(12) United States Patent
Feinstein et al.

(10) Patent No.: US 8,614,311 B2
(45) Date of Patent: Dec. 24, 2013

(54) RTP801L SIRNA COMPOUNDS AND METHODS OF USE THEREOF

(71) Applicant: Quark Pharmaceuticals, Inc., Fremont, CA (US)

(72) Inventors: Elena Feinstein, Rehovot (IL); Igor Mett, Rehovot (IL); Hagar Kalinski, Rishon-le-Zion (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

(21) Appl. No.: 13/651,123

(22) Filed: Oct. 12, 2012

(65) Prior Publication Data

US 2013/0131143 A1    May 23, 2013

Related U.S. Application Data

(63) Continuation-in-part of application No. 12/735,061, filed as application No. PCT/IL2008/001606 on Dec. 11, 2008, now abandoned.

(60) Provisional application No. 61/007,480, filed on Dec. 12, 2007.

(51) Int. Cl.
*C07H 21/04* (2006.01)

(52) U.S. Cl.
USPC .......................................................... 536/24.5

(58) Field of Classification Search
USPC .......................................................... 536/24.5
See application file for complete search history.

(56) References Cited

U.S. PATENT DOCUMENTS

| | | | |
|---|---|---|---|
| 5,753,789 A | 5/1998 | Chu et al. |
| 5,874,277 A | 2/1999 | Shintani et al. |
| 5,891,683 A | 4/1999 | Usman et al. |
| 5,898,031 A | 4/1999 | Crooke |
| 5,998,203 A | 12/1999 | Matulic-Adamic et al. |
| 6,107,094 A | 8/2000 | Crooke |
| 6,117,657 A | 9/2000 | Usman et al. |
| 6,235,886 B1 | 5/2001 | Manoharan et al. |
| 6,251,666 B1 | 6/2001 | Beigelman |
| 6,268,490 B1 | 7/2001 | Imanishi et al. |
| 6,372,249 B1 | 4/2002 | Smith et al. |
| 6,455,674 B1 | 9/2002 | Einat et al. |
| 6,506,559 B1 | 1/2003 | Fire et al. |
| 6,555,667 B1 | 4/2003 | Einat et al. |
| 6,586,238 B1 | 7/2003 | Matulic-Adamic et al. |
| 6,602,858 B2 | 8/2003 | Beigelman |
| 6,673,549 B1 | 1/2004 | Furness et al. |
| 6,740,738 B2 | 5/2004 | Einat et al. |
| 7,056,704 B2 | 6/2006 | Tuschl et al. |
| 7,078,196 B2 | 7/2006 | Tuschl et al. |
| 7,335,765 B2 | 2/2008 | Kaneko et al. |
| 7,452,987 B2 | 11/2008 | Giese et al. |
| 7,626,015 B2 | 12/2009 | Feinstein et al. |
| 7,629,456 B2 | 12/2009 | Lange et al. |
| 7,723,052 B2 | 5/2010 | Wechsler et al. |
| 7,741,299 B2 | 6/2010 | Feinstein et al. |
| 7,872,119 B2 | 1/2011 | Feinstein et al. |
| 7,893,245 B2 | 2/2011 | Giese et al. |
| 8,017,764 B2 | 9/2011 | Feinstein et al. |
| 8,067,570 B2 | 11/2011 | Feinstein et al. |
| 8,090,542 B2 | 1/2012 | Khvorova et al. |
| 8,097,710 B2 | 1/2012 | Baulcombe et al. |
| 2002/0119463 A1 | 8/2002 | Faris |
| 2002/0137077 A1 | 9/2002 | Hopkins et al. |
| 2003/0027783 A1 | 2/2003 | Zernicka-Goetz et al. |
| 2003/0104973 A1 | 6/2003 | Einat et al. |
| 2003/0108871 A1 | 6/2003 | Kaser |
| 2003/0108923 A1 | 6/2003 | Tuschl et al. |
| 2003/0165864 A1 | 9/2003 | Lasek et al. |
| 2004/0180351 A1 | 9/2004 | Giese et al. |
| 2004/0192626 A1 | 9/2004 | McSwiggen et al. |
| 2004/0229266 A1 | 11/2004 | Tuschl et al. |
| 2004/0265839 A1 | 12/2004 | Mello et al. |
| 2005/0004064 A1 | 1/2005 | Tei et al. |
| 2005/0020525 A1 | 1/2005 | McSwiggen et al. |
| 2005/0037988 A1 | 2/2005 | Zamore et al. |
| 2005/0080246 A1 | 4/2005 | Allerson et al. |
| 2005/0181382 A1 | 8/2005 | Zamore et al. |
| 2005/0223427 A1 | 10/2005 | Leake et al. |
| 2005/0233342 A1 | 10/2005 | Manoharan et al. |
| 2005/0255487 A1 | 11/2005 | Khvorova et al. |
| 2006/0058266 A1 | 3/2006 | Manoharan et al. |
| 2006/0069056 A1 | 3/2006 | Feinstein et al. |
| 2006/0217329 A1 | 9/2006 | Feinstein |
| 2006/0241072 A1 | 10/2006 | Baker |

(Continued)

FOREIGN PATENT DOCUMENTS

CA    2343602    4/2001
DE    19816395    10/1999

(Continued)

OTHER PUBLICATIONS

Amarzguioui et al., (2003) "Tolerance for Mutations and Chemical Modifications in a siRNA". Nucleic Acids Research, 31(2):589-95.
Barik, (2005) "Silence of the transcripts; RNA Interference in Medicine". Mol. Med, 83:764-773.
Bartel. (2004) "MicroRNAs: Genomics Biogenisis, Mechanism, and Function," Cell, 116:281-97.
Bernstein et al. (2001). "Role for a Bidentate Ribinuclease in the Intiation Step RNA Interference," Nature, 409: 363-66.
Bitko et al. (2004). "Inhibiton of Respiratory Viruses by Nassaly Administered siRNA," Nature Medicine, 11(1) :50-5.
Brafman et al. (2004) "Inhibition of Oxygen-Induced Retinopathy in RTP801-Deficient Mice," Investigative Optjamology & Visual Science, 45(10): 3796-3805.
Bass (2001) "The short answer". Nature 411:428-29.
Braasch et al., (2003) "RNA Interference in Mammalian Cells by Chemically-Modified RNA". Biochemistry, 42:7967-7975.

(Continued)

*Primary Examiner* — Jon E Angell
(74) *Attorney, Agent, or Firm* — John P. White; Cooper & Dunham LLP

(57) ABSTRACT

The invention provides chemically modified siRNA oligonucleotides that target RTP801L, compositions comprising same and to the use of such molecules to treat, inter alia, respiratory diseases including acute and chronic pulmonary disorders, eye diseases including glaucoma and ION, microvascular disorders, angiogenesis- and apoptosis-related conditions, and hearing impairments.

19 Claims, 11 Drawing Sheets

(56) References Cited

U.S. PATENT DOCUMENTS

| | | |
|---|---|---|
| 2007/0031844 A1 | 2/2007 | Khvorova et al. |
| 2007/0032441 A1 | 2/2007 | McSwiggen et al. |
| 2007/0185017 A1 | 8/2007 | Aggarwal et al. |
| 2007/0185047 A1 | 8/2007 | Bhat |
| 2007/0224201 A1 | 9/2007 | Wu et al. |
| 2007/0270579 A1 | 11/2007 | Jadhav et al. |
| 2007/0281326 A1 | 12/2007 | Wechsler et al. |
| 2008/0014599 A1 | 1/2008 | Wechsler et al. |
| 2008/0064650 A1 | 3/2008 | Feinstein et al. |
| 2009/0162365 A1 | 6/2009 | Feinstein et al. |
| 2010/0292301 A1 | 11/2010 | Feinstein et al. |
| 2011/0112168 A1 | 5/2011 | Feinstein et al. |
| 2012/0108647 A1 | 5/2012 | Feinstein et al. |

FOREIGN PATENT DOCUMENTS

| | | |
|---|---|---|
| EP | 0540742 A1 | 5/1993 |
| EP | 1 394 274 A2 | 3/2004 |
| EP | 1009753 B1 | 4/2005 |
| EP | 1 104 808 A1 | 9/2005 |
| EP | 1 580 263 A1 | 9/2005 |
| JP | 2003-259877 | 9/2003 |
| WO | WO 00/14283 | 3/2000 |
| WO | WO 00/44895 | 8/2000 |
| WO | WO 00/44914 | 8/2000 |
| WO | WO 00/61620 | 10/2000 |
| WO | WO 00/77022 A1 | 12/2000 |
| WO | WO 01/36646 A1 | 5/2001 |
| WO | WO 01/68836 | 9/2001 |
| WO | WO 01/70979 A2 | 9/2001 |
| WO | WO 01/75164 | 10/2001 |
| WO | WO 01/77289 A2 | 10/2001 |
| WO | WO 01/12659 A2 | 12/2001 |
| WO | WO 01/96391 | 12/2001 |
| WO | WO 02/31111 A2 | 4/2002 |
| WO | WO 02/44321 A2 | 6/2002 |
| WO | WO 02/46465 A2 | 6/2002 |
| WO | WO 02/055693 | 7/2002 |
| WO | WO 02/068579 A2 | 9/2002 |
| WO | WO 02/101075 A2 | 12/2002 |
| WO | WO 03/010205 A1 | 2/2003 |
| WO | WO 03/025138 | 3/2003 |
| WO | WO 03/029271 A2 | 4/2003 |
| WO | WO 03/064621 | 8/2003 |
| WO | WO 03/070918 | 8/2003 |
| WO | WO 03/074654 | 9/2003 |
| WO | WO 03/087768 A2 | 10/2003 |
| WO | WO 03/101283 | 12/2003 |
| WO | WO 2004/015107 | 2/2004 |
| WO | WO 2004/018999 A2 | 3/2004 |
| WO | WO 2004/031237 | 4/2004 |
| WO | WO 2004/045545 A2 | 6/2004 |
| WO | WO 2004/048368 A2 | 6/2004 |
| WO | WO 2004/060270 A2 | 7/2004 |
| WO | WO 2004/076633 A2 | 9/2004 |
| WO | WO 2004/091383 A2 | 10/2004 |
| WO | WO 2005/016000 A1 | 2/2005 |
| WO | WO 2005/044981 A2 | 5/2005 |
| WO | WO 2005/110464 | 11/2005 |
| WO | WO 2007/087451 | 8/2007 |

OTHER PUBLICATIONS

Brugarolas et al., (2004) "Regulation of Mtor Function in Response to Hypoxia by Reddi and the TSC1/TSC2 Tumor Suppressor Complex," Genes & Development, 18:2893-2904.

Brummelkamp et al. (2002). A System for Stable Expression of Short Interfering RNAs in Mammalian Cells Science, 296-550-553.

Caplen et al., (2001) "Specific Inhibition of Gene Expression by Small Double-Stranded RNAs in Invertebrate Vertebrate Systems". Proc Natl. Acad Sci, 98(17):9742-9747.

Chakraborty (2007) "Potentiality of Small Interfering RNAs- (siRNA)as Recent Therapeutic Targets for Gene-Silencing". Current Drug Targets, 8(3) :469-82.

Chalk et al. (2004). "Improved and Autonated Prediction of Effective siRNA," Biochemical and Biophysical Research Communications, 319: 264-274.

Chiu and Rana, (2002) "RNAi in Human Cells: basic Structural and Function Features of Small Interfering RNA" Molecular Cell, vol. 19, pp. 549-561.

Chiu and Rana, (2003) "siRNA function in RNAi: a chemical modification analysis". RNA, 9 (9) :1034-48.

Corradetti, (2005) The stress-inducted proteins RT801 and RTP801L are negative regulators of the mammalian target of rapamycin pathway. Biol Chem. Mar. 18; 280(11): 9769-72.

Cuaz-Perolin et al., (2004) REDD2 gene is upregulated by modified LDL or hypoxia and mediates human macrophage cell death. Arterioscler Thromb Vasc Biol. Oct.; 24(10) :1830-5. Epub Aug. 12, 2004.

Czauderna et al., (2003) "Structural Variations and Stabilising Modifications of Synthetic siRNAs in Mammalian Cells". NAR 31 (11):2705-16.

Damha et al., (1991) "Oligonucleotides containing unnatural L-2'-deoxyribose". Tetrahedron Letters 32(23) :2573-76.

Damha et al., (1994) "Antisense L/D-Oligodeoxynucleotide Chimeras: Nuclease Stability, Base-Pairing Properties, and Activity at Directing Ribonuclease H". Biochem 33 :7877-7885.

Dudek et al. (2004) TROD: T7 RNAi Oligio Designer, Nucleic Acids Research, 32:W121-W123.

Elbashir et al., (2001) "RNA Interference is Mediated by 21-and 22-nucleotide RNAs" Genes & Development, 15:188-200.

Elbashir et al., (2001) "Functional Anatomy of siRNAs for Mediating Efficient RNAi Drosophila melanogaster Embryo Lysate". EMBO Journal, 20(23) :6877-88.

Elbashir et al., (2001) "Duplexes of 21-nucleotide Mediated RNA Interference in Cultured Mammalian Cells" Nature 411:494-498.

Ellisen (2002) "Redd1, A Developmentally Regulated Transcriptional Target of p63 and p53, Links p63 to Regulation of Reactive Oxygen Species," Molecular Cell, 10: 995-1005.

Ellisen (2005) Growth control under stress: mTOR regulation through REDD1-TSC pathway. Cell Cycle. Nov.; 4(11) : 1500-02.

Elmen et al. (2005) "Locked nucleic acid (LNA) mediated improvements in siRNA stability and functionality." NAR 33 (1) :439-47.

Fire et al., (1998) "Potent and Specific Genetic Interference by Double-Stranded RNA in Caenorhabditis elegans". Nature, vol. 391:806-811.

Frovlov (2003) "Response markers and the Molecular mechanism of Action of Gleevac in Gastrointestinal Stromal Tumors," Molecular Cancer Therapeutics, 2: 699-709.

Honore et al. (2005): Understanding microtubule dynamics for improved cancer therapy. Cell Mol Life Sci. Dec.: 62(24): 3039-56. Review.

Garbesi et al., (1993) "L-DNAs as potential antimessenger oligonucleotides: a reassessment". Nuc. Acids Res. 21(18) :4159-65.

Hohjoh (2004) "Enhancement of RNAi activity by improved siRNA duplexes", FEBS Lett. 557(1-3):193-8.

Holen et al., (2002) "Positional effects of short interfering RNAs targeting the human coagulation trigger Tissue Factor". NAR. 30(8):1757-66.

International Search Report issued Oct. 20, 2010 in respect of International application PCT/IL2007/000695 (WO 2007/141796).

International Preliminary Report on Patentability issued Nov. 9, 2010 by the International Searching Authority (ISA/US) and Written Opinion issued Oct. 20, 2010 in connection with International Application PCT/IL2007/000695 (WO 2007/141796).

International Preliminary Report on Patentability by the International Searching Authority (ISA/US) on Oct. 20, 2009 in connection with International Application PCT/IL08/01606.

International Search Report issued Oct. 20, 2009 in connection with International Application PCT/IL2008/001606 (WO 2009/074990).

International Preliminary Report on Patentability issued Jun. 15, 2010 by the International Searching Authority (ISA/US) and Written Opinion issued on Oct. 20, 2009 in connection with International Application PCT/IL2008/001606 (WO 2009/074990).

International Search Report issued Oct. 7, 2008 in connection with PCT/IL2007/001278 (WO 2008/050329).

(56) References Cited

OTHER PUBLICATIONS

International Preliminary Report on Patentability issued Apr. 28, 2009 including Written Opinion issued Oct. 7, 2008 in connection with PCT/IL2007/001278 (WO2008/050329).
International Search Report issued Dec. 12, 2008 in connection with PCT/IL2008/000248 (WO 2007/091269).
International Preliminary Report on Patentability issued Jan. 19, 2010 including Written Opinion issued Nov. 8, 2008 in connection with PCT/IL2008/000248 (WO 2008/104978).
International Search Report issued Mar. 30, 2009 connection with PCT/IL2008/001197 (WO 2009/044392).
International Preliminary Report on Patentability issued Apr. 7, 2010 including Written Opinion issued Mar. 30, 2009 in connection with PCT/IL2008/001197 (WO 2009/044392).
Jozwiak et al. (2005): Positive and negative regulation of TSC2 activity and its effects on downstream effectors of the mTOR pathway. Neuromolecular Med. 7(4): 287-96.
Kawakami et al., (2005) Thermodynamic analysis of duplex formation of heterochiral DNA with L-deoxyadenosine. Analyt Sci. Feb. 2005 (21):77-82.
Kim et al., (2003) "Identification of Amyloid β-peptide Responsive Genes by cDNA Microarray Technology: Involvement of RTP801 in Amyloid β-peptide Toxicity," Experimental and Molecular Medicine, 35(5): 403-11.
Kurreck (2006) "siRNA efficiency: structure or sequence-that is the question". J Biomed Biotechnol 2006;2006(4):83757.
Lal et al., (2001) "Transcriptional Response to Hypoxia in Human Tumors," Journal of the National Cancer Institute, 93(17): 1337-1343.
Lee et al., (2003), "The nuclear Rnase III Drosha intiates microRNA processing," Nature, 425:415-419.
Lee et al., (2004) Spl-Dependent Regulation of the RTP801 Promoter and Its Application to Hypoxia Inducible VEGF Plasmid for Ischemic Disease, Pharmaceutical Research, 21 (5) 7 736-741.
Levenkova et al., (2004). "Gene specific siRNA selector," Bioinformatics, 20(3) 430-432.
Levkovitch-Verbin (2004) "Animal models of optic nerve diseases". Eye 18:1066-1074.
Liu et al. (2006). Mechanism of Aktl inhibition of breast cancer cell invasion reveals a protumorigenic role for TSC2. Proc Natl Aced Sci USA. Mar. 14; 103(11): 4134-9.
Mahato et al., (2005) "Modulation of Gene Expression by Antisense and Antigene Oligodeoxynucleotides and Small Interfering RNA". Expert Opinion on Drug Delivery 2(11:3-28.
McManus et al., (2002) "Gene Silencing in Mammals by Small Interfering RNAs". Nature Reviews Genetics, 3:737-747.
Morquette, et al. (2011) "mTOR Activity restores Retinal Ganglion Cell Dendritic Arbors and Glutamatergic Inputs After Injury In Vivo". May 3, 2011. Program # 2689/A170. Association for Research in Vision and Ophthalmology (ARVO), Inc., Sunday May 3, 2011.
Pisani et al., (2005) SMHS1 is involved in oxidative/glycolytic-energy metabolism balance of muscle fibers. Biochem Biophys Res Commun Jan. 28;326(4):788-93.
Prakash et al., (2005) "Positional effect of chemical modifications on short interference RNA activity in mammalian cells". J. Med Chem. :48(13)4247-53.
Prakash et al., (2006) "RNA interference by 2',5'-linked nucleic acid duplexes in mammalian cells". Bioorg Med. Cheer: Lett. 16(12):3238-40.
Rangsamy et al., (2004) "Genetic Ablation of Nrf2 Enhances Susceptibility to Cigarette Smoke-Induced Emphysema in Mice," The Journal of Clinical Investigation, 114(9): 1248-59.
Reich et al., (2003) Small interfering RNA (siRNA) targeting VEGF effectively inhibits ocular neovascularization in a mouse model, Molecular Vision, 9:210-216.
Reiling and Hafen (2004) "The Hypoxia-Induced Paralogs Scylla and Charybdis Inhibit Growth by Down-Regulating S6K Activity Upstream of TSC in *Drosophila*," Genes & Development, 18:2879-2892.

Richard et al. (2000) Nonhypoxix Pathway Mediates the Induction of Hypoxia- Inducible Factor 1α in Vascular Smooth Muscle Cells, The Journal of Biological Chemistry, 275(35): 26765-26771.
Sarbassov et al. (2006): Prolonged rapamycin treatment inhibits mTORC2 assembly and Akt/PKB. Mol Cell. Apr. 21;22(2): 159-68.
Schwarzer et al., (2005) "REDD1. Integrates Hypoxia-Mediated Survival Signaling Downstream of Phosphatidulinositol 3-kinase," Oncogene. 24: 1138-1149.
Scherer et al., (2003) "Approaches for the sequence-specific knockdown of mRNA". Nat. Biotechnol. 21(12):1457-1465.
Scherer and Rossi, (2004) "Therapeutic Applications of RNA Interferences: Recent Advances in siRNA Design". Advances in Genetics 22:1-21.
Shoshani et al., (2002) "Identification of a Novel Hypoxia-Induciblle Facto 1-Responsive Gene, RTP801, Involved in Apoptosis," Molecular and Cell Biology, 22(7): 2283-93.
Sioud et al., (2004) "Potential Design Rules and Enzymatic Synthesis of siRNAs" Methods in Molec. Biol., 252:457-468.
Sofer et al. (2005) Regulation of mTor and cell growth in response to energy stress by REDD1. Mol Cell Biol. Jul.; 25(14): 5834-45.
Strausberg et al., (2002) Generation and Initial Analysis of More Than 15,000 Full Length Human Mouse cDNA Sequences, Proceedings of the National Academy of Science of the United States of America, 99(26): 16899-16903.
Tee AR et al/ (2003): Tuberous sclerosis complex gene products, Tuberin and Hamartin, control mTOR signaling by acting as a GTPase-activating protien complex toward Rheb. Curr Biol. Aug. 5; 13(15): 1259-68.
Tolentino et al., (2004). Intravitreal Injection of Vascular Endothelial Growth Factor Small Interfering RNA Inhibits Growth and Leakage in a Nonhuman Primate, Laser-induced Model of Choroidal Neovascularization,: Retina, The Journal of Retinal and Vitreous Diseases, 24(1): 132-8.
Ui-Tei, Kumiko et al., (2004). "Guidelines for the selection of highly effective siRNA sequences for mammalian and chick RNA interference," Nucleic Acids Research, 32 (3) : 936-48.
Ui-Tei et al., (2006) "Essential notes regarding the design of functional siRNAs for efficient mammalian RNAi". J Biomed Biotechnol, 2006:65052.
Ui-Tei et al., (2008) "DNA-modified siRNA-dependent gene silencing with reduced off-target effect is induced through a pathway parallel to that for siRNA-mediated RNA interference." Proc 2008 Micro-NanoMechatronics and Human Science (MHS2008), 339-345.
Ui-Tei et al., (2008) "Functional dissection of siRNA sequence by systematic DNA substitution: modified siRNA with a DNA seed arm is a powerful tool for mammalian gene silencing with significantly reduced off-target effect". Nucleic Acids Res. 36(7):2136-51.
Urata et al., (1992) "Synthesis and properties of mirror-image DNA" Nucleic Acids Research 20(13)3325-3332.
Wang and Ortiz, (2003) "The Binding Sites on Human Heme Oxygenase-1 for Cytochrome P450 Reductase and Biliverdin Reductase," The American Society for Biochemistry and Molecular Biology, Inc., p. 1-38.
Wilson et al., (2009) "Targeted siRNA-Mediated Knockdown of Pro-Apoptotic Genes Delays Adult Retinal Ganglion Cell Death in vivo". Poster 111-A155. Association for Research in Vision and Ophthalmology (ARVO), Inc., Sunday May 3, 2009 Poster Session. p. 111-114.
Zamore et al., (2000) "RNAi: Double-Stranded RNA Directs the ATP-Dependent Cleavage of mRNA at 21 to 23 Nucleotide Intervals". Cell, 101:25-33.
Zhang et al., (2004) "Targeted Gene Silencing by Small Interfering RNA-Based Knock-Down Technology". Curr Pharmac Biotech, 5:1-7.
Non-Final Office Action issued Nov. 19, 2008 in connection with U.S. Appl. No. 11/811,112, filed Jun. 6, 2007.
Non-Final Office Action issued Jul. 25, 2008 in connection with U.S. Appl. No. 11/811,112, filed Jun. 6, 2007.
Notice of Allowance issued Jul. 16, 2009 in connection with U.S. Appl. No. 11/811,112, filed Jun. 6, 2007.
Non-Final Office Action issued Sep. 2, 2010 in connection with U.S. Appl. No. 12/589,972, filed Oct. 29, 2009.

(56) References Cited

OTHER PUBLICATIONS

Final Office Action issued Mar. 15, 2011 in connection with U.S. Appl. No. 12/589,972, filed Oct. 29, 2009.
Notice of Allowance issued May 3, 2011 in connection with U.S. Appl. No. 12/589,972, filed Oct. 29, 2009.
Non-Final Office Action issued Jun. 14, 2012 in connection with U.S. Appl. No. 12/735,061, filed Jan. 13, 2011.
Non-Final Office Action issued Mar. 1, 2012 in connection with U.S. Appl. No. 12/735,061, filed Jan. 13, 2011.
Non-Final Office Action issued Oct. 25, 2012 in connection with U.S. Appl. No. 13/218,053, filed Aug. 25, 2011.
Non-Final Office Action issued May 10, 2012 in connection with U.S. Appl. No. 13/218,053, filed Aug. 25, 2011.
Response filed Oct. 30, 2008 in connection with U.S. Appl. No. 11/811,112.
Response filed Mar. 23, 2009 in connection with U.S. Appl. No. 11/811,112.
Response filed Feb. 1, 2011 in connection with U.S. Appl. No. 12/589,972.
Response filed Jun. 1, 2012 in connection with U.S. Appl. No. 12/735,061.
Response filed Oct. 12, 2012 in connection with U.S. Appl. No. 12/735,061.
Response filed Aug. 27, 2012 in connection with U.S. Appl. No. 13/218,053.

Figure 1

Homo sapiens DNA-damage-inducible transcript 4-like (DDIT4L), mRNA.
ACCESSION   NM_145244
VERSION     NM_145244.2  GI:34222182

```
AGCCGGCGCA GGGUGGCCGG GGAGGGGUGA GCAGGGUGCC GCUGGCUGCU GGGGUCUGCA
GGUCACCGAG UCCCCAGGAG AGGGGACUCC UAAGAAGCCA CCUGCCUGUG UUUACCCGGC
AGCGAGCGCG CAGGCCCCCG CGAACUCCUG GCAGCGCUCA GGAAAGGCCG UUGCGCCUCG
CGAAGGAAAC AGAGCCGUUG ACCAUGGUUG CAACUGGCAG UUUGAGCAGC AAGAACCCGG
CCAGCAUUUC AGAAUUGCUG GACUGUGGCU AUCACCCAGA GAGCCUGCUA AGUGAUUUUG
ACUACUGGGA UUAUGUUGUU CCUGAACCCA ACCUCAACGA GGUAAUAUUU GAGGAAUCAA
CUUGCCAGAA UUUGGUUAAA AUGCUGGAGA ACUGUCUGUC CAAAUCAAAG CAAACUAAAC
UUGGUUGCUC AAAGGUCCUU GUCCCUGAGA ACUGACCCA GAGAAUUGCU CAAGAUGUCC
UGCGGCUUUC CUCAACGGAG CCCUGCGGCU UGCGAGGUUG UGUUAUGCAC GUGAACUUGG
AAAUUGAAAA UGUAUGUAAA AAGCUGGAUA GGAUUGUGUG UGAUUCUAGC GUCGUACCUA
CUUUUGAGCU UACACUUGUG UUUAAGCAGG AGAACUGCUC AUGGACUAGC UUCAGGGACU
UUUUCUUUAG UAGAGGUCGC UUCUCCUCUG GUUUCAGGAG AACUCUGAUC CUCAGCUCAG
GAUUUCGACU UGUUAAGAAA AAACUUUACU CACUGAUUGG AACAACAGUG AUUGAAGGGU
CCUAAAAAGG GAAAAUAUAU AAAGAUUAUU UCAUGAUUGG GUAGUAAAAC UAUUCAGCUA
GUCAGCUAAA GUCAUUUGUA GUUUGCCCCA CCUGCCCUAA AUAAGAAACC CCAAAUGUAG
UCUCUUUUCU UUCUGUGUUU CACAUUCAUA GCAACUGCAG CUAACAGGCU GAUUUUCUGG
CCUUUGGAGA AGUGAUUCAA AAUAGUGUAG AUUUUCUGCA UAGAUCCCAU UUUUGUACAG
AAUUGAAUGG GAUGGAAUAG GUAAGCAAAA GUAGAAGCCC AUUUGAGUUU UACAUUUGAU
UCCACAAUUU GGUUUCAGGU AGGCUUGGUA AUAGACUAUA UAAACCAGAU UUGCCUAUUU
UGAUUUUCAU AUGGCUUUUU UUUCUCUAAG UUUUCAGAGG AUUUUUUAAA UCACAGAAUC
AUACUAAAUG AUAUUUAGCU UAUCAAAACU UCCAAAAGCC CACACCACCA GUUCCUGACU
CAAAUUUGAA GGGUUUUUAG ACAGGAAGGU AGGAUUAAGU AGGUGAGUUU AAUUAAAGCU
UAACCCUAGG UAAGAGUAAA UGAGAAAUAU UACGGCAAUA AUGGAACUGC UUCACUGUUU
CUUGGUGACU UCCUCACUCU AAUGUUUUAA AGAGGCAACA AAAGCUUGUG GUGCCAUUUC
AGUAACCACG GUGUUGUUUU AGAUGCCUUU AUAAGCUCAG UUUCCCCUGU UCUUAAGUGU
UGAAUACUGU CUUUAAACUA GAAAAAUGCA AAAUAUUGAA CUGAUAUUUU UGUGUGUAGU
UGAUUACUCU UCCAUUGAGU GAAUGAUGAA UACCUGUGAG GAUAGGAAAU UAGUUCUGAG
AUCUAGUCCC UCUCUGAUUC ACUUAGUAAU CUAUCCUCUU UUCAGUAUUA CAUGUGCUUA
AUCUCAGAUG AACCAUUUCA CCAUGGCAGU GUUAUCUCAU CUCUGGGCUU UUCUGGGAAU
UGAAGUAUCU CUCCUUAACC CCAAUUGUCA AGGGUAGUAG CUGUAUACUA CCACUUUGAA
UUAUUGAAAC GGGUCAAUUU ACGAAGUCUG CAUUGGCUAU GGAGAUAUGG UUUAUAGUAC
AGCCUAGAGA AUGAAACUCA CCGUCCAGAU AACCAUGCAU GCACCCAGAU UUUUUCCACC
UUGGAUACCU GUCACUAGGG AAUAAUAAAG GCCUUAUUUU UUGUCUUAUU CCAACUAAGU
AGAUCAUUAU CUCUUUCCUU UUUUAUGUUA AUGAGAGAAU UUAGCCUCCA CUCAACAAUG
UUCAAUUCAG CAAGGCUUUC AUAUCCUUGC UGUGGGUCGU GGAUAAGGAG CUUAUUCAGG
UUUCCUGCCC UAGCUAUUAG CUCCACUUCA CAUGCUGGAG ACCGGCUAG GGACAGAUGU
AUUCAUCCUG GUGUUACUGA AAAACAGGUG UGAUCCUGUU ACUGAUACUA UAAGUGACCU
AAAAUGUCAC UGUUCAAAUU AGCCAGUGUU CUAACAAACU AAACUCUUCA AAUGCUUGGA
AAGAUACUAC AAAGCCAAUC UUUAUAGAAU UGGGCCAAGA UAAAUCAAUG UUGUUUUGCA
UGUCUAUUGU UAAGCUCCAA AGGUUCACUG UGUUUCUGCC GCUGUCCUGG AGUUGUCACC
ACUGACUGGG CAAGGCUUCU UGGGCAUCGA UGUAGAACUG UUGUCCUUUU UCCACUAACA
GUUAUCUUUG ACUCUCUUGC CUGUUAUGCU UACAAAAUGG UGAUGGCUUA UGGAAGGCUG
UUAAAUUAAU AUUCCUGUUA AAGGAAAUUA AAGUUUGUCU AUUUUUGACA AUAAAACAUU
AUAUAUUUUU AAAAAAAAAA AAAAAA
```

Figure 2

Table F – Preferred siRNA sequences

| Name | Sense 5' – 3' | AnUisense 5'-3' | Other ID |
|---|---|---|---|
| DDIT4L_6 | CCCAGAGAAUUGCUCAAGA | UCUUGAGCAAUUCUCUGGG | DDIT4L_228; #73 in Table A |
| DDIT4L_12 | CGUGAACUUGGAAAUUGAA | UUCAAUUUCCAAGUUCACG | #4 in Table B |
| DDIT4L_14 | ACGUGAACUUGGAAAUUGA | UCAAUUUCCAAGUUCACGU | #22 in Table B |
| DDIT4L_15 | UGGAGAACUGUCUGUCCAA | UUGGACAGACAGUUCUCCA | #69 in Table B |
| DDIT4L_20 | GUAAAAAGCUGGAUAGGAU | AUCCUAUCCAGCUUUUUAC | #172 in Table A |
| DDIT4L_21 | UGAACUUGGAAAUUGAAAA | UUUUCAAUUUCCAAGUUCA | |
| DDIT4L_22 | GUAUGUAAAAAGCUGGAUA | UAUCCAGCUUUUUACAUAC | #583 in Table A |
| DDIT4L_23 | GAUUUCGACUUGUUAAGAA | UUCUUAACAAGUCGAAAUC | #755 in Table A |
| DDIT4L_24 | GAACUUGGAAAUUGAAAAU | AUUUUCAAUUUCCAAGUUC | |
| DDIT4L_25 | GGAUUUCGACUUGUUAAGA | UCUUAACAAGUCGAAAUCC | #850 in Table A |
| DDIT4L_26 | GCACGUGAACUUGGAAAUU | AAUUUCCAAGUUCACGUGC | #345 in Table A |
| DDIT4L_27 | CCUGAGAAACUGACCCAGA | UCUGGGUCAGUUUCUCAGG | #264 in Table B |
| DDIT4L_28 | GAACUGUCUGUCCAAAUCA | UGAUUUGGACAGACAGUUC | |
| DDIT4L_29 | CUCAGGAUUUCGACUUGUU | AACAAGUCGAAAUCCUGAG | |
| DDIT4L_30 | GCUCAGGAUUUCGACUUGU | ACAAGUCGAAAUCCUGAGC | |
| DDIT4L_31 | GACUUGUUAAGAAAAAACU | AGUUUUUUCUUAACAAGUC | |

Table G    Fig. 3A

| Name | SEQ ID NO: | Sense 5->3 | SEQ ID NO: | AntiSense 5->3 | *1 | *2 | *3 | *4 | *5 |
|---|---|---|---|---|---|---|---|---|---|
| DDIT4L_12_S211 | 6928 | rC;rG;rU;rG;rA;rA;rC;rU;rU;rG;rG;rA;rA;dT;rU;rG;LdC;rA$ | 6966 | mU;rU;mC;rA;mA;rU;mU;rU;mC;rC;mA;rA;mG;rU;mU;rC;mA;rC;mG$ | | | 36 | 62 | |
| DDIT4L_12_S215M1 | 6929 | rC;rG;rU;rG;rA;rA;rC;rU;rU;rG;rG;rA;rA;dT;LdC;rG;LdC;rA$ | 6966 | mU;rU;mC;rA;mA;rU;mU;rU;mC;rC;mA;rA;mG;rU;mU;rC;mA;rC;mG$ | | | 71 | 60 | |
| DDIT4L_12_S219 | 6930 | iB;rC;rG;rU;rG;rA;rA;rC;rU;rU;rG;rG;rA;rA;dT;rU;rG;LdC;rA$ | 6966 | mU;rU;mC;rA;mA;rU;mU;rU;mC;rC;mA;rA;mG;rU;mU;rC;mA;rC;mG$ | | | 66 | 63 | |
| DDIT4L_12_S220M1 | 6931 | LdC;rC;rG;rU;rG;rA;rA;rC;rU;rU;rG;rG;rA;rA;dT;LdC;rG;LdC;rA$ | 6966 | mU;rU;mC;rA;mA;rU;mU;rU;mC;rC;mA;rA;mG;rU;mU;rC;mA;rC;mG$ | | | 55 | 102 | |
| DDIT4L_12_S221 | 6932 | c6Np;rC;rG;rU;rG;rA;rA;rC;rU;rU;rG;rG;rA;rA;dT;rU;rG;LdC;rA$ | 6966 | mU;rU;mC;rA;mA;rU;mU;rU;mC;rC;mA;rA;mG;rU;mU;rC;mA;rC;mG$ | | | 50 | 56 | |
| DDIT4L_12_S222M1 | 6933 | c6Np;rC;rG;rU;rG;rA;rA;rC;rU;rU;rG;rG;rA;rA;dT;LdC;rG;LdC;rA$ | 6966 | mU;rU;mC;rA;mA;rU;mU;rU;mC;rC;mA;rA;mG;rU;mU;rC;mA;rC;mG$ | | | 93 | 104 | |
| DDIT4L_12_S224M1 | 6934 | rC;LdC;rU;rG;rA;rA;rC;rU;rU;rG;rG;rA;rA;dT;rU;rG;LdC;rA$ | 6966 | mU;rU;mC;rA;mA;rU;mU;rU;mC;rC;mA;rA;mG;rU;mU;rC;mA;rC;mG$ | | | 76 | 110 | |
| DDIT4L_12_S225M1 | 6935 | rC;LdC;rU;rG;rA;rA;rC;rU;rU;rG;rG;rA;rA;dT;LdC;rG;LdC;rA$ | 6966 | mU;rU;mC;rA;mA;rU;mU;rU;mC;rC;mA;rA;mG;rU;mU;rC;mA;rC;mG$ | | | 114 | 134 | |
| DDIT4L_12_S389 | 6928 | rC;rG;rU;rG;rA;rA;rC;rU;rU;rG;rG;rA;rA;dT;rU;rG;LdC;rA$ | 6967 | rU;mU;rC;mA;rA;mU;rU;mU;rC;mC;mA;rA;mG;rU;mU;rC;mA;rC;mG$ | | | 72 | 71 | |
| DDIT4L_12_S234M1 | 6929 | rC;rG;rU;rG;rA;rA;rC;rU;rU;rG;rG;rA;rA;dT;LdC;rG;LdC;rA$ | 6967 | rU;mU;rC;mA;rA;mU;rU;mU;rC;mC;mA;rA;mG;rU;mU;rC;mA;rC;mG$ | | | 95 | 89 | |
| DDIT4L_12_S458 | 6930 | iB;rC;rG;rU;rG;rA;rA;rC;rU;rU;rG;rG;rA;rA;dT;rU;rG;LdC;rA$ | 6967 | rU;mU;rC;mA;rA;mU;rU;mU;rC;mC;mA;rA;mG;rU;mU;rC;mA;rC;mG$ | | | 47 | 74 | |
| DDIT4L_12_S381M1 | 6931 | LdC;rC;rG;rU;rG;rA;rA;rC;rU;rU;rG;rG;rA;rA;dT;LdC;rG;LdC;rA$ | 6967 | rU;mU;rC;mA;rA;mU;rU;mU;rC;mC;mA;rA;mG;rU;mU;rC;mA;rC;mG$ | | | 57 | 71 | |
| DDIT4L_12_S382 | 6932 | c6Np;rC;rG;rU;rG;rA;rA;rC;rU;rU;rG;rG;rA;rA;dT;rU;rG;LdC;rA$ | 6967 | rU;mU;rC;mA;rA;mU;rU;mU;rC;mC;mA;rA;mG;rU;mU;rC;mA;rC;mG$ | | | 71 | 49 | |
| DDIT4L_12_S383M1 | 6933 | c6Np;rC;rG;rU;rG;rA;rA;rC;rU;rU;rG;rG;rA;rA;dT;LdC;rG;LdC;rA$ | 6967 | rU;mU;rC;mA;rA;mU;rU;mU;rC;mC;mA;rA;mG;rU;mU;rC;mA;rC;mG$ | | | 46 | 91 | |
| DDIT4L_12_S384M1 | 6934 | rC;LdC;rU;rG;rA;rA;rC;rU;rU;rG;rG;rA;rA;dT;rU;rG;LdC;rA$ | 6967 | rU;mU;rC;mA;rA;mU;rU;mU;rC;mC;mA;rA;mG;rU;mU;rC;mA;rC;mG$ | | | 75 | 86 | |

Fig. 3B

| | | | | | | | |
|---|---|---|---|---|---|---|---|
| DDIT4L_12_S230M1 | 6935 | rC;LdC;rU;rG;rA;rA;rC;rU;rG;rG;rA;rA;dT;LdC;rG;LdC;rA$ | 6967 | rU;mU;rC;mA;rA;mU;rU;mU;rC;rC;mA;rA;mG;rU;mU;rC;mA;rC;mG$ | | 109 | 86 | 3 |
| DDIT4L_20_S211 | 6936 | rG;rA;rA;rA;rA;rA;rA;rG;rC;rU;rG;rA;rU;dA;rG;rG;LdC;rU$ | 6968 | mA;rU;mC;mU;rC;mU;rA;mU;rC;mC;rA;mG;rC;mU;rU;mU;rA;mC$ | 25 | 32 | 28 | 49 |
| DDIT4L_20_S213 | 6937 | rG;rA;rA;rA;rA;rA;rA;rG;rC;rU;rG;rA;rU;dA;rG;LdC;LdC;rU$ | 6968 | mA;rU;mC;rC;mU;rA;mU;rC;mC;rA;mG;rC;mU;rU;mU;rA;mC$ | 28 | 35 | 23 | 31 | — |
| DDIT4L_21_S211 | 6938 | rU;rG;rA;rA;rC;rU;rG;rG;rG;rA;rA;LdC;rA$ | 6969 | mU;rU;mU;rU;mC;rA;mA;rU;mU;rU;rC;mA$ | 22 | 28 | 32 | 40 | — |
| DDIT4L_21_S213 | 6939 | rU;rG;rA;rA;rC;rU;rG;rG;rG;rA;rA;LdC;LdC;rA$ | 6969 | mU;rU;mU;rU;mC;rA;mA;rU;mU;rU;rC;mA$ | 30 | 38 | 55 | 73 |
| DDIT4L_22_S211 | 6940 | rU;rG;rA;rU;rG;rU;rA;rA;rA;rA;LdC;rA$ | 6970 | mU;rU;mU;mC;rA;mG;rC;mU;rU;rC;mA$ | | | | |
| DDIT4L_22_S213 | 6941 | rG;rU;rA;rG;rU;rU;rG;LdC;LdC;LdC;rA$ | 6970 | mU;rU;mU;rA;mU;rA;mC;rA;mG;rC;mU;rU;rC;mA$ | 22 | 21 | 22 | 32 |
| DDIT4L_23_S211 | 6942 | rG;rC;rU;rG;rU;rA;rC;rG;rA;rC;rU;rU$ | 6971 | mU;rU;mC;rG;mA;rA;mC;mA;rU;mC$ | 32 | 51 | 38 | 44 |
| DDIT4L_23_S213 | 6943 | rG;rU;rU;rU;rU;rA;rC;rC;rC;rA;LdC;LdC;LdC;rU$ | 6971 | mU;rU;mC;rC;mA;mA;mC;rA;mU;mC$ | 26 | 23 | 17 | 22 |
| DDIT4L_24_S211 | 6944 | rG;rA;rA;rC;rU;rU;rU;rG;rA;rA;LdC;rA$ | 6972 | mA;rU;mC;mC;rA;mA;rA;mU;rU;rC$ | 40 | 43 | 37 | 34 |
| DDIT4L_24_S213 | 6945 | rG;rA;rA;rC;rU;rU;rU;rG;rG;rA;rA;LdC;rA$ | 6972 | mA;rU;mC;mC;rA;mA;rA;mU;rU;rC$ | 22 | 23 | 19 | 21 |
| DDIT4L_25_S211 | 6946 | rG;rG;rA;rU;rU;rU;rC;rG;rA;rC;LdC;LdC;rU$ | 6973 | mU;rC;mG;rU;mA;rA;mC;rA;mC;rG$ | 29 | 36 | 25 | 28 |
| DDIT4L_25_S213 | 6947 | rU;rG;rG;rU;rU;rC;rA;LdC;LdC;rA$ | 6973 | mU;rC;mG;rU;mA;rA;mC;mA;rC$ | 13 | 21 | 20 | 29 |
| DDIT4L_26_S211 | 6948 | rG;rA;rC;rG;rG;rA;rA;rA;LdC;rU$ | 6974 | mA;rA;mU;rU;mU;rC;mC;rA;mA;rC$ | 33 | 27 | 27 | 26 | — |
| DDIT4L_26_S213 | 6949 | rC;rU;rG;rA;rC;rA;rA;rA;LdC;rA$ | 6974 | mA;rA;mU;rU;mU;rC;mC;rA;mA;rC$ | 49 | 36 | 74 | 72 |
| DDIT4L_27_S211 | 6950 | rC;rC;rU;rG;rA;rA;rA;rA;LdC;rU$ | 6975 | mU;rU;mU;rC;mG;rG;mU;rC;mU;rG$ | 61 | 63 | 78 | 114 |
| DDIT4L_27_S213 | 6951 | rG;rA;rC;rC;rC;rU;rA;LdC;rA$ | 6975 | mU;rU;mU;rC;mU;rG;mA;rG$ | | | | |

Fig. 3C

| | | | | | | |
|---|---|---|---|---|---|---|
| DDIT4L_28_S211 | 6952 | rG;rA;rC;rA;rG;rU;rC;rU;rG;rU;rC;rG;rA;dA;rA;rU;LdC;rA$ | 6976 | mU;rG;mA;rU;mU;rU;mG;rG;mA;rC;mA;rG;mA;rC;rU;mA;rG;mU;rU;mC$ | 40 | 35 | | |
| DDIT4L_28_S213 | 6953 | rG;rA;rC;rU;rG;rU;rC;rG;rU;rG;rU;rC;rC;rA;dA;rA;LdC;LdC;rA$ | 6976 | mU;rG;mA;rU;mU;rG;rG;mA;rC;mA;rG;mU;rU;mC$ | 68 | 73 | | |
| DDIT4L_29_S211 | 6954 | rC;rU;rC;rA;rG;rA;rU;rU;rU;rC;rA;rC;rU;rG;LdC;LdC;rU$ | 6977 | mA;rA;mC;rA;mA;rU;rC;mG;rU;mC;rG;rA;mG$ | 41 | 40 | | |
| DDIT4L_29_S213 | 6955 | rC;rU;rC;rA;rG;rA;rU;rU;rU;rC;rG;rA;rC;dT;rU;LdC;LdC;rU$ | 6977 | mA;rA;mC;rA;mA;rG;mU;rC;mG;rA;mG$ | 38 | 40 | | |
| DDIT4L_30_S211 | 6956 | rG;rC;rU;rC;rA;rG;rA;rU;rU;rU;rC;rA;rU;rG;LdC;LdC;rU$ | 6978 | mA;rC;mA;rA;rG;mA;rG;mA;rC;mU;rU;mG;mA;rA;rG;mU$ | 43 | 31 | | |
| DDIT4L_30_S213 | 6957 | rC;rG;rA;rC;rG;rU;rC;rC;rA;rG;rU;rU;rC;rG;LdC;LdC;rU$ | 6978 | mA;rC;mA;rA;mG;rC;mU;rG;mA;rC;mG;rA;mG;mU$ | 24 | 49 | | |
| DDIT4L_31_S211 | 6958 | rG;rA;rC;rU;rC;rA;rG;rA;rU;rA;rA;rU;rA;LdC;LdC;rU$ | 6979 | mA;rG;mA;rU;mU;mU;rC;mC;rU;mU;mU;rU;mC$ | 41 | 40 | 63 | 67 | 13 | 16 |
| DDIT4L_31_S213 | 6959 | rG;rA;rC;rU;rC;rG;rU;rC;rG;rU;rA;rA;rA;LdC;LdC;rU$ | 6979 | mA;rA;mA;rC;mA;rA;mG;mU;rU;mU;rU;mC$ | 112 | 71 | 122 | 86 | 22 | 24 |
| DDIT4L_14_S211 | 6960 | rA;rC;rU;rG;rU;rA;rG;rU;rA;rC;rU;rG;rU;rG;LdC;LdC;rU;rG$ | 6980 | mU;rC;mA;rA;rU;mU;rU;mC;rG;mC;mU;rU;mU$ | 24 | 38 | 7 | 13 | 8 | 10 |
| DDIT4L_14_S213 | 6961 | rA;rC;rG;rA;rC;rU;rG;rU;rC;rU;rG;rU;rG;LdC;LdC;rA$ | 6980 | mU;rC;mA;rA;rU;mU;rU;mC;rG;mC;rA;mU$ | 51 | 32 | 8 | 22 | | |
| DDIT4L_15_S211 | 6962 | rU;rG;rG;rA;rG;rA;rC;rU;rU;rG;rC;rU;rG;rT;rC;LdC;LdC;rA$ | 6981 | mU;rG;mU;rU;mG;mA;rC;mA;rG;mA;rC;rG;mC$ | 67 | 66 | 59 | 83 | | 10 |
| DDIT4L_15_S213 | 6963 | rU;rG;rG;rA;rG;rA;rA;rC;rU;rC;rG;rU;dT;rC;LdC;LdC;rU$ | 6981 | mU;rU;mG;mU;rG;mA;rC;mA;rG;mA;rC;mA$ | 28 | 29 | 18 | 28 | | 10 |
| DDIT4L_6_S211 | 6964 | rC;rG;rC;rU;rC;rA;rG;rA;rA;rG;rA;rA;rG;LdC;LdC;rA$ | 6982 | mA;rU;rC;mA;rC;mU;rU;mG;rA;mG;rA;mG;rA;mU$ | 22 | 26 | | | | 3 |
| DDIT4L_6_S213 | 6965 | rC;rG;rC;rU;rC;rA;rG;rA;rA;rG;rA;rA;rG;LdC;LdC;rA$ | 6982 | mU;rG;mU;rU;mC;mU;rU;mC;mU;rU;mC;rU;mG;rG$ | 49 | 41 | | | | — |

Activity of REDD2 siRNAs on the endogenous REDD2 gene in wt MEF cells following H2O2 treatment Results are presented as residual REDD2 expression.

Dose dependent activity of REDD2 siRNA oligos as measured in 801 wt MEF cells. Results are presented as residual REDD2 expression.

Activity of REDD2 siRNAs on the endogenous REDD2 gene in wt 293T Results are presented as residual REDD2 expression.

Dose dependent activity of RTP801L siRNA as measured in 293T cells. Results are presented as residual RTP801L expression.

Figure 8A

| siRNA duplex name | SEQ ID NO: | N-DNA; N-2'Ome<br>n- L-DNA | Activity at 20nM-% of control |
|---|---|---|---|
| DDIT4L_20_S1-DS | 131726 | 6936 GUAAAAAGCUGGAU*A*GG*c*U<br>6968 AU<u>CC</u>U<u>A</u>U<u>CC</u>A<u>G</u>CUU<u>U</u>U<u>U</u>A<u>C</u> | 25-hum<br>28-rat |
| DDIT4L_20_S2-DS | 131727 | 6937 GUAAAAAGCUGGAU*A*G*cc*U<br>6968 AU<u>CC</u>U<u>A</u>U<u>CC</u>A<u>G</u>CUU<u>U</u>U<u>U</u>A<u>C</u> | 28-hum<br>23-rat |
| DDIT4L_21_S1-DS | 131728 | 6938 UGAACUUGGAAAUU*GA*A*c*A<br>6969 UU<u>U</u>U<u>C</u>A<u>A</u>U<u>U</u>U<u>CC</u>A<u>A</u>G<u>UU</u>C<u>A</u> | 22-hum<br>32-rat |
| DDIT4L_21_S2-DS | 131729 | 6939 UGAACUUGGAAAUU*GA*A*c*A<br>6969 UU<u>U</u>U<u>C</u>A<u>A</u>U<u>U</u>U<u>CC</u>A<u>A</u>G<u>UU</u>C<u>A</u> | 30-hum<br>55-rat |
| DDIT4L_23_S1-DS | 131732 | 6942 GAUUUCGACUUGUU*AA*G*c*A<br>6971 UU<u>C</u>U<u>U</u>A<u>A</u>C<u>AA</u>G<u>U</u>C<u>G</u>A<u>AA</u>U<u>C</u> | 22-hum<br>22-rat |
| DDIT4L_23_S2-DS | 131733 | 6943 GAUUUCGACUUGUU*AA*cc*A<br>6971 UU<u>C</u>U<u>U</u>A<u>A</u>C<u>AA</u>G<u>U</u>C<u>G</u>A<u>AA</u>U<u>C</u> | 32-hum<br>38-rat |
| DDIT4L_24_S1-DS | 131734 | 6944 GAACUUGGAAAUUG*A*A*c*U<br>6972 AU<u>U</u>U<u>U</u>C<u>A</u>A<u>U</u>U<u>U</u>C<u>C</u>A<u>A</u>G<u>UU</u>C | 26-hum<br>17-rat |
| DIT4L_24_S2-DS | 131735 | 6945 GAACUUGGAAAUUG*A*A*cc*U<br>6972 AU<u>U</u>U<u>U</u>C<u>A</u>A<u>U</u>U<u>U</u>C<u>C</u>A<u>A</u>G<u>UU</u>C | 40-hum<br>37-rat |
| DDIT4L_25_S1-DS | 131736 | 6946 GGAUUUCGACUUGU*TA*A*c*A<br>6973 U<u>C</u>U<u>U</u>A<u>A</u>C<u>AA</u>G<u>U</u>C<u>G</u>A<u>AA</u>U<u>CC</u> | 22-hum<br>19-rat |
| DDIT4L_25_S2-DS | 131737 | 6947 GGAUUUCGACUUGU*TA*cc*A<br>6973 U<u>C</u>U<u>U</u>A<u>A</u>C<u>AA</u>G<u>U</u>C<u>G</u>A<u>AA</u>U<u>CC</u> | 29-hum<br>25-rat |
| DDIT4L_26_S1-DS | 131738 | 6948 GCACGUGAACUUGG*AA*A*c*U<br>6974 A<u>A</u>U<u>U</u>U<u>CC</u>A<u>A</u>G<u>UU</u>C<u>A</u>C<u>G</u>U<u>G</u>C | 13-hum<br>20-rat |
| DDIT4L_26_S2-DS | 131739 | 6949 GCACGUGAACUUGG*AA*cc*U<br>6974 A<u>A</u>U<u>U</u>U<u>CC</u>A<u>A</u>G<u>UU</u>C<u>A</u>C<u>G</u>U<u>G</u>C | 33-hum<br>27-rat |

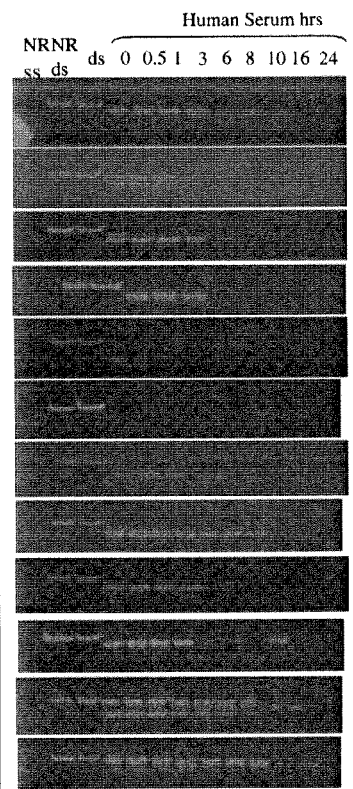

Figure 8B

| siRNA duplex name | ID | SEQ ID NO: | N-DNA; N=2'-5'-nucs; N-LNA; N-2'Ome<br>n- L-DNA; C6-Im-Pi -C6-IminoPi | Activity at 20nM-% of target gene |
|---|---|---|---|---|
| DDIT4L_14_S1 | 128339 | 6960<br>6980 | ACGUGAACUUGGAAA*U*U*c*A<br>U<u>C</u>A<u>A</u>U<u>UU</u>C<u>C</u>A<u>A</u>G<u>UU</u>C<u>A</u>C<u>G</u>U | 24-hum<br>7-rat |
| DDIT4L_14_S2 | 128340 | 6961<br>6980 | ACGUGAACUUGGAAA*U*cc*A<br>U<u>C</u>A<u>A</u>U<u>UU</u>C<u>C</u>A<u>A</u>G<u>UU</u>C<u>A</u>C<u>G</u>U | 32-hum<br>8-rat |
| DDIT4L_15_S1 | 128341 | 6962<br>6981 | UGGAGAACUGUCUG*U*CC*c*A<br>U<u>U</u>G<u>G</u>A<u>C</u>A<u>G</u>A<u>C</u>A<u>G</u>U<u>U</u>C<u>U</u>C<u>C</u>A | 28-hum |
| DDIT4L_15_S2 | 128343 | 6963<br>6981 | UGGAGAACUGUCUGUC*cc*A<br>U<u>U</u>G<u>G</u>A<u>C</u>A<u>G</u>A<u>C</u>A<u>G</u>U<u>U</u>C<u>U</u>C<u>C</u>A | 67<br>59-rat |
| DDIT4L_6_S1 | 128344 | 6964<br>6982 | CCCAGAGAAUUGCUCA*A*c*A<br>U<u>C</u>U<u>U</u>G<u>A</u>G<u>C</u>A<u>A</u>U<u>U</u>C<u>U</u>C<u>U</u>G<u>G</u>G | 22-hum |
| DDIT4L_6_S2 | 128345 | 6965<br>6982 | CCCAGAGAAUUGCUCA*cc*A<br>U<u>C</u>U<u>U</u>G<u>A</u>G<u>C</u>A<u>A</u>U<u>U</u>C<u>U</u>C<u>U</u>G<u>G</u>G | 49-hum |

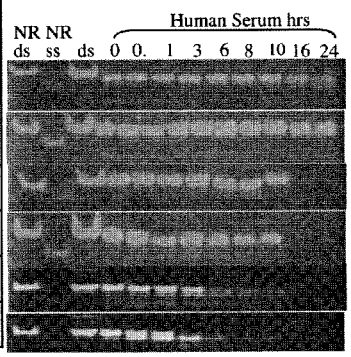

RTP801L SIRNA COMPOUNDS AND METHODS OF USE THEREOF

This application is a continuation-in-part of U.S. Ser. No. 12/735,061, filed Jan. 13, 2011, which is a §371 national stage of PCT International Application No. PCT/IL2008/001606, filed Dec. 11, 2008, claiming the benefit of U.S. Provisional Application No. 61/007,480, filed Dec. 12, 2007, the content of all of which are hereby incorporated by reference into the subject application.

This application incorporates-by-reference nucleotide and/or amino acid sequences which are present in the file named "121012_2094_76494-B-PCT-US_Sequence_Listing_SZ.txt," which is 1.27 megabytes in size, was created on Sep. 13, 2012, in the IBM-PCT machine format, having an operating system compatibility with MS-Windows and is contained in the text file submitted Oct. 12, 2012 as part of the above-identified application.

FIELD OF THE INVENTION

The present invention relates to double stranded oligonucleotide inhibitors of RTP801L (RTP801-like; REDD2, DNA-damage-inducible transcript 4-like, DDIT4_L), pharmaceutical compositions comprising same and methods of use thereof. The compounds and compositions are thus useful in the treatment of subjects suffering from diseases or conditions and or symptoms associated with such diseases or conditions in which RTP801L expression has adverse consequences. In particular embodiments, the invention provides chemically modified siRNA oligonucleotides, compositions comprising same and to the use of such molecules to treat, inter alia, respiratory disorders of all types (including acute and chronic pulmonary disorders), eye diseases including glaucoma and ION, microvascular disorders, angiogenesis- and apoptosis-related conditions, and hearing impairments.

BACKGROUND OF THE INVENTION siRNAs and RNA Interference

RNA interference (RNAi) is a phenomenon involving double-stranded (ds) RNA-dependent gene specific posttranscriptional silencing. Originally, attempts to study this phenomenon and to manipulate mammalian cells experimentally were frustrated by an active, non-specific antiviral defense mechanism which was activated in response to long dsRNA molecules (see Gil et al. 2000, *Apoptosis*, 5:107-114). Later it was discovered that synthetic duplexes of 21 nucleotide RNAs could mediate gene specific RNAi in mammalian cells, without the stimulation of the generic antiviral defense mechanisms (see Elbashir et al., 2001. *Nature*, 411:494-498 and Caplen et al., 2001. *PNAS*, 98:9742-9747). As a result, small interfering RNAs (siRNAs), which are short double-stranded RNAs, have become powerful tools in attempting to understand gene function. Thus RNA interference (RNAi) refers to the process of sequence-specific post-transcriptional gene silencing in mammals mediated by small interfering RNAs (siRNAs) (Fire et al, 1998, *Nature* 391:806) or microRNAs (miRNAs) (Ambros, 2004. *Nature* 431:7006, 350-355; and Bartel, 2004. *Cell*. 116(2):281-97). The corresponding process in plants is commonly referred to as specific post transcriptional gene silencing or RNA silencing and is also referred to as quelling in fungi.

An siRNA is a double-stranded RNA molecule which down-regulates or silences (prevents) the expression of a gene/mRNA of its endogenous or cellular counterpart. The mechanism of RNA interference is detailed infra.

siRNA has been successfully used for inhibition in primates; (for further details see Tolentino et al., 2004. *Retina* 24(1):132-138). Several studies have revealed that siRNA therapeutic agents are effective in vivo in both mammals and in humans. Bitko et al., have shown that specific siRNA molecules directed against the respiratory syncytial virus (RSV) nucleocapsid N gene are effective in treating mice when administered intranasally (Bitko et al., 2005. *Nat. Med.* 11(1):50-55). Reviews of the use of siRNA as a therapeutic agent recently published (see for example Barik 2005. *J. Mol. Med.* 83:764-773 and Dykxhoorn et al., 2006. *Gene Therapy* 13:541-552). In addition, clinical studies with short siRNAs that target the VEGFR1 receptor for the treatment of Age-Related Macular Degeneration (AMD) have been conducted in human patients. (Kaiser, 2006. *Am. J Ophthalmol.* 142(4): 660-8).

Chemically Modified siRNA

The selection and synthesis of siRNA corresponding to known genes has been widely reported; (see for example Ui-Tei et al., 2006. *J Biomed Biotechnol.*; 2006:65052; Chalk et al., 2004. *BBRC*. 319(1): 264-74; Sioud & Leirdal, 2004. *Met. Mol Biol.*; 252:457-69; Levenkova et al., 2004, *Bioinform.* 20(3):430-2; Ui-Tei et al., 2004. *NAR* 32(3):936-48).

For examples of the use of, and production of, modified siRNA see for example Braasch et al., 2003. *Biochem.*, 42(26):7967-75; Chiu et al., 2003, *RNA*, 9(9):1034-48; PCT publications WO 2004/015107 (atugen AG) and WO 02/44321 (Tuschl et al). U.S. Pat. Nos. 5,898,031 and 6,107, 094 teach chemically modified oligomers. US patent publication 2005/0080246 relates to oligomeric compounds having an alternating motif. US patent publication 2005/0042647 describes dsRNA compounds having chemically modified internucleoside linkages.

The inclusion of a 5'-phosphate moiety was shown to enhance activity of siRNAs in *Drosophila* embryos (Boutla, et al., 2001, *Curr. Biol.* 11:1776-1780) and is required for siRNA function in human HeLa cells (Schwarz et al., 2002, *Mol. Cell*, 10:537-548).

Amarzguoui et al., (2003, *NAR*, 31(2):589-595) showed that siRNA activity depended on the positioning of the 2'-O-methyl modifications. Holen et al (2003, *NAR*, 31(9):2401-2407) report that an siRNA having small numbers of 2'-O-methyl modified nucleosides gave good activity compared to wild type but that the activity decreased as the numbers of 2'-O-methyl modified nucleosides was increased. Chiu and Rana (2003, *RNA*, 9:1034-1048) teach that incorporation of 2'-O-methyl modified nucleosides in the sense or antisense strand (fully modified strands) severely reduced siRNA activity relative to unmodified siRNA. The placement of a 2'-O-methyl group at the 5'-terminus on the antisense strand was reported to severely limit activity whereas placement at the 3'-terminus of the antisense and at both termini of the sense strand was tolerated (Czauderna et al., 2003, *NAR*, 31(11), 2705-2716).

PCT Patent Publication Nos. PCT/IL2008/000248 and PCT/IL2008/001197 assigned to the assignee of the present invention disclose motifs useful in the preparation of chemically modified siRNA compounds.

RTP801L

Gene RTP801 (REDD1, DDIT4), was first reported by the assignee of the instant application. U.S. Pat. Nos. 6,455,674, 6,555,667, and 6,740,738, all assigned to the assignee of the instant application, disclose and claim per se the RTP801 polynucleotide and polypeptide, and antibodies directed toward the polypeptide. RTP801 represents a unique gene target for hypoxia-inducible factor-1 (HIF-1) that may regulate hypoxia-induced pathogenesis independent of growth factors such as VEGF. Further discoveries relating to gene RTP801, as discovered by the assignee of the instant application, were reported in Shoshani, et al. 2002. *Mol. Cell. Biol.*, 22(7):2283-2293; this paper, co-authored by the inventor of the present invention, details the discovery of the RTP801 gene. Gene RTP801L, so named because of its resemblance to RTP801, was also first reported by the assignee of the instant application, and given Pubmed accession No. NM_145244 subsequent to said report.

While RTP801 and RTP801L share sequence homology of about 65% at the amino acid level, indicating a possible similarity of function, and while the assignee of the present invention has found that both RTP801 and RTP801L interact with TSC2 and affect the mTOR pathway, the inventors of the present invention have found that the embryological expression pattern of the two polypeptides differs, and that, contrary to RTP801, RTP801L is not induced by hypoxia in all conditions which induce RTP801 expression; it is, however, induced in MEFs as a result of $H_2O_2$ treatment (hypoxia treatment), and the induction follows kinetics similar to those of RTP801 expression induction under the same conditions. Additionally, the inventors of the present invention have found that RTP801 polypeptide is more abundantly expressed than RTP801L. Thus, RTP801L may serve as a target in the treatment of conditions for which RTP801 is a target, and may have the added benefit of a similar, yet different, target.

The following patent applications and publications give aspects of background information relating to RTP801L: Patent application/publication Nos. EP1580263, WO2003029271, WO2001096391, WO2003087768, WO2004048938, WO2005044981, WO2003025138, WO2002068579, EP1104808 and CA2343602 all disclose a nucleic acid or polypeptide which is homologous to RTP801L. Various groups have studied the mechanism of action of RTP801L (Corradetti et al., 2005. *J Biol. Chem.* 280(11):9769-72; Pisani et al., 2005. *BBRC* 326(4):788-93; Cuaz-perolin et al., 2004 *Arterioscler Thromb Vasc Biol.* 24(10):1830-5; Sofer et al., 2005 *Mol Cell Biol.* 25(14):5834-45).

Inhibitors of RTP801L are disclosed in PCT patent publication WO 2007/141796, assigned to the assignee of the present invention and incorporated herein by reference in its entirety. Use of those inhibitors in treating numerous indications is disclosed therein.

SUMMARY OF THE INVENTION

The present invention relates in part to chemically modified RTP801L siRNA, and in particular to chemically modified RTP801L siRNA oligonucleotides having sense and antisense sequences set forth in Tables A-F. The chemically modified siRNA compounds disclosed herein are useful in down regulating RTP801L expression. The compounds according to the present invention exhibit properties that render them useful as therapeutic agents for treatment of a subject suffering from a disease or disorder associated with RTP801L expression. Specifically the compounds exhibit high activity, and/or serum stability and/or reduced off-target effects and/or reduced adverse immune response as compared to an unmodified siRNA compound. The present invention additionally provides novel RTP801L siRNA oligonucleotide pairs shown in Tables B-F and set forth in SEQ ID NOS:1852-6927. PCT patent publication WO 2007/141796, incorporated by reference herein, discloses the oligonucleotide pairs shown in Table A set forth in SEQ ID NO: 2-1851.

The present invention provides pharmaceutical compositions comprising one or more such oligonucleotides. The present invention further relates to methods for treating or preventing the incidence or severity of various diseases or conditions in a subject in need thereof wherein the disease or condition and/or symptoms associated therewith is selected from the group consisting of an ophthalmic disease or condition, a respiratory disease, an ischemic disease, a microvascular disease, an angiogenesis- and an apoptosis-related condition, a hearing impairment or any other disease, condition or combination of conditions as disclosed herein. Such methods involve administering to a mammal in need of such treatment a prophylactically or therapeutically effective amount of one or more such chemically modified siRNA compound, which inhibits or reduces expression or activity of RTP801L.

In one aspect the present invention provides a compound having the following structure:

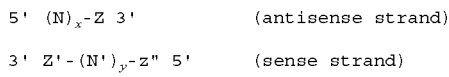

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present; wherein z" may be present or absent, but if present is a capping moiety covalently attached at the 5' terminus of (N') y;
each of x and y is independently an integer between 18 and 40;
wherein the sequence of (N)x is substantially complementary to the sequence of (N')y; and the sequence of (N')y is substantially identical to any one of the sense sequences set forth in any one of Tables B-F.

In certain preferred embodiments the present invention provides an siRNA compound comprising an antisense strand (N)x and its substantially complementary sense strand (N')y, set forth in any one of SEQ ID NOS:1852-6927. The siRNA compounds consist of unmodified ribonucleotides or a combination of unmodified ribonucleotides and ribonucleotides and or unconventional moieties.

In some embodiments the chemically modified siRNA compounds according to the present invention comprise the oligonucleotides disclosed in Tables B-F.

In some embodiments, the present invention provides a chemically modified siRNA compound having the following structure:

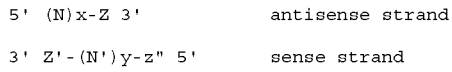

wherein each of N and N' is a nucleotide selected from an unmodified ribonucleotide and a modified ribonucleotide;
wherein each of (N)x and (N')y is an oligomer in which each consecutive ribonucleotide is joined to the next ribonucleotide by a covalent bond;
wherein each of x and y is independently an integer between 18 and 40;
wherein in each of (N)x and (N')y the ribonucleotides alternate between modified ribonucleotides and unmodified ribonucleotides each modified ribonucleotide being modified so as to have a 2'-O-methyl on its sugar and the ribonucleotide located at the middle position of (N)x being unmodified and the ribonucleotide located at the middle position of (N')y being modified;
wherein each of Z and Z' may be present or absent, but if present is 1-5 deoxyribonucleotides covalently attached at the 3' terminus of the oligomer to which it is attached;
wherein the sequence of (N)x is substantially complementary to the sequence of (N')y; and wherein the sequence of (N')y is substantially identical to any one of the sense sequences set forth in any one of Tables B-F.

The present invention provides additional chemically modified RTP801L siRNA compounds. In some embodiments, the present invention provides a compound having the following structure:

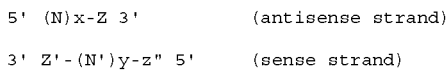

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent, but if present is a capping moiety covalently attached at the 5' terminus of (N')y;
wherein each of x and y is independently an integer between 18 and 40;
wherein (N)x comprises modified and unmodified ribonucleotides, each modified ribonucleotide having a 2'-O-methyl on its sugar, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide;
wherein in (N')y at least one unconventional moiety is present, which unconventional moiety may be a modified or unmodified deoxyribonucleotide, a mirror nucleotide, or a nucleotide joined to an adjacent nucleotide by a 2'-5' internucleotide phosphate bond;
wherein the sequence of (N)x is substantially complementary to the sequence of (N')y; and the sequence of (N')y is substantially identical to a sequence of identical length of consecutive ribonucleotides in the mRNA set forth in SEQ ID NO:1.

In various embodiments the compound of the invention comprises an antisense sequence (N)x present in any one of Tables A-F, set forth in SEQ ID NOS:2-6927. In certain embodiments (N)x comprising the oligonucleotide set forth in SEQ ID NO:999 or SEQ ID NO:1000. In other embodiments (N)x comprising the oligonucleotide set forth in SEQ ID NO:6914 or SEQ ID NO:6915.

In some embodiments the covalent bond joining each consecutive N or N' is a phosphodiester bond. In various embodiments all the covalent bonds are phosphodiester bonds.

In various embodiments x=y and each of x and y is 19, 20, 21, 22 or 23. In some embodiments x=y=23. In other embodiments x=y=19.

In one embodiment of the above structure, the compound comprises at least one mirror nucleotide at one or both termini in (N')y. In various embodiments the compound comprises two consecutive mirror nucleotides, one at the 3' penultimate position and one at the 3' terminus in (N')y. In one preferred embodiment x=y=19 and (N')y comprises an L-deoxyribonucleotide at position 18.

In some embodiments the mirror nucleotide is selected from an L-ribonucleotide and an L-deoxyribonucleotide. In various embodiments the mirror nucleotide is an L-deoxyribonucleotide. In some embodiments y=19 and (N')y, consists of unmodified ribonucleotides at positions 1-17 and 19 and one L-DNA at the 3' penultimate position (position 18). In other embodiments y=19 and (N')y consists of unmodified ribonucleotides at position 1-16 and 19 and two consecutive L-DNA at the 3' penultimate position (positions 17 and 18).

In another embodiment of the above structure, (N')y further comprises one or more nucleotides containing an intra-sugar bridge at one or both termini.

In another embodiment of the above structure, (N')y comprises at least two consecutive nucleotide joined together to the next nucleotide by a 2'-5' phosphodiester bond at one or both termini. In certain preferred embodiments in (N')y the 3' penultimate nucleotide is linked to the 3' terminal nucleotide with a 2'-5' phosphodiester bridge.

In certain preferred embodiments the compound of the invention is a blunt-ended (z", Z and Z' are absent), double stranded oligonucleotide structure, x=y and x=19 or 23, wherein (N')y comprises unmodified ribonucleotides in which three consecutive nucleotides at the 3' terminus are joined together by two 2'-5' phosphodiester bonds; and an antisense strand (AS) of alternating unmodified and 2'-O methyl sugar-modified ribonucleotides.

In additional embodiments (N)x comprises modified ribonucleotides in alternating positions wherein each N at the 5' and 3' termini are modified in their sugar residues and the middle ribonucleotide is not modified, e.g. ribonucleotide in position 10 in a 19-mer strand or position 12 in a 23-mer strand.

In some embodiments, neither (N)x nor (N')y are phosphorylated at the 3' and 5' termini. In other embodiments either or both (N)x and (N')y are phosphorylated at the 3' termini.

In various embodiments the compound comprises an antisense and sense oligonucleotide pair present in any one of Tables A-G set forth in SEQ ID NOS:2-6927.

In certain embodiments for all the above-mentioned structures, the compound is blunt ended, for example wherein both Z and Z' are absent. In an alternative embodiment, the compound comprises at least one 3' overhang, wherein at least one of Z or Z' is present. Z and Z' can independently comprise one or more covalently linked modified or non-modified nucleotides, for example inverted dT or dA; dT, LNA, mirror nucleotide and the like. In some embodiments each of Z and Z' are independently selected from dT and dTdT.

In some embodiments the present invention provides an expression vector comprising an antisense sequence present in any one of Tables B-F.

In a second aspect the present invention provides a pharmaceutical composition comprising one or more compounds of the present invention, in an amount effective to inhibit RTP801L human gene expression and a pharmaceutically acceptable carrier.

In another aspect, the present invention relates to a method for the treatment of a subject in need of treatment for a disease or disorder or symptoms or conditions associated with the disease or disorder, associated with the expression of RTP801L comprising administering to the subject an amount of an siRNA which reduces or inhibits expression of RTP801L.

More specifically, the present invention provides methods, compounds and compositions useful in therapy for treating a subject suffering from acute renal failure (ARF), hearing loss, glaucoma, acute respiratory distress syndrome (ARDS) and other acute lung and respiratory injuries, injury (e.g. ischemia-reperfusion injury) in organ transplant including lung, kidney, bone marrow, heart, pancreas, cornea or liver transplantation, nephrotoxicity, spinal cord injury, pressure sores, dry eye syndrome, oral mucositis and chronic obstructive pulmonary disease (COPD). The methods of the invention comprise administering to the subject one or more siRNA compounds which inhibit expression of RTP801L in a therapeutically effective dose so as to thereby treat the patient.

According to one embodiment the compound consists of an antisense strand having an oligomer sequence set forth in SEQ ID NO:1000 and a sense strand having an oligomer sequence set forth in SEQ ID NO:75. According to one embodiment the compound consists of an antisense strand having an oligomer sequence set forth in SEQ ID NO:999 and a sense strand having an oligomer sequence set forth in SEQ ID NO:74. According to another embodiment, the compound consists of an antisense strand having an oligomer sequence set forth in SEQ ID NO:6914 and a sense strand having an oligomer sequence set forth in SEQ ID NO:6898 (DDIT4L_14 in Table F). According to another embodiment, the compound consists of an antisense strand having an oligomer sequence set forth in SEQ ID NO:6915 and a sense strand having an oligomer sequence set forth in SEQ ID NO:6899 (DDIT4L_15 in Table F).

In various embodiments the siRNA compound is selected from any one of the compounds shown in Table G (FIG. 3).

In certain preferred embodiments the siRNA compounds indicated above are modified so at to have antisense strand comprising alternating 2'OMe and unmodified ribonucleotides, and a sense strand comprising unmodified ribonucleotides and an L-DNA moiety at position 18 or at positions 17 and 18. In some embodiments the sense strand further includes a deoxyribonucleotide at position 15.

In another aspect the present invention provides a pharmaceutical composition comprising on or more RTP801L siRNA inhibitors of the invention; and a pharmaceutically acceptable excipient.

In another aspect, the present invention provides a method of treating a patient suffering from a microvascular disorder, macular degeneration or a respiratory disorder, comprising administering to the patient a pharmaceutical composition comprising one or more RTP801L inhibitor.

Another embodiment of the present invention concerns a method for treating a patient suffering from COPD, comprising administering to the patient a pharmaceutical composition comprising a therapeutically effective amount of one or more siRNA RTP801L inhibitor. In one embodiment the inhibitor is selected from the group consisting of an siRNA molecule, an antisense molecule, and a ribozyme or a combination thereof.

Another embodiment of the present invention concerns a method for treating a patient suffering from Acute Lung Injury (ALI), comprising administering to the patient a pharmaceutical composition comprising a therapeutically effective amount of one or more RTP801L inhibitor. In one embodiment the inhibitor selected from the group consisting of an siRNA molecule, an antisense molecule, and a ribozyme or a combination thereof.

Another embodiment of the present invention concerns a method for treating a patient suffering from macular degeneration, comprising administering to the patient a pharmaceutical composition comprising a therapeutically effective amount of one or more RTP801L inhibitor. In one embodiment the inhibitor is an siRNA molecule, an antisense molecule, or a ribozyme or a combination thereof.

Another embodiment of the present invention concerns a method for treating a patient suffering from a microvascular disorder, comprising administering to the patient a pharmaceutical composition comprising a therapeutically effective amount of one or more RTP801L inhibitor. In one embodiment the inhibitor is an siRNA molecule, an antisense molecule, or a ribozyme or a combination thereof.

An additional embodiment of the present invention provides for the use of a therapeutically effective amount of an RTP801L inhibitor for the preparation of a medicament for promoting recovery in a patient suffering from a respiratory disorder. In one embodiment the respiratory disorder is COPD and the inhibitor is preferably one or more siRNA. In another embodiment the respiratory disorder is ALI and the inhibitor is preferably one or more siRNA.

An additional embodiment of the present invention provides for the use of a therapeutically effective dose of one or more RTP801L inhibitor for the preparation of a medicament for promoting recovery in a patient suffering from macular degeneration. In one embodiment the macular degeneration is AMD and the inhibitor is preferably one or more siRNA.

An additional embodiment of the present invention provides for the use of a therapeutically effective dose of one or more RTP801L inhibitor for the preparation of a medicament for promoting recovery in a patient suffering from glaucoma. In one embodiment the inhibitor is preferably one or more siRNA. In various embodiments the present invention is useful in therapy for treating a patient in need of neuroprotection. In some embodiments the siRNA compound is therapeutically effective in neuroprotection of the optic nerve.

An additional embodiment of the present invention provides for the use of a therapeutically effective dose of one or more RTP801L inhibitor for the preparation of a medicament for promoting recovery in a patient suffering from an eye disorder secondary to diabetes. In one embodiment the inhibitor is preferably one or more siRNA.

An additional embodiment of the present invention provides for the use of a therapeutically effective amount of one or more RTP801L inhibitor for the preparation of a medicament for promoting recovery in a patient suffering from a microvascular disorder. In one embodiment the microvascular disorder is diabetic retinopathy and the inhibitor is preferably one or more siRNA. In another embodiment the disorder is Acute Renal Failure and the inhibitor is preferably one or more siRNA.

The present invention also relates generally to methods and compositions for treating or preventing the incidence or severity of hearing impairment (or balance impairment), particularly hearing impairment associated with cell death of the inner ear hair cells. The methods and compositions involve administering to a mammal in need of such treatment a prophylactically or therapeutically effective amount of one or more compounds which down-regulate expression of the RTP801L gene, particularly novel small interfering RNAs (siRNAs).

More specifically, the present invention provides methods and compositions for treating a patient suffering from hearing impairment, or other oto-pathologies associated with cell death of inner ear hair cells. Such oto-pathologies may be the result of acoustic trauma, mechanical trauma, age (presbycusis) or ototoxin-induced hearing loss. The methods of the invention comprising administering to the patient one or more compounds which down-regulate expression of the RTP801L gene, particularly siRNAs that inhibit RTP801L typically as a pharmaceutical composition, in a therapeutically effective dose so as to thereby treat the patient.

In one embodiment, the present invention provides for improved compositions and methods for treatments requiring administration of a pharmaceutical drug having an ototoxic, hearing-impairing side-effect, in combination with a therapeutically effective amount of one or more siRNA molecules that inhibit RTP801L, to treat or prevent the ototoxicity induced by the pharmaceutical drug. The compositions of the invention can be administered at a suitable interval(s) either prior to, subsequent to, or substantially concurrent with the administration of the ototoxic, hearing-impairing drug that induces inner ear apoptotic tissue damage.

Accordingly, it is an object of the invention to provide an improved composition containing a therapeutically effective amount of one or more siRNA molecules that inhibit RTP801L in combination with an ototoxic, hearing-impairing pharmaceutical drug for administration to a mammal. Said combination drugs may be administered separately; the siRNA molecules that inhibit RTP801L would then be administered locally while the ototoxic, hearing-impairing pharmaceutical drug is administered systemically. The siRNA molecules may be administered prior to, simultaneously with or subsequent to the ototoxic drug. Such combination compositions can further contain a pharmaceutically acceptable carrier. The pharmaceutical composition will have lower ototoxicity than the ototoxic pharmaceutical alone, and preferably, will have a higher dosage of the ototoxic pharmaceutical than typically used. Examples of such improved compositions include cisplatin or other ototoxic neoplastic agent or an aminoglycoside antibiotic(s) in combination with the therapeutically effective amount of one or more siRNA molecules that inhibit RTP801L.

Still further, the invention relates to the use of the compositions of the invention in cases where diuretics are needed. The present invention provides a solution to the art that has long sought a therapy and a medicament which can treat the ototoxic effects currently associated with certain diuretics, and particular with the more popular and commonly used loop-diuretics, without sacrificing their diuretic effectiveness.

Still further, the invention relates to the use of the compositions of the invention in cases where quinine or quinine-like compounds are needed. The present invention provides a solution to the art that has long sought a therapy and a medicament which can treat the ototoxic effects currently associated with certain quinines without sacrificing their effectiveness.

The present invention further relates to methods and compositions for treating or preventing the incidence or severity of pressure sores. The methods and compositions involve administering to a mammal in need of such treatment a prophylactically or therapeutically effective amount of one or more compounds which down-regulate expression of the RTP801L gene, particularly novel small interfering RNAs (siRNAs).

Further, the present invention relates to methods and compositions for the treatment of any ischemic or ischemia-reperfusion injuries or conditions, as described herein. Said methods and compositions involve administering to a mammal in need of such treatment a prophylactically or therapeutically effective amount of one or more compounds which down-regulate expression of the RTP801L gene, particularly novel small interfering RNAs (siRNAs).

BRIEF DESCRIPTION OF THE FIGURES

FIG. 1 provides the polynucleotide sequence of REDD2 full length mRNA (SEQ ID NO:1);

FIG. 2 provides Table F, a list of certain preferred siRNA RTP801L oligonucleotide pairs.

FIG. 3a-3c provide Table G, a list of certain preferred chemically modified RTP801L siRNA. "r" preceeding A, C, G or U refers to an unmodified ribonucleotide; "m" preceeding A, C, G or U refers to a 2'OMe modified ribonucleotide; LdC refers to L-deoxycytidine, which substituted some of the A, C, G or U in the sense strands.

FIG. 8 Shows structure, activity and stability results for certain RTP801L siRNA compounds of the present invention. Lower case italic "c" refers to L-deoxycytidine, which substituted some of the A, C, G or U in the sense strands.

DETAILED DESCRIPTION OF THE INVENTION

Figure 4:
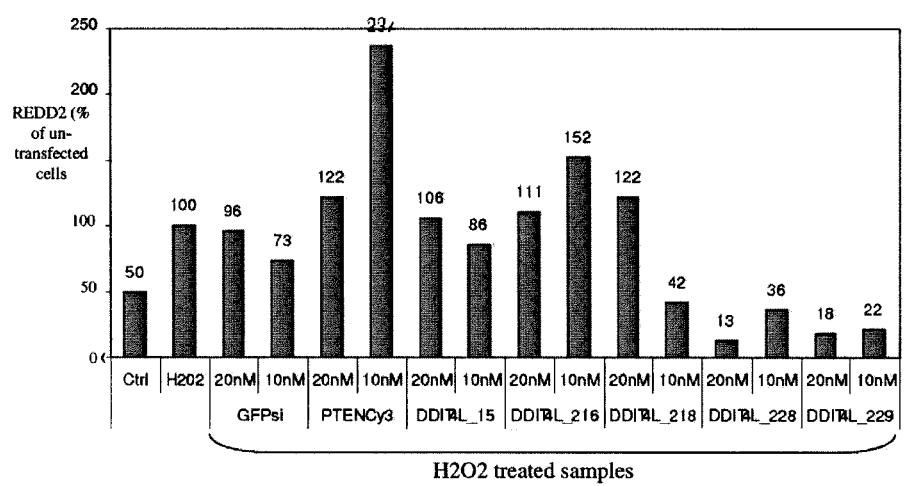
FIG. 4 details the activity results of RTP801L siRNAs on the endogenous RTP801L gene in wild type MEF cells following $H_2O_2$ treatment.
Figure 5:
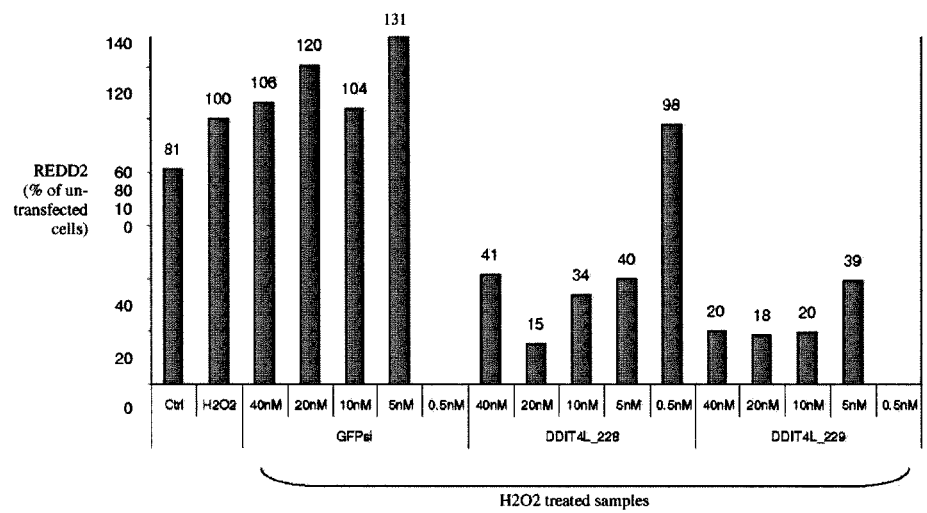
FIG. 5 demonstrates dose dependent activity of RTP801L siRNAs as measured in 801 wt MEF cells.
Figure 6:
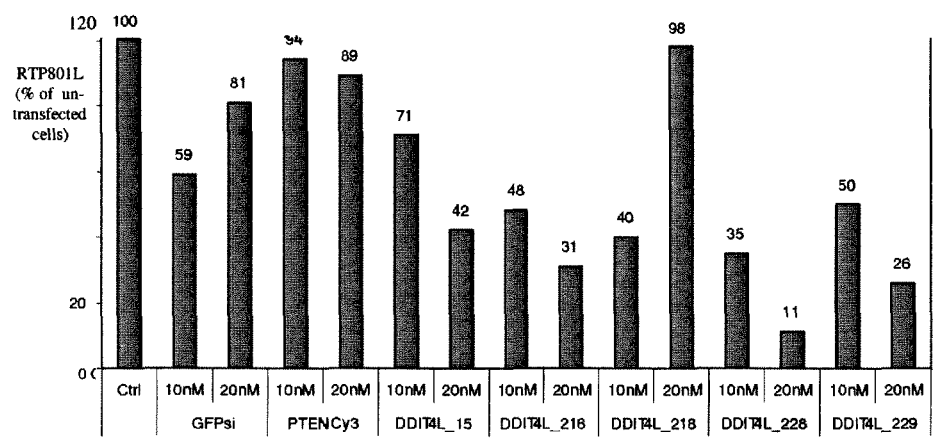
FIG. 6 shows activity results of RTP801L siRNAs on the endogenous RTP801L gene in wt 293 T cells.
Figure 7:
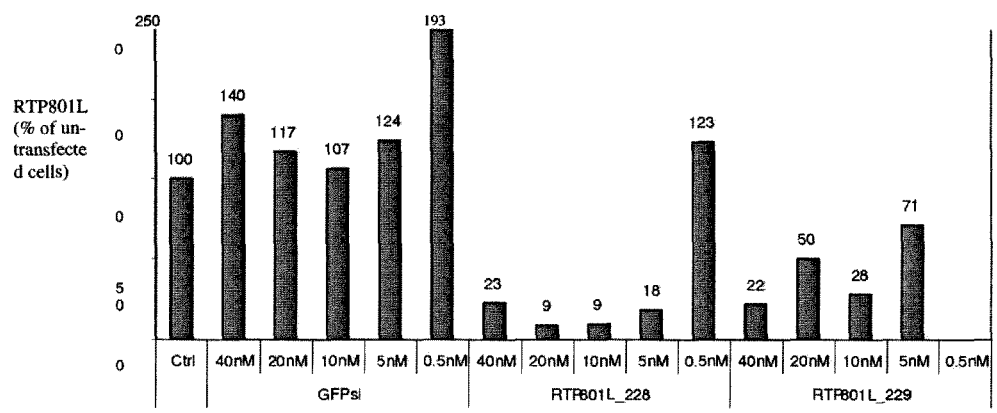
FIG. 7 demonstrates dose dependent activity of RTP801L siRNA as measured in 293T cells.
Figure 9:
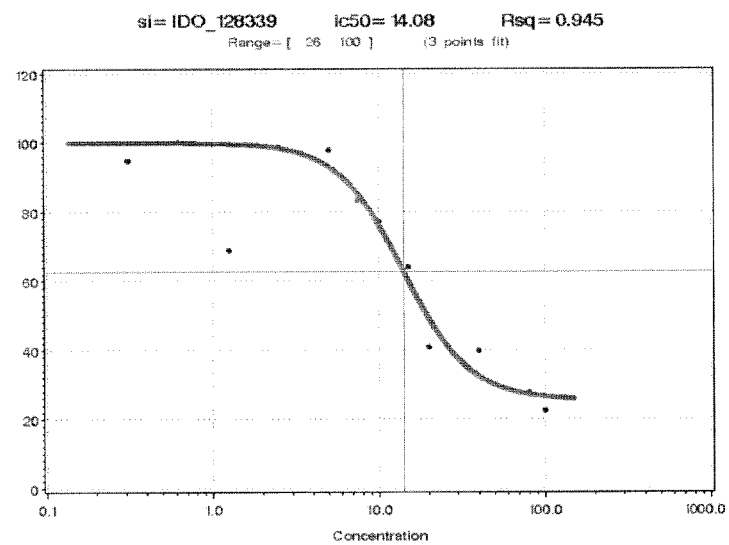
FIG. 9 shows IC50 results for an siRNA compound of the present invention.

The present invention, relates to novel oligonucleotide compounds useful in inhibiting the RTP801L gene for the treatment of eye diseases, respiratory disorders, microvascular disorders, hearing disorders and ischemic conditions, inter alia. As will be described herein, the preferred inhibitors to be used with the present invention are chemically modified siRNA.

Compounds and compositions comprising same which inhibit RTP801L are discussed herein at length, and any of said compounds and/or compositions may be beneficially employed in the treatment of a patient suffering from a disease or disorder associated with RTP801L expression.

The siRNAs of the present invention possess structures and modifications which may increase activity, increase stability, and or minimize toxicity; the novel modifications of the siRNAs of the present invention can be beneficially applied to double stranded RNA useful in preventing or attenuating RTP801L expression.

According to one aspect the present invention provides inhibitory oligonucleotide compounds comprising unmodified and modified nucleotides and or unconventional moieties. The compound comprises at least one modified nucleotide selected from the group consisting of a sugar modification, a base modification and an internucleotide linkage modification and may contain DNA, and modified nucleotides such as LNA (locked nucleic acid), ENA (ethylene-bridged nucleic acid), PNA (peptide nucleic acid), arabinoside, PACE, mirror nucleotide, or nucleotides with a 6 carbon sugar.

In one embodiment the compound comprises a 2' modification on the sugar moiety of at least one ribonucleotide ("2' sugar modification"). In certain embodiments the compound comprises 2'O-alkyl or 2'-fluoro or 2'O-allyl or any other 2' modification, optionally on alternate positions. Other stabilizing modifications are also possible (e.g. terminal modifications). In some embodiments the backbone of the oligonucleotides is modified and comprises phosphate-D-ribose entities but may also contain thiophosphate-D-ribose entities, triester, thioate, 2'-5' bridged backbone (also may be referred to as 5'-2'), PACE or any other type of modification.

Other modifications include terminal modifications on the 5' and/or 3' part of the oligonucleotides. Such terminal modifications may be lipids, peptides, sugars or other molecules.

Further, an additional embodiment of the present invention concerns a method for treating a patient suffering from a microvascular disorder, an eye disease, a respiratory disorder, a hearing disorder or a spinal cord injury or other wound, comprising administering to the patient a pharmaceutical composition comprising a therapeutically effective dose of an RTP801L inhibitor comprising an siRNA molecule, optionally an siRNA molecule detailed in any one of Tables A-G, in a dosage and over a period of time so as to thereby treat the patient.

An additional method for treating a patient suffering from a microvascular disorder, an eye disease, a respiratory disorder, a hearing disorder or a spinal cord injury or other wound is provided, comprising administering to the patient a pharmaceutical composition comprising a therapeutically effective dose of an RNA molecule which targets the RTP801L gene mRNA in a dosage and over a period of time so as to thereby treat the patient. The RNA molecule may be an siRNA molecule, such as an siRNA molecule detailed in any one of Tables A-G, preferably siRNA Nos:72 or 73. In one embodiment, the compound consists of an antisense strand having an oligomer sequence set forth in SEQ ID NO:6914 and a sense strand having an oligomer sequence set forth in SEQ ID NO:6898 (DDIT4L__14 in Table F). According to another embodiment, the compound consists of an antisense strand having an oligomer sequence set forth in SEQ ID NO:6915 and a sense strand having an oligomer sequence set forth in SEQ ID NO:6899 (DDIT4L__15 in Table F). In certain preferred embodiments the siRNA is modified so at to have antisense strand comprising alternating 2'OMe and unmodified ribonucleotides, and a sense strand comprising unmodified ribonucleotides and an L-DNA moiety at position 18 or at positions 17 and 18. In some embodiments the sense strand further includes a deoxyribonucleotide at position 15.

The present invention further provides a method for treating a patient suffering from a microvascular disorder, an eye disease, an ischemic disease, a kidney disorder, a respiratory disorder, a hearing disorder or a spinal cord injury or other wound or any of the conditions disclosed herein, comprising administering to the patient a pharmaceutical composition comprising a therapeutically effective dose of an siRNA molecule which targets the RTP801L gene mRNA, optionally an siRNA molecule detailed in any one of Tables A-G, in a dosage and over a period of time so as to thereby treat the patient. Further, the eye disease may be macular degeneration such as age-related macular degeneration (AMD) or glaucoma; the microvascular disorder may be diabetic retinopathy or acute renal failure; the ischemic disease may be ischemia—reperfusion or organ transplant related; the kidney disorder may be nephrotoxicity; the respiratory disorder may be COPD or ALI; and the hearing disorder may be noise—induced deafness, chemically induced deafness such as cisplatin-induced deafness or age-related deafness.

The present invention additionally relates to the use of the novel siRNAs disclosed herein in the treatment of hearing impairment in which inhibition of RTP801L expression is beneficial. In one embodiment, the present invention constitutes a method for treating a mammal having or prone to a hearing (or balance) impairment or treating a mammal prophylactically in conditions where inhibition of RTP801L expression is beneficial. The method of this embodiment of the present invention would prevent or reduce the occurrence or severity of a hearing (or balance) impairment that would result from inner ear cell injury, loss, or degeneration, in particular caused by an ototoxic agent or by aging. In this embodiment, the method of the invention includes administering a therapeutically effective amount of one or more compounds which down-regulate expression of the RTP801L gene, particularly the novel siRNAs of the present invention.

In one embodiment, it is the object of the present invention to provide a method for treating a mammal, to prevent, reduce, or treat a hearing impairment, disorder or imbalance, preferably an ototoxin-induced hearing condition, by administering to a mammal in need of such treatment a composition of the invention. One embodiment is a method for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds. These methods are especially effective when the ototoxic compound is an antibiotic, preferably an aminoglycoside antibiotic. Ototoxic aminoglycoside antibiotics include but are not limited to neomycin, paromomycin, ribostamycin, lividomycin, kanamycin, amikacin, tobramycin, viomycin, gentamycin, sisomycin, netilmycin, streptomycin, dibekacin, fortimycin, and dihydrostreptomycin, or combinations thereof. Particular antibiotics include neomycin B, kanamycin A, kanamycin B, gentamycin C1, gentamycin C1a, and gentamycin C2. The methods of the invention are also effective when the ototoxic compound is a neoplastic agent such as vincristine, vinblastine, cisplatin and cisplatin-like compounds and taxol and taxol-like compounds In some embodiments aimed at treating or preventing a hearing disorder, the composition of the invention is co-administered with an ototoxin. For example, an improved method is provided for treatment of infection of a mammal by administration of an aminoglycoside antibiotic, the improvement comprising administering a therapeutically effective amount of one or more compounds which down-regulate expression of the RTP801L gene particularly novel siRNAs, to the patient in need of such treatment to reduce or prevent ototoxin-induced hearing impairment associated with the antibiotic. The compounds which reduce or prevent the ototoxin-induced hearing impairment, particularly the novel siRNAs are preferably administered locally within the inner ear. In yet another embodiment is provided an improved method for treatment of cancer in a mammal by administration of a chemotherapeutic compound, the improvement comprises administering a therapeutically effective amount of a composition of the invention to the patient in need of such treatment to reduce or prevent ototoxin-induced hearing impairment associated with the chemotherapeutic drug. In another embodiment the methods of treatment are applied to hearing impairments resulting from the administration of a chemotherapeutic agent to treat its ototoxic side effect. Ototoxic chemotherapeutic agents amenable to the methods of the invention include, but are not limited to an antineoplastic agent, including cisplatin or cisplatin-like compounds, taxol or taxol-like compounds, and other chemotherapeutic agents believed to cause ototoxin-induced hearing impairments, e.g., vincristine, an antineoplastic drug used to treat hematological malignancies and sarcomas. Cisplatin-like compounds include carboplatin (Paraplatin®), tetraplatin, oxaliplatin, aroplatin and transplatin inter alia. In another embodiment the methods of the invention are applied to hearing impairments resulting from the administration of quinine and its synthetic substitutes, typically used in the treatment of malaria, to treat its ototoxic side-effect. In another embodiment the methods of the invention are applied to hearing impairments resulting from administration of a diuretic. Diuretics, particularly "loop" diuretics, i.e. those that act primarily in the Loop of Henle, are candidate ototoxins. Illustrative examples, not limiting to the invention method, include furosemide, ethacrylic acid, and mercurials. Diuretics are typically used to prevent or eliminate edema. Diuretics are also used in nonedematous states for example hypertension, hypercalcemia, idiopathic hypercalciuria, and nephrogenic diabetes insipidus.

In another embodiment, the methods of the invention are applied to treating or preventing the incidence or severity of pressure sores. The methods and compositions involve administering to a mammal in need of such treatment a prophylactically or therapeutically effective amount of one or more compounds which down-regulate expression of the RTP801L gene, particularly novel small interfering RNAs (siRNAs). The compounds which treat or prevent the incidence or severity of pressure sores, particularly the novel siRNAs are preferably administered locally within the damaged area. The methods and compositions of the present invention are effective in the treatment and prevention of pressure sores or pressure ulcers developed when sustained pressure (usually from a bed or wheelchair) cuts off circulation to vulnerable parts of the body. The methods and compositions are effective in patients with diminished or absent sensation or who are debilitated, emaciated, paralyzed, or long bedridden. The compositions of the present invention are effective also in improving the healing of pressure sores using the compositions. The compositions may be used at any particular stage in the healing process including the stage before any healing has initiated or even before a specific sore is made (prophylactic treatment).

Other kinds of wounds to be treated according to the invention include i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions.

The methods and compositions of the present invention are also effective in the treatment and prevention of any chronic wounds including inter alia pressure sores, venous ulcers, and diabetic ulcers. In all these chronic wound types, the underlying precipitating event is a period of ischemia followed by a period of reperfusion. These ischemia-reperfusion events are usually repetitive, which means the deleterious effects of ischemia-reperfusion are potentiated and eventually sufficient to cause ulceration. For both pressure sores and diabetic foot ulcers, the ischemic event is the result of prolonged pressure sufficient to prevent tissue perfusion, and when the pressure is finally relieved, the reperfusion injury occurs. The present compositions are effective in inhibiting the damage caused by ischemia-reperfusion in chronic wounds.

The present compositions are also effective in other conditions associated with ischemia-reperfusion such as but not limited to: organ transplantation, intestinal and colon anastamoses, operations on large blood vessels, stitching detached limbs, balloon angioplasty or any cardiac surgery, stroke or brain trauma, limb transplantation, pulmonary hypertension, hypoxemia, and noncardiogenic pulmonary edema, acute renal failure, acute glaucoma, diabetic retinopathy, hypertensive retinopathy, and retinal vascular occlusion, cochlear ischemia, microvascular surgery and ischemic lesions in scleroderma.

The methods and compositions of the present invention are also effective in the treatment of acoustic trauma or mechanical trauma, preferably acoustic or mechanical trauma that leads to inner ear hair cell loss. Acoustic trauma to be treated in the present invention may be caused by a single exposure to an extremely loud sound, or following long-term exposure to everyday loud sounds above 85 decibels. Mechanical inner ear trauma to be treated in the present invention is for example the inner ear trauma following an operation of electronic device insertion in the inner ear. The compositions of the present invention prevent or minimize the damage to inner ear hair cells associated with the operation. The compounds which reduce or prevent the ototoxin-induced hearing impairment, particularly the novel siRNAs are preferably administered locally within the inner ear.

Additionally, as detailed above, the compound of the present invention can be used to treat any condition in which ischemia is involved, optionally ischemia-reperfusion. Such condition include ischemia or ischemia-reperfusion resulting from an angioplasty, cardiac surgery or thrombolysis; organ transplant; as a result of plastic surgery; during severe compartment syndrome; during re-attachment of severed limbs; as a result of multiorgan failure syndrome; in the brain as a result of stroke or brain trauma; in connection with chronic wounds such as pressure sores, venous ulcers and diabetic ulcers; during skeletal muscle ischemia or limb transplantation; as a result of mesenteric ischemia or acute ischemic bowel disease; respiratory failure as a result of lower torso ischemia, leading to pulmonary hypertension, hypoxemia, and noncardiogenic pulmonary edema; acute renal failure as observed after renal transplantation, major surgery, trauma, and septic as well as hemorrhagic shock; Sepsis; Retinal ischemia occurring as a result of acute vascular occlusion, leading to loss of vision in a number of ocular diseases such as acute glaucoma, diabetic retinopathy, hypertensive retinopathy, and retinal vascular occlusion; Cochlear ischemia; flap failure in microvascular surgery for head and neck defects; Raynaud's phenomenon and the associated digital ischemic lesions in scleroderma; spinal cord injury; vascular surgery; Traumatic rhabdomyolysis (crush syndrome); and myoglobinuria. Further, ischemia/reperfusion may be involved in the following conditions: hypertension, hypertensive cerebral vascular disease, rupture of aneurysm, a constriction or obstruction of a blood vessel—as occurs in the case of a thrombus or embolus, angioma, blood dyscrasias, any form of compromised cardiac function including cardiac arrest or failure, systemic hypotension, cardiac arrest, cardiogenic shock, septic shock, spinal cord trauma, head trauma, seizure, bleeding from a tumor; and diseases such as stroke, Parkinson's disease, epilepsy, depression, ALS, Alzheimer's disease, Huntington's disease and any other disease-induced dementia (such as HIV induced dementia for example). Additionally, an ischemic episode may be caused by a mechanical injury to the Central Nervous System, such as results from a blow to the head or spine. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracranial hematoma or edema). Similarly, traumatic constriction or compression can arise from the presence of a mass of abnormal tissue, such as a metastatic or primary tumor.

"Treating a disease" refers to administering a therapeutic substance effective to ameliorate symptoms associated with a disease, to lessen the severity or cure the disease, or to prevent the disease from occurring. "Treatment" refers to both therapeutic treatment and prophylactic or preventative measures, wherein the object is to prevent or slow down (lessen) a disease or disorder.

A "therapeutically effective dose" refers to an amount of a pharmaceutical compound or composition which is effective to achieve an improvement in a patient or his physiological systems including, but not limited to, improved survival rate, more rapid recovery, or improvement or elimination of symptoms, and other indicators as are selected as appropriate determining measures by those skilled in the art.

The methods of treating the diseases disclosed herein and included in the present invention may include administering an RTP801L inhibitor in conjunction with an additional RTP801L inhibitor, a substance which improves the pharmacological properties of the active ingredient as detailed below, or an additional compound known to be effective in the treatment of the disease to be treated, such as macular degeneration, glaucoma, COPD, ALI, ARF, DR, cisplatin-induced deafness, and age-related deafness, inter alia. By "in conjunction with" is meant prior to, simultaneously or subsequent to. Further detail on exemplary conjoined therapies is given below.

In another embodiment, the present invention provides for the use of a therapeutically effective dose of an RTP801L inhibitor for the preparation of a medicament for promoting recovery in a patient suffering from macular degeneration, glaucoma, COPD, ALI, ARF, DR, cisplatin-induced deafness, age-related deafness or any eye disease, microvascular or respiratory condition or hearing disorder as detailed above, and the use of a therapeutically effective dose of an RTP801L inhibitor for the preparation of a medicament for treating said diseases and conditions. In this embodiment, the RTP801L inhibitor may comprise a polynucleotide which comprises consecutive nucleotides having a sequence which comprises an antisense sequence to the sequence set forth in FIG. 1 (SEQ ID No: 1). Additionally, the RTP801L inhibitor may be an expression vector comprising a polynucleotide having a sequence which is an antisense sequence to the sequence set forth in FIG. 1 (SEQ ID No:1). Additionally, the RTP801L inhibitor may be an RNA molecule which targets the RTP801L gene mRNA such as a ribozyme or an siRNA, optionally an siRNA comprising consecutive nucleotides having a sequence identical to any one of the sequences set forth in any one of Tables A-G (SEQ ID NOs:3-6927) and preferably, siRNA Nos:72 and 73 of Table A, or DDIT4L__14 or DDIT4L__15 in Table F.

Thus, according to the information disclosed herein, the RTP801L inhibitor to be used with any of the methods disclosed herein, in any of the uses disclosed herein and in any of the pharmaceutical compositions disclosed herein, may be selected from the group consisting of an siRNA molecule, a vector comprising an siRNA molecule, a vector which can express an siRNA molecule and any molecule which is endogenously processed into an siRNA molecule. As detailed herein, said siRNA molecule is preferably an siRNA comprising consecutive nucleotides having a sequence identical to any one of the sequences set forth in any one of Tables A-G and preferably siRNA Nos:72 and 73 of Table A, or DDIT4L__14 or DDIT4L__15 in Table F.

"Respiratory disorder" refers to conditions, diseases or syndromes of the respiratory system including but not limited to pulmonary disorders of all types including chronic obstructive pulmonary disease (COPD), acute lung injury (ALI), emphysema, chronic bronchitis, asthma and lung cancer, inter alia. Emphysema and chronic bronchitis may occur as part of COPD or independently. Conditions resulting from lung transplantation may also be viewed as such.

"Ischemic diseases/conditions" relates to any disease in which ischemia is involved, as well as ischemia-reperfusion injury and ischemia in connection with organ transplantation.

"Microvascular disorder" refers to any condition that affects microscopic capillaries and lymphatics, in particular vasospastic diseases, vasculitic diseases and lymphatic occlusive diseases. Examples of microvascular disorders include, inter alia: eye disorders such as Amaurosis Fugax (embolic or secondary to SLE), apla syndrome, Prot CS and ATIII deficiency, microvascular pathologies caused by IV drug use, dysproteinemia, temporal arteritis, anterior ischemic optic neuropathy, optic neuritis (primary or secondary to autoimmune diseases), glaucoma, von Hippel Lindau syndrome, corneal disease, corneal transplant rejection cataracts, Eales' disease, frosted branch angiitis, encircling buckling operation, uveitis including pars planitis, choroidal melanoma, choroidal hemangioma, optic nerve aplasia; retinal conditions such as retinal artery occlusion, retinal vein occlusion, retinopathy of prematurity, HIV retinopathy, Purtscher retinopathy, retinopathy of systemic vasculitis and autoimmune diseases, diabetic retinopathy, hypertensive retinopathy, radiation retinopathy, branch retinal artery or vein occlusion, idiopathic retinal vasculitis, aneurysms, neuroretinitis, retinal embolization, acute retinal necrosis, Birdshot retinochoroidopathy, long-standing retinal detachment; systemic conditions such as Diabetes mellitus, diabetic retinopathy (DR), diabetes-related microvascular pathologies (as detailed herein), hyperviscosity syndromes, aortic arch syndromes and ocular ischemic syndromes, carotid-cavernous fistula, multiple sclerosis, systemic lupus erythematosus, arteriolitis with SS-A autoantibody, acute multifocal hemorrhagic vasculitis, vasculitis resulting from infection, vasculitis resulting from Behcet's disease, sarcoidosis, coagulopathies, neuropathies, nephropathies, microvascular diseases of the kidney, acute renal failure and ischemic microvascular conditions, inter alia.

Microvascular disorders may comprise a neovascular element. The term "neovascular disorder" refers to those conditions where the formation of blood vessels (neovascularization) is harmful to the patient. Examples of ocular neovascularization include: retinal diseases (diabetic retinopathy, diabetic Macular Edema, chronic glaucoma, retinal detachment, and sickle cell retinopathy); rubeosis iritis; proliferative vitreo-retinopathy; inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve; and neovascularization due to penetration of the eye or contusive ocular injury. All these neovascular conditions may be treated using the compounds and pharmaceutical compositions of the present invention.

"Eye disease" refers to refers to conditions, diseases or syndromes of the eye including but not limited to any conditions involving choroidal neovascularization (CNV), wet and dry AMD, ocular histoplasmosis syndrome, angiod streaks, ruptures in Bruch's membrane, myopic degeneration, ocular tumors, retinal degenerative diseases, glaucoma, ION, and retinal vein occlusion (RVO). Some conditions disclosed herein, such as DR, which may be treated according to the methods of the present invention have been regarded as either a microvascular disorder and an eye disease, or both, under the definitions presented herein.

Hearing impairments relevant to the invention may be due to end-organ lesions involving inner ear hair cells, e.g., acoustic trauma, viral endolymphatic labyrinthitis, Meniere's disease. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chicken pox, mononucleosis and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome. The hearing loss can be noise-induced, generally due to a noise greater than 85 decibels (db) that damages the inner ear. Preferably, the hearing loss is caused by aging (presbycusis) or an ototoxic drug that affects the auditory portion of the inner ear, particularly inner ear hair cells. Incorporated herein by reference are Chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

Hearing disorders or impairments (or balance impairment) to be treated or prevented in the context of the present invention are preferably, without being bound by theory, trauma-induced deafness, age-related deafness and ototoxin-induced inner ear hair cells apoptotic damage. Those in need of treatment include those already experiencing a hearing impairment, those prone to having the impairment, and those in which the impairment is to be prevented. Without being bound by theory, the hearing impairments may be due to apoptotic inner ear hair cell damage or loss, wherein the damage or loss is caused by infection, mechanical injury, loud sound, aging, or, in particular, chemical-induced ototoxicity. Ototoxins include therapeutic drugs including antineoplastic agents, salicylates, quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition is given immediately after the exposure to prevent or reduce the ototoxic effect. More preferably, treatment is provided prophylactically, either by administration of the composition prior to or concomitantly with the ototoxic pharmaceutical or the exposure to the ototoxin.

The hearing impairment may be induced by chemotherapy. In more detail, hearing impairment may be caused by chemotherapeutic agents such as etoposide, 5-FU (5-fluorouracil), cis-platinum, doxorubicin, a ulna alkaloid, vincristine, vinblastine, vinorelbine, taxol, cyclophosphamide, ifosfamide, chlorambucil, busulfan, mechlorethamine, mitomycin, dacarbazine, carboplatinum, thiotepa, daunorubicin, idarubicin, mitoxantrone, bleomycin, esperamicin A1, dactinomycin, plicamycin, carmustine, lomustine, tauromustine, streptozocin, melphalan, dactinomycin, procarbazine, dexamethasone, prednisone, 2-chlorodeoxyadenosine, cytarabine, docetaxel, fludarabine, gemcitabine, herceptin, hydroxyurea, irinotecan, methotrexate, oxaliplatin, rituxin, semustine, epirubicin, etoposide, tomudex and topotecan, or a chemical analog of one of these chemotherapeutic agents. The chemotherapeutic agents most likely to cause hearing impairment is cisplatinum (cisplatin) and cisplatin-like compounds.

By "ototoxin" in the context of the present invention is meant a substance that through its chemical action injures, impairs or inhibits the activity of the sound receptors of the nervous system related to hearing, which in turn impairs hearing (and/or balance). In the context of the present invention, ototoxicity includes a deleterious effect on the inner ear hair cells. Ototoxic agents that cause hearing impairments include, but are not limited to, neoplastic agents such as vincristine, vinblastine, cisplatin and cisplatin-like compounds, taxol and taxol-like compounds, dideoxy-compounds, e.g., dideoxyinosine; alcohol; metals; industrial toxins involved in occupational or environmental exposure; contaminants of food or medicinals; and over-doses of vitamins or therapeutic drugs, e.g., antibiotics such as penicillin or chloramphenicol, and megadoses of vitamins A, D, or B6, salicylates, quinines and loop diuretics. By "exposure to an ototoxic agent" is meant that the ototoxic agent is made available to, or comes into contact with, a mammal. Exposure to an ototoxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure.

An "inhibitor" is a compound which is capable of reducing the expression of a gene or the activity of the product of such gene to an extent sufficient to achieve a desired biological or physiological effect. The term "inhibitor" as used herein refers to one or more of an oligonucleotide inhibitor, including siRNA, shRNA, aptamers, antisense molecules, miRNA and ribozymes, as well as antibodies. The inhibitor may cause complete or partial inhibition.

The term "inhibit" as used herein refers to reducing the expression of a gene or the activity of the product of such gene to an extent sufficient to achieve a desired biological or physiological effect. Inhibition may be complete or partial.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application mRNA sequences are set forth as representing the corresponding genes.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds of the present invention encompass molecules comprising deoxyribonucleotides, ribonucleotides, modified deoxyribonucleotides, modified ribonucleotides and combinations thereof. See below for in depth description of oligonucleotides.

RTP801L mRNA sequence, refers to the mRNA sequence shown in FIG. 1 (SEQ ID NO:1), or any homologous sequence thereof preferably having at least 70% identity, more preferable 80% identity, even more preferably 90% or 95% identity. This encompasses any sequences derived from SEQ ID NO:1 which have undergone mutations, alterations or modifications as described herein. Thus, in a preferred embodiment RTP801l is encoded by a nucleic acid sequence according to SEQ. ID. NO. 1. It is also within the present invention that the nucleic acids according to the present invention are only complementary and identical, respectively, to a part of the nucleic acid coding for RTP801L as, preferably, the first stretch and first strand is typically shorter than the nucleic acid according to the present invention. It is also to be acknowledged that based on the amino acid sequence of RTP801L any nucleic acid sequence coding for such amino acid sequence can be perceived by the one skilled in the art based on the genetic code. However, due to the assumed mode of action of the nucleic acids according to the present invention, it is most preferred that the nucleic acid coding for RTP801L, preferably the mRNA thereof, is the one present in the organism, tissue and/or cell, respectively, where the expression of RTP801L is to be reduced.

"RTP801L polypeptide" refers to the polypeptide of the RTP801L gene, and is understood to include, for the purposes of the instant invention, the terms "RTP777", "DDIT4L" "REDD2", and "SMHS1", derived from any organism, optionally man, splice variants and fragments thereof retaining biological activity, and homologs thereof, preferably having at least 70%, more preferably at least 80%, even more preferably at least 90% or 95% homology thereto. In addition, this term is understood to encompass polypeptides resulting from minor alterations in the RTP801L coding sequence, such as, inter alia, point mutations, substitutions, deletions and insertions which may cause a difference in a few amino acids between the resultant polypeptide and the naturally occurring RTP801L. Polypeptides encoded by nucleic acid sequences which bind to the RTP801L coding sequence or genomic sequence under conditions of highly stringent hybridization, which are well-known in the art (for example Ausubel et al., Current Protocols in Molecular Biology, John Wiley and Sons, Baltimore, Md. (1988), updated in 1995 and 1998), are also encompassed by this term. Chemically modified RTP801L or chemically modified fragments of RTP801L are also included in the term, so long as the biological activity is retained. RTP801L preferably has or comprises an amino acid sequence according to SEQ. ID. NO. 2. It is acknowledged that there might be differences in the amino acid sequence among various tissues of an organism and among different organisms of one species or among different species to which the nucleic acid according to the present invention can be applied in various embodiments of the present invention. However, based on the technical teaching provided herein, the respective sequence can be taken into consideration accordingly when designing any of the nucleic acids according to the present invention.

Without being bound by theory, RTP801L may be a factor acting in the fine-tuning of cell response to energy disbalance. As such, it is a target suitable for treatment of any disease where cells should be rescued from apoptosis due to stressful conditions (e.g. diseases accompanied by death of normal cells) or where cells, which are adapted to stressful conditions due to changes in RTP801L expression (e.g. cancer cells), should be killed. In the latter case, RTP801L may be viewed as a survival factor for cancer cells and its inhibitors may treat cancer as a monotherapy or as sensitising drugs in combination with chemotherapy or radiotherapy. The assignee of the present invention has previously discovered gene RTP801 (see above) and molecules effective in inhibiting gene RTP801 (see co-assigned PCT publication No. WO06/023544A2 and PCT Application No. PCT/US2007/01468, hereby incorporated by reference in their entirety). Although RTP801L shares sequence and functional homology with RTP801, the assignee of the present invention has discovered that inhibition of RTP801 does not cause simultaneous inhibition of RTP801L, and vice versa. Therefore, RTP801L is an excellent target for inhibition in the conditions disclosed herein, and its inhibition is gene-specific. Tandem therapies which inhibit both RTP801 and RTP801L can have additional advantages and are discussed herein blow.

The term "amino acid" refers to a molecule which consists of any one of the 20 naturally occurring amino acids, amino acids which have been chemically modified (see below), or synthetic amino acids.

The term "polypeptide" refers to a molecule composed of two or more amino acids residues. The term includes peptides, polypeptides, proteins and peptidomimetics.

By "biological effect of RTP801L" or "RTP801L biological activity" is meant, without being bound by theory, the effect of RTP801L on apoptosis, such as apoptosis of alveolar cells in respiratory disorders; apoptosis of inner ear hair cells in hearing disorders, apoptosis of macular cells in macular degeneration, apoptosis of cells related to ischemia in any diseases or conditions, inter alia. The effect of RTP801L on apoptosis may be direct or indirect, and includes, without being bound by theory, any effect of RTP801L of induced by hypoxic or hyperoxic conditions. The indirect effect includes, but is not limited to, RTP801L binding to or having an effect on one of several molecules, which are involved in a signal transduction cascade resulting in apoptosis.

"Apoptosis" refers to a physiological type of cell death which results from activation of some cellular mechanisms, i.e. death that is controlled by the machinery of the cell. Apoptosis may, for example, be the result of activation of the cell machinery by an external trigger, e.g. a cytokine or anti-FAS antibody, which leads to cell death or by an internal signal. The term "programmed cell death" may also be used interchangeably with "apoptosis".

"Apoptosis-related disease" refers to a disease whose etiology is related either wholly or partially to the process of apoptosis. The disease may be caused either by a malfunction of the apoptotic process (such as in cancer or an autoimmune disease) or by overactivity of the apoptotic process (such as in certain neurodegenerative diseases). Many diseases in which RTP801L is involved are apoptosis-related diseases. For example, apoptosis is a significant mechanism in dry AMD, whereby slow atrophy of photoreceptor and pigment epithelium cells, primarily in the central (macular) region of retina takes place. Neuroretinal apoptosis is also a significant mechanism in diabetic retinopathy.

An "RTP801L inhibitor" is a compound which is capable of inhibiting the activity of the RTP801L gene or RTP801L gene product, particularly the human RTP801L gene or gene product. Such inhibitors include substances that affect the transcription or translation of the gene as well as substances that affect the activity of the gene product. An RTP801L inhibitor may also be an inhibitor of the RTP801L promoter. Examples of such inhibitors may include, inter alia: polynucleotides such as antisense (AS) fragments, siRNA, or vectors comprising them; catalytic RNAs such as ribozymes.

Specific siRNA RTP801L inhibitors are provided herein.

"Expression vector" refers to a vector that has the ability to incorporate and express heterologous DNA fragments in a foreign cell. Many prokaryotic and eukaryotic expression vectors are known and/or commercially available. Selection of appropriate expression vectors is within the knowledge of those having skill in the art.

The present invention also relates to functional nucleic acids comprising a double-stranded structure, their use for the manufacture of a medicament, a pharmaceutical composition comprising such functional nucleic acids and a method for the treatment of a patient.

Hypoxia has been recognised as a key element in the pathomechanism of quite a number of diseases such as stroke, emphysema and infarct which are associated with sub-optimum oxygen availability and tissue damaging responses to the hypoxia conditions. In fast-growing tissues, including tumor, a sub-optimum oxygen availability is compensated by undesired neo-angiogenesis. Therefore, at least in case of cancer diseases, the growth of vasculature is undesired.

In view of this, the inhibition of angiogenesis and vascular growth, respectively, is subject to intense research. Already today some compounds are available which inhibit undesired angiogenesis and vascular growth. Some of the more prominent compounds are those inhibiting VEGF and the VEGF receptor. In both cases, the effect of VEGF is avoided by either blocking VEGF as such, for example by using an antibody directed against VEGF such as pursued by Genentech's AVASTIN™ (monoclonal AB specific for VEGF) (Ferrara N.; *Endocr Rev.* 2004 25(4):581-611), or by blocking the corresponding receptor, i.e. the VEGF receptor (Traxler P; *Cancer Res.* 2004 64(14):4931-41; or Stadler W M et al., *Clin Cancer Res.* 2004; 10(10):3365-70).

As, however, angiogenesis and the growth of vasculature is a very basic and vital process in any animal and human being, the effect of this kind of compound has to be focused at the particular site where angiogenesis and vascular growth is actually undesired which renders appropriate targeting or delivery a critical issue in connection with this kind of therapeutic approach.

It is thus an objective of the present invention to provide further means for the treatment of diseases involving undesired growth of vasculature and angiogenesis, respectively.

By "small interfering RNA" (siRNA) is meant an RNA molecule which decreases or silences (prevents) the expression of a gene/mRNA of its endogenous cellular counterpart. The term is understood to encompass "RNA interference" (RNAi). RNA interference (RNAi) refers to the process of sequence-specific post transcriptional gene silencing in mammals mediated by small interfering RNAs (siRNAs) (Fire et al, 1998, *Nature* 391, 806). The corresponding process in plants is commonly referred to as specific post transcriptional gene silencing or RNA silencing and is also referred to as quelling in fungi. The RNA interference response may feature an endonuclease complex containing an siRNA, commonly referred to as an RNA-induced silencing complex (RISC), which mediates cleavage of single-stranded RNA having sequence complementary to the antisense strand of the siRNA duplex. Cleavage of the target RNA may take place in the middle of the region complementary to the antisense strand of the siRNA duplex (Elbashir et al 2001, *Genes Dev.,* 15, 188). For recent information on these terms and proposed mechanisms, see Bernstein E., et al., 2001 November; 7(11):1509-21; and Nishikura K.: *Cell.* 2001. 107(4):415-8. Examples of siRNA molecules which are used in the present invention are given in Tables A-G.

During recent years, RNAi has emerged as one of the most efficient methods for inactivation of genes (*Nature Reviews,* 2002, v. 3, p. 737-47; *Nature,* 2002, v. 418, p. 244-51). As a method, it is based on the ability of dsRNA species to enter a specific protein complex, where it is then targeted to the complementary cellular RNA and specifically degrades it. In more detail, dsRNAs are digested into short (17-29 bp) inhibitory RNAs (siRNAs) by type III RNAses (DICER, Drosha, etc) (*Nature,* 2001, v. 409, p. 363-6; *Nature,* 2003, 425, p. 415-9). These fragments and complementary mRNA are recognized by the specific RISC protein complex. The whole process is culminated by endonuclease cleavage of target mRNA (*Nature Reviews,* 2002, v. 3, p. 737-47; *Curr Opin Mol Ther.* 2003 5(3):217-24).

For delivery of siRNAs, see, for example, Shen et al *FEBS letters* 539: 111-114 (2003), Xia et al., *Nat Biotech* 20: 1006-1010 (2002), Reich et al., *Molec. Vision* 9: 210-216 (2003), Sorensen et al. *J. Mol. Biol.* 327: 761-766 (2003), Lewis et al., *Nat Genet.* 32: 107-108 (2002) and Simeoni et al., *NAR* 31, 11: 2717-2724 (2003). siRNA has been successfully used for inhibition in primates; for further details see Tolentino et al., 2004 *Retina* 24(1): 132-138.

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

RNA interference (RNAi) is based on the ability of dsRNA species to enter a cytoplasmic protein complex, where it is then targeted to the complementary cellular RNA and specifically degrade it. The RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al., *Genes Dev.,* 2001, 15(2): 188-200). In more detail, longer dsRNAs are digested into short (17-29 bp) dsRNA fragments (also referred to as short inhibitory RNAs, "siRNAs") by type III RNAses (DICER, DROSHA, etc.; Bernstein et al., *Nature,* 2001, 409(6818): 363-6; Lee et al., *Nature,* 2003, 425(6956):415-9). The RISC protein complex recognizes these fragments and complementary mRNA. The whole process is culminated by endonuclease cleavage of target mRNA (McManus & Sharp, *Nature Rev Genet,* 2002, 3(10):737-47; Paddison & Hannon, *Curr Opin Mol Ther.* 2003, 5(3):217-24). (For additional information on these terms and proposed mechanisms, see for example Bernstein et al., *RNA* 2001, 7(11):1509-21; Nishikura, *Cell* 2001, 107(4):415-8 and PCT publication WO 01/36646).

"Nucleotide" is meant to encompass deoxyribonucleotides and ribonucleotides, which may be natural or synthetic, and or modified or unmodified. Modifications include changes and substitutions to the sugar moiety, the base moiety and/or the internucleotide linkages.

All analogs of, or modifications to, a nucleotide/oligonucleotide may be employed with the present invention, provided that said analog or modification does not substantially adversely affect the function of the nucleotide/oligonucleotide. Acceptable modifications include modifications of the sugar moiety, modifications of the base moiety, modifications in the internucleotide linkages and combinations thereof.

The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. Abasic nucleotides are encompassed by the present invention, as well as molecules comprising alternating RNA and DNA nucleotides.

In addition, analogs of polynucleotides can be prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA is replaced with a polyamide backbone which is similar to that found in peptides. PNA analogs have been shown to be resistant to enzymatic degradation and to have extended lives in vivo and in vitro. Mirror nucleotides ("L-nucleotides") may also be employed.

Possible modifications to the sugar residue are manifold and include 2'-O alkyl, locked nucleic acid (LNA), glycol nucleic acid (GNA), threose nucleic acid (TNA), arabinoside, altritol (ANA) and other 6-membered sugars including morpholinos, and cyclohexinyls.

Examples of siRNA compounds comprising LNA nucleotides are disclosed in Elmen et al., (NAR 2005. 33(1):439-447).

The compounds of the present invention can be synthesized using one or more inverted nucleotides, for example inverted thymidine or inverted adenine (for example see Takei, et al., 2002. JBC 277(26):23800-06.)

Certain structures include siRNA compounds having one or a plurality of 2'-5' internucleotide linkages (bridges or backbone).

In the context of the present invention, a "mirror" nucleotide also referred to as a Spiegelmer, is a nucleotide with reverse chirality to the naturally occurring or commonly employed nucleotide, i.e., a mirror image of the naturally occurring or commonly employed nucleotide. The mirror nucleotide can be a ribonucleotide (L-RNA) or a deoxyribonucleotide (L-DNA) and may further comprise at least one sugar, base and or backbone modification. U.S. Pat. No. 6,602,858 discloses nucleic acid catalysts comprising at least one L-nucleotide substitution.

Backbone modifications, such as ethyl (resulting in a phospho-ethyl triester); propyl (resulting in a phospho-propyl triester); and butyl (resulting in a phospho-butyl triester) are also possible. Other backbone modifications include polymer backbones, cyclic backbones, acyclic backbones, thiophosphate-D-ribose backbones, amidates, phosphonoacetates.

Other possible backbone modifications include thioate modifications or 2'-5' bridged backbone modifications.

Additional modifications which may be present in the molecules of the present invention include nucleoside modifications such as artificial nucleic acids, peptide nucleic acid (PNA), morpholino and locked nucleic acid (LNA), glycol nucleic acid (GNA), threose nucleic acid (TNA), arabinoside, and mirror nucleoside (for example, beta-L-deoxynucleoside instead of beta-D-deoxynucleoside Further, said molecules may additionally contain modifications on the sugar, such as 2' alkyl, 2' fluoro, 2'O allyl 2' amine and 2' alkoxy. Many additional sugar modifications are discussed herein.

Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of a internucleotide linkage between two adjacent nucleotides in one strand. Any of the molecules of the present invention may contain one or more gaps and/or one or more nicks.

Further provided by the present invention is an siRNA encoded by any of the molecules disclosed herein, a vector encoding any of the molecules disclosed herein, and a pharmaceutical composition comprising any of the molecules disclosed herein or the vectors encoding them; and a pharmaceutically acceptable carrier.

Oligonucleotides

The siRNA compounds useful in the present invention include unmodified and chemically and or structurally modified compounds.

The selection and synthesis of siRNA corresponding to known genes has been widely reported; see for example Ui-Tei et al., J Biomed Biotechnol. 2006; 65052; Chalk et al., BBRC. 2004, 319(1):264-74; Sioud & Leirdal, Met. Mol Biol. 2004, 252:457-69; Levenkova et al., Bioinform. 2004, 20(3): 430-2; Ui-Tei et al., NAR. 2004, 32(3):936-48. For examples of the use and production of modified siRNA see for example Braasch et al., Biochem. 2003, 42(26):7967-75; Chiu et al., RNA. 2003, 9(9):1034-48; PCT Publication Nos. WO 2004/015107 and WO 02/44321 and U.S. Pat. Nos. 5,898,031 and 6,107,094.

Tables A-G comprise nucleic acid sequences of sense and corresponding antisense oligonucleotides useful in preparing corresponding siRNA compounds.

The present invention provides double-stranded oligonucleotides (e.g. siRNAs), which down-regulate the expression of RTP801L. A siRNA of the invention is a duplex oligoribonucleotide in which the sense strand is derived from the mRNA sequence of RTP801L, and the antisense strand is complementary to the sense strand. In general, some deviation from the target mRNA sequence is tolerated without compromising the siRNA activity (see e.g. Czauderna et al., 2003, NAR 31(11), 2705-2716). An siRNA of the invention inhibits RTP801L gene expression on a post-transcriptional level with or without destroying the mRNA. Without being bound by theory, siRNA may target the mRNA for specific cleavage and degradation and/or may inhibit translation from the targeted message.

In some embodiments the oligonucleotide according to the present invention comprises modified siRNA, having one or more of any of the modifications disclosed herein. In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid which is mRNA transcribed from RTP801L, and the second strand comprises a ribonucleotide sequence at least partially complementary to the first strand and wherein said first strand or said second strand comprises a plurality of groups of modified ribonucleotides, optionally having a modification at the 2'-position of the sugar moiety whereby within each strand each group of modified ribonucleotides is flanked on one or both sides by a group of flanking nucleotides, optionally ribonucleotides, whereby each ribonucleotide forming the group of flanking ribonucleotides is selected from an unmodified ribonucleotide or a ribonucleotide having a modification different from the modification of the groups of modified ribonucleotides.

The group of modified ribonucleotides and/or the group of flanking nucleotides may comprise a number of ribonucleotides selected from the group consisting of an integer from 1 to 12. Accordingly, the group thus comprises one nucleotide, two nucleotides, three nucleotides, four nucleotides, five nucleotides, six nucleotides, seven nucleotides, eight nucleotides, nine nucleotides, ten nucleotides, eleven nucleotides or twelve nucleotides.

The groups of modified nucleotides and flanking nucleotides may be organized in a pattern on only one of the strands. In some embodiments the sense or the antisense strand comprises a pattern of modified nucleotides. In some preferred embodiments the middle ribonucleotide in the antisense strand is an unmodified nucleotide. For example, in a 19-oligomer antisense strand, ribonucleotide number 10 is unmodified; in a 21-oligomer antisense strand, ribonucleotide number 11 is unmodified; and in a 23-oligomer antisense strand, ribonucleotide number 12 is unmodified. The modifications or pattern of modification, if any, of the siRNA must be planned to allow for this. In an even numbered oligomer e.g. a 22 mer, the middle nucleotide may be number 11 or 12.

Possible modifications on the 2' moiety of the sugar residue include amino, fluoro, methoxy alkoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O-, S-, or N-alkyl; O—, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1. One or more deoxyribonucleotides are also tolerated in the compounds of the present invention. As used herein, in the description of any strategy for the design of molecules, RNAi or any embodiment of RNAi disclosed herein, the term "end modification" means a chemical entity added to the terminal 5' or 3' nucleotide of the sense and/or antisense strand. Examples for such end modifications include, but are not limited to, 3' or 5' phosphate, inverted abasic, abasic, amino, fluoro, chloro, bromo, CN, $CF_3$, methoxy, imidazolyl, carboxylate, phosphorothioate, $C_1$ to $C_{22}$ and lower alkyl, lipids, sugars and polyaminoacids (i.e. peptides), substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterocycloalkyl; heterocycloalkaryl; aminoalkylamino; polyalkylamino or substituted silyl, as, among others, described in European patents EP 0 586 520 B1 or EP 0 618 925 B1.

In some embodiments the siRNA is blunt ended, i.e. Z and Z' are absent, on one or both ends. More specifically, the siRNA may be blunt ended on the end defined by the 5'-terminus of the first strand and the 3'-terminus of the second strand, and/or the end defined by the 3'-terminus of the first strand and the 5'-terminus of the second strand.

In other embodiments at least one of the two strands may have an overhang of at least one nucleotide at the 5'-terminus; the overhang may consist of at least one deoxyribonucleotide. At least one of the strands may also optionally have an overhang of at least one nucleotide at the 3'-terminus. The overhang may consist of from about 1 to about 5 nucleotides.

The length of RNA duplex is from about 18 to about 40 ribonucleotides, preferably 19, 21 or 23 ribonucleotides. Further, the length of each strand may independently have a length selected from the group consisting of about 15 to about 40 bases, preferably 18 to 23 bases and more preferably 19, 21 or 23 ribonucleotides.

In certain embodiments the complementarity between said first strand and the target nucleic acid is perfect. In some embodiments, the strands are substantially complementary, i.e. having one, two or up to three mismatches between said first strand and the target nucleic acid. Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

In some embodiments the first strand and the second strand are linked by a loop structure, which is comprised of a non-nucleic acid polymer such as, inter alia, polyethylene glycol. Alternatively, the loop structure is comprised of a nucleic acid, including modified and non-modified ribonucleotides and modified and non-modified deoxyribonucleotides.

Further, the 5'-terminus of the first strand of the siRNA may be linked to the 3'-terminus of the second strand, or the 3'-terminus of the first strand are linked to the 5'-terminus of the second strand, said linkage being via a nucleic acid linker typically having a length between 2-100 nucleobases, preferably about 2 to about 30 nucleobases.

In preferred embodiments of the compounds of the invention having alternating ribonucleotides modified in at least one of the antisense and the sense strands of the compound, for 19 mer and 23 mer oligomers the ribonucleotides at the 5' and 3' termini of the antisense strand are modified in their sugar residues, and the ribonucleotides at the 5' and 3' termini of the sense strand are unmodified in their sugar residues. For 21 mer oligomers the ribonucleotides at the 5' and 3' termini of the sense strand are modified in their sugar residues, and the ribonucleotides at the 5' and 3' termini of the antisense strand are unmodified in their sugar residues, or may have an optional additional modification at the 3' terminus. As mentioned above, it is preferred that the middle nucleotide of the antisense strand is unmodified.

Additionally, the invention provides siRNA comprising a double stranded nucleic acid molecule wherein 1, 2, or 3 of the nucleotides in one strand or both strands are substituted thereby providing at least one base pair mismatch. The substituted nucleotides in each strand are preferably in the terminal region of one strand or both strands.

According to one preferred embodiment of the invention, the antisense and the sense strands of the oligonucleotide/siRNA are phosphorylated only at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

Any siRNA sequence disclosed herein can be prepared having any of the modifications/structures disclosed herein. The combination of sequence plus structure is novel and can be used in the treatment of the conditions disclosed herein.

Other modifications have been disclosed. The inclusion of a 5'-phosphate moiety was shown to enhance activity of siRNAs in *Drosophila* embryos (Boutla, et al., *Curr. Biol.* 2001, 11:1776-1780) and is required for siRNA function in human HeLa cells (Schwarz et al., *Mol. Cell*, 2002, 10:537-48). Amarzguioui et al., (*NAR*, 2003, 31(2):589-95) showed that siRNA activity depended on the positioning of the 2'-O-methyl modifications. Holen et at (NAR. 2003, 31(9):2401-07) report that an siRNA having small numbers of 2'-O-methyl modified nucleosides gave good activity compared to wild type but that the activity decreased as the numbers of 2'-O-methyl modified nucleosides was increased. Chiu and Rana (*RNA*. 2003, 9:1034-48) teach that incorporation of 2'-O-methyl modified nucleosides in the sense or antisense strand (fully modified strands) severely reduced siRNA activity relative to unmodified siRNA. The placement of a 2'-O-methyl group at the 5'-terminus on the antisense strand was reported to severely limit activity whereas placement at the 3'-terminus of the antisense and at both termini of the sense strand was tolerated (Czauderna et al., *NAR*. 2003, 31(11):2705-16). The molecules of the present invention offer an advantage in that they are active and or stable, are non-toxic and may be formulated as pharmaceutical compositions for treatment of various diseases.

In addition, analogues of polynucleotides can be prepared wherein the structure of one or more nucleotide is fundamentally altered and better suited as therapeutic or experimental reagents.

Possible modifications to the sugar residue are manifold and include 2'-0 alkyl, locked nucleic acid (LNA), glycol nucleic acid (GNA), threose nucleic acid (TNA), arabinoside, altritol (ANA) and other, 6-membered sugars including morpholinos, and cyclohexinyls.

LNA compounds are disclosed in International Patent Publication Nos. WO 00/47599, WO 99/14226, and WO 98/39352. Examples of siRNA compounds comprising LNA nucleotides are disclosed in Elmen et al., (NAR 2005. 33(1): 439-447) and in PCT Patent Publication No. WO 2004/083430.

The compounds of the present invention can be synthesized using one or more inverted nucleotides, for example inverted thymidine or inverted adenine (for example see Takei, et al., 2002. JBC 277(26):23800-06.

Backbone modifications, such as ethyl (resulting in a phospho-ethyl triester); propyl (resulting in a phospho-propyl triester); and butyl (resulting in a phospho-butyl triester) are also possible. Other backbone modifications include polymer backbones, cyclic backbones, acyclic backbones, thiophosphate-D-ribose backbones, amidates, phosphonoacetate derivatives. Certain structures include siRNA compounds having one or a plurality of 2'-5' internucleotide linkages (bridges or backbone).

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; bridged nucleic acids including LNA and ethylene bridged nucleic acids.

The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyriboabasic 5'-phosphate.

Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

The molecules of the present invention may comprise siRNAs, synthetic siRNAs, shRNAs and synthetic shRNAs, in addition to other nucleic acid sequences or molecules which encode such molecules or other inhibitory nucleotide molecules.

The compounds of the present invention may further comprise an end modification. A biotin group may be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned modifications.

The various end modifications as disclosed herein are preferably located at the ribose moiety of a nucleotide of the nucleic acid according to the present invention. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasic or abasic are nucleotides, either deoxyribonucleotides or ribonucleotides which do not have a nucleobase moiety. This kind of compound is, inter alia, described in Sternberger, et al., (Antisense Nucleic Acid Drug Dev, 2002.12, 131-43).

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks. Further provided by the present invention is an siRNA encoded by any of the molecules disclosed herein, a vector encoding any of the molecules disclosed herein, and a pharmaceutical composition comprising any of the molecules disclosed herein or the vectors encoding them; and a pharmaceutically acceptable carrier.

Particular molecules to be administered according to the methods of the present invention are disclosed below under the heading "structural motifs". For the sake of clarity, any of these molecules can be administered according to any of the methods of the present invention.

Structural Motifs

According to the present invention the siRNA compounds are chemically and or structurally modified according to one of the following modifications set forth in Structures (A)-(P) or as tandem siRNA or RNAstar.

In one aspect the present invention provides a compound set forth as Structure (A):

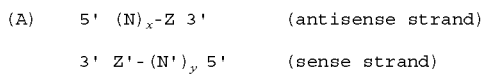

(A)    5'  $(N)_x$-Z 3'       (antisense strand)

3'  Z'-$(N')_y$ 5'     (sense strand)

wherein each of N and N' is a nucleotide selected from an unmodified ribonucleotide, a modified ribonucleotide, an unmodified deoxyribonucleotide and a modified deoxyribonucleotide;
wherein each of $(N)_x$ and $(N')_y$ is an oligonucleotide in which each consecutive N or N' is joined to the next N or N' by a covalent bond;
wherein each of x and y is an integer between 18 and 40;
wherein each of Z and Z' may be present or absent, but if present is 1-5 consecutive nucleotides covalently attached at the 3' terminus of the strand in which it is present; and
and wherein the sequence of $(N)_x$ comprises an antisense sequence substantially complementary to about 18 to about 40 consecutive ribonucleotides in an mRNA transcribed from the RTP801L gene.

In certain embodiments the present invention provides a compound having structure B (structures having alternating 2'-O-methyl modification in both strands):

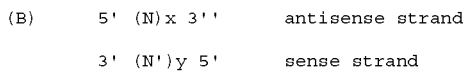

(B)    5'  (N)x 3''     antisense strand

3'  (N')y 5'     sense strand wherein each of $(N)_x$ and $(N')_y$ is an oligonucleotide in which each consecutive N or N' is an unmodified ribonucleotide or a modified ribonucleotide joined to the next N or N' by a covalent bond;
wherein each of x and y=19, 21 or 23 and $(N)_x$ and $(N')_y$ are fully complementary
wherein alternating ribonucleotides in each of $(N)_x$ and $(N')_y$ are modified to result in a 2'-O-methyl modification in the sugar residue of the ribonucleotides;
wherein the sequence of $(N')_y$ is a sequence complementary to (N)x; and wherein the sequence of $(N)_x$ comprises an antisense sequence substantially complementary to about 18 to about 40 consecutive ribonucleotides in an mRNA transcribed from the RTP801L gene. In some embodiments each of $(N)_x$ and $(N')_y$ is independently phosphorylated or non-phosphorylated at the 3' and 5' termini.

In certain embodiments of the invention, alternating ribonucleotides are modified in both the antisense and the sense strands of the compound.

In certain embodiments wherein each of x and y=19 or 23, each N at the 5' and 3' termini of $(N)_x$ is modified; and each N' at the 5' and 3' termini of $(N')_y$ is unmodified.

In certain embodiments wherein each of x and y=21, each N at the 5' and 3' termini of $(N)_x$ is unmodified; and each N' at the 5' and 3' termini of $(N')_y$ is modified.

In particular embodiments, when x and y=19, the siRNA is modified such that a 2%0-methyl (2'-OMe) group is present on the first, third, fifth, seventh, ninth, eleventh, thirteenth, fifteenth, seventeenth and nineteenth nucleotide of the antisense strand $(N)_x$, and whereby the very same modification, i.e. a 2'-OMe group, is present at the second, fourth, sixth, eighth, tenth, twelfth, fourteenth, sixteenth and eighteenth nucleotide of the sense strand $(N')_y$. In various embodiments these particular siRNA compounds are blunt ended at both termini.

In some embodiments, the present invention provides a compound having Structure (C):

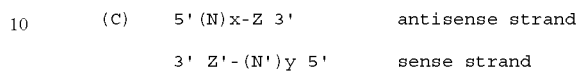

(C)    5' (N)x-Z 3'       antisense strand

3' Z'-(N')y 5'     sense strand wherein each of N and N' is a nucleotide independently selected from an unmodified ribonucleotide, a modified ribonucleotide, an unmodified deoxyribonucleotide and a modified deoxyribonucleotide;
wherein each of (N)x and (N')y is an oligomer in which each consecutive nucleotide is joined to the next nucleotide by a covalent bond and each of x and y is an integer between 18 and 40;
wherein in (N)x the nucleotides are unmodified or (N)x comprises alternating modified ribonucleotides and unmodified ribonucleotides; each modified ribonucleotide being modified so as to have a 2'-O-methyl on its sugar and the ribonucleotide located at the middle position of (N)x being modified or unmodified preferably unmodified;
wherein (N')y comprises unmodified ribonucleotides further comprising one modified nucleotide at a terminal or penultimate position, wherein the modified nucleotide is selected from the group consisting of a mirror nucleotide, a bicyclic nucleotide, a 2'-sugar modified nucleotide, an altritol nucleotide, or a nucleotide joined to an adjacent nucleotide by an internucleotide linkage selected from a 2'-5' phosphodiester bond, a P-alkoxy linkage or a PACE linkage;
wherein if more than one nucleotide is modified in (N')y, the modified nucleotides may be consecutive;
wherein each of Z and Z' may be present or absent, but if present is 1-5 deoxyribonucleotides covalently attached at the 3' terminus of any oligomer to which it is attached;
wherein the sequence of $(N')_y$ comprises a sequence substantially complementary to (N)x; and wherein the sequence of $(N)_x$ comprises an antisense sequence substantially complementary to about 18 to about 40 consecutive ribonucleotides in an mRNA transcribed from the RTP801L gene.

In particular embodiments, x=y=19 and in (N)x each modified ribonucleotide is modified so as to have a 2'-O-methyl on its sugar and the ribonucleotide located at the middle of (N)x is unmodified. Accordingly, in a compound wherein x=19, (N)x comprises 2'-O-methyl sugar modified ribonucleotides at positions 1, 3, 5, 7, 9, 11, 13, 15, 17 and 19. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 5. In other embodiments, (N)x comprises 2'O Me modified ribonucleotides at positions 2, 4, 8, 11, 13, 15, 17 and 19 and may further comprise at least one abasic or inverted abasic pseudo-nucleotide for example in position 6. In other embodiments, (N)x comprises 2'O Me modified ribonucleotides at positions 2, 4, 6, 8, 11, 13, 17 and 19 and may further comprise at least one abasic or inverted abasic pseudo-nucleotide for example in position 15. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 14. In other embodiments, (N)x comprises 2'O Me modified ribonucleotides at positions 1, 2, 3, 7, 9, 11, 13, 15, 17 and 19 and may further comprise at least one abasic or inverted abasic pseudo-nucleotide for example in position 5. In other embodiments, (N)x comprises 2'O Me modified ribonucleotides at positions 1, 2, 3, 5, 7, 9, 11, 13, 15, 17 and 19 and may further comprise at least one abasic or inverted abasic pseudo-nucleotide for example in position 6. In other embodiments, (N)x comprises 2'O Me modified ribonucleotides at positions 1, 2, 3, 5, 7, 9, 11, 13, 17 and 19 and may further comprise at least one abasic or inverted abasic pseudo-nucleotide for example in position 15. In other embodiments, (N)x comprises 2'O Me modified ribonucleotides at positions 1, 2, 3, 5, 7, 9, 11, 13, 15, 17 and 19 and may further comprise at least one abasic or inverted abasic pseudo-nucleotide for example in position 14. In other embodiments, (N)x comprises 2'O Me modified ribonucleotides at positions 2, 4, 6, 7, 9, 11, 13, 15, 17 and 19 and may further comprise at least one abasic or inverted abasic pseudo-nucleotide for example in position 5. In other embodiments, (N)x comprises 2'O Me modified ribonucleotides at positions 1, 2, 4, 6, 7, 9, 11, 13, 15, 17 and 19 and may further comprise at least one abasic or inverted abasic pseudo-nucleotide for example in position 5. In other embodiments, (N)x comprises 2'O Me modified ribonucleotides at positions 2, 4, 6, 8, 11, 13, 14, 16, 17 and 19 and may further comprise at least one abasic or inverted abasic pseudo-nucleotide for example in position 15. In other embodiments, (N)x comprises 2'O Me modified ribonucleotides at positions 1, 2, 3, 5, 7, 9, 11, 13, 14, 16, 17 and 19 and may further comprise at least one abasic or inverted abasic pseudo-nucleotide for example in position 15. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 7. In other embodiments, (N)x comprises 2'O Me modified ribonucleotides at positions 2, 4, 6, 11, 13, 15, 17 and 19 and may further comprise at least one abasic or inverted abasic pseudo-nucleotide for example in position 8. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 9. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 10. In other embodiments, (N)x comprises 2'O Me modified ribonucleotides at positions 2, 4, 6, 8, 13, 15, 17 and 19 and may further comprise at least one abasic or inverted abasic pseudo-nucleotide for example in position 11. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 12. In other embodiments, (N)x comprises 2'O Me modified ribonucleotides at positions 2, 4, 6, 8, 11, 15, 17 and 19 and may further comprise at least one abasic or inverted abasic pseudo-nucleotide for example in position 13.

In yet other embodiments (N)x comprises at least one nucleotide mismatch relative to the RTP801L gene. In certain preferred embodiments, (N)x comprises a single nucleotide mismatch on position 5, 6, or 14. In one embodiment of Structure (C), at least two nucleotides at either or both the 5' and 3' termini of (N')y are joined by a 2'-5' phosphodiester bond. In certain preferred embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and three nucleotides at the 3' terminus of (N')y are joined by two 2'-5' phosphodiester bonds (set forth herein as Structure I). In other preferred embodiments, x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and four consecutive nucleotides at the 5' terminus of (N')y are joined by three 2'-5' phosphodiester bonds. In a further embodiment, an additional nucleotide located in the middle position of (N)y may be modified with 2'-O-methyl on its sugar. In another preferred embodiment, in (N)x the nucleotides alternate between 2'-O-methyl modified ribonucleotides and unmodified ribonucleotides, and in (N')y four consecutive nucleotides at the 5' terminus are joined by three 2'-5' phosphodiester bonds and the 5' terminal nucleotide or two or three consecutive nucleotides at the 5' terminus comprise 3'-O-methyl modifications.

In certain preferred embodiments of Structure C, x=y=19 and in (N')y, at least one position comprises an abasic or inverted abasic pseudo-nucleotide, preferably five positions comprises an abasic or inverted abasic pseudo-nucleotides. In various embodiments, the following positions comprise an abasic or inverted abasic: positions 1 and 16-19, positions 15-19, positions 1-2 and 17-19, positions 1-3 and 18-19, positions 1-4 and 19 and positions 1-5. (N')y may further comprise at least one LNA nucleotide.

In certain preferred embodiments of Structure C, x=y=19 and in (N')y the nucleotide in at least one position comprises a mirror nucleotide, a deoxyribonucleotide and a nucleotide joined to an adjacent nucleotide by a 2'-5' internucleotide bond.

In certain preferred embodiments of Structure C, x=y=19 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA at position 18. In other embodiments (N')y comprises L-DNA at positions 17 and 18. In certain embodiments (N')y comprises L-DNA substitutions at positions 2 and at one or both of positions 17 and 18. In certain embodiments (N')y further comprises a 5' terminal cap nucleotide such as 5'-O-methyl DNA or an abasic or inverted abasic pseudo-nucleotide as an overhang.

In yet other embodiments (N')y comprises at least one nucleotide mismatch relative to the RTP801L gene. In certain preferred embodiments, (N')y comprises a single nucleotide mismatch on position 6, 14, or 15.

In yet other embodiments (N')y comprises a DNA at position 15 and L-DNA at one or both of positions 17 and 18. In that structure, position 2 may further comprise an L-DNA or an abasic pseudo-nucleotide.

Other embodiments of Structure C are envisaged wherein x=y=21 or wherein x=y=23; in these embodiments the modifications for (N')y discussed above instead of being on positions 15, 16, 17, 18 are on positions 17, 18, 19, 20 for 21 mer and on positions 19, 20, 21, 22 for 23 mer; similarly the modifications at one or both of positions 17 and 18 are on one or both of positions 19 or 20 for the 21 mer and one or both of positions 21 and 22 for the 23 mer. All modifications in the 19 mer are similarly adjusted for the 21 and 23 mers.

According to various embodiments of Structure (C), in (N')y 2, 3, 4, 5, 6, 7, 8, 9, 10, 11, 12, 13 or 14 consecutive ribonucleotides at the 3' terminus are linked by 2'-5' internucleotide linkages In one preferred embodiment, four consecutive nucleotides at the 3' terminus of (N')y are joined by three 2'-5' phosphodiester bonds, wherein one or more of the 2'-5' nucleotides which form the 2'-5' phosphodiester bonds further comprises a 3'-O-methyl sugar modification. Preferably the 3' terminal nucleotide of (N')y comprises a 2'-O-methyl sugar modification. In certain preferred embodiments of Structure C, x=y=19 and in (N')y two or more consecutive nucleotides at positions 15, 16, 17, 18 and 19 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments the nucleotides at positions 17 and 18 in (N')y are joined by a 2'-5' internucleotide bond. In other embodiments the nucleotides at positions 16, 17, 18, 16-17, 17-18, or 16-18 in (N')y are joined by a 2'-5' internucleotide bond.

In certain embodiments (N')y comprises an L-DNA at position 2 and 2'-5' internucleotide bonds at positions 16, 17, 18, 16-17, 17-18, or 16-18. In certain embodiments (N')y comprises 2'-5' internucleotide bonds at positions 16, 17, 18, 16-17, 17-18, or 16-18 and a 5' terminal cap nucleotide.

According to various embodiments of Structure (C), in (N')y 2, 3, 4, 5, 6, 7, 8, 9, 10, 11, 12, 13 or 14 consecutive nucleotides at either terminus or 2-8 modified nucleotides at each of the 5' and 3' termini are independently mirror nucleotides. In some embodiments the mirror nucleotide is an L-ribonucleotide. In other embodiments the mirror nucleotide is an L-deoxyribonucleotide. The mirror nucleotide may further be modified at the sugar or base moiety or in an internucleotide linkage.

In one preferred embodiment of Structure (C), the 3' terminal nucleotide or two or three consecutive nucleotides at the 3' terminus of (N')y are L-deoxyribonucleotides.

In other embodiments of Structure (C), in (N')y 2, 3, 4, 5, 6, 7, 8, 9, 10, 11, 12, 13 or 14 consecutive ribonucleotides at either terminus or 2-8 modified nucleotides at each of the 5' and 3' termini are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe). In one series of preferred embodiments, three, four or five consecutive nucleotides at the 5' terminus of (N')y comprise the 2'-OMe modification. In another preferred embodiment, three consecutive nucleotides at the 3' terminus of (N')y comprise the 2'-O-methyl modification.

In some embodiments of Structure (C), in (N')y 2, 3, 4, 5, 6, 7, 8, 9, 10, 11, 12, 13 or 14 consecutive ribonucleotides at either or 2-8 modified nucleotides at each of the 5' and 3' termini are independently bicyclic nucleotide. In various embodiments the bicyclic nucleotide is a locked nucleic acid (LNA). A 2'-O, 4'-C-ethylene-bridged nucleic acid (ENA) is a species of LNA (see below).

In various embodiments (N')y comprises modified nucleotides at the 5' terminus or at both the 3' and 5' termini.

In some embodiments of Structure (C), at least two nucleotides at either or both the 5' and 3' termini of (N')y are joined by P-ethoxy backbone modifications. In certain preferred embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle position of (N)x being unmodified; and four consecutive nucleotides at the 3' terminus or at the 5' terminus of (N')y are joined by three P-ethoxy backbone modifications. In another preferred embodiment, three consecutive nucleotides at the 3' terminus or at the 5' terminus of (N')y are joined by two P-ethoxy backbone modifications.

In some embodiments of Structure (C), in (N')y 2, 3, 4, 5, 6, 7 or 8, consecutive ribonucleotides at each of the 5' and 3' termini are independently mirror nucleotides, nucleotides joined by 2'-5' phosphodiester bond, 2' sugar modified nucleotides or bicyclic nucleotide. In one embodiment, the modification at the 5' and 3' termini of (N')y is identical. In one preferred embodiment, four consecutive nucleotides at the 5' terminus of (N')y are joined by three 2'-5' phosphodiester bonds and three consecutive nucleotides at the 3' terminus of (N')y are joined by two 2'-5' phosphodiester bonds. In another embodiment, the modification at the 5' terminus of (N')y is different from the modification at the 3' terminus of (N')y. In one specific embodiment, the modified nucleotides at the 5' terminus of (N')y are mirror nucleotides and the modified nucleotides at the 3' terminus of (N')y are joined by 2'-5' phosphodiester bond. In another specific embodiment, three consecutive nucleotides at the 5' terminus of (N')y are LNA nucleotides and three consecutive nucleotides at the 3' terminus of (N')y are joined by two 2'-5' phosphodiester bonds. In (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified, or the ribonucleotides in (N)x being unmodified In another embodiment of Structure (C), the present invention provides a compound wherein x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; three nucleotides at the 3' terminus of (N')y are joined by two 2'-5' phosphodiester bonds and three nucleotides at the 5' terminus of (N')y are LNA such as ENA.

In another embodiment of Structure (C), five consecutive nucleotides at the 5' terminus of (N')y comprise the 2'-O-methyl sugar modification and two consecutive nucleotides at the 3' terminus of (N')y are L-DNA.

In yet another embodiment, the present invention provides a compound wherein x=y=19 or x=y=23; (N)x consists of unmodified ribonucleotides; three consecutive nucleotides at the 3' terminus of (N')y are joined by two 2'-5' phosphodiester bonds and three consecutive nucleotides at the 5' terminus of (N')y are LNA such as ENA.

According to other embodiments of Structure (C), in (N')y the 5' or 3' terminal nucleotide, or 2, 3, 4, 5 or 6 consecutive nucleotides at either termini or 1-4 modified nucleotides at each of the 5' and 3' termini are independently phosphonocarboxylate or phosphinocarboxylate nucleotides (PACE nucleotides). In some embodiments the PACE nucleotides are deoxyribonucleotides. In some preferred embodiments in (N')y, 1 or 2 consecutive nucleotides at each of the 5' and 3' termini are PACE nucleotides. Examples of PACE nucleotides and analogs are disclosed in U.S. Pat. Nos. 6,693,187 and 7,067,641 both incorporated by reference.

In additional embodiments, the present invention provides a compound having Structure (D):

(D)  5' (N)x-Z 3'      antisense strand

3' Z'-(N')y 5'    sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein (N)x comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence having substantial identity to about 18 to about 40 consecutive ribonucleotides in an mRNA transcribed from the RTP801L gene.

In one embodiment of Structure (D), x=y=19 or x=y=23; (N)x comprises unmodified ribonucleotides in which two consecutive nucleotides linked by one 2'-5' internucleotide linkage at the 3' terminus; and (N')y comprises unmodified ribonucleotides in which two consecutive nucleotides linked by one 2'-5' internucleotide linkage at the 5' terminus.

In some embodiments, x=y=19 or x=y=23; (N)x comprises unmodified ribonucleotides in which three consecutive nucleotides at the 3' terminus are joined together by two 2'-5' phosphodiester bonds; and (N')y comprises unmodified ribonucleotides in which four consecutive nucleotides at the 5' terminus are joined together by three 2'-5' phosphodiester bonds (set forth herein as Structure II).

According to various embodiments of Structure (D) 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are linked by 2'-5' internucleotide linkages.

According to one preferred embodiment of Structure (D), four consecutive nucleotides at the 5' terminus of (N')y are joined by three 2'-5' phosphodiester bonds and three consecutive nucleotides at the 3' terminus of (N')x are joined by two 2'-5' phosphodiester bonds. Three nucleotides at the 5' terminus of (N')y and two nucleotides at the 3' terminus of (N')x may also comprise 3'-O-methyl modifications.

According to various embodiments of Structure (D), 2, 3, 4, 5, 6, 7, 8, 9, 10, 11, 12, 13 or 14 consecutive nucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently mirror nucleotides. In some embodiments the mirror is an L-ribonucleotide.

In other embodiments the mirror nucleotide is L-deoxyribonucleotide.

In other embodiments of Structure (D), 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In one preferred embodiment of Structure (D), five consecutive nucleotides at the 5' terminus of (N')y comprise the 2'-O-methyl modification and five consecutive nucleotides at the 3' terminus of (N')x comprise the 2'-O-methyl modification. In another preferred embodiment of Structure (D), ten consecutive nucleotides at the 5' terminus of (N')y comprise the 2'-O-methyl modification and five consecutive nucleotides at the 3' terminus of (N')x comprise the 2'-O-methyl modification. In another preferred embodiment of Structure (D), thirteen consecutive nucleotides at the 5' terminus of (N')y comprise the 2'-O-methyl modification and five consecutive nucleotides at the 3' terminus of (N')x comprise the 2'-O-methyl modification.

In some embodiments of Structure (D), in (N')y 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (D), (N')y comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a phosphodiester bond, a P-alkoxy linkage or a PACE linkage;

In various embodiments of Structure (D), (N)x comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In embodiments wherein each of the 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In one specific embodiment of Structure (D), five consecutive nucleotides at the 5' terminus of (N')y comprise the 2'-O-methyl modification and two consecutive nucleotides at the 3' terminus of (N')y are L-DNA. In addition, the compound may further comprise five consecutive 2'-O-methyl modified nucleotides at the 3' terminus of (N')x.

In various embodiments of Structure (D), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (E):

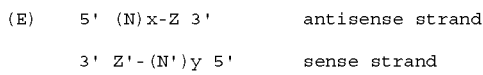

```
(E)    5' (N)x-Z 3'        antisense strand
       3' Z'-(N')y 5'      sense strand
``` wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein (N)x comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein (N')y comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein in each of (N)x and (N')y modified and unmodified nucleotides are not alternating;
wherein each of Z and Z' may be present or absent, but if present is 1-5 deoxyribonucleotides covalently attached at the 3' terminus of any oligomer to which it is attached;
wherein the sequence of (N')$_y$ is a sequence substantially complementary to (N)x; and wherein the sequence of (N)$_x$ comprises an antisense sequence having substantial identity to about 18 to about 40 consecutive ribonucleotides in an mRNA transcribed from the RTP801L gene.

In certain preferred embodiments the ultimate nucleotide at the 5' terminus of (N)x is unmodified.

According to various embodiments of Structure (E) 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are linked by 2'-5' internucleotide linkages.

According to various embodiments of Structure (E), 2, 3, 4, 5, 6, 7, 8, 9, 10, 11, 12, 13 or 14 consecutive nucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive nucleotides starting at the ultimate or penultimate position of the 3' terminus of (N')y are independently mirror nucleotides. In some embodiments the mirror is an L-ribonucleotide. In other embodiments the mirror nucleotide is L-deoxyribonucleotide.

In other embodiments of Structure (E), 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In some embodiments of Structure (E), in (N')y 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (E), (N')y comprises modified nucleotides selected from a bicyclic nucleotide, a 2' sugar modified nucleotide, a mirror nucleotide, an altritol nucleotide, a nucleotide joined to an adjacent nucleotide by a P-alkoxy backbone modification or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In various embodiments of Structure (E), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where both 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (E), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (F):

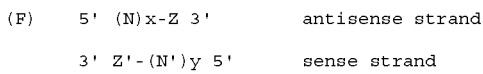

```
(F)    5' (N)x-Z 3'        antisense strand
       3' Z'-(N')y 5'      sense strand
``` wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;

wherein each of (N)x and (N')y comprise unmodified ribonucleotides in which each of (N)x and (N')y independently comprise one modified nucleotide at the 3' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a nucleotide joined to an adjacent nucleotide by a 2'-5' phosphodiester bond;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence having substantial identity to about 18 to about 40 consecutive ribonucleotides in an mRNA transcribed from the RTP801L gene.

In some embodiments of Structure (F), x=y=19 or x=y=23; (N')y comprises unmodified ribonucleotides in which two consecutive nucleotides at the 3' terminus comprises two consecutive mirror deoxyribonucleotides; and (N)x comprises unmodified ribonucleotides in which one nucleotide at the 3' terminus comprises a mirror deoxyribonucleotide (set forth as Structure III).

According to various embodiments of Structure (F) 2, 3, 4, 5, 6, 7, 8, 9, 10, 11, 12, 13 or 14 consecutive ribonucleotides independently beginning at the ultimate or penultimate position of the 3' termini of (N)x and (N')y are linked by 2'-5' internucleotide linkages.

According to one preferred embodiment of Structure (F), three consecutive nucleotides at the 3' terminus of (N')y are joined by two 2'-5' phosphodiester bonds and three consecutive nucleotides at the 3' terminus of (N')x are joined by two 2'-5' phosphodiester bonds.

According to various embodiments of Structure (F), 2, 3, 4, 5, 6, 7, 8, 9, 10, 11, 12, 13 or 14 consecutive nucleotides independently beginning at the ultimate or penultimate position of the 3' termini of (N)x and (N')y are independently mirror nucleotides. In some embodiments the mirror nucleotide is an L-ribonucleotide. In other embodiments the mirror nucleotide is an L-deoxyribonucleotide.

In other embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In some embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (F), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at both the 3' and 5' termini.

In various embodiments of Structure (F), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (F), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (G):

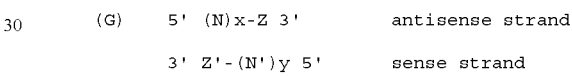

wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein each of (N)x and (N')y comprise unmodified ribonucleotides in which each of (N)x and (N')y independently comprise one modified nucleotide at the 5' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a nucleotide joined to an adjacent nucleotide by a 2'-5' phosphodiester bond;

wherein for (N)x the modified nucleotide is preferably at penultimate position of the 5' terminal;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence having substantial identity to about 18 to about 40 consecutive ribonucleotides in an mRNA transcribed from the RTP801L gene.

In some embodiments of Structure (G), x=y=19 or x=y=23.

According to various embodiments of Structure (G) 2, 3, 4, 5, 6, 7, 8, 9, 10, 11, 12, 13 or 14 consecutive ribonucleotides independently beginning at the ultimate or penultimate position of the 5' termini of (N)x and (N')y are linked by 2'-5' internucleotide linkages. For (N)x the modified nucleotides preferably starting at the penultimate position of the 5' terminal.

According to various embodiments of Structure (G), 2, 3, 4, 5, 6, 7, 8, 9, 10, 11, 12, 13 or 14 consecutive nucleotides independently beginning at the ultimate or penultimate position of the 5' termini of (N)x and (N')y are independently mirror nucleotides. In some embodiments the mirror nucleotide is an L-ribonucleotide. In other embodiments the mirror nucleotide is an L-deoxyribonucleotide. For (N)x the modified nucleotides preferably starting at the penultimate position of the 5' terminal.

In other embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe). In some preferred embodiments the consecutive modified nucleotides preferably begin at the penultimate position of the 5' terminus of (N)x.

In one preferred embodiment of Structure (G), five consecutive ribonucleotides at the 5' terminus of (N')y comprise a 2'-O-methyl modification and one ribonucleotide at the 5' penultimate position of (N')x comprises a 2'-O-methyl modification. In another preferred embodiment of Structure (G), five consecutive ribonucleotides at the 5' terminus of (N')y comprise a 2'-O-methyl modification and two consecutive ribonucleotides at the 5' terminal position of (N')x comprise a 2'-O-methyl modification.

In some embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are bicyclic nucleotides. In various embodiments the bicyclic nucleotide is a locked nucleic acid (LNA) such as a 2'-O, 4'-C-ethylene-bridged nucleic acid (ENA). In some preferred embodiments the consecutive modified nucleotides preferably begin at the penultimate position of the 5' terminus of (N)x.

In various embodiments of Structure (G), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In various embodiments of Structure (G), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond. In various embodiments of Structure (G), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (H):

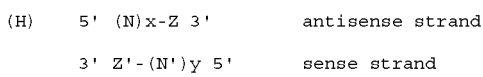

(H)  5' (N)x-Z 3'       antisense strand
     3' Z'-(N')y 5'     sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein (N)x comprises unmodified ribonucleotides further comprising one modified nucleotide at the 3' terminal or penultimate position or the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at an internal position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence having substantial identity to about 18 to about 40 consecutive ribonucleotides in an mRNA transcribed from the RTP801L gene.

In one embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or both termini of (N)x are independently 2' sugar modified nucleotides, bicyclic nucleotides, mirror nucleotides, altritol nucleotides or nucleotides joined to an adjacent nucleotide by a 2'-5' phosphodiester bond and 2, 3, 4, 5, 6, 7, 8, 9, 10, 11, 12, 13 or 14 consecutive internal ribonucleotides in (N')y are independently 2' sugar modified nucleotides, bicyclic nucleotides, mirror nucleotides, altritol nucleotides or nucleotides joined to an adjacent nucleotide by a 2'-5' phosphodiester bond. In some embodiments the 2' sugar modification comprises the presence of an amino, a fluoro, an alkoxy or an alkyl moiety. In certain embodiments the 2' sugar modification comprises a methoxy moiety (2'-OMe).

In another embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or 2-8 consecutive nucleotides at each of 5' and 3' termini of (N')y are independently 2' sugar modified nucleotides, bicyclic nucleotides, mirror nucleotides, altritol nucleotides or nucleotides joined to an adjacent nucleotide by a 2'-5' phosphodiester bond, and 2, 3, 4, 5, 6, 7, 8, 9, 10, 11, 12, 13 or 14 consecutive internal ribonucleotides in (N)x are independently 2' sugar modified nucleotides, bicyclic nucleotides, mirror nucleotides, altritol nucleotides or nucleotides joined to an adjacent nucleotide by a 2'-5' phosphodiester bond.

In one embodiment wherein each of 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (H), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In one preferred embodiment of Structure (H), x=y=19; three consecutive ribonucleotides at the 9-11 nucleotide positions 9-11 of (N')y comprise 2'-O-methyl modification and five consecutive ribonucleotides at the 3' terminal position of (N')x comprise 2'-O-methyl modification.

For all the above Structures (A)-(H), in various embodiments x=y and each of x and y is 19, 20, 21, 22 or 23. In certain embodiments, x=y=19. In yet other embodiments x=y=23. In additional embodiments the compound comprises modified ribonucleotides in alternating positions wherein each N at the 5' and 3' termini of (N)x are modified in their sugar residues and the middle ribonucleotide is not modified, e.g. ribonucleotide in position 10 in a 19-mer strand, position 11 in a 21 mer and position 12 in a 23-mer strand.

In some embodiments where x=y=21 or x=y=23 the position of modifications in the 19 mer are adjusted for the 21 and 23 mers with the proviso that the middle nucleotide of the antisense strand is preferably not modified.

In some embodiments, neither (N)x nor (N')y are phosphorylated at the 3' and 5' termini. In other embodiments either or both (N)x and (N')y are phosphorylated at the 3' termini. In yet another embodiment, either or both (N)x and (N')y are phosphorylated at the 3' termini using non-cleavable phosphate groups. In yet another embodiment, either or both (N)x and (N')y are phosphorylated at the terminal 2' termini position using cleavable or non-cleavable phosphate groups. These particular siRNA compounds are also blunt ended and are non-phosphorylated at the termini; however, comparative experiments have shown that siRNA compounds phosphorylated at one or both of the 3'-termini have similar activity in vivo compared to the non-phosphorylated compounds.

In certain embodiments for all the above-mentioned Structures, the compound is blunt ended, for example wherein both Z and Z' are absent. In an alternative embodiment, the compound comprises at least one 3' overhang, wherein at least one of Z or Z' is present. Z and Z' independently comprises one or more covalently linked modified or non-modified nucleotides, for example inverted dT or dA; dT, LNA, mirror nucleotide and the like. In some embodiments each of Z and Z' are independently selected from dT and dTdT. siRNA in which Z and/or Z' is present have similar activity and stability as siRNA in which Z and Z' are absent.

In certain embodiments for all the above-mentioned Structures, the compound comprises one or more phosphonocarboxylate and/or phosphinocarboxylate nucleotides (PACE nucleotides). In some embodiments the PACE nucleotides are deoxyribonucleotides and the phosphinocarboxylate nucleotides are phosphinoacetate nucleotides. Examples of PACE nucleotides and analogs are disclosed in U.S. Pat. Nos. 6,693,187 and 7,067,641, both incorporated herein by reference.

In certain embodiments for all the above-mentioned Structures, the compound comprises one or more locked nucleic acids (LNA) also defined as bridged nucleic acids or bicyclic nucleotides. Preferred locked nucleic acids are 2'-O, 4'-C-ethylene nucleosides (ENA) or 2'-O, 4'-C-methylene nucleosides. Other examples of LNA and ENA nucleotides are disclosed in WO 98/39352, WO 00/47599 and WO 99/14226, all incorporated herein by reference.

In certain embodiments for all the above-mentioned Structures, the compound comprises one or more altritol monomers (nucleotides), also defined as 1,5 anhydro-2-deoxy-D-altrito-hexitol (see for example, Allan, et al., 1998. Nucleosides & Nucleotides 17:1523-1526; Herdewijn et al., 1999. Nucleosides & Nucleotides 18:1371-1376; Fisher et al., 2007, NAR 35(4):1064-1074; all incorporated herein by reference).

The present invention explicitly excludes compounds in which each of N and/or N' is a deoxyribonucleotide (D-A, D-C, D-G, D-T). In certain embodiments (N)x and (N')y may comprise independently 1, 2, 3, 4, 5, 6, 7, 8, 9 or more deoxyribonucleotides. In certain embodiments the present invention provides a compound wherein each of N is an unmodified ribonucleotide and the 3' terminal nucleotide or 2, 3, 4, 5, 6, 7, 8, 9, 10, 11, 12, 13 or 14 consecutive nucleotides at the 3' terminus of (N')y are deoxyribonucleotides. In yet other embodiments each of N is an unmodified ribonucleotide and the 5' terminal nucleotide or 2, 3, 4, 5, 6, 7, 8, 9, 10, 11, 12, 13 or 14 consecutive nucleotides at the 5' terminus of (N')y are deoxyribonucleotides. In further embodiments the 5' terminal nucleotide or 2, 3, 4, 5, 6, 7, 8, or 9 consecutive nucleotides at the 5' terminus and 1, 2, 3, 4, 5, or 6 consecutive nucleotides at the 3' termini of (N)x are deoxyribonucleotides and each of N' is an unmodified ribonucleotide. In yet further embodiments (N)x comprises unmodified ribonucleotides and 1 or 2, 3 or 4 consecutive deoxyribonucleotides independently at each of the 5' and 3' termini and 1 or 2, 3, 4, 5 or 6 consecutive deoxyribonucleotides in internal positions; and each of N' is an unmodified ribonucleotide. In certain embodiments the 3' terminal nucleotide or 2, 3, 4, 5, 6, 7, 8, 9, 10, 11, 12 13 or 14 consecutive nucleotides at the 3' terminus of (N')y and the terminal 5' nucleotide or 2, 3, 4, 5, 6, 7, 8, 9, 10, 11, 12 13 or 14 consecutive nucleotides at the 5' terminus of (N)x are deoxyribonucleotides. The present invention excludes compounds in which each of N and/or N' is a deoxyribonucleotide. In some embodiments the 5' terminal nucleotide of N or 2 or 3 consecutive of N and 1,2, or 3 of N' is a deoxyribonucleotide. Certain examples of active DNA/RNA siRNA chimeras are disclosed in US patent publication 2005/0004064, and Ui-Tei, 2008 (NAR 36(7):2136-2151) incorporated herein by reference in their entirety.

Unless otherwise indicated, in preferred embodiments of the structures discussed herein the covalent bond between each consecutive N or N' is a phosphodiester bond.

An additional novel molecule provided by the present invention is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker.

Thus, one molecule provided by the present invention is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove. This molecule forms a "star"-like structure, and may also be referred to herein as RNAstar. Such structures are disclosed in PCT patent publication WO 2007/091269, assigned to the assignee of the present invention and incorporated herein in its entirety by reference.

A covalent bond refers to an internucleotide linkage linking one nucleotide monomer to an adjacent nucleotide monomer. A covalent bond includes for example, a phosphodiester bond, a phosphorothioate bond, a P-alkoxy bond, a P-carboxy bond and the like. The normal internucleoside linkage of RNA and DNA is a 3' to 5' phosphodiester linkage. In certain preferred embodiments a covalent bond is a phosphodiester bond. Covalent bond encompasses non-phosphorous-containing internucleoside linkages, such as those disclosed in WO 2004/041924 inter alia. Unless otherwise indicated, in preferred embodiments of the structures discussed herein the covalent bond between each consecutive N or N' is a phosphodiester bond.

For all of the structures above, in some embodiments the oligonucleotide sequence of (N)x is fully complementary to the oligonucleotide sequence of (N')y. In other embodiments (N)x and (N')y are substantially complementary. In certain embodiments (N)x is fully complementary to a target sequence. In other embodiments (N)x is substantially complementary to a target sequence.

In some embodiments, neither (N)x nor (N')y are phosphorylated at the 3' and 5' termini. In other embodiments either or both (N)x and (N')y are phosphorylated at the 3' termini (3' Pi). In yet another embodiment, either or both (N)x and (N')y are phosphorylated at the 3' termini with non-cleavable phosphate groups. In yet another embodiment, either or both (N)x and (N')y are phosphorylated at the terminal 2' termini position using cleavable or non-cleavable phosphate groups. Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks.

In one aspect the present invention provides a compound having Structure (I) set forth below:

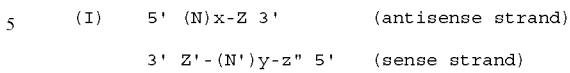

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent, but if present is a capping moiety covalently attached at the 5' terminus of (N') y;
wherein x=18 to 27;
wherein y=18 to 27;
wherein (N)x comprises modified and unmodified ribonucleotides, each modified ribonucleotide having a 2'-O-methyl on its sugar, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide;
wherein in (N')y at least one unconventional moiety is present, which unconventional moiety may be an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond; and
wherein the sequence of (N)x is substantially complementary to the sequence of (N')y; and the sequence of (N')y is substantially identical to the sequence of an mRNA encoded by the RTP801L gene.

In some embodiments x=y=19. In other embodiments x=y=23. In some embodiments the at least one unconventional moiety is present at positions 15, 16, 17, or 18 in (N')y. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18.

In other embodiments the unconventional moiety is an abasic moiety. In various embodiments (N')y comprises at least five abasic ribose moieties or abasic deoxyribose moieties.

In yet other embodiments (N')y comprises at least five abasic ribose moieties or abasic deoxyribose moieties and at least one of N' is an LNA.

In some embodiments of Structure (IX) (N)x comprises nine alternating modified ribonucleotides. In other embodiments of Structure (I) (N)x comprises nine alternating modified ribonucleotides further comprising a 2'O modified nucleotide at position 2. In some embodiments (N)x comprises 2'O Me modified ribonucleotides at the odd numbered positions 1, 3, 5, 7, 9, 11, 13, 15, 17, 19. In other embodiments (N)x further comprises a 2'O Me modified ribonucleotide at one or both of positions 2 and 18. In yet other embodiments (N)x comprises 2'O Me modified ribonucleotides at positions 2, 4, 6, 8, 11, 13, 15, 17, 19.

In various embodiments z" is present and is selected from an abasic ribose moiety, a deoxyribose moiety; an inverted abasic ribose moiety, a deoxyribose moiety; C6-amino-Pi; a mirror nucleotide.

In another aspect the present invention provides a compound having Structure (J) set forth below:

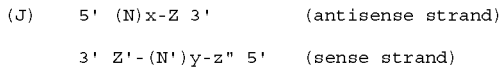

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent but if present is a capping moiety covalently attached at the 5' terminus of (N')y;
wherein x=18 to 27;
wherein y=18 to 27;
wherein (N)x comprises modified or unmodified ribonucleotides, and optionally at least one unconventional moiety;
wherein in (N')y at least one unconventional moiety is present, which unconventional moiety may be an abasic ribose moiety, an abasic deoxyribose moiety, a modified or unmodified deoxyribonucleotide, a mirror nucleotide, a non-base pairing nucleotide analog or a nucleotide joined to an adjacent nucleotide by a 2'-5' internucleotide phosphate bond; and
wherein the sequence of (N)x is substantially complementary to the sequence of (N')y; and the sequence of (N')y is substantially identical to the sequence of an mRNA encoded by the RTP801L gene.

In some embodiments x=y=19. In other embodiments x=y=23. In some preferred embodiments (N)x comprises modified and unmodified ribonucleotides, and at least one unconventional moiety.

In some embodiments in (N)x the N at the 3' terminus is a modified ribonucleotide and (N)x comprises at least 8 modified ribonucleotides. In other embodiments at least 5 of the at least 8 modified ribonucleotides are alternating beginning at the 3' end. In some embodiments (N)x comprises an abasic moiety in one of positions 5, 6, 7, 8, 9, 10, 11, 12, 13, 14 or 15.

In some embodiments the at least one unconventional moiety in (N')y is present at positions 15, 16, 17, or 18. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18. In other embodiments the at least one unconventional moiety in (N')y is an abasic ribose moiety or an abasic deoxyribose moiety.

In various embodiments of Structure (X) z" is present and is selected from an abasic ribose moiety, a deoxyribose moiety; an inverted abasic ribose moiety, a deoxyribose moiety; C6-amino-Pi; a mirror nucleotide.

In yet another aspect the present invention provides a compound having Structure (K) set forth below:

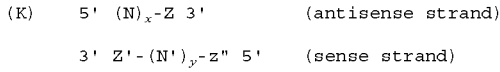

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent but if present is a capping moiety covalently attached at the 5' terminus of (N')y;
wherein x=18 to 27;
wherein y=18 to 27;
wherein (N)x comprises a combination of modified or unmodified ribonucleotides and unconventional moieties, any modified ribonucleotide having a 2'-O-methyl on its sugar;
wherein (N')y comprises modified or unmodified ribonucleotides and optionally an unconventional moiety, any modified ribonucleotide having a 2'OMe on its sugar;
wherein the sequence of (N)x is substantially complementary to the sequence of (N')y; and the sequence of (N')y is substantially identical to the sequence of an mRNA encoded by the RTP801L gene; and wherein there are less than 15 consecutive nucleotides complementary to the mRNA.

In some embodiments x=y=19. In other embodiments x=y=23. In some preferred embodiments the at least one preferred one unconventional moiety is present in (N)x and is an abasic ribose moiety or an abasic deoxyribose moiety. In other embodiments the at least one unconventional moiety is present in (N)x and is a non-base pairing nucleotide analog. In various embodiments (N')y comprises unmodified ribonucleotides. In some embodiments (N)x comprises at least five abasic ribose moieties or abasic deoxyribose moieties or a combination thereof. In certain embodiments (N)x and/or (N')y comprise modified ribonucleotides which do not base pair with corresponding modified or unmodified ribonucleotides in (N')y and/or (N)x.

In various embodiments the present invention provides an siRNA set forth in Structure (L):

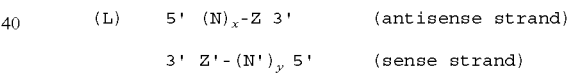

wherein each of N and N' is a nucleotide selected from an unmodified ribonucleotide, a modified ribonucleotide, an unmodified deoxyribonucleotide and a modified deoxyribonucleotide;
wherein each of (N)$_x$ and (N')$_y$ is an oligonucleotide in which each consecutive N or N' is joined to the next N or N' by a covalent bond;
wherein Z and Z' are absent;
wherein x=y=19;
wherein in (N')y the nucleotide in at least one of positions 15, 16, 17, 18 and 19 comprises a nucleotide selected from an abasic pseudo-nucleotide, a mirror nucleotide, a deoxyribonucleotide and a nucleotide joined to an adjacent nucleotide by a 2'-5' internucleotide bond;
wherein (N)x comprises alternating modified ribonucleotides and unmodified ribonucleotides each modified ribonucleotide being modified so as to have a 2'-O-methyl on its sugar and the ribonucleotide located at the middle position of (N)x being modified or unmodified, preferably unmodified; and
wherein the sequence of (N)x is substantially complementary to the sequence of (N')y; and the sequence of (N')y is substantially identical to the mRNA of the RTP801L gene.

In some embodiments of Structure (L), in (N')y the nucleotide in one or both of positions 17 and 18 comprises a modified nucleotide selected from an abasic pseudo-nucleotide, a mirror nucleotide and a nucleotide joined to an adjacent nucleotide by a 2'-5' internucleotide bond. In some embodiments the mirror nucleotide is selected from L-DNA and L-RNA. In various embodiments the mirror nucleotide is L-DNA.

In various embodiments (N')y comprises a modified nucleotide at position 15 wherein the modified nucleotide is selected from a mirror nucleotide and a deoxyribonucleotide.

In certain embodiments (N')y further comprises a modified nucleotide or pseudo nucleotide at position 2 wherein the pseudo nucleotide may be an abasic pseudo-nucleotide analog and the modified nucleotide is optionally a mirror nucleotide.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments (N)x further comprises 2'O-Me modified ribonucleotides at one or both positions 2 and 18. In other embodiments (N)x comprises 2'O Me modified ribonucleotides at positions 2, 4, 6, 8, 11, 13, 15, 17, 19.

Other embodiments of Structures (L), (I) and (J) are envisaged wherein x=y=21 or wherein x=y=23; in these embodiments the modifications for (N')y discussed above instead of being in positions 17 and 18 are in positions 19 and 20 for 21-mer oligonucleotide and 21 and 22 for 23 mer oligonucleotide; similarly the modifications in positions 15, 16, 17, 18 or 19 are in positions 17, 18, 19, 20 or 21 for the 21-mer oligonucleotide and positions 19, 20, 21, 22, or 23 for the 23-mer oligonucleotide. The 2'O Me modifications on the antisense strand are similarly adjusted. In some embodiments (N)x comprises 2'O Me modified ribonucleotides at the odd numbered positions (5' to 3'; positions 1, 3, 5, 7, 9, 12, 14, 16, 18, 20 for the 21 mer oligonucleotide [nucleotide at position 11 unmodified] and 1, 3, 5, 7, 9, 11, 13, 15, 17, 19, 21, 23 for the 23 mer oligonucleotide [nucleotide at position 12 unmodified]. In other embodiments (N)x comprises 2'O Me modified ribonucleotides at positions 2, 4, 6, 8, 10, 12, 14, 16, 18, 20 [nucleotide at position 11 unmodified for the 21 mer oligonucleotide and at positions 2, 4, 6, 8, 10, 13, 15, 17, 19, 21, 23 for the 23 mer oligonucleotide [nucleotide at position 12 unmodified].

In some embodiments (N')y further comprises a 5' terminal cap nucleotide. In various embodiments the terminal cap moiety is selected from an abasic pseudo-nucleotide analog, an inverted abasic pseudo-nucleotide analog, an L-DNA nucleotide, and a C6-imine phosphate (C6 amino linker with phosphate at terminus).

In other embodiments the present invention provides a compound having Structure (M) set forth below:

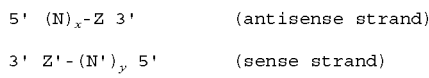

wherein each of N and N' is selected from a pseudo-nucleotide and a nucleotide;
wherein each nucleotide is selected from an unmodified ribonucleotide, a modified ribonucleotide, an unmodified deoxyribonucleotide and a modified deoxyribonucleotide;
wherein each of (N)x and (N')y is an oligonucleotide in which each consecutive N or N' is joined to the next N or N' by a covalent bond;
wherein Z and Z' are absent;
wherein x=18 to 27;
wherein y=18 to 27;
wherein the sequence of (N)x is substantially complementary to the sequence of (N')y; and the sequence of (N')y is substantially identical to an mRNA of the RTP801L gene;
wherein at least one of N is selected from an abasic pseudo nucleotide, a non-pairing nucleotide analog and a nucleotide mismatch to the mRNA of the RTP801L gene in a position of (N)x such that (N)x comprises less than 15 consecutive nucleotides complementary to the mRNA of the RTP801L gene.

In other embodiments the present invention provides a double stranded compound having Structure (N) set forth below:

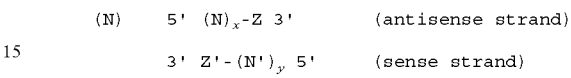

wherein each of N and N' is a nucleotide selected from an unmodified ribonucleotide, a modified ribonucleotide, an unmodified deoxyribonucleotide and a modified deoxyribonucleotide;
wherein each of (N)x and (N')y is an oligonucleotide in which each consecutive N or N' is joined to the next N or N' by a covalent bond;
wherein Z and Z' are absent;
wherein each of x and y is an integer between 18 and 40;
wherein the sequence of (N)x is substantially complementary to the sequence of (N')y; and the sequence of (N')y is substantially identical to an mRNA of the RTP801L gene;
wherein (N)x, (N')y or (N)x and (N')y comprise non base-pairing modified nucleotides such that (N)x and (N')y form less than 15 base pairs in the double stranded compound.

In other embodiments the present invention provides a compound having Structure (O) set forth below:

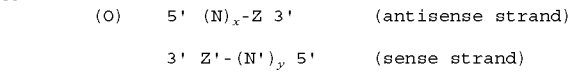

wherein each of N is a nucleotide selected from an unmodified ribonucleotide, a modified ribonucleotide, an unmodified deoxyribonucleotide and a modified deoxyribonucleotide;
wherein each of N' is a nucleotide analog selected from a six membered sugar nucleotide, seven membered sugar nucleotide, morpholino moiety, peptide nucleic acid and combinations thereof;
wherein each of (N)x and (N')y is an oligonucleotide in which each consecutive N or N' is joined to the next N or N' by a covalent bond;
wherein Z and Z" are absent;
wherein each of x and y is an integer between 18 and 40;
wherein the sequence of (N)x is substantially complementary to the sequence of (N')y; and the sequence of (N')y is substantially identical to an mRNA of the RTP801L gene.

In other embodiments the present invention provides a compound having Structure (P) set forth below:

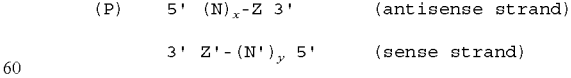

wherein each of N and N' is a nucleotide selected from an unmodified ribonucleotide, a modified ribonucleotide, an unmodified deoxyribonucleotide and a modified deoxyribonucleotide;
wherein each of (N)x and (N')y is an oligonucleotide in which each consecutive N or N' is joined to the next N or N' by a covalent bond;

wherein Z and Z' are absent;
wherein each of x and y is an integer between 18 and 40;
wherein one of N or N' in an internal position of (N)x or (N')y or one or more of N or N' at a terminal position of (N)x or (N')y comprises an abasic moiety or a 2' modified nucleotide; wherein the sequence of (N)x is substantially complementary to the sequence of (N')y; and the sequence of (N')y is substantially identical to an mRNA of the RTP801L gene.

In various embodiments (N')y comprises a modified nucleotide at position 15 wherein the modified nucleotide is selected from a mirror nucleotide and a deoxyribonucleotide.

In certain embodiments (N')y further comprises a modified nucleotide at position 2 wherein the modified nucleotide is selected from a mirror nucleotide and an abasic pseudonucleotide analog.

In various embodiments the antisense strand (N)x comprises 2'O-Me modified ribonucleotides at the odd numbered positions (5' to 3'; positions 1, 3, 5, 7, 9, 11, 13, 15, 17, 19), In some embodiments $(N)_x$ further comprises 2'O-Me modified ribonucleotides at one or both positions 2 and 18. In other embodiments (N)x comprises 2'O Me modified ribonucleotides at positions 2, 4, 6, 8, 11, 13, 15, 17, 19.

The Structural motifs described above are useful with any oligonucleotide pair (sense and antisense strands) to a mammalian RTP801L gene, and preferably to the human RTP801L gene.

Any siRNA sequence disclosed herein can be prepared having any of the modifications/structures disclosed herein.

In another aspect the present invention provides a pharmaceutical composition comprising a modified or unmodified compound of the present invention, in an amount effective to inhibit human RTP801L gene expression wherein the compound comprises an antisense sequence, $(N)_x$; and a pharmaceutically acceptable carrier.

In yet another aspect the present invention provides a pharmaceutical composition comprising one or more modified compounds of the present invention, in an amount effective to inhibit human RTP801L gene expression wherein the compound comprises an antisense sequence, $(N)_x$; and a pharmaceutically acceptable carrier.

In another aspect, the present invention relates to a method for the treatment of a subject in need of treatment for a disease or disorder or symptoms associated with the disease or disorder, associated with the expression of the RTP801L gene comprising administering to the subject an amount of an siRNA, according to the present invention, in a therapeutically effective dose so as to thereby treat the subject.

The methods of the invention comprise administering to the subject one or more siRNA compounds which inhibit expression of the RTP801L gene. The novel structures disclosed herein, when integrated into antisense and corresponding sense nucleic acid sequences, provide siRNA compounds useful in reducing expression of the RTP801L gene.

Pharmaceutical Compositions

The present invention provides a pharmaceutical composition comprising one or more of the compounds of the invention; and a pharmaceutically acceptable carrier. Such compositions may comprise a mixture of two or more different oligonucleotides/siRNAs.

The invention further provides a pharmaceutical composition comprising at least one compound of the invention covalently or non-covalently bound to one or more compounds of the invention in an amount effective to inhibit RTP801L; and a pharmaceutically acceptable carrier. Endogenous cellular complexes to produce one or more oligoribonucleotides of the invention may process the compound intracellularly.

The present invention also provides for a process of preparing a pharmaceutical composition, which comprises:
providing one or more siRNA compounds of the invention; and
admixing said compound with a pharmaceutically acceptable carrier.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

Additionally, the invention provides a method of inhibiting the expression of the genes of the present invention by at least 50% as compared to a control comprising contacting an mRNA transcript of the gene of the present invention with one or more of the compounds of the invention.

In one embodiment the oligoribonucleotide is inhibiting the RTP801L gene, whereby the inhibition is selected from the group comprising inhibition of gene function, inhibition of polypeptide and inhibition of mRNA expression.

In one embodiment the compound is inhibiting expression of a polypeptide, whereby the inhibition is selected from the group comprising inhibition of function (which may be examined by an enzymatic assay or a binding assay with a known interactor of the native gene/polypeptide, inter alia), inhibition of protein (which may be examined by Western blotting, ELISA or immuno-precipitation, inter alia) and inhibition of mRNA expression (which may be examined by Northern blotting, quantitative RT-PCR, in-situ hybridisation or microarray hybridisation, inter alia).

In additional embodiments the invention provides a method of treating a subject suffering from a disease accompanied by an elevated level of the RTP801L gene/polypeptide, the method comprising administering to the subject a compound of the invention in a therapeutically effective dose thereby treating the subject.

More particularly, the invention provides a chemically modified double stranded oligoribonucleotide wherein one strand comprises consecutive nucleotides having, from 5' to 3', the sequence set forth in any one of Tables A-G or a homolog thereof wherein in up to two of the ribonucleotides in each terminal region is altered.

Additionally, further nucleic acids according to the present invention comprise at least 14 contiguous nucleotides of any one of the oligomers set forth in any one of Tables A-G and more preferably 14 contiguous nucleotide base pairs at any end of the double-stranded structure comprised of the first strand and second strand as described above.

Delivery

The siRNA molecules of the present invention may be delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

However, in some embodiments the siRNA molecules of the invention are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003. 327: 761-766; Lewis et al., Nat. Gen. 2002, 32: 107-108 and Simeoni et al., *NAR* 2003, 31, 11:2717-2724).

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations may be selected. The siRNAs or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer.

The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal, inhalation, transtympanic administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In a particular embodiment, the administration comprises intravenous administration. In another embodiment the administration comprises topical or local administration.

In addition, in certain embodiments the compositions for use in the novel treatments of the present invention may be formed as aerosols, for example for intranasal administration.

In certain embodiments, oral compositions (such as tablets, suspensions, solutions) may be effective for local delivery to the oral cavity such as oral composition suitable for mouthwash for the treatment of oral mucositis.

The compounds of the present invention can be administered topically to the surface of the eye. It should be noted that the compound is preferably administered as the compound or as pharmaceutically acceptable salt active ingredient in combination with pharmaceutically acceptable carriers, solvents, diluents, excipients, adjuvants and or vehicles. According to the present invention the preferred method of delivery is topical administration for topical delivery to the eye.

Liquid forms are prepared for drops or spray. The liquid compositions include aqueous solutions, with and without organic co-solvents, aqueous or oil suspensions, emulsions with oils, as well as similar pharmaceutical vehicles. In some embodiments administration comprises topical or local administration.

These compounds are administered to humans and other animals for therapy by any suitable route of administration to the eye, as by, for example, a spray or drops, and topically, as by ointments, suspensions or drops.

In preferred embodiments the subject being treated is a warm-blooded animal and, in particular, mammals including human.

Methods of Treatment

In one aspect, the present invention relates to a method for the treatment of a subject in need of treatment for a disease or disorder associated with expression of the RTP801L gene, comprising administering to the subject an amount of at least one chemically modified siRNA which inhibits expression of RTP801L. In certain preferred embodiments more than one siRNA compound is administered.

In preferred embodiments the subject being treated is a warm-blooded animal and, in particular, mammals including human.

The methods of the invention comprise administering to the subject one or more RTP801L siRNA compounds which down-regulate expression of the RTP801L gene; and in particular east one siRNA in a therapeutically effective dose so as to thereby treat the subject.

The term "treatment" refers to both therapeutic treatment and prophylactic or preventative measures, wherein the object is to prevent or slow down, attenuate the related disorder as listed above. Those in need of treatment include those already experiencing the disease or condition, those prone to having the disease or condition, and those in which the disease or condition is to be prevented. The compounds of the invention may be administered before, during or subsequent to the onset of the disease or condition or symptoms associated therewith. In cases where treatment is for the purpose of prevention, then the present invention relates to a method for delaying the onset of or averting the development of the disease or disorder.

In general, the method includes administering oligoribonucleotides, such as small interfering RNAs (i.e., siRNAs) that are targeted to a particular mRNA and hybridize to it, or nucleic acid material that can produce siRNAs in a cell, in an amount sufficient to down-regulate expression of a target gene by an RNA interference mechanism. In particular, the subject method can be used to inhibit expression of the RTP801L gene for treatment of respiratory disorders, microvascular disorders, eye disorders and hearing impairments.

Thus, in one embodiment the present invention provides for a method of treating a patient suffering from a microvascular disorder, an eye disease a respiratory disorder, a hearing disorder or a spinal cord injury or other wound, comprising administering to the patient a pharmaceutical composition comprising an RTP801L inhibitor in a therapeutically effective amount so as to thereby treat the patient. The invention further provides a method of treating a patient suffering from a microvascular disorder, an eye disease, a respiratory disorder, a hearing disorder or a spinal cord injury or other wound, or an ischemic disease, comprising administering to the patient a pharmaceutical composition comprising an RTP801L inhibitor, in a dosage and over a period of time sufficient to promote recovery. The eye disease may be macular degeneration such as age-related macular degeneration (AMD), or glaucoma, inter alia. The microvascular disorder may be diabetic retinopathy or acute renal failure, inter alia. The respiratory disorder may be chronic obstructive pulmonary disease (COPD), acute lung injury (ALI), Acute Respiratory Distress Syndrome (ARDS), Lung transplantation, emphysema, chronic bronchitis, asthma and lung cancer, inter alia. The hearing disorder may be trauma-induced deafness, age-related deafness or cisplatin-induced deafness, inter alia. Thus, a list of conditions to be treated includes ARF, hearing loss, Acute Respiratory Distress Syndrome, Glaucoma, AMD, COPD, nephrotoxicity, lung transplantation, and Ischemia/reperfusion injury. Oligonucleotide sequences of RTP801L siRNA inhibitors are set forth below and in any one of Tables A-G (SEQ ID NOs:2-6927).

The present invention further relates to the use of any of the compounds disclosed herein, particularly to novel small interfering RNAs (siRNAs), in the treatment of diseases and disorders associated with RTP801L expression.

A further end modification is a biotin group. Such biotin group may preferably be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned end modifications.

The various end modifications as disclosed herein are preferably located at the ribose moiety of a nucleotide of the nucleic acid according to the present invention. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasic or abasic are nucleotides, either deoxyribonucleotides or ribonucleotides which do not have a nucleobase moiety. This kind of compound is, inter alia, described in Sternberger, M., et al., (2002. *Antisense Nucleic Acid Drug Dev,* 12, 131-43).

A further form of nucleotides used may be siNA which is, among others, described in international patent application WO 03/070918.

It is to be understood that, in the context of the present invention, any of the siRNA molecules disclosed herein, or any long double-stranded RNA molecules (typically 25-500 nucleotides in length) which are processed by endogenous cellular complexes (such as DICER—see above) to form the siRNA molecules disclosed herein, or molecules which comprise the siRNA molecules disclosed herein, can be incorporated into the molecules of the present invention to form additional novel molecules, and can employed in the treatment of the diseases or disorders described herein.

In particular, it is envisaged that a long oligonucleotide (typically about 80-500 nucleotides in length) comprising one or more stem and loop structures, where stem regions comprise the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence. Any molecules, such as, for example, antisense DNA molecules which comprise the inhibitory sequences disclosed herein (with the appropriate nucleic acid modifications) are particularly desirable and may be used in the same capacity as their corresponding RNAs/siRNAs for all uses and methods disclosed herein.

In addition, analogs of polynucleotides can be prepared wherein the structure of the nucleotide is fundamentally altered and that are better suited as therapeutic or experimental reagents. An example of a nucleotide analog is a peptide nucleic acid (PNA) wherein the deoxyribose (or ribose) phosphate backbone in DNA (or RNA is replaced with a polyamide backbone which is similar to that found in peptides. PNA analogs have been shown to be resistant to degradation by enzymes and to extend lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones.

In a particularly preferred embodiment the compounds of the present invention possess a sequence present in Table F (SEQ ID NOS: 6896-6927). In other preferred embodiments the RTP801L compound is selected from any one of the compounds set forth in Table G.

In one preferred embodiment the siRNA used in the methods of the present invention is one of a pair of oligonucleotides set forth in Table F. In another preferred embodiment the siRNA compound is selected from a compound set forth in Table G.

Thus, in a particularly preferred embodiment, the present invention comprises a compound having an oligonucleotide sequence and chemical modifications as shown in FIG. 8. In some preferred embodiments the compound is ID 128339 x=y=19; wherein (N)x comprises alternating unmodified and 2'OMe sugar modified ribonucleotides and wherein (N')y comprises unmodified ribonucleotides and an L-deoxyribonucleotide at position 18 and an optional deoxyribonucleotide at position 15. siRNA compound 128339 exhibits good activity (knockdown of about 75% at 20 nM) in human cells and stability in human serum.

And a compound having the structure

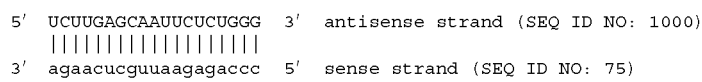

wherein in (N)x the ribonucleotides alternate between modified ribonucleotides and unmodified ribonucleotides each modified ribonucleotide being modified so as to have a 2'-O-methyl on its sugar and the ribonucleotide located at the middle position being unmodified;

wherein in (N')y the nucleotide at position 18 or 17 and 18 is a mirror nucleotide and the nucleotide at position 15 is optionally an unmodified ribonucleotide or a deoxyribonucleotide; and wherein the antisense and the sense strands are unphosphorylated or phosphorylated at the 3' termini.

And a compound having the structure

```
5'  AUCUUGAGCAAUUCUCUGG  3'  antisense strand (SEQ ID NO: 999)
    |||||||||||||||||||
3'  UAGAACUCGUUAAGAGACC  5'  sense strand (SEQ ID NO: 74)
``` wherein in (N)x the ribonucleotides alternate between modified ribonucleotides and unmodified ribonucleotides each modified ribonucleotide being modified so as to have a 2'-O-methyl on its sugar and the ribonucleotide located at the middle position being unmodified;

wherein in (N')y the nucleotide at position 18 or 17 and 18 is a mirror nucleotide and the nucleotide at position 15 is optionally an unmodified ribonucleotide or a deoxyribonucleotide; and wherein the antisense and the sense strands are unphosphorylated or phosphorylated at the 3' termini.

And a compound having the structure

```
5'  UCAAUUUCCAAGUUCACGU  3'  antisense strand (SEQ ID NO: 6914)
    |||||||||||||||||||
3'  AGUUAAAGGUUCAAGUGCA  5'  sense strand (SEQ ID NO: 6898)
``` wherein in (N)x the ribonucleotides alternate between modified ribonucleotides and unmodified ribonucleotides each modified ribonucleotide being modified so as to have a 2'-O-methyl on its sugar and the ribonucleotide located at the middle position being unmodified;

wherein in (N')y the nucleotide at position 18 or 17 and 18 is a mirror nucleotide and the nucleotide at position 15 is optionally an unmodified ribonucleotide or a deoxyribonucleotide; and wherein the antisense and the sense strands are unphosphorylated or phosphorylated at the 3' termini.

And a compound having the structure

```
5'  UUGGACAGACAGUUCUCCA  3'  antisense strand (SEQ ID NO: 6915)
    |||||||||||||||||||
3'  AACCUGUCUGUCAAGAGGU  5'  sense strand (SEQ ID NO: 6899)
``` wherein in (N)x the ribonucleotides alternate between modified ribonucleotides and unmodified ribonucleotides each modified ribonucleotide being modified so as to have a 2'-O-methyl on its sugar and the ribonucleotide located at the middle position being unmodified;

wherein in (N')y the nucleotide at position 18 or 17 and 18 is a mirror nucleotide and the nucleotide at position 15 is optionally an unmodified ribonucleotide or a deoxyribonucleotide; and wherein the antisense and the sense strands are unphosphorylated or phosphorylated at the 3' termini.

Further, the present invention provides for a pharmaceutical composition comprising any one of the above compounds and a pharmaceutically acceptable excipient.

The siRNA molecules having antisense strand SEQ ID NO:999 and sense strand SEQ ID NO:74 or antisense strand SEQ ID NO:1000 and sense strand SEQ ID NO:75 or antisense strand SEQ ID NO:6914 and sense strand SEQ ID NO:6898 or antisense strand SEQ ID NO:6915 and sense strand SEQ ID NO:6899 comprise any of the additional modifications disclosed herein, and are used in the treatment of any of the indications disclosed herein, such as the following diseases or conditions: hearing loss, acute renal failure (ARF), glaucoma, acute respiratory distress syndrome (ARDS) and other acute lung and respiratory injuries, ischemia-reperfusion injury following lung transplantation, organ transplantation including lung, liver, heart, bone marrow, pancreas, cornea and kidney transplantation, spinal cord injury, pressure sores, age-related macular degeneration (AMD), dry eye syndrome, oral mucositis and chronic obstructive pulmonary disease (COPD). Other indications include cancer of all types, chemical-induced nephrotoxicity and chemical-induced neurotoxicity, for example toxicity induced by cisplatin and cisplatin-like compounds, by aminoglycosides, by loop diuretics, and by hydroquinone and their analogs.

These compounds and pharmaceuticals are used to treat a patient suffering from any one of the diseases or conditions disclosed herein; further, any of the siRNAs in any one of Tables A-G are used in the same marnier.

Additionally, the invention provides a method of down-regulating the expression of the RTP801L gene by at least 50% as compared to a control comprising contacting an mRNA transcript of the RTP801L gene with one or more of the compounds of the invention.

In one embodiment the oligoribonucleotide is down-regulating the RTP801L gene, whereby the down-regulation is selected from the group comprising down-regulation of gene function, down-regulation of polypeptide and down-regulation of mRNA expression.

In one embodiment the compound is down-regulating the RTP801L polypeptide, whereby the down-regulation is selected from the group comprising down-regulation of function (which may be examined by an enzymatic assay or a binding assay with a known interactor of the native gene/polypeptide, inter alia), down-regulation of protein (which may be examined by Western blotting, ELISA or immunoprecipitation, inter alia) and down-regulation of mRNA expression (which may be examined by Northern blotting, quantitative RT-PCR, in-situ hybridization or microarray hybridisation, inter alia).

In additional embodiments the invention provides a method of treating a patient suffering from a disease accompanied by an elevated level of RTP801L, the method comprising administering to the patient a compound of the invention in a therapeutically effective dose thereby treating the patient.

More particularly, the invention provides an oligoribonucleotide wherein one strand comprises consecutive nucleotides having, from 5' to 3', the sequence set forth in any one of Tables A-G, or a homolog thereof wherein in up to two of the ribonucleotides in each terminal region is altered.

The terminal region of the oligoribonucleotide refers to bases 1-4 and/or 16-19 in the 19-mer sequence and to bases 1-4 and/or 18-21 in the 21-mer sequence, and to bases 1-4 and/or 20-23 in the 23 mer sequence.

When the nucleic acid according to the present invention is manufactured or expressed, preferably expressed in vivo, more preferably in a patient who is in need of the nucleic acid according to the present invention, such manufacture or expression preferably uses an expression vector, preferably a mammalian expression vector. Expression vectors are known in the art and preferably comprise plasmids, cosmids, viral expression systems. Preferred viral expression systems include, but are not limited to, adenovirus, retrovirus and lentivirus.

Methods are known in the art to introduce the vectors into cells or tissues. Such methods can be found generally described in Sambrook et al., Molecular cloning: A Laboratory Manual, Cold Springs Harbour Laboratory, New York (1983, 1992), or in Ausubel et al., Current Protocols in Molecular Biology, John Wiley and Sons, Baltimore, Md., 1998.

Suitable methods comprise, among others, transfection, lipofection, electroporation and infection with recombinant viral vectors. In connection with the present invention, an additional feature of the vector is in one embodiment an expression limiting feature such as a promoter and regulatory element, respectively, that are specific for the desired cell type thus allowing the expression of the nucleic acid sequence according to the present invention only once the background is provided which allows the desired expression.

In a further aspect the present invention is related to a pharmaceutical composition comprising a nucleic acid according to the present invention and/or a vector according to the present invention and, optionally, a pharmaceutically acceptable carrier, diluent or adjuvants or other vehicle(s). Preferably, such carrier, diluents, adjuvants and vehicles are inert, and non-toxic. The pharmaceutical composition is in its various embodiments adapted for administration in various ways. Such administration comprises systemic and local administration as well as oral, subcutaneous, parenteral, intravenous, intraarterial, intramuscular, intraperitonial, intranasal, and intrategral.

In particular embodiments the RTP801L siRNA is formulated as eye drops for administration to the surface of the eye. In other embodiments the RTP801L siRNA compound is administered to the lung by inhalation. In yet other embodiments the RTP801L siRNA compound is formulated for delivery to the inner ear by transtympanic injection or via ear drops.

It will be acknowledged by the one skilled in the art that the amount of the pharmaceutical composition and the respective siRNA depends on the clinical condition of the individual patient, the site and method of administration, scheduling of administration, patient age, sex, bodyweight and other factors known to medical practitioners. The pharmaceutically effective amount for purposes of prevention and/or treatment is thus determined by such considerations as are known in the medical arts. Preferably, the amount is effective to achieve improvement including but limited to improve the diseased condition or to provide for a more rapid recovery, improvement or elimination of symptoms and other indicators as are selected as appropriate measures by those skilled in the medical arts.

In a preferred embodiment, the pharmaceutical composition according to the present invention may comprise other pharmaceutically active compounds. Preferably, such other pharmaceutically active compounds are selected from the group comprising compounds which allow for uptake intracellular cell delivery, compounds which allow for endosomal release, compounds which allow for, longer circulation time and compounds which allow for targeting of endothelial cells or pathogenic cells. Preferred compounds for endosomal release are chloroquine, and inhibitors of ATP dependent $H^+$ pumps.

The pharmaceutical composition is preferably formulated so as to provide for a single dosage administration or a multi-dosage administration.

The pharmaceutical composition according to the present invention can also be used in a method for preventing and/or treating a disease as disclosed herein, whereby the method comprises the administration of a nucleic acid according to the present invention, a vector according to the present invention or a pharmaceutical composition or medicament according to the present invention for any of the diseases described herein.

In a further aspect, the present invention is related to a method for designing or screening a nucleic acid which is suitable to down-regulate RTP801L, more particularly to down-regulate RTP801L function. This method comprises the use of a nucleic acid sequence as disclosed herein and the assessment of such nucleic acid in a suitable assay. Such assay is known in the art and, for example, described in the example part of this application. In a further step, a double-stranded nucleic acid is designed, preferably according to the design principles as laid down herein, which is suitable to down-regulate RTP801L, preferably in connection with a post transcriptional gene silencing mechanism such as RNA interference. Also the thus obtained, i.e. designed or screened, nucleic acid is assessed in the respective assay and the result, i.e. the effect of both the nucleic acid according to the present invention as well as the newly designed or screened nucleic acid in such assay compared. Preferably, the designed or screened nucleic acid is more suitable in case it is either more stable or more effective, preferably both. It will be acknowledged that the method will be particularly effective if any of the nucleic acids according to the present invention is used as a starting point. It is thus within the present invention that new nucleic acid molecules will be designed based on the principles disclosed herein, whereby the target sequence on the RTP801L mRNA will be slightly shifted relative to the target sequence on the RTP801L mRNA for the corresponding nucleic acid according to the present invention. Preferably the new nucleic acid will be shifted by at least one or more nucleotides relative to the stretch on the target mRNA in either the 5' or the 3' direction of the mRNA coding for RTP801L. It is however with in the present invention that the shift occurs in both directions simultaneously which means that the new nucleic acid incorporates the nucleic acid according to the present invention used as a starting point. It is also within the present invention that the elongation of the nucleic acid according to the present invention and used as a starting point is biased to either the 3' end or the 5' end. In case of such as bias either the 3' end or the 5' end of the new nucleic acid is longer, i.e. more extended than the other end. When the new nucleic acid molecule is generated by extending either the 3' end of the 5' end of the antisense strand and/or the sense strand, the following sequence of steps is typically applied. If the shift is to the 5' end of the mRNA of RTP801L, the 3' end of the antisense strand has to be extended by the number of the nucleotides by which the 5' end of the mRNA of RTP801L is shifted. The nucleotide(s) thus to be added to the 3' end of the antisense strand of the new nucleic acid is/are complementary to those nucleotides following at the 5' end of the target sequence on the RTP801L mRNA used for the nucleic acid molecule according to the present invention used as a starting point. The same has to be done to the sense strand. However the nucleotides to be added to the sense strand have to correspond, i.e. be complementary to the nucleotides newly added to the 3' end of the antisense strand which means that they have to be added to the 5' end of the sense strand. The latter step on the sense strand, however has to be done only to the extent that apart from the antisense strand also the sense strand shall be shifted, which is the case in preferred embodiments of the present invention. Although this shifting can be done to an extent defined by the ones skilled in the art, more preferably the shift shall be done such that also the new nucleic acid still contains a stretch of at least 14 nucleotides, preferably 14 contiguous nucleotides as exhibited by any of the nucleic acid molecules disclosed herein.

The synthesis of any of the nucleic acids described herein is within the skills of the one of the art. Such synthesis is, among others, described in Beaucage S. L. and Iyer R. P., Tetrahedron 1992; 48: 2223-2311, Beaucage S. L. and Iyer R. P., Tetrahedron 1993; 49: 6123-6194 and Caruthers M. H. et. al., Methods Enzymol. 1987; 154: 287-313, the synthesis of thioates is, among others, described in Eckstein F., Annu. Rev. Biochem. 1985; 54: 367-402, the synthesis of RNA molecules is described in Sproat B., in Humana Press 2005 Edited by Herdewijn P.; Kap. 2: 17-31 and respective downstream processes are, among others, described in Pingoud A. et. al., in IRL Press 1989 Edited by Oliver R. W. A.; Kap. 7: 183-208 and Sproat B., in Humana Press 2005 Edited by Herdewijn P.; Kap. 2: 17-31 (supra).

siRNA for RTP801L can be made using methods known in the art as described above, based on the known sequence of RTP801L (SEQ ID NO:1), and can be made stable by various modifications as described above. For further information, see Example 5.

Combination Therapy

The present invention provides for combination therapy for all the conditions disclosed herein and in particular conditions involving choroidal neovascularization. In said combination therapy, both the RTP801L and VEGFR genes are inhibited in order to ameliorate the symptoms of the disease being treated. These genes are inhibited with a combination of siRNAs or antibodies (including aptamer antibodies) or both. The present invention therefore also provides for a novel pharmaceutical composition comprising an RTP801L inhibitor and a VEGF or VEGF-1 inhibitor, the RTP801L inhibitor preferable being an siRNA, more preferably an siRNA molecule detailed in any one of Tables A-G, optionally-selected from the group consisting of the siRNAs of Table F, and the VEGF/VEGFR-1 inhibitor optionally being an antibody or aptamer. The combined use of said compounds (i.e., RTP801L siRNA and VEGF antibody or any other combined example disclosed herein) in the preparation of a medicament is also part of the present invention.

Thus, RTP801L siRNA such as an siRNA molecule detailed herein and in any one of Tables A-G and optionally siRNA Nos: DDIT4L__14 or DDIT4L__15 of Table F, are administered in conjunction with agents which target VEGF or VEGF receptor 1 (VEGFR1). Such agents currently exist on the market or in various stages of approval and work through different mechanisms. Antibodies and antibody fragments such as ranibizumab (Lucentis, Genentech) attach to released VEGF to inhibit binding of VEGF to active receptors. An aptamer which can act like a ligand/antibody (Macugen, Eyetech/Pfizer, approved recently by the FDA for wet AMD) is also a possibility. Macugen bonds with extracellular VEGF to block its activity. These drugs are administered locally by intravitreal injection. Anti-VEGF siRNA based compounds (such as Acuity's Cand5 inhibitor of VEGF or SIRNA's 027 inhibitor of VEGFR-1) are also available. Additionally, the small molecule aminosterol Squalamine (Genaera) which is administered systemically reportedly interferes in multiple facets of the angiogenic process, including inhibiting VEGF and other growth factor signaling in endothelial cells.

The conjoined administration of an RTP801L siRNA, and any of the above VEGF/VEGFR-1 inhibitory agents can have an additive or even synergistic effect whereby said combined treatment is more effective than treatment by any of these individual compositions, irrespective of dosage in the single therapy option. RTP801L siRNA has a different mechanism of action and is potentially additive or even synergistic with VEGF-VEGFR inhibitors.

Additional disorders which can be treated by the molecules and compositions of the present invention include all types of choroidal neovascularization (CNV), which occurs not only in wet AMD but also in other ocular pathologies such as ocular histoplasmosis syndrome, angiod streaks, ruptures in Bruch's membrane, myopic degeneration, ocular tumors and some retinal degenerative diseases.

An additional aspect of the present invention provides for methods of treating an apoptosis related disease. Methods for therapy of diseases or disorders associated with uncontrolled, pathological cell growth, e.g. cancer, psoriasis, autoimmune diseases, inter alia, and methods for therapy of diseases associated with ischemia and lack of proper blood flow, e.g. myocardial infarction (MI) and stroke, are provided. "Cancer" or "Tumor" refers to an uncontrolled growing mass of abnormal cells. These terms include both primary tumors, which may be benign or malignant, as well as secondary tumors, or metastases which have spread to other sites in the body. Examples of cancer-type diseases include, inter alia: carcinoma (e.g.: breast, colon and lung), leukemia such as B cell leukemia, lymphoma such as B-cell lymphoma, blastoma such as neuroblastoma and melanoma and sarcoma. It will be acknowledged that the pharmaceutical composition according to the present invention can be used for any disease which involves undesired development or growth of vasculature including angiogenesis, as well as any of the diseases and conditions described herein. Preferably, these kind of diseases are tumor diseases. Among tumor diseases, the following tumors are most preferred: endometrial cancer, colorectal carcinomas, gliomas, endometrial cancers, adenocarcinomas, endometrial hyperplasias, Cowden's syndrome, hereditary non-polyposis colorectal carcinoma, Li-Fraumene's syndrome, breast-ovarian cancer, prostate cancer (Ali, I. U., Journal of the National Cancer Institute, Vol. 92, no. 11, Jun. 7, 2000, page 861-863), Bannayan-Zonana syndrome, LDD (Lhermitte-Duklos' syndrome) (Macleod, K., supra) hamartoma-macrocephaly diseases including Cow disease (CD) and Bannayan-Ruvalcaba-Rily syndrome (BRR), mucocutaneous lesions (e.g. trichilemmonmas), macrocephaly, mental retardation, gastrointestinal harmatomas, lipomas, thyroid adenomas, fibrocystic disease of the breast, cerebellar dysplastic gangliocytoma and breast and thyroid malignancies (Vazquez, F., Sellers, W. R., supra).

The invention also provides a composition comprising one or more of the compounds of the invention in a carrier, preferably a pharmaceutically acceptable carrier. This composition may comprise a mixture of two or more siRNAs for different genes or different siRNAs for the same gene. A composition comprising siRNA for the RTP801L gene and siRNA for the VEGF gene and/or the VEGF-R1 gene is envisaged.

This invention also comprises a tandem double-stranded structure which comprises two or more siRNA sequences, which is processed intracellularly to form two or more different siRNAs, one inhibiting RTP801L and a second inhibiting VEGF/VEGFR-1 In a related aspect, this invention also comprises a tandem double-stranded structure which comprises two or more siRNA sequences, which is degraded intracellularly to form two or more different siRNAs, both inhibiting RTP801L.

In particular, it is envisaged that a long oligonucleotide (typically about 80-500 nucleotides in length) comprising one or more stem and loop structures, where stem regions comprise the sequences of the oligonucleotides of the invention, are delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of an 801 gene. In particular, it is envisaged that this oligonucleotide comprises sense and antisense siRNA sequences as depicted in any one of Tables A-G. Alternatively, the tandem shRNA construct may comprise sense and complementary antisense siRNA sequence corresponding to an 801L gene and additionally sense and complementary antisense siRNA sequence corresponding to a different gene such as 801, VEGF or VEGF-R1.

As mentioned herein, siRNA against RTP801L are the main active component in a pharmaceutical composition, or are one active component of a pharmaceutical composition containing two or more siRNAs (or molecules which encode or endogenously produce two or more siRNAs, be it a mixture of molecules or one or more tandem molecule which encodes two or more siRNAs), said pharmaceutical composition further being comprised of one or more additional siRNA molecule which targets one or more additional gene. Simultaneous inhibition of RTP801L and said additional gene(s) has an additive or synergistic effect for treatment of the diseases disclosed herein, according to the following:

Acute Renal Failure (ARF) and other microvascular disorders: the pharmaceutical composition for treatment of ARF comprises of the following compound combinations: 1) RTP801L siRNA and p53 siRNA dimers; 2) RTP801L and Fas siRNA dimers; 3) RTP801L and Bax siRNA dimers; 4) p53 and Fas siRNA dimers; 5) RTP801L and Bax siRNA dimers; 6) RTP801L and Noxa siRNA dimers; 7) RTP801L and Puma siRNA dimers; 8) RTP801L (REDD1) and RTP801LL (REDD2) siRNA dimers; 9) RTP801L siRNA, Fas siRNA and any of RTP801LL siRNA p53 siRNA, Bax siRNA, Noxa siRNA or Puma siRNA to form timers or polymers (i.e., tandem molecules which encode three siRNAs).

Macular degeneration (MD), diabetic retinopathy (DR), spinal cord injury: pharmaceutical compositions for treatment of MD, DR and spinal cord injury comprises of the following compound combinations: 1) RTP801L siRNA combined with either of VEGF siRNA, VEGF-R1 siRNA, VEGF R2 siRNA, PKCbeta siRNA, MCP1 siRNA, eNOS siRNA, KLF2 siRNA, RTP801 siRNA (either physically mixed or in a tandem molecule); 2) RTP801L siRNA in combination with two or more siRNAs of the above list (physically mixed or in a tandem molecule encoding three siRNAs, or a combination thereof).

COPD and respiratory disorders: the pharmaceutical composition for treatment of respiratory disorders comprises of the following compound combinations: RTP801L siRNA combined with siRNA against one or more of the following genes: elastases, matrix metalloproteases, phospholipases, caspases, sphingomyelinase, RTP801 and ceramide synthase.

Further, a combination (tandem) siRNA directed against both RTP801 and RTP801L can be used to treat any of the conditions disclosed herein. For Example, the siRNA directed against RTP801 termed REDD14 (sense sequence: 5' GUGCCAACCUGAUGCAGCU 3' and antisense sequence 5' AGCUGCAUCAGGUUGGCAC 3') can be joined in tandem with any of the RTP801L siRNAs disclosed herein, such as an siRNA of Table F, or any other siRNA present in any one of Tables A-G.

Additionally, RTP801L siRNA or any nucleic acid molecule comprising or encoding RTP801L siRNA can be linked (covalently or non-covalently) to antibodies, in order to achieve enhanced targeting for treatment of the diseases disclosed herein, according to the following:
ARF: anti-Fas antibody (preferably neutralizing antibodies). Macular degeneration, diabetic retinopathy, spinal cord injury: anti-Fas antibody, anti-MCP1 antibody, anti-VEGFR1 and anti-VEGFR2 antibody. The antibodies should be preferably be neutralizing antibodies.

Any molecules, such as, for example, antisense DNA molecules which comprise the siRNA sequences disclosed herein (with the appropriate nucleic acid modifications) are particularly desirable and are used in the same capacity as their corresponding siRNAs for all uses and methods disclosed herein.

The invention also comprises a method of treating a patient suffering from a disorder such as the disorders described herein comprising administering to the patient the above composition or compound in a therapeutically effective dose so as to thereby treat the patient.
Macular Degeneration The most common cause of decreased best-corrected vision in individuals over 65 years of age in the US is the retinal disorder known as age-related macular degeneration (AMD). As AMD progresses, the disease is characterized by loss of sharp, central vision. The area of the eye affected by AMD is the Macula, a small area in the center of the retina, composed primarily of photoreceptor cells. So-called "dry" AMD, accounting for about 85%-90% of AMD patients, involves alterations in eye pigment distribution, loss of photoreceptors and diminished retinal function due to overall atrophy of cells. So-called "wet" AMD involves proliferation of abnormal choroidal vessels leading to clots or scars in the sub-retinal space. Thus, the onset of wet AMD occurs because of the formation of an abnormal choroidal neovascular network (choroidal neovascularization, CNV) beneath the neural retina. The newly formed blood vessels are excessively leaky. This leads to accumulation of subretinal fluid and blood leading to loss of visual acuity. Eventually, there is total loss of functional retina in the involved region, as a large disciform scar involving choroids and retina forms. While dry AMD patients may retain vision of decreased quality, wet AMD often results in blindness. (Hamdi & Kenney, May 2003. *Frontiers in Bioscience*, e305-314).

Acuity Pharmaceuticals and Sirna Therapeutics, have both recently filed an IND for siRNA molecules inhibiting VEGF and VEGF-R1 (Flt-1), respectively, for treatment of AMD. These molecules are termed Cand5 and Sirna-027 respectively.

Glaucoma

Glaucoma is one of the leading causes of blindness in the world. It affects approximately 66.8 million people worldwide. At least 12,000 Americans are blinded by this disease each year (Kahn and Milton, 1980. *Am J Epidemiol.* 111(6): 769-76). Glaucoma is characterized by the degeneration of axons in the optic nerve head, primarily due to elevated intraocular pressure (IOP). One of the most common forms of glaucoma, known as primary open-angle glaucoma (POAG), results from the increased resistance of aqueous humor outflow in the trabecular meshwork (TM), causing IOP elevation and eventual optic nerve damage. Mucke (IDrugs 2007, 10(1):37-41) reviews current therapeutics, including siRNA to various targets for the treatment of ocular diseases, for example, age-related macular degeneration (AMD) and glaucoma. Administration of neuroprotective agents has also been shown to be a viable treatment for glaucoma. The present invention provides RTP801L siRNA useful as a neuroprotective agent in the treatment of ION, AION, and glaucoma.

Ischemic Optic Neuropathy (ION)

A severely blinding disease resulting from loss of the arterial blood supply to the optic nerve (usually in one eye), as a result of occlusive disorders of the nutrient arteries. Optic neuropathy can be anterior (AION), which causes a pale edema of the optic disc, or posterior, in which the optic disc is not swollen and the abnormality occurs between the eyeball and the optic chiasm. Ischemic anterior optic neuropathy usually causes a loss of vision that may be sudden or occur over several days. Ischemic posterior optic neuropathy is uncommon, and the diagnosis depends largely upon exclusion of other causes, chiefly stroke and brain tumor.

Dry-Eye Syndrome

Dry eye syndrome is a common problem usually resulting from a decrease in the production of tear film that lubricates the eyes. Most patients with dry eye experience discomfort, and no vision loss; although in severe cases, the cornea may become damaged or infected. Wetting drops (artificial tears) may be used for treatment while lubricating ointments may help more severe cases.

Microvascular Disorders

Microvascular disorders are composed of a broad group of conditions that primarily affect the microscopic capillaries and lymphatics and are therefore outside the scope of direct surgical intervention. Microvascular disease can be broadly grouped into the vasospastic, the vasculitis and lymphatic occlusive. Additionally, many of the known vascular conditions have a microvascular element to them.

Microvascular Pathologies Associated with Diabetes

Diabetes is the leading cause of blindness, the major cause of amputations and impotence, and one of the most frequently occurring chronic childhood diseases. Diabetes is also the leading cause of end-stage renal disease in the United States, with a prevalence rate of 31% compared with other renal diseases. Diabetes is also the most frequent indication for kidney transplantation, accounting for 22% of all transplantation operations.

In general, diabetic complications can be classified broadly as microvascular or macrovascular disease. Microvascular complications include neuropathy (nerve damage), nephropathy (kidney disease) and vision disorders (e.g. retinopathy, glaucoma, cataract and corneal disease). In the retina, glomerulus, and vasa nervorum, similar pathophysiologic features characterize diabetes-specific microvascular disease. All the above listed conditions and pathologies are also be referred to herein as conditions "secondary to diabetes".

Emphysema and COPD

Among the mechanisms that underlie lung destruction in emphysema, excessive formation of reactive oxygen species (ROS) should be first of all mentioned. It is well established that prooxidant/antioxidant imbalance exists in the blood and in the lung tissue of smokers (Hulea S A, et al: 1995. *J Environ Pathol Toxicol Oncol.* 14(3-4):173-80; Rahman I, MacNee W. 1999. *Am J. Physiol.* 277(6 Pt 1):L1067-88; MacNee W. 2000 *Chest.* 117(5 Suppl 1):303S-17S; Marwick J A, et al., 2002. *Ann N Y Acad. Sci.* 973:278-83; Aoshiba K, et al., 2003. *Inhal Toxicol.* (10):1029-38; Dekhuijzen P N. 2004. *Eur Respir J.* 23(4):629-36; Tuder R M, et al., 2003. *Am J Respir Cell Mol Biol,* 29:88-97). After one hour exposure of mice to CS, there is a dramatic increase of 8-hydroxy-2'-deoxyguanosine (8-OHdG) in the alveolar epithelial cells, particularly of type II (see *Inhal Toxicol.* 2003 15(10):1029-38, above).

Overproduced reactive oxygen species are known for their cytotoxic activity, which stems from a direct DNA damaging effect and from the activation of apoptotic signal transduction pathways (Takahashi et al., 2004. *Brain Res Bull.* 62(6):497-504; Taniyama Y, Griendling K K. 2003. *Hypertension.* 42(6): 1075-81; Higuchi Y. 2003. *Biochem Pharmacol.* 66(8):1527-35; Punj V, Chakrabarty A M. 2003. *Cell Microbiol.* (4):225-31; Ueda et al., 2002 *Antioxid Redox Signal.* 4(3):405-14).

Both reactive oxygen species (ROS) from inhaled cigarette smoke and those endogenously formed by inflammatory cells contribute to an increased intrapulmonary oxidant burden.

One additional pathogenic factor with regards to COPD pathogenesis is the observed decreased expression of VEGF and VEGFRII in lungs of emphysematous patients (Kasahara, et al., 2001, *Am J Respir Crit Care Med.* 163:737-744). Moreover, inhibition of VEGF signaling using chemical VEGFR inhibitor leads to alveolar septal endothelial and then to epithelial cell apoptosis, probably due to disruption of intimate structural/functional connection of both types of cells within alveoli (Kasahara, et al., 2000. *J. Clin. Invest.* 106:1311-1319; Voelkel N F, Cool C D. 2003. *Eur Respir J Suppl.* 46:28s-32s).

Diabetic Neuropathy

Diabetic neuropathies are neuropathic disorders (peripheral nerve damage) associated with diabetes mellitus. These conditions usually result from diabetic microvascular injury involving small blood vessels that supply nerves (vasa nervorum). Relatively common conditions which are associated with diabetic neuropathy include third nerve palsy; mononeuropathy; mononeuropathy multiplex; diabetic amyotrophy; a painful polyneuropathy; autonomic neuropathy; and thoracoabdominal neuropathy and the most common form, peripheral neuropathy, which mainly affects the feet and legs. There are four factors involved in the development of diabetic neuropathy: microvascular disease, advanced glycated end products, protein kinase C, and the polyol pathway. The compounds of the present invention are useful in treating microvascular disease in diabetic neuropathy.

Neuropathy is a common complication of diabetes occurring over time in more than half of patients with type 2 diabetes. Nerve conduction studies demonstrate that neuropathy is already present in 10-18% of patients at the time of diabetes diagnosis, suggesting that peripheral nerve injury occurs at early stages of disease and with milder glycemic dysregulation. The concept that neuropathy is an early clinical sign of diabetes was proposed >40 years ago, and most studies report an association between IGT and neuropathy. Most patients with IGT and associated neuropathy have a symmetric, distal sensory polyneuropathy with prominent neuropathic pain. IGT neuropathy (Singleton, J R et al. 2003. 1: Diabetes 52(12):2867-73) is phenotypically similar to early diabetic neuropathy, which also causes sensory symptoms, including pain, and autonomic dysfunction.

Autonomic dysfunction, particularly erectile dysfunction and altered cardiac vagal response, are common early features of neuropathic injury in diabetes. Work with IGT patients also suggests prevalent vagal dysautonoinia: separate studies have found abnormal heart rate recovery following exercise, blunted R-R interval variability to deep breathing, and reduced expiration to inspiration ratio (all measures of vagal dysautonomia) in a greater fraction of IGT patients than age-matched normoglycemic control subjects.

For further information, see American Journal of Surgery, Volume 187• Number 5 Suppl 1• May 1, 2004, Elsevier.

Coronary Microvascular Dysfunction in Diabetes

The correlation between histopathology and microcirculatory dysfunction in diabetes is well known from old experimental studies and from autopsy, where thickening of the basal membrane, perivascular fibrosis, vascular rarefication, and capillary hemorrhage are frequently found. The following papers relate to microvascular dysfunction (Am J Physiol 2003; 285; Hypert Res 2002; 25:893; Sambuceti et al., Circulation 2001. 104:1129; Stone 2002; Feldmann Circulation 2003; Herrmann, Circulation 2001).

Diabetic Nephropathy (Renal Dysfunction in Patients with Diabetes)

Diabetic nephropathy encompasses microalbuminuria (a microvascular disease effect), proteinuria and ESRD. Diabetes is the most common cause of kidney failure, accounting for more than 40 percent of new cases. Even when drugs and diet are able to control diabetes, the disease can lead to nephropathy and kidney failure. Most people with diabetes do not develop nephropathy that is severe enough to cause kidney failure. About 16 million people in the United States have diabetes, and about 100,000 people have kidney failure as a result of diabetes.

Diabetic Retinopathy

In the diabetic state, hyperglycemia leads to decreased retinal blood flow, retinal hyperpermeability, delays in photoreceptor nerve conduction, and retinal neuronal cell death. In short duration diabetes, neuronal cell death has been identified within the inner nuclear layer of the retina. Specifically, apoptosis has been localized to glial cells such as Mueller cells and astrocytes and has been shown to occur within 1 month of diabetes in the STZ-induced diabetic rat model. The cause of these events is multi-factorial including activation of the diacylglycerol/PKC pathway, oxidative stress, and non-enzymatic glycosylation. The combination of these events renders the retina hypoxic and ultimately leads to the development of diabetic retinopathy. One possible connection between retinal ischemia and the early changes in the diabetic retina is the hypoxia-induced production of growth factors such as VEGF. The master regulator of the hypoxic response has been identified as hypoxia inducible factor-1 (HIF-1), which controls genes that regulate cellular proliferation and angiogenesis. Prior studies have demonstrated that inhibition of HIF-1 ubiquitination leads to binding with hypoxia responsive elements (HRE) and production of VEGF mRNA.

Diabetic Retinopathy is defined as the progressive dysfunction of the retinal vasculature caused by chronic hyperglycemia. Key features of diabetic retinopathy include microaneurysms, retinal hemorrhages, retinal lipid exudates, cotton-wool spots, capillary nonperfusion, macular edema and neovascularization. Associated features include vitreous hemorrhage, retinal detachment, neovascular glaucoma, premature cataract and cranial nerve palsies.

A microvascular disease that primarily affects the capillaries, diabetes mellitus affects the eye by destroying the vasculature in the conjunctiva, retina and central nervous system.

Neuropathy

Neuropathy affects all peripheral nerves: pain fibers, motor neurons, autonomic nerves. It therefore necessarily can affect all organs and systems since all are innervated. There are several distinct syndromes based on the organ systems and members affected, but these are by no means exclusive. A patient can have sensorimotor and autonomic neuropathy or any other combination. Despite advances in the understanding of the metabolic causes of neuropathy, treatments aimed at interrupting these pathological processes have been limited by side effects and lack of efficacy. Thus, treatments are symptomatic and do not address the underlying problems. Agents for pain caused by sensorimotor neuropathy include tricyclic antidepressants (TCAs), serotonin reuptake inhibitors (SSRIs) and antiepileptic drugs (AEDs). None of these agents reverse the pathological processes leading to diabetic neuropathy and none alter the relentless course of the illness. Thus, it would be useful to have a pharmaceutical composition that could better treat these conditions and/or alleviate the symptoms.

Retinal Microvasculopathy (AIDS Retinopathy)

Retinal microvasculopathy is seen in 100% of AIDS patients. It is characterized by intraretinal hemorrhages, microaneurysms, Roth spots, cotton-wool spots (microinfarctions of the nerve fiber layer) and perivascular sheathing. The etiology of the retinopathy is unknown though it has been thought to be due to circulating immune complexes, local release of cytotoxic substances, abnormal hemorheology, and HIV infection of endothelial cells. AIDS retinopathy is now so common that cotton wool spots in a patient without diabetes or hypertension but at risk for HIV should prompt the physician to consider viral testing. There is no specific treatment for AIDS retinopathy but its continued presence may prompt a physician to reexamine the efficacy of the HIV therapy and patient compliance.

Bone Marrow Transplantation (BMT) Retinopathy

Bone marrow transplantation retinopathy was first reported in 1983. It typically occurs within six months, but it can occur as late as 62 months after BMT. Risk factors such as diabetes and hypertension may facilitate the development of BMT retinopathy by heightening the ischemic microvasculopathy. There is no known age, gender or race predilection for development of BMT retinopathy. Patients present with decreased visual acuity and/or visual field deficit. Posterior segment findings are typically bilateral and symmetric. Clinical manifestations include multiple cotton wool spots, telangiectasia, microaneurysms, macular edema, hard exudates and retinal hemorrhages. Fluorescein angiography demonstrates capillary nonperfusion and dropout, intraretinal microvascular abnormalities, microaneurysms and macular edema. Although the precise etiology of BMT retinopathy has not been elucidated, it appears to be affected by several factors: cyclosporine toxicity, total body irradiation (TBI), and chemotherapeutic agents. Cyclosporine is a powerful immunomodulatory agent that suppresses graft-versus-host immune response. It may lead to endothelial cell injury and neurologic side effects, and as a result, it has been suggested as the cause of BMT retinopathy. However, BMT retinopathy can develop in the absence of cyclosporine use, and cyclosporine has not been shown to cause BMT retinopathy in autologous or syngeneic bone marrow recipients. Cyclosporine does not, therefore, appear to be the sole cause of BMT retinopathy. Total body irradiation (TBI) has also been implicated as the cause of BMT retinopathy.

Radiation injures the retinal microvasculature and leads to ischemic vasculopathy. Variables such as the total dose of radiation and the time interval between radiation and bone marrow ablation appear to be important. However, BMT retinopathy can occur in patients who did not receive TBI, and BMT retinopathy is not observed in solid organ transplant recipients who received similar doses of radiation. Thus, TBI is not the sole cause, but it is another contributing factor in development of BMT retinopathy. Chemotherapeutic agents have been suggested as a potential contributing factor in BMT retinopathy. Medications such as cisplatin, carmustine, and cyclophosphamide can cause ocular side effects including papilledema, optic neuritis, visual field deficit and cortical blindness. It has been suggested that these chemotherapeutic drugs may predispose patients to radiation-induced retinal damages and enhance the deleterious effect of radiation. In general, patients with BMT retinopathy have a good prognosis. The retinopathy usually resolves within two to four months after stopping or lowering the dosage of cyclosporine. In one report, 69 percent of patients experienced complete resolution of the retinal findings, and 46 percent of patients fully recovered their baseline visual acuity. Because of the favorable prognosis and relatively non-progressive nature of BMT retinopathy, aggressive intervention is usually not necessary.

Microvascular Diseases of the Kidney

The kidney is involved in a number of discreet clinicopathologic conditions that affect systemic and renal microvasculature. Certain of these conditions are characterized by primary injury to endothelial cells, such as: Hemolytic-uremic syndrome (HUS) and thrombotic thrombocytopenic purpura (TTP) and Radiation nephritis—The long-term consequences of renal irradiation in excess of 2500 rad.

In other kidney diseases, the microvasculature of the kidney is involved in autoimmune disorders, such as systemic sclerosis (scleroderma). Kidney involvement in systemic sclerosis manifests as a slowly progressing chronic renal disease or as scleroderma renal crisis (SRC), which is characterized by malignant hypertension and acute azotemia. It is postulated that SRC is caused by a Raynaud-like phenomenon in the kidney. Severe vasospasm leads to cortical ischemia and enhanced production of renin and angiotensin II, which in turn perpetuate renal vasoconstriction. Hormonal changes (pregnancy), physical and emotional stress, or cold temperature may trigger the Raynaud-like arterial vasospasm. The role of the renin-angiotensin system in perpetuating renal ischemia is underscored by the significant benefit of ACE inhibitors in treating SRC. In patients with SRC who progress to severe renal insufficiency despite antihypertensive treatment, dialysis becomes a necessity. Both peritoneal dialysis and hemodialysis have been employed. The End-Stage Renal Disease (ESRD) Network report on 311 patients with systemic sclerosis-induced ESRD dialyzed between 1983 and 1985 revealed a 33% survival rate at 3 years.

The renal microcirculation can also be affected in sickle cell disease, to which the kidney is particularly susceptible because of the low oxygen tension attained in the deep vessels of the renal medulla as a result of countercurrent transfer of oxygen along the vasa recta. The smaller renal arteries and arterioles can also be the site of thromboembolic injury from cholesterol-containing material dislodged from the walls of the large vessels.

Taken as a group, diseases that cause transient or permanent occlusion of renal microvasculature uniformly result in disruption of glomerular perfusion, and hence of the glomerular filtration rate, thereby constituting a serious threat to systemic homeostasis.

An additional embodiment of the present invention provides for the use of a therapeutically effective dose of an RTP801L inhibitor for the preparation of a medicament for promoting recovery in a patient suffering from any of the diseases or conditions described herein e.g. spinal cord disease or injury. In one embodiment the inhibitor is preferably an siRNA. In another embodiment the inhibitor is preferably Structure A depicted herein.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

Throughout this application, various publications, including United States patents, are referenced by author and year and patents by number. The disclosures of these publications and patents and patent applications in their entireties are hereby incorporated by reference into this application in order to more fully describe the state of the art to which this invention pertains.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

The present invention is illustrated in detail below with reference to examples, but is not to be construed as being limited thereto.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988).

Standard organic synthesis protocols known in the art not specifically described herein are generally followed essentially as in *Organic Syntheses*: Vol. 1-79, editors vary, J. Wiley, New York, (1941-2003); Gewert et al., *Organic synthesis workbook*, Wiley-VCH, Weinheim (2000); Smith & March, *Advanced Organic Chemistry*, Wiley-*Interscience*; 5th ed. (2001).

Standard medicinal chemistry methods known in the art not specifically described herein are generally followed essentially as in the series "Comprehensive Medicinal Chemistry", by various authors and editors, published by Pergamon Press.

The features of the present invention disclosed in the specification, the claims and/or the drawings may both separately and in any combination thereof be material for realizing the invention in various forms thereof.

General Materials and Methods

Cell Culture

The first human cell line, namely HeLa cells (American Type Culture Collection) were cultured as follows: Hela cells (American Type Culture Collection) were cultured as described in Czauderna F et al. (Czauderna, F., et al., 2003. Nucleic Acids Res, 31, 670-82).

The second human cell line was a human keratinozyte cell line which was cultivated as follows: Human keratinocytes were cultured at 37° C. in Dulbecco's modified Eagle medium (DMEM) containing 10% FCS. The mouse cell line was B16V (American Type Culture Collection) cultured at 37° C. in Dulbecco's modified Eagle medium (DMEM) containing 10% FCS. Culture conditions were as described in Methods Find Exp Clin Pharmacol. 1997 19(4):231-9.

In each case, the cells were subject to the experiments as described herein at a density of about 50,000 cells per well and the double-stranded nucleic acid according to the present invention was added at 20 nM, whereby the double-stranded nucleic acid was complexed using 1 µg/ml of a proprietary lipid.

Induction of Hypoxia-Like Condition

The cells were treated with $CoCl_2$ for inducing a hypoxia-like condition as follows: siRNA transfections were carried out in 10-cm plates (30-50% confluency) as described by (Czauderna et al., 2003; Kretschmer et al., 2003). Briefly, siRNA were transfected by adding a preformed 10× concentrated complex of GB and lipid in serum-free medium to cells in complete medium. The total transfection volume was 10 ml. The final lipid concentration was 1.0 µg/ml; the final siRNA concentration was 20 nM unless otherwise stated. Induction of the hypoxic responses was carried out by adding $CoCl_2$ (100 µM) directly to the tissue culture medium 24 h before lysis.

Preparation of Cell Extracts and Immuno Blotting

The preparation of cell extracts and immuno blot analysis were carried out essentially as described by Klippel et al. (Klippel, A., et al., 1998. Mol Cell Biol, 18, 5699-711; Klippel, A., et al., 1996. Mol Cell Biol, 16, 4117-27). Polyclonal antibodies against full length RTP801L were generated by immunising rabbits with recombinant RTP801L protein producing bacteria from pET19-b expression vector (Merck Biosciences GmbH, Germany). The murine monoclonal anti-p110α and anti-p85 antibodies have been described by Klippel et al. (supra).

In Vitro Testing of siRNA Compounds

About 1.5-2×10⁵ tested cells (HeLa cells and/or 293T cells for siRNA targeting human genes and NRK52 (normal rat kidney proximal tubule cells) cells and/or NMuMG cells (mouse mammary epithelial cell line) for siRNA targeting the rat/mouse gene) were seeded per well in 6 wells plate (70-80% confluent). See also Example 14 hereinbelow.

About 24 hours later, cells were transfected with siRNA compounds using the Lipofectamine™ 2000 reagent (Invitrogen) at final concentrations of 5 nM or 20 nM. The cells were incubated at 37° C. in a $CO_2$ incubator for 72 h.

As positive control for transfection PTEN-Cy3 labeled siRNA compounds were used. Various chemically modified blunt ended siRNA compounds having alternating modified and unmodified ribonucleotides (modified at the 2' position of the sugar residue in both the antisense and the sense strands, wherein the moiety at the 2' position of the sugar is methoxy) and wherein the ribonucleotides at the 5' and 3' termini of the antisense strand are modified in their sugar residues, and the ribonucleotides at the 5' and 3' termini of the sense strand are unmodified in their sugar residues were tested. Another siRNA compound comprised a blunt ended structure having an antisense with an alternating pattern of methoxy moieties and a sense strand with three ribonucleotides linked by two 2'5' bridges at the 3' terminus; and another siRNA compound comprising antisense and sense strands having three ribonucleotides linked by 2'5' bridges at the 3' terminus was used. Some of the tested compounds comprised a blunt ended structure having an antisense with an alternating pattern of methoxy moieties and a sense strand with one or two L-deoxynucleotides at the 3' terminal or 3' penultimate positions.

GFP siRNA compounds were used as negative control for siRNA activity.

At 72 h after transfection cells were harvested and RNA was extracted from cells. Transfection efficiency was tested by fluorescent microscopy.

The percent of inhibition of gene expression using specific preferred siRNA structures was determined using qPCR analysis of a target gene in cells expressing the endogenous gene.

In general, the siRNAs having specific sequences that were selected for in vitro testing were specific for human and a second species such as non-human primate, rat or rabbit genes. Similar results are obtained using siRNAs having these RNA sequences and modified as described herein.

Serum Stability Experiments

Chemically modified siRNA compounds according to the present invention were tested for duplex stability in human serum, as follows:

siRNA molecules at final concentration of 7 uM were incubated at 37° C. in 100% human serum (Sigma Cat# H4522). (siRNA stock 100 uM diluted in human serum 1:14.29).

5 ul were added to 15 ul 1.5XTBE-loading buffer at different time points (0, 30 min, 1 h, 3 h, 6 h, 8 h, 10 h, 16 h and 24 h)

Samples were immediately frozen in liquid nitrogen and were kept at −20° C.

Each sample was loaded onto a non-denaturing 20% acrylamide gel, prepared according to methods known in the art.

The oligos were visualized with Ethidium bromide under UV light.

Example 1

Chemically Modified RTP801L siRNA

Table 1 hereinbelow provides a code of the modified nucleotides/unconventional moieties utilized in preparing the siRNA ologonucleotides of the present invention.

TABLE 1

| Code Nuc | modification |
|---|---|
| 5medG | 5-methyl-deoxyriboguanosine-3'-phosphate |
| c6Np | Amino modifier C6 (Glen Research 10-1906-xx) |
| dA | deoxyriboadenosine-3'-phosphate |
| dB | abasic deoxyribose-3'-phosphate |
| dC | deoxyribocytidine-3'-phosphate |
| dG | deoxyriboguanosine-3'-phosphate |
| dT | thymidine-3'-phosphate |
| dT$ | thymidine (no phosphate) |
| enaA$ | ethylene-bridged nucleic acid adenosine (no phosphate) |
| enaC | ethylene-bridged nucleic acid cytidine 3' phosphate |
| enaG | ethylene-bridged nucleic acid guanosine 3' phosphate |
| enaT | ethylene-bridged nucleic acid thymidine 3' phosphate |

TABLE 1-continued

| Code Nuc | modification |
|---|---|
| iB | inverted deoxyabasic |
| LdA | L-deoxyriboadenosine-3'-phosphate (mirror image dA) |
| LdA$ | L-deoxyriboadenosine (no phosphate) (mirror image dA) |
| LdC | L-deoxyribocytidine-3'-phosphate (mirror image dC) |
| LdC$ | L-deoxyribocytidine (no phosphate) (mirror image dC) |
| LdG | L-deoxyriboguanosine-3'-phosphate (mirror image dG) |
| LdT | L-deoxyribothymidine-3'-phosphate (mirror image dT) |
| LdT$ | L-deoxyribothymidine (no phosphate) (mirror image dT) |
| mA | 2'-O-methyladenosine-3'-phosphate |
| mA$ | 2'-O-methyladenosine (no phosphate) |
| mC | 2'-O-methylcytidine-3'-phosphate |
| mC$ | 2'-O-methylcytidine (no 3'-phosphate) |
| mG | 2'-O-methylguanosine-3'-phosphate |
| mG$ | 2'-O-methylguanosine (no phosphate) |
| mU | 2'-O-methyluridine-3'-phosphate |
| mU$ | 2'-O-methyluridine (no phosphate) |
| rA | riboadenosine-3'-phosphate |
| rA$ | riboadenosine (no phosphate) |
| rC | ribocytidine-3'-phosphate |
| rC$ | ribocytidine (no phosphate) |
| rC2p | ribocytidine-2'-phosphate |
| rG | riboguanosine-3'-phosphate |
| rG2p | riboguanosine-2'-phosphate |
| rU | ribouridine-3'-phosphate |
| rU$ | ribouridine (no phosphate) |
| rU2p | ribouridine-2'-phosphate |

Tables A-E provide antisense and sense pairs of oligonucleotides useful in synthesis of the siRNA compounds according to the present invention. All oligonucleotides are presented as 5'-3' sequences. (Hum=human, chin=chinchilla, chimp=chimpanzee, ms=mouse). Table F (FIG. 2) provides certain preferred sense and corresponding antisense oligonucleotides useful in the preparation of siRNA compounds. Table G, (FIG. 3) provides chemically modified siRNA compounds, whereby the sense and antisense sequences are provided in code according to Table 1 above. In vitro activity of the compounds is also presented in Table G. The legend for Table G is as follows:

1: Activity in 293 human cells at 20 nM. % residual transcript relative to untreated control;
2: Activity in 293 human cells at 5 nM—% residual transcript relative to untreated control;
3: Activity in rat C6 cells at 20 nM—% residual transcript relative to untreated control
4: Activity in rat C6 cells at 5 nM—% residual transcript relative to untreated control;
5. Stability in Human serum (hours) "-" refers to less than 3 hours duplex stability in 100% human serum.

FIG. 8 shows the sequence, structure, activity and serum stability of siRNA compounds according to the present invention. The oligonucleotides are presented 5'-3', with sense strand above the antisense strand.

Example 2

Experimental Models, Methods and Results Relating to Ocular Disease

The compounds of the present invention are tested in the following animal model of Choroidal neovascularization (CNV). This hallmark of wet AMD is induced in model animals by laser treatment.

A) Mouse Model

Choroidal neovascularization (CNV) induction: Choroid neovascularization (CNV), a hallmark of wet AMD, is triggered by laser photocoagulation (532 nm, 200 mW, 100 ms, 75 µm) (OcuLight GL, Iridex, Mountain View, Calif.) performed on both eyes of each mouse on day 0 by a single individual masked to drug group assignment. Laser spots are applied in a standardized fashion around the optic nerve, using a slit lamp delivery system and a cover slip as a contact lens.

Treatment Groups

CNV is induced in the following groups of mice (males 6-8 weeks of age): Both eyes of each mouse are laser-treated.
12 WT mice;
12 RTP801L Knock-Out mice;
12 WT mice injected with 0.25 µg of synthetic stabilized active anti-RTP801L siRNA in one eye and inactive anti-RTP801L siRNA (REDD8—negative control) in the fellow eye, at days 0 and 7;
12 WT mice injected with 0.25 µg of synthetic stabilized active anti-RTP801L siRNA in one eye and inactive anti-GFP siRNA (negative control) in the fellow eye at days 0 and 7;
12 WT mice injected with either 0.1 µg of synthetic stabilized active anti-RTP801L siRNA in one eye and PBS (negative control) in the fellow eye at days 0 and 7; 12 WT mice injected with either 0.05 µg of synthetic stabilized active anti-RTP801L siRNA in one eye and PBS (negative control) in the fellow eye at days 0 and 7.

Evaluation: The experiment is terminated at day 14. For evaluation, the eyes are enucleated and fixed with 4% paraformaldehyde for 30 min at 4° C. The neurosensory retina is detached and severed from the optic nerve. The remaining RPE-choroid-sclera complex is flat mounted in Immu-Mount (Vectashield Mounting Medium, Vector) and coverslipped. Flat mounts are examined with a scanning laser confocal microscope (TCS SP, Leica, Germany). Vessels are visualized by exciting with blue argon laser. Horizontal optical sections (1 µm step) are obtained from the surface of the RPE-choroid-sclera complex. The deepest focal plane in which the surrounding choroidal vascular network connecting to the lesion can be identified is judged to be the floor of the lesion. Any vessel in the laser treated area and superficial to this reference plane is judged as CNV. Images of each section are digitally stored. The area of CNV-related fluorescence is measured by computerized image analysis using the Leica TCS SP software. The summation of whole fluorescent area in each horizontal section is used as an index for the volume of CNV.

Separate WT mice are used for evaluating RTP801L mRNA expression in CNV (as well as the expression of other genes relevant to AMD) (untreated and treated with siRNA) using real-time PCR on RNA extracted from RPE/choroids, or from neural retina.

Expression profiling conducted in the mouse model of CNV revealed that the RTP801L transcript level is gradually increased in mouse Retina following CNV induction, thus indicating that RTP801L is a good target for inhibition in the treatment of AMD and other conditions which involve choroidal neovascularization.

B) Non-Human Primate Model

CNV induction: Choroidal neovascularization (CNV) is induced by perimacular laser treatment of both eyes prior to dose administration. Nine lesions are placed in the macula with a laser [OcuLight GL (532 nm) Laser Photo-coagulator with an IRIS Medical®Portable Slit Lamp Adaptor], and laser spots in the right eye mirror the placement in the left eye. The approximate laser parameters are as follows: spot size: 50-100 µm diameter; laser power: 300-700 milliwatts; exposure time: 0.1 seconds.

Treatment: Immediately following laser treatment, both eyes of all animals are subjected to a single intravitreal injection. Left eye is typically dosed with 350 ug of synthetic stabilized siRNA against RTP801L in the final volume of 50 ul, whereas the contralateral eye receives 50 ul of PBS (vehicle).

Evaluation
1. All the animals are subjected to daily examination of food consumption and body weight measurements.
2. two monkeys are euthanized at day 6 following CNV induction. Their eyes are enucleated and the posterior pole is flattened. Then the fovea region is excised and separated into choroids and neuroretina which are separately (for every animal) frozen in liquid nitrogen to be subsequently used for RNA extraction and real time PCR evaluation of RTP801L expression.
3. Fluorescein angiograms are performed pre-study, and at the end of weeks 1, 2, and 3 following CNV induction. Photographs are taken, using a fundus camera (TRC-50EX Retina Camera). Images are captured using the TOPCON IMAGEnet™ system. Fluorescein dye (10% fluorescein sodium, approximately 0.1 mL/kg) is injected via vascular access ports. Photographs are taken at several timepoints following dye injection, to include the arterial phase, early arteriovenous phase and several late arteriovenous phases in order to evaluate neovascularization and to monitor leakage of fluorescein associated with CNV lesions. Interpretation and analysis of the fluorescein angiograms is independently conducted by two ophthalmologists.

Neovascularization (NV) is assessed in early angiograms and every spot is graded according to the following scheme:
0—no signs of NV
0.5—suspicious spot
1—"hot" spot
2—NV in the laser burn
3—evident NV Leakage is assessed according to the following scheme:
0—no leakage
0.5—suspicious spot
1—evident small spot leakage
2—leakage growing with time
3—leakage greater than previous borders (evidently)

In addition, the size of every spot is compared between the early and the late angiograms using morphometric measurements, and the increase in the spot's size resulting from the leakage is calculated.

Electroretinograms (ERGs) are recorded using an Epic 2000 electroretinograph according to Sierra's SOPs and the study-specific SOP, including the use of the Ganzfield apparatus, at prestudy and in the end of week 3. The tabulated ERG data are evaluated by a veterinary ophthalmologist.

C) Efficacy of Combination Therapy of RTP801L siRNA and Anti-VEGF Antibody

The efficacy of combination therapy of RTP801L siRNA and anti-VEGF antibody or aptamer (such as macugen) in the treatment of diseases in which CNV occurs is tested in the above mouse CNV model.

A) CNV volume studies: The volume of choroidal neovascularization (CNV) 3 weeks after laser injury is computed byconfocal fluorescence microscopy as previously described (Sakurai et al. *IOVS* 2003; 44: 3578-85 & Sakurai et al. *IOVS* 2003; 44: 2743-2749).

B) CNV leakage studies

Experiment 1

This experiment was designed in order to identify a potential additive or synergistic therapeutic effect of inhibition of VEGF and RTP801L in the model of laser-induced choroid neovascularization in mice Materials: Chemically modified RTP801L siRNA; negative control siRNA (GFP or scrambled); Anti-VEGF antibodies or Macugen™ and negative control.

CNV is induced on day zero as described above; the test material is injected to the subjects on day zero and day 7.

The results are evaluated by Fluorescein angiography on weeks 1, 2, 3, and by CNV volume measurement on week 3.

Experimental Groups:
VEGF Ab or macugen 0.5 ng/eye
VEGF Ab or macugen 1 ng/eye
VEGF Ab or macugen 2 ng/eye
VEGF Ab 4 or macugen ng/eye
RTP801L siRNA 0.05 ug/eye
RTP801L siRNA 0.1 ug/eye
RTP801L siRNA 0.25 ug/eye
RTP801L siRNA 0.05 ug/eye+VEGF Ab or macugen 1 ng/eye
RTP801L siRNA 0.1 ug/eye+VEGF Ab or macugen 1 ng/eye
RTP801L siRNA 0.25 ug/eye+VEGF Ab or macugen 1 ng/eye Control Groups:
PBS
Non-specific IgG 2 ng/eye
negative control 0.1 ug/eye
negative control 0.1 ug/eye+VEGF Ab or macugen 1 ng/eye The results show an additive or synergistic therapeutic effect of inhibition of VEGF and RTP801L Experiment 2

This experiment was designed in order to study the effect of RTP801L siRNA on gene expression in RPE and neural retina.

Experimental Design

Groups:
PBS
RTP801L siRNA 0.25 mg

CNV is induced by laser treatment as described above on day zero; the test material is also injected on day zero, and the effect evaluated by qPCR analysis of gene expression in RPE and neural retina on days zero and 5.

Additional AMD models which are used to test the methods of the present invention:

Ccl-2 or Ccr-2 deficient animals—deficiency in either of these proteins causes the development of some of the main features of AMD. Animals deficient in these proteins can be used to test the methods of the present invention.

For further information on AMD animal models, see: Chader, *Vision research* 42 (2002) 393-399; Ambati et al., *Nature Medicine* 9(11) (2003) 1390-1397; Tolentino et al., *Retina* 24 (2004) 132-138.

Example 3

Models and Results Relating to COPD and Emphysema

The compounds of the present invention are tested in the following an animal models and are shown to prevent emphysema:

Cigarette smoke-induced emphysema model: chronic exposure to cigarette smoke causes emphysema in several animals such as, inter alia, mouse, guinea pig.
Lung protease activity as a trigger of emphysema.
VEGFR inhibition model of emphysema.
Bronchial instillation with human neutrophil/pancreatic elastase in rodents.
MMP (matrix metalloprotease)-induced emphysema.
Inflammation-induced emphysema.

Additionally, emphysema models are generated through genetic means (e.g., mice carrying the TSK mutation), and emphysematous animals may be generated by known modifiers of susceptibility to emphysema such as, inter alia, lung injury, alveolar hypoplasia, hyperoxia, glucocorticoid treatment and nutrition.

Evaluation of the influence of lack of RTP801L on disease progression in mouse models of emphysema by inhibiting endogenous RTP801L employing intralung delivery RTP801L-inactivating siRNA CS-induced inflammation is induced by 7 day smoking in 2 groups of C57BL6 mice, 10 mice per group. Group 1: CS+delivery of control siRNA; Group 2: CS+RTP801L siRNA. Control groups of mice are instilled with either type of siRNA but kept in room air conditions. The lungs are subsequently agarose-inflated, fixed and imbedded in paraffin, and development oxidative stress in the KO mice is assessed by:

a) immunohistochemical localization and quantitation of 8-oxo-dG in the lung sections;
 b) immunohistochemical localization and quantitation of active caspase 3 in the lung sections using specific antibodies, or quantitative evaluation of the number of TUNEL-positive cells;
 c) measurement of ceramide concentration in the lung extracts;
 d) measurement of caspase activity in the lung extracts.

Methods

Exposure to Cigarette Smoking (CS)

Exposure is carried out (7 h/day, 7 days/week) by burning 2R4F reference cigarettes (2.45 mg nicotine per cigarette; purchased from the Tobacco Research Institute, University of Kentucky, Lexington, Ky., USA) using a smoking machine (Model TE-10, Teague Enterprises, Davis, Calif., USA). Each smoldering cigarette is puffed for 2 s, once every minute for a total of eight puffs, at a flow rate of 1.05 L/min, to provide a standard puff of 35 cm3. The smoke machine is adjusted to produce a mixture of sidestream smoke (89%) and mainstream smoke (11%) by burning five cigarettes at one time. Chamber atmosphere is monitored for total suspended particulates and carbon monoxide, with concentrations of 90 mg/m3 and 350 ppm, respectively.

Morphologic and Morphometric Analyses

After exposing the mice to CS or instillation of chemically modified RTP801L the mice are anesthetized with halothane and the lungs are inflated with 0.5% low-melting agarose at a constant pressure of 25 cm as previously described. The inflated lungs are fixed in 10% buffered formalin and embedded in paraffin. Sections (5 μm) are stained with hematoxylin and eosin. Mean alveolar diameter, alveolar length, and mean linear intercepts are determined by computer-assisted morphometry with the Image Pro Plus software (Media Cybernetics, Silver Spring, Md., USA). The lung sections in each group are coded and representative images (15 per lung section) are acquired by an investigator masked to the identity of the slides, with a Nikon E800 microscope, 20× lens. The results show that siRNA to 801L prevents emphysema caused by smoking as measured by the four parameters described above.

Bronchoalveolar Lavage (BAL) and Phenotyping

Following exposure to CS or instillation of chemically modified RTP801L, the mice are anesthetized with sodium pentobarbital. The BAL fluid collected from the lungs of the mice is centrifuged (500 'g at 4° C.), and the cell pellet is resuspended in phosphate-buffered saline. The total number of cells in the lavage fluid is determined, and 2×104 cells are cytocentrifuged (Shandon Southern Products, Pittsburgh, Pa., USA) onto glass slides and stained with Wright-Giemsa stain. Differential cell counts are performed on 300 cells, according to standard cytologic techniques.

Identification of Alveolar Apoptotic Cell Populations in the Lungs.

To identify the different alveolar cell types undergoing apoptosis in the lungs, an immunohistochemical staining of active caspase 3 is performed in the lung sections from the room air (RA) as well as CS exposed mice. To identify the apoptotic type II epithelial cells in the lungs, after active caspase 3 labeling, the lung sections are incubated first with anti-mouse surfactant protein C (SpC) antibody and then with an anti-rabbit Texas red antibody. Apoptotic endothelial cells are identified by incubating the sections first with the anti-mouse CD 31 antibody and then with the biotinylated rabbit anti-mouse secondary antibody. The lung sections are rinsed in PBS and then incubated with the streptavidin-Texas red conjugated complex. The apoptotic macrophages in the lungs are identified by incubating the sections first with the rat anti-mouse Mac-3 antibody and then with the anti-rat Texas red antibody. Finally, DAPI is applied to all lung sections, incubated for 5 minutes, washed and mounted with Vectashield HardSet mounting medium. DAPI and fluorescein are visualized at 330-380 nm and 465-495 nm, respectively. Images of the lung sections are acquired with the Nikon E800 microscope, 40× lens.

Immunohistochemical Localization of Active Caspase-3

Immunohistochemical staining of active caspase-3 assay is performed using anti-active caspase-3 antibody and the active caspase-3-positive cells are counted with a macro, using Image Pro Plus program. The counts are normalized by the sum of the alveolar profiles herein named as alveolar length and expressed in μm. Alveolar length correlates inversely with mean linear intercept, i.e., as the alveolar septa are destroyed, mean linear intercepts increases as total alveolar length, i.e., total alveolar septal length decreases.

Caspase 3 Activity Assay

The caspase-3/7 activity is measured in lung tissue extracts using a fluorometric assay according to the manufacturer's instructions. Snap-frozen lung tissue (n=3 per group) was homogenized with the assay buffer, followed by sonication and centrifugation at 800×g. After removal of nuclei and cellular debris, the supernatant (300 μg protein) is then incubated with the pro-fluorescent substrate at room temperature for 1 h and the fluorescence intensity was measured utilizing a Typhoon phosphoimager (Amersham Biosciences, Inc., Piscataway, N.J., USA). The results are expressed as the rate of specific caspase-3 substrate cleavage, expressed in units of caspase 3 enzymatic activity, normalized by total protein concentration. Active recombinant caspase 3 was utilized as the assay standard (0-4 U). Tissue lysates without substrate, assay buffer alone, and lysates with caspase 3 inhibitor were utilized as negative controls.

Immunohistochemical Localization of 8-Oxo-dG

For the immunohistochemical localization and quantification of 8-oxo-dG, lung sections from the mice exposed to CS or instilled with chemically modified RTP801L are incubated with anti-8-oxo-dG antibody and stained using InnoGenex™ Iso-IHC DAB kit using mouse antibodies. The 8-oxo-dG-positive cells are counted with a macro (using Image Pro Plus), and the counts were normalized by alveolar length as described.

Installation of siRNA into Mouse Lungs

Chemically modified RTP801L (50 ug) is delivered in 80 ul sterile perfluorocarbon. The oxygen carrying properties of perfluorocarbon make it well-tolerated at these volumes, while its physical-chemical properties allow for extremely efficient distal lung delivery when instilled intratracheally.

Mice are anesthetized by brief inhalational halothane exposure, the tongue is gently pulled forward by forceps and the trachea instilled with perfluorocarbon solution applied at the base of the tongue via a blunt angiocatheter.

Mice are anesthetized with an intra-peritoneal injection of Ketamine/Xylazine (115/22 mg/kg). 50 µg of siRNA is instilled intranasally in 50 µl volume of 0.9% NaCl by delivering five consecutive 10 µl portions. At the end of the intranasal instillation, the mouse's head is held straight up for 1 minute to ensure that all the instilled solution drains inside.

For further information, see: Rangasamy T, et al., 2004. *J.C.I.* 114(9):1248-59; Kasahara, Y et al., *Am J Respir Crit. Care Med* Vol 163. pp 737-744, 2001; Kasahara, Y et al., 2000. *J. Clin. Invest.* 106:1311-1319; and Tuder, R M et al., *Pulmonary Pharmacology & Therpaeutics* 2002.

Example 4

Models and Results Relating to Microvascular Disorders

The compounds of the present invention are tested in animal models of a range of microvascular disorders as described below.

1. Diabetic Retinopathy

RTP801L promotes neuronal cell apoptosis and generation of reactive oxygen species in vitro. Experiment 1: Diabetes is induced in 8 wk old RTP801L KO and C57/129sv wildtype (WT) littermate mice by intraperitoneal injection of STZ. After 4 weeks, ERG (single white flash, $1.4 \times 10^4$ ftc, 5 ms) is obtained from the left eye after 1 hour of dark adaptation. RVP is assessed from both eyes using the Evans-blue albumin permeation technique.

Experiment 2: Diabetes is induced in RTP801L knockout and in control wild type mice with the matched genetic background. In addition, it is induced in C57B16 mice, which are subsequently used for intravitreal injection of anti-RTP801L and control siRNAs. For diabetes induction, the mice are injected with streptozotocin (STZ 90 mg/kg/d for 2 days after overnight fast). Animal physiology is monitored throughout the study for changes in blood glucose, body weight, and hematocrit. Vehicle-injected mice serve as controls. The appropriate animals are treated by intravitreal injections of 1µg of RTP801L siRNA or 1µg of GFP control siRNA. siRNA is injected twice in the course of the study—on day 0, when the first STZ injection is performed, and on day 14 after the STZ injection.

Retinal vascular leakage is measured using the Evans-blue (EB) dye technique on the animals after 4 weeks duration of diabetes. Mice have a catheter implanted into the right jugular vein 24 hours prior to Evans Blue (EB) measurements. Retinal permeability measurements in both eyes of each animal follows a standard Evans-blue protocol.

2. Retinopathy of Prematurity

Retinopathy of prematurity is induced by exposing the test animals to hypoxic and hyperoxic conditions, and subsequently testing the effects on the retina.

3. Myocardial Infarction

Myocardial infarction is induced by Left Anterior Descending artery ligation in mice, both short term and long term.

4. Microvascular Ischemic Conditions

Animal models for assessing ischemic conditions include:

1. Closed Head Injury (CHI)—Experimental TBI produces a series of events contributing to neurological and neurometabolic cascades, which are related to the degree and extent of behavioral deficits. CHI is induced under anesthesia, while a weight is allowed to free-fall from a prefixed height (Chen et al, J. Neurotrauma 13, 557, 1996) over the exposed skull covering the left hemisphere in the midcoronal plane.

2. Transient middle cerebral artery occlusion (MCAO)— a 90 to 120 minutes transient focal ischemia is performed in adult, male Sprague Dawley rats, 300-370 gr. The method employed is the intraluminal suture MCAO (Longa et al., Stroke, 30, 84, 1989, and Dogan et al., J. Neurochem. 72, 765, 1999). Briefly, under halothane anesthesia, a 3-0-nylon suture material coated with Poly-L-Lysine is inserted into the right internal carotid artery (ICA) through a hole in the external carotid artery. The nylon thread is pushed into the ICA to the right MCA origin (20-23 mm). 90-120 minutes later the thread is pulled off, the animal is closed and allowed to recover.

3. Permanent middle cerebral artery occlusion (MCAO)— occlusion is permanent, unilateral-induced by electrocoagulation of MCA. Both methods lead to focal brain ischemia of the ipsilateral side of the brain cortex leaving the contralateral side intact (control). The left MCA is exposed via a temporal craniectomy, as described for rats by Tamura A., et al., *J Cereb Blood Flow Metab.* 1981; 1:53-60. The MCA and its lenticulostriatal branch are occluded proximally to the medial border of the olfactory tract with microbipolar coagulation. The wound is sutured, and animals returned to their home cage in a room warmed at 26° C. to 28° C. The temperature of the animals is maintained all the time with an automatic thermostat.

5. Acute Renal Failure (ARF)

Testing active siRNA for treating ARF is done using sepsis-induced ARF or ischemia-reperfusion-induced ARF.

1. Sepsis induced ARF

Two predictive animal models of sepsis-induced ARF are described by Miyaji T, et al., Kidney Int. 64(5):1620-31. These two models are lipopolysaccharide administration and cecal ligation puncture in mice, preferably in aged mice.

2. Ischemia-Reperfusion-Induced ARF

This predictive animal model is described by Kelly K J, et al., 2003. J Am Soc Nephrol.; 14(1):128-38.

Ischemia-reperfusion injury is induced in rats following 45 minutes bilateral kidney arterial clamp and subsequent release of the clamp to allow 24 hours of reperfusion. RTP801L siRNA or GFP siRNA (negative control) are injected into the jugular vein 2 hrs prior to and 30 minutes following the clamp. Additional siRNA is given via the tail vein at 4 and 8 hrs after the clamp. ARF progression is monitored by measurement of serum creatinine levels before and 24 hrs post surgery. At the end of the experiment, the rats are perfused via an indwelling femoral line with warm PBS followed by 4% paraformaldehyde. The left kidneys are removed and stored in 4% paraformaldehyde for subsequent histological analysis. Acute renal failure is frequently defined as an acute increase of the serum creatinine level from baseline. An increase of at least 0.5 mg per dL or 44.2 µmol per L of serum creatinine is considered as an indication for acute renal failure. Serum creatinine is measured at time zero before the surgery and at 24 hours post ARF surgery. siRNA to 801L prevents production of ARF in this model.

To study the distribution of siRNA in the rat kidney, Cy3-labeled 19-mer blunt-ended siRNA molecules (2 mg/kg) having alternating O-methyl modification in the sugar residues were administered iv for 3-5 min, after which in vivo imaging was conducted using two-photon confocal microscopy. The confocal microscopy analysis revealed that the majority of siRNA in the kidneys is concentrated in the endosomal compartment of proximal tubular cells. Both endosomal and cytoplasmic siRNA fluorescence were relatively stable during the first 2 hrs post delivery and disappeared at 24 hrs.

The expression of RTP801L during ischemia-reperfurion induced ARF was examined in rat kidneys. In both kidney regions, cortex and medulla, RTP801L transcript level is decreased in the ARF-10 hr group relative to the control group transcript level. RTP801L transcript level is also elevated (up-regulated) in the kidney medulla, 3 and 6 hrs following the ARF operation (bilateral renal artery clamp).

Example 5

Selection and Preparation of siRNAs

Using proprietary algorithms and the known sequence of the mRNA of gene RTP801L (SEQ ID NO:1), the sequences of many potential siRNAs were generated. siRNA molecules according to the above specifications were prepared essentially as described herein.

The siRNAs of the present invention can be synthesized by any of the methods which are well-known in the art for synthesis of ribonucleic (or deoxyribonucleic) oligonucleotides. For example, a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The siRNA molecules of the invention are synthesized by procedures known in the art e.g. the procedures as described in Usman et al., 1987, *J. Am. Chem. Soc.,* 109, 7845; Scaringe et al., 1990, *Nucleic Acids Res.,* 18, 5433; Wincott et al., 1995, *Nucleic Acids Res,* 23, 2677-2684; and Wincott et al., 1997, *Methods Mol. Bio.,* 74, 59, and may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

Alternatively, the nucleic acid molecules of the present invention can be synthesized separately and joined together post-synthetically, for example, by ligation (Moore et al., 1992, *Science* 256, 9923; Draper et al., International PCT publication No. WO93/23569; Shabarova et al., 1991, *Nucleic Acids Research* 19, 4247; Bellon et al., 1997, *Nucleosides & Nucleotides,* 16, 951; Bellon et al., 1997, *Bioconjugate Chem.* 8, 204), or by hybridization following synthesis and/or deprotection.

The siRNA molecules of the invention can also be synthesized via a tandem synthesis methodology, as described in US patent application publication No. US2004/0019001 (McSwiggen) wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker. Note that in the attached Table A, the sense and antisense strands of siRNAs have SEQ ID NOS: 2-1851.

Similarly, the sense and antisense strands of the siRNAs in attached tables B-F have SEQ ID NOS:1852-6927.

Further note that the coding region of gene RTP801L, as presented in FIG. 1, is between nucleotides 204-785. Therefore, any siRNA within this region targets the coding region of RTP801L, and any siRNA outside this region targets the non-coding region of RTP801L i.e. the 5'UTR or the 3' UTR. The exact region targeted by each siRNA is given in the above Tables.

Additionally, sequences presented in the Tables are depicted in the 5' to 3' direction.

Example 6

Pharmacology and Drug Delivery

The compounds or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

The treatment generally has a length proportional to the length of the disease process and drug effectiveness and the patient species being treated. It is noted that humans are treated generally longer than the mice or other experimental animals exemplified herein.

The compounds of the present invention are administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms are prepared for injection, the term including subcutaneous, transdermal, intravenous, intramuscular, intrathecal, and other parental routes of administration. The liquid compositions include aqueous solutions, with and without organic cosolvents, aqueous or oil suspensions, emulsions with edible oils, as well as similar pharmaceutical vehicles. In addition, under certain circumstances the compositions for use in the novel treatments of the present invention are formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention.

When administering the compound of the present invention parenterally, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions.

The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compound in tablets, suspensions, solutions, emulsions, capsules, powders, syrups and the like are usable. Known techniques which deliver it orally or intravenously and retain the biological activity are preferred. In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-2 weeks or longer, preferably for 24- to 48 hrs or by continuous infusion during a period of 1-2 weeks or longer.

Administration of Compounds of the Present Invention to the Eye

The compounds of the present invention can be administered to the eye topically or in the form of an injection, such as an intravitreal injection, a sub-retinal injection or a bilateral injection. Preferred methods of delivery to the eye is using siRNA dormulated as eye drops.

Further information on administration of the compounds of the present invention can be found in Tolentino et al., *Retina* 24 (2004) 132-138; Reich et al., *Molecular vision* 9 (2003) 210-216.

Pulmonary Administration of Compounds of the Present Invention

The therapeutic compositions of the present invention are preferably administered into the lung by inhalation of an aerosol containing these compositions/compounds, or by intranasal or intratracheal instillation of said compositions. Formulating the compositions in liposomes may benefit absorption. Additionally, the compositions may include a PFC liquid such as perflubron, and the compositions formulated as a complex of the compounds of the invention with polyethylemeimine (PEI).

For further information on pulmonary delivery of pharmaceutical compositions see Weiss et al., *Human gene therapy* 10:2287-2293 (1999); Densmore et al., *Molecular therapy* 1:180-188 (1999); Gautam et al., *Molecular therapy* 3:551-556 (2001); and Shahiwala & Misra, *AAPS PharmSciTech* 5 (2004). Additionally, respiratory formulations for siRNA are described in U.S. patent application No. 2004/0063654 of Davis et el.

Further, the compounds of the present invention are administered topically where appropriate (such as in the case of diabetic foot ulcers for example), optionally in a lipid/liposome formulation, or for use in iontophoresis.

A preferred administration mode is topical delivery of the RTP801L inhibitors onto the round window membrane of the cochlea as disclosed for example in Tanaka et al. (*Hear Res.* 2003; 177(1-2):21-31). Preferred delivery to the inner ear comprising administering the siRNA as an ear drop formulation.

In the treatment of pressure sores or other wounds, the administration of the pharmaceutical composition is preferably by topical application to the damages area, but the compositions may also be administered systemically.

Additional formulations for improved delivery of the compounds of the present invention can include non-formulated compounds, compounds covalently bound to cholesterol, and compounds bound to targeting antibodies (Song et al., 2005. *Nat. Biotechnol.* 23(6):709-17).

Example 7

Model Systems for Pressure Sores or Pressure Ulcers

Pressure sores or pressure ulcers including diabetic ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's situation.

Testing the active inhibitors of the invention (such as siRNA) for treating pressure sore, ulcers and similar wounds is done in the mouse model described in Reid R R, et al., J Surgical Research. 116: 172-180, 2004.

Additionally, a rabbit model is described by Mustoe et al, JCI, 1991; Ahn & Mustoe, Ann PI Surg, 1991 and is used for testing the siRNAs of the invention.

Example 8

Model Systems for Spinal Cord Injury

Spinal cord injury, or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases which can affect the spinal cord include polio, spina bifida, tumors and Friedreich's ataxia.

Testing the active inhibitors of the invention (such as siRNA) for treating spinal cord injury is done in the rat spinal cord contusion model as described by Young, W. in *Prog Brain Res.* 2002; 137:231-55. Other predictive animal models of spinal cord injury are described in the following references: Gruner, J A 1992. *J Neurotrauma* 9(2): 123; Hasegawa, K. and M. Grumet 2003. *J Neurosurg* 98(5): 1065-71; and Huang, P P and W. Young (1994). *J Neurotrauma* 11(5): 547.

Example 9

Model Systems for Glaucoma

Testing the active inhibitors of the invention (such as siRNA) for treating or preventing Glaucoma is done in the animal model for example as described by Pease et al., J. Glaucoma, 2006, 15(6):512-9 (Manometric calibration and comparison of TonoLab and TonoPen tonometers in rats with experimental glaucoma and in normal mice).
Rat Optic Nerve Crush (ONC) Model: Intravitreal siRNA Delivery and Eye Drop Delivery For optic nerve transsection the orbital optic nerve (ON) of anesthetized rats is exposed through a supraorbital approach, the meninges severed and all axons in the ON transected by crushing with forceps for 10 seconds, 2 mm from the lamina cribrosa.

The siRNA compounds are delivered alone or in combination in 5 uL volume (10 ug/uL) as eye drops. Immediately after optic nerve crush (ONC), 20 ug/10 ul test siRNA or 10 ul PBS is administered to one or both eyes of adult Wistar rats and the levels of siRNA taken up into the dissected and snap frozen whole retinae at 5 h and 1 d, and later at 2 d, 4 d, 7 d, 14 d and 21 d post injection is determined. Similar experiments are performed in order to test activity and efficacy of siRNA administered via eye drops.

Example 10

Model Systems for Ischemia and Reperfusion Injury Following Lung Transplantation in Rats Testing the active inhibitors of e invention (such as siRNA) for treating or preventing Ischemia and reperfusion injury following lung transplantation is done in the animal model for example as described by Mizobuchi et al., J. Heart Lung Transplant 2004: 23:889-93.

Example 11

Model Systems for Acute Lung Injury (ALI)

Intratracheal (i.t) administration of LPS (Lipopolysaccharide), a bacterial cell wall component, is an accepted experimental model of acute lung injury (ALI), as LPS stimulates profound lung recruitment of inflammatory cells and the subsequent development of systemic inflammation.

(See, for example, Fang W F, et al., Am J Physiol Lung Cell Mol. Physiol. 2007 293(2):L336-44; Hagiwara S, Iwasaka H, Noguchi T. J Anesth. 2007; 21(2):164-70).

Time-dependent changes of RTP801L gene expression in mice lungs during the first 24 hours (time points 0.5; 1; 2; 4; 8 & 24 hours), after Intratracheal (i.t) administration of LPS was assessed. The assessment of gene expression was done using qPCR.

The results indicate that the level of the RTP801L transcript is gradually decreased following LPS instillation.

Example 12

Model Systems for Acute Respiratory Distress Syndrome

Testing the active inhibitors of the invention (such as siRNA) for treating Acute respiratory distress syndrome is performed, inter alia, in the animal model as described by Chen et al. in J Biomed Sci. 2003; 10(6 Pt 1):588-92.

Example 13

Model Systems for Hearing Loss Conditions (i) Animal Model of Carboplatin-Induced or Cisplatin-Induced Hair Cell Death in the Cochlea of Chinchilla:

Chinchillas are pre-treated by direct administration of specific siRNAs to RTP801L in saline to the left ear of each animal. Saline is given to the right ear of each animal as placebo. Two days following the administration of the specific siRNA, the animals are treated with carboplatin (75 mg/kg ip) or cisplatin (intraperitoneal infusion of 13 mg/kg over 30 minutes). After sacrifice of the chinchillas (two weeks post carboplatin treatment) the percentage of dead cells of inner hair cells (IHC) and outer hair cells (OHC) is calculated in the left ear (siRNA treated) and in the right ear (saline treated). The percentage of dead cells is lower in the siRNA treated ear than in the control (ii) Animal Model of Acoustic-Induced Hair Cell Death in the Cochlea of Chinchilla:

The activity of specific siRNA to RTP801L (e.g. chemically modified siRNA Nos: 72 or 73 in Table A) in an acoustic trauma model is studied in chinchilla. The animals are exposed to an octave band of noise centered at 4 kHz for 2.5 h at 105 dB. The left ear of the noise-exposed chinchillas is pre-treated (48 h before the acoustic trauma) with 30 μg of either siRNA in ~10 μL of saline; the right ear is pre-treated with vehicle (saline). The compound action potential (CAP) is a convenient and reliable electrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear is assessed 2.5 weeks after the acoustic trauma. Specifically, the mean threshold of the compound action potential recorded from the round window is determined 2.5 weeks after the acoustic trauma in order to determine if the thresholds in the siRNA-treated ear are lower (better) than the untreated (saline) ear. In addition, the amount of inner and outer hair cell loss is determined in the siRNA-treated and the control ear. It is found that the thresholds in the siRNA-treated ear are lower than the untreated (saline) ear Also, the amount of hair cell loss is lower in the siRNA-treated ear than in the control ear.

Example 14

RTP801L siRNA Structures and Activity

In addition to Example 1 the siRNA compounds of the present invention are tested in the following model. The following negative controls were used:
a) Cy3-labeled synthetic stabilized siRNA against human, mouse and rat PTEN gene (PTEN-Cy3). Stock solution 20 mg/ml in double distilled.
b) Synthetic stabilized siRNA against GFP (GFP siRNA). Stock solution 20 mg/ml in double distilled.
The cells used in the experiment were 801 wt and Ko mouse embryonic fibroblasts (MEF) cells and 293T embryonic kidney cells.

The transfection reagent used was Lipofectamine™ 2000 (Invitrogen, Cat#11668-019).

Methods: $3 \times 10^5$ and $1 \times 10^5$ 801 wt MEF and 293T cells were seeded per well of the 6 wells plate, respectively. 24 h subsequently, cells were transfected with:
RTP801L siRNA molecules at final concentrations per well of 0.5-40 nM
GFP siRNA molecules at final concentrations per well of 0.5-40 nM
PTEN-Cy3 siRNA at final concentrations per well of 20-40 nM
Transfection mixture per each well contained 3 ul lipofectamine 2000 reagent (in 250 ul serum free medium).

RNA was extracted from cells 72 h following transfection. In the last 8 h of incubation, 500 uM $H_2O_2$ was added to wt MEF cells.

RNA was prepared from the cells and processed, and qPCR was performed for the evaluation of RTP801L mRNA levels, using mouse or human RTP801L-specific oligonucleotides and Cyclophylin as a reference gene.

TABLE A 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 1 | Hum | GCCAGUGUUCUAACAAACU | AGUUUGUUAGAACACUGGC | [2242-2260] | — | — | — | — |
| 2 | Hum | UAGCCAGUGUUCUAACAAA | UUUGUUAGAACACUGGCUA | [2240-2258] | — | — | — | — |
| 3 | Hum | GUGACUUCCUCACUCUAAU | AUUAGAGUGAGGAAGUCAC | [1385-1403] | — | — | — | — |
| 4 | Hum | AGCCAGUGUUCUAACAAAC | GUUUGUUAGAACACUGGCU | [2241-2259] | — | — | — | — |
| 5 | Hum | GAGUGAAUGAUGAAUACCU | AGGUAUUCAUCAUUCACUC | [1577-1595] | — | — | — | — |
| 6 | Hum | GACUUCCUCACUCUAAUGU | ACAUUAGAGUGAGGAAGUC | [1387-1405] | — | — | — | — |
| 7 | Hum | GUUCUAACAAACUAAACUC | GAGUUUAGUUUGUUAGAAC | [2248-2266] | — | — | [531-541] (11/11) | — |
| 8 | Hum | GAAUGAUGAAUACCUGUGA | UCACAGGUAUUCAUCAUUC | [1581-1599] | — | — | — | — |
| 9 | Hum | UCCUCACUCUAAUGUUUUA | UAAAACAUUAGAGUGAGGA | [1391-1409] | — | — | — | — |
| 10 | Hum, ms, rat, chimp | GCCAGAAUUUGGUUAAAAU | AUUUUAACCAAAUUCUGGC | [364-382] | [362-380] | [243-261] | [484-502] | — |
| 11 | Hum | ACGGGUCAAUUUACGAAGU | ACUUCGUAAAUUGACCCGU | [1809-1827] | — | — | — | — |
| 12 | Hum | UCCAUUGAGUGAAUGAUGA | UCAUCAUUCACUCAAUGGA | [1571-1589] | — | — | — | — |
| 13 | Hum | UUCCUCACUCUAAUGUUUU | AAAACAUUAGAGUGAGGAA | [1390-1408] | — | — | — | — |
| 14 | Hum | GCACCCAGAUUUUUCCAC | GUGGAAAAAUCUGGGUGC | [1901-1919] | — | — | — | — |
| 15 | Hum | GUGGUGCCAUUUCAGUAAC | GUUACUGAAAUGGCACCAC | [1428-1446] | — | — | — | — |
| 16 | Hum | CCUCACUCUAAUGUUUUAA | UUAAAACAUUAGAGUGAGG | [1392-1410] | — | — | — | — |
| 17 | Hum | CUUCCUCACUCUAAUGUUU | AAACAUUAGAGUGAGGAAG | [1389-1407] | — | — | — | — |
| 18 | Hum | GGCUUUUUUUCUCUAAGU | ACUUAGAGAAAAAAGCC | [1153-1171] | — | — | — | — |
| 19 | Hum | UCCAUUUUGUACAGAAU | AUUCUGUACAAAAUGGGA | [1005-1023] | — | — | — | — |
| 20 | Hum | GAGAAGUGAUUCAAAAUAG | CUAUUUUGAAUCACUUCUC | [967-985] | — | — | — | — |

TABLE A-continued

| | | | | 19 mer | | | | |
|---|---|---|---|---|---|---|---|---|
| No | Sp-Source | Sense siRNA | AntiSense siRNA | Hum 34222182 cds = 204-785 | Mouse 31541838 | rat 62644440 | chimp 55622975 | dog 74002279 |
| 21 | Hum | GGAGAAGUGAUUCAAAAUA | UAUUUUGAAUCACUUCUCC | [966-984] | — | — | — | — |
| 22 | Hum | GUCAGCUAAAGUCAUUUGU | ACAAAUGACUUUAGCUGAC | [841-859] | — | — | — | — |
| 23 | Hum, chimp | CCGGCCAGCAUUUCAGAAU | AUUCUGAAAUGCUGGCCGG | [237-255] | [235-251] (17/17) | [117-132] (16/16) | [357-375] | — |
| 24 | Hum, chimp, dog | AUGCUGGAGAACUGUCUGU | ACAGACAGUUCUCCAGCAU | [381-399] | [383-397] (15/15) | [264-278] (15/15) | [501-519] | [363-381] |
| 25 | Hum, chimp, dog | AAAUGCUGGAGAACUGUCU | AGACAGUUCUCCAGCAUUU | [379-397] | [377-395] (18/19) | [258-276] (18/19) | [499-517] | [361-379] |
| 26 | Hum, chimp | UGGUUAAAAUGCUGGAGAA | UUCUCCAGCAUUUUAACCA | [373-391] | [371-389] (18/19) | [252-270] (18/19) | [493-511] | [359-373] (15/15) |
| 27 | Hum, chimp | UUGGUUAAAAUGCUGGAGA | UCUCCAGCAUUUUAACCAA | [372-390] | [370-388] (18/19) | [251-269] (18/19) | [492-510] | [354-372] (18/19) |
| 28 | Hum | UAGCUCCACUUCACAUGCU | AGCAUGUGAAGUGGAGCUA | [2118-2136] | — | — | — | — |
| 29 | Hum | AGCCUCCACUCAACAAUGU | ACAUUGUUGAGUGGAGGCU | [2023-2041] | — | — | — | — |
| 30 | Hum | ACCCAGAUUUUUUCCACCU | AGGUGGAAAAAAUCUGGGU | [1903-1921] | — | — | — | — |
| 31 | Hum | UGCACCCAGAUUUUUUCCA | UGGAAAAAAUCUGGGUGCA | [1900-1918] | — | — | — | — |
| 32 | Hum | AAACGGGUCAAUUUACGAA | UUCGUAAAUUGACCCGUUU | [1807-1825] | — | — | — | — |
| 33 | Hum | AUGAUGAAUACCUGUGAGG | CCUCACAGGUAUUCAUCAU | [1583-1601] | — | — | — | — |
| 34 | Hum | UUGAGUGAAUGAUGAAUAC | GUAUUCAUCAUUCACUCAA | [1575-1593] | — | — | — | — |
| 35 | Hum | CGGCAAUAAUGGAACUGCU | AGCAGUUCCAUUAUUGCCG | [1353-1371] | — | — | — | — |
| 36 | Hum | GCCUAUCAAAACUUCCAAA | UUUGGAAGUUUUGAUAGGC | [1218-1236] | — | — | — | [1182-1194] (13/13) |
| 37 | Hum | UGGCUUUUUUUUCUCUAAG | CUUAGAGAAAAAAAGCCA | [1152-1170] | — | — | — | — |
| 38 | Hum | GCCCAUUUGAGUUUUACAU | AUGUAAAACUCAAAUGGGC | [1057-1075] | — | — | — | — |
| 39 | Hum, chimp | GGCCAGCAUUUCAGAAUUG | CAAUUCUGAAAUGCUGGCC | [239-257] | [237-251] (15/15) | [118-132] (15/15) | [359-377] | — |
| 40 | Hum, chimp | CGGCCAGCAUUUCAGAAUU | AAUUCUGAAAUGCUGGCCG | [238-256] | [236-251] (16/16) | [117-132] (16/16) | [358-376] | — |
| 41 | Hum | GCGUCGUACCUACUUUUGA | UCAAAAGUAGGUACGACGC | [589-607] | — | — | [711-727] (16/17) | — |
| 42 | Hum | UAGCGUCGUACCUACUUUU | AAAAGUAGGUACGACGCUA | [587-605] | — | — | — | — |
| 43 | Hum, rat, dog | AUGCACGUGAACUUGGAAA | UUUCCAAGUUCACGUGCAU | [525-543] | [523-539] (17/17) | [404-422] | [645-663] (18/19) | [507-525] |
| 44 | Hum | UUGUCCUUUUUCCACUAAC | GUUAGUGGAAAAAGGACAA | [2441-2459] | — | — | — | — |
| 45 | Hum | GUUGUCCUUUUUCCACUAA | UUAGUGGAAAAAGGACAAC | [2440-2458] | — | — | — | — |
| 46 | Hum | CUGUUGUCCUUUUUCCACU | AGUGGAAAAAGGACAACAG | [2438-2456] | — | — | — | — |
| 47 | Hum, chimp, dog | CUGGAGAACUGUCUGUCCA | UGGACAGACAGUUCUCCAG | [384-402] | [383-400] (18/18) | [264-281] (18/18) | [504-522] | [366-384] |

TABLE A-continued

19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 48 | Hum | GCCAAUCUUUAUAGAAUUG | CAAUUCUAUAAAGAUUGGC | [2294-2312] | — | — | — | — |
| 49 | Hum | GUUCAAAUUAGCCAGUGUU | AACACUGGCUAAUUUGAAC | [2232-2250] | — | — | — | — |
| 50 | Hum, ms, rat, chimp | UGCCAGAAUUUGGUUAAAA | UUUUAACCAAAUUCUGGCA | [363-381] | [361-379] | [242-260] | [483-501] | — |
| 51 | Hum | CCCAGAUUUUUUCCACCUU | AAGGUGGAAAAAAUCUGGG | [1904-1922] | — | — | — | — |
| 52 | Hum | CACCCAGAUUUUUUCCACC | GGUGGAAAAAAUCUGGGUG | [1902-1920] | — | — | — | — |
| 53 | Hum | CAAUUUACGAAGUCUGCAU | AUGCAGACUUCGUAAAUUG | [1815-1833] | — | — | — | — |
| 54 | Hum | GGGUCAAUUUACGAAGUCU | AGACUUCGUAAAUUGACCC | [1811-1829] | — | — | — | — |
| 55 | Hum | AACGGGUCAAUUUACGAAG | CUUCGUAAAUUGACCCGUU | [1808-1826] | — | — | — | — |
| 56 | Hum | UGAAACGGGUCAAUUUACG | CGUAAAUUGACCCGUUUCA | [1805-1823] | — | — | — | — |
| 57 | Hum | UGGUGCCAUUUCAGUAACC | GGUUACUGAAAUGGCACCA | [1429-1447] | — | — | — | — |
| 58 | Hum | UGGAACUGCUUCACUGUUU | AAACAGUGAAGCAGUUCCA | [1362-1380] | — | — | — | [1333-1343] (11/11) |
| 59 | Hum | AAGGUAGGAUUAAGUAGGU | ACCACUUAAUCCUACCUU | [1286-1304] | — | — | — | — |
| 60 | Hum | CAGGAAGGUAGGAUUAAGU | ACUUAAUCCUACCUUCCUG | [1282-1300] | — | — | — | — |
| 61 | Hum | AGCCUAUCAAAACUUCCAA | UUGGAAGUUUUGAUAGGCU | [1217-135] | — | — | — | [1182-1194] (13/13) |
| 62 | Hum | AACCAGAUUUGCCUAUUUU | AAAAUAGGCAAAUCUGGUU | [1123-1141] | — | — | — | — |
| 63 | Hum | GUACAGAAUUGAAUGGGAU | AUCCCAUUCAAUUCUGUAC | [1015-1033] | — | — | — | — |
| 64 | Hum | AUCCCAUUUUUGUACAGAA | UUCUGUACAAAAAUGGGAU | [1004-1022] | — | — | — | — |
| 65 | Hum | CAGCUAAAGUCAUUUGUAG | CUACAAAUGACUUUAGCUG | [843-861] | [845-856] (12/12) | — | — | [834-844] (11/11) |
| 66 | Hum | AUGAUUGGGUAGUAAAACU | AGUUUUACUACCCAAUCAU | [813-831] | — | — | — | — |
| 67 | Hum | AGGGUCCUAAAAAGGGAAA | UUUCCCUUUUUAGGACCCU | [776-794] | — | — | — | — |
| 68 | Hum, rat, dog | ACGUGAACUUGGAAAUUGA | UCAAUUUCCAAGUUCACGU | [529-547] | [527-545] (18/19) | [408-426] | [651-667] (17/17) | [511-529] |
| 69 | Hum, ms, chimp | GAAUUGCUCAAGAUGUCCU | AGGACAUCUUGAGCAAUUC | [463-481] | [461-479] | [342-360] | [583-601] | [447-463] (17/17) |
| 70 | Hum, ms, chimp | GAGAAUUGCUCAAGAUGUC | GACAUCUUGAGCAAUUCUC | [461-479] | [459-477] | — | [581-599] | [447-461] (15/15) |
| 71 | Hum, ms, chimp | AGAGAAUUGCUCAAGAUGU | ACAUCUUGAGCAAUUCUCU | [460-478] | [458-476] | — | [580-598] | [442-460] (18/19) |
| 72 | Hum, ms, chimp | CCAGAGAAUUGCUCAAGAU | AUCUUGAGCAAUUCUCUGG | [458-476] | [456-474] | [337-355] | [578-596] | [440-458] (18/19) |
| 73 | Hum, ms, chimp | CCCAGAGAAUUGCUCAAGA | UCUUGAGCAAUUCUCUGGG | [457-475] | [455-473] | [336-354] | [577-595] | [439-457] (18/19) |

TABLE A-continued 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 74 | Hum, chimp, dog | AACUGUCUGUCCAAAUCAA | UUGAUUUGGACAGACAGUU | [390-408] | [388-406] (18/19) | [269-287] (18/19) | [510-528] | [372-390] |
| 75 | Hum | UGUCCUUUUUCCACUAACA | UGUUAGUGGAAAAAGGACA | [2442-2460] | — | — | — | — |
| 76 | Hum | GAACUGUUGUCCUUUUUCC | GGAAAAGGACAACAGUUC | [2435-2453] | — | — | — | — |
| 77 | Hum, chimp, dog | GGAGAACUGUCUGUCCAAA | UUUGGACAGACAGUUCUCC | [366-404] | [384-400] (17/17) | [265-282] (18/18) | [506-524] | [368-386] |
| 78 | Hum | CAGUGUUCUAACAAACUAA | UUAGUUUGUUAGAACACUG | [2244-2262] | — | — | — | — |
| 79 | Hum | AAAUUAGCCAGUGUUCUAA | UUAGAACACUGGCUAAUUU | [2236-2254] | — | — | — | — |
| 80 | Hum | GACCUAAAAUGUCACUGUU | AACAGUGACAUUUUAGGUC | [2216-2234] | — | — | — | — |
| 81 | Hum, chimp | UUGCCAGAAUUUGGUUAAA | UUUAACCAAAUUCUGGCAA | [362-380] | [361-378] (18/18) | [242-259] (18/18) | [482-500] | — |
| 82 | Hum | UGGAUAAGGAGCUUAUUCA | UGAAUAAGCUCCUUAUCCA | [2080-2096] | — | — | — | — |
| 83 | Hum | AGCAAGGCUUUCAUAUCCU | AGGAUAUGAAAGCCUUGCU | [2049-2067] | — | — | — | — |
| 84 | Hum | CUCCACUCAACAAUGUUCA | UGAACAUUGUUGAGUGGAG | [2026-2044] | — | — | — | — |
| 85 | Hum | UUAGCCUCCACUCAACAAU | AUUGUUGAGUGGAGGCUAA | [2021-2039] | — | — | — | — |
| 86 | Hum | AGAGAAUUUAGCCUCCACU | AGUGGAGGCUAAAUUCUCU | [2014-2032] | — | — | — | — |
| 87 | Hum | AGAUCAUUAUCUCUUUCCU | AGGAAAGAGAUAAUGAUCU | [1981-1999] | — | — | — | — |
| 88 | Hum | GGCCUUAUUUUUGUCUUA | UAAGACAAAAAUAAGGCC | [1950-1968] | — | — | — | — |
| 89 | Hum | CAGAUUUUUCCACCUUGG | CCAAGGUGGAAAAAUCUG | [1906-1924] | — | — | — | — |
| 90 | Hum | CCAGAUUUUUCCACCUUG | CAAGGUGGAAAAAUCUGG | [1905-1923] | — | — | — | — |
| 91 | Hum | GCCUAGAGAAUGAAACUCA | UGAGUUUCAUUCUCUAGGC | [1862-1880] | — | — | — | — |
| 92 | Hum | UACGAAGUCUGCAUUGGCU | AGCCAAUGCAGACUUCGUA | [1820-1838] | — | — | — | — |
| 93 | Hum | CGGGUCAAUUUACGAAGGC | GACUUCGUAAAUUGACCCG | [1810-1828] | — | — | — | — |
| 94 | Hum | GAAACGGGUCAAUUUACGA | UCGUAAAUUGACCCGUUUC | [1806-1824] | — | — | — | — |
| 95 | Hum | GUCCCUCUCUGAUUCACUU | AAGUGAAUCAGAGAGGGAC | [1626-1644] | [1278-1288] (11/11) | — | — | — |
| 96 | Hum | GAGAGGGACUCCUAAGAA | UUCUUAGGAGUCCCCUCUC | [78-96] | — | — | — | — |
| 97 | Hum | GAAGGUAGGAUUAAGUAGG | CCUACUUAAUCCUACCUUC | [1285-1303] | — | — | — | — |
| 98 | Hum | UAGCCUAUCAAAACUUCCA | UGGAAGUUUUGAUAGGCUA | [1216-1234] | — | — | — | [1182-1194] (13/13) |
| 99 | Hum | CCAUUUUUGUACAGAAUUG | CAAUUCUGUACAAAAAUGG | [1007-1025] | — | — | — | — |
| 100 | Hum | UAGAUCCCAUUUUUGUACA | UGUACAAAAAUGGGAUCUA | [1001-1019] | — | — | — | — |
| 101 | Hum | GCAGCUAACAGGCUGAUUU | AAAUCAGCCUGUUAGCUGC | [937-955] | — | — | — | — |
| 102 | Hum | GUGUUUCACAUUCAUAGCA | UGCUAUGAAUGUGAAACAC | [915-933] | — | — | — | — |
| 103 | Hum | GUCCUAAAAGGGAAAAUA | UAUUUUCCCUUUUAGGAC | [779-797] | — | — | — | — |
| 104 | Hum | GGGUCCUAAAAGGGAAAA | UUUUCCCUUUUAGGACCC | [777-795] | — | — | — | — |
| 105 | Hum | AAGGGUCCUAAAAGGGAA | UUCCCUUUUAGGACCCUU | [775-793] | — | — | — | — |

TABLE A-continued

| | | | | 19 mer | | | | |
|---|---|---|---|---|---|---|---|---|
| No | Sp-Source | Sense siRNA | AntiSense siRNA | Hum 34222182 cds = 204-785 | Mouse 31541838 | rat 62644440 | chimp 55622975 | dog 74002279 |
| 106 | Hum | CAGGGACUUUUUCUUUAGU | ACUAAAGAAAAAGUCCCUG | [653-671] | — | — | [773-789] (17/17) | — |
| 107 | Hum, rat, dog | UGCACGUGAACUUGGAAAU | AUUUCCAAGUUCACGUGCA | [526-544] | [524-539] (16/16) | [405-423] | [646-664] (18/19) | [508-526] |
| 108 | Hum, ms, rat, dog | GUGUUAUGCACGUGAACUU | AAGUUCACGUGCAUAACAC | [520-538] | [518-536] | [399-417] | — | [502-520] |
| 109 | Hum, ms | GUUGUGUUAUGCACGUGAA | UUCACGUGCAUAACACAAC | [517-535] | [515-533] | [398-414] (17/17) | [637-655] (18/19) | [501-517] (17/17) |
| 110 | Hum | GAGGUUGUGUUAUGCACGU | ACGUGCAUAACACAACCUC | [514-532] | [514-530] (17/17) | [398-411] (14/14) | [634-649] (16/16) | [496-514] (18/19) |
| 111 | Hum, ms, chimp | GACCCAGAGAAUUGCUCAA | UUGAGCAAUUCUCUGGGUC | [455-473] | [453-471] | [334-348] (15/15) | [575-593] | — |
| 112 | Hum, chimp | AAGCAAACUAAACUUGGUU | AACCAAGUUUAGUUUGCUU | [408-426] | — | — | [528-546] | — |
| 113 | Hum, chimp | CCAAAUCAAAGCAAACUAA | UUAGUUUGCUUUGAUUUGG | [400-418] | [402-413] (12/12) | [279-294] (15/16) | [520-538] | [382-397] (16/16) |
| 114 | Hum | GGAAGGCUGUUAAAUUAAU | AUUAAUUUAACAGCCUUCC | [2512-2530] | — | — | — | — |
| 115 | Hum | UGCCUGUUAUGCUUACAAA | UUUGUAAGCAUAACAGGCA | [2478-2496] | — | — | — | — |
| 116 | Hum | UUGCCUGUUAUGCUUACAA | UUGUAAGCAUAACAGGCAA | [2477-2495] | — | — | — | — |
| 117 | Hum | UGACUCUCUUGCCUGUUAU | AUAACAGGCAAGAGAGUCA | [2469-2487] | — | — | — | — |
| 118 | Hum | GUCCUUUUUCCACUAACAG | CUGUUAGUGGAAAAGGAC | [2443-2461] | — | — | — | — |
| 119 | Hum | UAGAACUGUUGUCCUUUUU | AAAAGGACAACAGUUCUA | [2433-2451] | — | — | — | — |
| 120 | Hum | GUAGAACUGUUGUCCUUUU | AAAAGGACAACAGUUCUAC | [2432-2450] | — | — | — | — |
| 121 | Hum, chimp, dog | GAGAACUGUCUGUCCAAAU | AUUUGGACAGACAGUUCUC | [387-405] | [385-400] (16/16) | [266-282] (17/17) | [507-525] | [369-387] |
| 122 | Hum | GCCAAGAUAAAUCAAUGUU | AACAUUGAUUUAUCUUGGC | [2314-2332] | — | — | — | — |
| 123 | Hum | ACAAAGCCAAUCUUUAUAG | CUAUAAAGAUUGGCUUUGU | [2289-2307] | — | — | — | — |
| 124 | Hum | AUGUCACUGUUCAAAUUAG | CUAAUUUGAACAGUGACAU | [2224-2242] | — | — | — | — |
| 125 | Hum | GUGAUCCUGUUACUGAUAC | GUAUCAGUAACAGGAUCAC | [2190-2208] | — | — | — | — |
| 126 | Hum, chimp | GAAUUGGUUAAAAUGCUG | CAGCAUUUUAACCAAUUC | [368-386] | [366-381] (16/16) | [247-262] (16/16) | [488-506] | — |
| 127 | Hum | AGGCUUUCAUAUCCUUGCU | AGCAAGGAUAUGAAAGCCU | [2053-2071] | — | — | — | — |
| 128 | Hum | CAGCAAGGCUUUCAUAUCC | GGAUAUGAAAGCCUUGCUG | [2048-2066] | — | — | — | — |
| 129 | Hum | GCCUCCACUCAACAAUGUU | AACAUUGUUGAGUGGAGGC | [2024-2042] | — | — | — | — |
| 130 | Hum | GAAUUUAGCCUCCACUCAA | UUGAGUGGAGGCUAAAUUC | [2017-2035] | — | — | — | — |
| 131 | Hum | GAGAGAAUUUAGCCUCCAC | GUGGAGGCUAAAUUCUCUC | [2013-2031] | — | — | — | — |
| 132 | Hum | UAGAUCAUUAUCUCUUUCC | GGAAAGAGAUAAUGAUCUA | [1980-1998] | — | — | — | — |

TABLE A-continued 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 133 | Hum | AGGCCUUAUUUUUUGUCUU | AAGACAAAAAAUAAGGCCU | [1949-1967] | — | — | — | — |
| 134 | Hum | AAGGCCUUAUUUUUUGUCU | AGACAAAAAAUAAGGCCUU | [1948-1966] | — | — | — | — |
| 135 | Hum | GCAUGCACCCAGAUUUUUU | AAAAAAUCUGGGUGCAUGC | [1897-1915] | — | — | — | — |
| 136 | Hum | GGUCAAUUUACGAAGUCUG | CAGACUUCGUAAAUUGACC | [1812-1830] | — | — | — | — |
| 137 | Hum | GGGCUUUUCUGGGAAUUGA | UCAAUUCCCAGAAAAGCCC | [1725-1743] | — | — | — | — |
| 138 | Hum | AUACCUGUGAGGAUAGGAA | UUCCUAUCCUCACAGGUAU | [1590-1608] | — | — | — | — |
| 139 | Hum | ACUCUUCCAUUGAGUGAAU | AUUCACUCAAUGGAAGAGU | [1566-1584] | — | — | — | — |
| 140 | Hum, chimp | GGGAUUAUGUUGUUCCUGA | UCAGGAACAACAUAAUCCC | [307-325] | [305-323] (18/19) | — | [427-445] | — |
| 141 | Hum | UGCCAUUUCAGUAACCACG | CGUGGUUACUGAAAUGGCA | [1432-1450] | — | — | — | — |
| 142 | Hum | UGUGGUGCCAUUUCAGUAA | UUACUGAAAUGGCACCACA | [1427-1445] | — | — | — | — |
| 143 | Hum | AGCUUGUGGUGCCAUUUCA | UGAAAUGGCACCACAAGCU | [1423-1441] | — | — | — | — |
| 144 | Hum | CUCUAAUGUUUUAAAGAGG | CCUCUUUAAAACAUUAGAG | [1397-1415] | — | — | — | — |
| 145 | Hum | GAACUGCUUCACUGUUUCU | AGAAACAGUGAAGCAGUUC | [1364-1382] | — | — | — | [1333-1345] (13/13) |
| 146 | Hum | GGAACUGCUUCACUGUUUC | GAAACAGUGAAGCAGUUCC | [1363-1381] | — | — | — | [1333-1344] (12/12) |
| 147 | Hum | ACGGCAAUAAUGGAACUGC | GCAGUUCCAUUAUUGCCGU | [1352-1370] | — | — | — | — |
| 148 | Hum | ACCCUAGGUAAGAGUAAAU | AUUUACUCUUACCUAGGGU | [1323-1341] | — | — | — | — |
| 149 | Hum | CUCUAAGUUUUCAGAGGAU | AUCCUCUGAAAACUUAGAG | [1164-1182] | — | — | — | — |
| 150 | Hum | GCUUGGUAAUAGACUAUAU | AUAUAGUCUAUUACCAAGC | [1103-1121] | — | — | — | — |
| 151 | Hum | AGGCUUGGUAAUAGACUAU | AUAGUCUAUUACCAAGCCU | [1101-1119] | — | — | — | — |
| 152 | Hum | GAGUUUUACAUUUGAUUCC | GGAAUCAAAUGUAAAACUC | [1065-1083] | — | — | — | — |
| 153 | Hum | GAAGCCCAUUUGAGUUUUA | UAAAACUCAAAUGGGCUUC | [1054-1072] | — | — | — | — |
| 154 | Hum, chimp | GAGCCUGCUAAGUGAUUUU | AAAAUCACUUAGCAGGCUC | [281-299] | [283-296] (14/14) | [164-177] (14/14) | [401-419] | [263-281] (18/19) |
| 155 | Hum | UGUACAGAAUUGAAUGGGA | UCCCAUUCAAUUCUGUACA | [1014-1032] | — | — | — | — |
| 156 | Hum | UUGUACAGAAUUGAAUGGG | CCCAUUCAAUUCUGUACAA | [1013-1031] | — | — | — | — |
| 157 | Hum | GUGAUUCAAAAUAGUGUAG | CUACACUAUUUUGAAUCAC | [972-990] | — | — | — | — |
| 158 | Hum | UUGGAGAAGUGAUUCAAAA | UUUUGAAUCACUUCUCCAA | [964-982] | — | — | — | — |
| 159 | Hum | CAGGCUGAUUUUCUGGCCU | AGGCCAGAAAAUCAGCCUG | [945-963] | [939-949] (11/11) | — | — | — |
| 160 | Hum | GCUAACAGGCUGAUUUUCU | AGAAAAUCAGCCUGUUAGC | [940-958] | [939-949] (11/11) | — | — | — |
| 161 | Hum | GCUAAAGUCAUUUGUAGUU | AACUACAAAUGACUUUAGC | [845-863] | [845-858] (14/14) | — | — | [834-845] (12/12) |
| 162 | Hum | UAGUCAGCUAAAGUCAUUU | AAAUGACUUUAGCUGACUA | [839-857] | — | — | — | — |
| 163 | Hum | CUAGUCAGCUAAAGUCAUU | AAUGACUUUAGCUGACUAG | [838-856] | — | — | — | — |

TABLE A-continued

19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 164 | Hum | UGAUUGGGUAGUAAAACUA | UAGUUUUACUACCCAAUCA | [814-832] | — | — | — | — |
| 165 | Hum, chimp | GCAUUCAGAAUUGCUGGA | UCCAGCAAUUCUGAAAUGC | [244-262] | — | — | [364-382] | — |
| 166 | Hum | GAAGGUCCUAAAAAGGGA | UCCCUUUUAGGACCUUC | [774-792] | — | — | — | — |
| 167 | Hum | GGUUUCAGGAGAACUCUGA | UCAGAGUUCUCCUGAAACC | [690-708] | — | — | — | — |
| 168 | Hum | UCCUCUGGUUUCAGGAGAA | UUCUCCUGAAACCAGAGGA | [684-702] | — | — | — | — |
| 169 | Hum | AGGGACUUUUUCUUUAGUA | UACUAAAGAAAAGUCCCU | [654-672] | — | — | [774-789] (16/16) | — |
| 170 | Hum, chimp | CUACUUUUGAGCUUACACU | AGUGUAAGCUCAAAAGUAG | [598-616] | — | — | [718-736] | — |
| 171 | Hum | CUAGCGUCGUACCUACUUU | AAAGUAGGUACGACGCUAG | [586-604] | — | — | — | — |
| 172 | Hum, ms, rat, chimp | GUAAAAGCUGGAUAGGAU | AUCCUAUCCAGCUUUUUAC | [556-574] | [554-572] | [435-453] | [676-694] | [538-552] (15/15) |
| 173 | Hum, ms, rat, dog | UUAUGCACGUGAACUUGGA | UCCAAGUUCACGUGCAUAA | [523-541] | [521-539] | [402-420] | [643-661] (18/19) | [505-523] |
| 174 | Hum, ms | GGUUGUGUUAUGCACGUGA | UCACGUGCAUAACACAACC | [516-534] | [514-532] | [398-413] (16/16) | [636-654] (18/19) | [501-516] (16/16) |
| 175 | Hum | GCGAGGUUGUGUUAUGCAC | GUGCAUAACACAACCUCGC | [512-530] | [514-528] (15/15) | [398-409] (12/12) | [632-649] (18/18) | [494-512] (18/19) |
| 176 | Hum, chimp | AAAGCAAACUAAACUUGGU | ACCAAGUUUAGUUUGCUUU | [407-425] | — | — | [527-545] | — |
| 177 | Hum | CUGUUAUGCUUACAAAAUG | CAUUUUGUAAGCAUAACAG | [2481-2499] | — | — | — | — |
| 178 | Hum | UCCUUUUUCCACUAACAGU | ACUGUUAGUGGAAAAAGGA | [2444-2462] | — | — | — | — |
| 179 | Hum | CAAUCUUUAUAGAAUUGGG | CCCAAUUCUAUAAAGAUUG | [2296-2314] | — | — | — | — |
| 180 | Hum | CCAAUCUUUAUAGAAUUGG | CCAAUUCUAUAAAGAUUGG | [2295-2313] | — | — | — | — |
| 181 | Hum | AUACUACAAAGCCAAUCUU | AAGAUUGGCUUUGUAGUAU | [2284-2302] | [1571-1581] (11/11) | — | — | — |
| 182 | Hum | CCAGUGUUCUAACAAACUA | UAGUUUGUUAGAACACUGG | [2243-2261] | — | — | — | — |
| 183 | Hum | ACUGUUCAAAUUAGCCAGU | ACUGGCUAAUUUGAACAGU | [2229-2247] | — | — | — | — |
| 184 | Hum | CCUAAAAUGUCACUGUUCA | UGAACAGUGACAUUUUAGG | [2218-2236] | — | — | — | — |
| 185 | Hum | UGACCUAAAAUGUCACUGU | ACAGUGACAUUUUAGGUCA | [2215-2233] | — | — | — | — |
| 186 | Hum | UAAGUGACCUAAAAUGUCA | UGACAUUUUAGGUCACUUA | [2211-2229] | — | — | — | — |
| 187 | Hum | CUAUAAGUGACCUAAAAUG | CAUUUUAGGUCACUUAUAG | [2208-2226] | — | — | — | — |
| 188 | Hum | GUGUGAUCCUGUUACUGAU | AUCAGUAACAGGAUCACAC | [2188-2206] | — | — | — | — |
| 189 | Hum | CCACUUCACAUGCUGGAGA | UCUCCAGCAUGUGAAGUGG | [2123-2141] | — | — | — | — |
| 190 | Hum | GGCUUUCAUAUCCUUGCUG | CAGCAAGGAUAUGAAAGCC | [2054-2072] | — | — | — | — |
| 191 | Hum | GCAAGGCUUUCAUAUCCUU | AAGGAUAUGAAAGCCUUGC | [2050-2068] | — | — | — | — |

TABLE A-continued 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 192 | Hum | CACUCAACAAUGUUCAAUU | AAUUGAACAUUGUUGAGUG | [2029-2047] | — | — | — | — |
| 193 | Hum | UAGCCUCCACUCAACAAUG | CAUUGUUGAGUGGAGGCUA | [2022-2040] | — | — | — | — |
| 194 | Hum | GUAGAUCAUUAUCUCUUUC | GAAAGAGAUAAUGAUCUAC | [1979-1997] | — | — | — | — |
| 195 | Hum | CCACCUUGGAUACCUGUCA | UGACAGGUAUCCAAGGUGG | [1916-1934] | — | — | — | — |
| 196 | Hum | AUGCAUGCACCCAGAUUUU | AAAAUCGGGUGCAUGCAU | [1895-1913] | — | — | — | — |
| 197 | Hum | UUGAAACGGGUCAAUUUAC | GUAAAUUGACCCGUUUCAA | [1804-1822] | — | — | — | — |
| 198 | Hum, chimp | UCAACGAGGUAAUAUUUGA | UCAAAUAUUACCUCGUUGA | [334-352] | — | — | [454-472] | — |
| 199 | Hum, chimp | ACCUCAACGAGGUAAUAUU | AAUAUUACCUCGUUGAGGU | [331-349] | [329-341] (13/13) | [210-222] (13/13) | [451-469] | — |
| 200 | Hum, chimp | CCAACCUCAACGAGGUAAU | AUUACCUCGUUGAGGUUGG | [328-346] | [326-341] (16/16) | [207-222] (16/16) | [448-466] | — |
| 201 | Hum | GUGCUUAAUCUCAGAUGAA | UUCAUCUGAGAUUAAGCAC | [1674-1692] | — | — | — | — |
| 202 | Hum | CUAGUCCCUCUCUGAUUCA | UGAAUCAGAGAGGGACUAG | [1623-1641] | [1278-1288] (11/11) | — | — | — |
| 203 | Hum | AUGAAUACCUGUGAGGAUA | UAUCCUCACAGGUAUUCAU | [1586-1604] | — | — | — | — |
| 204 | Hum | AGAGGGGACUCCUAAGAAG | CUUCUUAGGAGUCCCCUCU | [79-97] | — | — | — | — |
| 205 | Hum | GAUUACUCUUCCAUUGAGU | ACUCAAUGGAAGAGUAAUC | [1562-1580] | — | — | — | — |
| 206 | Hum | UGAUUACUCUUCCAUUGAG | CUCAAUGGAAGAGUAAUCA | [1561-1579] | — | — | — | — |
| 207 | Hum | UAGUUGAUUACUCUUCCAU | AUGGAAGAGUAAUCAACUA | [1557-1575] | — | — | — | — |
| 208 | Hum | GUAGUUGAUUACUCUUCCA | UGGAAGAGUAAUCAACUAC | [1556-1574] | — | — | — | — |
| 209 | Hum | GUGUUGAAUACUGUCUUUA | UAAAGACAGUAUUCAACAC | [1497-1515] | — | — | — | — |
| 210 | Hum | AAGCUCAGUUUCCCCUGUU | AACAGGGGAAACUGAGCUU | [1473-1491] | — | — | — | — |
| 211 | Hum | ACCACGGUGUUGUUUUAGA | UCUAAAACAACACCGUGGU | [1445-1463] | — | — | — | — |
| 212 | Hum | GUGCCAUUUCAGUAACCAC | GUGGUUACUGAAAUGGCAC | [1431-1449] | — | — | — | — |
| 213 | Hum | GGUGCCAUUUCAGUAACCA | UGGUUACUGAAAUGGCACC | [1430-1448] | — | — | — | — |
| 214 | Hum | CUGCUUCACUGUUUCUUGG | CCAAGAAACAGUGAAGCAG | [1367-1385] | — | — | — | [1333-1346] (14/14) |
| 215 | Hum | AACUGCUUCACUGUUUCUU | AAGAAACAGUGAAGCAGUU | [1365-1383] | — | — | — | [1333-1346] (14/14) |
| 216 | Hum | CAAUAAUGGAACUGCUUCA | UGAAGCAGUUCCAUUAUUG | [1356-1374] | — | — | — | — |
| 217 | Hum | AGGUAAGAGUAAAUGAGAA | UUCUCAUUUACUCUUACCU | [1328-1346] | — | — | — | — |
| 218 | Hum | GGAUUAAGUAGGUGAGUUU | AAACUCACCUACUUAAUCC | [1292-1310] | — | — | — | — |
| 219 | Hum | GACUCAAAUUUGAAGGGUU | AACCCUUCAAAUUUGAGUC | [1257-1275] | — | — | — | — |
| 220 | Hum | CAGAUUUGCCUAUUUUGAU | AUCAAAAUAGGCAAAUCUG | [1126-1144] | — | — | — | — |
| 221 | Hum | CCAGAUUUGCCUAUUUUGA | UCAAAAUAGGCAAAUCUGG | [1125-1143] | — | — | — | — |
| 222 | Hum | AUAUAAACCAGAUUUGCCU | AGGCAAAUCUGGUUUAUAU | [1118-1136] | — | — | — | — |
| 223 | Hum | GGCUUGGUAAUAGACUAUA | UAUAGUCUAUUACCAAGCC | [1102-1120] | — | — | — | — |

TABLE A-continued

| | | | | 19 mer | | | | |
|---|---|---|---|---|---|---|---|---|
| No | Sp-Source | Sense siRNA | AntiSense siRNA | Hum 34222182 cds = 204-785 | Mouse 31541838 | rat 62644440 | chimp 55622975 | dog 74002279 |
| 224 | Hum | UUCCACAAUUUGGUUUCAG | CUGAAACCAAAUUGUGGAA | [1080-1098] | — | — | — | — |
| 225 | Hum | UUUGAUUCCACAAUUUGGU | ACCAAAUUGUGGAAUCAAA | [1075-1093] | — | — | — | — |
| 226 | Hum | GGAAUAGGUAAGCAAAAGU | ACUUUUGCUUACCUAUUCC | [1034-1052] | — | — | — | — |
| 227 | Hum | CAGAAUUGAAUGGGAUGGA | UCCAUCCCAUUCAAUUCUG | [1018-1036] | — | — | — | — |
| 228 | Hum | GAUCCCAUUUUGUACAGA | UCUGUACAAAAUGGGAUC | [1003-1021] | — | — | — | — |
| 229 | Hum | AGAUCCCAUUUUGUACAG | CUGUACAAAAUGGGAUCU | [1002-1020] | — | — | — | — |
| 230 | Hum | GUGUAGAUUUCUGCAUAG | CUAUGCAGAAAUCUACAC | [985-1003] | — | — | — | — |
| 231 | Hum | AGGCUGAUUUUCUGGCCUU | AAGGCCAGAAAAUCAGCCU | [946-964] | [939-949] (11/11) | — | — | — |
| 232 | Hum | CACAUUCAUAGCAACUGCA | UGCAGUUGCUAUGAAUGUG | [921-939] | — | — | — | — |
| 233 | Hum | CCCCACCUGCCCUAAAUAA | UUAUUUAGGGCAGGUGGGG | [866-884] | — | — | — | — |
| 234 | Hum | AGCUAAAGUCAUUUGUAGU | ACUACAAAUGACUUUAGCU | [844-862] | [845-857] (13/13) | — | — | [834-845] (12/12) |
| 235 | Hum | UCAGCUAAAGUCAUUUGUA | UACAAAUGACUUUAGCUGA | [842-860] | [845-855] (11/11) | — | — | — |
| 236 | Hum | CAGCUAGUCAGCUAAAGUC | GACUUUAGCUGACUAGCUG | [835-853] | — | — | — | — |
| 237 | Hum | UGGGUAGUAAAACUAUUCA | UGAAUAGUUUUACUACCCA | [818-836] | — | — | — | — |
| 238 | Hum | GAUUAUUUCAUGAUUGGGU | ACCCAAUCAUGAAAUAAUC | [804-822] | — | — | — | — |
| 239 | Hum | GGUCCUAAAAAGGGAAAAU | AUUUUCCCUUUUUAGGACC | [778-796] | — | — | — | — |
| 240 | Hum, chimp | CAGCAUUUCAGAAUUGCUG | CAGCAAUUCUGAAAUGCUG | [242-260] | [240-251] (12/12) | [121-139] (18/19) | [362-380] | — |
| 241 | Hum, chimp | GCCAGCAUUUCAGAAUUGC | GCAAUUCUGAAAUGCUGGC | [240-258] | [38-251] (14/14) | [119-137] (18/19) | [360-378] | — |
| 242 | Hum | AGAACUCUGAUCCUCAGCU | AGCUGAGGAUCAGAGUUCU | [699-717] | — | [579-596] (18/18) | — | — |
| 243 | Hum | UAAGAAGCCACCUGCCUGU | ACAGGCAGGUGGCUUCUUA | [91-109] | — | — | — | — |
| 244 | Hum | CUCCUCUGGUUUCAGGAGA | UCUCCUGAAACCAGAGGAG | [683-701] | — | — | — | — |
| 245 | Hum | GGGACUUUUUCUUUAGUAG | CUACUAAAGAAAAGUCCC | [655-673] | — | — | [775-789] (15/15) | — |
| 246 | Hum, chimp | AGCUUACACUUGUGUUUAA | UUAAACACAAGUGUAAGCU | [607-625] | [613-623] (11/11) | — | [727-745] | [589-607] (18/19) |
| 247 | Hum | GUCGUACCUACUUUUGAGC | GCUCAAAAGUAGGUACGAC | [591-609] | — | — | [711-729] (18/19) | — |
| 248 | Hum | AGCGUCGUACCUACUUUUG | CAAAAGUAGGUACGACGCU | [588-606] | — | — | — | — |
| 249 | Hum, rat, chimp | AAGCUGGAUAGGAUUGUGU | ACACAAUCCUAUCCAGCUU | [561-579] | [559-577] (18/19) | [440-458] | [681-699] | — |
| 250 | Hum, chimp | UUGCGAGGUUGUGUUAUGC | GCAUAACACAACCUCGCAA | [510-528] | [514-526] (13/13) | — | [630-648] | — |
| 251 | Hum, ms, | UUGCUCAAGAUGUCCUGCG | CGCAGGACAUCUUGAGCAA | [466-484] | [464-482] | [345-363] (18/19) | [586-604] | [448-466] |

TABLE A-continued

| | | | | 19 mer | | | | |
|---|---|---|---|---|---|---|---|---|
| No | Sp-Source | Sense siRNA | AntiSense siRNA | Hum 34222182 cds = 204-785 | Mouse 31541838 | rat 62644440 | chimp 55622975 | dog 74002279 |
| | chimp, dog | | | | | | | |
| 252 | Hum, ms, chimp | ACCCAGAGAAUUGCUCAAG | CUUGAGCAAUUCUCUGGGU | [456-474] | [454-472] (18/19) | [335-353] | [576-594] | — |
| 253 | Hum, chimp | UCAAAGCAAACUAAACUUG | CAAGUUUAGUUUGCUUUGA | [405-423] | [403-421] (18/19) | [284-300] (16/17) | [525-543] | [387-397] (11/11) |
| 254 | Hum, chimp | UCCAAAUCAAAGCAAACUA | UAGUUUGCUUUGAUUUGGA | [399-417] | [397-413] (16/17) | [278-294] (16/17) | [519-537] | [381-397] (17/17) |
| 255 | Hum | AUGGAAGGCUGUUAAAUUA | UAAUUUAACAGCCUUCCAU | [2510-2528] | — | — | — | — |
| 256 | Hum, chimp, dog | CUGUCCAAAUCAAAGCAAA | UUUGCUUUGAUUUGGACAG | [396-414] | [394-412] (18/19) | — | [516-534] | [378-396] |
| 257 | Hum, chimp, dog | GUCUGUCCAAAUCAAAGCA | UGCUUUGAUUUGGACAGAC | [394-412] | — | — | [514-532] | [376-394] |
| 258 | Hum | GUUAUGCUUACAAAAUGGU | ACCAUUUUGUAAGCAUAAC | [2483-2501] | — | — | — | — |
| 259 | Hum | UUGACUCUCUUGCCUGUUA | UAACAGGCAAGAGAGUCAA | [2468-2486] | — | — | — | — |
| 260 | Hum | CCUUUUUCCACUAACAGUU | AACUGUUAGUGGAAAAAGG | [2445-2463] | — | — | — | — |
| 261 | Hum, chimp, dog | GAACUGUCUGUCCAAAUCA | UGAUUUGGACAGACAGUUC | [389-407] | [387-405] (18/19) | [268-282] (15/15) | [509-527] | [371-389] |
| 262 | Hum | UGGGCAUCGAUGUAGAACU | AGUUCUACAUCGAUGCCCA | [2421-2439] | — | — | — | — |
| 263 | Hum | AAAGGUUCACUGUGUUUCU | AGAAACACAGUGAACCUUU | [2359-2377] | — | — | — | — |
| 264 | Hum | UCCAAAGGUUCACUGUGUU | AACACAGUGAACCUUUGGA | [2356-2374] | — | — | — | — |
| 265 | Hum | GCAUGUCUAUUGUUAAGCU | AGCUUAACAAUAGACAUGC | [2338-2356] | — | — | — | — |
| 266 | Hum | UCAAUGUUGUUUUGCAUGU | ACAUGCAAAACAACAUUGA | [2325-2343] | — | — | — | — |
| 267 | Hum | UUGGGCCAAGAUAAAUCAA | UUGAUUUAUCUUGGCCCAA | [2310-2328] | — | — | — | — |
| 268 | Hum | AUUGGGCCAAGAUAAAUCA | UGAUUUAUCUUGGCCCAAU | [2309-2327] | — | — | — | — |
| 269 | Hum | CAAAGCCAAUCUUUAUAGA | UCUAUAAAGAUUGGCUUUG | [2290-2308] | — | — | — | — |
| 270 | Hum | CUACAAAGCCAAUCUUUAU | AUAAAGAUUGGCUUUGUAG | [2287-2305] | — | — | — | — |
| 271 | Hum | ACUAAACUCUUCAAAUGCU | AGCAUUUGAAGAGUUUAGU | [2258-2276] | — | — | — | — |
| 272 | Hum | GUGUUCUAACAAACUAAAC | GUUUAGUUUGUUAGAACAC | [2246-2264] | — | — | — | — |
| 273 | Hum | UCACUGUUCAAAUUAGCCA | UGGCUAAUUUGAACAGUGA | [2227-2245] | — | — | — | — |
| 274 | Hum | CUGUUACUGAUACUAUAAG | CUUAUAGUAUCAGUAACAG | [2196-2214] | — | — | — | — |
| 275 | Hum | UCCUGUUACUGAUACUAUA | UAUAGUAUCAGUAACAGGA | [2194-2212] | — | — | — | — |
| 276 | Hum | AUCCUGUUACUGAUACUAU | AUAGUAUCAGUAACAGGAU | [2193-2211] | — | — | — | — |
| 277 | Hum | CAGGUGUGAUCCUGUUACU | AGUAACAGGAUCACACCUG | [2185-2203] | — | — | — | — |
| 278 | Hum | UAGGGACAGAUGUAUUCAU | AUGAAUACAUCUGUCCCUA | [2148-2166] | — | — | — | — |
| 279 | Hum | GCUAUUAGCUCCACUUCAC | GUGAAGUGGAGCUAAUAGC | [2113-2131] | — | — | — | — |
| 280 | Hum | GCCCUAGCUAUUAGCUCCA | UGGAGCUAAUAGCUAGGGC | [2107-2125] | — | — | — | — |

TABLE A-continued 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 281 | Hum | UCGUGGAUAAGGAGCUUAU | AUAAGCUCCUUAUCCACGA | [2077-2095] | — | — | — | — |
| 282 | Hum | AAGGCUUUCAUAUCCUUGC | GCAAGGAUAUGAAAGCCUU | [2052-2070] | — | — | — | — |
| 283 | Hum | CCACUCAACAAUGUUCAAU | AUUGAACAUUGUUGAGUGG | [2028-2046] | — | — | — | — |
| 284 | Hum | CCUCCACUCAACAAUGUUC | GAACAUUGUUGAGUGGAGG | [2025-2043] | — | — | — | — |
| 285 | Hum | GGAUACCUGUCACUAGGGA | UCCCUAGUGACAGGUAUCC | [1923-1941] | — | — | — | — |
| 286 | Hum | ACCUUGGAUACCUGUCACU | AGUGACAGGUAUCCAAGGU | [1918-1936] | — | — | — | — |
| 287 | Hum | UCACCGUCCAGAUAACCAU | AUGGUUAUCUGGACGGUGA | [1878-1896] | — | — | — | — |
| 288 | Hum | AACUCACCGUCCAGAUAAC | GUUAUCUGGACGGUGAGUU | [1875-1893] | — | — | — | — |
| 289 | Hum | GAGAUAUGGUUUAUAGUAC | GUACUAUAAACCAUAUCUC | [1842-1860] | — | — | — | — |
| 290 | Hum | GCAUUGGCUAUGGAGAUAU | AUAUCUCCAUAGCCAAUGC | [1830-1848] | — | — | — | — |
| 291 | Hum, chimp | AACGAGGUAAUAUUUGAGG | CCUCAAAUAUUACCUCGUU | [336-354] | — | — | [456-474] | — |
| 292 | Hum, chimp | CAACGAGGUAAUAUUUGAG | CUCAAAUAUUACCUCGUUG | [335-353] | — | — | [455-473] | — |
| 293 | Hum | CUGUAUACUACCACUUUGA | UCAAAGUGGUAGUAUACAG | [1781-1799] | — | — | — | — |
| 294 | Hum | UAGCUGUAUACUACCACUU | AAGUGGUAGUAUACAGCUA | [1778-1796] | — | — | — | — |
| 295 | Hum | GUAGCUGUAUACUACCACU | AGUGGUAGUAUACAGCUAC | [1777-1795] | — | — | — | — |
| 296 | Hum | UGGCAGUGUUAUCUCAUCU | AGAUGAGAUAACACUGCCA | [1704-1722] | — | — | — | — |
| 297 | Hum | UCUCAGAUGAACCAUUUCA | UGAAAUGGUUCAUCUGAGA | [1682-1700] | — | — | — | — |
| 298 | Hum | UAAUCUCAGAUGAACCAUU | AAUGGUUCAUCUGAGAUUA | [1679-1697] | — | — | — | — |
| 299 | Hum | CCCUCUCUGAUUCACUUAG | CUAAGUGAAUCAGAGAGGG | [1628-1646] | — | — | — | — |
| 300 | Hum | AGUCCCUCUCUGAUUCACU | AGUGAAUCAGAGAGGGACU | [1625-1643] | [1278-1288] (11/11) | — | — | — |
| 301 | Hum | UAGUCCCUCUCUGAUUCAC | GUGAAUCAGAGAGGGACUA | [1624-1642] | [1278-1288] (11/11) | — | — | — |
| 302 | Hum | UUGAUUACUCUUCCAUUGA | UCAAUGGAAGAGUAAUCAA | [1560-1578] | — | — | — | — |
| 303 | Hum | GUGUAGUUGAUUACUCUUC | GAAGAGUAAUCAACUACAC | [1554-1572] | — | — | — | — |
| 304 | Hum | CCCCUGUUCUUAAGUGUUG | CAACACUUAAGAACAGGGG | [1484-1502] | — | — | — | — |
| 305 | Hum | UUCCCUGUUCUUAAGUGU | ACACUUAAGAACAGGGAA | [1482-1500] | — | — | — | — |
| 306 | Hum | CAGUUUCCCUGUUCUUAA | UUAAGAACAGGGAAACUG | [1478-1496] | — | — | — | — |
| 307 | Hum | GCCUUUAUAAGCUCAGUUU | AAACUGAGCUUAUAAAGGC | [1465-1483] | — | — | — | — |
| 308 | Hum | GUGUUGUUUUAGAUGCCUU | AAGGCAUCUAAAACAACAC | [1451-1469] | — | — | — | — |
| 309 | Hum | ACGGUGUUGUUUUAGAUGC | GCAUCUAAAACAACACCGU | [1448-1466] | — | — | — | — |
| 310 | Hum | CCACGGUGUUGUUUUAGAU | AUCUAAAACAACACCGUGG | [1446-1464] | — | — | — | — |
| 311 | Hum | UCAGUAACCACGGUGUUGU | ACAACACCGUGGUUACUGA | [1439-1457] | — | — | — | — |
| 312 | Hum | CCAUUUCAGUAACCACGGU | ACCGUGGUUACUGAAAUGG | [1434-1452] | — | — | — | — |
| 313 | Hum | GUAGGAUUAAGUAGGUGAG | CUCACCUACUUAAUCCUAC | [1289-1307] | — | — | — | — |
| 314 | Hum | GGUAGGAUUAAGUAGGUGA | UCACCUACUUAAUCCUACC | [1288-1306] | — | — | — | — |

TABLE A-continued

| | | | | Hum 34222182 cds = | | | | |
|---|---|---|---|---|---|---|---|---|
| No | Sp-Source | Sense siRNA | AntiSense siRNA | 204-785 | Mouse 31541838 | rat 62644440 | chimp 55622975 | dog 74002279 |
| 315 | Hum | AAGGGUUUUUAGACAGGAA | UUCCUGUCUAAAAACCCUU | [1269-1287] | — | — | — | — |
| 316 | Hum | UUGAAGGGUUUUUAGACAG | CUGUCUAAAAACCCUUCAA | [1266-1284] | — | — | — | — |
| 317 | Hum | CAGUUCCUGACUCAAAUUU | AAAUUUGAGUCAGGAACUG | [1249-1267] | — | — | — | — |
| 318 | Hum | ACCAGUUCCUGACUCAAAU | AUUUGAGUCAGGAACUGGU | [1247-1265] | — | — | — | — |
| 319 | Hum | CCUAUCAAACUUCCAAAA | UUUUGGAAGUUUGAUAGG | [1219-1237] | — | — | — | [1182-1194] (13/13) |
| 320 | Hum, chimp | UGCUAAGUGAUUUUGACUA | UAGUCAAAAUCACUUAGCA | [286-304] | [284-302] (18/19) | [165-183] (18/19) | [406-424] | [268-286] (18/19) |
| 321 | Hum | UCCACAAUUUGGUUUCAGG | CCUGAAACCAAAUUGUGGA | [1081-1099] | — | — | — | — |
| 322 | Hum | UGAUUCCACAAUUUGGUUU | AAACCAAAUUGUGGAAUCA | [1077-1095] | — | — | — | — |
| 323 | Hum | AUAGAUCCCAUUUUUGUAC | GUACAAAAAUGGGAUCUAU | [1000-1018] | — | — | — | — |
| 324 | Hum, chimp | CAGAGAGCCUGCUAAGUGA | UCACUUAGCAGGCUCUCUG | [277-295] | [283-293] (11/11) | [164-174] (11/11) | [397-415] | [263-273] (11/11) |
| 325 | Hum | GUAGAUUUUCUGCAUAGAU | AUCUAUGCAGAAAAUCUAC | [987-1005] | — | — | — | — |
| 326 | Hum | UAGUGUAGAUUUUCUGCAU | AUGCAGAAAAUCUACACUA | [983-1001] | — | — | — | — |
| 327 | Hum | AUAGUGUAGAUUUUCUGCA | UGCAGAAAAUCUACACUAU | [982-1000] | — | — | — | — |
| 328 | Hum | UGUUUCACAUUCAUAGCAA | UUGCUAUGAAUGUGAAACA | [916-934] | — | — | — | — |
| 329 | Hum | CACCUGCCCUAAAUAAGAA | UUCUUAUUUAGGGCAGGUG | [869-887] | — | — | — | — |
| 330 | Hum | AAAGUCAUUUGUAGUUUGC | GCAAACUACAAAUGACUUU | [848-866] | [845-861] (17/17) | — | — | [834-845] (12/12) |
| 331 | Hum | GCUAGUCAGCUAAAGUCAU | AUGACUUUAGCUGACUAGC | [837-855] | — | — | — | — |
| 332 | Hum | UCAGCUAGUCAGCUAAAGU | ACUUUAGCUGACUAGCUGA | [834-852] | — | — | — | — |
| 333 | Hum | GGGUAGUAAAACUAUUCAG | CUGAAUAGUUUUACUACCC | [819-837] | — | — | — | — |
| 334 | Hum, chimp | CCAGCAUUUCAGAAUUGCU | AGCAAUUCUGAAAUGCUGG | [241-259] | [239-251] (13/13) | [120-138] (18/19) | [361-379] | — |
| 335 | Hum, ms | CAGCUCAGGAUUUCGACUU | AAGUCGAAAUCCUGAGCUG | [713-731] | [711-729] | [592-610] (18/19) | — | — |
| 336 | Hum, rat | GAACUCUGAUCCUCAGCUC | GAGCUGAGGAUCAGAGUUC | [700-718] | — | [579-597] | — | — |
| 337 | Hum | CGCUUCUCCUCUGGUUUCA | UGAAACCAGAGGAGAAGCG | [678-696] | [676-686] (11/11) | — | — | — |
| 338 | Hum | GACUUUUUCUUUAGUAGAG | CUCUACUAAAGAAAAAGUC | [657-675] | — | — | [777-789] (13/13) | — |
| 339 | Hum | UCAGGGACUUUUUCUUUAG | CUAAAGAAAAAGUCCCUGA | [652-670] | — | — | [772-789] (18/18) | — |
| 340 | Hum, chimp | UUCAGGGACUUUUUCUUUA | UAAAGAAAAAGUCCCUGAA | [651-669] | — | — | [771-789] | — |
| 341 | Hum, chimp | CUUUUGAGCUUACACUUGU | ACAAGUGUAAGCUCAAAAG | [601-619] | — | — | [721-739] | — |

TABLE A-continued 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 342 | Hum | UACCUACUUUUGAGCUUAC | GUAAGCUCAAAAGUAGGUA | [595-613] | — | — | [717-733] (17/17) | — |
| 343 | Hum | GUACCUACUUUUGAGCUUA | UAAGCUCAAAAGUAGGUAC | [594-612] | — | — | [717-732] (16/16) | — |
| 344 | Hum, rat, chimp, dog | GUGAACUUGGAAAUUGAAA | UUUCAAUUUCCAAGUUCAC | [531-549] | [529-547] (18/19) | [410-428] | [651-669] | [513-531] |
| 345 | Hum, rat, dog | GCACGUGAACUUGGAAAUU | AAUUUCCAAGUUCACGUGC | [527-545] | [525-539] (15/15) | [406-424] | [651-665] (15/15) | [509-527] |
| 346 | Hum, ms, chimp, dog | UCCCUGAGAAACUGACCCA | UGGGUCAGUUUCUCAGGGA | [442-460] | [440-458] | [323-339] (17/17) | [562-580] | [424-442] |
| 347 | Hum, chimp | AGGUCCUUGUCCCUGAGAA | UUCUCAGGGACAAGGACCU | [433-451] | [439-449] (11/11) | — | [553-571] | [417-433] (17/17) |
| 348 | Hum, chimp | GCAAACUAAACUUGGUUGC | GCAACCAAGUUUAGUUUGC | [410-428] | [408-426] (18/19) | — | [530-548] | — |
| 349 | Hum, chimp | GUCCAAAUCAAAGCAAACU | AGUUUGCUUUGAUUUGGAC | [398-416] | [396-413] (17/18) | [277-294] (17/18) | [518-536] | [380-397] (18/18) |
| 350 | Hum, chimp, dog | UCUGUCCAAAUCAAAGCAA | UUGCUUUGAUUUGGACAGA | [395-413] | — | — | [515-533] | [377-395] |
| 351 | Hum | CCUGUUAUGCUUACAAAAU | AUUUUGUAAGCAUAACAGG | [2480-2496] | — | — | — | — |
| 352 | Hum | GCCUGUUAUGCUUACAAAA | UUUUGUAAGCAUAACAGGC | [2479-2497] | — | — | — | — |
| 353 | Hum | CAGUUAUCUUUGACUCUCU | AGAGAGUCAAAGAUAACUG | [2459-2477] | — | — | — | — |
| 354 | Hum | CACUAACAGUUAUCUUUGA | UCAAAGAUAACUGUUAGUG | [2453-2471] | — | — | — | — |
| 355 | Hum | UCCACUAACAGUUAUCUUU | AAAGAUAACUGUUAGUGGA | [2451-2469] | — | — | — | — |
| 356 | Hum, chimp, dog | AGAACUGUCUGUCCAAAUC | GAUUUGGACAGACAGUUCU | [388-406] | [386-400] (15/15) | [267-282] (16/16) | [508-526] | [370-388] |
| 357 | Hum | UGACUGGGCAAGGCUUCUU | AAGAAGCCUUGCCCAGUCA | [2403-2421] | — | — | — | — |
| 358 | Hum | UCACUGUGUUUCUGCCGCU | AGCGGCAGAAACACAGUGA | [2365-2383] | [2460-2470] (11/11) | — | — | — |
| 359 | Hum | AAGGUUCACUGUGUUUCUG | CAGAAACACAGUGAACCUU | [2360-2378] | [2460-2470] (11/11) | — | — | — |
| 360 | Hum | CCAAGAUAAAUCAAUGUUG | CAACAUUGAUUUAUCUUGG | [2315-2333] | — | — | — | — |
| 361 | Hum | GAUACUACAAAGCCAAUCU | AGAUUGGCUUUGUAGUAUC | [2283-2301] | [1571-1581] (11/11) | — | — | — |
| 362 | Hum | AAAGAUACUACAAAGCCAA | UUGGCUUUGUAGUAUCUUU | [2280-2298] | [1571-1581] (11/11) | — | — | — |
| 363 | Hum | GAAAGAUACUACAAAGCCA | UGGCUUUGUAGUAUCUUUC | [2279-2297] | [1571-1581] (11/11) | — | — | — |
| 364 | Hum | UGGAAAGAUACUACAAAGC | GCUUUGUAGUAUCUUUCCA | [2277-2295] | [1571-1581] (11/11) | — | — | — |

TABLE A-continued 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 365 | Hum | UUGGAAAGAUACUACAAAG | CUUUGUAGUAUCUUUCCAA | [2276-2294] | [1571-1581] (11/11) | — | — | — |
| 366 | Hum | UGCUUGGAAAGAUACUACA | UGUAGUAUCUUUCCAAGCA | [2273-2291] | — | — | — | — |
| 367 | Hum | AUGCUUGGAAAGAUACUAC | GUAGUAUCUUUCCAAGCAU | [2272-2290] | — | — | — | — |
| 368 | Hum | CUAAACUCUUCAAAUGCUU | AAGCAUUUGAAGAGUUUAG | [2259-2277] | — | — | — | — |
| 369 | Hum | AAGUGACCUAAAAUGUCAC | GUGACAUUUUAGGUCACUU | [2212-2230] | — | — | — | — |
| 370 | Hum | UGAUCCUGUUACUGAUACU | AGUAUCAGUAACAGGAUCA | [2191-2209] | — | — | — | — |
| 371 | Hum | ACAGGUGUGAUCCUGUUAC | GUAACAGGAUCACACCUGU | [2184-2202] | — | — | — | — |
| 372 | Hum | AUCCUGGUGUUACUGAAAA | UUUUCAGUAACACCAGGAU | [2165-2183] | — | — | — | — |
| 373 | Hum | GGACAGAUGUAUUCAUCCU | AGGAUGAAUACAUCUGUCC | [2151-2169] | — | — | — | — |
| 374 | Hum | AGCUCCACUUCACAUGCUG | CAGCAUGUGAAGUGGAGCU | [2119-2137] | — | — | — | — |
| 375 | Hum | AGCUAUUAGCUCCACUUCA | UGAAGUGGAGCUAAUAGCU | [2112-2130] | — | — | — | — |
| 376 | Hum, chimp | CUUGCCAGAAUUUGGUUAA | UUAACCAAAUUCUGGCAAG | [361-379] | [361-377] (17/17) | [242-258] (17/17) | [481-499] | — |
| 377 | Hum | AAGGAGCUUAUUCAGGUUU | AAACCUGAAUAAGCUCCUU | [2085-2103] | — | — | — | — |
| 378 | Hum | GCUUUCAUAUCCUUGCUGU | ACAGCAAGGAUAUGAAAGC | [2055-2073] | — | — | — | — |
| 379 | Hum | UGAGAGAAUUUAGCCUCCA | UGGAGGCUAAAUUCUCUCA | [2012-2030] | — | — | — | — |
| 380 | Hum | AUGAGAGAAUUUAGCCUCC | GGAGGCUAAAUUCUCUCAU | [2011-2029] | — | — | — | — |
| 381 | Hum, chimp | GGAAUCAACUUGCCAGAAU | AUUCUGGCAAGUUGAUUCC | [353-371] | — | — | [473-491] | [340-351] (12/12) |
| 382 | Hum | UAGGGAAUAAUAAAGGCCU | AGGCCUUUAUUAUUCCCUA | [1936-1954] | — | — | — | — |
| 383 | Hum | UCACUAGGGAAUAAUAAAG | CUUUAUUAUUCCCUAGUGA | [1932-1950] | — | — | — | — |
| 384 | Hum | ACCUGUCACUAGGGAAUAA | UUAUUCCCUAGUGACAGGU | [1927-1945] | — | — | — | — |
| 385 | Hum | AUACCUGUCACUAGGGAAU | AUUCCCUAGUGACAGGUAU | [1925-1943] | — | — | — | — |
| 386 | Hum | UUGGAUACCUGUCACUAGG | CCUAGUGACAGGUAUCCAA | [1921-1939] | — | — | — | — |
| 387 | Hum | CACCUUGGAUACCUGUCAC | GUGACAGGUAUCCAAGGUG | [1917-1935] | — | — | — | — |
| 388 | Hum | ACCGUCCAGAUAACCAUGC | GCAUGGUUAUCUGGACGGU | [1880-1896] | — | — | — | — |
| 389 | Hum | GAAGUCUGCAUUGGCUAUG | CAUAGCCAAUGCAGACUUC | [1823-1841] | — | — | — | — |
| 390 | Hum | GAAUUAUUGAAACGGGUCA | UGACCCGUUUCAAUAAUUC | [1796-1816] | — | — | — | — |
| 391 | Hum | UAGUAGCUGUAUACUACCA | UGGUAGUAUACAGCUACUA | [1775-1793] | — | — | — | — |
| 392 | Hum | GGGUAGUAGCUGUAUACUA | UAGUAUACAGCUACUACCC | [1772-1790] | — | — | — | — |
| 393 | Hum | GUCAAGGGUAGUAGCUGUA | UACAGCUACUACCCUUGAC | [1767-1785] | — | — | — | — |
| 394 | Hum | UGAAGUAUCUCUCCUUAAC | GUUAAGGAGAGAUACUUCA | [1741-1759] | — | — | — | — |
| 395 | Hum | UUGAAGUAUCUCUCCUUAA | UUAAGGAGAGAUACUUCAA | [1740-1758] | — | — | — | — |
| 396 | Hum | GGGAAUUGAAGUAUCUCUC | GAGAGAUACUUCAAUUCCC | [1735-1753] | — | — | — | — |
| 397 | Hum | UGGGAAUUGAAGUAUCUCU | AGAGAUACUUCAAUUCCCA | [1734-1752] | — | — | — | — |
| 398 | Hum | GGCUUUUCUGGGAAUUGAA | UUCAAUUCCCAGAAAAGCC | [1726-1744] | — | — | — | — |

TABLE A-continued

| | | | | 19 mer | | | | |
|---|---|---|---|---|---|---|---|---|
| No | Sp-Source | Sense siRNA | AntiSense siRNA | Hum 34222182 cds = 204-785 | Mouse 31541838 | rat 62644440 | chimp 55622975 | dog 74002279 |
| 399 | Hum, chimp | CCCAACCUCAACGAGGUAA | UUACCUCGUUGAGGUUGGG | [327-345] | [325-341] (17/17) | [206-222] (17/17) | [447-465] | [309-325] (16/17) |
| 400 | Hum | GCAGUGUUAUCUAUCUCU | AGAGAUGAGAUAACACUGC | [1706-1724] | — | — | — | — |
| 401 | Hum | CUCAGAUGAACCAUUUCAC | GUGAAAUGGUUCAUCUGAG | [1683-1701] | — | — | — | — |
| 402 | Hum, chimp | CUGAACCCAACCUCAACGA | UCGUUGAGGUUGGGUUCAG | [322-340] | [320-338] (18/19) | [206-219] (14/14) | [442-460] | [306-319] (14/14) |
| 403 | Hum | CUGAUUCACUUAGUAAUCU | AGAUUACUAAGUGAAUCAG | [1634-1652] | — | — | — | — |
| 404 | Hum | CUCUGAUUCACUUAGUAAU | AUUACUAAGUGAAUCAGAG | [1632-1650] | — | — | — | — |
| 405 | Hum | CCUCUGAUUCACUUAGU | ACUAAGUGAAUCAGAGAGG | [1629-1647] | — | — | — | — |
| 406 | Hum, chimp | AGGAAACAGAGCCGUUGAC | GUCAACGGCUCUGUUUCCU | [184-202] | [183-200] (18/18) | [64-81] (18/18) | [304-322] | [167-184] (18/18) |
| 407 | Hum | UACUCUUCCAUUGAGUGAA | UUCACUCAAUGGAAGAGUA | [1565-1583] | — | — | — | — |
| 408 | Hum | GUGUGUAGUUGAUUACUCU | AGAGUAAUCAACUACACAC | [1552-1570] | — | — | — | — |
| 409 | Hum | GAACUGAUAUUUUGUGUG | CACACAAAAUAUCAGUUC | [1538-1556] | — | — | — | — |
| 410 | Hum | AAGUGUUGAAUACUGUCUU | AAGACAGUAUUCAACACUU | [1495-1513] | — | — | — | — |
| 411 | Hum | UCCCCUGUUCUUAAGUGUU | AACACUUAAGAACAGGGGA | [1483-1501] | — | — | — | — |
| 412 | Hum | GCUCAGUUUCCCUGUUCU | AGAACAGGGGAAACUGAGC | [1475-1493] | — | — | — | — |
| 413 | Hum | AGCUCAGUUUCCCCUGUUC | GAACAGGGGAAACUGAGCU | [1474-1492] | — | — | — | — |
| 414 | Hum, chimp | GGAUUAUGUUGUUCCUGAA | UUCAGGAACAACAUAAUCC | [308-326] | [306-323] (17/18) | — | [428-446] | — |
| 415 | Hum | UAAGCUCAGUUUCCCCUGU | ACAGGGGAAACUGAGCUUA | [1472-1490] | — | — | — | — |
| 416 | Hum | UGCCUUUAUAAGCUCAGUU | AACUGAGCUUAUAAAGGCA | [1464-1482] | — | — | — | — |
| 417 | Hum | AGAUGCCUUUAUAAGCUCA | UGAGCUUAUAAAGGCAUCU | [1461-1479] | — | — | — | — |
| 418 | Hum | UUAGAUGCCUUUAUAAGCU | AGCUUAUAAAGGCAUCUAA | [1459-1477] | — | — | — | — |
| 419 | Hum | CGGUGUUGUUUUAGAUGCC | GGCAUCUAAAACAACACCG | [1449-1467] | — | — | — | — |
| 420 | Hum | UAACCACGGUGUUGUUUUA | UAAAACAACACCGUGGUUA | [1443-1461] | — | — | — | — |
| 421 | Hum, chimp | CUACUGGGAUUAUGUUGUU | AACAACAUAAUCCCAGUAG | [302-320] | [300-317] (18/18) | [181-195] (15/15) | [422-440] | [284-302] (18/19) |
| 422 | Hum, ms, chimp | ACUACUGGGAUUAUGUUGU | ACAACAUAAUCCCAGUAGU | [301-319] | [299-317] (16/16) | [180-195] | [421-439] | [283-301] (18/19) |
| 423 | Hum | AUGGAACUGCUUCACUGUU | AACAGUGAAGCAGUUCCAU | [1361-1379] | — | — | — | — |
| 424 | Hum | UUACGGCAAUAAUGGAACU | AGUUCCAUUAUUGCCGUAA | [1350-1368] | — | — | — | — |
| 425 | Hum | AGGUGAGUUUAAUUAAAGC | GCUUUAAUUAAACUCACCU | [1301-1319] | — | — | — | — |
| 426 | Hum | AGGAUUAAGUAGGUGAGUU | AACUCACCUACUUAAUCCU | [1291-1309] | — | — | — | — |
| 427 | Hum | ACAGGAAGGUAGGAUUAAG | CUUAAUCCUACCUUCCUGU | [1281-1299] | — | — | — | — |
| 428 | Hum | AGGGUUUUUAGACAGGAAG | CUUCCUGUCUAAAAACCCU | [1270-1288] | — | — | — | — |
| 429 | Hum | GAAGGGUUUUUAGACAGGA | UCCUGUCUAAAAACCCUUC | [1268-1286] | — | — | — | — |

TABLE A-continued 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 430 | Hum | UGAAGGGUUUUUAGACAGG | CCUGUCUAAAAACCCUUCA | [1267-1285] | — | — | — | — |
| 431 | Hum | UUUGAAGGGUUUUUAGACA | UGUCUAAAAACCCUUCAAA | [1265-1283] | — | — | — | — |
| 432 | Hum, chimp | GUGAUUUUGACUACUGGGA | UCCCAGUAGUCAAAAUCAC | [292-310] | [290-308] (18/19) | [171-189] (18/19) | [412-430] | [275-292] (18/18) |
| 433 | Hum | UCCUGACUCAAAUUUGAAG | CUUCAAAUUUGAGUCAGGA | [1253-1271] | — | — | — | — |
| 434 | Hum | UCUCUAAGUUUCAGAGGA | UCCUCUGAAAACUUAGAGA | [1163-1181] | — | — | — | — |
| 435 | Hum | AGGUAGGCUUGGUAAUAGA | UCUAUUACCAAGCCUACCU | [1097-1115] | — | — | — | — |
| 436 | Hum | ACAAUUUGGUUUCAGGUAG | CUACCUGAAACCAAAUUGU | [1084-1102] | — | — | — | — |
| 437 | Hum | GUUUUACAUUUGAUUCCAC | GUGGAAUCAAAUGUAAAAC | [1067-1085] | — | — | — | — |
| 438 | Hum | AAGCCCAUUUGAGUUUUAC | GUAAAACUCAAAUGGGCUU | [1055-1073] | — | — | — | — |
| 439 | Hum | UAGAAGCCCAUUUGAGUUU | AAACUCAAAUGGGCUUCUA | [1052-1070] | — | — | — | — |
| 440 | Hum | AAGCAAAAGUAGAAGCCCA | UGGGCUUCUACUUUUGCUU | [1043-1061] | — | — | — | — |
| 441 | Hum | UAGGUAAGCAAAAGUAGAA | UUCUACUUUUGCUUACCUA | [1038-1056] | — | — | — | — |
| 442 | Hum | GAAUAGGUAAGCAAAAGUA | UACUUUUGCUUACCUAUUC | [1035-1053] | — | — | — | — |
| 443 | Hum | GGAUGGAAUAGGUAAGCAA | UUGCUUACCUAUUCCAUCC | [1030-1048] | — | — | — | — |
| 444 | Hum | GGGAUGGAAUAGGUAAGCA | UGCUUACCUAUUCCAUCCC | [1029-1047] | — | — | — | — |
| 445 | Hum | AGAAUUGAAUGGGAUGGAA | UUCCAUCCCAUUCAAUUCU | [1019-1037] | — | — | — | — |
| 446 | Hum | CUGCAUAGAUCCCAUUUUU | AAAAAUGGGAUCUAUGCAG | [996-1014] | — | — | — | — |
| 447 | Hum | UAGAUUUUCUGCAUAGAUC | GAUCUAUGCAGAAAAUCUA | [968-1006] | — | — | — | — |
| 448 | Hum | GGCCUUUGGAGAAGUGAUU | AAUCACUUCUCCAAAGGCC | [959-977] | — | — | — | — |
| 449 | Hum, chimp | ACUGUGGCUAUCACCCAGA | UCUGGGUGAUAGCCACAGU | [262-280] | [263-275] (13/13) | — | [382-400] | — |
| 450 | Hum | GGCUGAUUUUCUGGCCUUU | AAAGGCCAGAAAAUCAGCC | [947-965] | — | — | — | — |
| 451 | Hum | ACAGGCUGAUUUUCUGGCC | GGCCAGAAAAUCAGCCUGU | [944-962] | [939-949] (11/11) | — | — | — |
| 452 | Hum | AACAGGCUGAUUUUCUGGC | GCCAGAAAAUCAGCCUGUU | [943-961] | [939-949] (11/11) | — | — | — |
| 453 | Hum | CUGCAGCUAACAGGCUGAU | AUCAGCCUGUUAGCUGCAG | [935-953] | — | — | — | — |
| 454 | Hum | AGCAACUGCAGCUAACAGG | CCUGUUAGCUGCAGUUGCU | [930-948] | — | — | — | — |
| 455 | Hum | UAGCAACUGCAGCUAACAG | CUGUUAGCUGCAGUUGCUA | [929-947] | — | — | — | — |
| 456 | Hum | UCAUAGCAACUGCAGCUAA | UUAGCUGCAGUUGCUAUGA | [926-944] | — | — | — | — |
| 457 | Hum | UCACAUUCAUAGCAACUGC | GCAGUUGCUAUGAAUGUGA | [920-938] | — | — | — | — |
| 458 | Hum, chimp | CAGAAUUGCUGGACUGUGG | CCACAGUCCAGCAAUUCUG | [250-268] | — | — | [370-388] | — |
| 459 | Hum | GCCCUAAAUAAGAAACCGC | GGGGUUUCUUAUUUAGGGC | [874-892] | — | — | — | — |
| 460 | Hum | CCACCUGCCCUAAAUAAGA | UCUUAUUUAGGGCAGGUGG | [868-886] | — | — | — | — |
| 461 | Hum | GUCAUUUGUAGUUUGCCCC | GGGGCAAACUACAAAUGAC | [851-889] | [846-862] (17/17) | — | — | [834-845] (12/12) |

TABLE A-continued

19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 462 | Hum | GUAAACUAUUCAGCUAGU | ACUAGCUGAAUAGUUUUAC | [824-642] | — | — | — | — |
| 463 | Hum | UUGGGUAGUAAACUAUUC | GAAUAGUUUUACUACCCAA | [817-835] | — | — | — | — |
| 464 | Hum | CCUCAGCUCAGGAUUUCGA | UGGAAAUCCUGAGCUGAGG | [710-728] | [709-726] (18/18) | — | — | — |
| 465 | Hum | GGAGAACUCUGAUCCUCAG | CUGAGGAUCAGAGUUCUCC | [697-715] | — | [579-594] (16/16) | — | — |
| 466 | Hum | UCGCUUCUCCUCUGGUUUC | GAAACCAGAGGAGAAGCGA | [677-695] | [675-686] (12/12) | — | — | — |
| 467 | Hum | GUCGCUUCUCCUCUGGUUU | AAACCAGAGGAGAAGCGAC | [676-694] | [674-688] (13/13) | — | — | — |
| 468 | Hum | GGACUUUUCUUUAGUAGA | UCUACUAAAGAAAAGUCC | [656-674] | — | — | [776-789] (14/14) | — |
| 469 | Hum, chimp | UGGACUAGCUUCAGGGACU | AGUCCCUGAAGCUAGUCCA | [642-660] | — | — | [762-780] | [624-640] (17/17) |
| 470 | Hum, chimp, dog | UGCUCAUGGACUAGCUUCA | UGAAGCUAGUCCAUGAGCA | [636-654] | — | — | [756-774] | [618-636] |
| 471 | Hum | ACCUACUUUUGAGCUUACA | UGUAAGCUCAAAAGUAGGU | [596-614] | — | — | [717-734] (18/18) | — |
| 472 | Hum | UCGUACCUACUUUUGAGCU | AGCUCAAAAGUAGGUACGA | [592-610] | — | — | [712-730] (18/19) | — |
| 473 | Hum | CGUCGUACCUACUUUUGAG | CUCAAAAGUAGGUACGACG | [590-608] | — | — | [711-728] (17/18) | — |
| 474 | Hum, rat, dog | CACGUGAACUUGGAAAUUG | CAAUUUCCAAGUUCACGUG | [528-546] | [526-544] (18/19) | [407-425] | [651-666] (16/16) | [510-528] |
| 475 | Hum, chimp | UGCGAGGUUGUGUUAUGCA | UGCAUAACACAACCUCGCA | [511-529] | [514-527] (14/14) | [398-408] (11/11) | [631-649] | [493-511] (18/19) |
| 476 | Hum, chimp, dog | UUGUCCCUGAGAAACUGAC | GUCAGUUUCUCAGGGACAA | [439-457] | [439-455] (17/17) | [323-336] (14/14) | [559-577] | [421-439] |
| 477 | Hum, chimp, dog | UCCUUGUCCCUGAGAAACU | AGUUUCUCAGGGACAAGGA | [436-454] | [439-452] (14/14) | [323-333] (11/11) | [556-574] | [418-436] |
| 478 | Hum, chimp | UGACCAUGGUUGCAACUGG | GCAGUUGCAACCAUGGUCA | [199-217] | [197-212] (16/16) | [78-93] (16/16) | [319-337] | — |
| 479 | Hum, chimp | AACUAAACUGGUUGCUCA | UGAGCAACCAAGUUUAGUU | [413-431] | [415-428] (14/14) | — | [533-551] | [402-413] (12/12) |
| 480 | Hum, chimp | AGCAAACUAAACUGGUUG | CAACCAAGUUUAGUUUGCU | [409-427] | [407-425] (18/19) | — | [529-547] | — |
| 481 | Hum | UGUUAUGCUUACAAAAUGG | CCAUUUUGUAAGCAUAACA | [2482-2500] | — | — | — | — |
| 482 | Hum, chimp, dog | ACUGUCUGUCCAAAUCAAA | UUUGAUUUGGACAGACAGU | [391-409] | [389-407] (18/19) | [270-288] (18/19) | [511-529] | [373-391] |

TABLE A-continued

19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 483 | Hum | CUAACAGUUAUCUUGACU | AGUCAAAGAUAACUGUUAG | [2455-2473] | — | — | — | — |
| 484 | Hum | GGGCAUCGAUGUAGAACUG | CAGUUCUACAUCGAUGCCC | [2422-2440] | — | — | — | — |
| 485 | Hum | UCCUGGAGUUGUCACCACU | AGUGGUGACAACUCCAGGA | [2385-2403] | — | — | — | — |
| 486 | Hum | UUGUUAAGCUCCAAAGGUU | AACCUUUGGAGCUUAACAA | [2347-2365] | — | — | — | — |
| 487 | Hum | UUGCAUGUCUAUUGUUAAG | CUUAACAAUAGACAUGCAA | [2336-2354] | — | — | — | — |
| 488 | Hum | AUGUUGUUUUGCAUGUCUA | UAGACAUGCAAAACAACAU | [2328-2348] | — | — | — | — |
| 489 | Hum | AAGAUACUACAAAGCCAAU | AUUGGCUUUGUAGUAUCUU | [2281-2299] | [1571-1581] (11/11) | — | — | — |
| 490 | Hum | CUUGGAAAGAUACUACAAA | UUUGUAGUAUCUUUCCAAG | [2275-2293] | — | — | — | — |
| 491 | Hum | UGUCACUGUUCAAAUUAGC | GCUAAUUUGAACAGUGACA | [2225-2243] | — | — | — | — |
| 492 | Hum | UGAUACUAUAAGUGACCUA | UAGGUCACUUAUAGUAUCA | [2203-2221] | — | — | — | — |
| 493 | Hum, ms, rat, chimp | CCGUUGACCAUGGUUGCAA | UUGCAACCAUGGUCAACGG | [195-213] | [193-211] | [74-92] | [315-333] | [177-195] (18/19) |
| 494 | Hum | GUGUUACUGAAAAACAGGU | ACCUGUUUUUCAGUAACAC | [2171-2189] | — | — | — | — |
| 495 | Hum | AGGGACAGAUGUAUUCAUC | GAUGAAUACAUCUGUCCCU | [2149-2167] | — | — | — | — |
| 496 | Hum | GGCGUAGGGACAGAUGUAU | AUACAUCUGUCCCUACGCC | [2144-2162] | — | — | — | — |
| 497 | Hum | CUCCACUUCACAUGCUGGA | UCCAGCAUGUGAAGUGGAG | [2121-2139] | — | — | — | — |
| 498 | Hum | UUCCUGCCCUAGCUAUUAG | CUAAUAGCUAGGGCAGGAA | [2102-2120] | — | — | — | — |
| 499 | Hum | AGGAGCUUAUUCAGGUUUC | GAAACCUGAAUAAGCUCCU | [2086-2104] | — | — | — | — |
| 500 | Hum | AUAAGGAGCUUAUUCAGGU | ACCUGAAUAAGCUCCUUAU | [2083-2101] | — | — | — | — |
| 501 | Hum, chimp | CAACUUGCCAGAAUUUGGU | ACCAAAUUCUGGCAAGUUG | [358-376] | [356-374] (18/19) | [237-255] (18/19) | [478-496] | [340-357] (17/18) |
| 502 | Hum | AAUUCAGCAAGGCUUUCAU | AUGAAAGCCUUGCUGAAUU | [2044-2062] | [2157-2167] (11/11) | — | — | — |
| 503 | Hum | UCAACAAUGUUCAAUUCAG | CUGAAUUGAACAUUGUUGA | [2032-2050] | — | — | — | — |
| 504 | Hum | UCCACUCAACAAUGUUCAA | UUGAACAUUGUUGAGUGGA | [2027-2045] | — | — | — | — |
| 505 | Hum | UUCCAACUAAGUAGAUCAU | AUGAUCUACUUAGUUGGAA | [1969-1987] | — | — | — | — |
| 506 | Hum | AGGGAAUAAUAAAGGCCUU | AAGGCCUUUAUUAUUCCCU | [1937-1955] | — | — | — | — |
| 507 | Hum | CACUAGGGAAUAAUAAAGG | CCUUUAUUAUUCCCUAGUG | [1933-1951] | — | — | — | — |
| 508 | Hum, chimp | GAGGAAUCAACUUGCCAGA | UCUGGCAAGUUGAUUCCUC | [351-369] | — | — | [471-489] | [340-351] (12/12) |
| 509 | Hum | CCUGUCACUAGGGAAUAAU | AUUAUUCCCUAGUGACAGG | [1928-1946] | — | — | — | — |
| 510 | Hum | CAUGCAUGCACCCAGAUUU | AAAUCUGGGUGCAUGCAUG | [1894-1912] | — | — | — | — |
| 511 | Hum | GUCCAGAUAACCAUGCAUG | CAUGCAUGGUUAUCUGGAC | [1883-1901] | — | — | — | — |
| 512 | Hum | CCGUCCAGAUAACCAUGCA | UGCAUGGUUAUCUGGACGG | [1881-1899] | — | — | — | — |
| 513 | Hum | GAAUGAAACUCACCGUCCA | UGGACGGUGAGUUUCAUUC | [1869-1887] | — | — | — | — |
| 514 | Hum | GAGAAUGAAACUCACCGUC | GACGGUGAGUUUCAUUCUC | [1867-1885] | — | — | — | — |

TABLE A-continued

| | | | | 19 mer | | | | |
|---|---|---|---|---|---|---|---|---|
| No | Sp-Source | Sense siRNA | AntiSense siRNA | Hum 34222182 cds = 204-785 | Mouse 31541838 | rat 62644440 | chimp 55622975 | dog 74002279 |
| 515 | Hum | ACAGCCUAGAGAAUGAAAC | GUUUCAUUCUCUAGGCUGU | [1859-1877] | — | — | — | — |
| 516 | Hum | CUGCAUUGGCUAUGGAGAU | AUCUCCAUAGCCAAUGCAG | [1828-1846] | — | — | — | — |
| 517 | Hum | AGUCUGCAUUGGCUAUGGA | UCCAUAGCCAAUGCAGACU | [1825-1843] | — | — | — | — |
| 518 | Hum | AAGUCUGCAUUGGCUAUGG | CCAUAGCCAAUGCAGACUU | [1824-1842] | — | — | — | — |
| 519 | Hum | UUGAAUUAUUGAAACGGGU | ACCCGUUUCAAUAAUUCAA | [1796-1814] | — | — | — | — |
| 520 | Hum | GCUGUAUACUACCACUUUG | CAAAGUGGUAGUAUACAGC | [1780-1798] | — | — | — | — |
| 521 | Hum | AAGGGUAGUAGCUGUAUAC | GUAUACAGCUACUACCCUU | [1770-1788] | — | — | — | — |
| 522 | Hum | GAAGUAUCUCUCCUUAACC | GGUUAAGGAGAGAUACUUC | [1742-1760] | — | — | — | — |
| 523 | Hum | UUCUGGGAAUUGAAGUAUC | GAUACUUCAAUUCCCAGAA | [1731-1749] | — | — | — | — |
| 524 | Hum, chimp | AACCCAACCUCAACGAGGU | ACCUCGUUGAGGUUGGGUU | [325-343] | [325-341] (17/17) | [206-222] (17/17) | [445-463] | [307-325] (18/19) |
| 525 | Hum | AUGAACCAUUUCACCAUGG | CCAUGGUGAAAUGGUUCAU | [1688-1706] | — | — | — | — |
| 526 | Hum | AGAUGAACCAUUUCACCAU | AUGGUGAAAUGGUUCAUCU | [1686-1704] | — | — | — | — |
| 527 | Hum | AAUCUCAGAUGAACCAUUU | AAAUGGUUCAUCUGAGAUU | [1680-1698] | — | — | — | — |
| 528 | Hum | UGUGCUUAAUCUCAGAUGA | UCAUCUGAGAUUAAGCACA | [1673-1691] | — | — | — | — |
| 529 | Hum | AUGUGCUUAAUCUCAGAUG | CAUCUGAGAUUAAGCACAU | [1672-1690] | — | — | — | — |
| 530 | Hum | ACAUGUGCUUAAUCUCAGA | UCUGAGAUUAAGCACAUGU | [1670-1688] | — | — | — | — |
| 531 | Hum | UACAUGUGCUUAAUCUCAG | CUGAGAUUAAGCACAUGUA | [1669-1687] | — | — | — | — |
| 532 | Hum | CCUCUUUUCAGUAUUACAU | AUGUAAUACUGAAAAGAGG | [1655-1673] | — | — | — | — |
| 533 | Hum | CUCUCUGAUUCACUUAGUA | UACUAAGUGAAUCAGAGAG | [1630-1648] | — | — | — | — |
| 534 | Hum, chimp | AUGUUGUUCCUGAACCCAA | UUGGGUUCAGGAACAACAU | [313-331] | — | — | [433-451] | — |
| 535 | Hum | CCCUGUUCUUAAGUGUUGA | UCAACACUUAAGAACAGGG | [1485-1503] | — | — | — | — |
| 536 | Hum | AUGCCUUUAUAAGCUCAGU | ACUGAGCUUAUAAAGGCAU | [1463-1481] | — | — | — | — |
| 537 | Hum, chimp | CUGGGAUUAUGUUGUUCCU | AGGAACAACAUAAUCCCAG | [305-323] | [303-317] (15/15) | [184-195] (12/12) | [425-443] | — |
| 538 | Hum | CUAAUGUUUUAAAGAGGCA | UGCCUCUUUAAAACAUUAG | [1399-1417] | — | — | — | — |
| 539 | Hum, chimp | UUGACUACUGGGAUUAUGU | ACAUAAUCCCAGUAGUCAA | [298-316] | [298-314] (17/17) | [179-195] (17/17) | [418-436] | [280-295] (16/16) |
| 540 | Hum | UGAGAAAUAUUACGGCAAU | AUUGCCGUAAUAUUUCUCA | [1341-1359] | — | — | — | — |
| 541 | Hum | AUGAGAAAUAUUACGGCAA | UUGCCGUAAUAUUUCUCAU | [1340-1358] | — | — | — | — |
| 542 | Hum | GGUAAGAGUAAAUGAGAAA | UUUCUCAUUUACUCUUACC | [1329-1347] | — | — | — | — |
| 543 | Hum | CUAGGUAAGAGUAAAUGAG | CUCAUUUACUCUUACCUAG | [1326-1344] | — | — | — | — |
| 544 | Hum | AACCCUAGGUAAGAGUAAA | UUUACUCUUACCUAGGGUU | [1322-1340] | — | — | — | — |
| 545 | Hum | GGUGAGUUUAAUUAAAGCU | AGCUUUAAUUAAACUCACC | [1302-1320] | — | — | — | — |
| 546 | Hum | UAGACAGGAAGGUAGGAUU | AAUCCUACCUUCCUGUCUA | [1278-1296] | — | — | — | — |
| 547 | Hum | UGACUCAAAUUUGAAGGGU | ACCCUUCAAAUUUGAGUCA | [1256-1274] | — | — | — | — |

TABLE A-continued 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 548 | Hum | CUGACUCAAAUUUGAAGGG | CCCUUCAAAUUUGAGUCAG | [1255-1273] | — | — | — | — |
| 549 | Hum | CACCAGUUCCUGACUCAAA | UUUGAGUCAGGAACUGGUG | [1246-1264] | — | — | — | — |
| 550 | Hum | ACCACCAGUUCCUGACUCA | UGAGUCAGGAACUGGUGGU | [1244-1262] | — | — | — | — |
| 551 | Hum | AAAGCCCACACCACCAGUU | AACUGGUGGUGUGGGCUUU | [1235-1253] | — | — | — | — |
| 552 | Hum | UAGGCUUGGUAAUAGACUA | UAGUCUAUUACCAAGCCUA | [1100-1118] | — | — | — | — |
| 553 | Hum | CAAUUUGGUUUCAGGUAGG | CCUACCUGAAACCAAAUUG | [1085-1103] | — | — | — | — |
| 554 | Hum | AGCCCAUUUGAGUUUUACA | UGUAAAACUCAAAUGGGCU | [1056-1074] | — | — | — | — |
| 555 | Hum, chimp | GCCUGCUAAGUGAUUUUGA | UCAAAAUCACUUAGCAGGC | [283-301] | [283-296] (14/14) | [164-177] (14/14) | [403-421] | — |
| 556 | Hum | AGCAAAAGUAGAAGCCCAU | AUGGGCUUCUACUUUUGCU | [1044-1062] | — | — | — | — |
| 557 | Hum | GUAAGCAAAAGUAGAAGCC | GGCUUCUACUUUUGCUUAC | [1041-1059] | — | — | — | — |
| 558 | Hum, chimp | GAGAGCCUGCUAAGUGAUU | AAUCACUUAGCAGGCUCUC | [279-297] | [283-295] (13/13) | [164-176] (13/13) | [399-417] | [263-279] (16/17) |
| 559 | Hum | GCAUAGAUCCCAUUUUUGU | ACAAAAAUGGGAUCUAUGC | [996-1016] | — | — | — | — |
| 560 | Hum | AGUGUAGAUUUUCUGCAUA | UAUGCAGAAAAUCUACACU | [984-1002] | — | — | — | — |
| 561 | Hum | UGGAGAAGUGAUUCAAAAU | AUUUUGAAUCACUUCUCCA | [965-983] | — | — | — | — |
| 562 | Hum | ACUGCAGCUAACAGGCUGA | UCAGCCUGUUAGCUGCAGU | [934-952] | — | — | — | — |
| 563 | Hum | CUGUGUUUCACAUUCAUAG | CUAUGAAUGUGAAACACAG | [913-931] | — | — | — | — |
| 564 | Hum | UUCUGUGUUUCACAUUCAU | AUGAAUGUGAAACACAGAA | [911-929] | — | — | — | — |
| 565 | Hum | CCCAAAUGUAGUCUCUUUU | AAAAGAGACUACAUUUGGG | [890-908] | — | — | — | — |
| 566 | Hum | CCCCAAAUGUAGUCUCUUU | AAAGAGACUACAUUUGGGG | [889-907] | — | — | — | — |
| 567 | Hum | AACCCCAAAUGUAGUCUCU | AGAGACUACAUUUGGGGUU | [887-905] | — | — | — | — |
| 568 | Hum | CUGCCUAAAUAAGAAACC | GGUUUCUUAUUUAGGGCAG | [872-890] | — | — | — | — |
| 569 | Hum | ACCUGCCCUAAAUAAGAAA | UUUCUUAUUUAGGGCAGGU | [870-888] | — | — | — | — |
| 570 | Hum | CCCACCUGCCCUAAAUAAG | CUUAUUUAGGGCAGGUGGG | [867-885] | — | — | — | — |
| 571 | Hum | CUCACUGAUUGGAACAACA | UGUUGUUCCAAUCAGUGAG | [749-767] | [751-761] (11/11) | [632-642] (11/11) | — | [736-749] (14/14) |
| 572 | Hum | CUCAGGAUUUCGACUUGUU | AACAAGUCGAAAUCCUGAG | [716-734] | [714-731] (18/18) | [599-613] (15/15) | — | — |
| 573 | Hum, ms | GCUCAGGAUUUCGACUUGU | ACAAGUCGAAAUCCUGAGC | [715-733] | [713-731] (18/19) | [594-612] (18/19) | — | — |
| 574 | Hum, ms | AGCUCAGGAUUUCGACUUG | CAAGUCGAAAUCCUGAGCU | [714-732] | [712-730] (18/19) | [593-611] (18/19) | — | — |
| 575 | Hum | AGGAGAACUCUGAUCCUCA | UGAGGAUCAGAGUUCUCCU | [696-714] | — | [579-593] (15/15) | — | — |
| 576 | Hum, chimp | GGCAGUUUGAGCAGCAAGA | UCUUGCUGCUCAAACUGCC | [216-234] | [214-232] (18/19) | [95-113] (18/19) | [336-354] | [198-216] (18/19) |
| 577 | Hum, chimp | UGAGCUUACACUUGUGUUU | AAACACAAGUGUAAGCUCA | [605-623] | — | — | [725-743] | [588-605] (17/18) |

TABLE A-continued

19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 578 | Hum, chimp | UUUGAGCUUACACUUGUGU | ACACAAGUGUAAGCUCAAA | [603-621] | — | — | [723-741] | — |
| 579 | Hum | GUGUGUGAUUCUAGCGUCG | CGACGCUAGAAUCACACAC | [576-594] | — | — | [696-714] (18/19) | [568-571] (14/14) |
| 580 | Hum | UUGUGUGUGAUUCUAGCGU | ACGCUAGAAUCACACACAA | [574-592] | — | [453-468] (15/16) | [694-709] (16/16) | [556-571] (16/16) |
| 581 | Hum, rat, chimp | UGGAUAGGAUUGUGUGUGA | UCACACACAAUCCUAUCCA | [565-583] | — | [444-462] | [685-703] | [547-565] (18/19) |
| 582 | Hum, rat, chimp | AAAAGCUGGAUAGGAUUGU | ACAAUCCUAUCCAGCUUUU | [559-577] | [557-572] (16/16) | [438-456] | [679-697] | [541-559] (18/19) |
| 583 | Hum, ms, chimp, dog | GUAUGUAAAAGCUGGAUA | UAUCCAGCUUUUUACAUAC | [552-570] | [550-568] | [434-449] (16/16) | [672-690] | [534-552] |
| 584 | Hum, ms, chimp | AUGUAUGUAAAAGCUGGA | UCCAGCUUUUUACAUACAU | [550-568] | [548-566] | [429-447] (18/19) | [670-688] | [534-550] (17/17) |
| 585 | Hum, ms, chimp | CUGACCCAGAGAAUUGCUC | GAGCAAUUCUCUGGGUCAG | [453-471] | [451-469] | [332-348] (17/17) | [573-591] | [435-453] (18/19) |
| 586 | Hum, chimp | AUGGUUGCAACUGGCAGUU | AACUGCCAGUUGCAACCAU | [204-222] | [202-220] (18/19) | [83-101] (18/19) | [324-342] | [186-204] (18/19) |
| 587 | Hum | UGGAAGGCUGUUAAAUUAA | UUAAUUUAACAGCCUUCCA | [2511-2529] | — | — | — | — |
| 588 | Hum | GCUUAUGGAAGGCUGUUAA | UUAACAGCCUUCCAUAAGC | [2506-2524] | — | — | — | — |
| 589 | Hum, chimp, dog | CUGUCUGUCCAAAUCAAAG | CUUUGAUUUGGACAGACAG | [392-410] | [390-408] (18/19) | [271-289] (18/19) | [512-530] | [374-392] |
| 590 | Hum | AUGUAGAACUGUUGUCCUU | AAGGACAACAGUUCUACAU | [2430-2448] | — | — | — | — |
| 591 | Hum | GCAUCGAUGUAGAACUGUU | AACAGUUCUACAUCGAUGC | [2424-2442] | — | — | — | — |
| 592 | Hum | AAUGUUGUUUGCAUGUCU | AGACAUGCAAAACAACAUU | [2327-2345] | — | — | — | — |
| 593 | Hum | UGGGCCAAGAUAAAUCAAU | AUUGAUUUAUCUUGGCCCA | [2311-2329] | — | — | — | — |
| 594 | Hum | GAAUUGGGCCAAGAUAAAU | AUUUAUCUUGGCCCAAUUC | [2307-2325] | — | — | — | — |
| 595 | Hum | AGAAUUGGGCCAAGAUAAA | UUUAUCUUGGCCCAAUUCU | [2306-2324] | — | — | — | — |
| 596 | Hum | CUCUUCAAAUGCUUGGAAA | UUUCCAAGCAUUUGAAGAG | [2264-2282] | — | — | — | — |
| 597 | Hum | ACUCUUCAAAUGCUUGGAA | UUCCAAGCAUUUGAAGAGU | [2263-2281] | — | — | — | — |
| 598 | Hum | GUCACUGUUCAAAUUAGCC | GGCUAAUUUGAACAGUGAC | [2226-2244] | — | — | — | — |
| 599 | Hum | GUGACCUAAAAUGUCACUG | CAGUGACAUUUUAGGUCAC | [2214-2232] | — | — | — | — |
| 600 | Hum | CUGAUACUAUAAGUGACCU | AGGUCACUUAUAGUAUCAG | [2202-2220] | — | — | — | — |
| 601 | Hum | ACUGAUACUAUAAGUGACC | GGUCACUUAUAGUAUCAGU | [2201-2219] | — | — | — | — |
| 602 | Hum | UACUGAUACUAUAAGUGAC | GUCACUUAUAGUAUCAGUA | [2200-2218] | — | — | — | — |
| 603 | Hum | GAUCCUGUUACUGAUACUA | UAGUAUCAGUAACAGGAUC | [2192-2210] | — | — | — | — |

TABLE A-continued 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 604 | Hum | GGUGUGAUCCUGUUACUGA | UCAGUAACAGGAUCACACC | [2187-2205] | — | — | — | — |
| 605 | Hum | CUGAAAAACAGGUGUGAUC | GAUCACACCUGUUUUUCAG | [2177-2195] | — | — | — | — |
| 606 | Hum | UGGUGUUACUGAAAAACAG | CUGUUUUUCAGUAACACCA | [2169-2187] | — | — | — | — |
| 607 | Hum | CUGGUGUUACUGAAAAACA | UGUUUUUCAGUAACACCAG | [2168-2186] | — | — | — | — |
| 608 | Hum | UCCUGGUGUUACUGAAAAA | UUUUUCAGUAACACCAGGA | [2166-2184] | — | — | — | — |
| 609 | Hum | ACAGAUGUAUUCAUCCUGG | CCAGGAUGAAUACAUCUGU | [2153-2171] | — | — | — | — |
| 610 | Hum | GACAGAUGUAUUCAUCCUG | CAGGAUGAAUACAUCUGUC | [2152-2170] | — | — | — | — |
| 611 | Hum | GCUAGGGACAGAUGUAUU | AAUACAUCUGUCCCUACGC | [2145-2163] | — | — | — | — |
| 612 | Hum | UCCUGCCCUAGCUAUUAGC | GCUAAUAGCUAGGGCAGGA | [2103-2121] | — | — | — | — |
| 613 | Hum | GUGGAUAAGGAGCUUAUUC | GAAUAAGCUCCUUAUCCAC | [2079-2097] | — | — | — | — |
| 614 | Hum | UGCUGUGGGUCGUGGAUAA | UUAUCCACGACCCACAGCA | [2068-2086] | — | — | — | — |
| 615 | Hum, chimp | GAAUCAACUUGCCAGAAUU | AAUUCUGGCAAGUUGAUUC | [354-372] | — | — | [474-492] | [340-351] (12/12) |
| 616 | Hum | CCAACUAAGUAGAUCAUUA | UAAUGAUCUACUUAGUUGG | [1971-1989] | — | — | — | — |
| 617 | Hum | AAAGGCCUUAUUUUUUGUC | GACAAAAAUAAGGCCUUU | [1947-1965] | — | — | — | — |
| 618 | Hum | GGAAUAAUAAAGGCCUUAU | AUAAGGCCUUUAUUAUUCC | [1939-1957] | — | — | — | — |
| 619 | Hum | GGGAAUAAUAAAGGCCUUA | UAAGGCCUUUAUUAUUCCC | [1938-1956] | — | — | — | — |
| 620 | Hum | AACCAUGCAUGCACCCAGA | UCUGGGUGCAUGCAUGGUU | [1891-1909] | — | — | — | — |
| 621 | Hum | CAGAUAACCAUGCAUGCAC | GUGCAUGCAUGGUUAUCUG | [1886-1904] | — | — | — | — |
| 622 | Hum | CUCACCGUCCAGAUAACCA | UGGUUAUCUGGACGGUGAG | [1877-1895] | — | — | — | — |
| 623 | Hum | AUGAAACUCACCGUCCAGA | UCUGGACGGUGAGUUUCAU | [1871-1889] | — | — | — | — |
| 624 | Hum | AGAGAAUGAAACUCACCGU | ACGGUGAGUUUCAUUCUCU | [1866-1884] | — | — | — | — |
| 625 | Hum | GUACAGCCUAGAGAAUGAA | UUCAUUCUCUAGGCUGUAC | [1857-1875] | — | — | — | — |
| 626 | Hum | AUGGUUUAUAGUACAGCCU | AGGCUGUACUAUAAACCAU | [1847-1865] | — | — | — | — |
| 627 | Hum | AUGGAGAUAUGGUUUAUAG | CUAUAAACCAUAUCUCCAU | [1839-1857] | — | — | — | — |
| 628 | Hum | UGGCUAUGGAGAUAUGGUU | AACCAUAUCUCCAUAGCCA | [1834-1852] | — | — | — | — |
| 629 | Hum | UGCAUUGGCUAUGGAGAUA | UAUCUCCAUAGCCAAUGCA | [1829-1847] | — | — | — | — |
| 630 | Hum | GUAUACUACCACUUUGAAU | AUUCAAAGUGGUAGUAUAC | [1783-1801] | — | — | — | — |
| 631 | Hum | AGCUGUAUACUACCACUUU | AAAGUGGUAGUAUACAGCU | [1779-1797] | — | — | — | — |
| 632 | Hum | GGUAGUAGCUGUAUACUAC | GUAGUAUACAGCUACUACC | [1773-1791] | — | — | — | — |
| 633 | Hum | CAAGGGUAGUAGCUGUAUA | UAUACAGCUACUACCCUUG | [1769-1787] | — | — | — | — |
| 634 | Hum | UCCUUAACCCAAUUGUCA | UGACAAUUGGGGUUAAGGA | [1752-1770] | — | — | — | — |
| 635 | Hum | AAGUAUCUCUCCUUAACCC | GGGUUAAGGAGAGAUACUU | [1743-1761] | — | — | — | — |
| 636 | Hum | UCUGGGAAUUGAAGUAUCU | AGAUACUUCAAUUCCCAGA | [1732-1750] | — | — | — | — |
| 637 | Hum | UUUCUGGGAAUUGAAGUAU | AUACUUCAAUUCCCAGAAA | [1730-1748] | — | — | — | — |
| 638 | Hum | GGCAGUGUUAUCUCAUCUC | GAGAUGAGAUAACACUGCC | [1705-1723] | — | — | — | — |

TABLE A-continued

| | | | | Hum 34222182 cds = | | | | |
|---|---|---|---|---|---|---|---|---|
| No | Sp-Source | Sense siRNA | AntiSense siRNA | 204-785 | Mouse 31541838 | rat 62644440 | chimp 55622975 | dog 74002279 |
| 639 | Hum | AUGGCAGUGUUAUCUCAUC | GAUGAGAUAACACUGCCAU | [1703-1721] | — | — | — | — |
| 640 | Hum | CACCAUGGCAGUGUUAUCU | AGAUAACACUGCCAUGGUG | [1699-1717] | — | — | — | — |
| 641 | Hum | UGCUUAAUCUCAGAUGAAC | GUUCAUCUGAGAUUAAGCA | [1675-1693] | — | — | — | — |
| 642 | Hum | CAUGUGCUUAAUCUCAGAU | AUCUGAGAUUAAGCACAUG | [1671-1689] | — | — | — | — |
| 643 | Hum | UUACAUGUGCUUAAUCUCA | UGAGAUUAAGCACAUGUAA | [1668-1686] | — | — | — | — |
| 644 | Hum | CAGUAUUACAUGUGCUUAA | UUAAGCACAUGUAAUACUG | [1663-1681] | — | — | — | — |
| 645 | Hum | UCACUUAGUAAUCUAUCCU | AGGAUAGAUUACUAAGUGA | [1639-1657] | — | — | — | — |
| 646 | Hum | CUGUGAGGAUAGGAAAUUA | UAAUUUCCUAUCCUCACAG | [1594-1612] | — | — | — | — |
| 647 | Hum | AGUGUUGAAUACUGUCUUU | AAAGACAGUAUUCAACACU | [1496-1514] | — | — | — | — |
| 648 | Hum | UAAGUGUUGAAUACUGUCU | AGACAGUAUUCAACACUUA | [1494-1512] | — | — | — | — |
| 649 | Hum | CUGUUCUUAAGUGUUGAAU | AUUCAACACUUAAGAACAG | [1487-1505] | — | — | — | — |
| 650 | Hum | CCUGUUCUUAAGUGUUGAA | UUCAACACUUAAGAACAGG | [1486-1504] | — | — | — | — |
| 651 | Hum | GAUGCCUUUAUAAGCUCAG | CUGAGCUUAUAAAGGCAUC | [1462-1480] | — | — | — | — |
| 652 | Hum | UAGAUGCCUUUAUAAGCUC | GAGCUUAUAAAGGCAUCUA | [1460-1478] | — | — | — | — |
| 653 | Hum | GGUGUUGUUUUAGAUGCCU | AGGCAUCUAAAACAACACC | [1450-1468] | — | — | — | — |
| 654 | Hum | UAAAGAGGCAACAAAAGCU | AGCUUUUGUUGCCUCUUUA | [1408-1426] | — | — | — | — |
| 655 | Hum | GUUUUAAAGAGGCAACAAA | UUUGUUGCCUCUUUAAAAC | [1404-1422] | — | — | — | — |
| 656 | Hum | AUGUUUUAAAGAGGCAACA | UGUUGCCUCUUUAAAACAU | [1402-1420] | — | — | — | — |
| 657 | Hum | GCUUCACUGUUUCUUGGUG | CACCAAGAAACAGUGAAGC | [1369-1387] | — | — | — | [1333-1346] (14/14) |
| 658 | Hum | GAGAAAUAUUACGGCAAUA | UAUUGCCGUAAUAUUUCUC | [1342-1360] | — | — | — | — |
| 659 | Hum | ACUCAAAUUUGAAGGGUUU | AAACCCUUCAAAUUUGAGU | [1258-1276] | — | — | — | — |
| 660 | Hum, chimp | AAGUGAUUUUGACUACUGG | CCAGUAGUCAAAAUCACUU | [290-308] | — | — | [410-428] | [275-290] (16/16) |
| 661 | Hum, chimp | UAAGUGAUUUUGACUACUG | CAGUAGUCAAAAUCACUUA | [289-307] | — | — | [409-427] | [275-289] (15/15) |
| 662 | Hum | CACAGAAUCAUACUAAAUG | CAUUUAGUAUGAUUCUGUG | [1192-1210] | — | — | — | — |
| 663 | Hum, chimp | GCUAAGUGAUUUUGACUAC | GUAGUCAAAAUCACUUAGC | [287-305] | [285-303] (18/19) | [166-184] (18/19) | [407-425] | [269-287] (18/19) |
| 664 | Hum | CAGGUAGGCUUGGUAAUAG | CUAUUACCAAGCCUACCUG | [1096-1114] | — | — | — | — |
| 665 | Hum | UGGGAUGGAAUAGGUAAGC | GCUUACCUAUUCCAUCCCA | [1028-1046] | — | — | — | — |
| 666 | Hum | AUGGGAUGGAAUAGGUAAG | CUUACCUAUUCCAUCCCAU | [1027-1045] | — | — | — | — |
| 667 | Hum | UAGUCUCUUUUCUUUCUGU | ACAGAAAGAAAAGAGACUA | [898-916] | — | — | — | — |
| 668 | Hum | AAGAAACCCCAAAUGUAGU | ACUACAUUUGGGGUUUCUU | [883-901] | — | — | — | [866-878] (13/13) |
| 669 | Hum | CCCUAAAUAAGAAACCCCA | UGGGGUUUCUUAUUUAGGG | [875-893] | — | — | — | — |

TABLE A-continued

| | | | | 19 mer | | | | |
|---|---|---|---|---|---|---|---|---|
| No | Sp-Source | Sense siRNA | AntiSense siRNA | Hum 34222182 cds = 204-785 | Mouse 31541838 | rat 62644440 | chimp 55622975 | dog 74002279 |
| 670 | Hum | GAACAACAGUGAUUGAAGG | CCUUCAAUCACUGUUGUUC | [760-778] | — | — | — | — |
| 671 | Hum | CUGAUUGGAACAACAGUGA | UCACUGUUGUUCCAAUCAG | [753-771] | [751-767] (16/17) | [632-648] (16/17) | — | [736-751] (16/16) |
| 672 | Hum | GAUCCUCAGCUCAGGAUUU | AAAUCCUGAGCUGAGGAUC | [707-725] | [709-723] (15/15) | [586-604] (18/19) | — | — |
| 673 | Hum | UUCAGGAGAACUCUGAUCC | GGAUCAGAGUUCUCCUGAA | [693-711] | — | [579-590] (12/12) | — | — |
| 674 | Hum | UAGUAGAGGUCGCUUCUCC | GGAGAAGCGACCUCUACUA | [668-686] | [670-684] (15/15) | [552-564] (13/13) | — | [657-667] (11/11) |
| 675 | Hum, chimp | GCUUCAGGGACUUUUUCUU | AAGAAAAAGUCCCUGAAGC | [649-667] | — | — | [769-787] | — |
| 676 | Hum, chimp, dog | AAGCAGGAGAACUGCUCAU | AUGAGCAGUUCUCCUGCUU | [624-642] | — | — | [744-762] | [608-624] |
| 677 | Hum, chimp | GAGCUUACACUUGUGUUUA | UAAACACAAGUGUAAGCUC | [606-624] | — | — | [726-744] | [588-606] (18/19) |
| 678 | Hum | GUGUGAUUCUAGCGUCGUA | UACGACGCUAGAAUCACAC | [578-596] | — | — | [698-715] (17/18) | [560-571] (12/12) |
| 679 | Hum, chimp | AGGAUUGUGUGUGAUUCUA | UAGAAUCACACACAAUCCU | [570-588] | — | [449-463] (15/15) | [690-708] | [554-570] (17/17) |
| 680 | Hum, chimp | GGUCCUUGUCCCUGAGAAA | UUUCUCAGGGACAAGGACC | [434-452] | [439-450] (12/12) | — | [554-572] | [417-434] (18/18) |
| 681 | Hum | ACAAAAUGGUGAUGGCUUA | UAAGCCAUCACCAUUUUGU | [2492-2510] | — | — | — | — |
| 682 | Hum | CUCUCUUGCCUGUUAUGCU | AGCAUAACAGGCAAGAGAG | [2472-2490] | — | — | — | — |
| 683 | Hum | AUCUUUGACUCUCUUGCCU | AGGCAAGAGAGUCAAAGAU | [2464-2482] | — | — | — | — |
| 684 | Hum | UUCCACUAACAGUUAUCUU | AAGAUAACUGUUAGUGGAA | [2450-2468] | — | — | — | — |
| 685 | Hum | UCGAUGUAGAACUGUUGUC | GACAACAGUUCUACAUCGA | [2427-2445] | — | — | — | — |
| 686 | Hum | UCUUGGGCAUCGAUGUAGA | UCUACAUCGAUGCCCAAGA | [2418-2436] | — | — | — | — |
| 687 | Hum | AAGGCUUCUGGGCAUCGA | UCGAUGCCCAAGAAGCCUU | [2412-2430] | — | — | — | — |
| 688 | Hum | GUCUAUUGUUAAGCUCCAA | UUGGAGCUUAACAAUAGAC | [2342-2360] | — | — | — | — |
| 689 | Hum | UGUCUAUUGUUAAGCUCCA | UGGAGCUUAACAAUAGACA | [2341-2359] | — | — | — | — |
| 690 | Hum | UGCAUGUCUAUUGUUAAGC | GCUUAACAAUAGACAUGCA | [2337-2355] | — | — | — | — |
| 691 | Hum | UGUUUUGCAUGUCUAUUGU | ACAAUAGACAUGCAAAACA | [2332-2350] | — | — | — | — |
| 692 | Hum | UUGUUUUGCAUGUCUAUUG | CAAUAGACAUGCAAAACAA | [2331-2349] | — | — | — | — |
| 693 | Hum | AGUGACCUAAAAUGUCACU | AGUGACAUUUUAGGUCACU | [2213-2231] | — | — | — | — |
| 694 | Hum | GUUACUGAUACUAUAAGUG | CACUUAUAGUAUCAGUAAC | [2198-2216] | — | — | — | — |
| 695 | Hum | AAACAGGUGUGAUCCUGUU | AACAGGAUCACACCUGUUU | [2182-2200] | — | — | — | — |
| 696 | Hum | UCAUCCUGGUGUUACUGAA | UUCAGUAACACCAGGAUGA | [2163-2181] | — | — | — | — |
| 697 | Hum | GAUGUAUUCAUCCUGGUGU | ACACCAGGAUGAAUACAUC | [2156-2174] | — | — | — | — |

TABLE A-continued

19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 698 | Hum | CUAGCUAUUAGCUCCACUU | AAGUGGAGCUAAUAGCUAG | [2110-2128] | — | — | — | — |
| 699 | Hum | UAAGGAGCUUAUUCAGGUU | AACCUGAAUAAGCUCCUUA | [2084-2102] | — | — | — | — |
| 700 | Hum | GUCGUGGAUAAGGAGCUUA | UAAGCUCCUUAUCCACGAC | [2076-2094] | — | — | — | — |
| 701 | Hum | UGUGGGUCGUGGAUAAGGA | UCCUUAUCCACGACCCACA | [2071-2089] | — | — | — | — |
| 702 | Hum | UUCAUAUCCUUGCUGUGGG | CCCACAGCAAGGAUAUGAA | [2058-2076] | — | — | — | — |
| 703 | Hum | UAAUGAGAGAAUUUAGCCU | AGGCUAAAUUCUCUCAUUA | [2009-2027] | — | — | — | — |
| 704 | Hum | GUUAAUGAGAGAAUUUAGC | GCUAAAUUCUCUCAUUAAC | [2007-2025] | — | — | — | — |
| 705 | Hum | CUUAUUCCAACUAAGUAGA | UCUACUUAGUUGGAAUAAG | [1965-1983] | — | — | — | — |
| 706 | Hum | UUGUCUUAUUCCAACUAAG | CUUAGUUGGAAUAAGACAA | [1961-1979] | — | — | — | — |
| 707 | Hum | GUCACUAGGGAAUAAUAAA | UUUAUUAUUCCCUAGUGAC | [1931-1949] | — | — | — | — |
| 708 | Hum | CUGUCACUAGGGAAUAAUA | UAUUAUUCCCUAGUGACAG | [1929-1947] | — | — | — | — |
| 709 | Hum | CGUCCAGAUAACCAUGCAU | AUGCAUGGUUAUCUGGACG | [1882-1900] | — | — | — | — |
| 710 | Hum | UAGAGAAUGAAACUCACCG | CGGUGAGUUUCAUUCUCUA | [1865-1883] | — | — | — | — |
| 711 | Hum | CUACCACUUUGAAUUAUUG | CAAUAAUUCAAAGUGGUAG | [1788-1806] | — | — | — | — |
| 712 | Hum | UGUCAAGGGUAGUAGCUGU | ACAGCUACUACCCUUGACA | [1766-1784] | — | — | — | — |
| 713 | Hum | CUCUCCUUAACCCCAAUUG | CAAUUGGGGUUAAGGAGAG | [1749-1767] | — | — | — | — |
| 714 | Hum | GAUGAACCAUUUCACCAUG | CAUGGUGAAAUGGUUCAUC | [1687-1705] | — | — | — | — |
| 715 | Hum | UUUCAGUAUUACAUGUGCU | AGCACAUGUAAUACUGAAA | [1660-1678] | — | — | — | — |
| 716 | Hum, chimp | UUCCUGAACCCAACCUCAA | UUGAGGUUGGGUUCAGGAA | [319-337] | [319-335] (16/17) | [206-216] (11-11) | [439-457] | [301-319] (18/19) |
| 717 | Hum | GUAAUCUAUCCUCUUUUCA | UGAAAAGAGGAUAGAUUAC | [1646-1664] | — | — | — | — |
| 718 | Hum, chimp | UUGUUCCUGAACCCAACCU | AGGUUGGGUUCAGGAACAA | [316-334] | — | — | [436-454] | [298-316] (18/19) |
| 719 | Hum | GGAAAUUAGUUCUGAGAUC | GAUCUCAGAACUAAUUUCC | [1605-1623] | — | — | — | — |
| 720 | Hum | AGGAUAGGAAAUUAGUUCU | AGAACUAAUUUCCUAUCCU | [1599-1617] | — | — | — | — |
| 721 | Hum | UGUGAGGAUAGGAAAUUAG | CUAAUUUCCUAUCCUCACA | [1595-1613] | — | — | — | — |
| 722 | Hum | CCUGUGAGGAUAGGAAAUU | AAUUUCCUAUCCUCACAGG | [1593-1611] | — | — | — | — |
| 723 | Hum | CUGAUAUUUUGUGUGUAG | CUACACACAAAAAUAUCAG | [1541-1559] | — | — | — | — |
| 724 | Hum | GUUCUUAAGUGUUGAAUAC | GUAUUCAACACUUAAGAAC | [1489-1507] | — | — | — | — |
| 725 | Hum, chimp | ACUGGGAUUAUGUUGUUCC | GGAACAACAUAAUCCCAGU | [304-322] | [302-317] (16/16) | [183-195] (13/13) | [424-442] | — |
| 726 | Hum | GGUGACUUCCUCACUCUAA | UUAGAGUGAGGAAGUCACC | [1384-1402] | — | — | — | — |
| 727 | Hum | UUGGUGACUUCCUCACUCU | AGAGUGAGGAAGUCACCAA | [1382-1400] | — | — | — | — |
| 728 | Hum | CACUGUUUCUUGGUGACUU | AAGUCACCAAGAAACAGUG | [1373-1391] | — | — | — | [1336-1346] (11/11) |
| 729 | Hum | CUUCACUGUUUCUUGGUGA | UCACCAAGAAACAGUGAAG | [1370-1388] | — | — | — | [1333-1346] (14/14) |

TABLE A-continued

19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 730 | Hum | UAUUACGGCAAUAAUGGAA | UUCCAUUAUUGCCGUAAUA | [1348-1366] | — | — | — | — |
| 731 | Hum | UAGGUAAGAGUAAAUGAGA | UCUCAUUUACUCUUACCUA | [1327-1345] | — | — | — | — |
| 732 | Hum | CCCUAGGUAAGAGUAAAUG | CAUUUACUCUUACCUAGGG | [1324-1342] | — | — | — | — |
| 733 | Hum | UUAGACAGGAAGGUAGGAU | AUCCUACCUUCCUGUCUAA | [1277-1295] | — | — | — | — |
| 734 | Hum, chimp | CUAAGUGAUUUUGACUACU | AGUAGUCAAAAUCACUUAG | [288-306] | [286-304] (18/19) | [167-185] (18/19) | [408-426] | [270-288] (18/19) |
| 735 | Hum | AGAAGCCCAUUUGAGUUUU | AAAACUCAAAUGGGCUUCU | [1053-1071] | — | — | — | — |
| 736 | Hum | GUAGAAGCCCAUUUGAGUU | AACUCAAAUGGGCUUCUAC | [1051-1069] | — | — | — | — |
| 737 | Hum | AAGUAGAAGCCCAUUUGAG | CUCAAAUGGGCUUCUACUU | [1049-1067] | — | — | — | — |
| 738 | Hum | CAAAGUAGAAGCCCAUUUU | AAAUGGGCUUCUACUUUUG | [1046-1064] | — | — | — | — |
| 739 | Hum, chimp | AGCCUGCUAAGUGAUUUUG | CAAAAUCACUUAGCAGGCU | [282-300] | [283-296] (14/14) | [164-177] (14/14) | [402-420] | — |
| 740 | Hum | GGUAAGCAAAAGUAGAAGC | GCUUCUACUUUUGCUUACC | [1040-1058] | — | — | — | — |
| 741 | Hum | AGGUAAGCAAAAGUAGAAG | CUUCUACUUUUGCUUACCU | [1039-1057] | — | — | — | — |
| 742 | Hum | UGGAAUAGGUAAGCAAAAG | CUUUUGCUUACCUAUUCCA | [1033-1051] | — | — | — | — |
| 743 | Hum | AUGGAAUAGGUAAGCAAAA | UUUUGCUUACCUAUUCCAU | [1032-1050] | — | — | — | — |
| 744 | Hum | UUGAAUGGGAUGGAAUAGG | CCUAUUCCAUCCCAUUCAA | [1023-1041] | — | — | — | — |
| 745 | Hum, chimp | AGAGCCUGCUAAGUGAUUU | AAAUCACUUAGCAGGCUCU | [280-298] | [283-296] (14/14) | [164-177] (14/14) | [400-418] | [263-280] (17/18) |
| 746 | Hum | UCUGCAUAGAUCCCAUUUU | AAAAUGGGAUCUAUGCAGA | [995-1013] | — | — | — | — |
| 747 | Hum | UUCUGGCCUUUGGAGAAGU | ACUUCUCCAAAGGCCAGAA | [955-973] | — | — | — | — |
| 748 | Hum | UUUCUGUGUUUCACAUUCA | UGAAUGUGAAACACAGAAA | [910-928] | — | — | — | — |
| 749 | Hum | GUAGUCUCUUUUCUUUCUG | CAGAAAGAAAAGAGACUAC | [897-915] | — | — | — | — |
| 750 | Hum | GAAACCCCAAAUGUAGUCU | AGACUACAUUUGGGGUUUC | [885-903] | — | — | — | [867-878] (12/12) |
| 751 | Hum | GUAGUAAAACUAUUCAGCU | AGCUGAAUAGUUUUACUAC | [821-839] | — | — | — | — |
| 752 | Hum | GGUAGUAAAACUAUUCAGC | GCUGAAUAGUUUUACUACC | [820-838] | — | — | — | — |
| 753 | Hum | GAUUGGAACAACAGUGAUU | AAUCACUGUUGUUCCAAUC | [755-773] | — | — | — | [737-751] (15/15) |
| 754 | Hum | UACUCACUGAUUGGAACAA | UUGUUCCAAUCAGUGAGUA | [747-765] | [745-761] (16/17) | [626-642] (16/17) | — | [736-747] (12/12) |
| 755 | Hum, rat | GAUUUCGACUUGUUAAGAA | UUCUUAACAAGUCGAAAUC | [721-739] | [719-737] (18/19) | [600-618] | — | — |
| 756 | Hum | AGGAUUUCGACUUGUUAAG | CUUAACAAGUCGAAAUCCU | [719-737] | [717-731] (15/15) | [599-616] (18/18) | — | — |
| 757 | Hum | UCAGGAGAACUCUGAUCCU | AGGAUCAGAGUUCUCCUGA | [694-712] | — | [579-591] (13/13) | — | — |

TABLE A-continued

| | | | | 19 mer | | | | |
|---|---|---|---|---|---|---|---|---|
| No | Sp-Source | Sense siRNA | AntiSense siRNA | Hum 34222182 cds = 204-785 | Mouse 31541838 | rat 62644440 | chimp 55622975 | dog 74002279 |
| 758 | Hum, chimp | GGACUAGCUUCAGGGACUU | AAGUCCCUGAAGCUAGUCC | [643-661] | — | — | [763-781] | [625-640] (16/16) |
| 759 | Hum, chimp, dog | CUCAUGGACUAGCUUCAGG | CCUGAAGCUAGUCCAUGAG | [638-656] | — | — | [758-776] | [620-638] |
| 760 | Hum, chimp, dog | GAGAACUGCUCAUGGACUA | UAGUCCAUGAGCAGUUCUC | [630-648] | — | — | [750-768] | [612-630] |
| 761 | Hum, chimp, dog | GGAGAACUGCUCAUGGACU | AGUCCAUGAGCAGUUCUCC | [629-647] | — | — | [749-767] | [611-629] |
| 762 | Hum, chimp, dog | CAGGAGAACUGCUCAUGGA | UCCAUGAGCAGUUCUCCUG | [627-645] | — | — | [747-765] | [609-627] |
| 763 | Hum, chimp | GCUUACACUUGUGUUUAAG | CUUAAACACAAGUGUAAGC | [608-626] | [613-624] (12/12) | — | [728-746] | [594-608] (15/15) |
| 764 | Hum, chimp | GGAUUGUGUGUGAUUCUAG | CUAGAAUCACACACAAUCC | [571-589] | — | [450-468] (18/19) | [691-709] | [554-571] (18/18) |
| 765 | Hum, rat, chimp | GGAUAGGAUUGUGUGUGAU | AUCACACACAAUCCUAUCC | [566-584] | — | [445-463] | [686-704] | [548-566] (18/19) |
| 766 | Hum, chimp | GGUUGCAACUGGCAGUUUG | CAAACUGCCAGUUGCAACC | [206-224] | — | — | [326-344] | [192-206] (15/15) |
| 767 | Hum, chimp | UAAACUUGGUUGCUCAAAG | CUUUGAGCAACCAAGUUUA | [416-434] | [415-428] (14/14) | — | [536-554] | [402-415] (14/14) |
| 768 | Hum | GGCUUAUGGAAGGCUGUUA | UAACAGCCUUCCAUAAGCC | [2505-2523] | — | — | — | — |
| 769 | Hum | AAAUGGUGAUGGCUUAUGG | CCAUAAGCCAUCACCAUUU | [2495-2513] | — | — | — | — |
| 770 | Hum | UCUCUUGCCUGUUAUGCUU | AAGCAUAACAGGCAAGAGA | [2473-2491] | — | — | — | — |
| 771 | Hum | UUCUGGGCAUCGAUGUAG | CUACAUCGAUGCCCAAGAA | [2417-2435] | — | — | — | — |
| 772 | Hum | AAGCUCCAAAGGUUCACUG | CAGUGAACCUUUGGAGCUU | [2352-2370] | — | — | — | — |
| 773 | Hum | UCUAUUGUUAAGCUCCAAA | UUUGGAGCUUAACAAUAGA | [2343-2361] | — | — | — | — |
| 774 | Hum | GGGCCAAGAUAAAUCAAUG | CAUUGAUUUAUCUUGGCCC | [2312-2330] | — | — | — | — |
| 775 | Hum | UAGAAUUGGGCCAAGAUAA | UUAUCUUGGCCCAAUUCUA | [2305-2323] | — | — | — | — |
| 776 | Hum | GGAAAGAUACUACAAAGCC | GGCUUUGUAGUAUCUUUCC | [2278-2296] | [1571-1581] (11/11) | — | — | — |
| 777 | Hum | UCAAAUGCUUGGAAAGAUA | UAUCUUUCCAAGCAUUUGA | [2268-2286] | — | — | — | — |
| 778 | Hum | GUUACUGAAAAACAGGUGU | ACACCUGUUUUUCAGUAAC | [2173-2191] | — | — | — | — |
| 779 | Hum | AUGUAUUCAUCCUGGUGUU | AACACCAGGAUGAAUACAU | [2157-2175] | — | — | — | — |
| 780 | Hum | CAGAUGUAUUCAUCCUGGU | ACCAGGAUGAAUACAUCUG | [2154-2172] | — | — | — | — |
| 781 | Hum | UGCCCUAGCUAUUAGCUCC | GGAGCUAAUAGCUAGGGCA | [2106-2124] | — | — | — | — |
| 782 | Hum | GAGCUUAUUCAGGUUUCCU | AGGAAACCUGAAUAAGCUC | [2088-2106] | — | — | — | — |
| 783 | Hum | GGAGCUUAUUCAGGUUUCC | GGAAACCUGAAUAAGCUCC | [2087-2105] | — | — | — | — |

TABLE A-continued

19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 784 | Hum | UCAUAUCCUUGCUGUGGGU | ACCCACAGCAAGGAUAUGA | [2059-2077] | — | — | — | — |
| 785 | Hum | GUUCAAUUCAGCAAGGCUU | AAGCCUUGCUGAAUUGAAC | [2040-2058] | [2152-2167] (15/16) | — | — | — |
| 786 | Hum | CAACAAUGUUCAAUUCAGC | GCUGAAUUGAACAUUGUUG | [2033-2051] | — | — | — | — |
| 787 | Hum | GUCUUAUUCCAACUAAGUA | UACUUAGUUGGAAUAAGAC | [1963-1981] | — | — | — | — |
| 788 | Hum | CUAGGGAAUAAUAAAGGCC | GGCCUUUAUUAUUCCCUAG | [1935-1953] | — | — | — | — |
| 789 | Hum | UAACCAUGCAUGCACCCAG | CUGGGUGCAUGCAUGGUUA | [1890-1908] | — | — | — | — |
| 790 | Hum | AGAUAACCAUGCAUGCACC | GGUGCAUGCAUGGUUAUCU | [1887-1905] | — | — | — | — |
| 791 | Hum | AGCCUAGAGAAUGAAACUC | GAGUUUCAUUCUCUAGGCU | [1861-1879] | — | — | — | — |
| 792 | Hum | UUAUAGUACAGCCUAGAGA | UCUCUAGGCUGUACUAUAA | [1852-1870] | — | — | — | — |
| 793 | Hum | GCUAUGGAGAUAUGGUUUA | UAAACCAUAUCUCCAUAGC | [1836-1854] | — | — | — | — |
| 794 | Hum | UCUCUCCUUAACCCCAAUU | AAUUGGGGUUAAGGAGAGA | [1748-1766] | — | — | — | — |
| 795 | Hum | AUCUCUCCUUAACCCCAAU | AUUGGGGUUAAGGAGAGAU | [1747-1765] | — | — | — | — |
| 796 | Hum | CUGGGCUUUUCUGGGAAUU | AAUUCCCAGAAAAGCCCAG | [1723-1741] | — | — | — | — |
| 797 | Hum | AACCAUUCACCAUGGCAG | CUGCCAUGGUGAAAUGGUU | [1691-1709] | — | — | — | — |
| 798 | Hum | UUCAGUAUUACAUGUGCUU | AAGCACAUGUAAUACUGAA | [1661-1679] | — | — | — | — |
| 799 | Hum | UCCUCUUUUCAGUAUUACA | UGUAAUACUGAAAAGAGGA | [1654-1672] | — | — | — | — |
| 800 | Hum | AUCCUCUUUUCAGUAUUAC | GUAAUACUGAAAAGAGGAU | [1653-1671] | — | — | — | — |
| 801 | Hum | CUAUCCUCUUUUCAGUAUU | AAUACUGAAAAGAGGAUAG | [1651-1669] | — | — | — | — |
| 802 | Hum | AAUCUAUCCUCUUUUCAGU | ACUGAAAAGAGGAUAGAUU | [1648-1666] | — | — | — | — |
| 803 | Hum | UUCACUUAGUAAUCUAUCC | GGAUAGAUUACUAAGUGAA | [1638-1656] | — | — | — | — |
| 804 | Hum | UAGGAAAUUAGUUCUGAGA | UCUCAGAACUAAUUUCCUA | [1603-1621] | — | — | — | — |
| 805 | Hum | GGAUAGGAAAUUAGUUCUG | CAGAACUAAUUUCCUAUCC | [1600-1618] | — | — | — | — |
| 806 | Hum | GAGGAUAGGAAAUUAGUUC | GAACUAAUUUCCUAUCCUC | [1598-1616] | — | — | — | — |
| 807 | Hum | GUGAGGAUAGGAAAUUAGU | ACUAAUUUCCUAUCCUCAC | [1596-1614] | — | — | — | — |
| 808 | Hum | GUAGGCUUGGUAAUAGACU | AGUCUAUUACCAAGCCUAC | [1099-1117] | — | — | — | — |
| 809 | Hum, chimp | CCUGCUAAGUGAUUUUGAC | GUCAAAAUCACUUAGCAGG | [284-302] | [283-296] (14/14) | [164-177] (14/14) | [404-422] | — |
| 810 | Hum | UGCAUAGAUCCCAUUUUUG | CAAAAAUGGGAUCUAUGCA | [997-1015] | — | — | — | — |
| 811 | Hum | UUCUUUCUGUGUUUCACAU | AUGUGAAACACAGAAAGAA | [907-925] | — | — | — | — |
| 812 | Hum | CAAAUGUAGUCUCUUUUCU | AGAAAAGAGACUACAUUUG | [892-910] | — | — | — | — |
| 813 | Hum | AAACCCCAAAUGUAGUCUC | GAGACUACAUUUGGGGUUU | [886-904] | — | — | — | [868-878] (11/11) |
| 814 | Hum | UGCCCUAAAUAAGAAACCC | GGGUUUCUUAUUUAGGGCA | [873-891] | — | — | — | — |
| 815 | Hum | AAACUAUUCAGCUAGUCAG | CUGACUAGCUGAAUAGUUU | [827-845] | — | — | — | — |
| 816 | Hum | GUGAUUGAAGGGUCCUAAA | UUUAGGACCCUUCAAUCAC | [768-786] | — | — | — | — |
| 817 | Hum | UCAGGAUUUCGACUUGUUA | UAACAAGUCGAAAUCCUGA | [717-735] | [715-731] (17/17) | [599-614] (16/16) | — | — |

TABLE A-continued 19 mer

| No | Sp-Source | Sense siRNA | AntiSense siRNA | Hum 34222182 cds = 204-785 | Mouse 31541838 | rat 62644440 | chimp 55622975 | dog 74002279 |
|---|---|---|---|---|---|---|---|---|
| 818 | Hum | UAGAGGUCGCUUCUCCUCU | AGAGGAGAAGCGACCUCUA | [671-689] | [670-686] (17/17) | [552-564] (13/13) | — | [657-667] (11/11) |
| 819 | Hum, chimp, dog | AACUGCUCAUGGACUAGCU | AGCUAGUCCAUGAGCAGUU | [633-651] | — | — | [753-771] | [615-633] |
| 820 | Hum | GGUGAUGGCUUAUGGAAGG | CCUUCCAUAAGCCAUCACC | [2499-2517] | — | — | — | — |
| 821 | Hum | AGGCUUCUUGGGCAUCGAU | AUCGAUGCCCAAGAAGCCU | [2413-2431] | — | — | — | — |
| 822 | Hum | UAAGCUCCAAAGGUUCACU | AGUGAACCUUUGGAGCUUA | [2351-2369] | — | — | — | — |
| 823 | Hum | GGCCAAGAUAAAUCAAUGU | ACAUUGAUUUAUCUUGGCC | [2313-2331] | — | — | — | — |
| 824 | Hum | UUCAAAUGCUUGGAAAGAU | AUCUUUCCAAGCAUUUGAA | [2267-2285] | — | — | — | — |
| 825 | Hum | GGGACAGAUGUAUUCAUCC | GGAUGAAUACAUCUGUCCC | [2150-2168] | — | — | — | — |
| 826 | Hum | AGCUUAUUCAGGUUUCCUG | CAGGAAACCUGAAUAAGCU | [2089-2107] | — | — | — | — |
| 827 | Hum | AUUCCAACUAAGUAGAUCA | UGAUCUACUUAGUUGGAAU | [1968-1986] | — | — | — | — |
| 828 | Hum | AGUACAGCCUAGAGAAUGA | UCAUUCUCUAGGCUGUACU | [1856-1874] | — | — | — | — |
| 829 | Hum | AUAGUACAGCCUAGAGAAU | AUUCUCUAGGCUGUACUAU | [1854-1872] | — | — | — | — |
| 830 | Hum | GGUUUAUAGUACAGCCUAG | CUAGGCUGUACUAUAAACC | [1849-1867] | — | — | — | — |
| 831 | Hum | GAUAUGGUUUAUAGUACAG | CUGUACUAUAAACCAUAUC | [1844-1862] | — | — | — | — |
| 832 | Hum | GGAGAUAUGGUUUAUAGUA | UACUAUAAACCAUAUCUCC | [1841-1859] | — | — | — | — |
| 833 | Hum | AACCCCAAUUGUCAAGGGU | ACCCUUGACAAUUGGGGUU | [1757-1775] | — | — | — | — |
| 834 | Hum | UAUCUCUCCUUAACCCCAA | UUGGGGUUAAGGAGAGAUA | [1746-1764] | — | — | — | — |
| 835 | Hum | GUAUCUCUCCUUAACCCCA | UGGGGUUAAGGAGAGAUAC | [1745-1763] | — | — | — | — |
| 836 | Hum | UCUGGGCUUUUCUGGGAAU | AUUCCCAGAAAAGCCCAGA | [1722-1740] | — | — | — | — |
| 837 | Hum | GAACCAUUUCACCAUGGCA | UGCCAUGGUGAAAUGGUUC | [1690-1708] | — | — | — | — |
| 838 | Hum | UCUAUCCUCUUUUCAGUAU | AUACUGAAAAGAGGAUAGA | [1650-1668] | — | — | — | — |
| 839 | Hum | UGUGUGUAGUUGAUUACUC | GAGUAAUCAACUACACACA | [1551-1569] | — | — | — | — |
| 840 | Hum | CUUAAGUGUUGAAUACUGU | ACAGUAUUCAACACUUAAG | [1492-1510] | — | — | — | — |
| 841 | Hum | UCUUAAGUGUUGAAUACUG | CAGUAUUCAACACUUAAGA | [1491-1509] | — | — | — | — |
| 842 | Hum | AAACCAGAUUUGCCUAUUU | AAAUAGGCAAAUCUGGUUU | [1122-1140] | — | — | — | — |
| 843 | Hum | CCUUUGGAGAAGUGAUUCA | UGAAUCACUUCUCCAAAGG | [961-979] | — | — | — | — |
| 844 | Hum | UGGCCUUUGGAGAAGUGAU | AUCACUUCUCCAAAGGCCA | [958-976] | — | — | — | — |
| 845 | Hum | UGUAGUCUCUUUUCUUUCU | AGAAAGAAAAGAGACUACA | [896-914] | — | — | — | — |
| 846 | Hum | CUAAAUAAGAAACCCCAAA | UUUGGGGUUUCUUAUUUAG | [877-895] | — | — | — | [866-877] (12/12) |
| 847 | Hum | CCUGCCCUAAAUAAGAAAC | GUUUCUUAUUUAGGGCAGG | [871-889] | — | — | — | — |
| 848 | Hum | AAACUUUACUCACUGAUUG | CAAUCAGUGAGUAAAGUUU | [741-759] | — | — | — | — |
| 849 | Hum | GAAAAACUUUACUCACUG | CAGUGAGUAAAGUUUUUC | [737-755] | — | — | — | — |
| 850 | Hum, rat | GGAUUUCGACUUGUUAAGA | UCUUAACAAGUCGAAAUCC | [720-738] | [718-736] (18/19) | [599-617] | — | — |

TABLE A-continued

| | | | | Hum 34222182 cds = | | | | |
|---|---|---|---|---|---|---|---|---|
| No | Sp-Source | Sense siRNA | AntiSense siRNA | 204-785 | Mouse 31541838 | rat 62644440 | chimp 55622975 | dog 74002279 |
| 851 | Hum | CAGGAUUUCGACUUGUUAA | UUAACAAGUCGAAAUCCUG | [718-736] | [716-731] (16/16) | [599-615] (17/17) | — | — |
| 852 | Hum, chimp | CUGGCAGUUUGAGCAGCAA | UUGCUGCUCAAACUGCCAG | [214-232] | [214-227] (14/14) | [95-108] (14/14) | [334-352] | [196-211] (16/16) |
| 853 | Hum, chimp | ACUGGCAGUUUGAGCAGCA | UGCUGCUCAAACUGCCAGU | [213-231] | [214-227] (14/14) | [95-108] (14/14) | [333-351] | [195-211] (17/17) |
| 854 | Hum, chimp | UAGGAUUGUGUGUGAUUCU | AGAAUCACACACAAUCCUA | [569-587] | — | [448-463] (16/16) | [689-707] | [554-569] (16/16) |
| 855 | Hum, rat, chimp | CUGGAUAGGAUUGUGUGUG | CACACACAAUCCUAUCCAG | [564-582] | [562-580] (18/19) | [443-461] | [684-702] | [546-564] (18/19) |
| 856 | Hum, chimp | CAAAGGUCCUUGUCCCUGA | UCAGGGACAAGGACCUUUG | [430-448] | — | — | [550-568] | [412-430] (18/19) |
| 857 | Hum, chimp | GUUGCUCAAAGGUCCUUGU | ACAAGGACCUUUGAGCAAC | [424-442] | [597-607] (11/11) | [478-488] (11/11) | [544-562] | — |
| 858 | Hum, chimp | AAACUUGGUUGCUCAAAGG | CCUUUGAGCAACCAAGUUU | [417-435] | [415-433] (18/19) | — | [537-555] | [402-415] (14/14) |
| 859 | Hum | UGGUGAUGGCUUAUGGAAG | CUUCCAUAAGCCAUCACCA | [2498-2516] | — | — | — | — |
| 860 | Hum | GGAGUUGUCACCACUGACU | AGUCAGUGGUGACAACUCC | [2389-2407] | — | — | — | — |
| 861 | Hum | ACAAUGUUCAAUUCAGCAA | UUGCUGAAUUGAACAUUGU | [2035-2053] | — | — | — | — |
| 862 | Hum, chimp | UGAGGAAUCAACUUGCCAG | CUGGCAAGUUGAUUCCUCA | [350-368] | — | — | [470-488] | [340-350] (11/11) |
| 863 | Hum | UGGAGAUAUGGUUUAUAGU | ACUAUAAACCAUAUCUCCA | [1840-1858] | — | — | — | — |
| 864 | Hum | CUAUGGAGAUAUGGUUUAU | AUAAACCAUAUCUCCAUAG | [1837-1855] | — | — | — | — |
| 865 | Hum | CCCCAAUUGUCAAGGGUAG | CUACCCUUGACAAUUGGGG | [1759-1777] | — | — | — | — |
| 866 | Hum | UAACCCCAAUUGUCAAGGG | CCCUUGACAAUUGGGGUUA | [1756-1774] | — | — | — | — |
| 867 | Hum | ACUUAGUAAUCUAUCCUCU | AGAGGAUAGAUUACUAAGU | [1641-1659] | — | — | — | — |
| 868 | Hum | CACUUAGUAAUCUAUCCUC | GAGGAUAGAUUACUAAGUG | [1640-1658] | — | — | — | — |
| 869 | Hum | AGGAAAUUAGUUCUGAGAU | AUCUCAGAACUAAUUUCCU | [1604-1622] | — | — | — | — |
| 870 | Hum | UGGUGACUUCCUCACUCUA | UAGAGUGAGGAAGUCACCA | [1383-1401] | — | — | — | — |
| 871 | Hum | GUUUCAGGUAGGCUUGGUA | UACCAAGCCUACCUGAAAC | [1092-1110] | — | — | — | — |
| 872 | Hum | AUAGGUAAGCAAAAGUAGA | UCUACUUUUGCUUACCUAU | [1037-1055] | — | — | — | — |
| 873 | Hum | ACAACAGUGAUUGAAGGGU | ACCCUUCAAUCACUGUUGU | [762-780] | — | — | — | — |
| 874 | Hum, chimp, dog | GAACUGCUCAUGGACUAGC | GCUAGUCCAUGAGCAGUUC | [632-650] | — | — | [752-770] | [614-632] |
| 875 | Hum, chimp, dog | GUGUUUAAGCAGGAGAACU | AGUUCUCCUGCUUAAACAC | [618-636] | [616-631] (16/16) | — | [738-756] | [600-618] |
| 876 | Hum, ms, | GAGAAACUGACCCAGAGAA | UUCUCUGGGUCAGUUUCUC | [447-465] | [445-463] | [326-344] | [567-585] | [429-445] |

TABLE A-continued

| | | | | Hum 34222182 cds = | | | | |
|---|---|---|---|---|---|---|---|---|
| No | Sp-Source | Sense siRNA | AntiSense siRNA | 204-785 | Mouse 31541838 | rat 62644440 | chimp 55622975 | dog 74002279 |
| | rat, chimp | | | | | | | (17/17) |
| 877 | Hum | CAAUGUUCAAUUCAGCAAG | CUUGCUGAAUUGAACAUUG | [2036-2054] | — | — | — | — |
| 878 | Hum | GGCUAUGGAGAUAUGGUUU | AAACCAUAUCUCCAUAGCC | [1835-1853] | — | — | — | — |
| 879 | Hum | AUAGGAAAUUAGUUCUGAG | CUCAGAACUAAUUUCCUAU | [1602-1620] | — | — | — | — |
| 880 | Hum | GAUAGGAAAUUAGUUCUGA | UCAGAACUAAUUUCCUAUC | [1601-1619] | — | — | — | — |
| 881 | Hum | AUAAACCAGAUUUGCCUAU | AUAGGCAAAUCUGGUUUAU | [1120-1138] | — | — | — | — |
| 882 | Hum | CAACAGUGAUUGAAGGGUC | GACCCUUCAAUCACUGUUG | [763-781] | — | — | — | — |
| 883 | Hum, chimp | UGGUUGCUCAAAGGUCCUU | AAGGACCUUUGAGCAACCA | [422-440] | [597-607] (11/11) | [478-488] (11/11) | [542-560] | [404-422] (18/19) |
| 884 | Hum, chimp | UUGGUUGCUCAAAGGUCCU | AGGACCUUUGAGCAACCAA | [421-439] | [597-607] (11/11) | [478-488] (11/11) | [541-559] | [403-421] (18/19) |
| 885 | Hum | AUGCUUACAAAAUGGUGAU | AUCACCAUUUUGUAAGCAU | [2486-2504] | — | — | — | — |
| 886 | Hum | CUGGAGUUGUCACCACUGA | UCAGUGGUGACAACUCCAG | [2387-2405] | — | — | — | — |
| 887 | Hum | CUCCAAAGGUUCACUGUGU | ACACAGUGAACCUUUGGAG | [2355-2373] | — | — | — | — |
| 888 | Hum, chimp | GAGGUAAUAUUUGAGGAAU | AUUCCUCAAAUAUUACCUC | [339-357] | — | — | [459-477] | [321-337] (16/17) |
| 889 | Hum, chimp | ACGAGGUAAUAUUUGAGGA | UCCUCAAAUAUUACCUCGU | [337-355] | — | — | [457-475] | [321-337] (16/17) |
| 890 | Hum | GUUCCUGACUCAAAUUUGA | UCAAAUUUGAGUCAGGAAC | [1251-1269] | — | — | — | — |
| 891 | Hum | CUGAUCCUCAGCUCAGGAU | AUCCUGAGCUGAGGAUCAG | [705-723] | [703-721] (18/19) | [584-602] (18/19) | — | — |
| 892 | Hum, chimp | AGGUAAUAUUUGAGGAAUC | GAUUCCUCAAAUAUUACCU | [340-358] | — | — | [460-478] | [322-337] (15/16) |
| 893 | Hum, chimp | CGAGGUAAUAUUUGAGGAA | UUCCUCAAAUAUUACCUCG | [338-356] | — | — | [458-476] | [321-337] (16/17) |
| 894 | Hum | AUCAAAACUUCCAAAAGCC | GGCUUUUGGAAGUUUUGAU | [1222-1240] | — | — | — | [1182-1200] (18/19) |
| 895 | Hum | UAUCAAAACUUCCAAAAGC | GCUUUUGGAAGUUUUGAUA | [1221-1239] | — | — | — | [1182-1199] (17/18) |
| 896 | Hum | CUGAUUUUCUGGCCUUUGG | CCAAAGGCCAGAAAAUCAG | [949-967] | — | — | — | — |
| 897 | Hum, chimp, dog | CACUGUGUUUAAGCAGGA | UCCUGCUUAAACACAAGUG | [613-631] | [613-629] (17/17) | — | [733-751] | [595-613] |
| 898 | Hum | UAUGCUUACAAAAUGGUGA | UCACCAUUUUGUAAGCAUA | [2485-2503] | — | — | — | — |
| 899 | Hum | GAAUUGAAGUAUCUCUCCU | AGGAGAGAUACUUCAAUUC | [1737-1755] | — | — | — | — |
| 900 | Hum | UUCCUGACUCAAAUUUGAA | UUCAAAUUUGAGUCAGGAA | [1252-1270] | — | — | — | — |
| 901 | Hum | UUCUCUAAGUUUUCAGAGG | CCUCUGAAAACUUAGAGAA | [1162-1180] | — | — | — | — |
| 902 | Hum | UGAAUGGGAUGGAAUAGGU | ACCUAUUCCAUCCCAUUCA | [1024-1042] | — | — | — | — |

TABLE A-continued

| | | | | 19 mer | | | | |
|---|---|---|---|---|---|---|---|---|
| No | Sp-Source | Sense siRNA | AntiSense siRNA | Hum 34222182 cds = 204-785 | Mouse 31541838 | rat 62644440 | chimp 55622975 | dog 74002279 |
| 903 | Hum | GAAGUGAUUCAAAAUAGUG | CACUAUUUUGAAUCACUUC | [969-987] | — | — | — | — |
| 904 | Hum | UUGAAGGGUCCUAAAAAGG | CCUUUUUAGGACCCUUCAA | [772-790] | — | — | — | — |
| 905 | Hum, rat | CGACUUGUUAAGAAAAAAC | GUUUUUUCUUAACAAGUCG | [726-744] | — | [605-623] | — | [708-724] (16/17) |
| 906 | Hum, chimp, dog | UUGUGUUUAAGCAGGAGAA | UUCUCCUGCUUAAACACAA | [616-634] | [614-631] (18/18) | — | [736-754] | [598-616] |
| 907 | Hum, chimp, dog | ACACUUGUGUUUAAGCAGG | CCUGCUUAAACACAAGUGU | [612-630] | [613-628] (16/16) | — | [732-750] | [594-612] |
| 908 | Hum, chimp | UUACACUUGUGUUUAAGCA | UGCUUAAACACAAGUGUAA | [610-628] | [613-626] (14/14) | — | [730-748] | [594-610] (17/17) |
| 909 | Hum, ms, rat, chimp | AGAAACUGACCCAGAGAAU | AUUCUCUGGGUCAGUUUCU | [448-466] | [446-464] | [327-345] | [568-586] | [430-445] (16/16) |
| 910 | Hum | CCAUGGCAGUGUUAUCUCA | UGAGAUAACACUGCCAUGG | [1701-1719] | — | — | — | — |
| 911 | Hum | AUUGAAGGGUCCUAAAAAG | CUUUUUAGGACCCUUCAAU | [771-789] | — | — | — | — |
| 912 | Hum | UGGAACAACAGUGAUUGAA | UUCAAUCACUGUUGUUCCA | [758-776] | — | — | — | [740-758] (18/19) |
| 913 | Hum, chimp, dog | GCAACUGGCAGUUUGAGCA | UGCUCAAACUGCCAGUUGC | [210-228] | [208-226] (18/19) | [89-107] (18/19) | [330-348] | [192-210] |
| 914 | Hum, chimp | GGUAAUAUUUGAGGAAUCA | UGAUUCCUCAAAUAUUACC | [341-359] | — | — | [461-479] | [327-337] (11/11) |
| 915 | Hum, ms, rat, chimp, dog | CUGAGAAACUGACCCAGAG | CUCUGGGUCAGUUUCUCAG | [445-463] | [443-461] | [324-342] | [565-583] | [427-445] |
| 916 | Hum | CUCUGGGCUUUUCUGGGAA | UUCCCAGAAAAGCCCAGAG | [1721-1739] | — | — | — | — |
| 917 | Hum | UUGGAACAACAGUGAUUGA | UCAAUCACUGUUGUUCCAA | [757-775] | — | — | — | [739-757] (18/19) |
| 918 | Hum | UGAUGGCUUAUGGAAGGCU | AGCCUUCCAUAAGCCAUCA | [2501-2519] | — | — | — | — |
| 919 | Hum | GUGAUGGCUUAUGGAAGGC | GCCUUCCAUAAGCCAUCAC | [2500-2518] | — | — | — | — |
| 920 | Hum | UUGGCUAUGGAGAUAUGGU | ACCAUAUCUCCAUAGCCAA | [1833-1851] | — | — | — | — |
| 921 | Hum | CUCUUUUCUUUCUGUGUUU | AAACACAGAAAGAAAAGAG | [902-920] | — | — | — | — |
| 922 | Hum | GGAACAACAGUGAUUGAAG | CUUCAAUCACUGUUGUUCC | [759-777] | — | — | — | [741-759] (18/19) |
| 923 | Hum | UCUCUGGGCUUUUCUGGGA | UCCCAGAAAAGCCCAGAGA | [1720-1738] | — | — | — | — |
| 924 | Hum | UCUCUUUUCUUUCUGUGUU | AACACAGAAAGAAAAGAGA | [901-919] | — | — | — | — |
| 925 | Hum | GUCUCUUUUCUUUCUGUGU | ACACAGAAAGAAAAGAGAC | [900-918] | — | — | — | — |

TABLE B additional 19 mers

| Number | Sense siRNA | AntiSense siRNA | Other Sp | Hum-34222182 ORF: 204-785 |
|---|---|---|---|---|
| 1 | CAGUGUUCUAACAAACUAA | UUAGUUUGUUAGAACACUG | | [2244-2262] 3'UTR |
| 2 | CCAGUGUUCUAACAAACUA | UAGUUUGUUAGAACACUGG | | [2243-2261] 3'UTR |
| 3 | GGCUUUUCUGGGAAUUGAA | UUCAAUUCCCAGAAAAGCC | | [1728-1744] 3'UTR |
| 4 | CGUGAACUUGGAAAUUGAA | UUCAAUUUCCAAGUUCACG | Dog, Chin, GP, Rat | [530-548] ORF |
| 5 | GGAUGGAAUAGGUAAGCAA | UUGCUUACCUAUUCCAUCC | | [1030-1048] 3'UTR |
| 6 | UAGCCAGUGUUCUAACAAA | UUUGUUAGAACACUGGCUA | | [2240-2258] 3'UTR |
| 7 | GAUUGAAGGGUCCUAAAAA | UUUUUAGGACCCUUCAAUC | | [770-788] ORF + 3'UTR |
| 8 | AGAAUUGGGCCAAGAUAAA | UUUAUCUUGGCCCAAUUCU | | [2306-2324] 3'UTR |
| 9 | UGCUGUGGGUCGUGGAUAA | UUAUCCACGACCCACAGCA | | [2068-2086] 3'UTR |
| 10 | AGGUAAGAGUAAAUGAGAA | UUCUCAUUUACUCUUACCU | | [1328-1346] 3'UTR |
| 11 | CUGUCCAAAUCAAAGCAAA | UUUGCUUUGAUUUGGACAG | Dog, Chimp | [396-414] ORF |
| 12 | UCAUGAUUGGGUAGUAAAA | UUUUACUACCCAAUCAUGA | | [811-829] 3'UTR |
| 13 | GCCAGUGUUCUAACAAACU | AGUUUGUUAGAACACUGGC | | [2242-2260] 3'UTR |
| 14 | GUGAUUGAAGGGUCCUAAA | UUUAGGACCCUUCAAUCAC | | [768-786] ORF + 3'UTR |
| 15 | GGAAGGCUGUUAAAUUAAU | AUUAAUUUAACAGCCUUCC | | [2512-2530] 3'UTR |
| 16 | GCUUAUGGAAGGCUGUUAA | UUAACAGCCUUCCAUAAGC | | [2506-2524] 3'UTR |
| 17 | UCCUGUUACUGAUACUAUA | UAUAGUAUCAGUAACAGGA | | [2194-2212] 3'UTR |
| 18 | GGUCCUUGUCCCUGAGAAA | UUUCUCAGGGACAAGGACC | Chimp | [434-452] ORF |
| 19 | UGGUUAAAAUGCUGGAGAA | UUCUCCAGCAUUUUAACCA | Chimp | [373-391] ORF |
| 20 | CCAUUGAGUGAAUGAUGAA | UUCAUCAUUCACUCAAUGG | | [1572-1590] 3'UTR |
| 21 | CAGGAUUUCGACUUGUUAA | UUAACAAGUCGAAAUCCUG | | [718-736] ORF |
| 22 | ACGUGAACUUGGAAAUUGA | UCAAUUUCCAAGUUCACGU | Dog, Chin, GP, Rat | [529-547] ORF |
| 23 | GUGUGAUCCUGUUACUGAU | AUCAGUAACAGGAUCACAC | | [2188-2206] 3'UTR |
| 24 | CGAGGUAAUAUUUGAGGAA | UUCCUCAAAUAUUACCUCG | Chimp | [338-356] ORF |
| 25 | GCUUGGAAAGAUACUACAA | UUGUAGUAUCUUUCCAAGC | | [2274-2292] 3'UTR |
| 26 | CUAAAAUGUCACUGUUCAA | UUGAACAGUGACAUUUUAG | | [2219-2237] 3'UTR |
| 27 | GUGACUUCCUCACUCUAAU | AUUAGAGUGAGGAAGUCAC | | [1385-1403] 3'UTR |
| 28 | GCCUGUUAUGCUUACAAAA | UUUUGUAAGCAUAACAGGC | | [2479-2497] 3'UTR |
| 29 | AGGUAGGCUUGGUAAUAGA | UCUAUUACCAAGCCUACCU | | [1097-1115] 3'UTR |
| 30 | GAUGAAUACCUGUGAGGAU | AUCCUCACAGGUAUUCAUC | | [1585-1603] 3'UTR |
| 31 | CUGUCACUAGGGAAUAAUA | UAUUAUUCCCUAGUGACAG | | [1929-1947] 3'UTR |
| 32 | GUUUUAAAGAGGCAACAAA | UUUGUUGCCUCUUUAAAAC | | [1404-1422] 3'UTR |
| 33 | GUGUUCUAACAAACUAAAC | GUUUAGUUUGUUAGAACAC | | [2246-2264] 3'UTR |
| 34 | GCUUGGUAAUAGACUAUAU | AUAUAGUCUAUUACCAAGC | | [1103-1121] 3'UTR |
| 35 | CAUCCUGGUGUUACUGAAA | UUUCAGUAACACCAGGAUG | | [2164-2182] 3'UTR |
| 36 | GCCUAUCAAAACUUCCAAA | UUUGGAAGUUUUGAUAGGC | | [1218-1236] 3'UTR |

TABLE B-continued additional 19 mers

| Number | Sense siRNA | AntiSense siRNA | Other Sp | Hum-34222182 ORF: 204-785 |
|---|---|---|---|---|
| 37 | UCCUGGUGUUACUGAAAAA | UUUUUCAGUAACACCAGGA | | [2166-2184] 3'UTR |
| 38 | CCACGGUGUUGUUUUAGAU | AUCUAAAACAACACCGUGG | | [1446-1464] 3'UTR |
| 39 | GCAGUUUGAGCAGCAAGAA | UUCUUGCUGCUCAAACUGC | Chimp | [217-235] ORF |
| 40 | CUUGGAAAGAUACUACAAA | UUUGUAGUAUCUUUCCAAG | | [2275-2293] 3'UTR |
| 41 | GUGUGAUUCUAGCGUCGUA | UACGACGCUAGAAUCACAC | | [578-596] ORF |
| 42 | CUUGGGCAUCGAUGUAGAA | UUCUACAUCGAUGCCCAAG | | [2419-2437] 3'UTR |
| 43 | GGGCUUUUCUGGGAAUUGA | UCAAUUCCCAGAAAAGCCC | | [1725-1743] 3'UTR |
| 44 | AACUGUCUGUCCAAAUCAA | UUGAUUUGGACAGACAGUU | Dog, Chimp | [390-408] ORF |
| 45 | AGCCAGUGUUCUAACAAAC | GUUUGUUAGAACACUGGCU | | [2241-2259] 3'UTR |
| 46 | GAAGGGUCCUAAAAAGGGA | UCCCUUUUUAGGACCCUUC | | [774-792] ORF + 3'UTR |
| 47 | AAAGCUUAACCCUAGGUAA | UUACCUAGGGUUAAGCUUU | | [1315-1333] 3'UTR |
| 48 | ACAUGUGCUUAAUCUCAGA | UCUGAGAUUAAGCACAUGU | | [1670-1688] 3'UTR |
| 49 | UCCUCACUCUAAUGUUUUA | UAAAACAUUAGAGUGAGGA | | [1391-1409] 3'UTR |
| 50 | GAAAGAUACUACAAAGCCA | UGGCUUUGUAGUAUCUUUC | | [2279-2297] 3'UTR |
| 51 | AAGGGUUUUUAGACAGGAA | UUCCUGUCUAAAAACCCUU | | [1269-1287] 3'UTR |
| 52 | UCAUCCUGGUGUUACUGAA | UUCAGUAACACCAGGAUGA | | [2163-2181] 3'UTR |
| 53 | CCUGUUACUGAUACUAUAA | UUAUAGUAUCAGUAACAGG | | [2195-2213] 3'UTR |
| 54 | CAUAGAUCCCAUUUUUGUA | UACAAAAUGGGAUCUAUG | | [999-1017] 3'UTR |
| 55 | AAUUGAAUGGGAUGGAAUA | UAUUCCAUCCCAUUCAAUU | | [1021-1039] 3'UTR |
| 56 | CUGUGAGGAUAGGAAAUUA | UAAUUUCCUAUCCUCACAG | | [1594-1612] 3'UTR |
| 57 | CCUAGGUAAGAGUAAAUGA | UCAUUUACUCUUACCUAGG | | [1325-1343] 3'UTR |
| 58 | CGUGGAUAAGGAGCUUAUU | AAUAAGCUCCUUAUCCACG | | [2078-2096] 3'UTR |
| 59 | CCAGAUUUGCCUAUUUUGA | UCAAAAUAGGCAAAUCUGG | | [1125-1143] 3'UTR |
| 60 | UUGGAGAAGUGAUUCAAAA | UUUUGAAUCACUUCUCCAA | | [964-982] 3'UTR |
| 61 | GAGGAAUCAACUUGCCAGA | UCUGGCAAGUUGAUUCCUC | Chimp | [351-389] ORF |
| 62 | GAGAAAUAUUACGGCAAUA | UAUUGCCGUAAUAUUUCUC | | [1342-1360] 3'UTR |
| 63 | AGAAUUGAAUGGGAUGGAA | UUCCAUCCCAUUCAAUUCU | | [1019-1037] 3'UTR |
| 64 | AUGGAAUAGGUAAGCAAAA | UUUUGCUUACCUAUUCCAU | | [1032-1050] 3'UTR |
| 65 | GUAAAAGCUGGAUAGGAU | AUCCUAUCCAGCUUUUUAC | Chin, GP, Chimp, Rat, Ms | [556-574] ORF |
| 66 | CCACCAGUUCCUGACUCAA | UUGAGUCAGGAACUGGUGG | | [1245-1263] 3'UTR |
| 67 | CAAAUUAGCCAGUGUUCUA | UAGAACACUGGCUAAUUUG | | [2235-2253] 3'UTR |
| 68 | CUCACUGAUUGGAACAACA | UGUUGUUCCAAUCAGUGAG | | [749-767] ORF |
| 69 | UGGAGAACUGUCUGUCCAA | UUGGACAGACAGUUCUCCA | Dog, GP, Chimp, Rat | [385-403] ORF |
| 70 | UAGAAUUGGGCCAAGAUAA | UUAUCUUGGCCCAAUUCUA | | [2305-2323] 3'UTR |
| 71 | CUCUUCAAAUGCUUGGAAA | UUUCCAAGCAUUUGAAGAG | | [2264-2282] 3'UTR |

TABLE B-continued additional 19 mers

| Number | Sense siRNA | AntiSense siRNA | Other Sp | Hum-34222182 ORF: 204-785 |
|---|---|---|---|---|
| 72 | UGUGGGUCGUGGAUAAGGA | UCCUUAUCCACGACCCACA | | [2071-2089] 3'UTR |
| 73 | CCUAAAAUGUCACUGUUCA | UGAACAGUGACAUUUUAGG | | [2218-2236] 3'UTR |
| 74 | UGAUUGAAGGGUCCUAAAA | UUUUAGGAGCCUUCAAUCA | | [769-787] ORF + 3'UTR |
| 75 | GAGAAACUGACCCAGAGAA | UUCUCUGGGUCAGUUUCUC | Chin, GP, Chimp, Rat, Ms | [447-465] ORF |
| 76 | CACCAGUUCCUGACUCAAA | UUUGAGUCAGGAACUGGUG | | [1246-1264] 3'UTR |
| 77 | CAAAGGUCCUUGUCCCUGA | UCAGGGACAAGGACCUUUG | Chimp | [430-448] ORF |
| 78 | GAGUGAAUGAUGAAUACCU | AGGUAUUCAUCAUUCACUC | | [1577-1595] 3'UTR |
| 79 | CAAUAAUGGAACUGCUUCA | UGAAGCAGUUCCAUUAUUG | | [1356-1374] 3'UTR |
| 80 | CACUAACAGUUAUCUUUGA | UCAAAGAUAACUGUUAGUG | | [2453-2471] 3'UTR |
| 81 | GCGUCGUACCUACUUUUGA | UCAAAAGUAGGUACGACGC | | [589-607] ORF |
| 82 | CGGCCAGCAUUUCAGAAUU | AAUUCUGAAAUGCUGGCCG | Chimp | [238-256] ORF |
| 83 | GUGCUUAAUCUCAGAUGAA | UUCAUCUGAGAUUAAGCAC | | [1674-1692] 3'UTR |
| 84 | GUUGUGUUAUGCACGUGAA | UUCACGUGCAUAACACAAC | Ms | [517-536] ORF |
| 85 | AGUACAGCCUAGAGAAUGA | UCAUUCUCUAGGCUGUACU | | [1856-1874] 3'UTR |
| 86 | ACUGUCUGUCCAAAUCAAA | UUUGAUUUGGACAGACAGU | Dog, Chimp | [391-409] ORF |
| 87 | AGCUUACACUUGUGUUUAA | UUAAACACAAGUGUAAGCU | Chimp | [607-625] ORF |
| 88 | GAUUGGGUAGUAAAACUAU | AUAGUUUUACUACCCAAUC | | [815-833] 3'UTR |
| 89 | GUGAACUUGGAAAUUGAAA | UUUCAAUUUCCAAGUUCAC | Dog, Chin, GP, Chimp, Rat | [531-549] ORF |
| 90 | GCCAGAAUUUGGUUAAAAU | AUUUUAACCAAAUUCUGGC | GP, Chimp, Rat, Ms | [364-382] ORF |
| 91 | CUGGCAGUUUGAGCAGCAA | UUGCUGCUCAAACUGCCAG | Chimp | [214-232] ORF |
| 92 | GAAUUGAAUGGGAUGGAAU | AUUCCAUCCCAUUCAAUUC | | [1020-1038] 3'UTR |
| 93 | GUCACUAGGGAAUAAUAAA | UUUAUUAUUCCCUAGUGAC | | [1931-1949] 3'UTR |
| 94 | AGAUCUAGUCCCUCUCUGA | UCAGAGAGGGACUAGAUCU | | [1619-1637] 3'UTR |
| 95 | UCUUGGGCAUCGAUGUAGA | UCUACAUCGAUGCCCAAGA | | [2418-2438] 3'UTR |
| 96 | CCAGAGAAUUGCUCAAGAU | AUCUUGAGCAAUUCUCUGG | Chimp, Ms | [458-476] ORF |
| 97 | CCCUGUUCUUAAGUGUUGA | UCAACACUUAAGAACAGGG | | [1485-1503] 3'UTR |
| 98 | GACCCAGAGAAUUGCUCAA | UUGAGCAAUUCUCUGGGUC | Chimp, Ms | [455-473] ORF |
| 99 | UUUGGAGAAGUGAUUCAAA | UUUGAAUCACUUCUCCAAA | | [963-981] 3'UTR |
| 100 | GUGAAUGAUGAAUACCUGU | ACAGGUAUUCAUCAUUCAC | | [1579-1597] 3'UTR |
| 101 | UCAGGAUUUCGACUUGUUA | UAACAAGUCGAAAUCCUGA | | [1717-735] ORF |
| 102 | AGUGAAUGAUGAAUACCUG | CAGGUAUUCAUCAUUCACU | | [1578-1596] 3'UTR |
| 103 | GACAGGAAGGUAGGAUUAA | UUAAUCCUACCUUCCUGUC | | [1280-1298] 3'UTR |
| 104 | GGGUCCUAAAAAGGGAAAA | UUUUCCCUUUUUAGGACCC | | [777-795] ORF + 3'UTR |
| 105 | GGAUAAGGAGCUUAUUCAG | CUGAAUAAGCUCCUUAUCC | | [2081-2099] 3'UTR |

TABLE B-continued additional 19 mers

| Number | Sense siRNA | AntiSense siRNA | Other Sp | Hum-34222182 ORF: 204-785 |
|---|---|---|---|---|
| 106 | CUUAUGGAAGGCUGUUAAA | UUUAACAGCCUUCCAUAAG | | [2507-2525] 3'UTR |
| 107 | CGAAGGAAACAGAGCCGUU | AACGGCUCUGUUUCCUUCG | Chimp | [181-199] 5'UTR |
| 108 | GUUCUAACAAACUAAACUC | GAGUUUAGUUUGUUAGAAC | | [2248-2266] 3'UTR |
| 109 | AAUGGGAUGGAAUAGGUAA | UUACCUAUUCCAUCCCAUU | | [1026-1044] 3'UTR |
| 110 | CCUGUUCUUAAGUGUUGAA | UUCAACACUUAAGAACAGG | | [1486-1504] 3'UTR |
| 111 | GGCCUUAUUUUUGUCUUA | UAAGACAAAAAUAAGGCC | | [1950-1968] 3'UTR |
| 112 | CUCUCUGAUUCACUUAGUA | UACUAAGUGAAUCAGAGAG | | [1630-1648] 3'UTR |
| 113 | GGCAGUUUGAGCAGCAAGA | UCUUGCUGCUCAAACUGCC | Chimp | [216-234] ORF |
| 114 | CGUCGUACCUACUUUUGAG | CUCAAAAGUAGGUACGAGG | | [590-608] ORF |
| 115 | GAAUGAAACUCACCGUCCA | UGGACGGUGAGUUUCAUUC | | [1869-1887] 3'UTR |
| 116 | GUCUAUUGUUAAGCUCCAA | UUGGAGCUUAACAAUAGAC | | [2342-2360] 3'UTR |
| 117 | CAACCUCAACGAGGUAAUA | UAUUACCUCGUUGAGGUUG | Chimp | [329-347] ORF |
| 118 | UAGGCUUGGUAAUAGACUA | UAGUCUAUUACCAAGCCUA | | [1100-1118] 3'UTR |
| 119 | GUAUGUAAAAGCUGGAUA | UAUCCAGCUUUUUACAUAC | Dog, Chimp, Ms | [552-570] ORF |
| 120 | GUUGCAACUGGCAGUUUGA | UCAAACUGCCAGUUGCAAC | Chimp | [207-225] ORF |
| 121 | CCUAGAGAAUGAAACUCAC | GUGAGUUUCAUUCUCUAGG | | [1863-1881] 3'UTR |
| 122 | GCCUGCUAAGUGAUUUUGA | UCAAAAUCACUUAGCAGGC | Chimp | [283-301] ORF |
| 123 | CUAUUAGCUCCACUUCACA | UGUGAAGUGGAGCUAAUAG | | [2114-2132] 3'UTR |
| 124 | AGUGAUUGAAGGGUCCUAA | UUAGGACCCUUCAAUCACU | | [767-785] ORF |
| 125 | GGGUAGUAGCUGUAUACUA | UAGUAUACAGCUACUACCC | | [1772-1790] 3'UTR |
| 126 | UGUUGUUUUGCAUGUCUAU | AUAGACAUGCAAAACAACA | | [2329-2347] 3'UTR |
| 127 | GUUCCUGACUCAAAUUUGA | UCAAAUUUGAGUCAGGAAC | | [1251-1269] 3'UTR |
| 128 | CAGUAACCACGGUGUUGUU | AACAACACCGUGGUUACUG | | [1440-1458] 3'UTR |
| 129 | AGAUUUUUCCACCUUGGA | UCCAAGGUGGAAAAAUCU | | [1907-1925] 3'UTR |
| 130 | CCCAGAGAAUUGCUCAAGA | UCUUGAGCAAUUCUCUGGG | Chimp, Ms | [457-475] ORF |
| 131 | CAGAUUUGCCUAUUUUGAU | AUCAAAAUAGGCAAAUCUG | | [1126-1144] 3'UTR |
| 132 | UGGAAGGCUGUUAAAUUAA | UUAAUUUAACAGCCUUCCA | | [2511-2529] 3'UTR |
| 133 | UAUAGUACAGCCUAGAGAA | UUCUCUAGGCUGUACUAUA | | [1853-1871] 3'UTR |
| 134 | GGUUGUGUUAUGCACGUGA | UCACGUGCAUAACACAACC | Ms | [516-534] ORF |
| 135 | GAUACCUGUCACUAGGGAA | UUCCCUAGUGACAGGUAUC | | [1924-1942] 3'UTR |
| 136 | CCUAUCAAAACUUCCAAAA | UUUUGGAAGUUUUGAUAGG | | [1219-1237] 3'UTR |
| 137 | GCGUAGGGACAGAUGUAUU | AAUACAUCUGUCCCUACGC | | [2145-2163] 3'UTR |
| 138 | GAUACUAUAAGUGACCUAA | UUAGGUCACUUAUAGUAUC | | [2204-2222] 3'UTR |
| 139 | CGAAGUCUGCAUUGGCUAU | AUAGCCAAUGCAGACUUCG | | [1822-1840] 3'UTR |
| 140 | GGAUAGGAUUGUGUGUGAU | AUCACACACAAUCCUAUCC | Chin, GP, Chimp, Rat | [566-584] ORF |
| 141 | GGCCUUUGGAGAAGUGAUU | AAUCACUUCUCCAAAGGCC | | [959-977] 3'UTR |

TABLE B-continued additional 19 mers

| Number | Sense siRNA | AntiSense siRNA | Other Sp | Hum-34222182 ORF: 204-785 |
|---|---|---|---|---|
| 142 | AUAGGUAAGCAAAAGUAGA | UCUACUUUUGCUUACCUAU | | [1037-1055] 3'UTR |
| 143 | GGUAGGAUUAAGUAGGUGA | UCACCUACUUAAUCCUACC | | [1288-1306] 3'UTR |
| 144 | GAUUAAGUAGGUGAGUUUA | UAAACUCACCUACUUAAUC | | [1293-1311] 3'UTR |
| 145 | AGGAAGGUAGGAUUAAGUA | UACUUAAUCCUACCUUCCU | | [1283-1301] 3'UTR |
| 146 | GGUGUGAUCCUGUUACUGA | UCAGUAACAGGAUCACACC | | [2187-2205] 3'UTR |
| 147 | CAUGGACUAGCUUCAGGGA | UCCCUGAAGCUAGUCCAUG | Dog, Chimp | [640-658] ORF |
| 148 | GAAGGGUUUUUAGACAGGA | UCCUGUCUAAAAACCCUUC | | [1268-1286] 3'UTR |
| 149 | CUUUGGAGAAGUGAUUCAA | UUGAAUCACUUCUCCAAAG | | [962-980] 3'UTR |
| 150 | UGGAGAAGUGAUUCAAAAU | AUUUUGAAUCACUUCUCCA | | [965-983] 3'UTR |
| 151 | CAGUGAUUGAAGGGUCCUA | UAGGACCCUUCAAUCACUG | | [766-784] ORF |
| 152 | UGUACAGAAUUGAAUGGGA | UCCCAUUCAAUUCUGUACA | | [1014-1032] 3'UTR |
| 153 | UCAACGAGGUAAUAUUUGA | UCAAAUAUUACCUCGUUGA | Chimp | [334-352] ORF |
| 154 | CUCUGGGCUUUUCUGGGAA | UUGCGAGAAAAGCCCAGAG | | [1721-1739] 3'UTR |
| 155 | GGCUUGCGAGGUUGUGUUA | UAACACAACCUCGCAAGCC | Chimp | [507-525] ORF |
| 156 | CGGCAAUAAUGGAACUGCU | AGCAGUUCCAUUAUUGCCG | | [1353-1371] 3'UTR |
| 157 | CUUUACUCACUGAUUGGAA | UUCCAAUCAGUGAGUAAAG | | [744-762] ORF |
| 158 | GGACUUUUUCUUUAGUAGA | UCUACUAAAGAAAAAGUCC | | [658-674] ORF |
| 159 | CUCUGAUUCACUUAGUAAU | AUUACUAAGUGAAUCAGAG | | [1632-1650] 3'UTR |
| 160 | GUACAGAAUUGAAUGGGAU | AUCCCAUUCAAUUCUGUAC | | [1015-1033] 3'UTR |
| 161 | GGGAAUAAUAAAGGCCUUA | UAAGGCCUUUAUUAUUCCC | | [1938-1956] 3'UTR |
| 162 | UACCUGUGAGGAUAGGAAA | UUUCCUAUCCUCACAGGUA | | [1591-1609] 3'UTR |
| 163 | GGAUACCUGUCACUAGGGA | UCCCUAGUGACAGGUAUCC | | [1923-1941] 3'UTR |
| 164 | CUAGCUUCAGGGACUUUUU | AAAAAGUCCCUGAAGCUAG | Chimp | [646-664] ORF |
| 165 | AAAGAUACUACAAAGCCAA | UUGGCUUUGUAGUAUCUUU | | [2280-2298] 3'UTR |
| 166 | UGUGGUGCCAUUUCAGUAA | UUACUGAAAUGGCACCACA | | [1427-1445] 3'UTR |
| 167 | AUAGAAUUGGGCCAAGAUA | UAUCUUGGCCCAAUUCUAU | | [2304-2322] 3'UTR |
| 168 | GUUUCAGGUAGGCUGGUA | UACCAAGCCUACCUGAAAC | | [1092-1110] 3'UTR |
| 169 | GGUCGUGGAUAAGGAGCUU | AAGCUCCUUAUCCACGACC | | [2075-2093] 3'UTR |
| 170 | AAUGGUGAUGGCUUAUGGA | UCCAUAAGCCAUCACCAUU | | [2496-2514] 3'UTR |
| 171 | GCUUGUGGUGCCAUUUCAG | CUGAAAUGGCACCACAAGC | | [1424-1442] 3'UTR |
| 172 | UGUGCUUAAUCUCAGAUGA | UCAUCUGAGAUUAAGCACA | | [1673-1691] 3'UTR |
| 173 | UAGGUAAGCAAAAGUAGAA | UUCUACUUUUGCUUACCUA | | [1038-1056] 3'UTR |
| 174 | UGAUUUCUGGCCUUUGGA | UCCAAAGGCCAGAAAUCA | | [950-968] 3'UTR |
| 175 | GCUUCUUGGGCAUCGAUGU | ACAUCGAUGCCCAAGAAGC | | [2415-2433] 3'UTR |
| 176 | CCGUCCAGAUAACCAUGCA | UGCAUGGUUAUCUGGACGG | | [1881-1899] 3'UTR |
| 177 | AACCAUGCAUGCACCCAGA | UCUGGGUGCAUGCAUGGUU | | [1891-1909] 3'UTR |
| 178 | CAGGAAGGUAGGAUUAAGU | ACUUAAUCCUACCUUCCUG | | [1282-1300] 3'UTR |

TABLE B-continued additional 19 mers

| Number | Sense siRNA | AntiSense siRNA | Other Sp | Hum-34222182 ORF: 204-785 |
|---|---|---|---|---|
| 179 | GAAUUGGGCCAAGAUAAAU | AUUUAUCUUGGCCCAAUUC | | [2307-2325] 3'UTR |
| 180 | GUGAGGAUAGGAAAUUAGU | ACUAAUUUCCUAUCCUCAC | | [1596-1614] 3'UTR |
| 181 | GAUUUUUCCACCUUGGAU | AUCCAAGGUGGAAAAAAUC | | [1908-1926] 3'UTR |
| 182 | GCAUGCACCCAGAUUUUUU | AAAAAAUCUGGGUGCAUGC | | [1897-1915] 3'UTR |
| 183 | CCUGCUAAGUGAUUUUGAC | GUCAAAAUCACUUAGCAGG | Chimp | [284-302] ORF |
| 184 | GGGAUUAUGUUGUUCCUGA | UCAGGAACAACAUAAUCCC | Chimp | [307-325] ORF |
| 185 | UGCCUGUUAUGCUUACAAA | UUUGUAAGCAUAACAGGCA | | [2478-2496] 3'UTR |
| 186 | CCACCUUGGAUACCUGUCA | UGACAGGUAUCCAAGGUGG | | [1916-1934] 3'UTR |
| 187 | UGGCCUUUGGAGAAGUGAU | AUCACUUCUCCAAAGGCCA | | [958-976] 3'UTR |
| 188 | CUGCAUAGAUCCCAUUUUU | AAAAAUGGGAUCUAUGCAG | | [996-1014] 3'UTR |
| 189 | CCAACCUCAACGAGGUAAU | AUUACCUCGUUGAGGUUGG | Chimp | [328-346] ORF |
| 190 | AGAAACUGACCCAGAGAAU | AUUCUCUGGGUCAGUUUCU | Chin, GP, Chimp, Rat, Ms | [448-466] ORF |
| 191 | UGGUGACUUCCUCACUCUA | UAGAGUGAGGAAGUCACCA | | [1383-1401] 3'UTR |
| 192 | AGGGAAUAAUAAAGGCCUU | AAGGCCUUUAUUAUUCCCU | | [1937-1955] 3'UTR |
| 193 | CCUGUUAUGCUUACAAAAU | AUUUUGUAAGCAUAACAGG | | [2480-2498] 3'UTR |
| 194 | AAAGUAGAAGCCCAUUUGA | UCAAAUGGGCUUCUACUUU | | [1048-1066] 3'UTR |
| 195 | GAUUUUGACUACUGGGAUU | AAUCCCAGUAGUCAAAAUC | Dog, Chimp | [294-312] ORF |
| 196 | GGCUUAUGGAAGGCUGUUA | UAACAGCCUUCCAUAAGCC | | [2505-2523] 3'UTR |
| 197 | UGUUGUCCUUUUUCCACUA | UAGUGGAAAAAGGACAACA | | [2439-2457] 3'UTR |
| 198 | GGCGUAGGGACAGAUGUAU | AUACAUCUGUCCCUACGCC | | [2144-2162] 3'UTR |
| 199 | AGUGUAGAUUUUCUGCAUA | UAUGCAGAAAAUCUACACU | | [984-1002] 3'UTR |
| 200 | CCUUGGAUACCUGUCACUA | UAGUGACAGGUAUCCAAGG | | [1919-1937] 3'UTR |
| 201 | CCAGAUUUUUCCACCUUG | CAAGGUGGAAAAAUCUGG | | [1905-1923] 3'UTR |
| 202 | UAGGUAAGAGUAAAUGAGA | UCUCAUUUACUCUUACCUA | | [1327-1345] 3'UTR |
| 203 | ACCUGCCCUAAAUAAGAAA | UUUCUUAUUUAGGGCAGGU | | [870-888] 3'UTR |
| 204 | UGAGGAUAGGAAAUUAGUU | AACUAAUUUCCUAUCCUCA | | [1597-1615] 3'UTR |
| 205 | GGCUUUUUUUCUCUAAGU | ACUUAGAGAAAAAAAGCC | | [1153-1171] 3'UTR |
| 206 | AAGGGUCCUAAAAGGGAA | UUCCCUUUUAGGACCCUU | | [775-793] ORF + 3'UTR |
| 207 | UAUGCACGUGAACUUGGAA | UUCCAAGUUCACGUGCAUA | Dog, Chin, GP, Rat | [524-542] ORF |
| 208 | GGCUUGGUAAUAGACUAUA | UAUAGUCUAUUACCAAGCC | | [1102-1120] 3'UTR |
| 209 | CGUUGACCAUGGUUGCAAC | GUUGCAACCAUGGUCAACG | Chimp, Rat, Ms | [196-214] 5'UTR + ORF |
| 210 | UGUCUAUUGUUAAGCUCCA | UGGAGCUUAACAAUAGACA | | [2341-2359] 3'UTR |
| 211 | GCAUAGAUCCCAUUUUUGU | ACAAAAAUGGGAUCUAUGC | | [998-1016] 3'UTR |
| 212 | CAAUUUACGAAGUCUGCAU | AUGCAGACUUCGUAAAUUG | | [1815-1833] 3'UTR |
| 213 | GGAAUAGGUAAGCAAAAGU | ACUUUUGCUUACCUAUUCC | | [1034-1052] 3'UTR |

TABLE B-continued additional 19 mers

| Number | Sense siRNA | AntiSense siRNA | Other Sp | Hum-34222182 ORF: 204-785 |
|---|---|---|---|---|
| 214 | UCAGCUAAAGUCAUUUGUA | UACAAAUGACUUUAGCUGA | | [842-860] 3'UTR |
| 215 | GCUGGAUAGGAUUGUGUGU | ACACACAAUCCUAUCCAGC | Chin, GP, Chimp, Rat | [563-581] ORF |
| 216 | GGAAGGUAGGAUUAAGUAG | CUACUUAAUCCUACCUUCC | | [1284-1302] 3'UTR |
| 217 | GUACAGCCUAGAGAAUGAA | UUCAUUCUCUAGGCUGUAC | | [1857-1875] 3'UTR |
| 218 | GAUUCUAGCGUCGUACCUA | UAGGUACGACGCUAGAAUC | | [582-600] ORF |
| 219 | GAUCUAGUCCCUCUCUGAU | AUCAGAGAGGGACUAGAUC | | [1620-1638] 3'UTR |
| 220 | GACUCAAAUGUGAAGGGUU | AACCCUUCAAAUUUGAGUC | | [1257-1275] 3'UTR |
| 221 | UCCACUCAACAAUGUUCAA | UUGAACAUUGUUGAGUGGA | | [2027-2045] 3'UTR |
| 222 | UGUAGAUUUCUGCAUAGA | UCUAUGCAGAAAAUCUACA | | [986-1004] 3'UTR |
| 223 | UCGUGGAUAAGGAGCUUAU | AUAAGCUCCUUAUCCACGA | | [2077-2095] 3'UTR |
| 224 | UGGAGAUAUGGUUUAUAGU | ACUAUAAACCAUAUCUCCA | | [1840-1858] 3'UTR |
| 225 | GUAUACUACCACUUUGAAU | AUUCAAAGUGGUAGUAUAC | | [1783-1801] 3'UTR |
| 226 | CCGUUGACCAUGGUUGCAA | UUGCAACCAUGGUCAACGG | Chimp, Rat, Ms | [195-213] 5'UTR + ORF |
| 227 | GGGAUGGAAUAGGUAAGCA | UGCUUACCUAUUCCAUCCC | | [1029-1047] 3'UTR |
| 228 | GAAUUAUUGAAACGGGUCA | UGACCCGUUUCAAUAAUUC | | [1798-1816] 3'UTR |
| 229 | CUAUGGAGAUAUGGUUUAU | AUAAACCAUAUCUCCAUAG | | [1837-1855] 3'UTR |
| 230 | CCUUUGGAGAAGUGAUUCA | UGAAUCACUUCUCCAAAGG | | [961-979] 3'UTR |
| 231 | AGCCCAUUUGAGUUUUACA | UGUAAAACUCAAAUGGGCU | | [1056-1074] 3'UTR |
| 232 | AGGAUUGUGUGUGAUUCUA | UAGAAUCACACACAAUCCU | Chimp | [570-588] ORF |
| 233 | UGCUUGGAAAGAUACUACA | UGUAGUAUCUUUCCAAGCA | | [2273-2291] 3'UTR |
| 234 | ACCAGUUCCUGACUCAAAU | AUUUGAGUCAGGAACUGGU | | [1247-1265] 3'UTR |
| 235 | GGCUAUGGAGAUAUGGUUU | AAACCAUAUCUCCAUAGCC | | [1836-1853] 3'UTR |
| 236 | CUUUUCCACUAACAGUUA | UAACUGUUAGUGGAAAAAG | | [2446-2464] 3'UTR |
| 237 | CCCAGAUUUUUUCCACCUU | AAGGUGGAAAAAAUCUGGG | | [1904-1922] 3'UTR |
| 238 | GGUCCUAAAAAGGGAAAAU | AUUUUCCCUUUUUAGGACC | | [778-796] ORF + 3'UTR |
| 239 | GCUUCAGGGACUUUUUCUU | AAGAAAAAGUCCCUGAAGC | Chimp | [649-687] ORF |
| 240 | UGUUUUAAAGAGGCAACAA | UUGUUGCCUCUUUAAAACA | | [1403-1421] 3'UTR |
| 241 | GGAAUAAUAAAGGCCUUAU | AUAAGGCCUUUAUUAUUCC | | [1939-1957] 3'UTR |
| 242 | GCAUGUCUAUUGUUAAGCU | AGCUUAACAAUAGACAUGC | | [2338-2356] 3'UTR |
| 243 | AGGUCCUUGUCCCUGAGAA | UUCUCAGGGACAAGGACCU | Chimp | [433-451] ORF |
| 244 | UGAUGAAUACCUGUGAGGA | UCCUCACAGGUAUUCAUCA | | [1584-1602] 3'UTR |
| 245 | CUGUAUACUACCACUUUGA | UCAAAGUGGUAGUAUACAG | | [1781-1799] 3'UTR |
| 246 | GUAGAUUUUCUGCAUAGAU | AUCUAUGCAGAAAAUCUAC | | [967-1005] 3'UTR |
| 247 | UUAUGCACGUGAACUUGGA | UCCAAGUUCACGUGCAUAA | Dog, Chin, GP, Rat, Ms | [523-541] ORF |

TABLE B-continued additional 19 mers

| Number | Sense siRNA | AntiSense siRNA | Other Sp | Hum-34222182 ORF: 204-785 |
|---|---|---|---|---|
| 248 | GAAACUGACCCAGAGAAUU | AAUUCUCUGGGUCAGUUUC | Chin, GP, Chimp, Rat, Ms | [449-467] ORF |
| 249 | CCAGUUCCUGACUCAAAUU | AAUUUGAGUCAGGAACUGG | | [1248-1266] 3'UTR |
| 250 | GAAACAGAGCCGUUGACCA | UGGUCAACGGCUCUGUUUC | Dog, Chimp, Rat, Ms | [186-204] 5'UTR |
| 251 | GAGAACUGUCUGUCCAAAU | AUUUGGACAGACAGUUCUC | Dog, Chimp | [387-405] ORF |
| 252 | UGUCACUAGGGAAUAAUAA | UUAUUAUUCCCUAGUGACA | | [1930-1948] 3'UTR |
| 253 | CAUUGAGUGAAUGAUGAAU | AUUCAUCAUUCACUCAAUG | | [573-1591] 3'UTR |
| 254 | UACAGCCUAGAGAAUGAAA | UUUCAUUCUCUAGGCUGUA | | [1858-1876] 3'UTR |
| 255 | GGAGAACUCUGAUCCUCAG | CUGAGGAUCAGAGUUCUCC | | [697-715] ORF |
| 256 | ACGAGGUAAUAUUUGAGGA | UCCUCAAAUAUUACCUCGU | Chimp | [337-355] ORF |
| 257 | CAGGGACUUUUCUUUAGU | ACUAAAGAAAAGUCCCUG | | [653-671] ORF |
| 258 | AGUUGAUUACUCUUCCAUU | AAUGGAAGAGUAAUCAACU | | [1558-1576] 3'UTR |
| 259 | GGAACAACAGUGAUUGAAG | CUUCAAUCACUGUUGUUCC | | [759-777] ORF |
| 260 | AAGGAAACAGAGCCGUUGA | UCAACGGCUCUGUUUCCUU | Chimp | [183-201] 5'UTR |
| 261 | CAAAGCCAAUCUUUAUAGA | UCUAUAAAGAUUGGCUUUG | | [2290-2308] 3'UTR |
| 262 | AAACGGGUCAAUUUACGAA | UUCGUAAAUUGACCCGUUU | | [1807-1825] 3'UTR |
| 263 | AAGGCUUCUUGGGCAUCGA | UCGAUGCCCAAGAAGCCUU | | [2412-2430] 3'UTR |
| 264 | CCUGAGAAACUGACCCAGA | UCUGGGUCAGUUUCUCAGG | Dog, Chin, GP, Chimp, Ms | [444-462] ORF |
| 265 | CUGCAUUGGCUAUGGAGAU | AUCUCCAUAGCCAAUGCAG | | [1828-1846] 3'UTR |
| 266 | GAUUGUGUGUGAUUCUAGC | GCUAGAAUCACACACAAUC | | [572-59] ORF |
| 267 | GCUAGUCAGCUAAAGUCAU | AUGACUUUAGCUGACUAGC | | [837-855] 3'UTR |
| 268 | UAUUCAUCCUGGUGUUACU | AGUAACACCAGGAUGAAUA | | [2160-2178] 3'UTR |
| 269 | GGGUAGUAAAACUAUUCAG | CUGAAUAGUUUUACUACCC | | [819-837] 3'UTR |
| 270 | ACCACGGUGUUGUUUUAGA | UCUAAAACAACACCGUGGU | | [1445-1463] 3'UTR |
| 271 | CAGUUAUCUUUGACUCUCU | AGAGAGUCAAAGAUAACUG | | [2459-2477] 3'UTR |
| 272 | CACAAUUUGGUUUCAGGUA | UACCUGAAACCAAAUUGUG | | [1083-1101] 3'UTR |
| 273 | UGAUUGGGUAGUAAAACUA | UAGUUUUACUACCCAAUCA | | [814-832] 3'UTR |
| 274 | CUUCUUGGGCAUCGAUGUA | UACAUCGAUGCCCAAGAAG | | [2416-2434] 3'UTR |
| 275 | GCUUUUCUGGGAAUUGAAG | CUUCAAUUCCCAGAAAAGC | | [1727-1745] 3'UTR |
| 276 | GGAUUGUGUGUGAUUCUAG | CUAGAAUCACACACAAUCC | Chimp | [571-589] ORF |
| 277 | AGUCUGCAUUGGCUAUGGA | UCCAUAGCCAAUGCAGACU | | [1825-1843] 3'UTR |
| 278 | ACUACAAAGCCAAUCUUUA | UAAAGAUUGGCUUUGUAGU | | [2286-2304] 3'UTR |
| 279 | UAGUGUAGAUUUCUGCAU | AUGCAGAAAAUCUACACUA | | [983-1001] 3'UTR |
| 280 | GCAAAAGUAGAAGCCCAUU | AAUGGGCUUCUACUUUUGC | | [1045-1063] 3'UTR |
| 281 | GGGUCAAUUUACGAAGUCU | AGACUUCGUAAAUUGACCC | | [1811-1829] 3'UTR |
| 282 | AGGCUUCUUGGGCAUCGAU | AUCGAUGCCCAAGAAGCCU | | [2413-2431] 3'UTR |

TABLE B-continued additional 19 mers

| Number | Sense siRNA | AntiSense siRNA | Other Sp | Hum-34222182 ORF: 204-785 |
|---|---|---|---|---|
| 283 | UGAUUGGAACAACAGUGAU | AUCACUGUUGUUCCAAUCA | | [754-772] ORF |
| 284 | AAUUCAGCAAGGCUUUCAU | AUGAAAGCCUUGCUGAAUU | | [2044-2062] 3'UTR |
| 285 | AAUGAUGAAUACCUGUGAG | CUCACAGGUAUUCAUCAUU | | [1582-1600] 3'UTR |
| 286 | AUACCUGUGAGGAUAGGAA | UUCCUAUCCUCACAGGUAU | | [1590-1608] 3'UTR |
| 287 | UUCAUGAUUGGGUAGUAAA | UUUACUACCCAAUCAUGAA | | [810-828] 3'UTR |
| 288 | CUACAAAGCCAAUCUUUAU | AUAAAGAUUGGCUUUGUAG | | [2287-2305] 3'UTR |
| 289 | GAGCCUGCUAAGUGAUUUU | AAAAUCACUUAGCAGGCUC | Chimp | [281-299] ORF |
| 290 | AACCCUAGGUAAGAGUAAA | UUUACUCUUACCUAGGGUU | | [1322-1340] 3'UTR |
| 291 | UAACCCUAGGUAAGAGUAA | UUACUCUUACCUAGGGUUA | | [1321-1339] 3'UTR |
| 292 | CAAAAUGGUGAUGGCUUAU | AUAAGCCAUCACCAUUUUG | | [2493-2511] 3'UTR |
| 293 | UUAGCCAGUGUUCUAACAA | UUGUUAGAACACUGGCUAA | | [2239-2257] 3'UTR |
| 294 | AACUGUUGUCCUUUUUCCA | UGGAAAAAGGACAACAGUU | | [2436-2454] 3'UTR |
| 295 | GCAUUCAGAAUUGCUGGA | UCCAGCAAUUCUGAAAUGC | Chimp | [244-262] ORF |
| 296 | GUACCUACUUUUGAGCUUA | UAAGCUCAAAAGUAGGUAC | | [594-812] ORF |
| 297 | CUGUCUGUCCAAAUCAAAG | CUUUGAUUUGGACAGACAG | Dog, Chimp | [392-410] ORF |
| 298 | GUCUUAUUCCAACUAAGUA | UACUUAGUUGGAAUAAGAC | | [1963-1981] 3'UTR |
| 299 | UUGUGUUUAAGCAGGAGAA | UUCUCCUGCUUAAACACAA | Dog, Chimp | [616-634] ORF |
| 300 | UGCCAGAAUUUGGUUAAAA | UUUUAACCAAAUUCUGGCA | GP, Chimp, Rat, Ms | [363-381] ORF |
| 301 | CUAAUGUUUAAAGAGGCA | UGCCUCUUUAAACAUUAG | | [1399-1417] 3'UTR |
| 302 | CUAAGUUUUCAGAGGAUUU | AAAUCCUCUGAAAACUUAG | | [1166-1184] 3'UTR |
| 303 | GGUUUAUAGUACAGCCUAG | CUAGGCUGUACUAUAAACC | | [1849-1867] 3'UTR |
| 304 | ACAGGAAGGUAGGAUUAAG | CUUAAUCCUACCUUCCUGU | | [1281-1299] 3'UTR |
| 305 | UCCUCUGGUUUCAGGAGAA | UUCUCCUGAAACCAGAGGA | | [684-702] ORF |
| 306 | UGUUGUUUUAGAUGCCUUU | AAAGGCAUCUAAAACAACA | | [1452-1470] 3'UTR |
| 307 | UCUCUGAUUCACUUAGUAA | UUACUAAGUGAAUCAGAGA | | [1631-1649] 3'UTR |
| 308 | UGAUUUUGACUACUGGGAU | AUCCCAGUAGUCAAAAUCA | Dog, Chimp | [293-311] ORF |
| 309 | AGAGAGCCUGCUAAGUGAU | AUCACUUAGCAGGCUCUCU | Chimp | [278-296] ORF |
| 310 | GGUGAUGGCUUAUGGAAGG | CCUUCCAUAAGCCAUCACC | | [2499-2517] 3'UTR |
| 311 | UGUCAAGGGUAGUAGCUGU | ACAGCUACUACCCUUGACA | | [1766-1784] 3'UTR |
| 312 | CGCUUCUCCUCUGGUUUCA | UGAAACCAGAGGAGAAGCG | | [678-698] ORF |
| 313 | AUGUUGUUUUGCAUGUCUA | UAGACAUGCAAAACAACAU | | [2328-2346] 3'UTR |
| 314 | CUAGCGUCGUACCUACUUU | AAAGUAGGUACGACGCUAG | | [586-604] ORF |
| 315 | CCAGAUAACCAUGCAUGCA | UGCAUGCAUGGUUAUCUGG | | [1885-1903] 3'UTR |
| 316 | CUUCCAAAAGCCCACACCA | UGGUGUGGGCUUUUGGAAG | | [1229-1247] 3'UTR |
| 317 | AGUUAUCUUUGACUCUCUU | AAGAGAGUCAAAGAUAACU | | [2460-2478] 3'UTR |
| 318 | CUUAAGUGUUGAAUACUGU | ACAGUAUUCAACACUUAAG | | [1492-1510] 3'UTR |
| 319 | CAUAGCAACUGCAGCUAAC | GUUAGCUGCAGUUGCUAUG | | [927-945] 3'UTR |

TABLE B-continued additional 19 mers

| Number | Sense siRNA | AntiSense siRNA | Other Sp | Hum-34222182 ORF: 204-785 |
|---|---|---|---|---|
| 320 | CCGGCCAGCAUUUCAGAAU | AUUCUGAAAUGCUGGCCGG | Chimp | [237-255] ORF |
| 321 | GGCCAAGAUAAAUCAAUGU | ACAUUGAUUUAUCUUGGCC | | [2313-2331] 3'UTR |
| 322 | AUAUUACGGCAAUAAUGGA | UCCAUUAUUGCCGUAAUAU | | [1347-1365] 3'UTR |
| 323 | ACUUCCUCACUCUAAUGUU | AACAUUAGAGUGAGGAAGU | | [1388-1406] 3'UTR |
| 324 | UAAAAAGCUGGAUAGGAUU | AAUCCUAUCCAGCUUUUUA | Chin, GP, Chimp, Rat | [557-575] ORF |
| 325 | AUGUUGUUCCUGAACCCAA | UUGGGUUCAGGAACAACAU | Chimp | [313-331] ORF |
| 326 | GGUUUCAGGAGAACUCUGA | UCAGAGUUCUCCUGAAACC | | [690-708] ORF |
| 327 | CAUGGUUGCAACUGGCAGU | ACUGCCAGUUGCAACCAUG | Chimp | [203-221] 5'UTR + ORF |
| 328 | UUUCAGGUAGGCUUGGUAA | UUACCAAGCCUACCUGAAA | | [1093-1111] 3'UTR |
| 329 | UGUGAUCCUGUUACUGAUA | UAUCAGUAACAGGAUCACA | | [2189-2207] 3'UTR |
| 330 | UUUCAUGAUUGGGUAGUAA | UUACUACCCAAUCAUGAAA | | [809-827] 3'UTR |
| 331 | GUUUUUAGACAGGAAGGUA | UACCUUCCUGUCUAAAAAC | | [1273-1291] 3'UTR |
| 332 | AGGUUUCCUGCCCUAGCUA | UAGCUAGGGCAGGAAACCU | | [2098-2116] 3'UTR |
| 333 | CAACAAUGUUCAAUUCAGC | GCUGAAUUGAACAUUGUUG | | [2033-2051] 3'UTR |
| 334 | CCUCUUUUCAGUAUUACAU | AUGUAAUACUGAAAAGAGG | | [1655-1673] 3'UTR |
| 335 | GUCAAGGGUAGUAGCUGUA | UACAGCUACUACCCUUGAC | | [1767-1785] 3'UTR |
| 336 | AGUGUUGAAUACUGUCUUU | AAAGACAGUAUUCAACACU | | [1496-1514] 3'UTR |
| 337 | GAACAACAGUGAUUGAAGG | CCUUCAAUCACUGUUGUUC | | [760-778] ORF |
| 338 | UCCUCUUUUCAGUAUUACA | UGUAAUACUGAAAAGAGGA | | [1654-1672] 3'UTR |
| 339 | AGGAAUCAACUUGCCAGAA | UUCUGGCAAGUUGAUUCCU | Chimp | [352-370] ORF |
| 340 | CGUCCAGAUAACCAUGCAU | AUGCAUGGUUAUCUGGACG | | [1882-1900] 3'UTR |
| 341 | CCUUUUUCCACUAACAGUU | AACUGUUAGUGGAAAAAGG | | [2445-2463] 3'UTR |
| 342 | CAGAAUUGAAUGGGAUGGA | UCCAUCCCAUUCAAUUCUG | | [1018-1036] 3'UTR |
| 343 | UUUUCUGGCCUUUGGAGAA | UUCUCCAAAGGCCAGAAAA | | [953-971] 3'UTR |
| 344 | CCUCUCUGAUUCACUUAGU | ACUAAGUGAAUCAGAGAGG | | [1629-1647] 3'UTR |
| 345 | GUCCCUCUCUGAUUCACUU | AAGUGAAUCAGAGAGGGAC | | [1626-1644] 3'UTR |
| 346 | AGGGUCCUAAAAAGGGAAA | UUUCCCUUUUUAGGACCCU | | [776-794] ORF + 3'UTR |
| 347 | UAUAGAAUUGGGCCAAGAU | AUCUUGGCCCAAUUCUAUA | | [2303-2321] 3'UTR |
| 348 | GUUUCAGGAGAACUCUGAU | AUCAGAGUUCUCCUGAAAC | | [691-709] ORF |
| 349 | GCUAUUAGCUCCACUUCAC | GUGAAGUGGAGCUAAUAGC | | [2113-2131] 3'UTR |
| 350 | UGGGCCAAGAUAAAUCAAU | AUUGAUUUAUCUUGGCCCA | | [2311-2329] 3'UTR |
| 351 | ACUCAAAUUUGAAGGGUUU | AAACCCUUCAAAUUUGAGU | | [1258-1276] 3'UTR |
| 352 | CUAACAGGCUGAUUUUCUG | CAGAAAAUCAGCCUGUUAG | | [941-959] 3'UTR |
| 353 | CAAUGUUCAAUUCAGCAAG | CUUGCUGAAUUGAACAUUG | | [2036-2054] 3'UTR |
| 354 | UGGUGUUACUGAAAAACAG | CUGUUUUUCAGUAACACCA | | [2169-2187] 3'UTR |
| 355 | GUUCCUGAACCCAACCUCA | UGAGGUUGGGUUCAGGAAC | Chimp | [318-336] ORF |

TABLE B-continued additional 19 mers

| Number | Sense siRNA | AntiSense siRNA | Other Sp | Hum-34222182 ORF: 204-785 |
|---|---|---|---|---|
| 356 | AGGAGAACUCUGAUCCUCA | UGAGGAUCAGAGUUCUCCU | | [696-714] ORF |
| 357 | UUGCCAGAAUUUGGUUAAA | UUUAACCAAAUUCUGGCAA | Chimp | [362-380] ORF |
| 358 | UGUAUACUACCACUUUGAA | UUCAAAGUGGUAGUAUACA | | [1782-1800] 3'UTR |
| 359 | AUCCUGGUGUUACUGAAAA | UUUUCAGUAACACCAGGAU | | [2165-2183] 3'UTR |
| 360 | CAGCUAACAGGCUGAUUUU | AAAAUCAGCCUGUUAGCUG | | [938-956] 3'UTR |
| 361 | CCCAAAUGUAGUCuCUUUU | AAAAGAGACUACAUUUGGG | | [890-908] 3'UTR |
| 362 | CCAUGCAUGCACCCAGAUU | AAUCUGGGUGCAUGCAUGG | | [1893-1911] 3'UTR |
| 363 | AUGGUGAUGGCUUAUGGAA | UUCCAUAAGCCAUCACCAU | | [2497-2515] 3'UTR |
| 364 | GAACCAUUUCACCAUGGCA | UGCCAUGGUGAAAUGGUUC | | [1690-1708] 3'UTR |
| 365 | ACUAAACUUGGUUGCUCAA | UUGAGCAACCAAGUUUAGU | Chimp | [414-432] ORF |
| 366 | UUUUCUGCAUAGAUCCCAU | AUGGGAUCUAUGCAGAAAA | | [992-1010] 3'UTR |
| 367 | ACGAAGUCUGCAUUGGCUA | UAGCCAAUGCAGACUUCGU | | [1821-1839] 3'UTR |
| 368 | GAUCAUUAUCUCUUUCCUU | AAGGAAAGAGAUAAUGAUC | | [1962-2000] 3'UTR |
| 369 | UGGCUAUGGAGAUAUGGUU | AACCAUAUCUCCAUAGCCA | | [1834-1852] 3'UTR |
| 370 | GGUAGUAGCUGUAUAUACC | GUAGUAUACAGCUACUACC | | [1773-1791] 3'UTR |
| 371 | UUGGGCCAAGAUAAAUCAA | UUGAUUUAUCUUGGCCCAA | | [2310-2328] 3'UTR |
| 372 | CCAAUUGUCAAGGGUAGUA | UACUACCCUUGACAAUUGG | | [1761-1779] 3'UTR |
| 373 | CUUAGUAAUCUAUCCUCUU | AAGAGGAUAGAUUACUAAG | | [1642-1660] 3'UTR |
| 374 | UGGUGAUGGCUUAUGGAAG | CUUCCAUAAGCCAUCACCA | | [2496-2516] 3'UTR |
| 375 | CUGGAGUUGUCACCACUGA | UCAGUGGUGACAACUCCAG | | [2387-2405] 3'UTR |
| 376 | CACUGAUUGGAACAACAGU | ACUGUUGUUCCAAUCAGUG | | [751-769] ORF |
| 377 | CAGUUUGAGCAGCAAGAAC | GUUCUUGCUGCUCAAACUG | Chimp | [218-236] ORF |
| 378 | UAGGGACAGAUGUAUUCAU | AUGAAUACAUCUGUCCCUA | | [2148-2166] 3'UTR |
| 379 | CAAUCUUUAUAGAAUUGGG | CCCAAUUCUAUAAAGAUUG | | [2296-2314] 3'UTR |
| 380 | UGUCCUUUUCCACUAACA | UGUUAGUGGAAAAGGACA | | [2442-2460] 3'UTR |
| 381 | GUCCUAAAAGGGAAAAUA | UAUUUUCCCUUUUUAGGAC | | [779-797] ORF + 3'UTR |
| 382 | GGUUGCAACUGGCAGUUUG | CAAACUGCCAGUUGCAACC | Chimp | [206-224] ORF |
| 383 | AGCCUAUCAAAACUUCCAA | UUGGAAGUUUUGAUAGGCU | | [1217-1235] 3'UTR |
| 384 | CUAAACUCUUCAAAUGCUU | AAGCAUUUGAAGAGUUUAG | | [2259-2277] 3'UTR |
| 385 | CUUGGAUACCUGUCACUAG | CUAGUGACAGGUAUCCAAG | | [1920-1938] 3'UTR |
| 386 | CAACGAGGUAAUAUUUGAG | CUCAAAUAUUACCUCGUUG | Chimp | [335-353] ORF |
| 387 | GAGGUUGUGUUAUGCACGU | ACGUGCAUAACACAACCUC | | [514-532] ORF |
| 388 | CUUGCCAGAAUUUGGUUAA | UUAACCAAAUUCUGGCAAG | Chimp | [361-379] ORF |
| 389 | AAAAGCUUGUGGUGCCAUU | AAUGGCACCACAAGCUUUU | | [1420-1438] 3'UTR |
| 390 | GCAAGGCUUUCAUAUCCUU | AAGGAUAUGAAAGCCUUGC | | [2050-2068] 3'UTR |
| 391 | ACCUGUCACUAGGGAAUAA | UUAUUCCCUAGUGACAGGU | | [1927-1945] 3'UTR |
| 392 | AGCUUGUGGUGCCAUUUCA | UGAAAUGGCACCACAAGCU | | [1423-1441] 3'UTR |

TABLE B-continued additional 19 mers

| Number | Sense siRNA | AntiSense siRNA | Other Sp | Hum-34222182 ORF: 204-785 |
|---|---|---|---|---|
| 393 | GGGACUUUUCUUUAGUAG | CUACUAAAGAAAAAGUCCC | | [665-673] ORF |
| 394 | CUAGGUAAGAGUAAAUGAG | CUCAUUUACUCUUACCUAG | | [1326-1344] 3'UTR |
| 395 | CGUACCUACUUUUGAGCUU | AAGCUCAAAAGUAGGUACG | | [593-611] ORF |
| 396 | AAGAUACUACAAAGCCAAU | AUUGGCUUUGUAGUAUCUU | | [2281-2299] 3'UTR |
| 397 | CUCAGGAUUUCGACUUGUU | AACAAGUCGAAAUCCUGAG | | [716-734] ORF |
| 398 | CUUUAUAGAAUUGGGCCAA | UUGGCCCAAUUCUAUAAAG | | [2300-2318] 3'UTR |
| 399 | CCCAUUUUUGUACAGAAUU | AAUUCUGUACAAAAAUGGG | | [1006-1024] 3'UTR |
| 400 | UUGUGGUGCCAUUUCAGUA | UACUGAAAUGGCACCACAA | | [1426-1444] 3'UTR |
| 401 | GUGUGUAGUUGAUUACUCU | AGAGUAAUCAACUACACAC | | [1552-1570] 3'UTR |
| 402 | GUUUAUAGUACAGCCUAGA | UCUAGGCUGUACUAUAAAC | | [1850-1868] 3'UTR |
| 403 | AUGAGAAAUAUUACGGCAA | UUGCCGUAAUAUUUCUCAU | | [1340-1358] 3'UTR |
| 404 | CACCCAGAUUUUUUCCACC | GGUGGAAAAAUCUGGGUG | | [1902-1920] 3'UTR |
| 405 | AUCCCAUUUUUGUACAGAA | UUCUGUACAAAAAUGGGAU | | [1004-1022] 3'UTR |
| 406 | CAGAAUUGCUGGACUGUGG | CCACAGUCCAGCAAUUCUG | Chimp | [250-258] ORF |
| 407 | UGACUACUGGGAUUAUGUU | AACAUAAUCCCAGUAGUCA | Chimp | [299-317] ORF |
| 408 | GAUCCUGUUACUGAUACUA | UAGUAUCAGUAACAGGAUC | | [2192-2210] 3'UTR |
| 409 | UCCAAAUCAAAGCAAACUA | UAGUUUGCUUUGAUUUGGA | Chimp | [399-417] ORF |
| 410 | UCUGGGCUUUUCUGGGAAU | AUUCCCAGAAAAGCCCAGA | | [1722-1740] 3'UTR |
| 411 | CCAUUUUUGUACAGAAUUG | CAAUUCUGUACAAAAAUGG | | [1007-1025] 3'UTR |
| 412 | CUGGCCUUUGGAGAAGUGA | UCACUUCUCCAAAGGCCAG | | [957-975] 3'UTR |
| 413 | UAGGAAAUUAGUUCUGAGA | UCUCAGAACUAAUUUCCUA | | [1603-1621] 3'UTR |
| 414 | CUUAAUCUCAGAUGAACCA | UGGUUCAUCUGAGAUUAAG | | [1677-1695] 3'UTR |
| 415 | AGGAAAUUAGUUCUGAGAU | AUCUCAGAACUAAUUUCCU | | [1604-1622] 3'UTR |
| 416 | AGGCUUGGUAAUAGACUAU | AUAGUCUAUUACCAAGCCU | | [1101-1119] 3'UTR |
| 417 | GAAUUUGGUUAAAAUGCUG | CAGCAUUUUAACCAAAUUC | Chimp | [368-388] ORF |
| 418 | UAGACAGGAAGGUAGGAUU | AAUCCUACCUUCCUGUCUA | | [1278-1296] 3'UTR |
| 419 | UUGAAGUAUCUCUCCUUAA | UUAAGGAGAGAUACUUCAA | | [1740-1758] 3'UTR |
| 420 | CUUUGACUCUCUUGCCUGU | ACAGGCAAGAGAGUCAAAG | | [2466-2484] 3'UTR |
| 421 | UGUGGCUAUCACCCAGAGA | UCUCUGGGUGAUAGCCACA | Chimp | [264-282] ORF |
| 422 | AGGCCUUAUUUUUGUCUU | AAGACAAAAAUAAGGCCU | | [1949-1967] 3'UTR |
| 423 | CAGUGUUAUCUCAUCUCUG | CAGAGAUGAGAUAACACUG | | [1707-1725] 3'UTR |
| 424 | UGAGAAACUGACCCAGAGA | UCUCUGGGUCAGUUUCUCA | Chin, GP, Chimp, Rat, Ms | [446-464] ORF |
| 425 | UGUUGUUCCUGAACCCAAC | GUUGGGUUCAGGAACAACA | Chimp | [314-332] ORF |
| 426 | GUUGUCCUUUUUCCACUAA | UUAGUGGAAAAAGGACAAC | | [2440-2458] 3'UTR |
| 427 | GGCAAUAAUGGAACUGCUU | AAGCAGUUCCAUUAUUGCC | | [1354-1372] 3'UTR |
| 428 | ACAAUGUUCAAUUCAGCAA | UUGCUGAAUUGAACAUUGU | | [2035-2053] 3'UTR |

TABLE B-continued additional 19 mers

| Number | Sense siRNA | AntiSense siRNA | Other Sp | Hum-34222182 ORF: 204-785 |
|---|---|---|---|---|
| 429 | GCAACUGGCAGUUUGAGCA | UGCUCAAACUGCCAGUUGC | Dog, Chimp | [210-228] ORF |
| 430 | GGGUUUUUAGACAGGAAGG | CCUUCCUGUCUAAAAACCC | | [1271-1289] 3'UTR |
| 431 | GUAGGAUUAAGUAGGUGAG | CUCACCUACUUAAUCCUAC | | [1289-1307] 3'UTR |
| 432 | UGAAACUCACCGUCCAGAU | AUCUGGACGGUGAGUUUCA | | [1872-1890] 3'UTR |
| 433 | UGAUCCUGUUACUGAUACU | AGUAUCAGUAACAGGAUCA | | [2191-2209] 3'UTR |
| 434 | AUUUCAUGAUUGGGUAGUA | UACUACCCAAUCAUGAAAU | | [808-826] 3'UTR |
| 435 | AGAUGCCUUUAUAAGCUCA | UGAGCUUAUAAAGGCAUCU | | [1461-1479] 3'UTR |
| 436 | CCUCAACGAGGUAAUAUUU | AAAUAUUACCUCGUUGAGG | Chimp | [332-350] ORF |
| 437 | GUUAAGCUCCAAAGGUUCA | UGAACCUUUGGAGCUUAAC | | [2349-2367] 3'UTR |
| 438 | CCUAGCUAUUAGCUCCACU | AGUGGAGCUAAUAGCUAGG | | [2109-2127] 3'UTR |
| 439 | GUAGGGACAGAUGUAUUCA | UGAAUACAUCUGUCCCUAC | | [2147-2165] 3'UTR |
| 440 | UUCUGUGUUUCACAUUCAU | AUGAAUGUGAAACACAGAA | | [911-929] 3'UTR |
| 441 | GGUAGGCUUGGUAAUAGAC | GUCUAUUACCAAGCCUACC | | [1098-1116] 3'UTR |
| 442 | CAGGUGUGAUCCUGUUACU | AGUAACAGGAUCACACCUG | | [2185-2203] 3'UTR |
| 443 | UAUUCAGCUAGUCAGCUAA | UUAGCUGACUAGCUGAAUA | | [831-849] 3'UTR |
| 444 | ACUCUUCAAAUGCUUGGAA | UUCCAAGCAUUUGAAGAGU | | [2263-2281] 3'UTR |
| 445 | UGGACUAGCUUCAGGGACU | AGUCCCUGAAGCUAGUCCA | Chimp | [642-680] ORF |
| 446 | UGCACGUGAACUUGGAAAU | AUUUCCAAGUUCACGUGCA | Dog, Chin, GP, Rat | [526-544] ORF |
| 447 | CAUCGAUGUAGAACUGUUG | CAACAGUUCUACAUCGAUG | | [2425-2443] 3'UTR |
| 448 | GAGCUUACACUUGUGUUUA | UAAACACAAGUGUAAGCUC | Chimp | [606-624] ORF |
| 449 | UGUUUCACAUUCAUAGCAA | UUGCUAUGAAUGUGAAACA | | [916-934] 3'UTR |
| 450 | CCUCACUCUAAUGUUUUAA | UUAAAACAUUAGAGUGAGG | | [1392-1410] 3'UTR |
| 451 | GGCUGAUUUUCUGGCCUUU | AAAGGCCAGAAAAUCAGCC | | [947-965] 3'UTR |
| 452 | UCUGGGAAUUGAAGUAUCU | AGAUACUUCAAUUCCCAGA | | [1732-1750] 3'UTR |
| 453 | CUUUUGAGCUUACACUUGU | ACAAGUGUAAGCUCAAAAG | Chimp | [601-619] ORF |
| 454 | CACUGUUUCUUGGUGACUU | AAGUCACCAAGAAACAGUG | | [1373-1391] 3'UTR |
| 455 | UGUUCAAAUUAGCCAGUGU | ACACUGGCUAAUUUGAACA | | [2231-2249] 3'UTR |
| 456 | AAUGAGAAAUAUUACGGCA | UGCCGUAAUAUUUCUCAUU | | [1339-1357] 3'UTR |
| 457 | CAUGGCAGUGUUAUCUCAU | AUGAGAUAACACUGCCAUG | | [1702-1720] 3'UTR |
| 458 | CUGUUAUGCUUACAAAAUG | CAUUUUGUAAGCAUAACAG | | [2481-2499] 3'UTR |
| 459 | GCUUUCAUAUCCUUGCUGU | ACAGCAAGGAUAUGAAAGC | | [2055-2073] 3'UTR |
| 460 | AGCUAAAGUCAUUUGUAGU | ACUACAAAUGACUUUAGCU | | [844-862] 3'UTR |
| 461 | UCUGUGUUUCACAUUCAUA | UAUGAAUGUGAAACACAGA | | [912-930] 3'UTR |
| 462 | AUUAGCCAGUGUUCUAACA | UGUUAGAACACUGGCUAAU | | [2238-2256] 3'UTR |
| 463 | AGUAGAAGCCCAUUUGAGU | ACUCAAAUGGGCUUCUACU | | [1050-1068] 3'UTR |
| 464 | AUGUAUUCAUCCUGGUGUU | AACACCAGGAUGAAUACAU | | [2157-2175] 3'UTR |
| 465 | GUAGUUGAUUACUCUUCCA | UGGAAGAGUAAUCAACUAC | | [1556-1574] 3'UTR |

TABLE B-continued additional 19 mers

| Number | Sense siRNA | AntiSense siRNA | Other Sp | Hum-34222182 ORF: 204-785 |
|---|---|---|---|---|
| 466 | UGUAAAAAGCUGGAUAGGA | UCCUAUCCAGCUUUUUACA | Chin, GP, Chimp, Rat, Ms | [555-573] ORF |
| 467 | UGUUUUGCAUGUCUAUUGU | ACAAUAGACAUGCAAAACA | | [2332-2350] 3'UTR |
| 468 | CUUCAAAUGCUUGGAAAGA | UCUUUCCAAGCAUUUGAAG | | [2266-2284] 3'UTR |
| 469 | UCAUAGCAACUGCAGCUAA | UUAGCUGCAGUUGCUAUGA | | [926-944] 3'UTR |
| 470 | CAGCCUAGAGAAUGAAACU | AGUUUCAUUCUCUAGGCUG | | [1860-1878] 3'UTR |
| 471 | UAUUACGGCAAUAAUGGAA | UUCCAUUAUUGCCGUAAUA | | [1348-1366] 3'UTR |
| 472 | AAAGGUUCACUGUGUUUCU | AGAAACACAGUGAACCUUU | | [2359-2377] 3'UTR |
| 473 | GUGAUUUUGACUACUGGGA | UCCCAGUAGUCAAAAUCAC | Chimp | [292-310] ORF |
| 474 | AAGCAAAAGUAGAAGCCCA | UGGGCUUCUACUUUUGCUU | | [1043-1061] 3'UTR |
| 475 | GGUUUCCUGCCCUAGCUAU | AUAGCUAGGGCAGGAAACC | | [2099-2117] 3'UTR |
| 476 | CUCUUUUCUUUCUGUGUUU | AAACACAGAAAGAAAAGAG | | [902-920] 3'UTR |
| 477 | GCCCUAGCUAUUAGCUCCA | UGGAGCUAAUAGCUAGGGC | | [2107-2125] 3'UTR |
| 478 | CCAGCAUUUCAGAAUUGCU | AGCAAUUCUGAAAUGCUGG | Chimp | [241-259] ORF |
| 479 | AGGGACUUUUUCUUUAGUA | UACUAAAGAAAAAGUCCCU | | [654-672] ORF |
| 480 | CAAAUGUAGUCUCUUUUCU | AGAAAAGAGACUACAUUUG | | [892-910] 3'UTR |
| 481 | CCAAGAUAAAUCAAUGUUG | CAACAUUGAUUUAUCUUGG | | [2315-2333] 3'UTR |
| 482 | AUGUAUGUAAAAGCUGGA | UCCAGCUUUUUACAUACAU | Chimp, Ms | [550-568] ORF |
| 483 | CGGUGUUGUUUUAGAUGCC | GGCAUCUAAAACAACACCG | | [1449-1467] 3'UTR |
| 484 | CAGAUUUUUUCCACCUUGG | CCAAGGUGGAAAAAAUCUG | | [1906-1924] 3'UTR |
| 485 | CAAAAGUAGAAGCCCAUUU | AAAUGGGCUUCUACUUUUG | | [1048-1064] 3'UTR |
| 486 | UUAUAGAAUUGGGCCAAGA | UCUUGGCCCAAUUCUAUAA | | [2302-2320] 3'UTR |
| 487 | AAGGUAGGAUUAAGUAGGU | ACCUACUUAAUCCUACCUU | | [1296-1304] 3'UTR |
| 488 | UAAGGAGCUUAUUCAGGUU | AACCUGAAUAAGCUCCUUA | | [2084-2102] 3'UTR |
| 489 | GUGUUGUUUUAGAUGCCUU | AAGGCAUCUAAAACAACAC | | [1451-1469] 3'UTR |
| 490 | GUUUCCUGCCCUAGCUAUU | AAUAGCUAGGGCAGGAAAC | | [2100-2118] 3'UTR |
| 491 | AUUCAGCAAGGCUUUCAUA | UAUGAAAGCCUUGCUGAAU | | [2945-2063] 3'UTR |
| 492 | CAAUUGGUUUCAGGUAGG | CCUACCUGAAACCAAUUG | | [1085-1103] 3'UTR |
| 493 | GUUGUUUUAGAUGCCUUUA | UAAAGGCAUCUAAAACAAC | | [1453-1471] 3'UTR |
| 494 | GCAUUGGCUAUGGAGAUAU | AUAUCUCCAUAGCCAAUGC | | [1830-1848] 3'UTR |
| 495 | CUGAGAAACUGACCCAGAG | CUCUGGGUCAGUUUCUCAG | Dog, Chin, GP, Chimp, Rat, Ms | [445-463] ORF |
| 496 | UAUGCUUACAAAAUGGUGA | UCACCAUUUUGUAAGCAUA | | [2485-2503] 3'UTR |
| 497 | AACUAAACUUGGUUGCUCA | UGAGCAACCAAGUUUAGUU | Chimp | [413-431] ORF |
| 498 | AAUGCUUGGAAAGAUACUA | UAGUAUCUUUCCAAGCAUU | | [2271-2289] 3'UTR |
| 499 | GUCUGUCCAAAUCAAAGCA | UGCUUUGAUUUGGACAGAC | Dog, Chimp | [394-412] ORF |
| 500 | AUUGCUGGACUGUGGCUAU | AUAGCCACAGUCCAGCAAU | Chimp | [254-272] ORF |

TABLE C

21 mers

| Number | Sense siRNA | AntiSense siRNA | Other Sp | Hum-34222182 ORF: 204-785 |
|---|---|---|---|---|
| 1 | GCCAGUGUUCUAACAAACUAA | UUAGUUUGUUAGAACACUGGC | | [2242-2262](21/21) 3'UTR |
| 2 | GGAUGGAAUAGGUAAGCAAAA | UUUUGCUUACCUAUUCCAUCC | | [1030-1050](21/21) 3'UTR |
| 3 | GGAUUAAGUAGGUGAGUUUAA | UUAAACUCACCUACUUAAUCC | | [1292-1312](21/21) 3'UTR |
| 4 | CCACCUGCCCUAAAUAAGAAA | UUUCUUAUUUAGGGCAGGUGG | | [868-888](21/21) 3'UTR |
| 5 | CAGUGUUCUAACAAACUAAAC | GUUUAGUUUGUUAGAACACUG | | [2244-2264](21/21) 3'UTR |
| 6 | CAGUGAUUGAAGGGUCCUAAA | UUUAGGACCCUUCAAUCACUG | | [766-786](21/21) ORF + 3'UTR |
| 7 | GCUGGAGAACUGUCUGUCCAA | UUGGACAGACAGUUCUCCAGC | Dog, Chimp | [383-403](21/21) ORF |
| 8 | GAGUGAAUGAUGAAUACCUGU | ACAGGUAUUCAUCAUUCACUC | | [1577-1597](21/21) 3'UTR |
| 9 | GGAUUUCGACUUGUUAAGAAA | UUUCUUAACAAGUCGAAAUCC | Rat | [720-740](21/21) ORF |
| 10 | GGAAAUUAGUUCUGAGAUCUA | UAGAUCUCAGAACUAAUUUCC | | [1605-1625](21/21) 3'UTR |
| 11 | ACGUGAACUUGGAAAUUGAAA | UUUCAAUUUCCAAGUUCACGU | Dog, Chin, GP, Rat | [529-549](21/21) ORF |
| 12 | UAGCCAGUGUUCUAACAAACU | AGUUUGUUAGAACACUGGCUA | | [2240-2260](21/21) 3'UTR |
| 13 | CAUCCUGGUGUUACUGAAAAA | UUUUUCAGUAACACCAGGAUG | | [2164-2184](21/21) 3'UTR |
| 14 | AGCCAGUGUUCUAACAAACUA | UAGUUUGUUAGAACACUGGCU | | [2241-2261](21/21) 3'UTR |
| 15 | CGUGAACUUGGAAAUUGAAAA | UUUUCAAUUUCCAAGUUCACG | Dog, Chin, GP, Rat | [530-550](21/21) ORF |
| 16 | UGGGCUUUUCUGGGAAUUGAA | UUCAAUUCCCAGAAAAGCCCA | | [1724-1744](21/21) 3'UTR |
| 17 | GGAAAGAUACUACAAAGCCAA | UUGGCUUUGUAGUAUCUUUCC | | [2278-2298](21/21) 3'UTR |
| 18 | CACGUGAACUUGGAAAUUGAA | UUCAAUUUCCAAGUUCACGUG | Dog, Chin, GP, Rat | [528-548](21/21) ORF |
| 19 | GCACGUGAACUUGGAAAUUGA | UCAAUUUCCAAGUUCACGUGC | Dog, Chin, GP, Rat | [527-547](21/21) ORF |
| 20 | GGCUUAUGGAAGGCUGUUAAA | UUUAACAGCCUUCCAUAAGCC | | [2505-2525](21/21) 3'UTR |
| 21 | GGAGAUAUGGUUUAUAGUACA | UGUACUAUAAACCAUAUCUCC | | [1841-1861](21/21) 3'UTR |
| 22 | GGGAUGGAAUAGGUAAGCAAA | UUUGCUUACCUAUUCCAUCCC | | [1029-1049](21/21) 3'UTR |
| 23 | CAAUGUUGUUUUGCAUGUCUA | UAGACAUGCAAAACAACAUUG | | [2326-2346](21/21) 3'UTR |
| 24 | AGUACAGCCUAGAGAAUGAAA | UUUCAUUCUCUAGGCUGUACU | | [1856-1876](21/21) 3'UTR |
| 25 | CUUUGGAGAAGUGAUUCAAAA | UUUUGAAUCACUUCUCCAAAG | | [962-982](21/21) 3'UTR |
| 26 | CCUUUGGAGAAGUGAUUCAAA | UUUGAAUCACUUCUCCAAAGG | | [961-981](21/21) 3'UTR |
| 27 | CAGAAUUGAAUGGGAUGGAAU | AUUCCAUCCCAUUCAAUUCUG | | [1018-1038](21/21) 3'UTR |
| 28 | UGGGAUGGAAUAGGUAAGCAA | UUGCUUACCUAUUCCAUCCCA | | [1028-1048](21/21) 3'UTR |
| 29 | CCAGAUUUUUCCACCUUGGA | UCCAAGGUGGAAAAAUCUGG | | [1905-1925](21/21) 3'UTR |
| 30 | GAAGGGUCCUAAAAAGGGAAA | UUUCCCUUUUUAGGACCCUUC | | [774-794](21/21) ORF + 3'UTR |
| 31 | CUUCCUCACUCUAAUGUUUUA | UAAAACAUUAGAGUGAGGAAG | | [1389-1409](21/21) 3'UTR |
| 32 | GAACUGUCUGUCCAAAUCAAA | UUUGAUUUGGACAGACAGUUC | Dog, Chimp | [389-409](21/21) ORF |
| 33 | CAACAAUGUUCAAUUCAGCAA | UUGCUGAAUUGAACAUUGUUG | | [2033-2053](21/21) 3'UTR |
| 34 | CUAGGUAAGAGUAAAUGAGAA | UUCUCAUUUACUCUUACCUAG | | [1326-1346](21/21) 3'UTR |
| 35 | AGUGAUUGAAGGGUCCUAAAA | UUUUAGGACCCUUCAAUCACU | | [767-787](21/21) ORF + 3'UTR |
| 36 | GUGAUUGAAGGGUCCUAAAAA | UUUUUAGGACCCUUCAAUCAC | | [768-788](21/21) ORF + 3'UTR |
| 37 | GAAUGAUGAAUACCUGUGAGG | CCUCACAGGUAUUCAUCAUUC | | [1581-1601](21/21) 3'UTR |
| 38 | CCUCUCUGAUUCACUUAGUAA | UUACUAAGUGAAUCAGAGAGG | | [1629-1649](21/21) 3'UTR |

TABLE C-continued 21 mers

| Number | Sense siRNA | AntiSense siRNA | Other Sp | Hum-34222182 ORF: 204-785 |
|---|---|---|---|---|
| 39 | AGAUUUUUCCACCUUGGAUA | UAUCCAAGGUGGAAAAAAUCU | | [1907-1927](21/21) 3'UTR |
| 40 | GAAUUUAGCCUCCACUCAACA | UGUUGAGUGGAGGCUAAAUUC | | [2017-2037](21/21) 3'UTR |
| 41 | GAAUAGGUAAGCAAAAGUAGA | UCUACUUUUGCUUACCUAUUC | | [1035-1055](21/21) 3'UTR |
| 42 | GGUCGUGGAUAAGGAGCUUAU | AUAAGCUCCUUAUCCACGACC | | [2075-2095](21/21) 3'UTR |
| 43 | GGCUUGGUAAUAGACUAUAUA | UAUAUAGUCUAUUACCAAGCC | | [1102-1122](21/21) 3'UTR |
| 44 | CUGUCACUAGGGAAUAAUAAA | UUUAUUAUUCCCUAGUGACAG | | [1929-1949](21/21) 3'UTR |
| 45 | CUUGGUGACUUCCUCACUCUA | UAGAGUGAGGAAGUCACCAAG | | [1381-1401](21/21) 3'UTR |
| 46 | CCUAGGUAAGAGUAAAUGAGA | UCUCAUUUACUCUUACCUAGG | | [1325-1345](21/21) 3'UTR |
| 47 | GCUUGUGGUGCCAUUUCAGUA | UACUGAAAUGGCACCACAAGC | | [1424-1444](21/21) 3'UTR |
| 48 | GAUGAAUACCUGUGAGGAUAG | CUAUCCUCACAGGUAUUCAUC | | [1585-1605](21/21) 3'UTR |
| 49 | GGUGUGAUCCUGUUACUGAUA | UAUCAGUAACAGGAUCACACC | | [2187-2207](21/21) 3'UTR |
| 50 | GGGUCGUGGAUAAGGAGCUUA | UAAGCUCCUUAUCCACGACCC | | [2074-2094](21/21) 3'UTR |
| 51 | ACCUAAAAUGUCACUGUUCAA | UUGAACAGUGACAUUUUAGGU | | [2217-2237](21/21) 3'UTR |
| 52 | GAUCCUGUUACUGAUACUAUA | UAUAGUAUCAGUAACAGGAUC | | [2192-2212](21/21) 3'UTR |
| 53 | CAAAGGUCCUUGUCCCUGAGA | UCUCAGGGACAAGGACCUUUG | Chimp | [430-450](21/21) ORF |
| 54 | AAAUGGUGAUGGCUUAUGGAA | UUCCAUAAGCCAUCACCAUUU | | [2495-2515](21/21) 3'UTR |
| 55 | CGUAGGGACAGAUGUAUUCAU | AUGAAUACAUCUGUCCCUACG | | [2146-2166](21/21) 3'UTR |
| 56 | AUAGAAUUGGGCCAAGAUAAA | UUUAUCUUGGCCCAAUUCUAU | | [2304-2324](21/21) 3'UTR |
| 57 | GAAAGAUACUACAAAGCCAAU | AUUGGCUUUGUAGUAUCUUUC | | [2279-2299](21/21) 3'UTR |
| 58 | GCUUCAGGGACUUUUUCUUUA | UAAAGAAAAGUCCCUGAAGC | Chimp | [649-669](21/21) ORF |
| 59 | CAUGAUUGGGUAGUAAAACUA | UAGUUUUACUACCCAAUCAUG | | [812-832](21/21) 3'UTR |
| 60 | AAUUAGCCAGUGUUCUAACAA | UUGUUAGAACACUGGCUAAUU | | [2237-2257](21/21) 3'UTR |
| 61 | UCAGGUAGGCUUGGUAAUAGA | UCUAUUACCAAGCCUACCUGA | | [1095-1115](21/21) 3'UTR |
| 62 | UGAAUGGGAUGGAAUAGGUAA | UUACCUAUUCCAUCCCAUUCA | | [1024-1044](21/21) 3'UTR |
| 63 | CGGUGUUGUUUUAGAUGCCUU | AAGGCAUCUAAAACAACACCG | | [1449-1469](21/21) 3'UTR |
| 64 | GGUUUCAGGUAGGCUUGGUAA | UUACCAAGCCUACCUGAAACC | | [1091-1111](21/21) 3'UTR |
| 65 | GCUGAUUUUCUGGCCUUUGGA | UCCAAAGGCCAGAAAAUCAGC | | [948-968](21/21) 3'UTR |
| 66 | CCUCCACUCAACAAUGUUCAA | UUGAACAUUGUUGAGUGGAGG | | [2025-2045](21/21) 3'UTR |
| 67 | GCUGUAUACUACCACUUUGAA | UUCAAAGUGGUAGUAUACAGC | | [1780-1800](21/21) 3'UTR |
| 68 | CGAAGGAAACAGAGCCGUUGA | UCAACGGCUCUGUUUCCUUCG | Chimp | [181-201](21/21) 5'UTR |
| 69 | UGAGCUUACACUUGUGUUUAA | UUAAACACAAGUGUAAGCUCA | Chimp | [605-625](21/21) ORF |
| 70 | CGGCGUAGGGACAGAUGUAUU | AAUACAUCUGUCCCUACGCCG | | [2143-2163](21/21) 3'UTR |
| 71 | AGAAUUGAAUGGGAUGGAAUA | UAUUCCAUCCCAUUCAAUUCU | | [1019-1039](21/21) 3'UTR |
| 72 | CAGAGAGCCUGCUAAGUGAUU | AAUCACUUAGCAGGCUCUCUG | Chimp | [277-297](21/21) ORF |
| 73 | UAUAGAAUUGGGCCAAGAUAA | UUAUCUUGGCCCAAUUCUAUA | | [2303-2323](21/21) 3'UTR |
| 74 | CUCAGGAUUUCGACUUGUUAA | UUAACAAGUCGAAAUCCUGAG | | [716-736](21/21) ORF |
| 75 | CUUCAAAUGCUUGGAAAGAUA | UAUCUUUCCAAGCAUUUGAAG | | [2266-2286](21/21) 3'UTR |
| 76 | GGUCCUAAAAAGGGAAAAUAU | AUAUUUUCCCUUUUUAGGACC | | [778-796](21/21) ORF + 3'UTR |

TABLE C-continued 21 mers

| Number | Sense siRNA | AntiSense siRNA | Other Sp | Hum-34222182 ORF: 204-785 |
|---|---|---|---|---|
| 77 | UGGAGAACUGUCUGUCCAAAU | AUUUGGACAGACAGUUCUCCA | Dog, Chimp | [385-405](21/21) ORF |
| 78 | GCUCAGGAUUUCGACUUGUUA | UAACAAGUCGAAAUCCUGAGC | | [715-735](21/21) ORF |
| 79 | GAGCCUGCUAAGUGAUUUGA | UCAAAAUCACUUAGCAGGCUC | Chimp | [281-301](21/21) ORF |
| 80 | UGAUGAAUACCUGUGAGGAUA | UAUCCUCACAGGUAUUCAUCA | | [1584-1604](21/21) 3'UTR |
| 81 | GAGAAUUUAGCCUCCACUCAA | UUGAGUGGAGGCUAAAUUCUC | | [2015-2035](21/21) 3'UTR |
| 82 | GGCCUUUGGAGAAGUGAUUCA | UGAAUCACUUCUCCAAAGGCC | | [959-979](21/21) 3'UTR |
| 83 | UGAAGGGUUUUUAGACAGGAA | UUCCUGUCUAAAAACCCUUCA | | [1267-1287](21/21) 3'UTR |
| 84 | GAGGAAUCAACUUGCCAGAAU | AUUCUGGCAAGUUGAUUCCUC | Chimp | [351-371](21/21) ORF |
| 85 | AGGAUUUCGACUUGUUAAGAA | UUCUUAACAAGUCGAAAUCCU | | [719-739](21/21) ORF |
| 86 | AGUUCCUGACUCAAAUUUGAA | UUCAAAUUUGAGUCAGGAACU | | [1250-1270](21/21) 3'UTR |
| 87 | ACAGGAAGGUAGGAUUAAGUA | UACUUAAUCCUACCUUCCUGU | | [1281-1301](21/21) 3'UTR |
| 88 | CUUGCUGUGGGUCGUGGAUAA | UUAUCCACGACCCACAGCAAG | | [2066-2086](21/21) 3'UTR |
| 89 | GCUGGAUAGGAUUGUGUGUGA | UCACACACAAUCCUAUCCAGC | Chin, GP, Chimp, Rat | [563-583](21/21) ORF |
| 90 | UUAUGUUGUUCCUGAACCCAA | UUGGGUUCAGGAACAACAUAA | Chimp | [311-331](21/21) ORF |
| 91 | CCUAAAAUGUCACUGUUCAAA | UUUGAACAGUGACAUUUUAGG | | [2218-2238](21/21) 3'UTR |
| 92 | GAUAGGAAAUUAGUUCUGAGA | UCUCAGAACUAAUUUCCUAUC | | [1601-1621](21/21) 3'UTR |
| 93 | GUUUCAGGUAGGCUUGGUAAU | AUUACCAAGCCUACCUGAAAC | | [1092-1112](21/21) 3'UTR |
| 94 | GAUUUUCUGGCCUUUGGAGAA | UUCUCCAAAGGCCAGAAAAUC | | [951-971](21/21) 3'UTR |
| 95 | CUGUGAGGAUAGGAAAUUAGU | ACUAAUUUCCUAUCCUCACAG | | [1594-1614](21/21) 3'UTR |
| 96 | GGUAGGCUUGGUAAUAGACUA | UAGUCUAUUACCAAGCCUACC | | [1098-1118](21/21) 3'UTR |
| 97 | GAAUGAAACUCACCGUCCAGA | UCUGGACGGUGAGUUUCAUUC | | [1869-1889](21/21) 3'UTR |
| 98 | CGUGGAUAAGGAGCUUAUUCA | UGAAUAAGCUCCUUAUCCACG | | [2078-2098](21/21) 3'UTR |
| 99 | GUGAAUGAUGAAUACCUGUGA | UCACAGGUAUUCAUCAUUCAC | | [1579-1599](21/21) 3'UTR |
| 100 | AAUUUAGCCUCCACUCAACAA | UUGUUGAGUGGAGGCUAAAUU | | [2018-2038](21/21) 3'UTR |
| 101 | GGAGAAGUGAUUCAAAAUAGU | ACUAUUUUGAAUCACUUCUCC | | [966-986](21/21) 3'UTR |
| 102 | CCACCAGUUCCUGACUCAAAU | AUUUGAGUCAGGAACUGGUGG | | [1245-1265](21/21) 3'UTR |
| 103 | UAGACAGGAAGGUAGGAUUAA | UUAAUCCUACCUUCCUGUCUA | | [1278-1298](21/21) 3'UTR |
| 104 | UGGGAUUAUGUUGUUCCUGAA | UUCAGGAACAACAUAAUCCCA | Chimp | [306-326](21/21) ORF |
| 105 | AAUGGGCCAAGAUAAAUCAA | UUGAUUUAUCUUGGCCCAAUU | | [2308-2328](21/21) 3'UTR |
| 106 | GGAUAAGGAGCUUAUUCAGGU | ACCUGAAUAAGCUCCUUAUCC | | [2081-2101](21/21) 3'UTR |
| 107 | AUUAGCCAGUGUUCUAACAAA | UUUGUUAGAACACUGGCUAAU | | [2238-2258](21/21) 3'UTR |
| 108 | UGGCUAUGGAGAUAUGGUUUA | UAAACCAUAUCUCCAUAGCCA | | [1834-1854](21/21) 3'UTR |
| 109 | GUCCAAAUCAAAGCAAACUAA | UUAGUUUGCUUUGAUUUGGAC | Chimp | [398-418](21/21) ORF |
| 110 | UGGAUACCUGUCACUAGGGAA | UUCCCUAGUGACAGGUAUCCA | | [1922-1942](21/21) 3'UTR |
| 111 | CCACCUUGGAUACCUGUCACU | AGUGACAGGUAUCCAAGGUGG | | [1916-1936](21/21) 3'UTR |
| 112 | AUGUGCUUAAUCUCAGAUGAA | UUCAUCUGAGAUUAAGCACAU | | [1672-1692](21/21) 3'UTR |
| 113 | CCAUUGAGUGAAUGAUGAAUA | UAUUCAUCAUUCACUCAAUGG | | [1572-1592](21/21) 3'UTR |
| 114 | CCUUUUUCCACUAACAGUUAU | AUAACUGUUAGUGGAAAAAGG | | [2445-2465](21/21) 3'UTR |

TABLE C-continued 21 mers

| Number | Sense siRNA | AntiSense siRNA | Other Sp | Hum-34222182 ORF: 204-785 |
|---|---|---|---|---|
| 115 | GGUCAAUUUACGAAGUCUGCA | UGCAGACUUCGUAAAUUGACC | | [1812-1832](21/21) 3'UTR |
| 116 | CCCUCUCUGAUUCACUUAGUA | UACUAAGUGAAUCAGAGAGGG | | [1628-1648](21/21) 3'UTR |
| 117 | CUGUUGUCCUUUUUCCACUAA | UUAGUGGAAAAAGGACAACAG | | [2438-2458](21/21) 3'UTR |
| 118 | UGCUUGGAAAGAUACUACAAA | UUUGUAGUAUCUUUCCAAGCA | | [2273-2293](21/21) 3'UTR |
| 119 | CAAUUCAGCAAGGCUUUCAUA | UAUGAAAGCCUUGCUGAAUUG | | [2043-2063](21/21) 3'UTR |
| 120 | GUGUGUGAUUCUAGCGUCGUA | UACGACGCUAGAAUCACACAC | | [576-596](21/21) ORF |
| 121 | CCUGCUAAGUGAUUUGACUA | UAGUCAAAAUCACUUAGCAGG | Chimp | [284-304](21/21) ORF |
| 122 | CUCUCUUGCCUGUUAUGCUUA | UAAGCAUAACAGGCAAGAGAG | | [2472-2492](21/21) 3'UTR |
| 123 | GUUAUGCACGUGAACUUGGAA | UUCCAAGUUCACGUGCAUAAC | Dog, Chin, GP, Rat | [522-542](21/21) ORF |
| 124 | CAAAGUAGAAGCCCAUUUGA | UCAAAUGGGCUUCUACUUUUG | | [1046-1066](21/21) 3'UTR |
| 125 | GCUAUUAGCUCCACUUCACAU | AUGUGAAGUGGAGCUAAUAGC | | [2113-2133](21/21) 3'UTR |
| 126 | AGUUGAUUACUCUUCCAAUUGA | UCAAUGGAAGAGUAAUCAACU | | [1558-1578](21/21) 3'UTR |
| 127 | GAAUUUGGUUAAAAUGCUGGA | UCCAGCAUUUUAACCAAAUUC | Chimp | [368-388](21/21) ORF |
| 128 | GGGCUUUUCUGGGAAUUGAAG | CUUCAAUUCCCAGAAAAGCCC | | [1725-1745](21/21) 3'UTR |
| 129 | UUGCCUGUUAUGCUUACAAAA | UUUUGUAAGCAUAACAGGCAA | | [2477-2497](21/21) 3'UTR |
| 130 | GAGGUUGUGUUAUGCACGUGA | UCACGUGCAUAACACAACCUC | | [514-534](21/21) ORF |
| 131 | GAAGCCCAUUUGAGUUUUACA | UGUAAAACUCAAAUGGGCUUC | | [1054-1074](21/21) 3'UTR |
| 132 | GGCUUUUCUGGGAAUUGAAGU | ACUUCAAUUCCCAGAAAAGCC | | [1726-1746](21/21) 3'UTR |
| 133 | CCAAAUGUAGUCUCUUUUCUU | AAGAAAAGAGACUACAUUUGG | | [891-911](21/21) 3'UTR |
| 134 | AGCUGUAUACUACCACUUUGA | UCAAAGUGGUAGUAUACAGCU | | [1779-1799](21/21) 3'UTR |
| 135 | UAACCAUGCAUGCACCCAGAU | AUCUGGGUGCAUGCAUGGUUA | | [1890-1910](21/21) 3'UTR |
| 136 | CUGGGAUUAUGUUGUUCCUGA | UCAGGAACAACAUAAUCCCAG | Chimp | [305-325](21/21) ORF |
| 137 | GGGCAUCGAUGUAGAACUGUU | AACAGUUCUACAUCGAUGCCC | | [2422-2442](21/21) 3'UTR |
| 138 | CUGAGAAACUGACCCAGAAA | UUCUCUGGGUCAGUUUCUCAG | Chin, GP, Chimp, Rat, Ms | [445-465](21/21) ORF |
| 139 | GGUGUUGUUUAGAUGCCUUU | AAAGGCAUCUAAAACAACACC | | [1450-1470](21/21) 3'UTR |
| 140 | CUGGCAGUUUGAGCAGCAAGA | UCUUGCUGCUCAAACUGCCAG | Chimp | [214-234](21/21) ORF |
| 141 | CAUUUCACCAUGGCAGUGUUA | UAACACUGCCAUGGUGAAAUG | | [1694-1714](21/21) 3'UTR |
| 142 | UUCCAUUGAGUGAAUGAUGAA | UUCAUCAUUCACUCAAUGGAA | | [1570-1590](21/21) 3'UTR |
| 143 | GGUUGUGUUAUGCACGUGAAC | GUUCACGUGCAUAACACAACC | Ms | [516-536](21/21) ORF |
| 144 | CAGUAACCACGGUGUUGUUUU | AAAACAACACCGUGGUUACUG | | [1440-1460](21/21) 3'UTR |
| 145 | AGGAGAACUGCUCAUGGACUA | UAGUCCAUGAGCAGUUCUCCU | Dog, Chimp | [628-648](21/21) ORF |
| 146 | CCUGUUCUUAAGUGUUGAAUA | UAUUCAACACUUAAGAACAGG | | [1486-1506](21/21) 3'UTR |
| 147 | UCAUCCUGGUGUUACUGAAAA | UUUUCAGUAACACCAGGAUGA | | [2163-2183](21/21) 3'UTR |
| 148 | UGAAGGGUCCUAAAAGGGAA | UUCCCUUUUAGGACCCUUCA | | [773-793](21/21) ORF + 3'UTR |
| 149 | GCUAUGGAGAUAUGGUUUAUA | UAUAAACCAUAUCUCCAUAGC | | [1836-1856](21/21) 3'UTR |
| 150 | UUAGCCAGUUCUAACAAAC | GUUUGUUAGAACACUGGCUAA | | [2239-2259](21/21) 3'UTR |
| 151 | GGGUUUUUAGACAGGAAGGUA | UACCUUCCUGUCUAAAAACCC | | [1271-1291](21/21) 3'UTR |
| 152 | UGUCUAUUGUUAAGCUCCAAA | UUUGGAGCUUAACAAUAGACA | | [2341-2361](21/21) 3'UTR |

TABLE C-continued 21 mers

| Number | Sense siRNA | AntiSense siRNA | Other Sp | Hum-34222182 ORF: 204-785 |
|---|---|---|---|---|
| 153 | GAAUACCUGUGAGGAUAGGAA | UUCCUAUCCUCACAGGUAUUC | | [1588-1608](21/21) 3'UTR |
| 154 | CCUGUCACUAGGGAAUAAUAA | UUAUUAUUCCCUAGUGACAGG | | [1928-1948](21/21) 3'UTR |
| 155 | UAUUCAUCCUGGUGUUACUGA | UCAGUAACACCAGGAUGAAUA | | [2160-2180](21/21) 3'UTR |
| 156 | GGAAUCAACUUGCCAGAAUUU | AAAUUCUGGCAAGUUGAUUCC | Chimp | [353-373](21/21) ORF |
| 157 | UGUAAAAAGCUGGAUAGGAUU | AAUCCUAUCCAGCUUUUUACA | Chin, GP, Chimp, Rat | [555-575](21/21) ORF |
| 158 | UGGAUAGGAUUGUGUGUGAUU | AAUCACACACAAUCCUAUCCA | Chimp | [565-585](21/21) ORF |
| 159 | CUGUAUACUACCACUUUGAAU | AUUCAAAGUGGUAGUAUACAG | | [1781-1801](21/21) 3'UTR |
| 160 | GGAUAGGAAAUUAGUUCUGAG | CUCAGAACUAAUUUCCUAUCC | | [1600-1620](21/21) 3'UTR |
| 161 | AAACUAAACUUGGUUGCUCAA | UUGAGCAACCAAGUUUAGUUU | Chimp | [412-432](21/21) ORF |
| 162 | CAGAUUUUUCCACCUUGGAU | AUCCAAGGUGGAAAAAUCUG | | [1906-1926](21/21) 3'UTR |
| 163 | AAGGUAGGAUUAAGUAGGUGA | UCACCUACUUAAUCCUACCUU | | [1286-1306](21/21) 3'UTR |
| 164 | AGAACUGUCUGUCCAAAUCAA | UUGAUUUGGACAGACAGUUCU | Dog, Chimp | [388-408](21/21) ORF |
| 165 | CAUAGAUCCCAUUUUUGUACA | UGUACAAAAAUGGGAUCUAUG | | [999-1019](21/21) 3'UTR |
| 166 | GAUUCUAGCGUCGUACCUACU | AGUAGGUACGACGCUAGAAUC | | [582-602](21/21) ORF |
| 167 | CCAGAGAGCCUGCUAAGUGAU | AUCACUUAGCAGGCUCUCUGG | Chimp | [276-296](21/21) ORF |
| 168 | CACUUAGUAAUCUAUCCUCUU | AAGAGGAUAGAUUACUAAGUG | | [1640-1660](21/21) 3'UTR |
| 169 | ACUUCCUCACUCUAAUGUUUU | AAAACAUUAGAGUGAGGAAGU | | [1388-1408](21/21) 3'UTR |
| 170 | CCUGAGAAACUGACCCAGAGA | UCUCUGGGUCAGUUUCUCAGG | Chin, GP, Chimp, Rat, Ms | [444-464](21/21) ORF |
| 171 | AGGUUGUGUUAUGCACGUGAA | UUCACGUGCAUAACACAACCU | | [515-535](21/21) ORF |
| 172 | GCCUUUGGAGAAGUGAUUCAA | UUGAAUCACUUCUCCAAAGGC | | [960-980](21/21) 3'UTR |
| 173 | GAGAACUGUCUGUCCAAAUCA | UGAUUUGGACAGACAGUUCUC | Dog, Chimp | [387-407](21/21) ORF |
| 174 | AACUCUUCAAAUGCUGGAAA | UUUCCAAGCAUUUGAAGAGUU | | [2262-2282](21/21) 3'UTR |
| 175 | CAACGAGGUAAUAUUUGAGGA | UCCUCAAAUAUUACCUCGUUG | Chimp | [335-355](21/21) ORF |
| 176 | GGAAUAGGUAAGCAAAAGUAG | CUACUUUUGCUUACCUAUUCC | | [1034-1054](21/21) 3'UTR |
| 177 | GUGUAGAUUUUCUGCAUAGAU | AUCUAUGCAGAAAAUCUACAC | | [985-1005](21/21) 3'UTR |
| 178 | CACUCAACAAUGUUCAAUUCA | UGAAUUGAACAUUGUUGAGUG | | [2029-2049](21/21) 3'UTR |
| 179 | UCAACAAUGUUCAAUUCAGCA | UGCUGAAUUGAACAUUGUUGA | | [2032-2052](21/21) 3'UTR |
| 180 | GAAUUGGGCCAAGAUAAAUCA | UGAUUUAUCUUGGCCCAAUUC | | [2307-2327](21/21) 3'UTR |
| 181 | CUGUUAUGCUUACAAAAUGGU | ACCAUUUUGUAAGCAUAACAG | | [2481-2501](21/21) 3'UTR |
| 182 | GUCUGUCCAAAUCAAAGCAAA | UUUGCUUUGAUUUGGACAGAC | Dog, Chimp | [394-414](21/21) ORF |
| 183 | GGAAUUGAAGUAUCUCUCCUU | AAGGAGAGAUACUUCAAUUCC | | [1736-1756](21/21) 3'UTR |
| 184 | GAAGUCUGCAUUGGCUAUGGA | UCCAUAGCCAAUGCAGACUUC | | [1823-1843](21/21) 3'UTR |
| 185 | CUCUCUGAUUCACUUAGUAAU | AUUACUAAGUGAAUCAGAGAG | | [1630-1650](21/21) 3'UTR |
| 186 | AGUCCCUCUCUGAUUCACUUA | UAAGUGAAUCAGAGAGGGACU | | [1625-1645](21/21) 3'UTR |
| 187 | GGGUCCUAAAAGGGAAAAUA | UAUUUUCCCUUUUAGGACCC | | [777-797](21/21) ORF + 3'UTR |
| 188 | CAACCUCAACGAGGUAAUAUU | AAUAUUACCUCGUUGAGGUUG | Chimp | [329-349](21/21) ORF |
| 189 | CUAUUCAGCUAGUCAGCUAAA | UUUAGCUGACUAGCUGAAUAG | | [830-850](21/21) 3'UTR |
| 190 | GAUUGGAACAACAGUGAUUGA | UCAAUCACUGUUGUUCCAAUC | | [755-775](21/21) ORF |

TABLE C-continued 21 mers

| Number | Sense siRNA | AntiSense siRNA | Other Sp | Hum-34222182 ORF: 204-785 |
|---|---|---|---|---|
| 191 | AGAUCUAGUCCCUCUCUGAUU | AAUCAGAGAGGGACUAGAUCU | | [1619-1639](21/21) 3'UTR |
| 192 | UUACGAAGUCUGCAUUGGCUA | UAGCCAAUGCAGACUUCGUAA | | [1819-1839](21/21) 3'UTR |
| 193 | GCUUUUCUGGGAAUUGAAGUA | UACUUCAAUUCCCAGAAAAGC | | [1727-1747](21/21) 3'UTR |
| 194 | GAAGGGUUUUUAGACAGGAAG | CUUCCUGUCUAAAAACCCUUC | | [1268-1288](21/21) 3'UTR |
| 195 | GGCUUCUUGGGCAUCGAUGUA | UACAUCGAUGCCCAAGAAGCC | | [2414-2434](21/21) 3'UTR |
| 196 | UGGUUGCAACUGGCAGUUUGA | UCAAACUGCCAGUUGCAACCA | Chimp | [205-225](21/21) ORF |
| 197 | ACCAGAUUUGCCUAUUUUGAU | AUCAAAAUAGGCAAAUCUGGU | | [1124-1144](21/21) 3'UTR |
| 198 | UGUUAUGCACGUGAACUUGGA | UCCAAGUUCACGUGCAUAACA | Dog, Chin, GP, Rat, Ms | [521-541](21/21) ORF |
| 199 | UGGUGACUUCCUCACUCUAAU | AUUAGAGUGAGGAAGUCACCA | | [1383-1403](21/21) 3'UTR |
| 200 | CAUGCACCCAGAUUUUUUCCA | UGGAAAAAUCUGGGUGCAUG | | [1898-1918](21/21) 3'UTR |
| 201 | UGGCUUAUGGAAGGCUGUUAA | UUAACAGCCUUCCAUAAGCCA | | [2504-2524](21/21) 3'UTR |
| 202 | UGUUCCUGAACCCAACCUCAA | UUGAGGUUGGGUUCAGGAACA | Chimp | [317-337](21/21) ORF |
| 203 | GACAGGAAGGUAGGAUUAAGU | ACUUAAUCCUACCUUCCUGUC | | [1280-1300](21/21) 3'UTR |
| 204 | CUUAACCCUAGGUAAGAGUAA | UUACUCUUACCUAGGGUUAAG | | [1319-1339](21/21) 3'UTR |
| 205 | CUUUACUCACUGAUUGGAACA | UGUUCCAAUCAGUGAGUAAAG | | [744-764](21/21) ORF |
| 206 | ACCACCAGUUCCUGACUCAAA | UUUGAGUCAGGAACUGGUGGU | | [1244-1264](21/21) 3'UTR |
| 207 | GGGCCAAGAUAAAUCAAUGUU | AACAUUGAUUUAUCUUGGCCC | | [2312-2332](21/21) 3'UTR |
| 208 | UGAAACGGGUCAAUUUACGAA | UUCGUAAAUUGACCCGUUUCA | | [1805-1825](21/21) 3'UTR |
| 209 | CAAGGCUUCUUGGGCAUCGAU | AUCGAUGCCCAAGAAGCCUUG | | [2411-2431](21/21) 3'UTR |
| 210 | CACCACCAGUUCCUGACUCAA | UUGAGUCAGGAACUGGUGGUG | | [1243-1263](21/21) 3'UTR |
| 211 | UGAGGAAUCAACUUGCCAGAA | UUCUGGCAAGUUGAUUCCUCA | Chimp | [350-370](21/21) ORF |
| 212 | AAUUCAGCAAGGCUUUCAUAU | AUAUGAAAGCCUUGCUGAAUU | | [2044-2064](21/21) 3'UTR |
| 213 | CUUUAUAGAAUUGGGCCAAGA | UCUUGGCCCAAUUCUAUAAAG | | [2300-2320](21/21) 3'UTR |
| 214 | UGACCAUGGUUGCAACUGGCA | UGCCAGUUGCAACCAUGGUCA | Chimp | [199-219](21/21) 5'UTR + ORF |
| 215 | UGAUUUCUGGCCUUUGGAGA | UCUCCAAAGGCCAGAAAAUCA | | [950-970](21/21) 3'UTR |
| 216 | UAGGGAAUAAUAAAGGCCUUA | UAAGGCCUUUAUUAUUCCCUA | | [1936-1956](21/21) 3'UTR |
| 217 | CCUCAACGAGGUAAUAUUUGA | UCAAAUAUUACCUCGUUGAGG | Chimp | [332-352](21/21) ORF |
| 218 | GGGAAUAAUAAAGGCCUUAUU | AAUAAGGCCUUUAUUAUUCCC | | [1938-1958](21/21) 3'UTR |
| 219 | GUAGGCUUGGUAAUAGACUAU | AUAGUCUAUUACCAAGCCUAC | | [1099-1119](21/21) 3'UTR |
| 220 | UGUCUGUCCAAAUCAAAGCAA | UUGCUUUGAUUUGGACAGACA | Dog, Chimp | [393-413](21/21) ORF |
| 221 | CUUGUGGUGCCAUUUCAGUAA | UUACUGAAAUGGCACCACAAG | | [1425-1445](21/21) 3'UTR |
| 222 | CCCAUUUUUGUACAGAAUUGA | UCAAUUCUGUACAAAAAUGGG | | [1006-1026](21/21) 3'UTR |
| 223 | GGUAGUAAAACUAUUCAGCUA | UAGCUGAAUAGUUUUACUACC | | [820-840](21/21) 3'UTR |
| 224 | UUAUGCACGUGAACUUGGAAA | UUUCCAAGUUCACGUGCAUAA | Dog, Chin, GP, Rat | [523-543](21/21) ORF |
| 225 | UUGGUGACUUCCUCACUCUAA | UUAGAGUGAGGAAGUCACCAA | | [1382-1402](21/21) 3'UTR |
| 226 | UUGAAUGGGAUGGAAUAGGUA | UACCUAUUCCAUCCCAUUCAA | | [1023-1043](21/21) 3'UTR |
| 227 | UGGAAUAGGUAAGCAAAAGUA | UACUUUUGCUUACCUAUUCCA | | [1033-1053](21/21) 3'UTR |
| 228 | AAUGCUUGGAAAGAUACUACA | UGUAGUAUCUUUCCAAGCAUU | | [2271-2291](21/21) 3'UTR |

TABLE C-continued 21 mers

| Number | Sense siRNA | AntiSense siRNA | Other Sp | Hum-34222182 ORF: 204-785 |
|---|---|---|---|---|
| 229 | UUGUCAAGGGUAGUAGCUGUA | UACAGCUACUACCCUUGACAA | | [1765-1785](21/21) 3'UTR |
| 230 | GCUUCUCCUCUGGUUUCAGGA | UCCUGAAACCAGAGGAGAAGC | | [679-699](21/21) ORF |
| 231 | GGACUAGCUUCAGGGACUUUU | AAAAGUCCCUGAAGCUAGUCC | Chimp | [643-663](21/21) ORF |
| 232 | GGUUUUUAGACAGGAAGGUAG | CUACCUUCCUGUCUAAAAACC | | [1272-1292](21/21) 3'UTR |
| 233 | CAACUUGCCAGAAUUUGGUUA | UAACCAAAUUCUGGCAAGUUG | Chimp | [358-378](21/21) ORF |
| 234 | UUCUUGGGCAUCGAUGUAGAA | UUCUACAUCGAUGCCCAAGAA | | [2417-2437](21/21) 3'UTR |
| 235 | UAACCACGGUGUUGUUUUAGA | UCUAAAACAACACCGUGGUUA | | [1443-1463](21/21) 3'UTR |
| 236 | UGGUUUCAGGUAGGCUUGGUA | UACCAAGCCUACCUGAAACCA | | [1090-1110](21/21) 3'UTR |
| 237 | CUAGCUAUUAGCUCCACUUCA | UGAAGUGGAGCUAAUAGCUAG | | [2110-2130](21/21) 3'UTR |
| 238 | ACUGAUACUAUAAGUGACCUA | UAGGUCACUUAUAGUAUCAGU | | [2201-2221](21/21) 3'UTR |
| 239 | CUUGCCAGAAUUUGGUUAAAA | UUUUAACCAAAUUCUGGCAAG | Chimp | [361-381](21/21) ORF |
| 240 | CCCACCUGCCCUAAAUAAGAA | UUCUUAUUUAGGGCAGGUGGG | | [867-887](21/21) 3'UTR |
| 241 | CAGGAAGGUAGGAUUAAGUAG | CUACUUAAUCCUACCUUCCUG | | [1282-1302](21/21) 3'UTR |
| 242 | CGGCUUGCGAGGUUGUGUUAU | AUAACACAACCUCGCAAGCCG | Chimp | [506-526](21/21) ORF |
| 243 | AAUACCUGUGAGGAUAGGAAA | UUUCCUAUCCUCACAGGUAUU | | [1589-1609](21/21) 3'UTR |
| 244 | GAUAGGAUUGUGUGUGAUUCU | AGAAUCACACACAAUCCUAUC | Chimp | [567-587](21/21) ORF |
| 245 | GACUCAAAUUUGAAGGGUUUU | AAAACCCUUCAAAUUUGAGUC | | [1257-1277](21/21) 3'UTR |
| 246 | CUUGCCUGUUAUGCUUACAAA | UUUGUAAGCAUAACAGGCAAG | | [2476-2496](21/21) 3'UTR |
| 247 | CAGCUAGUCAGCUAAAGUCAU | AUGACUUUAGCUGACUAGCUG | | [835-855](21/21) 3'UTR |
| 248 | GUACCUACUUUUGAGCUUACA | UGUAAGCUCAAAAGUAGGUAC | | [594-614](21/21) ORF |
| 249 | UCAGGAGAACUCUGAUCCUCA | UGAGGAUCAGAGUUCUCCUGA | | [694-714](21/21) ORF |
| 250 | GAGGUAAUAUUUGAGGAAUCA | UGAUUCCUCAAAUAUUACCUC | Chimp | [339-359](21/21) ORF |
| 251 | CGAGGUAAUAUUUGAGGAAUC | GAUUCCUCAAAUAUUACCUCG | Chimp | [338-358](21/21) ORF |
| 252 | CAAUAAUGGAACUGCUUCACU | AGUGAAGCAGUUCCAUUAUUG | | [1356-1376](21/21) 3'UTR |
| 253 | AAAGGUCCUUGUCCCUGAGAA | UUCUCAGGGACAAGGACCUUU | Chimp | [431-451](21/21) ORF |
| 254 | UAGCGUCGUACCUACUUUUGA | UCAAAAGUAGGUACGACGCUA | | [587-607](21/21) ORF |
| 255 | CCAGAUUUGCCUAUUUUGAUU | AAUCAAAAUAGGCAAAUCUGG | | [1125-1145](21/21) 3'UTR |
| 256 | CAGGUUUCCUGCCCUAGCUAU | AUAGCUAGGGCAGGAAACCUG | | [2097-2117](21/21) 3'UTR |
| 257 | GUUUAUAGUACAGCCUAGAGA | UCUCUAGGCUGUACUAUAAAC | | [1850-1870](21/21) 3'UTR |
| 258 | GACAGAUGUAUUCAUCCUGGU | ACCAGGAUGAAUACAUCUGUC | | [2152-2172](21/21) 3'UTR |
| 259 | GUGUUCUAACAAACUAAACUC | GAGUUUAGUUUGUUAGAACAC | | [2246-2266](21/21) 3'UTR |
| 260 | GGAAGGUAGGAUUAAGUAGGU | ACCACUUAAUCCUACCUUCC | | [1284-1304](21/21) 3'UTR |
| 261 | AACGAGGUAAUAUUUGAGGAA | UUCCUCAAAUAUUACCUCGUU | Chimp | [336-356](21/21) ORF |
| 262 | UAGUACAGCCUAGAGAAUGAA | UUCAUUCUCUAGGCUGUACUA | | [1855-1875](21/21) 3'UTR |
| 263 | AGCUCAGGAUUUCGACUUGUU | AACAAGUCGAAAUCCUGAGCU | | [714-734](21/21) ORF |
| 264 | CAGGUAGGCUUGGUAAUAGAC | GUCUAUUACCAAGCCUACCUG | | [1096-1116](21/21) 3'UTR |
| 265 | AAGGGUCCUAAAAAGGGAAAA | UUUUCCCUUUUUAGGACCCUU | | [775-795](21/21) ORF + 3'UTR |
| 266 | AGAUCCCAUUUUUGUACAGAA | UUCUGUACAAAAAUGGGAUCU | | [1002-1022](21/21) 3'UTR |

TABLE C-continued

21 mers

| Number | Sense siRNA | AntiSense siRNA | Other Sp | Hum-34222182 ORF: 204-785 |
|---|---|---|---|---|
| 267 | GCUUAAUCUCAGAUGAACCAU | AUGGUUCAUCUGAGAUUAAGC | | [1676-1696](21/21) 3'UTR |
| 268 | GGAUACCUGUCACUAGGGAAU | AUUCCCUAGUGACAGGUAUCC | | [1923-1943](21/21) 3'UTR |
| 269 | CACCAGUUCCUGACUCAAAUU | AAUUUGAGUCAGGAACUGGUG | | [1246-1266](21/21) 3'UTR |
| 270 | CUUCCAUUGAGUGAAUGAUGA | UCAUCAUUCACUCAAUGGAAG | | [1569-1589](21/21) 3'UTR |
| 271 | CUUUGAAUUAUUGAAACGGGU | ACCCGUUUCAAUAAUUCAAAG | | [1794-1814](21/21) 3'UTR |
| 272 | GCCUGCUAAGUGAUUUUGACU | AGUCAAAAUCACUUAGCAGGC | Chimp | [283-303](21/21) ORF |
| 273 | CAAAUUAGCCAGUGUUCUAAC | GUUAGAACACUGGCUAAUUUG | | [2235-2255](21/21) 3'UTR |
| 274 | CUUUGACUCUCUUGCCUGUUA | UAACAGGCAAGAGAGUCAAAG | | [2466-2486](21/21) 3'UTR |
| 275 | CAGGUGUGAUCCUGUUACUGA | UCAGUAACAGGAUCACACCUG | | [2185-2205](21/21) 3'UTR |
| 276 | AACUUUACUCACUGAUUGGAA | UUCCAAUCAGUGAGUAAAGUU | | [742-762](21/21) ORF |
| 277 | UCCUUGUCCCUGAGAAACUGA | UCAGUUUCUCAGGGACAAGGA | Dog, Chimp | [436-456](21/21) ORF |
| 278 | AAAUGGUGAUGGCUUAUGGA | UCCAUAAGCCAUCACCAUUUU | | [2494-2514](21/21) 3'UTR |
| 279 | AAAUUAGCCAGUGUUCUAACA | UGUUAGAACACUGGCUAAUUU | | [2236-2256](21/21) 3'UTR |
| 280 | GAAUGGGAUGGAAUAGGUAAG | CUUACCUAUUCCAUCCCAUUC | | [1025-1045](21/21) 3'UTR |
| 281 | GCUUAUGGAAGGCUGUUAAAU | AUUUAACAGCCUUCCAUAAGC | | [2506-2526](21/21) 3'UTR |
| 282 | AAGGGUAGUAGCUGUAUACUA | UAGUAUACAGCUACUACCCUU | | [1770-1790](21/21) 3'UTR |
| 283 | UGAAACUCACCGUCCAGAUAA | UUAUCUGGACGGUGAGUUUCA | | [1872-1892](21/21) 3'UTR |
| 284 | CUAGCUUCAGGGACUUUUUCU | AGAAAAAGUCCCUGAAGCUAG | Chimp | [646-666](21/21) ORF |
| 285 | UACUCACUGAUUGGAACAACA | UGUUGUUCCAAUCAGUGAGUA | | [747-767](21/21) ORF |
| 286 | AAGUGAUUUUGACUACUGGGA | UCCCAGUAGUCAAAAUCACUU | Chimp | [290-310](21/21) ORF |
| 287 | GGCAAUAAUGGAACUGCUUCA | UGAAGCAGUUCCAUUAUUGCC | | [1354-1374](21/21) 3'UTR |
| 288 | GGGUAGUAAAACUAUUCAGCU | AGCUGAAUAGUUUUACUACCC | | [819-839](21/21) 3'UTR |
| 289 | CUGCAUAGAUCCCAUUUUUGU | ACAAAAAUGGGAUCUAUGCAG | | [996-1016](21/21) 3'UTR |
| 290 | GUUUUAAAGAGGCAACAAAAG | CUUUUGUUGCCUCUUUAAAAC | | [1404-1424](21/21) 3'UTR |
| 291 | GAACCCAACCUCAACGAGGUA | UACCUCGUUGAGGUUGGGUUC | Chimp | [324-344](21/21) ORF |
| 292 | AGCUAUUAGCUCCACUUCACA | UGUGAAGUGGAGCUAAUAGCU | | [2112-2132](21/21) 3'UTR |
| 293 | CUUUCUGUGUUUCACAUUCAU | AUGAAUGUGAAACACAGAAAG | | [909-929](21/21) 3'UTR |
| 294 | CAGAAUUGCUGGACUGUGGCU | AGCCACAGUCCAGCAAUUCUG | Chimp | [250-270](21/21) ORF |
| 295 | CAAACUAAACUUGGUUGCUCA | UGAGCAACCAAGUUUAGUUUG | Chimp | [411-431](21/21) ORF |
| 296 | CUUCUUGGGCAUCGAUGUAGA | UCUACAUCGAUGCCCAAGAAG | | [2416-2436](21/21) 3'UTR |
| 297 | GUCAAGGGUAGUAGCUGUAUA | UAUACAGCUACUACCCUUGAC | | [1767-1787](21/21) 3'UTR |
| 298 | UCAGGUUUCCUGCCCUAGCUA | UAGCUAGGGCAGGAAACCUGA | | [2096-2116](21/21) 3'UTR |
| 299 | CGAUGUAGAACUGUUGUCCUU | AAGGACAACAGUUCUACAUCG | | [2428-2448](21/21) 3'UTR |
| 300 | UGGGCAUCGAUGUAGAACUGU | ACAGUUCUACAUCGAUGCCCA | | [2421-2441](21/21) 3'UTR |
| 301 | GGUAGUAGCUGUAUACUACCA | UGGUAGUAUACAGCUACUACC | | [1773-1793](21/21) 3'UTR |
| 302 | CUCUUUUCUUCUGUGUUUCA | UGAAACACAGAAGAAAAGAG | | [902-922](21/21) 3'UTR |
| 303 | CUGGAGAACUGUCUGUCCAAA | UUUGGACAGACAGUUCUCCAG | Dog, Chimp | [384-404](21/21) ORF |
| 304 | UUGUCACCACUGACUGGGCAA | UUGCCCAGUCAGUGGUGACAA | | [2393-2413](21/21) 3'UTR |

TABLE C-continued 21 mers

| Number | Sense siRNA | AntiSense siRNA | Other Sp | Hum-34222182 ORF: 204-785 |
|---|---|---|---|---|
| 305 | CCAAAUCAAAGCAAACUAAAC | GUUUAGUUUGCUUUGAUUUGG | Chimp | [400-420](21/21) ORF |
| 306 | GCUUGGAAAGAUACUACAAAG | CUUUGUAGUAUCUUUCCAAGC | | [2274-2294](21/21) 3'UTR |
| 307 | GGCAGUGUUAUCUCAUCUCUG | CAGAGAUGAGAUAACACUGCC | | [1705-1725](21/21) 3'UTR |
| 308 | ACAGAAUUGAAUGGGAUGGAA | UUCCAUCCCAUUCAAUUCUGU | | [1017-1037](21/21) 3'UTR |
| 309 | CACUGAUUGGAACAACAGUGA | UCACUGUUGUUCCAAUCAGUG | | [751-771](21/21) ORF |
| 310 | GCUUAACCCUAGGUAAGAGUA | UACUCUUACCUAGGGUUAAGC | | [1318-1338](21/21) 3'UTR |
| 311 | UCUUGCCUGUUAUGCUUACAA | UUGUAAGCAUAACAGGCAAGA | | [2475-2495](21/21) 3'UTR |
| 312 | CACUAACAGUUAUCUUUGACU | AGUCAAAGAUAACUGUUAGUG | | [2453-2473](21/21) 3'UTR |
| 313 | GAGAGCCUGCUAAGUGAUUUU | AAAAUCACUUAGCAGGCUCUC | Chimp | [279-299](21/21) ORF |
| 314 | ACACCACCAGUUCCUGACUCA | UGAGUCAGGAACUGGUGGUGU | | [1242-1262](21/21) 3'UTR |
| 315 | GAUUAUUUCAUGAUUGGGUAG | CUACCCAAUCAUGAAAUAAUC | | [804-824](21/21) 3'UTR |
| 316 | AUGCUUGGAAAGAUACUACAA | UUGUAGUAUCUUUCCAAGCAU | | [2272-2292](21/21) 3'UTR |
| 317 | UGCAUAGAUCCCAUUUUUGUA | UACAAAAUGGGAUCUAUGCA | | [997-1017](21/21) 3'UTR |
| 318 | UAGGCUUGGUAAUAGACUAUA | UAUAGUCUAUUACCAAGCCUA | | [1100-1120](21/21) 3'UTR |
| 319 | UGAUUUGACUACUGGGAUUA | UAAUCCCAGUAGUCAAAAUCA | Dog, Chimp | [293-313](21/21) ORF |
| 320 | UGGUUUUAUAGUACAGCCUAGA | UCUAGGCUGUACUAUAAACCA | | [1848-1868](21/21) 3'UTR |
| 321 | CUGCAUUGGCUAUGGAGAUAU | AUAUCUCCAUAGCCAAUGCAG | | [1828-1848](21/21) 3'UTR |
| 322 | UUAUAGAAUUGGGCCAAGAUA | UAUCUUGGCCCAAUUCUAUAA | | [2302-2322](21/21) 3'UTR |
| 323 | GAUACUACAAAGCCAAUCUUU | AAAGAUUGGCUUUGUAGUAUC | | [2283-2303](21/21) 3'UTR |
| 324 | CAGCAAGGCUUUCAUAUCCUU | AAGGAUAUGAAAGCCUUGCUG | | [2048-2068](21/21) 3'UTR |
| 325 | GAAUUGCUGGACUGUGGCUAU | AUAGCCACAGUCCAGCAAUUC | Chimp | [252-272](21/21) ORF |
| 326 | CAGGAUUUCGACUUGUUAAGA | UCUUAACAAGUCGAAAUCCUG | | [718-738](21/21) ORF |
| 327 | GGUCCUUGUCCCUGAGAAACU | AGUUUCUCAGGGACAAGGACC | Chimp | [434-454](21/21) ORF |
| 328 | UGGUGUUACUGAAAAACAGGU | ACCUGUUUUUCAGUAACACCA | | [2169-2189](21/21) 3'UTR |
| 329 | AGUGAAUGAUGAAUACCUGUG | CACAGGUAUUCAUCAUUCACU | | [1578-1598](21/21) 3'UTR |
| 330 | CAGUUAUCUUUGACUCUCUUG | CAAGAGAGUCAAAGAUAACUG | | [2459-2479](21/21) 3'UTR |
| 331 | ACGGCAAUAAUGGAACUGCUU | AAGCAGUUCCAUUAUUGCCGU | | [1352-1372](21/21) 3'UTR |
| 332 | AUUUGAGGAAUCAACUUGCCA | UGGCAAGUUGAUUCCUCAAAU | Chimp | [347-367](21/21) ORF |
| 333 | CCAACCUCAACGAGGUAAUAU | AUAUUACCUCGUUGAGGUUGG | Chimp | [328-348](21/21) ORF |
| 334 | CCCUGUUCUUAAGUGUUGAAU | AUUCAACACUUAAGAACAGGG | | [1485-1505](21/21) 3'UTR |
| 335 | GAACCAUUUCACCAUGGCAGU | ACUGCCAUGGUGAAAUGGUUC | | [1690-1710](21/21) 3'UTR |
| 336 | CAGCCUAGAGAAUGAAACUCA | UGAGUUUCAUUCUCUAGGCUG | | [1860-1880](21/21) 3'UTR |
| 337 | AGCCUAUCAAAACUUCCAAAA | UUUUGGAAGUUUUGAUAGGCU | | [1217-1237](21/21) 3'UTR |
| 338 | CUUGCGAGGUUGUGUUAUGCA | UGCAUAACACAACCUCGCAAG | Chimp | [509-529](21/21) ORF |
| 339 | UAGAAGCCCAUUUGAGUUUUA | UAAAACUCAAAUGGGCUUCUA | | [1052-1072](21/21) 3'UTR |
| 340 | ACCUGUCACUAGGGAAUAUAU | AUAUAUUCCCUAGUGACAGGU | | [1927-1947](21/21) 3'UTR |
| 341 | AGUCAGCUAAAGUCAUUUGUA | UACAAAUGACUUUAGCUGACU | | [840-860](21/21) 3'UTR |
| 342 | CAGUAUUACAUGUGCUUAAUC | GAUUAAGCACAUGUAAUACUG | | [1663-1683](21/21) 3'UTR |

TABLE C-continued

21 mers

| Number | Sense siRNA | AntiSense siRNA | Other Sp | Hum-34222182 ORF: 204-785 |
|---|---|---|---|---|
| 343 | CACCCAGAUUUUUCCACCUU | AAGGUGGAAAAAAUCUGGGUG | | [1902-1922](21/21) 3'UTR |
| 344 | CUUACAAAAUGGUGAUGGCUU | AAGCCAUCACCAUUUUGUAAG | | [2489-2509](21/21) 3'UTR |
| 345 | UUUGGUUAAAAUGCUGGAGAA | UUCUCCAGCAUUUUAACCAAA | Chimp | [371-391](21/21) ORF |
| 346 | GAUUACUCUUCCAUUGAGUGA | UCACUCAAUGGAAGAGUAAUC | | [1562-1582](21/21) 3'UTR |
| 347 | CAUGUCUAUUGUUAAGCUCCA | UGGAGCUUAACAAUAGACAUG | | [2339-2359](21/21) 3'UTR |
| 348 | GCGUAGGGACAGAUGUAUUCA | UGAAUACAUCUGUCCCUACGC | | [2145-2165](21/21) 3'UTR |
| 349 | AGCCGUUGACCAUGGUUGCAA | UUGCAACCAUGGUCAACGGCU | Chimp, Rat, Ms | [193-213](21/21) 5'UTR + ORF |
| 350 | UUACAUGUGCUUAAUCUCAGA | UCUGAGAUUAAGCACAUGUAA | | [1668-1688](21/21) 3'UTR |
| 351 | AUCUCUGGGCUUUUCUGGGAA | UUCCCAGAAAAGCCCAGAGAU | | [1719-1739](21/21) 3'UTR |
| 352 | CCUUGUCCCUGAGAAACUGAC | GUCAGUUUCUCAGGGACAAGG | Dog, Chimp | [437-457](21/21) ORF |
| 353 | UAGAAUUGGGCCAAGAUAAAU | AUUUAUCUUGGCCCAAUUCUA | | [2305-2325](21/21) 3'UTR |
| 354 | AGGGACUUUUUCUUUAGUAGA | UCUACUAAAGAAAAAGUCCCU | | [654-674](21/21) ORF |
| 355 | UUGAGUGAAUGAUGAAUACCU | AGGUAUUCAUCAUUCACUCAA | | [1575-1595](21/21) 3'UTR |
| 356 | GCAUCGAUGUAGAACUGUUGU | ACAACAGUUCUACAUCGAUGC | | [2424-2444](21/21) 3'UTR |
| 357 | UUGAAACGGGUCAAUUUACGA | UCGUAAAUUGACCCGUUUCAA | | [1804-1824](21/21) 3'UTR |
| 358 | AAGUCUGCAUUGGCUAUGGAG | CUCCAUAGCCAAUGCAGACUU | | [1824-1844](21/21) 3'UTR |
| 359 | AUGUCUAUUGUUAAGCUCCAA | UUGGAGCUUAACAAUAGACAU | | [2340-2360](21/21) 3'UTR |
| 360 | AUUGGGCCAAGAUAAAUCAAU | AUUGAUUUAUCUUGGCCCAAU | | [2309-2329](21/21) 3'UTR |
| 361 | UGCUUAAUCUCAGAUGAACCA | UGGUUCAUCUGAGAUUAAGCA | | [1675-1695](21/21) 3'UTR |
| 362 | CAGCUAAAGUCAUUUGUAGUU | AACUACAAAUGACUUUAGCUG | | [843-863](21/21) 3'UTR |
| 363 | GAGAAUUGCUCAAGAUGUCCU | AGGACAUCUUGAGCAAUUCUC | Chimp, Ms | [461-481](21/21) ORF |
| 364 | GGCUAUGGAGAUAUGGUUUAU | AUAAACCAUAUCUCCAUAGCC | | [1835-1855](21/21) 3'UTR |
| 365 | GCCCUAGCUAUUAGCUCCACU | AGUGGAGCUAAUAGCUAGGGC | | [2107-2127](21/21) 3'UTR |
| 366 | CAGCAUUUCAGAAUUGCUGGA | UCCAGCAAUUCUGAAAUGCUG | Chimp | [242-262](21/21) ORF |
| 367 | CCUACUUUUGAGCUUACACUU | AAGUGUAAGCUCAAAAGUAGG | Chimp | [597-617](21/21) ORF |
| 368 | CCAGAGAAUUGCUCAAGAUGU | ACAUCUUGAGCAAUUCUCUGG | Chimp, Ms | [458-478](21/21) ORF |
| 369 | AGGUAGGCUUGGUAAUAGACU | AGUCUAUUACCAAGCCUACCU | | [1097-1117](21/21) 3'UTR |
| 370 | GAUUUUGACUACUGGGAUUAU | AUAAUCCCAGUAGUCAAAAUC | Chimp | [294-314](21/21) ORF |
| 371 | AUGAUGAAUACCUGUGAGGAU | AUCCUCACAGGUAUUCAUCAU | | [1583-1603](21/21) 3'UTR |
| 372 | GCUCCAAAGGUUCACUGUGUU | AACACAGUGAACCUUUGGAGC | | [2354-2374](21/21) 3'UTR |
| 373 | UGAUCCUGUUACUGAUACUAU | AUAGUAUCAGUAACAGGAUCA | | [2191-2211](21/21) 3'UTR |
| 374 | GUCAAUUUACGAAGUCUGCAU | AUGCAGACUUCGUAAAUUGAC | | [1813-1833](21/21) 3'UTR |
| 375 | GGAAACAGAGCCGUUGACCAU | AUGGUCAACGGCUCUGUUUCC | Dog, Chimp, Rat, Ms | [185-205](21/21) 5'UTR + ORF |
| 376 | GAAAACAGGUGUGAUCCUGU | ACAGGAUCACACCUGUUUUC | | [2179-2199](21/21) 3'UTR |
| 377 | UCAGGGACUUUUUCUUUAGUA | UACUAAAGAAAAAGUCCCUGA | | [652-672](21/21) ORF |
| 378 | UCAUGAUUGGGUAGUAAACU | AGUUUACUACCCAAUCAUGA | | [811-831](21/21) 3'UTR |
| 379 | CAUGGACUAGCUUCAGGGACU | AGUCCCUGAAGCUAGUCCAUG | Chimp | [640-660](21/21) ORF |
| 380 | GCGAGGUUGUGUUAUGCACGU | ACGUGCAUAACACAACCUCGC | | [512-532](21/21) ORF |

TABLE C-continued

21 mers

| Number | Sense siRNA | AntiSense siRNA | Other Sp | Hum-34222182 ORF: 204-785 |
|---|---|---|---|---|
| 381 | AACCCAACCUCAACGAGGUAA | UUACCUCGUUGAGGUUGGGUU | Chimp | [325-345](21/21) ORF |
| 382 | GAGAUAUGGUUUAUAGUACAG | CUGUACUAUAAACCAUAUCUC | | [1842-1862](21/21) 3'UTR |
| 383 | AGGUGUGAUCCUGUUACUGAU | AUCAGUAACAGGAUCACACCU | | [2186-2206](21/21) 3'UTR |
| 384 | GAGAAACUGACCCAGAGAAUU | AAUUCUCUGGGUCAGUUUCUC | Chin, GP, Chimp, Rat, Ms | [447-467](21/21) ORF |
| 385 | AGAUUUUCUGCAUAGAUCCCA | UGGGAUCUAUGCAGAAAAUCU | | [989-1009](21/21) 3'UTR |
| 386 | AGGAAUCAACUUGCCAGAAUU | AAUUCUGGCAAGUUGAUUCCU | Chimp | [352-372](21/21) ORF |
| 387 | CCAUGCAUGCACCCAGAUUUU | AAAAUCGGGUGCAUGCAUGG | | [1893-1913](21/21) 3'UTR |
| 388 | ACUGUUGUCCUUUUUCCACUA | UAGUGGAAAAAGGACAACAGU | | [2437-2457](21/21) 3'UTR |
| 389 | UAACCCUAGGUAAGAGUAAAU | AUUUACUCUUACCUAGGGUUA | | [1321-1341](21/21) 3'UTR |
| 390 | AUUCAUCCUGGUGUUACUGAA | UUCAGUAACACCAGGAUGAAU | | [2161-2181](21/21) 3'UTR |
| 391 | AGGGAAUAAUAAAGGCCUUAU | AUAAGGCCUUUAUUAUUCCCU | | [1937-1957](21/21) 3'UTR |
| 392 | UUGUUAAGCUCCAAAGGUUCA | UGAACCUUUGGAGCUUAACAA | | [2347-2367](21/21) 3'UTR |
| 393 | CUGGUUUCAGGAGAACUCUGA | UCAGAGUUCUCCUGAAACCAG | | [688-708](21/21) ORF |
| 394 | UGGAAAGAUACUACAAAGCCA | UGGCUUUGUAGUAUCUUUCCA | | [2277-2297](21/21) 3'UTR |
| 395 | CUCUGAUCCUCAGCUCAGGAU | AUCCUGAGCUGAGGAUCAGAG | | [703-723](21/21) ORF |
| 396 | CAACUGGCAGUUUGAGCAGCA | UGCUGCUCAAACUGCCAGUUG | Chimp | [211-231](21/21) ORF |
| 397 | UAAGCAAAAGUAGAAGCCCAU | AUGGGCUUCUACUUUUGCUUA | | [1042-1062](21/21) 3'UTR |
| 398 | GAUUUUCUGCAUAGAUCCCAU | AUGGGAUCUAUGCAGAAAAUC | | [990-1010](21/21) 3'UTR |
| 399 | GAGUUUUACAUUUGAUUCCAC | GUGGAAUCAAAUGUAAAACUC | | [1065-1085](21/21) 3'UTR |
| 400 | CUGCCCUAGCUAUUAGCUCCA | UGGAGCUAAUAGCUAGGGCAG | | [2105-2125](21/21) 3'UTR |
| 401 | UCCACUAACAGUUAUCUUUGA | UCAAAGAUAACUGUUAGUGGA | | [2451-2471](21/21) 3'UTR |
| 402 | AGGCUUGGUAAUAGACUAUAU | AUAUAGUCUAUUACCAAGCCU | | [1101-1121](21/21) 3'UTR |
| 403 | AAAGCUUGUGGUGCCAUUUCA | UGAAAUGGCACCACAAGCUUU | | [1421-1441](21/21) 3'UTR |
| 404 | UAGCCUAUCAAAACUUCCAAA | UUUGGAAGUUUUGAUAGGCUA | | [1216-1236](21/21) 3'UTR |
| 405 | GUCUUAUUCCAACUAAGUAGA | UCUACUUAGUUGGAAUAAGAC | | [1963-1983](21/21) 3'UTR |
| 406 | UCAGCUAAAGUCAUUUGUAGU | ACUACAAAUGACUUUAGCUGA | | [842-862](21/21) 3'UTR |
| 407 | CAACUGCAGCUAACAGGCUGA | UCAGCCUGUUAGCUGCAGUUG | | [932-952](21/21) 3'UTR |
| 408 | CGUCGUACCUACUUUUGAGCU | AGCUCAAAAGUAGGUACGACG | | [590-610](21/21) ORF |
| 409 | CAACAGUGAUUGAAGGGUCCU | AGGACCCUUCAAUCACUGUUG | | [763-783](21/21) ORF |
| 410 | GGAACUGCUUCACUGUUUCUU | AAGAAACAGUGAAGCAGUUCC | | [1363-1383](21/21) 3'UTR |
| 411 | CCCAGAUUUUUUCCACCUUGG | CCAAGGUGGAAAAAAUCUGGG | | [1904-1924](21/21) 3'UTR |
| 412 | CUUAAUCUCAGAUGAACCAUU | AAUGGUUCAUCUGAGAUUAAG | | [1677-1697](21/21) 3'UTR |
| 413 | AAAACAGGUGUGAUCCUGUUA | UAACAGGAUCACACCUGUUUU | | [2181-2201](21/21) 3'UTR |
| 414 | UGAGAUCUAGUCCCUCUCUGA | UCAGAGAGGGACUAGAUCUCA | | [1617-1637](21/21) 3'UTR |
| 415 | CAAAGCAAACUAAACUUGGUU | AACCAAGUUUAGUUUGCUUUG | Chimp | [406-426](21/21) ORF |
| 416 | UGGCAGUUUGAGCAGCAAGAA | UUCUUGCUGCUCAAACUGCCA | Chimp | [215-235](21/21) ORF |
| 417 | UGUUUCUGGUGACUUCCUCA | UGAGGAAGUCACCAAGAAACA | | [1376-1396](21/21) 3'UTR |
| 418 | UUCAAAUUAGCCAGUGUUCUA | UAGAACACUGGCUAAUUUGAA | | [2233-2253](21/21) 3'UTR |

TABLE C-continued 21 mers

| Number | Sense siRNA | AntiSense siRNA | Other Sp | Hum-34222182 ORF: 204-785 |
|---|---|---|---|---|
| 419 | ACUGCUUCACUGUUUCUUGGU | ACCAAGAAACAGUGAAGCAGU | | [1366-1386](21/21) 3'UTR |
| 420 | GACCCAGAGAAUUGCUCAAGA | UCUUGAGCAAUUCUCUGGGUC | Chimp, Ms | [455-475](21/21) ORF |
| 421 | GAAUUGAAGUAUCUCUCCUUA | UAAGGAGAGAUACUUCAAUUC | | [1737-1757](21/21) 3'UTR |
| 422 | AUCUAGUCCCUCUCUGAUUCA | UGAAUCAGAGAGGGACUAGAU | | [1621-1641](21/21) 3'UTR |
| 423 | UCAAAUGCUUGGAAAGAUACU | AGUAUCUUUCCAAGCAUUUGA | | [2268-2288](21/21) 3'UTR |
| 424 | CAAUUGUCAAGGGUAGUAGCU | AGCUACUACCCUUGACAAUUG | | [1762-1782](21/21) 3'UTR |
| 425 | CUGACUCAAAUUUGAAGGGUU | AACCCUUCAAAUUUGAGUCAG | | [1255-1275](21/21) 3'UTR |
| 426 | UUACAAAAUGGUGAUGGCUUA | UAAGCCAUCACCAUUUUGUAA | | [2490-2510](21/21) 3'UTR |
| 427 | UCUCUGGGCUUUUCGGGAAU | AUUCCCAGAAAAGCCCAGAGA | | [1720-1740](21/21) 3'UTR |
| 428 | CAAAAGCCCACACCACCAGUU | AACUGGUGGUGUGGGCUUUUG | | [1233-1253](21/21) 3'UTR |
| 429 | UAGGAUUGUGUGUGAUUCUAG | CUAGAAUCACACACAAUCCUA | Chimp | [569-589](21/21) ORF |
| 430 | CAAAUGCUUGGAAAGAUACUA | UAGUAUCUUUCCAAGCAUUUG | | [2269-2289](21/21) 3'UTR |
| 431 | CCUGUUACUGAUACUAUAAGU | ACUUAUAGUAUCAGUAACAGG | | [2195-2215](21/21) 3'UTR |
| 432 | GCACCCAGAUUUUUUCCACCU | AGGUGGAAAAAUCUGGGUGC | | [1901-1921](21/21) 3'UTR |
| 433 | CUCUAAUGUUUAAAGAGGCA | UGCCUCUUUAAAACAUUAGAG | | [1397-1417](21/21) 3'UTR |
| 434 | CAGUUCCUGACUCAAAUUUGA | UCAAAUUUGAGUCAGGAACUG | | [1249-1269](21/21) 3'UTR |
| 435 | GUCUCUUUUCUUCUGUGUUU | AAACACAGAAAGAAAAGAGAC | | [900-920](21/21) 3'UTR |
| 436 | UAGUGUAGAUUUUCUGCAUAG | CUAUGCAGAAAAUCUACACUA | | [983-1003](21/21) 3'UTR |
| 437 | GGUAGGAUUAAGUAGGUGAGU | ACUCACCUACUUAAUCCUACC | | [1288-1308](21/21) 3'UTR |
| 438 | GUGAUUCUAGCGUCGUACCUA | UAGGUACGACGCUAGAAUCAC | | [580-600](21/21) ORF |
| 439 | GGUUAAAAUGCUGGAGAACUG | CAGUUCUCCAGCAUUUUAACC | Chimp | [374-394](21/21) ORF |
| 440 | CUCAGAUGAACCAUUUCACCA | UGGUGAAAUGGUUCAUCUGAG | | [1683-1703](21/21) 3'UTR |
| 441 | UGAGAAACUGACCCAGAGAAU | AUUCUCUGGGUCAGUUUCUCA | Chin, GP, Chimp, Rat, Ms | [446-466](21/21) ORF |
| 442 | ACUUGGUUGCUCAAAGGUCCU | AGGACCUUUGAGCAACCAAGU | Chimp | [419-439](21/21) ORF |
| 443 | UAGGAUUAAGUAGGUGAGUUU | AAACUCACCUACUUAAUCCUA | | [1290-1310](21/21) 3'UTR |
| 444 | AGGAUUAAGUAGGUGAGUUUA | UAAACUCACCUACUUAAUCCU | | [1291-1311](21/21) 3'UTR |
| 445 | UCCUUUUUCCACUAACAGUUA | UAACUGUUAGUGGAAAAAGGA | | [2444-2464](21/21) 3'UTR |
| 446 | GAAGCCACCUGCUGUGUUUA | UAAACACAGCAGGUGGCUUC | | [94-114](21/21) 5'UTR |
| 447 | GCUUCUUGGGCAUCGAUGUAG | CUACAUCGAUGCCCAAGAAGC | | [2415-2435](21/21) 3'UTR |
| 448 | CUGUCUGUCCAAAUCAAAGCA | UGCUUUGAUUUGGACAGACAG | Dog, Chimp | [392-412](21/21) ORF |
| 449 | CUGGAUAGGAUUGUGUGUGAU | AUCACACACAAUCCUAUCCAG | Chin, GP, Chimp, Rat | [564-584](21/21) ORF |
| 450 | CUGGGCUUUUCGGGAAUUGA | UCAAUUCCCAGAAAAGCCCAG | | [1723-1743](21/21) 3'UTR |
| 451 | CUAACAGUUAUCUUUGACUCU | AGAGUCAAAGAUAACUGUUAG | | [2455-2475](21/21) 3'UTR |
| 452 | AUGUAAAAGCUGGAUAGGAU | AUCCUAUCCAGCUUUUUACAU | Chimp, Ms | [554-574](21/21) ORF |
| 453 | UCUCCUCUGGUUUCAGGAGAA | UUCUCCUGAAACCAGAGGAGA | | [682-702](21/21) ORF |
| 454 | GAUUUUUCCACCUUGGAUAC | GUAUCCAAGGUGGAAAAAUC | | [1908-1928](21/21) 3'UTR |
| 455 | AACUCACCGUCCAGAUAACCA | UGGUUAUCUGGACGGUGAGUU | | [1875-1895](21/21) 3'UTR |
| 456 | AGUGAUUUUGACUACUGGGAU | AUCCCAGUAGUCAAAAUCACU | Chimp | [291-311](21/21) ORF |

TABLE C-continued 21 mers

| Number | Sense siRNA | AntiSense siRNA | Other Sp | Hum-34222182 ORF: 204-785 |
|---|---|---|---|---|
| 457 | AUGGAAUAGGUAAGCAAAAGU | ACUUUUGCUUACCUAUUCCAU | | [1032-1052](21/21) 3'UTR |
| 458 | GAUGGAAUAGGUAAGCAAAAG | CUUUUGCUUACCUAUUCCAUC | | [1031-1051](21/21) 3'UTR |
| 459 | GGUUUAUAGUACAGCCUAGAG | CUCUAGGCUGUACUAUAAACC | | [1849-1869](21/21) 3'UTR |
| 460 | GAUUGUGUGUGAUUCUAGCGU | ACGCUAGAAUCACACACAAUC | | [572-592](21/21) ORF |
| 461 | CGGCAAUAAUGGAACUGCUUC | GAAGCAGUUCCAUUAUUGCCG | | [1353-1373](21/21) 3'UTR |
| 462 | CUCCAAAGGUUCACUGUGUUU | AAACACAGUGAACCUUUGGAG | | [2355-2375](21/21) 3'UTR |
| 463 | AGAAGCCACCUGCCUGUGUUU | AAACACAGGCAGGUGGCUUCU | | [93-113](21/21) 5'UTR |
| 464 | UGUCAAGGGUAGUAGCUGUAU | AUACAGCUACUACCCUUGACA | | [1766-1786](21/21) 3'UTR |
| 465 | CAUUGAGUGAAUGAUGAAUAC | GUAUUCAUCAUUCACUCAAUG | | [1573-1593](21/21) 3'UTR |
| 466 | AGGUUUCCUGCCCUAGCUAUU | AAUAGCUAGGGCAGGAAACCU | | [2098-2118](21/21) 3'UTR |
| 467 | UCCUGAACCCAACCUCAACGA | UCGUUGAGGUUGGGUUCAGGA | Chimp | [320-340](21/21) ORF |
| 468 | AGUAGAAGCCCAUUUGAGUUU | AAACUCAAAUGGGCUUCUACU | | [1050-1070](21/21) 3'UTR |
| 469 | GCCUCCACUCAACAAUGUUCA | UGAACAUUGUUGAGUGGAGGC | | [2024-2044](21/21) 3'UTR |
| 470 | GUUAAAAUGCUGGAGAACUGU | ACAGUUCUCCAGCAUUUUAAC | Chimp | [375-395](21/21) ORF |
| 471 | AUACCUGUGAGGAUAGGAAAU | AUUUCCUAUCCUCACAGGUAU | | [1590-1610](21/21) 3'UTR |
| 472 | UGUACAGAAUUGAAUGGGAUG | CAUCCCAUUCAAUUCUGUACA | | [1014-1034](21/21) 3'UTR |
| 473 | CAGUGUUAUCUCAUCUCUGGG | CCCAGAGAUGAGAUAACACUG | | [1707-1727](21/21) 3'UTR |
| 474 | UGGACUAGCUUCAGGGACUUU | AAAGUCCCUGAAGCUAGUCCA | Chimp | [642-662](21/21) ORF |
| 475 | UGUGAGGAUAGGAAAUUAGUU | AACUAAUUUCCUAUCCUCACA | | [1595-1615](21/21) 3'UTR |
| 476 | GAGGCAACAAAAGCUUGUGGU | ACCACAAGCUUUUGUUGCCUC | | [1412-1432](21/21) 3'UTR |
| 477 | UCUGGCCUUUGGAGAAGUGAU | AUCACUUCUCCAAAGGCCAGA | | [956-976](21/21) 3'UTR |
| 478 | CAUCUCUGGGCUUUUCUGGGA | UCCCAGAAAAGCCCAGAGAUG | | [1718-1738](21/21) 3'UTR |
| 479 | GAGAAUGAAACUCACCGUCCA | UGGACGGUGAGUUUCAUUCUC | | [1867-1887](21/21) 3'UTR |
| 480 | UUUAUAGUACAGCCUAGAGAA | UUCUCUAGGCUGUACUAUAAA | | [1851-1871](21/21) 3'UTR |
| 481 | AGAACUGUUGUCCUUUUUCCA | UGGAAAAAGGACAACAGUUCU | | [2434-2454](21/21) 3'UTR |
| 482 | AACUAAACUGGUUGCUCAAA | UUUGAGCAACCAAGUUUAGUU | Chimp | [413-433](21/21) ORF |
| 483 | GUGACUUCCUCACUCUAAUGU | ACAUUAGAGUGAGGAAGUCAC | | [1385-1405](21/21) 3'UTR |
| 484 | ACAAAAGCUUGUGGUGCCAUU | AAUGGCACCACAAGCUUUUGU | | [1418-1438](21/21) 3'UTR |
| 485 | CUGACCCAGAGAAUUGCUCAA | UUGAGCAAUUCUCUGGGUCAG | Chimp, Ms | [453-473](21/21) ORF |
| 486 | UCAGGAUUUCGACUUGUUAAG | CUUAACAAGUCGAAAUCCUGA | | [717-737](21/21) ORF |
| 487 | ACUCUUCCAUUGAGUGAAUGA | UCAUUCACUCAAUGGAAGAGU | | [1566-1586](21/21) 3'UTR |
| 488 | GCUAAAGUCAUUUGUAGUUUG | CAAACUACAAAUGACUUUAGC | | [845-865](21/21) 3'UTR |
| 489 | CAUUGGCUAUGGAGAUAUGGU | ACCAUAUCUCCAUAGCCAAUG | | [1831-1851](21/21) 3'UTR |
| 490 | GAACUGCUCAUGGACUAGCUU | AAGCUAGUCCAUGAGCAGUUC | Dog, Chimp | [632-652](21/21) ORF |
| 491 | CUUGGUUGCUCAAAGGUCCUU | AAGGACCUUUGAGCAACCAAG | Chimp | [420-440](21/21) ORF |
| 492 | GAUACCUGUCACUAGGGAAUA | UAUUCCCUAGUGACAGGUAUC | | [1924-1944](21/21) 3'UTR |
| 493 | AAGGUCCUUGUCCCUGAGAAA | UUUCUCAGGGACAAGGACCUU | Chimp | [432-452](21/21) ORF |
| 494 | GGCAGUUUGAGCAGCAAGAAC | GUUCUUGCUGCUCAAACUGCC | Chimp | [216-236](21/21) ORF |

TABLE C-continued

21 mers

| Number | Sense siRNA | AntiSense siRNA | Other Sp | Hum-34222182 ORF: 204-785 |
|---|---|---|---|---|
| 495 | CUGGCCUUUGGAGAAGUGAUU | AAUCACUUCUCCAAAGGCCAG | | [957-977](21/21) 3'UTR |
| 496 | AUUGGAACAACAGUGAUUGAA | UUCAAUCACUGUUGUUCCAAU | | [756-776](21/21) ORF |
| 497 | GAUGUAUUCAUCCUGGUGUUA | UAACACCAGGAUGAAUACAUC | | [2156-2176](21/21) 3'UTR |
| 498 | CCGUUGACCAUGGUUGCAACU | AGUUGCAACCAUGGUCAACGG | Chimp | [195-215](21/21) 5'UTR + ORF |
| 499 | CUAUAUAAACCAGAUUUGCCU | AGGCAAAUCUGGUUUAUAUAG | | [1116-1136](21/21) 3'UTR |
| 500 | GAUGUAGAACUGUUGUCCUUU | AAAGGACAACAGUUCUACAUC | | [2429-2449](21/21) 3'UTR |

TABLE D

23 mers

| Number | Sense siRNA | AntiSense siRNA | Other Sp | Hum-34222182 ORF: 204-785 |
|---|---|---|---|---|
| 1 | GAGUUUUACAUUUGAUUCCACAA | UUGUGGAAUCAAAUGUAAAACUC | | [1065-1087](23/23) 3'UTR |
| 2 | GGUAAUAGACUAUAUAAACCAGA | UCUGGUUUAUAUAGUCUAUUACC | | [1107-1129](23/23) 3'UTR |
| 3 | GGGAAUUGAAGUAUCUCUCCUUA | UAAGGAGAGAUACUUCAAUUCCC | | [1735-1757](23/23) 3'UTR |
| 4 | GAAAAUGUAUGUAAAAGCUGGA | UCCAGCUUUUUACAUACAUUUUC | Chimp, Ms | [546-568](23/23) ORF |
| 5 | CAGAGGAUUUUUAAAUCACAGA | UCUGUGAUUUAAAAAUCCUCUG | | [1175-1197](23/23) 3'UTR |
| 6 | GGCUGUUAAAUUAAUAUUCCUGU | ACAGGAAUAUUAAUUUAACAGCC | | [2516-2538](23/23) 3'UTR |
| 7 | GCCUUAUUUUUGUCUUAUUCCA | UGGAAUAAGACAAAAAUAAGGC | | [1951-1973](23/23) 3'UTR |
| 8 | CAAAUUUGAAGGGUUUUUAGACA | UGUCUAAAAACCCUUCAAAUUUG | | [1261-1283](23/23) 3'UTR |
| 9 | CUAAGUGAUUUGACUACUGGGA | UCCCAGUAGUCAAAUCACUUAG | Chimp | [288-310](23/23) ORF |
| 10 | CUAUCACCCAGAGAGCCUGCUAA | UUAGCAGGCUCUCUGGGUGAUAG | Chimp | [269-291](23/23) ORF |
| 11 | AGAUGUCCUGCGGCUUUCCUCAA | UUGAGGAAAGCCGCAGGACAUCU | Chimp | [473-495](23/23) ORF |
| 12 | AACUAUUCAGCUAGUCAGCUAAA | UUUAGCUGACUAGCUGAAUAGUU | | [828-850](23/23) 3'UTR |
| 13 | GUUGUUUUGCAUGUCUAUUGUUA | UAACAAUAGACAUGCAAAACAAC | | [2330-2352](23/23) 3'UTR |
| 14 | UGAGUUUUACAUUUGAUUCCACA | UGUGGAAUCAAAUGUAAAACUCA | | [1064-1086](23/23) 3'UTR |
| 15 | GGUAGUAAAACUAUUCAGCUAGU | ACUAGCUGAAUAGUUUUACUACC | | [820-842](23/23) 3'UTR |
| 16 | AGUAUUACAUGUGCUUAAUCUCA | UGAGAUUAAGCACAUGUAAUACU | | [1664-1686](23/23) 3'UTR |
| 17 | CUGUUAUGCUUACAAAAUGGUGA | UCACCAUUUUGUAAGCAUAACAG | | [2481-2503](23/23) 3'UTR |
| 18 | UCUCUUGCCUGUUAUGCUUACAA | UUGUAAGCAUAACAGGCAAGAGA | | [2473-2495](23/23) 3'UTR |
| 19 | CCAUUUCACCAUGGCAGUGUUAU | AUAACACUGCCAUGGUGAAAUGG | | [1693-1715](23/23) 3'UTR |
| 20 | UGAUCCUCAGCUCAGGAUUUCGA | UCGAAAUCCUGAGCUGAGGAUCA | | [706-728](23/23) ORF |
| 21 | CAAAAUAGUGUAGAUUUUCUGCA | UGCAGAAAAUCUACACUAUUUUG | | [978-1000](23/23) 3'UTR |
| 22 | GGUUAAAAUGCUGGAGAACUGUC | GACAGUUCUCCAGCAUUUUAACC | Chimp | [374-396](23/23) ORF |
| 23 | CUGAUAUUUUGUGUGUAGUUGA | UCAACUACACACAAAAAUAUCAG | | [1541-1563](23/23) 3'UTR |
| 24 | GUAGGUGAGUUUAAUUAAAGCUU | AAGCUUUAAUUAAACUCACCUAC | | [1299-1321](23/23) 3'UTR |
| 25 | ACAAACUAAACUCUUCAAAUGCU | AGCAUUUGAAGAGUUUAGUUUGU | | [2254-2276](23/23) 3'UTR |
| 26 | CCUACUUUUGAGCUUACACUUGU | ACAAGUGUAAGCUCAAAAGUAGG | Chimp | [597-619](23/23) ORF |
| 27 | GCCCAUUUGAGUUUUACAUUUGA | UCAAAUGUAAAACUCAAAUGGGC | | [1057-1079](23/23) 3'UTR |

TABLE D-continued

| | | 23 mers | | |
|---|---|---|---|---|
| Number | Sense siRNA | AntiSense siRNA | Other Sp | Hum-34222182 ORF: 204-785 |
| 28 | GAUUACUCUUCCAUUGAGUGAAU | AUUCACUCAAUGGAAGAGUAAUC | | [1562-1584](23/23) 3'UTR |
| 29 | UGUUAUGCUUACAAAAUGGUGAU | AUCACCAUUUUGUAAGCAUAACA | | [2482-2504](23/23) 3'UTR |
| 30 | AGUUGUCACCACUGACUGGGCAA | UUGCCCAGUCAGUGGUGACAACU | | [2391-2413](23/23) 3'UTR |
| 31 | CUCAAAUUUGAAGGGUUUUUAGA | UCUAAAACCCUUCAAAUUUGAG | | [1259-1281](23/23) 3'UTR |
| 32 | GCUUCUCCUCUGGUUUCAGGAGA | UCUCCUGAAACCAGAGGAGAAGC | | [679-701](23/23) ORF |
| 33 | GCAACUGCAGCUAACAGGCUGAU | AUCAGCCUGUUAGCUGCAGUUGC | | [931-953](23/23) 3'UTR |
| 34 | GACAGAUGUAUUCAUCCUGGUGU | ACACCAGGAUGAAUACAUCUGUC | | [2152-2174](23/23) 3'UTR |
| 35 | GAACUGCUCAUGGACUAGCUUCA | UGAAGCUAGUCCAUGAGCAGUUC | Dog, Chimp | [632-654](23/23) ORF |
| 36 | UAUUUAGCCUAUCAAACUUCCA | UGGAAGUUUUGAUAGGCUAAAUA | | [1212-1234](23/23) 3'UTR |
| 37 | CCCAUUUGAGUUUUACAUUUGAU | AUCAAAUGUAAAACUCAAAUGGG | | [1058-1080](23/23) 3'UTR |
| 38 | CUAAGAAGCCACCUGCCUGUGUU | AACACAGGCAGGUGGCUUCUUAG | | [90-112](23/23) 5'UTR |
| 39 | CUAUCAAAACUUCCAAAAGCCCA | UGGGCUUUUGGAAGUUUUGAUAG | | [1220-1242](23/23) 3'UTR |
| 40 | UGAUUACUCUUCCAUUGAGUGAA | UUCACUCAAUGGAAGAGUAAUCA | | [1561-1583](23/23) 3'UTR |
| 41 | UAAUUAAAGCUUACCCUAGGUA | UACCUAGGGUUAAGCUUUAAUUA | | [1310-1332](23/23) 3'UTR |
| 42 | CCCUAGCUAUUAGCUCCACUUCA | UGAAGUGGAGCUAAUAGCUAGGG | | [2108-2130](23/23) 3'UTR |
| 43 | GGGACAGAUGUAUUCAUCCUGGU | ACCAGGAUGAAUACAUCUGUCCC | | [2150-2172](23/23) 3'UTR |
| 44 | UGAACCCAACCUCAACGAGGUAA | UUACCUCGUUGAGGUUGGGUUCA | Chimp | [323-345](23/23) ORF |
| 45 | AGGUAAGCAAAAGUAGAAGCCCA | UGGGCUUCUACUUUUGCUUACCU | | [1039-1061](23/23) 3'UTR |
| 46 | ACAAUUUGGUUUCAGGUAGGCUU | AAGCCUACCUGAAACCAAAUUGU | | [1084-1106](23/23) 3'UTR |
| 47 | GACUCUCUUGCCUGUUAUGCUUA | UAAGCAUAACAGGCAAGAGAGUC | | [2470-2492](23/23) 3'UTR |
| 48 | GUCUCUUUUCUUUCUGUGUUUCA | UGAAACACAGAAAGAAAAGAGAC | | [900-922](23/23) 3'UTR |
| 49 | CUCUGAUCCUCAGCUCAGGAUUU | AAAUCCUGAGCUGAGGAUCAGAG | | [703-725](23/23) ORF |
| 50 | GUUUAAGCAGGAGAACUGCUCAU | AUGAGCAGUUCUCCUGCUUAAAC | Dog, Chimp | [620-642](23/23) ORF |
| 51 | GGUAAGCAAAAGUAGAAGCCCAU | AUGGGCUUCUACUUUUGCUUACC | | [1040-1062](23/23) 3'UTR |
| 52 | GAACUCUGAUCCUCAGCUCAGGA | UCCUGAGCUGAGGAUCAGAGUUC | | [700-722](23/23) ORF |
| 53 | UCUGUGUUUCACAUUCAUAGCAA | UUGCUAUGAAUGUGAAACACAGA | | [912-934](23/23) 3'UTR |
| 54 | UGUUUUGCAUGUCUAUUGUUAAG | CUUAACAAUAGACAUGCAAAACA | | [2332-2354](23/23) 3'UTR |
| 55 | UGAAAAACAGGUGUGAUCCUGUU | AACAGGAUCACACCUGUUUUUCA | | [2178-2200](23/23) 3'UTR |
| 56 | CCUAUUUUGAUUUCAUAUGGCU | AGCCAUAUGAAAAUCAAAAUAGG | | [1134-1156](23/23) 3'UTR |
| 57 | CACUGUUCAAAUUAGCCAGUGUU | AACACUGGCUAAUUUGAACAGUG | | [2228-2250](23/23) 3'UTR |
| 58 | CAAAUGUAGUCUCUUUUCUUUCU | AGAAAGAAAAGAGACUACAUUUG | | [892-914](23/23) 3'UTR |
| 59 | CAGAUAACCAUGCAUGCACCCAG | CUGGGUGCAUGCAUGGUUAUCUG | | [1886-1908](23/23) 3'UTR |
| 60 | GUUGAAUACUGUCUUUAAACUAG | CUAGUUUAAAGACAGUAUUCAAC | | [1499-1521](23/23) 3'UTR |
| 61 | GCAACAAAGCUUGUGGUGCCAU | AUGGCACCACAAGCUUUUGUUGC | | [1415-1437](23/23) 3'UTR |
| 62 | GAUAUGGUUUAUAGUACAGCCUA | UAGGCUGUACUAUAAACCAUAUC | | [1844-1866](23/23) 3'UTR |
| 63 | GACUAUAUAAACCAGAUUUGCCU | AGGCAAAUCUGGUUUAUAUAGUC | | [1114-1136](23/23) 3'UTR |
| 64 | CUUAUUCCAACUAAGUAGAUCAU | AUGAUCUACUUAGUUGGAAUAAG | | [1965-1987](23/23) 3'UTR |

TABLE D-continued 23 mers

| Number | Sense siRNA | AntiSense siRNA | Other Sp | Hum-34222182 ORF: 204-785 |
|---|---|---|---|---|
| 65 | GUAUUACAUGUGCUUAAUCUCAG | CUGAGAUUAAGCACAUGUAAUAC | | [1665-1687](23/23) 3'UTR |
| 66 | AGUAAAACUAUUCAGCUAGUCAG | CUGACUAGCUGAAUAGUUUUACU | | [823-845](23/23) 3'UTR |
| 67 | CUCUCUUGCCUGUUAUGCUUACA | UGUAAGCAUAACAGGCAAGAGAG | | [2472-2494](23/23) 3'UTR |
| 68 | AGAUUAUUUCAUGAUUGGGUAGU | ACUACCCAAUCAUGAAAUAAUCU | | [803-825](23/23) 3'UTR |
| 69 | GUUAAAAUGCUGGAGAACUGUCU | AGACAGUUCUCCAGCAUUUUAAC | Chimp | [375-397](23/23) ORF |
| 70 | AAACUAUUCAGCUAGUCAGCUAA | UUAGCUGACUAGCUGAAUAGUUU | | [827-849](23/23) 3'UTR |
| 71 | GAAAAACAGGUGUGAUCCUGUUA | UAACAGGAUCACACCUGUUUUUC | | [2179-2201](23/23) 3'UTR |
| 72 | GCUUCACUGUUUCUUGGUGACUU | AAGUCACCAAGAAACAGUGAAGC | | [1369-1391](23/23) 3'UTR |
| 73 | AGAACCCGGCCAGCAUUUCAGAA | UUCUGAAAUGCUGGCCGGGUUCU | Chimp | [232-254](23/23) ORF |
| 74 | UAGCCUCCACUCAACAAUGUUCA | UGAACAUUGUUGAGUGGAGGCUA | | [2022-2044](23/23) 3'UTR |
| 75 | UGAACUGAUAUUUUGUGUGUAG | CUACACACAAAAAUAUCAGUUCA | | [1537-1559](23/23) 3'UTR |
| 76 | AGUAAUCUAUCCUCUUUUCAGUA | UACUGAAAAGAGGAUAGAUUACU | | [1645-1667](23/23) 3'UTR |
| 77 | GGUGAGUUUAAUUAAAGCUUAAC | GUUAAGCUUUAAUUAAACUCACC | | [1302-1324](23/23) 3'UTR |
| 78 | UGUUCAAUUCAGCAAGGCUUUCA | UGAAAGCCUUGCUGAAUUGAACA | | [2039-2061](23/23) 3'UTR |
| 79 | GUAAUCUAUCCUCUUUUCAGUAU | AUACUGAAAAGAGGAUAGAUUAC | | [1646-1668](23/23) 3'UTR |
| 80 | UCUUUCUGUGUUUCACAUUCAUA | UAUGAAUGUGAAACACAGAAAGA | | [908-930](23/23) 3'UTR |
| 81 | AGUAGGUGAGUUUAAUUAAAGCU | AGCUUUAAUUAAACUCACCUACU | | [1298-1320](23/23) 3'UTR |
| 82 | GAAAUUAGUUCUGAGAUCUAGUC | GACUAGAUCUCAGAACUAAUUUC | | [1606-1628](23/23) 3'UTR |
| 83 | UCACUAGGGAAUAAUAAGGCCU | AGGCCUUAUUAUUCCCUAGUGA | | [1932-1954](23/23) 3'UTR |
| 84 | AAACUCACCGUCCAGAUAACCAU | AUGGUUAUCUGGACGGUGAGUUU | | [1874-1896](23/23) 3'UTR |
| 85 | ACUGUUUCUUGGUGACUUCCUCA | UGAGGAAGUCACCAAGAAACAGU | | [1374-1396](23/23) 3'UTR |
| 86 | GUGUUAUCUCAUCUCUGGGCUUU | AAAGCCCAGAGAUGAGAUAACAC | | [1709-1731](23/23) 3'UTR |
| 87 | ACUAUAAGUGACCUAAAAUGUCA | UGACAUUUUAGGUCACUAUAGU | | [2207-2229](23/23) 3'UTR |
| 88 | UUAGCUCCACUUCACAUGCUGGA | UCCAGCAUGUGAAGUGGAGCUAA | | [2117-2139](23/23) 3'UTR |
| 89 | AAUGUCACUGUUCAAAUUAGCCA | UGGCUAAUUUGAACAGUGACAUU | | [2223-2245](23/23) 3'UTR |
| 90 | UGGGAAUUGAAGUAUCUCUCCUU | AAGGAGAGAUACUUCAAUUCCCA | | [1734-1756](23/23) 3'UTR |
| 91 | AAAACUAUUCAGCUAGUCAGCUA | UAGCUGACUAGCUGAAUAGUUUU | | [826-848](23/23) 3'UTR |
| 92 | CCACUCAACAAUGUUCAAUUCAG | CUGAAUUGAACAUUGUUGAGUGG | | [2028-2050](23/23) 3'UTR |
| 93 | CAUAUGGCUUUUUUUCUCUAAG | CUUAGAGAAAAAAAGCCAUAUG | | [1148-1170](23/23) 3'UTR |
| 94 | AAGCUUAACCCUAGGUAAGAGUA | UACUCUUACCUAGGGUUAAGCUU | | [1316-1338](23/23) 3'UTR |
| 95 | GAAUUGCUGGACUGUGGCUAUCA | UGAUAGCCACAGUCCAGCAAUUC | Chimp | [252-274](23/23) ORF |
| 96 | GCUAAGUGAUUUUGACUACUGGG | CCCAGUAGUCAAAAUCACUUAGC | Chimp | [287-309](23/23) ORF |
| 97 | AAACAGGUGUGAUCCUGUUACU | AGUAACAGGAUCACACCUGUUUU | | [2181-2203](23/23) 3'UTR |
| 98 | UGCUCAAGAUGUCCUGCGGCUUU | AAAGCCGCAGGACAUCUUGAGCA | Chimp | [467-489](23/23) ORF |
| 99 | GUGUUACUGAAAAACAGGUGUGA | UCACACCUGUUUUUCAGUAACAC | | [2171-2193](23/23) 3'UTR |
| 100 | AACUCUGAUCCUCAGCUCAGGAU | AUCCUGAGCUGAGGAUCAGAGUU | | [701-723](23/23) ORF |
| 101 | ACAGAUGUAUUCAUCCUGGUGUU | AACACCAGGAUGAAUACAUCUGU | | [2153-2175](23/23) 3'UTR |

TABLE D-continued 23 mers

| Number | Sense siRNA | AntiSense siRNA | Other Sp | Hum-34222182 ORF: 204-785 |
|---|---|---|---|---|
| 102 | UGUUUAAGCAGGAGAACUGCUCA | UGAGCAGUUCUCCUGCUUAAACA | Dog, Chimp | [619-641](23/23) ORF |
| 103 | ACUGCUUCACUGUUUCUUGGUGA | UCACCAAGAAACAGUGAAGCAGU | | [1366-1388](23/23) 3'UTR |
| 104 | AAGAAGCCACCUGCCUGUGUUUA | UAAACACAGGCAGGUGGCUUCUU | | [92-114](23/23) 5'UTR |
| 105 | CCACUUUGAAUUAUUGAAACGGG | CCCGUUUCAAUAAUUCAAAGUGG | | [1791-1813](23/23) 3'UTR |
| 106 | UCAAGAUGUCCUGCGGCUUUCCU | AGGAAAGCCGCAGGACAUCUUGA | Chimp | [470-492](23/23) ORF |
| 107 | GAGAUAUGGUUUAUAGUACAGCC | GGCUGUACUAUAAACCAUAUCUC | | [1842-1864](23/23) 3'UTR |
| 108 | UACACUUGUGUUUAAGCAGGAGA | UCUCCUGCUUAAACACAAGUGUA | Chimp | [611-633](23/23) ORF |
| 109 | GAUUCACUUAGUAAUCUAUCCUC | GAGGAUAGAUUACUAAGUGAAUC | | [1636-1658](23/23) 3'UTR |
| 110 | GGUGCCAUUUCAGUAACCACGGU | ACCGUGGUUACUGAAAUGGCACC | | [1430-1452](23/23) 3'UTR |
| 111 | AAUCAAUGUUGUUUGCAUGUCU | AGACAUGCAAAACAACAUUGAUU | | [2323-2345](23/23) 3'UTR |
| 112 | AAUAAUGGAACUGCUUCACUGUU | AACAGUGAAGCAGUUCCAUUAUU | | [1357-1379](23/23) 3'UTR |
| 113 | UAUCCUUGCUGUGGGUCGUGGAU | AUCCACGACCCACAGCAAGGAUA | | [2062-2084](23/23) 3'UTR |
| 114 | GAUUCCACAAUUUGGUUUCAGGU | ACCUGAAACCAAAUUGUGGAAUC | | [1078-1100](23/23) 3'UTR |
| 115 | UAGUAAAACUAUUCAGCUAGUCA | UGACUAGCUGAAUAGUUUUACUA | | [822-844](23/23) 3'UTR |
| 116 | ACAUUUGAUUCCACAAUUUGGUU | AACCAAAUUGUGGAAUCAAAUGU | | [1072-1094](23/23) 3'UTR |
| 117 | CAAGGCUUUCAUAUCCUUGCUGU | ACAGCAAGGAUAUGAAAGCCUUG | | [2051-2073](23/23) 3'UTR |
| 118 | GAAGUGAUUCAAAAUAGUGUAGA | UCUACACUAUUUUGAAUCACUUC | | [969-991](23/23) 3'UTR |
| 119 | UGUGUUUCACAUUCAUAGCAACU | AGUUGCUAUGAAUGUGAAACACA | | [914-936](23/23) 3'UTR |
| 120 | GUUUCACAUUCAUAGCAACUGCA | UGCAGUUGCUAUGAAUGUGAAAC | | [917-939](23/23) 3'UTR |
| 121 | CUCAUCUCUGGGCUUUUCUGGGA | UCCCAGAAAAGCCCAGAGAUGAG | | [1716-1738](23/23) 3'UTR |
| 122 | UCUUAUUCCAACUAAGUAGAUCA | UGAUCUACUUAGUUGGAAUAAGA | | [1964-1986](23/23) 3'UTR |
| 123 | GUUUAAUUAAAGCUUAACCCUAG | CUAGGGUUAAGCUUUAAUUAAAC | | [1307-1329](23/23) 3'UTR |
| 124 | ACAUUCAUAGCAACUGCAGCUAA | UUAGCUGCAGUUGCUAUGAAUGU | | [922-944](23/23) 3'UTR |
| 125 | UUGAUUACUCUUCCAUUGAGUGA | UCACUCAAUGGAAGAGUAAUCAA | | [1560-1582](23/23) 3'UTR |
| 126 | GCUUGCGAGGUUGUGUUAUGCAC | GUGCAUAACACAACCUCGCAAGC | | [508-530](23/23) ORF |
| 127 | AGAAGCCACCUGCCUGUGUUUAC | GUAAACACAGGCAGGUGGCUUCU | | [93-115](23/23) 5'UTR |
| 128 | AAUGUAGUCUCUUUUCUUUCUGU | ACAGAAAGAAAAGAGACUACAUU | | [894-916](23/23) 3'UTR |
| 129 | UAAGAAGCCACCUGCCUGUGUUU | AAACACAGGCAGGUGGCUUCUUA | | [91-113](23/23) 5'UTR |
| 130 | AGAACUGCUCAUGGACUAGCUUC | GAAGCUAGUCCAUGAGCAGUUCU | Dog, Chimp | [631-653](23/23) ORF |
| 131 | CUAUAUAAACCAGAUUUGCCUAU | AUAGGCAAAUCUGGUUUAUAUAG | | [1116-1138](23/23) 3'UTR |
| 132 | UGGUAAUAGACUAUAUAAACCAG | CUGGUUUAUAUAGUCUAUUACCA | | [1106-1128](23/23) 3'UTR |
| 133 | GCCAAGAUAAAUCAAUGUUGUUU | AAACAACAUUGAUUUAUCUUGGC | | [2314-2336](23/23) 3'UTR |
| 134 | UCAGAGGAUUUUUAAAAUCACAG | CUGUGAUUUUAAAAAUCCUCUGA | | [1174-1196](23/23) 3'UTR |
| 135 | GAUAUUUAGCCUAUCAAAACUUC | GAAGUUUUGAUAGGCUAAAUAUC | | [1210-1232](23/23) 3'UTR |
| 136 | GAGAACUCUGAUCCUCAGCUCAG | CUGAGCUGAGGAUCAGAGUUCUC | | [698-720](23/23) ORF |
| 137 | CACUGUUUCUUGGUGACUUCCUC | GAGGAAGUCACCAAGAAACAGUG | | [1373-1395](23/23) 3'UTR |
| 138 | AGUAAAUGAGAAAUAUUACGGCA | UGCCGUAAUAUUUCUCAUUUACU | | [1335-1357](23/23) 3'UTR |

TABLE D-continued 23 mers

| Number | Sense siRNA | AntiSense siRNA | Other Sp | Hum-34222182 ORF: 204-785 |
|---|---|---|---|---|
| 139 | ACUAUAUAAACCAGAUUUGCCUA | UAGGCAAAUCUGGUUUAUAUAGU | | [1115-1137](23/23) 3'UTR |
| 140 | CAAUUUGGUUUCAGGUAGGCUUG | CAAGCCUACCUGAAACCAAAUUG | | [1085-1107](23/23) 3'UTR |
| 141 | CAAAGGUUCACUGUGUUUCUGCC | GGCAGAAACACAGUGAACCUUUG | | [2358-2380](23/23) 3'UTR |
| 142 | CAUUUCACCAUGGCAGUGUUAUC | GAUAACACUGCCAUGGUGAAAUG | | [1694-1716](23/23) 3'UTR |
| 143 | AAAAACUUUACUCACUGAUUGGA | UCCAAUCAGUGAGUAAAGUUUUU | | [739-761](23/23) ORF |
| 144 | UGUAGUCUCUUUUCUUUCUGUGU | ACACAGAAAGAAAAGAGACUACA | | [896-918](23/23) 3'UTR |
| 145 | GGUGUUACUGAAAAACAGGUGUG | CACACCUGUUUUUCAGUAACACC | | [2170-2192](23/23) 3'UTR |
| 146 | CUGUUCUUAAGUGUUGAAUACUG | CAGUAUUCAACACUUAAGAACAG | | [1487-1509](23/23) 3'UTR |
| 147 | GAAAAACUUUACUCACUGAUUG | CAAUCAGUGAGUAAAGUUUUUUC | | [737-759](23/23) ORF |
| 148 | GAACUGAUAUUUUGUGUGUAGU | ACUACACACAAAAAUAUCAGUUC | | [1538-1560](23/23) 3'UTR |
| 149 | CAUCGAUGUAGAACUGUUGUCCU | AGGACAACAGUUCUACAUCGAUG | | [2425-2447](23/23) 3'UTR |
| 150 | CUUGGUUGCUCAAAGGUCCUUGU | ACAAGGACCUUUGAGCAACCAAG | Chimp | [420-442](23/23) ORF |
| 151 | CAACUAAGUAGAUCAUUAUCUCU | AGAGAUAAUGAUCUACUUAGUUG | | [1972-1994](23/23) 3'UTR |
| 152 | UAAAAUGCUGGAGAACUGUCUGU | ACAGACAGUUCUCCAGCAUUUUA | Dog, Chimp | [377-399](23/23) ORF |
| 153 | GAUAAGGAGCUUAUUCAGGUUUC | GAAACCUGAAUAAGCUCCUUAUC | | [2082-2104](23/23) 3'UTR |
| 154 | AAACAGAGCCGUUGACCAUGGUU | AACCAUGGUCAACGGCUCUGUUU | Chimp, Rat, Ms | [187-209](23/23) 5'UTR + ORF |
| 155 | CUGCUAAGUGAUUUUGACUACUG | CAGUAGUCAAAAUCACUUAGCAG | Chimp | [285-307](23/23) ORF |
| 156 | CCUCACUCUAAUGUUUUAAAGAG | CUCUUUAAAACAUUAGAGUGAGG | | [1392-1414](23/23) 3'UTR |
| 157 | UUUUGAGCUUACACUUGUGUUUA | UAAACACAAGUGUAAGCUCAAAA | Chimp | [602-624](23/23) ORF |
| 158 | CUGAAAACAGGUGUGAUCCUGU | ACAGGAUCACACCUGUUUUUCAG | | [2177-2199](23/23) 3'UTR |
| 159 | UGCUUACAAAAUGGUGAUGGCUU | AAGCCAUCACCAUUUUGUAAGCA | | [2487-2509](23/23) 3'UTR |
| 160 | GUGAGUUUAAUUAAAGCUUAACC | GGUUAAGCUUUAAUUAAACUCAC | | [1303-1325](23/23) 3'UTR |
| 161 | GUGAUGGCUUAUGGAAGGCUGUU | AACAGCCUUCCAUAAGCCAUCAC | | [2500-2522](23/23) 3'UTR |
| 162 | CACUUUGAAUUAUUGAAACGGGU | ACCCGUUUCAAUAAUUCAAAGUG | | [1792-1814](23/23) 3'UTR |
| 163 | GUUCACUGUGUUUCUGCCGCUGU | ACAGCGGCAGAAACACAGUGAAC | | [2363-2385](23/23) 3'UTR |
| 164 | AAGAACCCGGCCAGCAUUUCAGA | UCUGAAAUGCUGGCCGGGUUCUU | Chimp, Ms | [231-253](23/23) ORF |
| 165 | UACUCUUCCAUUGAGUGAAUGAU | AUCAUUCACUCAAUGGAAGAGUA | | [1565-1587](23/23) 3'UTR |
| 166 | CUUGUCCCUGAGAAACUGACCCA | UGGGUCAGUUUCUCAGGGACAAG | Dog, Chimp | [438-460](23/23) ORF |
| 167 | AAGAUGUCCUGCGGCUUUCCUCA | UGAGGAAAGCCGCAGGACAUCUU | Chimp | [472-494](23/23) ORF |
| 168 | UAGUCUCUUUUCUUUCUGUGUUU | AAACACAGAAAGAAAAGAGACUA | | [898-920](23/23) 3'UTR |
| 169 | GUGUUGAAUACGUCUUUAAACU | AGUUUAAAGACGUAUUCAACAC | | [1497-1519](23/23) 3'UTR |
| 170 | AGCAACUGCAGCUAACAGGCUGA | UCAGCCUGUUAGCUGCAGUUGCU | | [930-952](23/23) 3'UTR |
| 171 | UGAAAUGUAUGUAAAAGCUGG | CCAGCUUUUUACAUACAUUUUCA | Chimp, Ms | [545-567](23/23) ORF |
| 172 | CUCUUUUCUUUCUGUGUUUCACA | UGUGAAACACAGAAAGAAAAGAG | | [902-924](23/23) 3'UTR |
| 173 | UGCCCUAGCUAUUAGCUCCACUU | AAGUGGAGCUAAUAGCUAGGGCA | | [2106-2128](23/23) 3'UTR |
| 174 | AGCAAACUAAACUUGGUUGCUCA | UGAGCAACCAAGUUUAGUUUGCU | Chimp | [409-431](23/23) ORF |
| 175 | CUAUUCAGCUAGUCAGCUAAAGU | ACUUUAGCUGACUAGCUGAAUAG | | [830-852](23/23) 3'UTR |

TABLE D-continued

23 mers

| Number | Sense siRNA | AntiSense siRNA | Other Sp | Hum-34222182 ORF: 204-785 |
|---|---|---|---|---|
| 176 | UAGAGGUCGCUUCUCCUCUGGUU | AACCAGAGGAGAAGCGACCUCUA | | [671-693](23/23) ORF |
| 177 | AAAAGCCCACACCACCAGUUCCU | AGGAACUGGUGGUGUGGGCUUUU | | [1234-1256](23/23) 3'UTR |
| 178 | GUCCUUGUCCCUGAGAAACUGAC | GUCAGUUUCUCAGGGACAAGGAC | Dog, Chimp | [435-457](23/23) ORF |
| 179 | GAACUGCUUCACUGUUUCUUGGU | ACCAAGAAACAGUGAAGCAGUUC | | [1364-1386](23/23) 3'UTR |
| 180 | AACAGAGCCGUUGACCAUGGUUG | CAACCAUGGUCAACGGCUCUGUU | Chimp, Rat, Ms | [188-210](23/23) 5'UTR + ORF |
| 181 | UGUGUAGUUGAUUACUCUUCCAU | AUGGAAGAGUAAUCAACUACACA | | [1553-1575](23/23) 3'UTR |
| 182 | CUGAACCCAACCUCAACGAGGUA | UACCUCGUUGAGGUUGGGUUCAG | Chimp | [322-344](23/23) ORF |
| 183 | UUUCUGGGAAUUGAAGUAUCUCU | AGAGAUACUUCAAUUCCCAGAAA | | [1730-1752](23/23) 3'UTR |
| 184 | GCUUUCAUAUCCUUGCUGUGGGU | ACCCACAGCAAGGAUAUGAAAGC | | [2055-2077](23/23) 3'UTR |
| 185 | UCUGAUUCACUUAGUAAUCUAUC | GAUAGAUUACUAAGUGAAUCAGA | | [1633-1655](23/23) 3'UTR |
| 186 | CAUUUCAGUAACCACGGUGUUGU | ACAACACCGUGGUUACUGAAAUG | | [1435-1457](23/23) 3'UTR |
| 187 | AAUGUUCAAUUCAGCAAGGCUUU | AAAGCCUUGCUGAAUUGAACAUU | | [2037-2059](23/23) 3'UTR |
| 188 | AGCUCCACUUCACAUGCUGGAGA | UCUCCAGCAUGUGAAGUGGAGCU | | [2119-2141](23/23) 3'UTR |
| 189 | AAACUGACCCAGAGAAUUGCUCA | UGAGCAAUUCUCUGGGUCAGUUU | Chimp, Ms | [450-472](23/23) ORF |
| 190 | CUUACACUUGUGUUUAAGCAGGA | UCCUGCUUAAACACAAGUGUAAG | Chimp | [609-631](23/23) ORF |
| 191 | UAAGCUCCAAAGGUUCACUGUGU | ACACAGUGAACCUUUGGAGCUUA | | [2351-2373](23/23) 3'UTR |
| 192 | ACUUUGAGCUUACACUUGUGUUU | AACACAAGUGUAAGCUCAAAAGU | Chimp | [600-622](23/23) ORF |
| 193 | UGUUACUGAAAAACAGGUGUGAU | AUCACACCUGUUUUUCAGUAACA | | [2172-2194](23/23) 3'UTR |
| 194 | UUUUUUCCACCUUGGAUACCUGU | ACAGGUAUCCAAGGUGGAAAAAA | | [1910-1932](23/23) 3'UTR |
| 195 | UUACUCUUCCAUUGAGUGAAUGA | UCAUUCACUCAAUGGAAGAGUAA | | [1564-1586](23/23) 3'UTR |

TABLE E additional 23 mers

| Number | Sense siRNA | AntiSense siRNA | Other Sp | Hum-34222182 ORF: 204-785 |
|---|---|---|---|---|
| 1 | CAGUGUUCUAACAAACUAAACUC | GAGUUUAGUUUGUUAGAACACUG | | [2244-2266] 3'UTR |
| 2 | CCAGUGUUCUAACAAACUAAACU | AGUUUAGUUUGUUAGAACACUGG | | [2243-2265] 3'UTR |
| 3 | GCCAGUGUUCUAACAAACUAAAC | GUUUAGUUUGUUAGAACACUGGC | | [2242-2264] 3'UTR |
| 4 | AGCCAGUGUUCUAACAAACUAAA | UUUAGUUUGUUAGAACACUGGCU | | [2241-2263] 3'UTR |
| 5 | UAGCCAGUGUUCUAACAAACUAA | UUAGUUUGUUAGAACACUGGCUA | | [2240-2262] 3'UTR |
| 6 | UUAGCCAGUGUUCUAACAAACUA | UAGUUUGUUAGAACACUGGCUAA | | [2239-2261] 3'UTR |
| 7 | GGAUUAUGUUGUUCCUGAACCCA | UGGGUUCAGGAACAACAUAAUCC | Chimp | [308-330] ORF |
| 8 | GGGAUUAUGUUGUUCCUGAACCC | GGGUUCAGGAACAACAUAAUCCC | Chimp | [307-329] ORF |
| 9 | UGGGAUUAUGUUGUUCCUGAACC | GGUUCAGGAACAACAUAAUCCCA | Chimp | [306-328] ORF |
| 10 | CUGGGAUUAUGUUGUUCCUGAAC | GUUCAGGAACAACAUAAUCCCAG | Chimp | [305-327] ORF |
| 11 | ACUGGGAUUAUGUUGUUCCUGAA | UUCAGGAACAACAUAAUCCCAGU | Chimp | [304-326] ORF |
| 12 | GGCUUUUCUGGGAAUUGAAGUAU | AUACUUCAAUUCCCAGAAAAGCC | | [1726-1748] 3'UTR |

TABLE E-continued additional 23 mers

| Number | Sense siRNA | AntiSense siRNA | Other Sp | Hum-34222182 ORF: 204-785 |
|---|---|---|---|---|
| 13 | GGGCUUUUCUGGGAAUUGAAGUA | UACUUCAAUUCCCAGAAAAGCCC | | [1725-1747] 3'UTR |
| 14 | UGGGCUUUUCUGGGAAUUGAAGU | ACUUCAAUUCCCAGAAAAGCCCA | | [1724-1746] 3'UTR |
| 15 | CUGGGCUUUUCUGGGAAUUGAAG | CUUCAAUUCCCAGAAAAGCCCAG | | [1723-1745] 3'UTR |
| 16 | UCUGGGCUUUUCUGGGAAUUGAA | UUCAAUUCCCAGAAAAGCCCAGA | | [1722-1744] 3'UTR |
| 17 | GAUGGAAUAGGUAAGCAAAAGUA | UACUUUGCUUACCUAUUCCAUC | | [1031-1053] 3'UTR |
| 18 | GGAUGGAAUAGGUAAGCAAAAGU | ACUUUGCUUACCUAUUCCAUCC | | [1030-1052] 3'UTR |
| 19 | GGGAUGGAAUAGGUAAGCAAAAG | CUUUGCUUACCUAUUCCAUCCC | | [1029-1051] 3'UTR |
| 20 | UGGGAUGGAAUAGGUAAGCAAAA | UUUGCUUACCUAUUCCAUCCCA | | [1028-1050] 3'UTR |
| 21 | AUGGGAUGGAAUAGGUAAGCAAA | UUUGCUUACCUAUUCCAUCCCAU | | [1027-1049] 3'UTR |
| 22 | CGUGAACUUGGAAAUUGAAAAUG | CAUUUUCAAUUUCCAAGUUCACG | Dog, Chin, GP, Rat | [530-552] ORF |
| 23 | ACGUGAACUUGGAAAUUGAAAAU | AUUUUCAAUUUCCAAGUUCACGU | Dog, Chin, GP, Rat | [529-551] ORF |
| 24 | CACGUGAACUUGGAAAUUGAAAA | UUUUCAAUUUCCAAGUUCACGUG | Dog, Chin, GP, Rat | [528-550] ORF |
| 25 | GCACGUGAACUUGGAAAUUGAAA | UUUCAAUUUCCAAGUUCACGUGC | Dog, Chin, GP, Rat | [527-549] ORF |
| 26 | UGCACGUGAACUUGGAAAUUGAA | UUCAAUUUCCAAGUUCACGUGCA | Dog, Chin, GP, Rat | [526-548] ORF |
| 27 | AAUGGGAUGGAAUAGGUAAGCAA | UUGCUUACCUAUUCCAUCCCAUU | | [1026-1048] 3'UTR |
| 28 | AUUAGCCAGUGUUCUAACAAACU | AGUUUGUUAGAACACUGGCUAAU | | [2238-2260] 3'UTR |
| 29 | AAUUAGCCAGUGUUCUAACAAAC | GUUUGUUAGAACACUGGCUAAUU | | [2237-2259] 3'UTR |
| 30 | AAAUUAGCCAGUGUUCUAACAAA | UUUGUUAGAACACUGGCUAAUUU | | [2236-2258] 3'UTR |
| 31 | GAUUGAAGGGUCCUAAAAAGGGA | UCCCUUUUUAGGACCCUUCAAUC | | [770-792] ORF + 3'UTR |
| 32 | UGAUUGAAGGGUCCUAAAAAGGG | CCCUUUUUAGGACCCUUCAAUCA | | [769-791] ORF + 3'UTR |
| 33 | GUGAUUGAAGGGUCCUAAAAAGG | CCUUUUUAGGACCCUUCAAUCAC | | [768-790] ORF + 3'UTR |
| 34 | AGUGAUUGAAGGGUCCUAAAAAG | CUUUUUAGGACCCUUCAAUCACU | | [767-789] ORF + 3'UTR |
| 35 | CAGUGAUUGAAGGGUCCUAAAAA | UUUUUAGGACCCUUCAAUCACUG | | [766-788] ORF + 3'UTR |
| 36 | GAAUGAUGAAUACCUGUGAGGAU | AUCCUCACAGGUAUUCAUCAUUC | | [1581-1603] 3'UTR |
| 37 | UGAAUGAUGAAUACCUGUGAGGA | UCCUCACAGGUAUUCAUCAUUCA | | [1580-1602] 3'UTR |
| 38 | GUGAAUGAUGAAUACCUGUGAGG | CCUCACAGGUAUUCAUCAUUCAC | | [1579-1601] 3'UTR |
| 39 | AGUGAAUGAUGAAUACCUGUGAG | CUCACAGGUAUUCAUCAUUCACU | | [1578-1600] 3'UTR |
| 40 | GAGUGAAUGAUGAAUACCUGUGA | UCACAGGUAUUCAUCAUUCACUC | | [1577-1599] 3'UTR |
| 41 | CAGAGAGCCUGCUAAGUGAUUUU | AAAAUCACUUAGCAGGCUCUCUG | Chimp | [277-299] ORF |
| 42 | CCAGAGAGCCUGCUAAGUGAUUU | AAAUCACUUAGCAGGCUCUCUGG | Chimp | [276-298] ORF |
| 43 | CCCAGAGAGCCUGCUAAGUGAUU | AAUCACUUAGCAGGCUCUCUGGG | Chimp | [275-297] ORF |
| 44 | ACCCAGAGAGCCUGCUAAGUGAU | AUCACUUAGCAGGCUCUCUGGGU | Chimp | [274-296] ORF |
| 45 | CACCCAGAGAGCCUGCUAAGUGA | UCACUUAGCAGGCUCUCUGGGUG | Chimp | [273-295] ORF |
| 46 | AGAAUUGGGCCAAGAUAAAUCAA | UUGAUUUAUCUUGGCCCAAUUCU | | [2306-2328] 3'UTR |
| 47 | UAGAAUUGGGCCAAGAUAAAUCA | UGAUUUAUCUUGGCCCAAUUCUA | | [2305-2327] 3'UTR |
| 48 | AUAGAAUUGGGCCAAGAUAAAUC | GAUUUAUCUUGGCCCAAUUCUAU | | [2304-2326] 3'UTR |
| 49 | UAUAGAAUUGGGCCAAGAUAAAU | AUUUAUCUUGGCCCAAUUCUAUA | | [2303-2325] 3'UTR |

TABLE E-continued additional 23 mers

| Number | Sense siRNA | AntiSense siRNA | Other Sp | Hum-34222182 ORF: 204-785 |
|---|---|---|---|---|
| 50 | UUAUAGAAUUGGGCCAAGAUAAA | UUUAUCUUGGCCCAAUUCUAUAA | | [2302-2324] 3'UTR |
| 51 | UGCUGUGGGUCGUGGAUAAGGAG | CUCCUUAUCCACGACCCACAGCA | | [2068-2090] 3'UTR |
| 52 | UUGCUGUGGGUCGUGGAUAAGGA | UCCUUAUCCACGACCCACAGCAA | | [2067-2089] 3'UTR |
| 53 | CUUGCUGUGGGUCGUGGAUAAGG | CCUUAUCCACGACCCACAGCAAG | | [2066-2088] 3'UTR |
| 54 | CCUUGCUGUGGGUCGUGGAUAAG | CUUAUCCACGACCCACAGCAAGG | | [2065-2087] 3'UTR |
| 55 | UCCUUGCUGUGGGUCGUGGAUAA | UUAUCCACGACCCACAGCAAGGA | | [2064-2086] 3'UTR |
| 56 | AGGUAAGAGUAAAUGAGAAAUAU | AUAUUUCUCAUUUACUCUUACCU | | [1328-1350] 3'UTR |
| 57 | UAGGUAAGAGUAAAUGAGAAAUA | UAUUUCUCAUUUACUCUUACCUA | | [1327-1349] 3'UTR |
| 58 | CUAGGUAAGAGUAAAUGAGAAAU | AUUUCUCAUUUACUCUUACCUAG | | [1326-1348] 3'UTR |
| 59 | CCUAGGUAAGAGUAAAUGAGAAA | UUUCUCAUUUACUCUUACCUAGG | | [1325-1347] 3'UTR |
| 60 | CCCUAGGUAAGAGUAAAUGAGAA | UUCUCAUUUACUCUUACCUAGGG | | [1324-1346] 3'UTR |
| 61 | CUGUCCAAAUCAAAGCAAACUAA | UUAGUUUGCUUUGAUUUGGACAG | Dog, Chimp | [396-418] ORF |
| 62 | UCUGUCCAAAUCAAAGCAAACUA | UAGUUUGCUUUGAUUUGGACAGA | Dog, Chimp | [395-417] ORF |
| 63 | GUCUGUCCAAAUCAAAGCAAACU | AGUUUGCUUUGAUUUGGACAGAC | Dog, Chimp | [394-416] ORF |
| 64 | UGUCUGUCCAAAUCAAAGCAAAC | GUUUGCUUUGAUUUGGACAGACA | Dog, Chimp | [393-415] ORF |
| 65 | CUGUCUGUCCAAAUCAAAGCAAA | UUUGCUUUGAUUUGGACAGACAG | Dog, Chimp | [392-414] ORF |
| 66 | UCAUGAUUGGGUAGUAAAACUAU | AUAGUUUUACUACCCAAUCAUGA | | [811-833] 3'UTR |
| 67 | UUCAUGAUUGGGUAGUAAAACUA | UAGUUUUACUACCCAAUCAUGAA | | [810-832] 3'UTR |
| 68 | UUUCAUGAUUGGGUAGUAAAACU | AGUUUUACUACCCAAUCAUGAAA | | [809-831] 3'UTR |
| 69 | AUUUCAUGAUUGGGUAGUAAAAC | GUUUUACUACCCAAUCAUGAAAU | | [808-830] 3'UTR |
| 70 | UAUUUCAUGAUUGGGUAGUAAAA | UUUUACUACCCAAUCAUGAAAUA | | [807-829] 3'UTR |
| 71 | ACAGUGAUUGAAGGGUCCUAAAA | UUUUAGGACCCUUCAAUCACUGU | | [765-787] ORF + 3'UTR |
| 72 | AACAGUGAUUGAAGGGUCCUAAA | UUUAGGACCCUUCAAUCACUGUU | | [764-786] ORF + 3'UTR |
| 73 | GGAAGGCUGUUAAAUUAAUAUUC | GAAUAUUAAUUUAACAGCCUUCC | | [2512-2534] 3'UTR |
| 74 | UGGAAGGCUGUUAAAUUAAUAUU | AAUAUUAAUUUAACAGCCUUCCA | | [2511-2533] 3'UTR |
| 75 | AUGGAAGGCUGUUAAAUUAAUAU | AUAUUAAUUUAACAGCCUUCCAU | | [2510-2532] 3'UTR |
| 76 | UAUGGAAGGCUGUUAAAUUAAUA | UAUUAAUUUAACAGCCUUCCAUA | | [2509-2531] 3'UTR |
| 77 | UUAUGGAAGGCUGUUAAAUUAAU | AUUAAUUUAACAGCCUUCCAUAA | | [2508-2530] 3'UTR |
| 78 | CAAGGGUAGUAGCUGUAUACUAC | GUAGUAUACAGCUACUACCCUUG | | [1769-1791] 3'UTR |
| 79 | UCAAGGGUAGUAGCUGUAUACUA | UAGUAUACAGCUACUACCCUUGA | | [1768-1790] 3'UTR |
| 80 | GUCAAGGGUAGUAGCUGUAUACU | AGUAUACAGCUACUACCCUUGAC | | [1767-1789] 3'UTR |
| 81 | UGUCAAGGGUAGUAGCUGUAUAC | GUAUACAGCUACUACCCUUGACA | | [1766-1788] 3'UTR |
| 82 | UUGUCAAGGGUAGUAGCUGUAUA | UAUACAGCUACUACCCUUGACAA | | [1765-1787] 3'UTR |
| 83 | CCAAAUCAAAGCAAACUAAACUU | AAGUUUAGUUUGCUUUGAUUUGG | Chimp | [400-422] ORF |
| 84 | UCCAAAUCAAAGCAAACUAAACU | AGUUUAGUUUGCUUUGAUUUGGA | Chimp | [399-421] ORF |
| 85 | GUCCAAAUCAAAGCAAACUAAAC | GUUUAGUUUGCUUUGAUUUGGAC | Chimp | [398-420] ORF |
| 86 | UGUCCAAAUCAAAGCAAACUAAA | UUUAGUUUGCUUUGAUUUGGACA | Chimp | [397-419] ORF |

TABLE E-continued additional 23 mers

| Number | Sense siRNA | AntiSense siRNA | Other Sp | Hum-34222182 ORF: 204-785 |
|---|---|---|---|---|
| 87 | GCUUAUGGAAGGCUGUUAAAUUA | UAAUUUAACAGCCUUCCAUAAGC | | [2506-2528] 3'UTR |
| 88 | GGCUUAUGGAAGGCUGUUAAAUU | AAUUUAACAGCCUUCCAUAAGCC | | [2505-2527] 3'UTR |
| 89 | UGGCUUAUGGAAGGCUGUUAAAU | AUUUAACAGCCUUCCAUAAGCCA | | [2504-2526] 3'UTR |
| 90 | AUGGCUUAUGGAAGGCUGUUAAA | UUUAACAGCCUUCCAUAAGCCAU | | [2503-2525] 3'UTR |
| 91 | GAUGGCUUAUGGAAGGCUGUUAA | UUAACAGCCUUCCAUAAGCCAUC | | [2502-2524] 3'UTR |
| 92 | UCCUGUUACUGAUACUAUAAGUG | CACUUAUAGUAUCAGUAACAGGA | | [2194-2216] 3'UTR |
| 93 | AUCCUGUUACUGAUACUAUAAGU | ACUUAUAGUAUCAGUAACAGGAU | | [2193-2215] 3'UTR |
| 94 | GAUCCUGUUACUGAUACUAUAAG | CUUAUAGUAUCAGUAACAGGAUC | | [2192-2214] 3'UTR |
| 95 | UGAUCCUGUUACUGAUACUAUAA | UUAUAGUAUCAGUAACAGGAUCA | | [2191-2213] 3'UTR |
| 96 | GUGAUCCUGUUACUGAUACUAUA | UAUAGUAUCAGUAACAGGAUCAC | | [2190-2212] 3'UTR |
| 97 | GGUCCUUGUCCCUGAGAAACUGA | UCAGUUUCUCAGGGACAAGGACC | Chimp | [434-456] ORF |
| 98 | AGGUCCUUGUCCCUGAGAAACUG | CAGUUUCUCAGGGACAAGGACCU | Chimp | [433-455] ORF |
| 99 | AAGGUCCUUGUCCCUGAGAAACU | AGUUUCUCAGGGACAAGGACCUU | Chimp | [432-454] ORF |
| 100 | AAAGGUCCUUGUCCCUGAGAAAC | GUUUCUCAGGGACAAGGACCUUU | Chimp | [431-453] ORF |
| 101 | CAAAGGUCCUUGUCCCUGAGAAA | UUUCUCAGGGACAAGGACCUUUG | Chimp | [430-452] ORF |
| 102 | CCAACUAAGUAGAUCAUUAUCUC | GAGAUAAUGAUCUACUUAGUUGG | | [1971-1993] 3'UTR |
| 103 | UCCAACUAAGUAGAUCAUUAUCU | AGAUAAUGAUCUACUUAGUUGGA | | [1970-1992] 3'UTR |
| 104 | UUCCAACUAAGUAGAUCAUUAUC | GAUAAUGAUCUACUUAGUUGGAA | | [1969-1991] 3'UTR |
| 105 | AUUCCAACUAAGUAGAUCAUUAU | AUAAUGAUCUACUUAGUUGGAAU | | [1968-1990] 3'UTR |
| 106 | UAUUCCAACUAAGUAGAUCAUUA | UAAUGAUCUACUUAGUUGGAAUA | | [1967-1989] 3'UTR |
| 107 | UGGUUAAAAUGCUGGAGAACUGU | ACAGUUCUCCAGCAUUUUAACCA | Chimp | [373-395] ORF |
| 108 | UUGGUUAAAAUGCUGGAGAACUG | CAGUUCUCCAGCAUUUUAACCAA | Chimp | [372-394] ORF |
| 109 | UUUGGUUAAAAUGCUGGAGAACU | AGUUCUCCAGCAUUUUAACCAAA | Chimp | [371-393] ORF |
| 110 | AUUUGGUUAAAAUGCUGGAGAAC | GUUCUCCAGCAUUUUAACCAAAU | Chimp | [370-392] ORF |
| 111 | AAUUUGGUUAAAAUGCUGGAGAA | UUCUCCAGCAUUUUAACCAAAUU | Chimp | [369-391] ORF |
| 112 | CCAUUGAGUGAAUGAUGAAUACC | GGUAUUCAUCAUUCACUCAAUGG | | [1572-1594] 3'UTR |
| 113 | UCCAUUGAGUGAAUGAUGAAUAC | GUAUUCAUCAUUCACUCAAUGGA | | [1571-1593] 3'UTR |
| 114 | UUCCAUUGAGUGAAUGAUGAAUA | UAUUCAUCAUUCACUCAAUGGAA | | [1570-1592] 3'UTR |
| 115 | CUUCCAUUGAGUGAAUGAUGAAU | AUUCAUCAUUCACUCAAUGGAAG | | [1569-1591] 3'UTR |
| 116 | UCUUCCAUUGAGUGAAUGAUGAA | UUCAUCAUUCACUCAAUGGAAGA | | [1568-1590] 3'UTR |
| 117 | GAAUUUAGCCUCCACUCAACAAU | AUUGUUGAGUGGAGGCUAAAUUC | | [2017-2039] 3'UTR |
| 118 | AGAAUUUAGCCUCCACUCAACAA | UUGUUGAGUGGAGGCUAAAUUCU | | [2016-2038] 3'UTR |
| 119 | GAGAAUUUAGCCUCCACUCAACA | UGUUGAGUGGAGGCUAAAUUCUC | | [2015-2037] 3'UTR |
| 120 | AGAGAAUUUAGCCUCCACUCAAC | GUUGAGUGGAGGCUAAAUUCUCU | | [2014-2036] 3'UTR |
| 121 | GAGAGAAUUUAGCCUCCACUCAA | UUGAGUGGAGGCUAAAUUCUCUC | | [2013-2035] 3'UTR |
| 122 | CAGGAUUUCGACUUGUUAAGAAU | UUUCUUAACAAGUCGAAAUCCUG | | [718-740] ORF |
| 123 | UCAGGAUUUCGACUUGUUAAGAA | UUCUUAACAAGUCGAAAUCCUGA | | [717-739] ORF |

TABLE E-continued additional 23 mers

| Number | Sense siRNA | AntiSense siRNA | Other Sp | Hum-34222182 ORF: 204-785 |
|---|---|---|---|---|
| 124 | CUCAGGAUUUCGACUUGUUAAGA | UCUUAACAAGUCGAAAUCCUGAG | | [716-738] ORF |
| 125 | GCUCAGGAUUUCGACUUGUUAAG | CUUAACAAGUCGAAAUCCUGAGC | | [715-737] ORF |
| 126 | AGCUCAGGAUUUCGACUUGUUAA | UUAACAAGUCGAAAUCCUGAGCU | | [714-736] ORF |
| 127 | AUGCACGUGAACUUGGAAAUUGA | UCAAUUUCCAAGUUCACGUGCAU | Dog, Chin, GP, Rat | [525-547] ORF |
| 128 | GUGUGAUCCUGUUACUGAUACUA | UAGUAUCAGUAACAGGAUCACAC | | [2188-2210] 3'UTR |
| 129 | GGUGUGAUCCUGUUACUGAUACU | AGUAUCAGUAACAGGAUCACACC | | [2187-2209] 3'UTR |
| 130 | AGGUGUGAUCCUGUUACUGAUAC | GUAUCAGUAACAGGAUCACACCU | | [2186-2208] 3'UTR |
| 131 | CAGGUGUGAUCCUGUUACUGAUA | UAUCAGUAACAGGAUCACACCUG | | [2185-2207] 3'UTR |
| 132 | ACAGGUGUGAUCCUGUUACUGAU | AUCAGUAACAGGAUCACACCUGU | | [2184-2206] 3'UTR |
| 133 | CAGUAUUACAUGUGCUUAAUCUC | GAGAUUAAGCACAUGUAAUACUG | | [1663-1685] 3'UTR |
| 134 | UCAGUAUUACAUGUGCUUAAUCU | AGAUUAAGCACAUGUAAUACUGA | | [1662-1684] 3'UTR |
| 135 | UUCAGUAUUACAUGUGCUUAAUC | GAUUAAGCACAUGUAAUACUGAA | | [1661-1683] 3'UTR |
| 136 | UUUCAGUAUUACAUGUGCUUAAU | AUUAAGCACAUGUAAUACUGAAA | | [1660-1682] 3'UTR |
| 137 | UUUUCAGUAUUACAUGUGCUUAA | UUAAGCACAUGUAAUACUGAAAA | | [1659-1681] 3'UTR |
| 138 | CCACCUGCCCUAAAUAAGAAACC | GGUUUCUUAUUUAGGGCAGGUGG | | [868-890] 3'UTR |
| 139 | CCCACCUGCCCUAAAUAAGAAAC | GUUUCUUAUUUAGGGCAGGUGGG | | [867-889] 3'UTR |
| 140 | CCCCACCUGCCCUAAAUAAGAAA | UUUCUUAUUUAGGGCAGGUGGGG | | [866-888] 3'UTR |
| 141 | GCCCCACCUGCCCUAAAUAAGAA | UUCUUAUUUAGGGCAGGUGGGGC | | [865-887] 3'UTR |
| 142 | UGCCCCACCUGCCCUAAAUAAGA | UCUUAUUUAGGGCAGGUGGGGCA | | [864-886] 3'UTR |
| 143 | GGUAAGAGUAAUGAGAAAUAUU | AAUAUUUCUCAUUUACUCUUACC | | [1329-1351] 3'UTR |
| 144 | GGAGAACUGUCUGUCCAAAUCAA | UUGAUUUGGACAGACAGUUCUCC | Dog, Chimp | [386-408] ORF |
| 145 | UGGAGAACUGUCUGUCCAAAUCA | UGAUUUGGACAGACAGUUCUCCA | Dog, Chimp | [385-407] ORF |
| 146 | CUGGAGAACUGUCUGUCCAAAUC | GAUUUGGACAGACAGUUCUCCAG | Dog, Chimp | [384-406] ORF |
| 147 | GCUGGAGAACUGUCUGUCCAAAU | AUUUGGACAGACAGUUCUCCAGC | Dog, Chimp | [383-405] ORF |
| 148 | UGCUGGAGAACUGUCUGUCCAAA | UUUGGACAGACAGUUCUCCAGCA | Dog, Chimp | [382-404] ORF |
| 149 | CGAGGUAAUAUUUGAGGAAUCAA | UUGAUUCCUCAAAUAUUACCUCG | Chimp | [338-360] ORF |
| 150 | ACGAGGUAAUAUUUGAGGAAUCA | UGAUUCCUCAAAUAUUACCUCGU | Chimp | [337-359] ORF |
| 151 | AACGAGGUAAUAUUUGAGGAAUC | GAUUCCUCAAAUAUUACCUCGUU | Chimp | [336-358] ORF |
| 152 | CAACGAGGUAAUAUUUGAGGAAU | AUUCCUCAAAUAUUACCUCGUUG | Chimp | [335-357] ORF |
| 153 | UCAACGAGGUAAUAUUUGAGGAA | UUCCUCAAAUAUUACCUCGUUGA | Chimp | [334-356] ORF |
| 154 | GCUUGGAAAGAUACUACAAAGCC | GGCUUUGUAGUAUCUUUCCAAGC | | [2274-2296] 3'UTR |
| 155 | UGCUUGGAAAGAUACUACAAAGC | GCUUUGUAGUAUCUUUCCAAGCA | | [2273-2295] 3'UTR |
| 156 | AUGCUUGGAAAGAUACUACAAAG | CUUUGUAGUAUCUUUCCAAGCAU | | [2272-2294] 3'UTR |
| 157 | AAUGCUUGGAAAGAUACUACAAA | UUUGUAGUAUCUUUCCAAGCAUU | | [2271-2293] 3'UTR |
| 158 | AAAUGCUUGGAAAGAUACUACAA | UUGUAGUAUCUUUCCAAGCAUUU | | [2270-2292] 3'UTR |
| 159 | CUAAAAUGUCACUGUUCAAAUUA | UAAUUUGAACAGUGACAUUUUAG | | [2219-2241] 3'UTR |
| 160 | CCUAAAAUGUCACUGUUCAAAUU | AAUUUGAACAGUGACAUUUUAGG | | [2218-2240] 3'UTR |

TABLE E-continued additional 23 mers

| Number | Sense siRNA | AntiSense siRNA | Other Sp | Hum-34222182 ORF: 204-785 | |
|---|---|---|---|---|---|
| 161 | ACCUAAAAUGUCACUGUUCAAAU | AUUUGAACAGUGACAUUUUAGGU | | [2217-2239] | 3'UTR |
| 162 | GACCUAAAAUGUCACUGUUCAAA | UUUGAACAGUGACAUUUUAGGUC | | [2216-2238] | 3'UTR |
| 163 | UGACCUAAAAUGUCACUGUUCAA | UUGAACAGUGACAUUUUAGGUCA | | [2215-2237] | 3'UTR |
| 164 | GUGACUUCCUCACUCUAAUGUUU | AAACAUUAGAGUGAGGAAGUCAC | | [1385-1407] | 3'UTR |
| 165 | GGUGACUUCCUCACUCUAAUGUU | AACAUUAGAGUGAGGAAGUCACC | | [1384-1406] | 3'UTR |
| 166 | UGGUGACUUCCUCACUCUAAUGU | ACAUUAGAGUGAGGAAGUCACCA | | [1383-1405] | 3'UTR |
| 167 | UUGGUGACUUCCUCACUCUAAUG | CAUUAGAGUGAGGAAGUCACCAA | | [1382-1404] | 3'UTR |
| 168 | CUUGGUGACUUCCUCACUCUAAU | AUUAGAGUGAGGAAGUCACCAAG | | [1381-1403] | 3'UTR |
| 169 | GAAUGGGAUGGAAUAGGUAAGCA | UGCUUACCUAUUCCAUCCCAUUC | | [1025-1047] | 3'UTR |
| 170 | UGAAUGGGAUGGAAUAGGUAAGC | GCUUACCUAUUCCAUCCCAUUCA | | [1024-1046] | 3'UTR |
| 171 | UUGAAUGGGAUGGAAUAGGUAAG | CUUACCUAUUCCAUCCCAUUCAA | | [1023-1045] | 3'UTR |
| 172 | AUUGAAUGGGAUGGAAUAGGUAA | UUACCUAUUCCAUCCCAUUCAAU | | [1022-1044] | 3'UTR |
| 173 | AAUUGAAUGGGAUGGAAUAGGUA | UACCUAUUCCAUCCCAUUCAAUU | | [1021-1043] | 3'UTR |
| 174 | GCCUGUUAUGCUUACAAAAUGGU | ACCAUUUGUAAGCAUAACAGGC | | [2479-2501] | 3'UTR |
| 175 | UGCCUGUUAUGCUUACAAAAUGG | CCAUUUGUAAGCAUAACAGGCA | | [2478-2500] | 3'UTR |
| 176 | UUGCCUGUUAUGCUUACAAAAUG | CAUUUGUAAGCAUAACAGGCAA | | [2477-2499] | 3'UTR |
| 177 | CUUGCCUGUUAUGCUUACAAAAU | AUUUGUAAGCAUAACAGGCAAG | | [2476-2498] | 3'UTR |
| 178 | UCUUGCCUGUUAUGCUUACAAAA | UUUUGUAAGCAUAACAGGCAAGA | | [2475-2497] | 3'UTR |
| 179 | AGGUAGGCUUGGUAAUAGACUAU | AUAGUCUAUUACCAAGCCUACCU | | [1097-1119] | 3'UTR |
| 180 | CAGGUAGGCUUGGUAAUAGACUA | UAGUCUAUUACCAAGCCUACCUG | | [1096-1118] | 3'UTR |
| 181 | UCAGGUAGGCUUGGUAAUAGACU | AGUCUAUUACCAAGCCUACCUGA | | [1095-1117] | 3'UTR |
| 182 | UUCAGGUAGGCUUGGUAAUAGAC | GUCUAUUACCAAGCCUACCUGAA | | [1094-1116] | 3'UTR |
| 183 | UUUCAGGUAGGCUUGGUAAUAGA | UCUAUUACCAAGCCUACCUGAAA | | [1093-1115] | 3'UTR |
| 184 | GAUGAAUACCUGUGAGGAUAGGA | UCCUAUCCUCACAGGUAUUCAUC | | [1585-1607] | 3'UTR |
| 185 | UGAUGAAUACCUGUGAGGAUAGG | CCUAUCCUCACAGGUAUUCAUCA | | [1584-1606] | 3'UTR |
| 186 | AUGAUGAAUACCUGUGAGGAUAG | CUAUCCUCACAGGUAUUCAUCAU | | [1583-1605] | 3'UTR |
| 187 | AAUGAUGAAUACCUGUGAGGAUA | UAUCCUCACAGGUAUUCAUCAUU | | [1582-1604] | 3'UTR |
| 188 | CUGUCACUAGGGAAUAAUAAAGG | CCUUUAUUAUUCCCUAGUGACAG | | [1929-1951] | 3'UTR |
| 189 | CCUGUCACUAGGGAAUAAUAAAG | CUUUAUUAUUCCCUAGUGACAGG | | [1928-1950] | 3'UTR |
| 190 | ACCUGUCACUAGGGAAUAAUAAA | UUUAUUAUUCCCUAGUGACAGGU | | [1927-1949] | 3'UTR |
| 191 | UACCUGUCACUAGGGAAUAAUAA | UUAUUAUUCCCUAGUGACAGGUA | | [1926-1948] | 3'UTR |
| 192 | AUACCUGUCACUAGGGAAUAAUA | UAUUAUUCCCUAGUGACAGGUAU | | [1925-1947] | 3'UTR |
| 193 | GUUUUAAAGAGGCAACAAAAGCU | AGCUUUUGUUGCCUCUUUAAAAC | | [1404-1426] | 3'UTR |
| 194 | UGUUUUAAAGAGGCAACAAAAGC | GCUUUUGUUGCCUCUUUAAAACA | | [1403-1425] | 3'UTR |
| 195 | AUGUUUUAAAGAGGCAACAAAAG | CUUUUGUUGCCUCUUUAAAACAU | | [1402-1424] | 3'UTR |
| 196 | AAUGUUUUAAAGAGGCAACAAAA | UUUUGUUGCCUCUUUAAAACAUU | | [1401-1423] | 3'UTR |
| 197 | UAAUGUUUUAAAGAGGCAACAAA | UUUGUUGCCUCUUUAAAACAUUA | | [1400-1422] | 3'UTR |

TABLE E-continued additional 23 mers

| Number | Sense siRNA | AntiSense siRNA | Other Sp | Hum-34222182 ORF: 204-785 |
|---|---|---|---|---|
| 198 | GUGUUCUAACAAACUAAACUCUU | AAGAGUUUAGUUUGUUAGAACAC | | [2246-2268] 3'UTR |
| 199 | AGUGUUCUAACAAACUAAACUCU | AGAGUUUAGUUUGUUAGAACACU | | [2245-2267] 3'UTR |
| 200 | GCUUGGUAAUAGACUAUAUAAAC | GUUUAUAGUCUAUUACCAAGC | | [1103-1125] 3'UTR |
| 201 | GGCUUGGUAAUAGACUAUAUAAA | UUUAUAGUCUAUUACCAAGCC | | [1102-1124] 3'UTR |
| 202 | AGGCUUGGUAAUAGACUAUAUA | UUAUAGUCUAUUACCAAGCCU | | [1101-1123] 3'UTR |
| 203 | UAGGCUUGGUAAUAGACUAUAUA | UAUAUAGUCUAUUACCAAGCCUA | | [1100-1122] 3'UTR |
| 204 | GUAGGCUUGGUAAUAGACUAUAU | AUAUAGUCUAUUACCAAGCCUAC | | [1099-1121] 3'UTR |
| 205 | CAUCCUGGUGUUACUGAAAAACA | UGUUUUCAGUAACACCAGGAUG | | [2164-2186] 3'UTR |
| 206 | UCAUCCUGGUGUUACUGAAAAAC | GUUUUCAGUAACACCAGGAUGA | | [2163-2185] 3'UTR |
| 207 | UUCAUCCUGGUGUUACUGAAAAA | UUUUCAGUAACACCAGGAUGAA | | [2162-2184] 3'UTR |
| 208 | AUUCAUCCUGGUGUUACUGAAAA | UUUUCAGUAACACCAGGAUGAAU | | [2161-2183] 3'UTR |
| 209 | UAUUCAUCCUGGUGUUACUGAAA | UUUCAGUAACACCAGGAUGAAUA | | [2160-2182] 3'UTR |
| 210 | GCCUAUCAAACUUCCAAAAGCC | GGCUUUUGGAAGUUUUGAUAGGC | | [1218-1240] 3'UTR |
| 211 | AGCCUAUCAAACUUCCAAAAGC | GCUUUUGGAAGUUUUGAUAGGCU | | [1217-1239] 3'UTR |
| 212 | UAGCCUAUCAAACUUCCAAAAG | CUUUUGGAAGUUUUGAUAGGCUA | | [1216-1238] 3'UTR |
| 213 | UUAGCCUAUCAAACUUCCAAAA | UUUUGGAAGUUUUGAUAGGCUAA | | [1215-1237] 3'UTR |
| 214 | UUUAGCCUAUCAAACUUCCAAA | UUUGGAAGUUUUGAUAGGCUAAA | | [1214-1236] 3'UTR |
| 215 | UCCUGGUGUUACUGAAAAACAGG | CCUGUUUUCAGUAACACCAGGA | | [2166-2188] 3'UTR |
| 216 | AUCCUGGUGUUACUGAAAAACAG | CUGUUUUCAGUAACACCAGGAU | | [2165-2187] 3'UTR |
| 217 | CCACGGUGUUGUUUUAGAUGCCU | AGGCAUCUAAAACAACACCGUGG | | [1446-1468] 3'UTR |
| 218 | ACCACGGUGUUGUUUUAGAUGCC | GGCAUCUAAAACAACACCGUGGU | | [1445-1467] 3'UTR |
| 219 | AACCACGGUGUUGUUUUAGAUGC | GCAUCUAAAACAACACCGUGGUU | | [1444-1466] 3'UTR |
| 220 | UAACCACGGUGUUGUUUUAGAUG | CAUCUAAAACAACACCGUGGUUA | | [1443-1465] 3'UTR |
| 221 | GUAACCACGGUGUUGUUUUAGAU | AUCUAAAACAACACCGUGGUUAC | | [1442-1464] 3'UTR |
| 222 | ACAAAAUGGUGAUGGCUUAUGGA | UCCAUAAGCCAUCACCAUUUUGU | | [2492-2514] 3'UTR |
| 223 | UACAAAAUGGUGAUGGCUUAUGG | CCAUAAGCCAUCACCAUUUUGUA | | [2491-2513] 3'UTR |
| 224 | UUACAAAAUGGUGAUGGCUUAUG | CAUAAGCCAUCACCAUUUUGUAA | | [2490-2512] 3'UTR |
| 225 | CUUACAAAAUGGUGAUGGCUUAU | AUAAGCCAUCACCAUUUUGUAAG | | [2489-2511] 3'UTR |
| 226 | GCUUACAAAAUGGUGAUGGCUUA | UAAGCCAUCACCAUUUUGUAAGC | | [2488-2510] 3'UTR |
| 227 | GCAGUUUGAGCAGCAAGAACCCG | CGGGUUCUUGCUGCUCAAACUGC | Chimp | [217-239] ORF |
| 228 | GGCAGUUUGAGCAGCAAGAACCC | GGGUUCUUGCUGCUCAAACUGCC | Chimp | [216-238] ORF |
| 229 | UGGCAGUUUGAGCAGCAAGAACC | GGUUCUUGCUGCUCAAACUGCCA | Chimp | [215-237] ORF |
| 230 | CUGGCAGUUUGAGCAGCAAGAAC | GUUCUUGCUGCUCAAACUGCCAG | Chimp | [214-236] ORF |
| 231 | ACUGGCAGUUUGAGCAGCAAGAA | UUCUUGCUGCUCAAACUGCCAGU | Chimp | [213-235] ORF |
| 232 | CUUGGAAAGAUACUACAAAGCCA | UGGCUUUGUAGUAUCUUUCCAAG | | [2275-2297] 3'UTR |
| 233 | GUGUGAUUCUAGCGUCGUACCUA | UAGGUACGACGCUAGAAUCACAC | | [578-600] ORF |
| 234 | UGUGUGAUUCUAGCGUCGUACCU | AGGUACGACGCUAGAAUCACACA | | [577-599] ORF |

TABLE E-continued additional 23 mers

| Number | Sense siRNA | AntiSense siRNA | Other Sp | Hum-34222182 ORF: 204-785 | |
|---|---|---|---|---|---|
| 235 | GUGUGUGAUUCUAGCGUCGUACC | GGUACGACGCUAGAAUCACACAC | | [576-598] | ORF |
| 236 | UGUGUGAUUCUAGCGUCGUAC | GUACGACGCUAGAAUCACACACA | | [575-597] | ORF |
| 237 | UUGUGUGAUUCUAGCGUCGUA | UACGACGCUAGAAUCACACACAA | | [574-596] | ORF |
| 238 | CUUGGGCAUCGAUGUAGAACUGU | ACAGUUCUACAUCGAUGCCCAAG | | [2419-2441] | 3'UTR |
| 239 | UCUUGGGCAUCGAUGUAGAACUG | CAGUUCUACAUCGAUGCCCAAGA | | [2418-2440] | 3'UTR |
| 240 | UUCUUGGGCAUCGAUGUAGAACU | AGUUCUACAUCGAUGCCCAAGAA | | [2417-2439] | 3'UTR |
| 241 | CUUCUUGGGCAUCGAUGUAGAAC | GUUCUACAUCGAUGCCCAAGAAG | | [2416-2438] | 3'UTR |
| 242 | GCUUCUUGGGCAUCGAUGUAGAA | UUCUACAUCGAUGCCCAAGAAGC | | [2415-2437] | 3'UTR |
| 243 | CUCUGGGCUUUUCUGGGAAUUGA | UCAAUUCCCAGAAAAGCCCAGAG | | [1721-1743] | 3'UTR |
| 244 | AACUGUCUGUCCAAAUCAAAGCA | UGCUUUGAUUUGGACAGACAGUU | Dog, Chimp | [390-412] | ORF |
| 245 | GAACUGUCUGUCCAAAUCAAAGC | GCUUUGAUUUGGACAGACAGUUC | Dog, Chimp | [389-411] | ORF |
| 246 | AGAACUGUCUGUCCAAAUCAAAG | CUUUGAUUUGGACAGACAGUUCU | Dog, Chimp | [388-410] | ORF |
| 247 | GAGAACUGUCUGUCCAAAUCAAA | UUUGAUUUGGACAGACAGUUCUC | Dog, Chimp | [387-409] | ORF |
| 248 | GAAGGGUCCUAAAAAGGGAAAAU | AUUUUCCCUUUUUAGGACCCUUC | | [774-796] | ORF + 3'UTR |
| 249 | UGAAGGGUCCUAAAAAGGGAAAA | UUUUCCCUUUUUAGGACCCUUCA | | [773-795] | ORF + 3'UTR |
| 250 | UUGAAGGGUCCUAAAAAGGGAAA | UUUCCCUUUUUAGGACCCUUCAA | | [772-794] | ORF + 3'UTR |
| 251 | AUUGAAGGGUCCUAAAAAGGGAA | UUCCCUUUUUAGGACCCUUCAAU | | [771-793] | ORF + 3'UTR |
| 252 | AAAGCUUAACCCUAGGUAAGAGU | ACUCUUACCUAGGGUUAAGCUUU | | [1315-1337] | 3'UTR |
| 253 | UAAAGCUUAACCCUAGGUAAGAG | CUCUUACCUAGGGUUAAGCUUUA | | [1314-1336] | 3'UTR |
| 254 | UUAAAGCUUAACCCUAGGUAAGA | UCUUACCUAGGGUUAAGCUUUAA | | [1313-1335] | 3'UTR |
| 255 | AUUAAAGCUUAACCCUAGGUAAG | CUUACCUAGGGUUAAGCUUUAAU | | [1312-1334] | 3'UTR |
| 256 | AAUUAAAGCUUAACCCUAGGUAA | UUACCUAGGGUUAAGCUUUAAUU | | [1311-1333] | 3'UTR |
| 257 | ACAUGUGCUUAAUCUCAGAUGAA | UUCAUCUGAGAUUAAGCACAUGU | | [1670-1692] | 3'UTR |
| 258 | UACAUGUGCUUAAUCUCAGAUGA | UCAUCUGAGAUUAAGCACAUGUA | | [1669-1691] | 3'UTR |
| 259 | UUACAUGUGCUUAAUCUCAGAUG | CAUCUGAGAUUAAGCACAUGUAA | | [1668-1690] | 3'UTR |
| 260 | AUUACAUGUGCUUAAUCUCAGAU | AUCUGAGAUUAAGCACAUGUAAU | | [1667-1689] | 3'UTR |
| 261 | UAUUACAUGUGCUUAAUCUCAGA | UCUGAGAUUAAGCACAUGUAAUA | | [1666-1688] | 3'UTR |
| 262 | GAAUCAACUUGCCAGAAUUUGGU | ACCAAAUUCUGGCAAGUUGAUUC | Chimp | [354-376] | ORF |
| 263 | GGAAUCAACUUGCCAGAAUUUGG | CCAAAUUCUGGCAAGUUGAUUCC | Chimp | [353-375] | ORF |
| 264 | AGGAAUCAACUUGCCAGAAUUUG | CAAAUUCUGGCAAGUUGAUUCCU | Chimp | [352-374] | ORF |
| 265 | GAGGAAUCAACUUGCCAGAAUUU | AAAUUCUGGCAAGUUGAUUCCUC | Chimp | [351-373] | ORF |
| 266 | UGAGGAAUCAACUUGCCAGAAUU | AAUUCUGGCAAGUUGAUUCCUCA | Chimp | [350-372] | ORF |
| 267 | UCCUCACUCUAAUGUUUUAAAGA | UCUUUAAAACAUUAGAGUGAGGA | | [1391-1413] | 3'UTR |
| 268 | UUCCUCACUCUAAUGUUUUAAAG | CUUUAAAACAUUAGAGUGAGGAA | | [1390-1412] | 3'UTR |
| 269 | CUUCCUCACUCUAAUGUUUUAAA | UUUAAAACAUUAGAGUGAGGAAG | | [1389-1411] | 3'UTR |
| 270 | ACUUCCUCACUCUAAUGUUUUAA | UUAAAACAUUAGAGUGAGGAAGU | | [1388-1410] | 3'UTR |
| 271 | GACUUCCUCACUCUAAUGUUUUA | UAAAACAUUAGAGUGAGGAAGUC | | [1387-1409] | 3'UTR |

TABLE E-continued additional 23 mers

| Number | Sense siRNA | AntiSense siRNA | Other Sp | Hum-34222182 ORF: 204-785 | |
|---|---|---|---|---|---|
| 272 | GAAAGAUACUACAAAGCCAAUCU | AGAUUGGCUUUGUAGUAUCUUUC | | [2279-2301] | 3'UTR |
| 273 | GGAAAGAUACUACAAAGCCAAUC | GAUUGGCUUUGUAGUAUCUUUCC | | [2278-2300] | 3'UTR |
| 274 | UGGAAAGAUACUACAAAGCCAAU | AUUGGCUUUGUAGUAUCUUUCCA | | [2277-2299] | 3'UTR |
| 275 | UUGGAAAGAUACUACAAAGCCAA | UUGGCUUUGUAGUAUCUUUCCAA | | [2276-2298] | 3'UTR |
| 276 | AAGGGUUUUUAGACAGGAAGGUA | UACCUUCCUGUCUAAAAACCCUU | | [1269-1291] | 3'UTR |
| 277 | GAAGGGUUUUUAGACAGGAAGGU | ACCUUCCUGUCUAAAAACCCUUC | | [1268-1290] | 3'UTR |
| 278 | UGAAGGGUUUUUAGACAGGAAGG | CCUUCCUGUCUAAAAACCCUUCA | | [1267-1289] | 3'UTR |
| 279 | UUGAAGGGUUUUUAGACAGGAAG | CUUCCUGUCUAAAAACCCUUCAA | | [1266-1288] | 3'UTR |
| 280 | UUUGAAGGGUUUUUAGACAGGAA | UUCCUGUCUAAAAACCCUUCAAA | | [1265-1287] | 3'UTR |
| 281 | GUAUUCAUCCUGGUGUUACUGAA | UUCAGUAACACCAGGAUGAAUAC | | [2159-2181] | 3'UTR |
| 282 | CCUGUUACUGAUACUAUAAGUGA | UCACUUAUAGUAUCAGUAACAGG | | [2195-2217] | 3'UTR |
| 283 | GGAGAUAUGGUUUAUAGUACAGC | GCUGUACUAUAAACCAUAUCUCC | | [1841-1863] | 3'UTR |
| 284 | UGGAGAUAUGGUUUAUAGUACAG | CUGUACUAUAAACCAUAUCUCCA | | [1840-1862] | 3'UTR |
| 285 | AUGGAGAUAUGGUUUAUAGUACA | UGUACUAUAAACCAUAUCUCCAU | | [1839-1861] | 3'UTR |
| 286 | UAUGGAGAUAUGGUUUAUAGUAC | GUACUAUAAACCAUAUCUCCAUA | | [1838-1860] | 3'UTR |
| 287 | CUAUGGAGAUAUGGUUUAUAGUA | UACUAUAAACCAUAUCUCCAUAG | | [1837-1859] | 3'UTR |
| 288 | CAUAGAUCCCAUUUUUGUACAGA | UCUGUACAAAAAUGGGAUCUAUG | | [999-1021] | 3'UTR |
| 289 | GCAUAGAUCCCAUUUUUGUACAG | CUGUACAAAAAUGGGAUCUAUGC | | [998-1020] | 3'UTR |
| 290 | UGCAUAGAUCCCAUUUUUGUACA | UGUACAAAAAUGGGAUCUAUGCA | | [997-1019] | 3'UTR |
| 291 | CUGCAUAGAUCCCAUUUUUGUAC | GUACAAAAAUGGGAUCUAUGCAG | | [996-1018] | 3'UTR |
| 292 | UCUGCAUAGAUCCCAUUUUUGUA | UACAAAAAUGGGAUCUAUGCAGA | | [995-1017] | 3'UTR |
| 293 | GAAUUGAAUGGGAUGGAAUAGGU | ACCUAUUCCAUCCCAUUCAAUUC | | [1020-1042] | 3'UTR |
| 294 | AGAAUUGAAUGGGAUGGAAUAGG | CCUAUUCCAUCCCAUUCAAUUCU | | [1019-1041] | 3'UTR |
| 295 | CAGAAUUGAAUGGGAUGGAAUAG | CUAUUCCAUCCCAUUCAAUUCUG | | [1018-1040] | 3'UTR |
| 296 | ACAGAAUUGAAUGGGAUGGAAUA | UAUUCCAUCCCAUUCAAUUCUGU | | [1017-1039] | 3'UTR |
| 297 | CUGUGAGGAUAGGAAAUUAGUUC | GAACUAAUUUCCUAUCCUCACAG | | [1594-1616] | 3'UTR |
| 298 | CCUGUGAGGAUAGGAAAUUAGUU | AACUAAUUUCCUAUCCUCACAGG | | [1593-1615] | 3'UTR |
| 299 | ACCUGUGAGGAUAGGAAAUUAGU | ACUAAUUUCCUAUCCUCACAGGU | | [1592-1614] | 3'UTR |
| 300 | UACCUGUGAGGAUAGGAAAUUAG | CUAAUUUCCUAUCCUCACAGGUA | | [1591-1613] | 3'UTR |
| 301 | AUACCUGUGAGGAUAGGAAAUUA | UAAUUUCCUAUCCUCACAGGUAU | | [1590-1612] | 3'UTR |
| 302 | ACCCUAGGUAAGAGUAAAUGAGA | UCUCAUUUACUCUUACCUAGGGU | | [1323-1345] | 3'UTR |
| 303 | AACCCUAGGUAAGAGUAAAUGAG | CUCAUUUACUCUUACCUAGGGUU | | [1322-1344] | 3'UTR |
| 304 | UAACCCUAGGUAAGAGUAAAUGA | UCAUUUACUCUUACCUAGGGUUA | | [1321-1343] | 3'UTR |
| 305 | UCAAAUGCUUGGAAAGAUACUAC | GUAGUAUCUUUCCAAGCAUUUGA | | [2268-2290] | 3'UTR |
| 306 | UUCAAAUGCUUGGAAAGAUACUA | UAGUAUCUUUCCAAGCAUUUGAA | | [2267-2289] | 3'UTR |
| 307 | CUUCAAAUGCUUGGAAAGAUACU | AGUAUCUUUCCAAGCAUUUGAAG | | [2266-2288] | 3'UTR |
| 308 | UCUUCAAAUGCUUGGAAAGAUAC | GUAUCUUUCCAAGCAUUUGAAGA | | [2265-2287] | 3'UTR |

TABLE E-continued additional 23 mers

| Number | Sense siRNA | AntiSense siRNA | Other Sp | Hum-34222182 ORF: 204-785 |
|---|---|---|---|---|
| 309 | CUCUUCAAAUGCUUGGAAAGAUA | UAUCUUUCCAAGCAUUUGAAGAG | | [2264-2286] 3'UTR |
| 310 | GGAGAAGUGAUUCAAAAUAGUGU | ACACUAUUUUGAAUCACUUCUCC | | [966-988] 3'UTR |
| 311 | UGGAGAAGUGAUUCAAAAUAGUG | CACUAUUUUGAAUCACUUCUCCA | | [965-987] 3'UTR |
| 312 | UUGGAGAAGUGAUUCAAAAUAGU | ACUAUUUUGAAUCACUUCUCCAA | | [964-986] 3'UTR |
| 313 | UUUGGAGAAGUGAUUCAAAAUAG | CUAUUUUGAAUCACUUCUCCAAA | | [963-985] 3'UTR |
| 314 | CUUUGGAGAAGUGAUUCAAAAUA | UAUUUUGAAUCACUUCUCCAAAG | | [962-984] 3'UTR |
| 315 | CGUGGAUAAGGAGCUUAUUCAGG | CCUGAAUAAGCUCCUUAUCCACG | | [2078-2100] 3'UTR |
| 316 | UCGUGGAUAAGGAGCUUAUUCAG | CUGAAUAAGCUCCUUAUCCACGA | | [2077-2099] 3'UTR |
| 317 | GUCGUGGAUAAGGAGCUUAUUCA | UGAAUAAGCUCCUUAUCCACGAC | | [2076-2098] 3'UTR |
| 318 | GGUCGUGGAUAAGGAGCUUAUUC | GAAUAAGCUCCUUAUCCACGACC | | [2075-2097] 3'UTR |
| 319 | GGGUCGUGGAUAAGGAGCUUAUU | AAUAAGCUCCUUAUCCACGACCC | | [2074-2096] 3'UTR |
| 320 | CCAGAUUUGCCUAUUUUGAUUUU | AAAAUCAAAAUAGGCAAAUCUGG | | [1125-1147] 3'UTR |
| 321 | ACCAGAUUUGCCUAUUUUGAUUU | AAAUCAAAAUAGGCAAAUCUGGU | | [1124-1146] 3'UTR |
| 322 | AACCAGAUUUGCCUAUUUUGAUU | AAUCAAAAUAGGCAAAUCUGGUU | | [1123-1145] 3'UTR |
| 323 | AAACCAGAUUUGCCUAUUUUGAU | AUCAAAAUAGGCAAAUCUGGUUU | | [1122-1144] 3'UTR |
| 324 | UAAACCAGAUUUGCCUAUUUUGA | UCAAAAUAGGCAAAUCUGGUUUA | | [1121-1143] 3'UTR |
| 325 | CCUUUGGAGAAGUGAUUCAAAAU | AUUUUGAAUCACUUCUCCAAAGG | | [961-983] 3'UTR |
| 326 | GCCUUUGGAGAAGUGAUUCAAAA | UUUUGAAUCACUUCUCCAAAGGC | | [960-982] 3'UTR |
| 327 | UUGAGGAAUCAACUUGCCAGAAU | AUUCUGGCAAGUUGAUUCCUCAA | Chimp | [349-371] ORF |
| 328 | UUUGAGGAAUCAACUUGCCAGAA | UUCUGGCAAGUUGAUUCCUCAAA | Chimp | [348-370] ORF |
| 329 | AUUUGAGGAAUCAACUUGCCAGA | UCUGGCAAGUUGAUUCCUCAAAU | Chimp | [347-369] ORF |
| 330 | GAGAAAUAUUACGGCAAUAAUGG | CCAUUAUUGCCGUAAUAUUUCUC | | [1342-1364] 3'UTR |
| 331 | UGAGAAAUAUUACGGCAAUAAUG | CAUUAUUGCCGUAAUAUUUCUCA | | [1341-1363] 3'UTR |
| 332 | AUGAGAAAUAUUACGGCAAUAAU | AUUAUUGCCGUAAUAUUUCUCAU | | [1340-1362] 3'UTR |
| 333 | AAUGAGAAAUAUUACGGCAAUAA | UUAUUGCCGUAAUAUUUCUCAUU | | [1339-1361] 3'UTR |
| 334 | AAAUGAGAAAUAUUACGGCAAUA | UAUUGCCGUAAUAUUUCUCAUUU | | [1338-1360] 3'UTR |
| 335 | UACAGAAUUGAAUGGGAUGGAAU | AUUCCAUCCCAUUCAAUUCUGUA | | [1016-1038] 3'UTR |
| 336 | GUACAGAAUUGAAUGGGAUGGAA | UUCCAUCCCAUUCAAUUCUGUAC | | [1015-1037] 3'UTR |
| 337 | AUGGAAUAGGUAAGCAAAAGUAG | CUACUUUUGCUUACCUAUUCCAU | | [1032-1054] 3'UTR |
| 338 | GUAAAAGCUGGAUAGGAUUGUG | CACAAUCCUAUCCAGCUUUUUAC | Chin, GP, Chimp, Rat, Ms | [556-578] ORF |
| 339 | UGUAAAAGCUGGAUAGGAUUGU | ACAAUCCUAUCCAGCUUUUUACA | Chin, GP, Chimp, Rat, Ms | [555-577] ORF |
| 340 | AUGUAAAAGCUGGAUAGGAUUG | CAAUCCUAUCCAGCUUUUUACAU | Chin, GP, Chimp, Rat, Ms | [554-576] ORF |
| 341 | UAUGUAAAAGCUGGAUAGGAUU | AAUCCUAUCCAGCUUUUUACAUA | Chin, GP, Chimp, Rat, Ms | [553-575] ORF |
| 342 | GUAUGUAAAAGCUGGAUAGGAU | AUCCUAUCCAGCUUUUUACAUAC | Chin, GP, Chimp, Rat, Ms | [552-574] ORF |
| 343 | CCACCAGUUCCUGACUCAAAUUU | AAAUUUGAGUCAGGAACUGGUGG | | [1245-1267] 3'UTR |
| 344 | ACCACCAGUUCCUGACUCAAAUU | AAUUUGAGUCAGGAACUGGUGGU | | [1244-1266] 3'UTR |
| 345 | CACCACCAGUUCCUGACUCAAAU | AUUUGAGUCAGGAACUGGUGGUG | | [1243-1265] 3'UTR |

TABLE E-continued additional 23 mers

| Number | Sense siRNA | AntiSense siRNA | Other Sp | Hum-34222182 ORF: 204-785 |
|---|---|---|---|---|
| 346 | ACACCACCAGUUCCUGACUCAAA | UUUGAGUCAGGAACUGGUGGUGU | | [1242-1264] 3'UTR |
| 347 | CACACCACCAGUUCCUGACUCAA | UUGAGUCAGGAACUGGUGGUGUG | | [1241-1263] 3'UTR |
| 348 | CAAAUUAGCCAGUGUUCUAACAA | UUGUUAGAACACUGGCUAAUUUG | | [2235-2257] 3'UTR |
| 349 | UCAAAUUAGCCAGUGUUCUAACA | UGUUAGAACACUGGCUAAUUUGA | | [2234-2256] 3'UTR |
| 350 | UUCAAAUUAGCCAGUGUUCUAAC | GUUAGAACACUGGCUAAUUUGAA | | [2233-2255] 3'UTR |
| 351 | GUUCAAAUUAGCCAGUGUUCUAA | UUAGAACACUGGCUAAUUUGAAC | | [2232-2254] 3'UTR |
| 352 | UGUUCAAAUUAGCCAGUGUUCUA | UAGAACACUGGCUAAUUUGAACA | | [2231-2253] 3'UTR |
| 353 | CACCUGCCCUAAAUAAGAAACCC | GGGUUUCUUAUUUAGGGCAGGUG | | [869-891] 3'UTR |
| 354 | CUCACUGAUUGGAACAACAGUGA | UCACUGUUGUUCCAAUCAGUGAG | | [749-771] ORF |
| 355 | ACUCACUGAUUGGAACAACAGUG | CACUGUUGUUCCAAUCAGUGAGU | | [748-770] ORF |
| 356 | UACUCACUGAUUGGAACAACAGU | ACUGUUGUUCCAAUCAGUGAGUA | | [747-769] ORF |
| 357 | UUACUCACUGAUUGGAACAACAG | CUGUUGUUCCAAUCAGUGAGUAA | | [746-768] ORF |
| 358 | UUUACUCACUGAUUGGAACAACA | UGUUGUUCCAAUCAGUGAGUAAA | | [745-767] ORF |
| 359 | AUGCUGGAGAACUGUCUGUCCAA | UUGGACAGACAGUUCUCCAGCAU | Dog, GP, Chimp, Rat | [381-403] ORF |
| 360 | UUUAUAGAAUUGGGCCAAGAUAA | UUAUCUUGGCCCAAUUCUAUAAA | | [2301-2323] 3'UTR |
| 361 | ACUCUUCAAAUGCUUGGAAAGAU | AUCUUUCCAAGCAUUUGAAGAGU | | [2263-2285] 3'UTR |
| 362 | AACUCUUCAAAUGCUUGGAAAGA | UCUUUCCAAGCAUUUGAAGAGUU | | [2262-2284] 3'UTR |
| 363 | AAACUCUUCAAAUGCUUGGAAAG | CUUUCCAAGCAUUUGAAGAGUUU | | [2261-2283] 3'UTR |
| 364 | UAAACUCUUCAAAUGCUUGGAAA | UUUCCAAGCAUUUGAAGAGUUUA | | [2260-2282] 3'UTR |
| 365 | UCUUGGUGACUUCCUCACUCUAA | UUAGAGUGAGGAAGUCACCAAGA | | [1380-1402] 3'UTR |
| 366 | GAGAACUGCUCAUGGACUAGCUU | AAGCUAGUCCAUGAGCAGUUCUC | Dog, Chimp | [630-652] ORF |
| 367 | GGAGAACUGCUCAUGGACUAGCU | AGCUAGUCCAUGAGCAGUUCUCC | Dog, Chimp | [629-651] ORF |
| 368 | AGGAGAACUGCUCAUGGACUAGC | GCUAGUCCAUGAGCAGUUCUCCU | Dog, Chimp | [628-650] ORF |
| 369 | CAGGAGAACUGCUCAUGGACUAG | CUAGUCCAUGAGCAGUUCUCCUG | Dog, Chimp | [627-649] ORF |
| 370 | GCAGGAGAACUGCUCAUGGACUA | UAGUCCAUGAGCAGUUCUCCUGC | Dog, Chimp | [626-648] ORF |
| 371 | UGUGGGUCGUGGAUAAGGAGCUU | AAGCUCCUUAUCCACGACCCACA | | [2071-2093] 3'UTR |
| 372 | CUGUGGGUCGUGGAUAAGGAGCU | AGCUCCUUAUCCACGACCCACAG | | [2070-2092] 3'UTR |
| 373 | GCUGUGGGUCGUGGAUAAGGAGC | GCUCCUUAUCCACGACCCACAGC | | [2069-2091] 3'UTR |
| 374 | GUGACCUAAAAUGUCACUGUUCA | UGAACAGUGACAUUUUAGGUCAC | | [2214-2236] 3'UTR |
| 375 | GAGAAACUGACCCAGAGAAUUGC | GCAAUUCUCUGGGUCAGUUUCUC | Chin, GP, Chimp, Rat, Ms | [447-469] ORF |
| 376 | UGAGAAACUGACCCAGAGAAUUG | CAAUUCUCUGGGUCAGUUUCUCA | Chin, GP, Chimp, Rat, Ms | [446-468] ORF |
| 377 | CUGAGAAACUGACCCAGAGAAUU | AAUUCUCUGGGUCAGUUUCUCAG | Chin, GP, Chimp, Rat, Ms | [445-467] ORF |
| 378 | CCUGAGAAACUGACCCAGAGAAU | AUUCUCUGGGUCAGUUUCUCAGG | Chin, GP, Chimp, Rat, Ms | [444-466] ORF |
| 379 | CCCUGAGAAACUGACCCAGAGAA | UUCUCUGGGUCAGUUUCUCAGGG | Chin, GP, Chimp, Rat, Ms | [443-465] ORF |
| 380 | CACCAGUUCCUGACUCAAAUUUG | CAAAUUUGAGUCAGGAACUGGUG | | [1246-1268] 3'UTR |
| 381 | UCAAAGGUCCUUGUCCCUGAGAA | UUCUCAGGGACAAGGACCUUUGA | Chimp | [429-451] ORF |
| 382 | CUCAAAGGUCCUUGUCCCUGAGA | UCUCAGGGACAAGGACCUUUGAG | Chimp | [428-450] ORF |

TABLE E-continued additional 23 mers

| Number | Sense siRNA | AntiSense siRNA | Other Sp | Hum-34222182 ORF: 204-785 |
|---|---|---|---|---|
| 383 | GCUCAAAGGUCCUUGUCCCUGAG | CUCAGGGACAAGGACCUUUGAGC | Chimp | [427-449] ORF |
| 384 | UGCUCAAAGGUCCUUGUCCCUGA | UCAGGGACAAGGACCUUUGAGCA | Chimp | [426-448] ORF |
| 385 | GAUUUCGACUUGUUAAGAAAAAA | UUUUUUCUUAACAAGUCGAAAUC | Rat | [721-743] ORF |
| 386 | GGAUUUCGACUUGUUAAGAAAAA | UUUUUCUUAACAAGUCGAAAUCC | Rat | [720-742] ORF |
| 387 | AGGAUUUCGACUUGUUAAGAAAA | UUUUCUUAACAAGUCGAAAUCCU | Rat | [719-741] ORF |
| 388 | UGAGUGAAUGAUGAAUACCUGUG | CACAGGUAUUCAUCAUUCACUCA | | [1576-1598] 3'UTR |
| 389 | UUGAGUGAAUGAUGAAUACCUGU | ACAGGUAUUCAUCAUUCACUCAA | | [1575-1597] 3'UTR |
| 390 | AUUGAGUGAAUGAUGAAUACCUG | CAGGUAUUCAUCAUUCACUCAAU | | [1574-1596] 3'UTR |
| 391 | CAUUGAGUGAAUGAUGAAUACCU | AGGUAUUCAUCAUUCACUCAAUG | | [1573-1595] 3'UTR |
| 392 | CAAUAAUGGAACUGCUUCACUGU | ACAGUGAAGCAGUUCCAUUAUUG | | [1356-1378] 3'UTR |
| 393 | GCAAUAAUGGAACUGCUUCACUG | CAGUGAAGCAGUUCCAUUAUUGC | | [1355-1377] 3'UTR |
| 394 | GGCAAUAAUGGAACUGCUUCACU | AGUGAAGCAGUUCCAUUAUUGCC | | [1354-1376] 3'UTR |
| 395 | CGGCAAUAAUGGAACUGCUUCAC | GUGAAGCAGUUCCAUUAUUGCCG | | [1353-1375] 3'UTR |
| 396 | ACGGCAAUAAUGGAACUGCUUCA | UGAAGCAGUUCCAUUAUUGCCGU | | [1352-1374] 3'UTR |
| 397 | CACUAACAGUUAUCUUUGACUCU | AGAGUCAAAGAUAACUGUUAGUG | | [2453-2475] 3'UTR |
| 398 | CCACUAACAGUUAUCUUUGACUC | GAGUCAAAGAUAACUGUUAGUGG | | [2452-2474] 3'UTR |
| 399 | UCCACUAACAGUUAUCUUUGACU | AGUCAAAGAUAACUGUUAGUGGA | | [2451-2473] 3'UTR |
| 400 | UUCCACUAACAGUUAUCUUUGAC | GUCAAAGAUAACUGUUAGUGGAA | | [2450-2472] 3'UTR |
| 401 | UUUCCACUAACAGUUAUCUUUGA | UCAAAGAUAACUGUUAGUGGAAA | | [2449-2471] 3'UTR |
| 402 | GCGUCGUACCUACUUUUGAGCUU | AAGCUCAAAAGUAGGUACGACGC | | [589-611] ORF |
| 403 | AGCGUCGUACCUACUUUUGAGCU | AGCUCAAAAGUAGGUACGACGCU | | [588-610] ORF |
| 404 | UAGCGUCGUACCUACUUUUGAGC | GCUCAAAAGUAGGUACGACGCUA | | [587-609] ORF |
| 405 | CUAGCGUCGUACCUACUUUUGAG | CUCAAAAGUAGGUACGACGCUAG | | [586-608] ORF |
| 406 | UCUAGCGUCGUACCUACUUUUGA | UCAAAAGUAGGUACGACGCUAGA | | [585-607] ORF |
| 407 | CGGCCAGCAUUUCAGAAUUGCUG | CAGCAAUUCUGAAAUGCUGGCCG | Chimp | [238-260] ORF |
| 408 | CCGGCCAGCAUUUCAGAAUUGCU | AGCAAUUCUGAAAUGCUGGCCGG | Chimp | [237-259] ORF |
| 409 | CCCGGCCAGCAUUUCAGAAUUGC | GCAAUUCUGAAAUGCUGGCCGGG | Chimp | [236-258] ORF |
| 410 | ACCCGGCCAGCAUUUCAGAAUUG | CAAUUCUGAAAUGCUGGCCGGGU | Chimp | [235-257] ORF |
| 411 | AACCCGGCCAGCAUUUCAGAAUU | AAUUCUGAAAUGCUGGCCGGGUU | Chimp | [234-256] ORF |
| 412 | GUGCUUAAUCUCAGAUGAACCAU | AUGGUUCAUCUGAGAUUAAGCAC | | [1674-1696] 3'UTR |
| 413 | UGUGCUUAAUCUCAGAUGAACCA | UGGUUCAUCUGAGAUUAAGCACA | | [1673-1695] 3'UTR |
| 414 | AUGUGCUUAAUCUCAGAUGAACC | GGUUCAUCUGAGAUUAAGCACAU | | [1672-1694] 3'UTR |
| 415 | CAUGUGCUUAAUCUCAGAUGAAC | GUUCAUCUGAGAUUAAGCACAUG | | [1671-1693] 3'UTR |
| 416 | GAAUAGGUAAGCAAAAGUAGAAG | CUUCUACUUUUGCUUACCUAUUC | | [1035-1057] 3'UTR |
| 417 | GGAAUAGGUAAGCAAAAGUAGAA | UUCUACUUUUGCUUACCUAUUCC | | [1034-1056] 3'UTR |
| 418 | UGGAAUAGGUAAGCAAAAGUAGA | UCUACUUUUGCUUACCUAUUCCA | | [1033-1055] 3'UTR |
| 419 | GUUGUGUUAUGCACGUGAACUUG | CAAGUUCACGUGCAUAACACAAC | Ms | [517-539] ORF |

TABLE E-continued additional 23 mers

| Number | Sense siRNA | AntiSense siRNA | Other Sp | Hum-34222182 ORF: 204-785 |
|---|---|---|---|---|
| 420 | GGUUGUGUUAUGCACGUGAACUU | AAGUUCACGUGCAUAACACAACC | Ms | [516-538] ORF |
| 421 | AGGUUGUGUUAUGCACGUGAACU | AGUUCACGUGCAUAACACAACCU | Ms | [515-537] ORF |
| 422 | GAGGUUGUGUUAUGCACGUGAAC | GUUCACGUGCAUAACACAACCUC | Ms | [514-536] ORF |
| 423 | CGAGGUUGUGUUAUGCACGUGAA | UUCACGUGCAUAACACAACCUCG | Ms | [513-535] ORF |
| 424 | AGUACAGCCUAGAGAAUGAAACU | AGUUUCAUUCUCUAGGCUGUACU | | [1856-1878] 3'UTR |
| 425 | UAGUACAGCCUAGAGAAUGAAAC | GUUUCAUUCUCUAGGCUGUACUA | | [1855-1877] 3'UTR |
| 426 | AUAGUACAGCCUAGAGAAUGAAA | UUUCAUUCUCUAGGCUGUACUAU | | [1854-1876] 3'UTR |
| 427 | UAUAGUACAGCCUAGAGAAUGAA | UUCAUUCUCUAGGCUGUACUAUA | | [1853-1875] 3'UTR |
| 428 | UUAUAGUACAGCCUAGAGAAUGA | UCAUUCUCUAGGCUGUACUAUAA | | [1852-1874] 3'UTR |
| 429 | ACUGUCUGUCCAAAUCAAAGCAA | UUGCUUUGAUUUGGACAGACAGU | Dog, Chimp | [391-413] ORF |
| 430 | AGCUUACACUUGUGUUUAAGCAG | CUGCUUAAACACAAGUGUAAGCU | Chimp | [607-629] ORF |
| 431 | GAGCUUACACUUGUGUUUAAGCA | UGCUUAAACACAAGUGUAAGCUC | Chimp | [606-628] ORF |
| 432 | UGAGCUUACACUUGUGUUUAAGC | GCUUAAACACAAGUGUAAGCUCA | Chimp | [605-627] ORF |
| 433 | UUGAGCUUACACUUGUGUUUAAG | CUUAAACACAAGUGUAAGCUCAA | Chimp | [604-626] ORF |
| 434 | UUUGAGCUUACACUUGUGUUUAA | UUAAACACAAGUGUAAGCUCAAA | Chimp | [603-625] ORF |
| 435 | GAUUGGGUAGUAAAACUAUUCAG | CUGAAUAGUUUUACUACCCAAUC | | [815-837] 3'UTR |
| 436 | UGAUUGGGUAGUAAAACUAUUCA | UGAAUAGUUUUACUACCCAAUCA | | [814-836] 3'UTR |
| 437 | AUGAUUGGGUAGUAAAACUAUUC | GAAUAGUUUUACUACCCAAUCAU | | [813-835] 3'UTR |
| 438 | CAUGAUUGGGUAGUAAAACUAUU | AAUAGUUUUACUACCCAAUCAUG | | [812-834] 3'UTR |
| 439 | GUGAACUUGGAAAUUGAAAAUGU | ACAUUUUCAAUUUCCAAGUUCAC | Dog, Chin, GP, Chimp, Rat | [531-553] ORF |
| 440 | GCCAGAAUUUGGUUAAAAUGCUG | CAGCAUUUUAACCAAAUUCUGGC | GP, Chimp, Rat, Ms | [364-386] ORF |
| 441 | UGCCAGAAUUUGGUUAAAAUGCU | AGCAUUUUAACCAAAUUCUGGCA | GP, Chimp, Rat, Ms | [363-385] ORF |
| 442 | UUGCCAGAAUUUGGUUAAAAUGC | GCAUUUUAACCAAAUUCUGGCAA | GP, Chimp, Rat, Ms | [362-384] ORF |
| 443 | CUUGCCAGAAUUUGGUUAAAAUG | CAUUUUAACCAAAUUCUGGCAAG | GP, Chimp, Rat, Ms | [361-383] ORF |
| 444 | ACUUGCCAGAAUUUGGUUAAAAU | AUUUUAACCAAAUUCUGGCAAGU | GP, Chimp, Rat, Ms | [360-382] ORF |
| 445 | AACUGGCAGUUUGAGCAGCAAGA | UCUUGCUGCUCAAACUGCCAGUU | Chimp | [212-234] ORF |
| 446 | CAACUGGCAGUUUGAGCAGCAAG | CUUGCUGCUCAAACUGCCAGUUG | Chimp | [211-233] ORF |
| 447 | GCAACUGGCAGUUUGAGCAGCAA | UUGCUGCUCAAACUGCCAGUUGC | Chimp | [210-232] ORF |
| 448 | GUCACUAGGGAAUAAUAAAGGCC | GGCCUUUAUUAUUCCCUAGUGAC | | [1931-1953] 3'UTR |
| 449 | UGUCACUAGGGAAUAAUAAAGGC | GCCUUUAUUAUUCCCUAGUGACA | | [1930-1952] 3'UTR |
| 450 | AGAUCUAGUCCCUCUCUGAUUCA | UGAAUCAGAGAGGGACUAGAUCU | | [1619-1641] 3'UTR |
| 451 | GAGAUCUAGUCCCUCUCUGAUUC | GAAUCAGAGAGGGACUAGAUCUC | | [1618-1640] 3'UTR |
| 452 | UGAGAUCUAGUCCCUCUCUGAUU | AAUCAGAGAGGGACUAGAUCUCA | | [1617-1639] 3'UTR |
| 453 | CUGAGAUCUAGUCCCUCUCUGAU | AUCAGAGAGGGACUAGAUCUCAG | | [1616-1638] 3'UTR |
| 454 | UCUGAGAUCUAGUCCCUCUCUGA | UCAGAGAGGGACUAGAUCUCAGA | | [1615-1637] 3'UTR |
| 455 | GGCUUCUUGGGCAUCGAUGUAGA | UCUACAUCGAUGCCCAAGAAGCC | | [2414-2436] 3'UTR |
| 456 | CCAGAGAAUUGCUCAAGAUGUCC | GGACAUCUUGAGCAAUUCUCUGG | Chimp, Ms | [458-480] ORF |

TABLE E-continued additional 23 mers

| Number | Sense siRNA | AntiSense siRNA | Other Sp | Hum-34222182 ORF: 204-785 |
|---|---|---|---|---|
| 457 | CCCAGAGAAUUGCUCAAGAUGUC | GACAUCUUGAGCAAUUCUCUGGG | Chimp, Ms | [457-479] ORF |
| 458 | ACCCAGAGAAUUGCUCAAGAUGU | ACAUCUUGAGCAAUUCUCUGGGU | Chimp, Ms | [456-478] ORF |
| 459 | GACCCAGAGAAUUGCUCAAGAUG | CAUCUUGAGCAAUUCUCUGGGUC | Chimp, Ms | [455-477] ORF |
| 460 | UGACCCAGAGAAUUGCUCAAGAU | AUCUUGAGCAAUUCUCUGGGUCA | Chimp, Ms | [454-476] ORF |
| 461 | CCCUGUUCUUAAGUGUUGAAUAC | GUAUUCAACACUUAAGAACAGGG |  | [1485-1507] 3'UTR |
| 462 | CCCCUGUUCUUAAGUGUUGAAUA | UAUUCAACACUUAAGAACAGGGG |  | [1484-1506] 3'UTR |
| 463 | UCCCCUGUUCUUAAGUGUUGAAU | AUUCAACACUUAAGAACAGGGGA |  | [1483-1505] 3'UTR |
| 464 | UUCCCCUGUUCUUAAGUGUUGAA | UUCAACACUUAAGAACAGGGGAA |  | [1482-1504] 3'UTR |
| 465 | UUUCCCCUGUUCUUAAGUGUUGA | UCAACACUUAAGAACAGGGGAAA |  | [1481-1503] 3'UTR |
| 466 | CUGACCCAGAGAAUUGCUCAAGA | UCUUGAGCAAUUCUCUGGGUCAG | Chimp, Ms | [453-475] ORF |
| 467 | ACUGACCCAGAGAAUUGCUCAAG | CUUGAGCAAUUCUCUGGGUCAGU | Chimp, Ms | [452-474] ORF |
| 468 | AACUGACCCAGAGAAUUGCUCAA | UUGAGCAAUUCUCUGGGUCAGUU | Chimp, Ms | [451-473] ORF |
| 469 | GGCCUUUGGAGAAGUGAUUCAAA | UUUGAAUCACUUCUCCAAAGGCC |  | [959-981] 3'UTR |
| 470 | CCAUGGCAGUGUUAUCUCAUCUC | GAGAUGAGAUAACACUGCCAUGG |  | [1701-1723] 3'UTR |
| 471 | ACCAUGGCAGUGUUAUCUCAUCU | AGAUGAGAUAACACUGCCAUGGU |  | [1700-1722] 3'UTR |
| 472 | CACCAUGGCAGUGUUAUCUCAUC | GAUGAGAUAACACUGCCAUGGUG |  | [1699-1721] 3'UTR |
| 473 | UCACCAUGGCAGUGUUAUCUCAU | AUGAGAUAACACUGCCAUGGUGA |  | [1698-1720] 3'UTR |
| 474 | UUCACCAUGGCAGUGUUAUCUCA | UGAGAUAACACUGCCAUGGUGAA |  | [1697-1719] 3'UTR |
| 475 | CAGCUCAGGAUUUCGACUUGUUA | UAACAAGUCGAAAUCCUGAGCUG |  | [713-735] ORF |
| 476 | GACAGGAAGGUAGGAUUAAGUAG | CUACUUAAUCCUACCUUCCUGUC |  | [1280-1302] 3'UTR |
| 477 | AGACAGGAAGGUAGGAUUAAGUA | UACUUAAUCCUACCUUCCUGUCU |  | [1279-1301] 3'UTR |
| 478 | UAGACAGGAAGGUAGGAUUAAGU | ACUUAAUCCUACCUUCCUGUCUA |  | [1278-1300] 3'UTR |
| 479 | UUAGACAGGAAGGUAGGAUUAAG | CUUAAUCCUACCUUCCUGUCUAA |  | [1277-1299] 3'UTR |
| 480 | UUUAGACAGGAAGGUAGGAUUAA | UUAAUCCUACCUUCCUGUCUAAA |  | [1276-1298] 3'UTR |
| 481 | GGGUCCUAAAAAGGGAAAAUAUA | UAUAUUUUCCCUUUUUAGGACCC |  | [777-799] ORF + 3'UTR |
| 482 | AGGGUCCUAAAAAGGGAAAAUAU | AUAUUUUCCCUUUUUAGGACCCU |  | [776-798] ORF + 3'UTR |
| 483 | AAGGGUCCUAAAAAGGGAAAAUA | UAUUUUCCCUUUUUAGGACCCUU |  | [775-797] ORF + 3'UTR |
| 484 | GGAUAAGGAGCUUAUUCAGGUUU | AAACCUGAAUAAGCUCCUUAUCC |  | [2081-2103] 3'UTR |
| 485 | UGGAUAAGGAGCUUAUUCAGGUU | AACCUGAAUAAGCUCCUUAUCCA |  | [2080-2102] 3'UTR |
| 486 | GUGGAUAAGGAGCUUAUUCAGGU | ACCUGAAUAAGCUCCUUAUCCAC |  | [2079-2101] 3'UTR |
| 487 | CUUAUGGAAGGCUGUUAAAUUAA | UUAAUUUAACAGCCUUCCAUAAG |  | [2507-2529] 3'UTR |
| 488 | CGAAGGAAACAGAGCCGUUGACC | GGUCAACGGCUCUGUUUCCUUCG | Chimp | [181-203] 5'UTR |
| 489 | GCGAAGGAAACAGAGCCGUUGAC | GUCAACGGCUCUGUUUCCUUCGC | Chimp | [180-202] 5'UTR |
| 490 | CGCGAAGGAAACAGAGCCGUUGA | UCAACGGCUCUGUUUCCUUCGCG | Chimp | [179-201] 5'UTR |
| 491 | UCGCGAAGGAAACAGAGCCGUUG | CAACGGCUCUGUUUCCUUCGCGA | Chimp | [178-200] 5'UTR |
| 492 | CUCGCGAAGGAAACAGAGCCGUU | AACGGCUCUGUUUCCUUCGCGAG | Chimp | [177-199] 5'UTR |
| 493 | GUUCUAACAAACUAAACUCUUCA | UGAAGAGUUUAGUUUGUUAGAAC |  | [2248-2270] 3'UTR |

TABLE E-continued additional 23 mers

| Number | Sense siRNA | AntiSense siRNA | Other Sp | Hum-34222182 ORF: 204-785 |
|---|---|---|---|---|
| 494 | UGUUCUAACAAACUAAACUCUUC | GAAGAGUUUAGUUUGUUAGAACA | | [2247-2269] 3'UTR |
| 495 | CCUGUUCUUAAGUGUUGAAUACU | AGUAUUCAACACUUAAGAACAGG | | [1486-1508] 3'UTR |
| 496 | GGCCUUAUUUUUGUCUUAUUCC | GGAAUAAGACAAAAAAUAAGGCC | | [1950-1972] 3'UTR |
| 497 | AGGCCUUAUUUUUGUCUUAUUC | GAAUAAGACAAAAAAUAAGGCCU | | [1949-1971] 3'UTR |
| 498 | AAGGCCUUAUUUUUGUCUUAUU | AAUAAGACAAAAAAUAAGGCCUU | | [1948-1970] 3'UTR |
| 499 | AAAGGCCUUAUUUUUGUCUUAU | AUAAGACAAAAAAUAAGGCCUUU | | [1947-1969] 3'UTR |
| 500 | UAAAGGCCUUAUUUUUGUCUUA | UAAGACAAAAAAUAAGGCCUUUA | | [1946-1968] 3'UTR |
| 501 | CUCUCUGAUUCACUUAGUAAUCU | AGAUUACUAAGUGAAUCAGAGAG | | [1630-1652] 3'UTR |
| 502 | CCUCUCUGAUUCACUUAGUAAUC | GAUUACUAAGUGAAUCAGAGAGG | | [1629-1651] 3'UTR |
| 503 | CCCUCUCUGAUUCACUUAGUAAU | AUUACUAAGUGAAUCAGAGAGGG | | [1628-1650] 3'UTR |
| 504 | UCCCUCUCUGAUUCACUUAGUAA | UUACUAAGUGAAUCAGAGAGGGA | | [1627-1649] 3'UTR |
| 505 | GUCCCUCUCUGAUUCACUUAGUA | UACUAAGUGAAUCAGAGAGGGAC | | [1626-1648] 3'UTR |
| 506 | GCAUCGAUGUAGAACUGUUGUCC | GGACAACAGUUCUACAUCGAUGC | | [2424-2446] 3'UTR |
| 507 | GGCAUCGAUGUAGAACUGUUGUC | GACAACAGUUCUACAUCGAUGCC | | [2423-2445] 3'UTR |
| 508 | GGGCAUCGAUGUAGAACUGUUGU | ACAACAGUUCUACAUCGAUGCCC | | [2422-2444] 3'UTR |
| 509 | UGGGCAUCGAUGUAGAACUGUUG | CAACAGUUCUACAUCGAUGCCCA | | [2421-2443] 3'UTR |
| 510 | UUGGGCAUCGAUGUAGAACUGUU | AACAGUUCUACAUCGAUGCCCAA | | [2420-2442] 3'UTR |
| 511 | CGUCGUACCUACUUUUGAGCUUA | UAAGCUCAAAAGUAGGUACGACG | | [590-612] ORF |
| 512 | GAAUGAAACUCACCGUCCAGAUA | UAUCUGGACGGUGAGUUUCAUUC | | [1869-1891] 3'UTR |
| 513 | AGAAUGAAACUCACCGUCCAGAU | AUCUGGACGGUGAGUUUCAUUCU | | [1868-1890] 3'UTR |
| 514 | GAGAAUGAAACUCACCGUCCAGA | UCUGGACGGUGAGUUUCAUUCUC | | [1867-1889] 3'UTR |
| 515 | AGAGAAUGAAACUCACCGUCCAG | CUGGACGGUGAGUUUCAUUCUCU | | [1866-1888] 3'UTR |
| 516 | UAGAGAAUGAAACUCACCGUCCA | UGGACGGUGAGUUUCAUUCUCUA | | [1865-1887] 3'UTR |
| 517 | GUCUAUUGUUAAGCUCCAAAGGU | ACCUUUGGAGCUUAACAAUAGAC | | [2342-2364] 3'UTR |
| 518 | UGUCUAUUGUUAAGCUCCAAAGG | CCUUUGGAGCUUAACAAUAGACA | | [2341-2363] 3'UTR |
| 519 | AUGUCUAUUGUUAAGCUCCAAAG | CUUUGGAGCUUAACAAUAGACAU | | [2340-2362] 3'UTR |
| 520 | CAUGUCUAUUGUUAAGCUCCAAA | UUUGGAGCUUAACAAUAGACAUG | | [2339-2361] 3'UTR |
| 521 | GCAUGUCUAUUGUUAAGCUCCAA | UUGGAGCUUAACAAUAGACAUGC | | [2338-2360] 3'UTR |
| 522 | CAACCUCAACGAGGUAAUAUUUG | CAAAUAUUACCUCGUUGAGGUUG | Chimp | [329-351] ORF |
| 523 | CCAACCUCAACGAGGUAAUAUUU | AAAUAUUACCUCGUUGAGGUUGG | Chimp | [328-350] ORF |
| 524 | CCCAACCUCAACGAGGUAAUAUU | AAUAUUACCUCGUUGAGGUUGGG | Chimp | [327-349] ORF |
| 525 | ACCCAACCUCAACGAGGUAAUAU | AUAUUACCUCGUUGAGGUUGGGU | Chimp | [326-348] ORF |
| 526 | AACCCAACCUCAACGAGGUAAUA | UAUUACCUCGUUGAGGUUGGGUU | Chimp | [325-347] ORF |
| 527 | GGGCCAAGAUAAAUCAAUGUUGU | ACAACAUUGAUUUAUCUUGGCCC | | [2312-2334] 3'UTR |
| 528 | UGGGCCAAGAUAAAUCAAUGUUG | CAACAUUGAUUUAUCUUGGCCCA | | [2311-2333] 3'UTR |
| 529 | UUGGGCCAAGAUAAAUCAAUGUU | AACAUUGAUUUAUCUUGGCCCAA | | [2310-2332] 3'UTR |
| 530 | AUUGGGCCAAGAUAAAUCAAUGU | ACAUUGAUUUAUCUUGGCCCAAU | | [2309-2331] 3'UTR |

TABLE E-continued additional 23 mers

| Number | Sense siRNA | AntiSense siRNA | Other Sp | Hum-34222182 ORF: 204-785 |
|---|---|---|---|---|
| 531 | AAUUGGGCCAAGAUAAAUCAAUG | CAUUGAUUUAUCUUGGCCCAAUU | | [2308-2330] 3'UTR |
| 532 | GGUAGGCUUGGUAAUAGACUAUA | UAUAGUCUAUUACCAAGCCUACC | | [1098-1120] 3'UTR |
| 533 | GGUAAUAUUUGAGGAAUCAACUU | AAGUUGAUUCCUCAAAUAUUACC | Chimp | [341-363] ORF |
| 534 | AGGUAAUAUUUGAGGAAUCAACU | AGUUGAUUCCUCAAAUAUUACCU | Chimp | [340-362] ORF |
| 535 | GAGGUAAUAUUUGAGGAAUCAAC | GUUGAUUCCUCAAAUAUUACCUC | Chimp | [339-361] ORF |
| 536 | UGUAUGUAAAAGCUGGAUAGGA | UCCUAUCCAGCUUUUUACAUACA | Dog, Chimp, Ms | [551-573] ORF |
| 537 | AUGUAUGUAAAAGCUGGAUAGG | CCUAUCCAGCUUUUUACAUACAU | Dog, Chimp, Ms | [550-572] ORF |
| 538 | AAUGUAUGUAAAAGCUGGAUAG | CUAUCCAGCUUUUUACAUACAUU | Dog, Chimp, Ms | [549-571] ORF |
| 539 | AAAUGUAUGUAAAAGCUGGAUA | UAUCCAGCUUUUUACAUACAUUU | Dog, Chimp, Ms | [548-570] ORF |
| 540 | GAAACGGGUCAAUUUACGAAGUC | GACUUCGUAAAUUGACCCGUUUC | | [1806-1828] 3'UTR |
| 541 | UGAAACGGGUCAAUUUACGAAGU | ACUUCGUAAAUUGACCCGUUUCA | | [1805-1827] 3'UTR |
| 542 | UUGAAACGGGUCAAUUUACGAAG | CUUCGUAAAUUGACCCGUUUCAA | | [1804-1826] 3'UTR |
| 543 | AUUGAAACGGGUCAAUUUACGAA | UUCGUAAAUUGACCCGUUUCAAU | | [1803-1825] 3'UTR |
| 544 | UAUUGAAACGGGUCAAUUUACGA | UCGUAAAUUGACCCGUUUCAAUA | | [1802-1824] 3'UTR |
| 545 | GUUGCAACUGGCAGUUUGAGCAG | CUGCUCAAACUGCCAGUUGCAAC | Chimp | [207-229] ORF |
| 546 | GGUUGCAACUGGCAGUUUGAGCA | UGCUCAAACUGCCAGUUGCAACC | Chimp | [206-228] ORF |
| 547 | UGGUUGCAACUGGCAGUUUGAGC | GCUCAAACUGCCAGUUGCAACCA | Chimp | [205-227] ORF |
| 548 | AUGGUUGCAACUGGCAGUUUGAG | CUCAAACUGCCAGUUGCAACCAU | Chimp | [204-226] ORF |
| 549 | CAUGGUUGCAACUGGCAGUUUGA | UCAAACUGCCAGUUGCAACCAUG | Chimp | [203-225] 5'UTR + ORF |
| 550 | CCUAGAGAAUGAAACUCACCGUC | GACGGUGAGUUUCAUUCUCUAGG | | [1863-1885] 3'UTR |
| 551 | GCCUAGAGAAUGAAACUCACCGU | ACGGUGAGUUUCAUUCUCUAGGC | | [1862-1884] 3'UTR |
| 552 | AGCCUAGAGAAUGAAACUCACCG | CGGUGAGUUUCAUUCUCUAGGCU | | [1861-1883] 3'UTR |
| 553 | CAGCCUAGAGAAUGAAACUCACC | GGUGAGUUUCAUUCUCUAGGCUG | | [1860-1882] 3'UTR |
| 554 | ACAGCCUAGAGAAUGAAACUCAC | GUGAGUUUCAUUCUCUAGGCUGU | | [1859-1881] 3'UTR |
| 555 | GCCUGCUAAGUGAUUUUGACUAC | GUAGUCAAAAUCACUUAGCAGGC | Chimp | [283-305] ORF |
| 556 | AGCCUGCUAAGUGAUUUUGACUA | UAGUCAAAAUCACUUAGCAGGCU | Chimp | [282-304] ORF |
| 557 | GAGCCUGCUAAGUGAUUUUGACU | AGUCAAAAUCACUUAGCAGGCUC | Chimp | [281-303] ORF |
| 558 | AGAGCCUGCUAAGUGAUUUUGAC | GUCAAAAUCACUUAGCAGGCUCU | Chimp | [280-302] ORF |
| 559 | GAGAGCCUGCUAAGUGAUUUUGA | UCAAAAUCACUUAGCAGGCUCUC | Chimp | [279-301] ORF |
| 560 | CUAUUAGCUCCACUUCACAUGCU | AGCAUGUGAAGUGGAGCUAAUAG | | [2114-2136] 3'UTR |
| 561 | GCUAUUAGCUCCACUUCACAUGC | GCAUGUGAAGUGGAGCUAAUAGC | | [2113-2135] 3'UTR |
| 562 | AGCUAUUAGCUCCACUUCACAUG | CAUGUGAAGUGGAGCUAAUAGCU | | [2112-2134] 3'UTR |
| 563 | UAGCUAUUAGCUCCACUUCACAU | AUGUGAAGUGGAGCUAAUAGCUA | | [2111-2133] 3'UTR |
| 564 | CUAGCUAUUAGCUCCACUUCACA | UGUGAAGUGGAGCUAAUAGCUAG | | [2110-2132] 3'UTR |
| 565 | CAACAGUGAUUGAAGGGUCCUAA | UUAGGACCCUUCAAUCACUGUUG | | [763-785] ORF |
| 566 | GGGUAGUAGCUGUAUACUACCAC | GUGGUAGUAUACAGCUACUACCC | | [1772-1794] 3'UTR |
| 567 | AGGGUAGUAGCUGUAUACUACCA | UGGUAGUAUACAGCUACUACCCU | | [1771-1793] 3'UTR |

TABLE E-continued additional 23 mers

| Number | Sense siRNA | AntiSense siRNA | Other Sp | Hum-34222182 ORF: 204-785 |
|---|---|---|---|---|
| 568 | AAGGGUAGUAGCUGUAUACUACC | GGUAGUAUACAGCUACUACCCUU | | [1770-1792] 3'UTR |
| 569 | GGAUUAAGUAGGUGAGUUUAAUU | AAUUAAACUCACCUACUUAAUCC | | [1292-1314] 3'UTR |
| 570 | AGGAUUAAGUAGGUGAGUUUAAU | AUUAAACUCACCUACUUAAUCCU | | [1291-1313] 3'UTR |
| 571 | UAGGAUUAAGUAGGUGAGUUUAA | UUAAACUCACCUACUUAAUCCUA | | [1290-1312] 3'UTR |
| 572 | GUAGGAUUAAGUAGGUGAGUUUA | UAAACUCACCUACUUAAUCCUAC | | [1289-1311] 3'UTR |
| 573 | GGUAGGAUUAAGUAGGUGAGUUU | AAACUCACCUACUUAAUCCUACC | | [1288-1310] 3'UTR |
| 574 | UGUUGUUUUGCAUGUCUAUUGUU | AACAAUAGACAUGCAAAACAACA | | [2329-2351] 3'UTR |
| 575 | AUGUUGUUUUGCAUGUCUAUUGU | ACAAUAGACAUGCAAAACAACAU | | [2328-2350] 3'UTR |
| 576 | AAUGUUGUUUUGCAUGUCUAUUG | CAAUAGACAUGCAAAACAACAUU | | [2327-2349] 3'UTR |
| 577 | CAAUGUUGUUUUGCAUGUCUAUU | AAUAGACAUGCAAAACAACAUUG | | [2326-2348] 3'UTR |
| 578 | UCAAUGUUGUUUUGCAUGUCUAU | AUAGACAUGCAAAACAACAUUGA | | [2325-2347] 3'UTR |
| 579 | GUUCCUGACUCAAAUUUGAAGGG | CCCUUCAAAUUUGAGUCAGGAAC | | [1251-1273] 3'UTR |
| 580 | AGUUCCUGACUCAAAUUUGAAGG | CCUUCAAAUUUGAGUCAGGAACU | | [1250-1272] 3'UTR |
| 581 | CAGUUCCUGACUCAAAUUUGAAG | CUUCAAAUUUGAGUCAGGAACUG | | [1249-1271] 3'UTR |
| 582 | CCAGUUCCUGACUCAAAUUUGAA | UUCAAAUUUGAGUCAGGAACUGG | | [1248-1270] 3'UTR |
| 583 | ACCAGUUCCUGACUCAAAUUUGA | UCAAAUUUGAGUCAGGAACUGGU | | [1247-1269] 3'UTR |
| 584 | AGUAACCACGGUGUUGUUUUAGA | UCUAAAACAACACCGUGGUUACU | | [1441-1463] 3'UTR |
| 585 | CAGUAACCACGGUGUUGUUUUAG | CUAAAACAACACCGUGGUUACUG | | [1440-1462] 3'UTR |
| 586 | UCAGUAACCACGGUGUUGUUUUA | UAAAACAACACCGUGGUUACUGA | | [1439-1461] 3'UTR |
| 587 | UUCAGUAACCACGGUGUUGUUUU | AAAACAACACCGUGGUUACUGAA | | [1438-1460] 3'UTR |
| 588 | UUUCAGUAACCACGGUGUUGUUU | AAACAACACCGUGGUUACUGAAA | | [1437-1459] 3'UTR |
| 589 | AUUUCAGUAACCACGGUGUUGUU | AACAACACCGUGGUUACUGAAAU | | [1436-1458] 3'UTR |
| 590 | AGAUUUUUUCCACCUUGGAUACC | GGUAUCCAAGGUGGAAAAAAUCU | | [1907-1929] 3'UTR |
| 591 | CAGAUUUUUUCCACCUUGGAUAC | GUAUCCAAGGUGGAAAAAAUCUG | | [1906-1928] 3'UTR |
| 592 | CCAGAUUUUUUCCACCUUGGAUA | UAUCCAAGGUGGAAAAAAUCUGG | | [1905-1927] 3'UTR |
| 593 | CCCAGAUUUUUUCCACCUUGGAU | AUCCAAGGUGGAAAAAAUCUGGG | | [1904-1926] 3'UTR |
| 594 | ACCCAGAUUUUUUCCACCUUGGA | UCCAAGGUGGAAAAAAUCUGGGU | | [1903-1925] 3'UTR |
| 595 | CAGAUUUGCCUAUUUUGAUUUUC | GAAAAUCAAAAUAGGCAAAUCUG | | [1126-1148] 3'UTR |
| 596 | UUUAUAGUACAGCCUAGAGAAUG | CAUUCUCUAGGCUGUACUAUAAA | | [1851-1873] 3'UTR |
| 597 | GUUUAUAGUACAGCCUAGAGAAU | AUUCUCUAGGCUGUACUAUAAAC | | [1850-1872] 3'UTR |
| 598 | GGUUUAUAGUACAGCCUAGAGAA | UUCUCUAGGCUGUACUAUAAACC | | [1849-1871] 3'UTR |
| 599 | GCGAGGUUGUGUUAUGCACGUGA | UCACGUGCAUAACACAACCUCGC | Ms | [512-534] ORF |
| 600 | GAUACCUGUCACUAGGGAAUAU | AUUAUUCCCUAGUGACAGGUAUC | | [1924-1946] 3'UTR |
| 601 | GGAUACCUGUCACUAGGGAAUAA | UUAUUCCCUAGUGACAGGUAUCC | | [1923-1945] 3'UTR |
| 602 | UGGAUACCUGUCACUAGGGAAUA | UAUUCCCUAGUGACAGGUAUCCA | | [1922-1944] 3'UTR |
| 603 | UUGGAUACCUGUCACUAGGGAAU | AUUCCCUAGUGACAGGUAUCCAA | | [1921-1943] 3'UTR |
| 604 | CUUGGAUACCUGUCACUAGGGAA | UUCCCUAGUGACAGGUAUCCAAG | | [1920-1942] 3'UTR |

TABLE E-continued additional 23 mers

| Number | Sense siRNA | AntiSense siRNA | Other Sp | Hum-34222182 ORF: 204-785 |
|---|---|---|---|---|
| 605 | UAAAUGAGAAAUAUUACGGCAAU | AUUGCCGUAAUAUUUCUCAUUUA | | [1337-1359] 3'UTR |
| 606 | CCUAUCAAAACUUCCAAAAGCCC | GGGCUUUUGGAAGUUUUGAUAGG | | [1219-1241] 3'UTR |
| 607 | GCGUAGGGACAGAUGUAUUCAUC | GAUGAAUACAUCUGUCCCUACGC | | [2145-2167] 3'UTR |
| 608 | GGCGUAGGGACAGAUGUAUUCAU | AUGAAUACAUCUGUCCCUACGCC | | [2144-2166] 3'UTR |
| 609 | CGGCGUAGGGACAGAUGUAUUCA | UGAAUACAUCUGUCCCUACGCCG | | [2143-2165] 3'UTR |
| 610 | CCGGCGUAGGGACAGAUGUAUUC | GAAUACAUCUGUCCCUACGCCGG | | [2142-2164] 3'UTR |
| 611 | ACCGGCGUAGGGACAGAUGUAUU | AAUACAUCUGUCCCUACGCCGGU | | [2141-2163] 3'UTR |
| 612 | GAUACUAUAAGUGACCUAAAAUG | CAUUUUAGGUCACUUAUAGUAUC | | [2204-2226] 3'UTR |
| 613 | UGAUACUAUAAGUGACCUAAAAU | AUUUUAGGUCACUUAUAGUAUCA | | [2203-2225] 3'UTR |
| 614 | CUGAUACUAUAAGUGACCUAAAA | UUUUAGGUCACUUAUAGUAUCAG | | [2202-2224] 3'UTR |
| 615 | ACUGAUACUAUAAGUGACCUAAA | UUUAGGUCACUUAUAGUAUCAGU | | [2201-2223] 3'UTR |
| 616 | UACUGAUACUAUAAGUGACCUAA | UUAGGUCACUUAUAGUAUCAGUA | | [2200-2222] 3'UTR |
| 617 | CGAAGUCUGCAUUGGCUAUGGAG | CUCCAUAGCCAAUGCAGACUUCG | | [1822-1844] 3'UTR |
| 618 | ACGAAGUCUGCAUUGGCUAUGGA | UCCAUAGCCAAUGCAGACUUCGU | | [1821-1843] 3'UTR |
| 619 | UACGAAGUCUGCAUUGGCUAUGG | CCAUAGCCAAUGCAGACUUCGUA | | [1820-1842] 3'UTR |
| 620 | UUACGAAGUCUGCAUUGGCUAUG | CAUAGCCAAUGCAGACUUCGUAA | | [1819-1841] 3'UTR |
| 621 | UUUACGAAGUCUGCAUUGGCUAU | AUAGCCAAUGCAGACUUCGUAAA | | [1818-1840] 3'UTR |
| 622 | GGAUAGGAUUGUGUGUGAUUCUA | UAGAAUCACACACAAUCCUAUCC | Chin, GP, Chimp, Rat | [566-588] ORF |
| 623 | UGGAUAGGAUUGUGUGUGAUUCU | AGAAUCACACACAAUCCUAUCCA | Chin, GP, Chimp, Rat | [565-587] ORF |
| 624 | CUGGAUAGGAUUGUGUGUGAUUC | GAAUCACACACAAUCCUAUCCAG | Chin, GP, Chimp, Rat | [564-586] ORF |
| 625 | GCUGGAUAGGAUUGUGUGUGAUU | AAUCACACACAAUCCUAUCCAGC | Chin, GP, Chimp, Rat | [563-585] ORF |
| 626 | AGCUGGAUAGGAUUGUGUGUGAU | AUCACACACAAUCCUAUCCAGCU | Chin, GP, Chimp, Rat | [562-584] ORF |
| 627 | UGGCCUUUGGAGAAGUGAUUCAA | UUGAAUCACUUCUCCAAAGGCCA | | [958-980] 3'UTR |
| 628 | CUGGCCUUUGGAGAAGUGAUUCA | UGAAUCACUUCUCCAAAGGCCAG | | [957-979] 3'UTR |
| 629 | UCUGGCCUUUGGAGAAGUGAUUC | GAAUCACUUCUCCAAAGGCCAGA | | [956-978] 3'UTR |
| 630 | UUCUGGCCUUUGGAGAAGUGAUU | AAUCACUUCUCCAAAGGCCAGAA | | [955-977] 3'UTR |
| 631 | AUAGGUAAGCAAAAGUAGAAGCC | GGCUUCUACUUUUGCUUACCUAU | | [1037-1059] 3'UTR |
| 632 | AAUAGGUAAGCAAAAGUAGAAGC | GCUUCUACUUUUGCUUACCUAUU | | [1036-1058] 3'UTR |
| 633 | AGGUAGGAUUAAGUAGGUGAGUU | AACUCACCUACUUAAUCCUACCU | | [1287-1309] 3'UTR |
| 634 | AAGGUAGGAUUAAGUAGGUGAGU | ACUCACCUACUUAAUCCUACCUU | | [1286-1308] 3'UTR |
| 635 | GAAGGUAGGAUUAAGUAGGUGAG | CUCACCUACUUAAUCCUACCUUC | | [1285-1307] 3'UTR |
| 636 | GGAAGGUAGGAUUAAGUAGGUGA | UCACCUACUUAAUCCUACCUUCC | | [1284-1306] 3'UTR |
| 637 | GAUUAAGUAGGUGAGUUUAAUUA | UAAUUAAACUCACCUACUUAAUC | | [1293-1315] 3'UTR |
| 638 | AGGAAGGUAGGAUUAAGUAGGUG | CACCUACUUAAUCCUACCUUCCU | | [1283-1305] 3'UTR |
| 639 | CAGGAAGGUAGGAUUAAGUAGGU | ACCUACUUAAUCCUACCUUCCUG | | [1282-1304] 3'UTR |
| 640 | ACAGGAAGGUAGGAUUAAGUAGG | CCUACUUAAUCCUACCUUCCUGU | | [1281-1303] 3'UTR |
| 641 | AACAGGUGUGAUCCUGUUACUGA | UCAGUAACAGGAUCACACCUGUU | | [2183-2205] 3'UTR |

TABLE E-continued additional 23 mers

| Number | Sense siRNA | AntiSense siRNA | Other Sp | Hum-34222182 ORF: 204-785 |
|---|---|---|---|---|
| 642 | CAUGGACUAGCUUCAGGGACUUU | AAAGUCCCUGAAGCUAGUCCAUG | Dog, Chimp | [640-662] ORF |
| 643 | UCAUGGACUAGCUUCAGGGACUU | AAGUCCCUGAAGCUAGUCCAUGA | Dog, Chimp | [639-661] ORF |
| 644 | CUCAUGGACUAGCUUCAGGGACU | AGUCCCUGAAGCUAGUCCAUGAG | Dog, Chimp | [638-660] ORF |
| 645 | GCUCAUGGACUAGCUUCAGGGAC | GUCCCUGAAGCUAGUCCAUGAGC | Dog, Chimp | [637-659] ORF |
| 646 | UGCUCAUGGACUAGCUUCAGGGA | UCCCUGAAGCUAGUCCAUGAGCA | Dog, Chimp | [636-658] ORF |
| 647 | AUUUGAAGGGUUUUUAGACAGGA | UCCUGUCUAAAAACCCUUCAAAU |  | [1264-1286] 3'UTR |
| 648 | ACAACAGUGAUUGAAGGGUCCUA | UAGGACCCUUCAAUCACUGUUGU |  | [762-784] ORF |
| 649 | UGUACAGAAUUGAAUGGGAUGGA | UCCAUCCCAUUCAAUUCUGUACA |  | [1014-1036] 3'UTR |
| 650 | UUGUACAGAAUUGAAUGGGAUGG | CCAUCCCAUUCAAUUCUGUACAA |  | [1013-1035] 3'UTR |
| 651 | UUUGUACAGAAUUGAAUGGGAUG | CAUCCCAUUCAAUUCUGUACAAA |  | [1012-1034] 3'UTR |
| 652 | UUUUGUACAGAAUUGAAUGGGAU | AUCCCAUUCAAUUCUGUACAAAA |  | [1011-1033] 3'UTR |
| 653 | UUUUUGUACAGAAUUGAAUGGGA | UCCCAUUCAAUUCUGUACAAAAA |  | [1010-1032] 3'UTR |
| 654 | CUCAACGAGGUAAUAUUUGAGGA | UCCUCAAAUAUUACCUCGUUGAG | Chimp | [333-355] ORF |
| 655 | CCUCAACGAGGUAAUAUUUGAGG | CCUCAAAUAUUACCUCGUUGAGG | Chimp | [332-354] ORF |
| 656 | ACCUCAACGAGGUAAUAUUUGAG | CUCAAAUAUUACCUCGUUGAGGU | Chimp | [331-353] ORF |
| 657 | AACCUCAACGAGGUAAUAUUUGA | UCAAAUAUUACCUCGUUGAGGUU | Chimp | [330-352] ORF |
| 658 | UCUCUGGGCUUUUCUGGGAAUUG | CAAUUCCCAGAAAAGCCCAGAGA |  | [1720-1742] 3'UTR |
| 659 | AUCUCUGGGCUUUUCUGGGAAUU | AAUUCCCAGAAAAGCCCAGAGAU |  | [1719-1741] 3'UTR |
| 660 | CAUCUCUGGGCUUUUCUGGGAAU | AUUCCCAGAAAAGCCCAGAGAUG |  | [1718-1740] 3'UTR |
| 661 | UCAUCUCUGGGCUUUUCUGGGAA | UUCCCAGAAAAGCCCAGAGAUGA |  | [1717-1739] 3'UTR |
| 662 | GGCUUGCGAGGUUGUGUUAUGCA | UGCAUAACACAACCUCGCAAGCC | Chimp | [507-529] ORF |
| 663 | CGGCUUGCGAGGUUGUGUUAUGC | GCAUAACACAACCUCGCAAGCCG | Chimp | [506-528] ORF |
| 664 | GCGGCUUGCGAGGUUGUGUUAUG | CAUAACACAACCUCGCAAGCCGC | Chimp | [505-527] ORF |
| 665 | UGCGGCUUGCGAGGUUGUGUUAU | AUAACACAACCUCGCAAGCCGCA | Chimp | [504-526] ORF |
| 666 | CUGCGGCUUGCGAGGUUGUGUUA | UAACACAACCUCGCAAGCCGCAG | Chimp | [503-525] ORF |
| 667 | UACGGCAAUAAUGGAACUGCUUC | GAAGCAGUUCCAUUAUUGCCGUA |  | [1351-1373] 3'UTR |
| 668 | UUACGGCAAUAAUGGAACUGCUU | AAGCAGUUCCAUUAUUGCCGUAA |  | [1350-1372] 3'UTR |
| 669 | AUUACGGCAAUAAUGGAACUGCU | AGCAGUUCCAUUAUUGCCGUAAU |  | [1349-1371] 3'UTR |
| 670 | CUUUACUCACUGAUUGGAACAAC | GUUGUUCCAAUCAGUGAGUAAAG |  | [744-766] ORF |
| 671 | ACUUUACUCACUGAUUGGAACAA | UUGUUCCAAUCAGUGAGUAAAGU |  | [743-765] ORF |
| 672 | AACUUUACUCACUGAUUGGAACA | UGUUCCAAUCAGUGAGUAAAGUU |  | [742-764] ORF |
| 673 | AAACUUUACUCACUGAUUGGAAC | GUUCCAAUCAGUGAGUAAAGUUU |  | [741-763] ORF |
| 674 | AAAACUUUACUCACUGAUUGGAA | UUCCAAUCAGUGAGUAAAGUUUU |  | [740-762] ORF |
| 675 | UUUUAGACAGGAAGGUAGGAUUA | UAAUCCUACCUUCCUGUCUAAAA |  | [1275-1297] 3'UTR |
| 676 | UGACUUCCUCACUCUAAUGUUUU | AAAACAUUAGAGUGAGGAAGUCA |  | [1386-1408] 3'UTR |
| 677 | GGACUUUUUCUUUAGUAGAGGUC | GACCUCUACUAAAGAAAAGUCC |  | [656-678] ORF |
| 678 | GGGACUUUUUCUUUAGUAGAGGU | ACCUCUACUAAAGAAAAGUCCC |  | [655-677] ORF |

TABLE E-continued additional 23 mers

| Number | Sense siRNA | AntiSense siRNA | Other Sp | Hum-34222182 ORF: 204-785 |
|---|---|---|---|---|
| 679 | AGGGACUUUUUCUUUAGUAGAGG | CCUCUACUAAAGAAAAAGUCCCU | | [654-676] ORF |
| 680 | CAGGGACUUUUUCUUUAGUAGAG | CUCUACUAAAGAAAAAGUCCCUG | | [653-675] ORF |
| 681 | UCAGGGACUUUUUCUUUAGUAGA | UCUACUAAAGAAAAAGUCCCUGA | | [652-674] ORF |
| 682 | CUCUGAUUCACUUAGUAAUCUAU | AUAGAUUACUAAGUGAAUCAGAG | | [1632-1654] 3'UTR |
| 683 | UCUCUGAUUCACUUAGUAAUCUA | UAGAUUACUAAGUGAAUCAGAGA | | [1631-1653] 3'UTR |
| 684 | GGGAAUAAUAAAGGCCUUAUUUU | AAAAUAAGGCCUUUAUUAUUCCC | | [1938-1960] 3'UTR |
| 685 | AGGGAAUAAUAAAGGCCUUAUUU | AAAUAAGGCCUUUAUUAUUCCCU | | [1937-1959] 3'UTR |
| 686 | UAGGGAAUAAUAAAGGCCUUAUU | AAUAAGGCCUUUAUUAUUCCCUA | | [1936-1958] 3'UTR |
| 687 | CUAGGGAAUAAUAAAGGCCUUAU | AUAAGGCCUUUAUUAUUCCCUAG | | [1935-1957] 3'UTR |
| 688 | ACUAGGGAAUAAUAAAGGCCUUA | UAAGGCCUUUAUUAUUCCCUAGU | | [1934-1956] 3'UTR |
| 689 | AAUACCUGUGAGGAUAGGAAAUU | AAUUUCCUAUCCUCACAGGUAUU | | [1589-1611] 3'UTR |
| 690 | GAAUACCUGUGAGGAUAGGAAAU | AUUUCCUAUCCUCACAGGUAUUC | | [1588-1610] 3'UTR |
| 691 | UGAAUACCUGUGAGGAUAGGAAA | UUUCCUAUCCUCACAGGUAUUCA | | [1587-1609] 3'UTR |
| 692 | CCUUGGAUACCUGUCACUAGGGA | UCCCUAGUGACAGGUAUCCAAGG | | [1919-1941] 3'UTR |
| 693 | CUAGCUUCAGGGACUUUUUCUUU | AAAGAAAAAGUCCCUGAAGCUAG | Chimp | [646-668] ORF |
| 694 | ACUAGCUUCAGGGACUUUUUCUU | AAGAAAAAGUCCCUGAAGCUAGU | Chimp | [645-667] ORF |
| 695 | GACUAGCUUCAGGGACUUUUUCU | AGAAAAAGUCCCUGAAGCUAGUC | Chimp | [644-666] ORF |
| 696 | GGACUAGCUUCAGGGACUUUUUC | GAAAAAGUCCCUGAAGCUAGUCC | Chimp | [643-665] ORF |
| 697 | UGGACUAGCUUCAGGGACUUUUU | AAAAAGUCCCUGAAGCUAGUCCA | Chimp | [642-664] ORF |
| 698 | AAAGAUACUACAAAGCCAAUCUU | AAGAUUGGCUUUGUAGUAUCUUU | | [2280-2302] 3'UTR |
| 699 | AAGCUGGAUAGGAUUGUGUGUGA | UCACACACAAUCCUAUCCAGCUU | Chin, GP, Chimp, Rat | [561-583] ORF |
| 700 | UGUGGUGCCAUUUCAGUAACCAC | GUGGUUACUGAAAUGGCACCACA | | [1427-1449] 3'UTR |
| 701 | UUGUGGUGCCAUUUCAGUAACCA | UGGUUACUGAAAUGGCACCACAA | | [1426-1448] 3'UTR |
| 702 | CUUGUGGUGCCAUUUCAGUAACC | GGUUACUGAAAUGGCACCACAAG | | [1425-1447] 3'UTR |
| 703 | GCUUGUGGUGCCAUUUCAGUAAC | GUUACUGAAAUGGCACCACAAGC | | [1424-1446] 3'UTR |
| 704 | AGCUUGUGGUGCCAUUUCAGUAA | UUACUGAAAUGGCACCACAAGCU | | [1423-1445] 3'UTR |
| 705 | CUUUAUAGAAUUGGGCCAAGAUA | UAUCUUGGCCCAAUUCUAUAAAG | | [2300-2322] 3'UTR |
| 706 | GUUUCAGGUAGGCUUGGUAAUAG | CUAUUACCAAGCCUACCUGAAAC | | [1092-1114] 3'UTR |
| 707 | GGUUUCAGGUAGGCUUGGUAAUA | UAUUACCAAGCCUACCUGAAACC | | [1091-1113] 3'UTR |
| 708 | UGGUUUCAGGUAGGCUUGGUAAU | AUUACCAAGCCUACCUGAAACCA | | [1090-1112] 3'UTR |
| 709 | UUGGUUUCAGGUAGGCUUGGUAA | UUACCAAGCCUACCUGAAACCAA | | [1089-1111] 3'UTR |
| 710 | UUUGGUUUCAGGUAGGCUUGGUA | UACCAAGCCUACCUGAAACCAAA | | [1088-1110] 3'UTR |
| 711 | UGGGUCGUGGAUAAGGAGCUAUU | AUAAGCUCCUUAUCCACGACCCA | | [2073-2095] 3'UTR |
| 712 | GUGGGUCGUGGAUAAGGAGCUUA | UAAGCUCCUUAUCCACGACCCAC | | [2072-2094] 3'UTR |
| 713 | AAUGGUGAUGGCUUAUGGAAGGC | GCCUUCCAUAAGCCAUCACCAUU | | [2496-2518] 3'UTR |
| 714 | AAAUGGUGAUGGCUUAUGGAAGG | CCUUCCAUAAGCCAUCACCAUUU | | [2495-2517] 3'UTR |
| 715 | AAAAUGGUGAUGGCUUAUGGAAG | CUUCCAUAAGCCAUCACCAUUUU | | [2494-2516] 3'UTR |

TABLE E-continued additional 23 mers

| Number | Sense siRNA | AntiSense siRNA | Other Sp | Hum-34222182 ORF: 204-785 |
|---|---|---|---|---|
| 716 | CAAAAUGGUGAUGGCUUAUGGAA | UUCCAUAAGCCAUCACCAUUUUG | | [2493-2515] 3'UTR |
| 717 | AAGCUUGUGGUGCCAUUUCAGUA | UACUGAAAUGGCACCACAAGCUU | | [1422-1444] 3'UTR |
| 718 | AAAGCUUGUGGUGCCAUUUCAGU | ACUGAAAUGGCACCACAAGCUUU | | [1421-1443] 3'UTR |
| 719 | AAAAGCUUGUGGUGCCAUUUCAG | CUGAAAUGGCACCACAAGCUUUU | | [1420-1442] 3'UTR |
| 720 | UAGGUAAGCAAAAGUAGAAGCCC | GGGCUUCUACUUUUGCUUACCUA | | [1038-1060] 3'UTR |
| 721 | UGAUUUUCUGGCCUUUGGAGAAG | CUUCUCCAAAGGCCAGAAAAUCA | | [950-972] 3'UTR |
| 722 | CUGAUUUUCUGGCCUUUGGAGAA | UUCUCCAAAGGCCAGAAAAUCAG | | [949-971] 3'UTR |
| 723 | GCUGAUUUUCUGGCCUUUGGAGA | UCUCCAAAGGCCAGAAAAUCAGC | | [948-970] 3'UTR |
| 724 | AGGCUGAUUUUCUGGCCUUUGGA | UCCAAAGGCCAGAAAAUCAGCCU | | [946-968] 3'UTR |
| 725 | AGGCUUCUUGGGCAUCGAUGUAG | CUACAUCGAUGCCCAAGAAGCCU | | [2413-2435] 3'UTR |
| 726 | AAGGCUUCUUGGGCAUCGAUGUA | UACAUCGAUGCCCAAGAAGCCUU | | [2412-2434] 3'UTR |
| 727 | CAAGGCUUCUUGGGCAUCGAUGU | ACAUCGAUGCCCAAGAAGCCUUG | | [2411-2433] 3'UTR |
| 728 | CCGUCCAGAUAACCAUGCAUCGA | UGCAUGCAUGGUUAUCUGGACGG | | [1881-1903] 3'UTR |
| 729 | ACCGUCCAGAUAACCAUGCAUGC | GCAUGCAUGGUUAUCUGGACGGU | | [1880-1902] 3'UTR |
| 730 | CACCGUCCAGAUAACCAUGCAUG | CAUGCAUGGUUAUCUGGACGGUG | | [1879-1901] 3'UTR |
| 731 | UCACCGUCCAGAUAACCAUGCAU | AUGCAUGGUUAUCUGGACGGUGA | | [1878-1900] 3'UTR |
| 732 | CUCACCGUCCAGAUAACCAUGCA | UGCAUGGUUAUCUGGACGGUGAG | | [1877-1899] 3'UTR |
| 733 | AACCAUGCAUGCACCCAGAUUUU | AAAAUCUGGGUGCAUGCAUGGUU | | [1891-1913] 3'UTR |
| 734 | UAACCAUGCAUGCACCCAGAUUU | AAAUCUGGGUGCAUGCAUGGUUA | | [1890-1912] 3'UTR |
| 735 | AUAACCAUGCAUGCACCCAGAUU | AAUCUGGGUGCAUGCAUGGUUAU | | [1889-1911] 3'UTR |
| 736 | GAUAACCAUGCAUGCACCCAGAU | AUCUGGGUGCAUGCAUGGUUAUC | | [1888-1910] 3'UTR |
| 737 | AGAUAACCAUGCAUGCACCCAGA | UCUGGGUGCAUGCAUGGUUAUCU | | [1887-1909] 3'UTR |
| 738 | GAAUUGGGCCAAGAUAAAUCAAU | AUUGAUUUAUCUUGGCCCAAUUC | | [2307-2329] 3'UTR |
| 739 | GUGAGGAUAGGAAAUUAGUUCUG | CAGAACUAAUUUCCUAUCCUCAC | | [1596-1618] 3'UTR |
| 740 | UGUGAGGAUAGGAAAUUAGUUCU | AGAACUAAUUUCCUAUCCUCACA | | [1595-1617] 3'UTR |
| 741 | GAUUUUUUCCACCUUGGAUACCU | AGGUAUCCAAGGUGGAAAAAAUC | | [1908-1930] 3'UTR |
| 742 | GAAGCCCAUUUGAGUUUUACAUU | AAUGUAAAACUCAAAUGGGCUUC | | [1054-1076] 3'UTR |
| 743 | AGAAGCCCAUUUGAGUUUUACAU | AUGUAAAACUCAAAUGGGCUUCU | | [1053-1075] 3'UTR |
| 744 | UAGAAGCCCAUUUGAGUUUUACA | UGUAAAACUCAAAUGGGCUUCUA | | [1052-1074] 3'UTR |
| 745 | GUAGAAGCCCAUUUGAGUUUUAC | GUAAAACUCAAAUGGGCUUCUAC | | [1051-1073] 3'UTR |
| 746 | AGUAGAAGCCCAUUUGAGUUUUA | UAAAACUCAAAUGGGCUUCUACU | | [1050-1072] 3'UTR |
| 747 | AGCAGGAGAACUGCUCAUGGACU | AGUCCAUGAGCAGUUCUCCUGCU | Dog, Chimp | [625-647] ORF |
| 748 | AAGCAGGAGAACUGCUCAUGGAC | GUCCAUGAGCAGUUCUCCUGCUU | Dog, Chimp | [624-646] ORF |
| 749 | UAAGCAGGAGAACUGCUCAUGGA | UCCAUGAGCAGUUCUCCUGCUUA | Dog, Chimp | [623-645] ORF |
| 750 | GCAUGCACCCAGAUUUUUUCCAC | GUGGAAAAAAUCUGGGUGCAUGC | | [1897-1919] 3'UTR |
| 751 | UGCAUGCACCCAGAUUUUUUCCA | UGGAAAAAAUCUGGGUGCAUGCA | | [1896-1918] 3'UTR |
| 752 | AUGCAUGCACCCAGAUUUUUUCC | GGAAAAAAUCUGGGUGCAUGCAU | | [1895-1917] 3'UTR |

TABLE E-continued additional 23 mers

| Number | Sense siRNA | AntiSense siRNA | Other Sp | Hum-34222182 ORF: 204-785 |
|---|---|---|---|---|
| 753 | CAUGCAUGCACCCAGAUUUUUC | GAAAAAUCUGGGUGCAUGCAUG | | [1894-1916] 3'UTR |
| 754 | CCAUGCAUGCACCCAGAUUUUU | AAAAAUCUGGGUGCAUGCAUGG | | [1893-1915] 3'UTR |
| 755 | CCUGCUAAGUGAUUUGACUACU | AGUAGUCAAAUCACUUAGCAGG | Chimp | [284-306] ORF |
| 756 | UACUGGGAUUAUGUUGUUCCUGA | UCAGGAACAACAUAAUCCCAGUA | Chimp | [303-325] ORF |
| 757 | CUCUUGCCUGUUAUGCUUACAAA | UUUGUAAGCAUAACAGGCAAGAG | | [2474-2496] 3'UTR |
| 758 | CCACCUUGGAUACCUGUCACUAG | CUAGUGACAGGUAUCCAAGGUGG | | [1916-1938] 3'UTR |
| 759 | UCCACCUUGGAUACCUGUCACUA | UAGUGACAGGUAUCCAAGGUGGA | | [1915-1937] 3'UTR |
| 760 | UUCCACCUUGGAUACCUGUCACU | AGUGACAGGUAUCCAAGGUGGAA | | [1914-1936] 3'UTR |
| 761 | UUUCCACCUUGGAUACCUGUCAC | GUGACAGGUAUCCAAGGUGGAAA | | [1913-1935] 3'UTR |
| 762 | UUUUCCACCUUGGAUACCUGUCA | UGACAGGUAUCCAAGGUGGAAAA | | [1912-1934] 3'UTR |
| 763 | UUUCUGGCCUUUGGAGAAGUGAU | AUCACUUCUCCAAAGGCCAGAAA | | [954-976] 3'UTR |
| 764 | UUCUGCAUAGAUCCCAUUUUUGU | ACAAAAUGGGAUCUAUGCAGAA | | [994-1016] 3'UTR |
| 765 | UUUCUGCAUAGAUCCCAUUUUUG | CAAAAUGGGAUCUAUGCAGAAA | | [993-1015] 3'UTR |
| 766 | UUUUCUGCAUAGAUCCCAUUUUU | AAAAUGGGAUCUAUGCAGAAAA | | [992-1014] 3'UTR |
| 767 | GAACCCAACCUCAACGAGGUAAU | AUUACCUCGUUGAGGUUGGGUUC | Chimp | [324-346] ORF |
| 768 | AGAAACUGACCCAGAGAAUUGCU | AGCAAUUCUCUGGGUCAGUUUCU | Chin, GP, Chimp, Rat, Ms | [448-470] ORF |
| 769 | UUCUUGGUGACUUCCUCACUCUA | UAGAGUGAGGAAGUCACCAAGAA | | [1379-1401] 3'UTR |
| 770 | CACUAGGGAAUAAUAAAGGCCUU | AAGGCCUUUAUUAUUCCCUAGUG | | [1933-1955] 3'UTR |
| 771 | CCUGUUAUGCUUACAAAAUGGUG | CACCAUUUUGUAAGCAUAACAGG | | [2480-2502] 3'UTR |
| 772 | AAAGUAGAAGCCCAUUUGAGUUU | AAACUCAAAUGGGCUUCUACUUU | | [1048-1070] 3'UTR |
| 773 | AAAAGUAGAAGCCCAUUUGAGUU | AACUCAAAUGGGCUUCUACUUUU | | [1047-1069] 3'UTR |
| 774 | CAAAAGUAGAAGCCCAUUUGAGU | ACUCAAAUGGGCUUCUACUUUUG | | [1046-1068] 3'UTR |
| 775 | GCAAAAGUAGAAGCCCAUUUGAG | CUCAAAUGGGCUUCUACUUUUGC | | [1045-1067] 3'UTR |
| 776 | AGCAAAAGUAGAAGCCCAUUUGA | UCAAAUGGGCUUCUACUUUUGCU | | [1044-1066] 3'UTR |
| 777 | GAUUUUGACUACUGGGAUUAUGU | ACAUAAUCCCAGUAGUCAAAAUC | Dog, Chimp | [294-316] ORF |
| 778 | UGAUUUUGACUACUGGGAUUAUG | CAUAAUCCCAGUAGUCAAAAUCA | Dog, Chimp | [293-315] ORF |
| 779 | GUGAUUUUGACUACUGGGAUUAU | AUAAUCCCAGUAGUCAAAAUCAC | Dog, Chimp | [292-314] ORF |
| 780 | AGUGAUUUUGACUACUGGGAUUA | UAAUCCCAGUAGUCAAAAUCACU | Dog, Chimp | [291-313] ORF |
| 781 | AAGUGAUUUUGACUACUGGGAUU | AAUCCCAGUAGUCAAAAUCACUU | Dog, Chimp | [290-312] ORF |
| 782 | UGAUGGCUUAUGGAAGGCUGUUA | UAACAGCCUUCCAUAAGCCAUCA | | [2501-2523] 3'UTR |
| 783 | UGUUGUCCUUUUUCCACUAACAG | CUGUUAGUGGAAAAGGACAACA | | [2439-2461] 3'UTR |
| 784 | CUGUUGUCCUUUUUCCACUAACA | UGUUAGUGGAAAAGGACAACAG | | [2438-2460] 3'UTR |
| 785 | ACUGUUGUCCUUUUUCCACUAAC | GUUAGUGGAAAAGGACAACAGU | | [2437-2459] 3'UTR |
| 786 | AACUGUUGUCCUUUUUCCACUAA | UUAGUGGAAAAGGACAACAGUU | | [2436-2458] 3'UTR |
| 787 | GAACUGUUGUCCUUUUUCCACUA | UAGUGGAAAAGGACAACAGUUC | | [2435-2457] 3'UTR |
| 788 | GACCGGCGUAGGGACAGAUGUAU | AUACAUCUGUCCCUACGCCGGUC | | [2140-2162] 3'UTR |
| 789 | AGUGUAGAUUUUCUGCAUAGAUC | GAUCUAUGCAGAAAAUCUACACU | | [984-1006] 3'UTR |

TABLE E-continued additional 23 mers

| Number | Sense siRNA | AntiSense siRNA | Other Sp | Hum-34222182 ORF: 204-785 |
|---|---|---|---|---|
| 790 | UAGUGUAGAUUUUCUGCAUAGAU | AUCUAUGCAGAAAAUCUACACUA | | [983-1005] 3'UTR |
| 791 | AUAGUGUAGAUUUUCUGCAUAGA | UCUAUGCAGAAAAUCUACACUAU | | [982-1004] 3'UTR |
| 792 | AAUAGUGUAGAUUUUCUGCAUAG | CUAUGCAGAAAAUCUACACUAUU | | [981-1003] 3'UTR |
| 793 | AAAUAGUGUAGAUUUUCUGCAUA | UAUGCAGAAAAUCUACACUAUUU | | [980-1002] 3'UTR |
| 794 | ACCUUGGAUACCUGUCACUAGGG | CCCUAGUGACAGGUAUCCAAGGU | | [1918-1940] 3'UTR |
| 795 | CACCUUGGAUACCUGUCACUAGG | CCUAGUGACAGGUAUCCAAGGUG | | [1917-1939] 3'UTR |
| 796 | CACCCAGAUUUUUCCACCUUGG | CCAAGGUGGAAAAAUCUGGGUG | | [1902-1924] 3'UTR |
| 797 | GCACCCAGAUUUUUCCACCUUG | CAAGGUGGAAAAAUCUGGGUGC | | [1901-1923] 3'UTR |
| 798 | GAUAGGAAAUUAGUUCUGAGAUC | GAUCUCAGAACUAAUUUCCUAUC | | [1601-1623] 3'UTR |
| 799 | GGAUAGGAAAUUAGUUCUGAGAU | AUCUCAGAACUAAUUUCCUAUCC | | [1600-1622] 3'UTR |
| 800 | AGGAUAGGAAAUUAGUUCUGAGA | UCUCAGAACUAAUUUCCUAUCCU | | [1599-1621] 3'UTR |
| 801 | GAGGAUAGGAAAUUAGUUCUGAG | CUCAGAACUAAUUUCCUAUCCUC | | [1598-1620] 3'UTR |
| 802 | UGAGGAUAGGAAAUUAGUUCUGA | UCAGAACUAAUUUCCUAUCCUCA | | [1597-1619] 3'UTR |
| 803 | ACCUGCCCUAAAUAAGAAACCCC | GGGGUUUCUUAUUUAGGGCAGGU | | [870-892] 3'UTR |
| 804 | CAGCUAAAGUCAUUUGUAGUUUG | CAAACUACAAAUGACUUUAGCUG | | [843-865] 3'UTR |
| 805 | UCAGCUAAAGUCAUUUGUAGUUU | AAACUACAAAUGACUUUAGCUGA | | [842-864] 3'UTR |
| 806 | GUCAGCUAAAGUCAUUUGUAGUU | AACUACAAAUGACUUUAGCUGAC | | [841-863] 3'UTR |
| 807 | AGUCAGCUAAAGUCAUUUGUAGU | ACUACAAAUGACUUUAGCUGACU | | [840-862] 3'UTR |
| 808 | UAGUCAGCUAAAGUCAUUUGUAG | CUACAAAUGACUUUAGCUGACUA | | [839-861] 3'UTR |
| 809 | GGCUUUUUUUCUCUAAGUUUUC | GAAAACUUAGAGAAAAAAAGCC | | [1153-1175] 3'UTR |
| 810 | UGGCUUUUUUUCUCUAAGUUUU | AAAACUUAGAGAAAAAAAGCCA | | [1152-1174] 3'UTR |
| 811 | AUGGCUUUUUUUCUCUAAGUUU | AAACUUAGAGAAAAAAAGCCAU | | [1151-1173] 3'UTR |
| 812 | UAUGGCUUUUUUUCUCUAAGUU | AACUUAGAGAAAAAAAGCCAUA | | [1150-1172] 3'UTR |
| 813 | AUAUGGCUUUUUUUCUCUAAGU | ACUUAGAGAAAAAAAGCCAUAU | | [1149-1171] 3'UTR |
| 814 | UAUGCACGUGAACUUGGAAAUUG | CAAUUUCCAAGUUCACGUGCAUA | Dog, Chin, GP, Rat | [524-546] ORF |
| 815 | UUAUGCACGUGAACUUGGAAAUU | AAUUUCCAAGUUCACGUGCAUAA | Dog, Chin, GP, Rat | [523-545] ORF |
| 816 | GUUAUGCACGUGAACUUGGAAAU | AUUUCCAAGUUCACGUGCAUAAC | Dog, Chin, GP, Rat | [522-544] ORF |
| 817 | UGUUAUGCACGUGAACUUGGAAA | UUUCCAAGUUCACGUGCAUAACA | Dog, Chin, GP, Rat | [521-543] ORF |
| 818 | GUGUUAUGCACGUGAACUUGGAA | UUCCAAGUUCACGUGCAUAACAC | Dog, Chin, GP, Rat | [520-542] ORF |
| 819 | AUGGACUAGCUUCAGGGACUUUU | AAAAGUCCCUGAAGCUAGUCCAU | Chimp | [641-663] ORF |
| 820 | CGUUGACCAUGGUUGCAACUGGC | GCCAGUUGCAACCAUGGUCAACG | Chimp, Rat, Ms | [196-218] 5'UTR + ORF |
| 821 | CCGUUGACCAUGGUUGCAACUGG | CCAGUUGCAACCAUGGUCAACGG | Chimp, Rat, Ms | [195-217] 5'UTR + ORF |
| 822 | GCCGUUGACCAUGGUUGCAACUG | CAGUUGCAACCAUGGUCAACGGC | Chimp, Rat, Ms | [194-216] 5'UTR + ORF |
| 823 | AGCCGUUGACCAUGGUUGCAACU | AGUUGCAACCAUGGUCAACGGCU | Chimp, Rat, Ms | [193-215] 5'UTR + ORF |
| 824 | GAGCCGUUGACCAUGGUUGCAAC | GUUGCAACCAUGGUCAACGGCUC | Chimp, Rat, Ms | [192-214] 5'UTR + ORF |
| 825 | UGCAUGUCUAUUGUUAAGCUCCA | UGGAGCUUAACAAUAGACAUGCA | | [2337-2359] 3'UTR |
| 826 | CAAUUUACGAAGUCUGCAUUGGC | GCCAAUGCAGACUUCGUAAAUUG | | [1815-1837] 3'UTR |

TABLE E-continued additional 23 mers

| Number | Sense siRNA | AntiSense siRNA | Other Sp | Hum-34222182 ORF: 204-785 |
|---|---|---|---|---|
| 827 | UCAAUUUACGAAGUCUGCAUUGG | CCAAUGCAGACUUCGUAAAUUGA | | [1814-1836] 3'UTR |
| 828 | GUCAAUUUACGAAGUCUGCAUUG | CAAUGCAGACUUCGUAAAUUGAC | | [1813-1835] 3'UTR |
| 829 | GGUCAAUUUACGAAGUCUGCAUU | AAUGCAGACUUCGUAAAUUGACC | | [1812-1834] 3'UTR |
| 830 | GGGUCAAUUUACGAAGUCUGCAU | AUGCAGACUUCGUAAAUUGACCC | | [1811-1833] 3'UTR |
| 831 | CUAGUCAGCUAAAGUCAUUUGUA | UACAAAUGACUUUAGCUGACUAG | | [838-860] 3'UTR |
| 832 | AAAGCUGGAUAGGAUUGUGUGUG | CACACACAAUCCUAUCCAGCUUU | Chin, GP, Chimp, Rat | [560-582] ORF |
| 833 | AAAAGCUGGAUAGGAUUGUGUGU | ACACACAAUCCUAUCCAGCUUUU | Chin, GP, Chimp, Rat | [559-581] ORF |
| 834 | GUACAGCCUAGAGAAUGAAACUC | GAGUUUCAUUCUCUAGGCUGUAC | | [1857-1879] 3'UTR |
| 835 | GAUUCUAGCGUCGUACCACUUU | AAAGUAGGUACGACGCUAGAAUC | | [582-604] ORF |
| 836 | UGAUUCUAGCGUCGUACCACUU | AAGUAGGUACGACGCUAGAAUCA | | [581-603] ORF |
| 837 | GUGAUUCUAGCGUCGUACCACU | AGUAGGUACGACGCUAGAAUCAC | | [580-602] ORF |
| 838 | UGUGAUUCUAGCGUCGUACCAC | GUAGGUACGACGCUAGAAUCACA | | [579-601] ORF |
| 839 | GAUCUAGUCCCUCUCUGAUUCAC | GUGAAUCAGAGAGGGACUAGAUC | | [1620-1642] 3'UTR |
| 840 | CUAACAAACUAAACUCUUCAAAU | AUUUGAAGAGUUUAGUUUGUUAG | | [2251-2273] 3'UTR |
| 841 | UCUAACAAACUAAACUCUUCAAA | UUUGAAGAGUUUAGUUUGUUAGA | | [2250-2272] 3'UTR |
| 842 | UUCUAACAAACUAAACUCUUCAA | UUGAAGAGUUUAGUUUGUUAGAA | | [2249-2271] 3'UTR |
| 843 | GACUCAAAUUUGAAGGGUUUUUA | UAAAAACCCUUCAAAUUUGAGUC | | [1257-1279] 3'UTR |
| 844 | UGACUCAAAUUUGAAGGGUUUUU | AAAAACCCUUCAAAUUUGAGUCA | | [1256-1278] 3'UTR |
| 845 | CUGACUCAAAUUUGAAGGGUUUU | AAAACCCUUCAAAUUUGAGUCAG | | [1255-1277] 3'UTR |
| 846 | CCUGACUCAAAUUUGAAGGGUUU | AAACCCUUCAAAUUUGAGUCAGG | | [1254-1276] 3'UTR |
| 847 | UCCUGACUCAAAUUUGAAGGGUU | AACCCUUCAAAUUUGAGUCAGGA | | [1253-1275] 3'UTR |
| 848 | UCCACUCAACAAUGUUCAAUUCA | UGAAUUGAACAUUGUUGAGUGGA | | [2027-2049] 3'UTR |
| 849 | CUCCACUCAACAAUGUUCAAUUC | GAAUUGAACAUUGUUGAGUGGAG | | [2026-2048] 3'UTR |
| 850 | CCUCCACUCAACAAUGUUCAAUU | AAUUGAACAUUGUUGAGUGGAGG | | [2025-2047] 3'UTR |
| 851 | GCCUCCACUCAACAAUGUUCAAU | AUUGAACAUUGUUGAGUGGAGGC | | [2024-2046] 3'UTR |
| 852 | AGCCUCCACUCAACAAUGUUCAA | UUGAACAUUGUUGAGUGGAGGCU | | [2023-2045] 3'UTR |
| 853 | UGUAGAUUUUCUGCAUAGAUCCC | GGGAUCUAUGCAGAAAAUCUACA | | [986-1008] 3'UTR |
| 854 | GUGUAGAUUUUCUGCAUAGAUCC | GGAUCUAUGCAGAAAAUCUACAC | | [985-1007] 3'UTR |
| 855 | GCUAUGGAGAUAUGGUUUAUAGU | ACUAUAAACCAUAUCUCCAUAGC | | [1836-1858] 3'UTR |
| 856 | GGCUAUGGAGAUAUGGUUUAUAG | CUAUAAACCAUAUCUCCAUAGCC | | [1835-1857] 3'UTR |
| 857 | UGGCUAUGGAGAUAUGGUUUAUA | UAUAAACCAUAUCUCCAUAGCCA | | [1834-1856] 3'UTR |
| 858 | UUGGCUAUGGAGAUAUGGUUUAU | AUAAACCAUAUCUCCAUAGCCAA | | [1833-1855] 3'UTR |
| 859 | AUUGGCUAUGGAGAUAUGGUUUA | UAAACCAUAUCUCCAUAGCCAAU | | [1832-1854] 3'UTR |
| 860 | GUAUACUACCACUUUGAAUUAUU | AAUAAUUCAAAGUGGUAGUAUAC | | [1783-1805] 3'UTR |
| 861 | UGUAUACUACCACUUUGAAUUAU | AUAAUUCAAAGUGGUAGUAUACA | | [1782-1804] 3'UTR |
| 862 | CUGUAUACUACCACUUUGAAUUA | UAAUUCAAAGUGGUAGUAUACAG | | [1781-1803] 3'UTR |
| 863 | GCUGUAUACUACCACUUUGAAUU | AAUUCAAAGUGGUAGUAUACAGC | | [1780-1802] 3'UTR |

TABLE E-continued additional 23 mers

| Number | Sense siRNA | AntiSense siRNA | Other Sp | Hum-34222182 ORF: 204-785 |
|---|---|---|---|---|
| 864 | AGCUGUAUACUACCACUUUGAAU | AUUCAAAGUGGUAGUAUACAGCU | | [1779-1801] 3'UTR |
| 865 | AGAGCCGUUGACCAUGGUUGCAA | UUGCAACCAUGGUCAACGGCUCU | Chimp, Rat, Ms | [191-213] 5'UTR + ORF |
| 866 | GAAUUAUUGAAACGGGUCAAUUU | AAAUUGACCCGUUUCAAUAAUUC | | [1798-1820] 3'UTR |
| 867 | UGAAUUAUUGAAACGGGUCAAUU | AAUUGACCCGUUUCAAUAAUUCA | | [1797-1819] 3'UTR |
| 868 | UUGAAUUAUUGAAACGGGUCAAU | AUUGACCCGUUUCAAUAAUUCAA | | [1796-1818] 3'UTR |
| 869 | UUUGAAUUAUUGAAACGGGUCAA | UUGACCCGUUUCAAUAAUUCAAA | | [1795-1817] 3'UTR |
| 870 | CUUUGAAUUAUUGAAACGGGUCA | UGACCCGUUUCAAUAAUUCAAAG | | [1794-1816] 3'UTR |
| 871 | AGCCCAUUUGAGUUUUACAUUUG | CAAAUGUAAAACUCAAAUGGGCU | | [1056-1078] 3'UTR |
| 872 | AAGCCCAUUUGAGUUUUACAUUU | AAAUGUAAAACUCAAAUGGGCUU | | [1055-1077] 3'UTR |
| 873 | AGGAUUGUGUGUGAUUCUAGCGU | ACGCUAGAAUCACACACAAUCCU | Chimp | [570-592] ORF |
| 874 | UAGGAUUGUGUGUGAUUCUAGCG | CGCUAGAAUCACACACAAUCCUA | Chimp | [569-591] ORF |
| 875 | AUAGGAUUGUGUGUGAUUCUAGC | GCUAGAAUCACACACAAUCCUAU | Chimp | [568-590] ORF |
| 876 | GAUAGGAUUGUGUGUGAUUCUAG | CUAGAAUCACACACAAUCCUAUC | Chimp | [567-589] ORF |
| 877 | CAAAUGCUUGGAAAGAUACUACA | UGUAGUAUCUUUCCAAGCAUUUG | | [2269-2291] 3'UTR |
| 878 | CAUUGGCUAUGGAGAUAUGGUUU | AAACCAUAUCUCCAUAGCCAAUG | | [1831-1853] 3'UTR |
| 879 | CUUUUUCCACUAACAGUUAUCUU | AAGAUAACUGUUAGUGGAAAAAG | | [2446-2468] 3'UTR |
| 880 | CCUUUUUCCACUAACAGUUAUCU | AGAUAACUGUUAGUGGAAAAAGG | | [2445-2467] 3'UTR |
| 881 | UCCUUUUUCCACUAACAGUUAUC | GAUAACUGUUAGUGGAAAAAGGA | | [2444-2466] 3'UTR |
| 882 | GUCCUUUUUCCACUAACAGUUAU | AUAACUGUUAGUGGAAAAAGGAC | | [2443-2465] 3'UTR |
| 883 | UGUCCUUUUUCCACUAACAGUUA | UAACUGUUAGUGGAAAAAGGACA | | [2442-2464] 3'UTR |
| 884 | UGCACCCAGAUUUUUUCCACCUU | AAGGUGGAAAAAAUCUGGGUGCA | | [1900-1922] 3'UTR |
| 885 | GGUCCUAAAAAGGGAAAAUAUAU | AUAUAUUUUCCCUUUUUAGGACC | | [778-800] ORF + 3'UTR |
| 886 | GCUUCAGGGACUUUUUCUUUAGU | ACUAAAGAAAAAGUCCCUGAAGC | Chimp | [649-671] ORF |
| 887 | AGCUUCAGGGACUUUUUCUUUAG | CUAAAGAAAAAGUCCCUGAAGCU | Chimp | [648-670] ORF |
| 888 | UAGCUUCAGGGACUUUUUCUUUA | UAAAGAAAAAGUCCCUGAAGCUA | Chimp | [647-669] ORF |
| 889 | CUAAUGUUUAAAGAGGCAACAA | UUGUUGCCUCUUUAAACAUUAG | | [1399-1421] 3'UTR |
| 890 | GGAAUAAUAAAGGCCUUAUUUUU | AAAAAUAAGGCCUUUAUUAUUCC | | [1939-1961] 3'UTR |
| 891 | UUGCAUGUCUAUUGUUAAGCUCC | GGAGCUUAACAAUAGACAUGCAA | | [2336-2358] 3'UTR |
| 892 | UUUGCAUGUCUAUUGUUAAGCUC | GAGCUUAACAAUAGACAUGCAAA | | [2335-2357] 3'UTR |
| 893 | UUUUGCAUGUCUAUUGUUAAGCU | AGCUUAACAAUAGACAUGCAAAA | | [2334-2356] 3'UTR |
| 894 | UAGCUGUAUACUACCACUUUGAA | UUCAAAGUGGUAGUAUACAGCUA | | [1778-1800] 3'UTR |
| 895 | GUAGCUGUAUACUACCACUUUGA | UCAAAGUGGUAGUAUACAGCUAC | | [1777-1799] 3'UTR |
| 896 | GUAGAUUUUCUGCAUAGAUCCCA | UGGGAUCUAUGCAGAAAAUCUAC | | [987-1009] 3'UTR |
| 897 | UGUGUUAUGCACGUGAACUUGGA | UCCAAGUUCACGUGCAUAACACA | Dog, Chin, GP, Rat, Ms | [519-541] ORF |
| 898 | GAAACUGACCCAGAGAAUUGCUC | GAGCAAUUCUCUGGGUCAGUUUC | Chin, GP, Chimp, Rat, Ms | [449-471] ORF |
| 899 | GAAACUCACCGUCCAGAUAACCA | UGGUUAUCUGGACGGUGAGUUUC | | [1873-1895] 3'UTR |
| 900 | UGAAACUCACCGUCCAGAUAACC | GGUUAUCUGGACGGUGAGUUUCA | | [1872-1894] 3'UTR |

TABLE E-continued additional 23 mers

| Number | Sense siRNA | AntiSense siRNA | Other Sp | Hum-34222182 ORF: 204-785 |
|---|---|---|---|---|
| 901 | AUGAAACUCACCGUCCAGAUAAC | GUUAUCUGGACGGUGAGUUUCAU | | [1871-1893] 3'UTR |
| 902 | AAUGAAACUCACCGUCCAGAUAA | UUAUCUGGACGGUGAGUUUCAUU | | [1870-1892] 3'UTR |
| 903 | GAAACAGAGCCGUUGACCAUGGU | ACCAUGGUCAACGGCUCUGUUUC | Dog, Chimp, Rat, Ms | [186-208] 5'UTR + ORF |
| 904 | GGAAACAGAGCCGUUGACCAUGG | CCAUGGUCAACGGCUCUGUUUCC | Dog, Chimp, Rat, Ms | [185-207] 5'UTR + ORF |
| 905 | AGGAAACAGAGCCGUUGACCAUG | CAUGGUCAACGGCUCUGUUUCCU | Dog, Chimp, Rat, Ms | [184-206] 5'UTR + ORF |
| 906 | AAGGAAACAGAGCCGUUGACCAU | AUGGUCAACGGCUCUGUUUCCUU | Dog, Chimp, Rat, Ms | [183-205] 5'UTR + ORF |
| 907 | GAAGGAAACAGAGCCGUUGACCA | UGGUCAACGGCUCUGUUUCCUUC | Dog, Chimp, Rat, Ms | [182-204] 5'UTR |
| 908 | UACAGCCUAGAGAAUGAAACUCA | UGAGUUUCAUUCUCUAGGCUGUA | | [1858-1880] 3'UTR |
| 909 | GGAGAACUCUGAUCCUCAGCUCA | UGAGCUGAGGAUCAGAGUUCUCC | | [697-719] ORF |
| 910 | AGGAGAACUCUGAUCCUCAGCUC | GAGCUGAGGAUCAGAGUUCUCCU | | [696-718] ORF |
| 911 | CAGGAGAACUCUGAUCCUCAGCU | AGCUGAGGAUCAGAGUUCUCCUG | | [695-717] ORF |
| 912 | UCAGGAGAACUCUGAUCCUCAGC | GCUGAGGAUCAGAGUUCUCCUGA | | [694-716] ORF |
| 913 | UUCAGGAGAACUCUGAUCCUCAG | CUGAGGAUCAGAGUUCUCCUGAA | | [693-715] ORF |
| 914 | UUCAGGGACUUUUUCUUUAGUAG | CUACUAAAGAAAAGUCCCUGAA | | [651-673] ORF |
| 915 | CUUCAGGGACUUUUUCUUUAGUA | UACUAAAGAAAAGUCCCUGAAG | | [650-672] ORF |
| 916 | AGUUGAUUACUCUUCCAUUGAGU | ACUCAAUGGAAGAGUAAUCAACU | | [1558-1580] 3'UTR |
| 917 | UAGUUGAUUACUCUUCCAUUGAG | CUCAAUGGAAGAGUAAUCAACUA | | [1557-1579] 3'UTR |
| 918 | GUAGUUGAUUACUCUUCCAUUGA | UCAAUGGAAGAGUAAUCAACUAC | | [1556-1578] 3'UTR |
| 919 | UGUAGUUGAUUACUCUUCCAUUG | CAAUGGAAGAGUAAUCAACUACA | | [1555-1577] 3'UTR |
| 920 | GUGUAGUUGAUUACUCUUCCAUU | AAUGGAAGAGUAAUCAACUACAC | | [1554-1576] 3'UTR |
| 921 | GGAACAACAGUGAUUGAAGGGUC | GACCCUUCAAUCACUGUUGUUCC | | [759-781] ORF |
| 922 | UGGAACAACAGUGAUUGAAGGGU | ACCCUUCAAUCACUGUUGUUCCA | | [758-780] ORF |
| 923 | UUGGAACAACAGUGAUUGAAGGG | CCCUUCAAUCACUGUUGUUCCAA | | [757-779] ORF |
| 924 | AUUGGAACAACAGUGAUUGAAGG | CCUUCAAUCACUGUUGUUCCAAU | | [756-778] ORF |
| 925 | GAUUGGAACAACAGUGAUUGAAG | CUUCAAUCACUGUUGUUCCAAUC | | [755-777] ORF |
| 926 | CAAAGCCAAUCUUUAUAGAAUUG | CAAUUCUAUAAAGAUUGGCUUUG | | [2290-2312] 3'UTR |
| 927 | ACAAAGCCAAUCUUUAUAGAAUU | AAUUCUAUAAAGAUUGGCUUUGU | | [2289-2311] 3'UTR |
| 928 | UACAAAGCCAAUCUUUAUAGAAU | AUUCUAUAAAGAUUGGCUUUGUA | | [2288-2310] 3'UTR |
| 929 | CUACAAAGCCAAUCUUUAUAGAA | UUCUAUAAAGAUUGGCUUUGUAG | | [2287-2309] 3'UTR |
| 930 | ACUACAAAGCCAAUCUUUAUAGA | UCUAUAAAGAUUGGCUUUGUAGU | | [2286-2308] 3'UTR |
| 931 | AAACGGGUCAAUUUACGAAGUCU | AGACUUCGUAAAUUGACCCGUUU | | [1807-1829] 3'UTR |
| 932 | GCAAGGCUUCUUGGGCAUCGAUG | CAUCGAUGCCCAAGAAGCCUUGC | | [2410-2432] 3'UTR |
| 933 | GGCAAGGCUUCUUGGGCAUCGAU | AUCGAUGCCCAAGAAGCCUUGCC | | [2409-2431] 3'UTR |
| 934 | GGGCAAGGCUUCUUGGGCAUCGA | UCGAUGCCCAAGAAGCCUUGCCC | | [2408-2430] 3'UTR |
| 935 | UCCCUGAGAAACUGACCCAGAGA | UCUCUGGGUCAGUUUCUCAGGGA | Dog, Chin, GP, Chimp, Rat, Ms | [442-464] ORF |
| 936 | GUCCCUGAGAAACUGACCCAGAG | CUCUGGGUCAGUUUCUCAGGGAC | Dog, Chin, GP, Chimp, Rat, Ms | [441-463] ORF |

TABLE E-continued additional 23 mers

| Number | Sense siRNA | AntiSense siRNA | Other Sp | Hum-34222182 ORF: 204-785 |
|---|---|---|---|---|
| 937 | UGUCCCUGAGAAACUGACCCAGA | UCUGGGUCAGUUUCUCAGGGACA | Dog, Chin, GP, Chimp, Rat, Ms | [440-462] ORF |
| 938 | CUGCAUUGGCUAUGGAGAUAUGG | CCAUAUCUCCAUAGCCAAUGCAG | | [1828-1850] 3'UTR |
| 939 | UCUGCAUUGGCUAUGGAGAUAUG | CAUAUCUCCAUAGCCAAUGCAGA | | [1827-1849] 3'UTR |
| 940 | GUCUGCAUUGGCUAUGGAGAUAU | AUAUCUCCAUAGCCAAUGCAGAC | | [1826-1848] 3'UTR |
| 941 | AGUCUGCAUUGGCUAUGGAGAUA | UAUCUCCAUAGCCAAUGCAGACU | | [1825-1847] 3'UTR |
| 942 | AAGUCUGCAUUGGCUAUGGAGAU | AUCUCCAUAGCCAAUGCAGACUU | | [1824-1846] 3'UTR |
| 943 | GAUUGUGUGUGAUUCUAGCGUCG | CGACGCUAGAAUCACACACAAUC | | [572-594] ORF |
| 944 | GGAUUGUGUGUGAUUCUAGCGUC | GACGCUAGAAUCACACACAAUCC | | [571-593] ORF |
| 945 | GCUAGUCAGCUAAAGUCAUUUGU | ACAAAUGACUUUAGCUGACUAGC | | [837-859] 3'UTR |
| 946 | AGCUAGUCAGCUAAAGUCAUUUG | CAAAUGACUUUAGCUGACUAGCU | | [836-858] 3'UTR |
| 947 | CAGCUAGUCAGCUAAAGUCAUUU | AAAUGACUUUAGCUGACUAGCUG | | [835-857] 3'UTR |
| 948 | UCAGCUAGUCAGCUAAAGUCAUU | AAUGACUUUAGCUGACUAGCUGA | | [834-856] 3'UTR |
| 949 | UUCAGCUAGUCAGCUAAAGUCAU | AUGACUUUAGCUGACUAGCUGAA | | [833-855] 3'UTR |
| 950 | UGUAUUCAUCCUGGUGUUACUGA | UCAGUAACACCAGGAUGAAUACA | | [2158-2180] 3'UTR |
| 951 | AUGUAUUCAUCCUGGUGUUACUG | CAGUAACACCAGGAUGAAUACAU | | [2157-2179] 3'UTR |
| 952 | GAUGUAUUCAUCCUGGUGUUACU | AGUAACACCAGGAUGAAUACAUC | | [2156-2178] 3'UTR |
| 953 | GGGUAGUAAAACUAUUCAGCUAG | CUAGCUGAAUAGUUUUACUACCC | | [819-841] 3'UTR |
| 954 | UGGGUAGUAAAACUAUUCAGCUA | UAGCUGAAUAGUUUUACUACCCA | | [818-840] 3'UTR |
| 955 | UUGGGUAGUAAAACUAUUCAGCU | AGCUGAAUAGUUUUACUACCCAA | | [817-839] 3'UTR |
| 956 | AUUGGGUAGUAAAACUAUUCAGC | GCUGAAUAGUUUUACUACCCAAU | | [816-838] 3'UTR |
| 957 | UGAUUGGAACAACAGUGAUUGAA | UUCAAUCACUGUUGUUCCAAUCA | | [754-776] ORF |
| 958 | CUGAUUGGAACAACAGUGAUUGA | UCAAUCACUGUUGUUCCAAUCAG | | [753-775] ORF |
| 959 | ACUGAUUGGAACAACAGUGAUUG | CAAUCACUGUUGUUCCAAUCAGU | | [752-774] ORF |
| 960 | CACUGAUUGGAACAACAGUGAUU | AAUCACUGUUGUUCCAAUCAGUG | | [751-773] ORF |
| 961 | CAGUUAUCUUUGACUCUCUUGCC | GGCAAGAGAGUCAAAGAUAACUG | | [2459-2481] 3'UTR |
| 962 | ACAGUUAUCUUUGACUCUCUUGC | GCAAGAGAGUCAAAGAUAACUGU | | [2458-2480] 3'UTR |
| 963 | AACAGUUAUCUUUGACUCUCUUG | CAAGAGAGUCAAAGAUAACUGUU | | [2457-2479] 3'UTR |
| 964 | UAACAGUUAUCUUUGACUCUCUU | AAGAGAGUCAAAGAUAACUGUUA | | [2456-2478] 3'UTR |
| 965 | CUAACAGUUAUCUUUGACUCUCU | AGAGAGUCAAAGAUAACUGUUAG | | [2455-2477] 3'UTR |
| 966 | CACAAUUUGGUUUCAGGUAGGCU | AGCCUACCUGAAACCAAAUUGUG | | [1083-1105] 3'UTR |
| 967 | CCACAAUUUGGUUUCAGGUAGGC | GCCUACCUGAAACCAAAUUGUGG | | [1082-1104] 3'UTR |
| 968 | UCCACAAUUUGGUUUCAGGUAGG | CCUACCUGAAACCAAAUUGUGGA | | [1081-1103] 3'UTR |
| 969 | UUCCACAAUUUGGUUUCAGGUAG | CUACCUGAAACCAAAUUGUGGAA | | [1080-1102] 3'UTR |
| 970 | AUUCCACAAUUUGGUUUCAGGUA | UACCUGAAACCAAAUUGUGGAAU | | [1079-1101] 3'UTR |
| 971 | GAGAAGUGAUUCAAAAUAGUGUA | UACACUAUUUUGAAUCACUUCUC | | [967-989] 3'UTR |
| 972 | GCUUUUCUGGGAAUUGAAGUAUC | GAUACUUCAAUUCCCAGAAAAGC | | [1727-1749] 3'UTR |
| 973 | GAAGUCUGCAUUGGCUAUGGAGA | UCUCCAUAGCCAAUGCAGACUUC | | [1823-1845] 3'UTR |

TABLE E-continued additional 23 mers

| Number | Sense siRNA | AntiSense siRNA | Other Sp | Hum-34222182 ORF: 204-785 |
|---|---|---|---|---|
| 974 | UACUACAAAGCCAAUCUUUAUAG | CUAUAAAGAUUGGCUUUGUAGUA | | [2285-2307] 3'UTR |
| 975 | AUACUACAAAGCCAAUCUUUAUA | UAUAAAGAUUGGCUUUGUAGUAU | | [2284-2306] 3'UTR |
| 976 | GAUACUACAAAGCCAAUCUUUAU | AUAAAGAUUGGCUUUGUAGUAUC | | [2283-2305] 3'UTR |
| 977 | AGAUACUACAAAGCCAAUCUUUA | UAAAGAUUGGCUUUGUAGUAUCU | | [2282-2304] 3'UTR |
| 978 | AAAAUAGUGUAGAUUUUCUGCAU | AUGCAGAAAAUCUACACUAUUUU | | [979-1001] 3'UTR |
| 979 | AAGCAAAAGUAGAAGCCCAUUUG | CAAAUGGGCUUCUACUUUUGCUU | | [1043-1065] 3'UTR |
| 980 | UAAGCAAAAGUAGAAGCCCAUUU | AAAUGGGCUUCUACUUUUGCUUA | | [1042-1064] 3'UTR |
| 981 | GUAAGCAAAAGUAGAAGCCCAUU | AAUGGGCUUCUACUUUUGCUUAC | | [1041-1063] 3'UTR |
| 982 | CGGGUCAAUUUACGAAGUCUGCA | UGCAGACUUCGUAAAUUGACCCG | | [1810-1832] 3'UTR |
| 983 | ACGGGUCAAUUUACGAAGUCUGC | GCAGACUUCGUAAAUUGACCCGU | | [1809-1831] 3'UTR |
| 984 | AACGGGUCAAUUUACGAAGUCUG | CAGACUUCGUAAAUUGACCCGUU | | [1808-1830] 3'UTR |
| 985 | UCACUGAUUGGAACAACAGUGAU | AUCACUGUUGUUCCAAUCAGUGA | | [750-772] ORF |
| 986 | AAUUCAGCAAGGCUUUCAUAUCC | GGAUAUGAAAGCCUUGCUGAAUU | | [2044-2066] 3'UTR |
| 987 | CAAUUCAGCAAGGCUUUCAUAUC | GAUAUGAAAGCCUUGCUGAAUUG | | [2043-2065] 3'UTR |
| 988 | UCAAUUCAGCAAGGCUUUCAUAU | AUAUGAAAGCCUUGCUGAAUUGA | | [2042-2064] 3'UTR |
| 989 | UUCAAUUCAGCAAGGCUUUCAUA | UAUGAAAGCCUUGCUGAAUUGAA | | [2041-2063] 3'UTR |
| 990 | GUUCAAUUCAGCAAGGCUUUCAU | AUGAAAGCCUUGCUGAAUUGAAC | | [2040-2062] 3'UTR |
| 991 | AUGAAUACCUGUGAGGAUAGGAA | UUCCUAUCCUCACAGGUAUUCAU | | [1586-1608] 3'UTR |
| 992 | UUAUUUCAUGAUUGGGUAGUAAA | UUUACUACCCAAUCAUGAAAUAA | | [806-828] 3'UTR |
| 993 | AGAGAGCCUGCUAAGUGAUUUUG | CAAAAUCACUUAGCAGGCUCUCU | Chimp | [278-300] ORF |
| 994 | UUAACCCUAGGUAAGAGUAAAUG | CAUUUACUCUUACCUAGGGUUAA | | [1320-1342] 3'UTR |
| 995 | CUUAACCCUAGGUAAGAGUAAAU | AUUUACUCUUACCUAGGGUUAAG | | [1319-1341] 3'UTR |
| 996 | GCUUAACCCUAGGUAAGAGUAAA | UUUACUCUUACCUAGGGUUAAGC | | [1318-1340] 3'UTR |
| 997 | AGCUUAACCCUAGGUAAGAGUAA | UUACUCUUACCUAGGGUUAAGCU | | [1317-1339] 3'UTR |
| 998 | AGAACUGUUGUCCUUUUUCCACU | AGUGGAAAAGGACAACAGUUCU | | [2434-2456] 3'UTR |
| 999 | UAGAACUGUUGUCCUUUUUCCAC | GUGGAAAAGGACAACAGUUCUA | | [2433-2455] 3'UTR |
| 1000 | GUAGAACUGUUGUCCUUUUUCCA | UGGAAAAGGACAACAGUUCUAC | | [2432-2454] 3'UTR |
| 1001 | GCAUUUCAGAAUUGCUGGACUGU | ACAGUCCAGCAAUUCUGAAAUGC | Chimp | [244-266] ORF |
| 1002 | AGCAUUUCAGAAUUGCUGGACUG | CAGUCCAGCAAUUCUGAAAUGCU | Chimp | [243-265] ORF |
| 1003 | CAGCAUUUCAGAAUUGCUGGACU | AGUCCAGCAAUUCUGAAAUGCUG | Chimp | [242-264] ORF |
| 1004 | CCAGCAUUUCAGAAUUGCUGGAC | GUCCAGCAAUUCUGAAAUGCUGG | Chimp | [241-263] ORF |
| 1005 | GCCAGCAUUUCAGAAUUGCUGGA | UCCAGCAAUUCUGAAAUGCUGGC | Chimp | [240-262] ORF |
| 1006 | GUACCUACUUUUGAGCUUACACU | AGUGUAAGCUCAAAAGUAGGUAC | | [594-616] ORF |
| 1007 | CGUACCUACUUUUGAGCUUACAC | GUGUAAGCUCAAAAGUAGGUACG | | [593-615] ORF |
| 1008 | UCGUACCUACUUUUGAGCUUACA | UGUAAGCUCAAAAGUAGGUACGA | | [592-614] ORF |
| 1009 | GUCGUACCUACUUUUGAGCUUAC | GUAAGCUCAAAAGUAGGUACGAC | | [591-613] ORF |
| 1010 | GUCUUAUUCCAACUAAGUAGAUC | GAUCUACUUAGUUGGAAUAAGAC | | [1963-1985] 3'UTR |

TABLE E-continued additional 23 mers

| Number | Sense siRNA | AntiSense siRNA | Other Sp | Hum-34222182 ORF: 204-785 |
|---|---|---|---|---|
| 1011 | UGUCUUAUUCCAACUAAGUAGAU | AUCUACUUAGUUGGAAUAAGACA | | [1962-1984] 3'UTR |
| 1012 | UUGUCUUAUUCCAACUAAGUAGA | UCUACUUAGUUGGAAUAAGACAA | | [1961-1983] 3'UTR |
| 1013 | UUUGUCUUAUUCCAACUAAGUAG | CUACUUAGUUGGAAUAAGACAAA | | [1960-1982] 3'UTR |
| 1014 | UUUUGUCUUAUUCCAACUAAGUA | UACUUAGUUGGAAUAAGACAAAA | | [1959-1981] 3'UTR |
| 1015 | UUGUGUUUAAGCAGGAGAACUGC | GCAGUUCUCCUGCUUAAACACAA | Dog, Chimp | [616-638] ORF |
| 1016 | CUUGUGUUUAAGCAGGAGAACUG | CAGUUCUCCUGCUUAAACACAAG | Dog, Chimp | [615-637] ORF |
| 1017 | ACUUGUGUUUAAGCAGGAGAACU | AGUUCUCCUGCUUAAACACAAGU | Dog, Chimp | [614-636] ORF |
| 1018 | CACUUGUGUUUAAGCAGGAGAAC | GUUCUCCUGCUUAAACACAAGUG | Dog, Chimp | [613-635] ORF |
| 1019 | ACACUUGUGUUUAAGCAGGAGAA | UUCUCCUGCUUAAACACAAGUGU | Dog, Chimp | [612-634] ORF |
| 1020 | AACUUGCCAGAAUUUGGUUAAAA | UUUUAACCAAAUUCUGGCAAGUU | GP, Chimp, Rat, Ms | [359-381] ORF |
| 1021 | UCUAAUGUUUAAAGAGGCAACA | UGUUGCCUCUUUAAACAUUAGA | | [1398-1420] 3'UTR |
| 1022 | CUCUAAUGUUUAAAGAGGCAAC | GUUGCCUCUUUAAACAUUAGAG | | [1397-1419] 3'UTR |
| 1023 | ACUCUAAUGUUUAAAGAGGCAA | UUGCCUCUUUAAACAUUAGAGU | | [1396-1418] 3'UTR |
| 1024 | CACUCUAAUGUUUAAAGAGGCA | UGCCUCUUUAAACAUUAGAGUG | | [1395-1417] 3'UTR |
| 1025 | CUAAGUUUUCAGAGGAUUUUUA | UAAAAAUCCUCUGAAAACUUAG | | [1166-1188] 3'UTR |
| 1026 | UCUAAGUUUUCAGAGGAUUUUU | AAAAAUCCUCUGAAAACUUAGA | | [1165-1187] 3'UTR |
| 1027 | CUCUAAGUUUUCAGAGGAUUUU | AAAAUCCUCUGAAAACUUAGAG | | [1164-1186] 3'UTR |
| 1028 | UCUCUAAGUUUUCAGAGGAUUU | AAAUCCUCUGAAAACUUAGAGA | | [1163-1185] 3'UTR |
| 1029 | UUCUCUAAGUUUUCAGAGGAUU | AAUCCUCUGAAAACUUAGAGAA | | [1162-1184] 3'UTR |
| 1030 | UGGUUUAUAGUACAGCCUAGAGA | UCUCUAGGCUGUACUAUAAACCA | | [1848-1870] 3'UTR |
| 1031 | AUGGUUUAUAGUACAGCCUAGAG | CUCUAGGCUGUACUAUAAACCAU | | [1847-1869] 3'UTR |
| 1032 | UAUGGUUUAUAGUACAGCCUAGA | UCUAGGCUGUACUAUAAACCAUA | | [1846-1868] 3'UTR |
| 1033 | AUAUGGUUUAUAGUACAGCCUAG | CUAGGCUGUACUAUAAACCAUAU | | [1845-1867] 3'UTR |
| 1034 | UCCUCUGGUUUCAGGAGAACUCU | AGAGUUCUCCUGAAACCAGAGGA | | [684-706] ORF |
| 1035 | CUCCUCUGGUUUCAGGAGAACUC | GAGUUCUCCUGAAACCAGAGGAG | | [683-705] ORF |
| 1036 | UCUCCUCUGGUUUCAGGAGAACU | AGUUCUCCUGAAACCAGAGGAGA | | [682-704] ORF |
| 1037 | UUCUCCUCUGGUUUCAGGAGAAC | GUUCUCCUGAAACCAGAGGAGAA | | [681-703] ORF |
| 1038 | CUUCUCCUCUGGUUUCAGGAGAA | UUCUCCUGAAACCAGAGGAGAAG | | [680-702] ORF |
| 1039 | UGUUGUUUUAGAUGCCUUUAUAA | UUAUAAAGGCAUCUAAAACAACA | | [1452-1474] 3'UTR |
| 1040 | GUGUUGUUUUAGAUGCCUUUAUA | UAUAAAGGCAUCUAAAACAACAC | | [1451-1473] 3'UTR |
| 1041 | GGUGUUGUUUUAGAUGCCUUUAU | AUAAAGGCAUCUAAAACAACACC | | [1450-1472] 3'UTR |
| 1042 | ACGGUGUUGUUUUAGAUGCCUUU | AAAGGCAUCUAAAACAACACCGU | | [1448-1470] 3'UTR |
| 1043 | UAAGUGAUUUGACUACUGGGAU | AUCCCAGUAGUCAAAUCACUUA | Dog, Chimp | [289-311] ORF |
| 1044 | GGUGAUGGCUUAUGGAAGGCUGU | ACAGCCUUCCAUAAGCCAUCACC | | [2499-2521] 3'UTR |
| 1045 | UGGUGAUGGCUUAUGGAAGGCUG | CAGCCUUCCAUAAGCCAUCACCA | | [2498-2520] 3'UTR |
| 1046 | AUGGUGAUGGCUUAUGGAAGGCU | AGCCUUCCAUAAGCCAUCACCAU | | [2497-2519] 3'UTR |
| 1047 | AUUGUCAAGGGUAGUAGCUGUAU | AUACAGCUACUACCCUUGACAAU | | [1764-1786] 3'UTR |

TABLE E-continued additional 23 mers

| Number | Sense siRNA | AntiSense siRNA | Other Sp | Hum-34222182 ORF: 204-785 |
|---|---|---|---|---|
| 1048 | AAUUGUCAAGGGUAGUAGCUGUA | UACAGCUACUACCCUUGACAAUU | | [1763-1785] 3'UTR |
| 1049 | CAAUUGUCAAGGGUAGUAGCUGU | ACAGCUACUACCCUUGACAAUUG | | [1762-1784] 3'UTR |
| 1050 | CGCUUCUCCUCUGGUUUCAGGAG | CUCCUGAAACCAGAGGAGAAGCG | | [678-700] ORF |
| 1051 | UCGCUUCUCCUCUGGUUUCAGGA | UCCUGAAACCAGAGGAGAAGCGA | | [677-699] ORF |
| 1052 | GUCGCUUCUCCUCUGGUUUCAGG | CCUGAAACCAGAGGAGAAGCGAC | | [676-698] ORF |
| 1053 | GGUCGCUUCUCCUCUGGUUUCAG | CUGAAACCAGAGGAGAAGCGACC | | [675-697] ORF |
| 1054 | AGGUCGCUUCUCCUCUGGUUUCA | UGAAACCAGAGGAGAAGCGACCU | | [674-696] ORF |
| 1055 | AUCAAUGUUGUUUUGCAUGUCUA | UAGACAUGCAAAACAACAUUGAU | | [2324-2346] 3'UTR |
| 1056 | UUCUAGCGUCGUACCUACUUUUG | CAAAAGUAGGUACGACGCUAGAA | | [584-606] ORF |
| 1057 | AUUCUAGCGUCGUACCUACUUUU | AAAAGUAGGUACGACGCUAGAAU | | [583-605] ORF |
| 1058 | CCAGAUAACCAUGCAUGCACCCA | UGGGUGCAUGCAUGGUUAUCUGG | | [1885-1907] 3'UTR |
| 1059 | UCCAGAUAACCAUGCAUGCACCC | GGGUGCAUGCAUGGUUAUCUGGA | | [1884-1906] 3'UTR |
| 1060 | GUCCAGAUAACCAUGCAUGCACC | GGUGCAUGCAUGGUUAUCUGGAC | | [1883-1905] 3'UTR |
| 1061 | CGUCCAGAUAACCAUGCAUGCAC | GUGCAUGCAUGGUUAUCUGGACG | | [1882-1904] 3'UTR |
| 1062 | CUUCCAAAAGCCCACACCACCAG | CUGGUGGUGUGGGCUUUUGGAAG | | [1229-1251] 3'UTR |
| 1063 | ACUUCCAAAAGCCCACACCACCA | UGGUGGUGUGGGCUUUUGGAAGU | | [1228-1250] 3'UTR |
| 1064 | AACUUCCAAAAGCCCACACCACC | GGUGGUGUGGGCUUUUGGAAGUU | | [1227-1249] 3'UTR |
| 1065 | AAACUUCCAAAAGCCCACACCAC | GUGGUGUGGGCUUUUGGAAGUUU | | [1226-1248] 3'UTR |
| 1066 | AAAACUUCCAAAAGCCCACACCA | UGGUGUGGGCUUUUGGAAGUUUU | | [1225-1247] 3'UTR |
| 1067 | AGUUAUCUUUGACUCUCUUGCCU | AGGCAAGAGAGUCAAAGAUAACU | | [2460-2482] 3'UTR |
| 1068 | CUUAAGUGUUGAAUACUGUCUUU | AAAGACAGUAUUCAACACUUAAG | | [1492-1514] 3'UTR |
| 1069 | UCUUAAGUGUUGAAUACUGUCUU | AAGACAGUAUUCAACACUUAAGA | | [1491-1513] 3'UTR |
| 1070 | UUCUUAAGUGUUGAAUACUGUCU | AGACAGUAUUCAACACUUAAGAA | | [1490-1512] 3'UTR |
| 1071 | GUUCUUAAGUGUUGAAUACUGUC | GACAGUAUUCAACACUUAAGAAC | | [1489-1511] 3'UTR |
| 1072 | UGUUCUUAAGUGUUGAAUACUGU | ACAGUAUUCAACACUUAAGAACA | | [1488-1510] 3'UTR |
| 1073 | CAUAGCAACUGCAGCUAACAGGC | GCCUGUUAGCUGCAGUUGCUAUG | | [927-949] 3'UTR |
| 1074 | UCAUAGCAACUGCAGCUAACAGG | CCUGUUAGCUGCAGUUGCUAUGA | | [926-948] 3'UTR |
| 1075 | UUCAUAGCAACUGCAGCUAACAG | CUGUUAGCUGCAGUUGCUAUGAA | | [925-947] 3'UTR |
| 1076 | AUUCAUAGCAACUGCAGCUAACA | UGUUAGCUGCAGUUGCUAUGAAU | | [924-946] 3'UTR |
| 1077 | CAUUCAUAGCAACUGCAGCUAAC | GUUAGCUGCAGUUGCUAUGAAUG | | [923-945] 3'UTR |
| 1078 | GAACCCGGCCAGCAUUUCAGAAU | AUUCUGAAAUGCUGGCCGGGUUC | Chimp | [233-255] ORF |
| 1079 | GGCCAAGAUAAAUCAAUGUUGUU | AACAACAUUGAUUUAUCUUGGCC | | [2313-2335] 3'UTR |
| 1080 | AUAUUACGGCAAUAAUGGAACUG | CAGUUCCAUUAUUGCCGUAAUAU | | [1347-1369] 3'UTR |
| 1081 | AAUAUUACGGCAAUAAUGGAACU | AGUUCCAUUAUUGCCGUAAUAUU | | [1346-1368] 3'UTR |
| 1082 | AAAUAUUACGGCAAUAAUGGAAC | GUUCCAUUAUUGCCGUAAUAUUU | | [1345-1367] 3'UTR |
| 1083 | GAAAUAUUACGGCAAUAAUGGAA | UUCCAUUAUUGCCGUAAUAUUUC | | [1344-1366] 3'UTR |
| 1084 | AGAAAUAUUACGGCAAUAAUGGA | UCCAUUAUUGCCGUAAUAUUUCU | | [1343-1365] 3'UTR |

TABLE E-continued additional 23 mers

| Number | Sense siRNA | AntiSense siRNA | Other Sp | Hum-34222182 ORF: 204-785 |
|---|---|---|---|---|
| 1085 | UAAAAAGCUGGAUAGGAUUGUGU | ACACAAUCCUAUCCAGCUUUUUA | Chin, GP, Chimp, Rat | [557-579] ORF |
| 1086 | AUGUUGUUCCUGAACCCAACCUC | GAGGUUGGGUUCAGGAACAACAU | Chimp | [313-335] ORF |
| 1087 | UAUGUUGUUCCUGAACCCAACCU | AGGUUGGGUUCAGGAACAACAUA | Chimp | [312-334] ORF |
| 1088 | UUAUGUUGUUCCUGAACCCAACC | GGUUGGGUUCAGGAACAACAUAA | Chimp | [311-333] ORF |
| 1089 | AUUAUGUUGUUCCUGAACCCAAC | GUUGGGUUCAGGAACAACAUAAU | Chimp | [310-332] ORF |
| 1090 | GAUUAUGUUGUUCCUGAACCCAA | UUGGGUUCAGGAACAACAUAAUC | Chimp | [309-331] ORF |
| 1091 | GGUUUCAGGAGAACUCUGAUCCU | AGGAUCAGAGUUCUCCUGAAACC | | [690-712] ORF |
| 1092 | UGGUUUCAGGAGAACUCUGAUCC | GGAUCAGAGUUCUCCUGAAACCA | | [689-711] ORF |
| 1093 | CUGGUUUCAGGAGAACUCUGAUC | GAUCAGAGUUCUCCUGAAACCAG | | [688-710] ORF |
| 1094 | UCUGGUUUCAGGAGAACUCUGAU | AUCAGAGUUCUCCUGAAACCAGA | | [687-709] ORF |
| 1095 | CUCUGGUUUCAGGAGAACUCUGA | UCAGAGUUCUCCUGAAACCAGAG | | [686-708] ORF |
| 1096 | CCAUGGUUGCAACUGGCAGUUUG | CAAACUGCCAGUUGCAACCAUGG | Chimp | [202-224] 5'UTR + ORF |
| 1097 | ACCAUGGUUGCAACUGGCAGUUU | AAACUGCCAGUUGCAACCAUGGU | Chimp | [201-223] 5'UTR + ORF |
| 1098 | GACCAUGGUUGCAACUGGCAGUU | AACUGCCAGUUGCAACCAUGGUC | Chimp | [200-222] 5'UTR + ORF |
| 1099 | UGACCAUGGUUGCAACUGGCAGU | ACUGCCAGUUGCAACCAUGGUCA | Chimp | [199-221] 5'UTR + ORF |
| 1100 | UGUGAUCCUGUUACUGAUACUAU | AUAGUAUCAGUAACAGGAUCACA | | [2189-2211] 3'UTR |
| 1101 | AUUAUUUCAUGAUUGGGUAGUAA | UUACUACCCAAUCAUGAAAUAAU | | [805-827] 3'UTR |
| 1102 | GUUUUUAGACAGGAAGGUAGGAU | AUCCUACCUUCCUGUCUAAAAAC | | [1273-1295] 3'UTR |
| 1103 | GGUUUUUAGACAGGAAGGUAGGA | UCCUACCUUCCUGUCUAAAAACC | | [1272-1294] 3'UTR |
| 1104 | GGGUUUUUAGACAGGAAGGUAGG | CCUACCUUCCUGUCUAAAAACCC | | [1271-1293] 3'UTR |
| 1105 | AGGGUUUUUAGACAGGAAGGUAG | CUACCUUCCUGUCUAAAAACCCU | | [1270-1292] 3'UTR |
| 1106 | AGGUUUCCUGCCCUAGCUAUUAG | CUAAUAGCUAGGGCAGGAAACCU | | [2098-2120] 3'UTR |
| 1107 | CAGGUUUCCUGCCCUAGCUAUUA | UAAUAGCUAGGGCAGGAAACCUG | | [2097-2119] 3'UTR |
| 1108 | UCAGGUUUCCUGCCCUAGCUAUU | AAUAGCUAGGGCAGGAAACCUGA | | [2096-2118] 3'UTR |
| 1109 | UUCAGGUUUCCUGCCCUAGCUAU | AUAGCUAGGGCAGGAAACCUGAA | | [2095-2117] 3'UTR |
| 1110 | AUUCAGGUUUCCUGCCCUAGCUA | UAGCUAGGGCAGGAAACCUGAAU | | [2094-2116] 3'UTR |
| 1111 | CAACAAUGUUCAAUUCAGCAAGG | CCUUGCUGAAUUGAACAUUGUUG | | [2033-2055] 3'UTR |
| 1112 | UCAACAAUGUUCAAUUCAGCAAG | CUUGCUGAAUUGAACAUUGUUGA | | [2032-2054] 3'UTR |
| 1113 | CUCAACAAUGUUCAAUUCAGCAA | UUGCUGAAUUGAACAUUGUUGAG | | [2031-2053] 3'UTR |
| 1114 | ACUCAACAAUGUUCAAUUCAGCA | UGCUGAAUUGAACAUUGUUGAGU | | [2030-2052] 3'UTR |
| 1115 | CACUCAACAAUGUUCAAUUCAGC | GCUGAAUUGAACAUUGUUGAGUG | | [2029-2051] 3'UTR |
| 1116 | CCUCUUUUCAGUAUUACAUGUGC | GCACAUGUAAUACUGAAAAGAGG | | [1655-1677] 3'UTR |
| 1117 | UCCUCUUUUCAGUAUUACAUGUG | CACAUGUAAUACUGAAAAGAGGA | | [1654-1676] 3'UTR |
| 1118 | AUCCUCUUUUCAGUAUUACAUGU | ACAUGUAAUACUGAAAAGAGGAU | | [1653-1675] 3'UTR |
| 1119 | UAUCCUCUUUUCAGUAUUACAUG | CAUGUAAUACUGAAAAGAGGAUA | | [1652-1674] 3'UTR |
| 1120 | CUAUCCUCUUUUCAGUAUUACAU | AUGUAAUACUGAAAAGAGGAUAG | | [1651-1673] 3'UTR |
| 1121 | AGUGUUGAAUACUGUCUUUAAAC | GUUUAAAGACAGUAUUCAACACU | | [1496-1518] 3'UTR |

TABLE E-continued additional 23 mers

| Number | Sense siRNA | AntiSense siRNA | Other Sp | Hum-34222182 ORF: 204-785 |
|---|---|---|---|---|
| 1122 | AAGUGUUGAAUACUGUCUUUAAA | UUUAAAGACAGUAUUCAACACUU | | [1495-1517] 3'UTR |
| 1123 | UAAGUGUUGAAUACUGUCUUUAA | UUAAAGACAGUAUUCAACACUUA | | [1494-1516] 3'UTR |
| 1124 | UUAAGUGUUGAAUACUGUCUUUA | UAAAGACAGUAUUCAACACUUAA | | [1493-1515] 3'UTR |
| 1125 | GAACAACAGUGAUUGAAGGGUCC | GGACCCUUCAAUCACUGUUGUUC | | [760-782] ORF |
| 1126 | UCUAUCCUCUUUUCAGUAUUACA | UGUAAUACUGAAAAGAGGAUAGA | | [1650-1672] 3'UTR |
| 1127 | GGAAAUUAGUUCUGAGAUCUAGU | ACUAGAUCUCAGAACUAAUUUCC | | [1605-1627] 3'UTR |
| 1128 | AGGAAAUUAGUUCUGAGAUCUAG | CUAGAUCUCAGAACUAAUUUCCU | | [1604-1626] 3'UTR |
| 1129 | UAGGAAAUUAGUUCUGAGAUCUA | UAGAUCUCAGAACUAAUUUCCUA | | [1603-1625] 3'UTR |
| 1130 | AUAGGAAAUUAGUUCUGAGAUCU | AGAUCUCAGAACUAAUUUCCUAU | | [1602-1624] 3'UTR |
| 1131 | UUGUCCUUUUUCCACUAACAGUU | AACUGUUAGUGGAAAAGGACAA | | [2441-2463] 3'UTR |
| 1132 | UUUUCUGGCCUUUGGAGAAGUGA | UCACUUCUCCAAAGGCCAGAAAA | | [953-975] 3'UTR |
| 1133 | AUUUUCUGGCCUUUGGAGAAGUG | CACUUCUCCAAAGGCCAGAAAAU | | [952-974] 3'UTR |
| 1134 | GAUUUUCUGGCCUUUGGAGAAGU | ACUUCUCCAAAGGCCAGAAAAUC | | [951-973] 3'UTR |
| 1135 | AGUCCUCUCUGAUUCACUUAGU | ACUAAGUGAAUCAGAGAGGGACU | | [1625-1647] 3'UTR |
| 1136 | UAGUCCCUCUCUGAUUCACUUAG | CUAAGUGAAUCAGAGAGGGACUA | | [1624-1646] 3'UTR |
| 1137 | CUAGUCCCUCUCUGAUUCACUUA | UAAGUGAAUCAGAGAGGGACUAG | | [1623-1645] 3'UTR |
| 1138 | UCUAGUCCCUCUCUGAUUCACUU | AAGUGAAUCAGAGAGGGACUAGA | | [1622-1644] 3'UTR |
| 1139 | UCUUUAUAGAAUUGGGCCAAGAU | AUCUUGGCCCAAUUCUAUAAAGA | | [2299-2321] 3'UTR |
| 1140 | GUUUCAGGAGAACUCUGAUCCUC | GAGGAUCAGAGUUCUCCUGAAAC | | [691-713] ORF |
| 1141 | CCUAGCUAUUAGCUCCACUUCAC | GUGAAGUGGAGCUAAUAGCUAGG | | [2109-2131] 3'UTR |
| 1142 | ACUCAAAUUUGAAGGGUUUUUAG | CUAAAACCCUUCAAAUUUGAGU | | [1258-1280] 3'UTR |
| 1143 | CUAACAGGCUGAUUUUCUGGCCU | AGGCCAGAAAAUCAGCCUGUUAG | | [941-963] 3'UTR |
| 1144 | GCUAACAGGCUGAUUUUCUGGCC | GGCCAGAAAAUCAGCCUGUUAGC | | [940-962] 3'UTR |
| 1145 | AGCUAACAGGCUGAUUUUCUGGC | GCCAGAAAAUCAGCCUGUUAGCU | | [939-961] 3'UTR |
| 1146 | CAGCUAACAGGCUGAUUUUCUGG | CCAGAAAAUCAGCCUGUUAGCUG | | [938-960] 3'UTR |
| 1147 | GCAGCUAACAGGCUGAUUUUCUG | CAGAAAAUCAGCCUGUUAGCUGC | | [937-959] 3'UTR |
| 1148 | CAAUGUUCAAUUCAGCAAGGCUU | AAGCCUUGCUGAAUUGAACAUUG | | [2036-2058] 3'UTR |
| 1149 | ACAAUGUUCAAUUCAGCAAGGCU | AGCCUUGCUGAAUUGAACAUUGU | | [2035-2057] 3'UTR |
| 1150 | AACAAUGUUCAAUUCAGCAAGGC | GCCUUGCUGAAUUGAACAUUGUU | | [2034-2056] 3'UTR |
| 1151 | UGGUGUUACUGAAAAACAGGUGU | ACACCUGUUUUUCAGUAACACCA | | [2169-2191] 3'UTR |
| 1152 | CUGGUGUUACUGAAAAACAGGUG | CACCUGUUUUUCAGUAACACCAG | | [2168-2190] 3'UTR |
| 1153 | CCUGGUGUUACUGAAAAACAGGU | ACCUGUUUUUCAGUAACACCAGG | | [2167-2189] 3'UTR |
| 1154 | GUUCCUGAACCCAACCUCAACGA | UCGUUGAGGUUGGGUUCAGGAAC | Chimp | [318-340] ORF |
| 1155 | UGUUCCUGAACCCAACCUCAACG | CGUUGAGGUUGGGUUCAGGAACA | Chimp | [317-339] ORF |
| 1156 | UUGUUCCUGAACCCAACCUCAAC | GUUGAGGUUGGGUUCAGGAACAA | Chimp | [316-338] ORF |
| 1157 | GUUGUUCCUGAACCCAACCUCAA | UUGAGGUUGGGUUCAGGAACAAC | Chimp | [315-337] ORF |
| 1158 | UGUUGUUCCUGAACCCAACCUCA | UGAGGUUGGGUUCAGGAACAACA | Chimp | [314-336] ORF |

TABLE E-continued additional 23 mers

| Number | Sense siRNA | AntiSense siRNA | Other Sp | Hum-34222182 ORF: 204-785 | |
|---|---|---|---|---|---|
| 1159 | UUUCAGGAGAACUCUGAUCCUCA | UGAGGAUCAGAGUUCUCCUGAAA | | [692-714] | ORF |
| 1160 | CAACUUGCCAGAAUUUGGUUAAA | UUUAACCAAAUUCUGGCAAGUUG | Chimp | [358-380] | ORF |
| 1161 | UGCAGCUAACAGGCUGAUUUUCU | AGAAAAUCAGCCUGUUAGCUGCA | | [936-958] | 3'UTR |
| 1162 | CUGCAGCUAACAGGCUGAUUUUC | GAAAAUCAGCCUGUUAGCUGCAG | | [935-957] | 3'UTR |
| 1163 | ACUGCAGCUAACAGGCUGAUUUU | AAAAUCAGCCUGUUAGCUGCAGU | | [934-956] | 3'UTR |
| 1164 | CCCAAAUGUAGUCUCUUUUCUUU | AAAGAAAAGAGACUACAUUUGGG | | [890-912] | 3'UTR |
| 1165 | CCCCAAAUGUAGUCUCUUUUCUU | AAGAAAAGAGACUACAUUUGGGG | | [889-911] | 3'UTR |
| 1166 | ACCCCAAAUGUAGUCUCUUUUCU | AGAAAAGAGACUACAUUUGGGGU | | [888-910] | 3'UTR |
| 1167 | AACCCCAAAUGUAGUCUCUUUUC | GAAAAGAGACUACAUUUGGGGUU | | [887-909] | 3'UTR |
| 1168 | AAACCCCAAAUGUAGUCUCUUUU | AAAAGAGACUACAUUUGGGGUUU | | [886-908] | 3'UTR |
| 1169 | ACCAUGCAUGCACCCAGAUUUUU | AAAAAUCUGGGUGCAUGCAUGGU | | [1892-1914] | 3'UTR |
| 1170 | GGAACUGCUUCACUGUUUCUUGG | CCAAGAAACAGUGAAGCAGUUCC | | [1363-1385] | 3'UTR |
| 1171 | UGGAACUGCUUCACUGUUUCUUG | CAAGAAACAGUGAAGCAGUUCCA | | [1362-1384] | 3'UTR |
| 1172 | AUGGAACUGCUUCACUGUUUCUU | AAGAAACAGUGAAGCAGUUCCAU | | [1361-1383] | 3'UTR |
| 1173 | AAUGGAACUGCUUCACUGUUUCU | AGAAACAGUGAAGCAGUUCCAUU | | [1360-1382] | 3'UTR |
| 1174 | UAAUGGAACUGCUUCACUGUUUC | GAAACAGUGAAGCAGUUCCAUUA | | [1359-1381] | 3'UTR |
| 1175 | CCAAAGGUUCACUGUGUUUCUGC | GCAGAAACACAGUGAACCUUUGG | | [2357-2379] | 3'UTR |
| 1176 | UCCAAAGGUUCACUGUGUUUCUG | CAGAAACACAGUGAACCUUUGGA | | [2356-2378] | 3'UTR |
| 1177 | CUCCAAAGGUUCACUGUGUUUCU | AGAAACACAGUGAACCUUUGGAG | | [2355-2377] | 3'UTR |
| 1178 | GCUCCAAAGGUUCACUGUGUUUC | GAAACACAGUGAACCUUUGGAGC | | [2354-2376] | 3'UTR |
| 1179 | AGCUCCAAAGGUUCACUGUGUUU | AAACACAGUGAACCUUUGGAGCU | | [2353-2375] | 3'UTR |
| 1180 | GAACCAUUUCACCAUGGCAGUGU | ACACUGCCAUGGUGAAAUGGUUC | | [1690-1712] | 3'UTR |
| 1181 | UGAACCAUUUCACCAUGGCAGUG | CACUGCCAUGGUGAAAUGGUUCA | | [1689-1711] | 3'UTR |
| 1182 | AUGAACCAUUUCACCAUGGCAGU | ACUGCCAUGGUGAAAUGGUUCAU | | [1688-1710] | 3'UTR |
| 1183 | GAUGAACCAUUUCACCAUGGCAG | CUGCCAUGGUGAAAUGGUUCAUC | | [1687-1709] | 3'UTR |
| 1184 | ACUAAACUUGGUUGCUCAAAGGU | ACCUUUGAGCAACCAAGUUUAGU | Chimp | [414-436] | ORF |
| 1185 | AACUAAACUUGGUUGCUCAAAGG | CCUUUGAGCAACCAAGUUUAGUU | Chimp | [413-435] | ORF |
| 1186 | AAACUAAACUUGGUUGCUCAAAG | CUUUGAGCAACCAAGUUUAGUUU | Chimp | [412-434] | ORF |
| 1187 | CAAACUAAACUUGGUUGCUCAAA | UUUGAGCAACCAAGUUUAGUUUG | Chimp | [411-433] | ORF |
| 1188 | GCAAACUAAACUUGGUUGCUCAA | UUGAGCAACCAAGUUUAGUUUGC | Chimp | [410-432] | ORF |
| 1189 | AUUUUCUGCAUAGAUCCCAUUUU | AAAUGGGAUCUAUGCAGAAAAU | | [991-1013] | 3'UTR |
| 1190 | GAUUUUCUGCAUAGAUCCCAUUU | AAAUGGGAUCUAUGCAGAAAAUC | | [990-1012] | 3'UTR |
| 1191 | AGAUUUUCUGCAUAGAUCCCAUU | AAUGGGAUCUAUGCAGAAAAUCU | | [989-1011] | 3'UTR |
| 1192 | UAGAUUUUCUGCAUAGAUCCCAU | AUGGGAUCUAUGCAGAAAAUCUA | | [988-1010] | 3'UTR |
| 1193 | AUUUACGAAGUCUGCAUUGGCUA | UAGCCAAUGCAGACUUCGUAAAU | | [1817-1839] | 3'UTR |
| 1194 | GAUCAUUAUCUCUUUCCUUUUUU | AAAAAGGAAAGAGAUAAUGAUC | | [1982-2004] | 3'UTR |
| 1195 | AGAUCAUUAUCUCUUUCCUUUUU | AAAAAGGAAAGAGAUAAUGAUCU | | [1981-2003] | 3'UTR |

TABLE E-continued additional 23 mers

| Number | Sense siRNA | AntiSense siRNA | Other Sp | Hum-34222182 ORF: 204-785 |
|---|---|---|---|---|
| 1196 | UAGAUCAUUAUCUCUUUCCUUUU | AAAAGGAAAGAGAUAAUGAUCUA | | [1980-2002] 3'UTR |
| 1197 | GUAGAUCAUUAUCUCUUUCCUUU | AAAGGAAAGAGAUAAUGAUCUAC | | [1979-2001] 3'UTR |
| 1198 | AGUAGAUCAUUAUCUCUUUCCUU | AAGGAAAGAGAUAAUGAUCUACU | | [1978-2000] 3'UTR |
| 1199 | GCAUUGGCUAUGGAGAUAUGGUU | AACCAUAUCUCCAUAGCCAAUGC | | [1830-1852] 3'UTR |
| 1200 | GGUAGUAGCUGUAUACUACCACU | AGUGGUAGUAUACAGCUACUACC | | [1773-1795] 3'UTR |
| 1201 | CCAAUUGUCAAGGGUAGUAGCUG | CAGCUACUACCCUUGACAAUUGG | | [1761-1783] 3'UTR |
| 1202 | CCCAAUUGUCAAGGGUAGUAGCU | AGCUACUACCCUUGACAAUUGGG | | [1760-1782] 3'UTR |
| 1203 | CCCCAAUUGUCAAGGGUAGUAGC | GCUACUACCCUUGACAAUUGGGG | | [1759-1781] 3'UTR |
| 1204 | ACCCCAAUUGUCAAGGGUAGUAG | CUACUACCCUUGACAAUUGGGGU | | [1758-1780] 3'UTR |
| 1205 | AACCCCAAUUGUCAAGGGUAGUA | UACUACCCUUGACAAUUGGGGUU | | [1757-1779] 3'UTR |
| 1206 | CUUAGUAAUCUAUCCUCUUUUCA | UGAAAGAGGAUAGAUUACUAAG | | [1642-1664] 3'UTR |
| 1207 | ACUUAGUAAUCUAUCCUCUUUUC | GAAAAGAGGAUAGAUUACUAAGU | | [1641-1663] 3'UTR |
| 1208 | CACUUAGUAAUCUAUCCUCUUUU | AAAAGAGGAUAGAUUACUAAGUG | | [1640-1662] 3'UTR |
| 1209 | UCACUUAGUAAUCUAUCCUCUUU | AAAGAGGAUAGAUUACUAAGUGA | | [1639-1661] 3'UTR |
| 1210 | UUCACUUAGUAAUCUAUCCUCUU | AAGAGGAUAGAUUACUAAGUGAA | | [1638-1660] 3'UTR |
| 1211 | CUGGAGUUGUCACCACUGACUGG | CCAGUCAGUGGUGACAACUCCAG | | [2387-2409] 3'UTR |
| 1212 | CCUGGAGUUGUCACCACUGACUG | CAGUCAGUGGUGACAACUCCAGG | | [2386-2408] 3'UTR |
| 1213 | UCCUGGAGUUGUCACCACUGACU | AGUCAGUGGUGACAACUCCAGGA | | [2385-2407] 3'UTR |
| 1214 | GUCCUGGAGUUGUCACCACUGAC | GUCAGUGGUGACAACUCCAGGAC | | [2384-2406] 3'UTR |
| 1215 | UGUCCUGGAGUUGUCACCACUGA | UCAGUGGUGACAACUCCAGGACA | | [2383-2405] 3'UTR |
| 1216 | CAGUUUGAGCAGCAAGAACCCGG | CCGGGUUCUUGCUGCUCAAACUG | Chimp | [218-240] ORF |
| 1217 | CUACUGGGAUUAUGUUGUUCCUG | CAGGAACAACAUAAUCCCAGUAG | Chimp | [302-324] ORF |
| 1218 | ACUACUGGGAUUAUGUUGUUCCU | AGGAACAACAUAAUCCCAGUAGU | Chimp | [301-323] ORF |
| 1219 | GACUACUGGGAUUAUGUUGUUCC | GGAACAACAUAAUCCCAGUAGUC | Chimp | [300-322] ORF |
| 1220 | UGACUACUGGGAUUAUGUUGUUC | GAACAACAUAAUCCCAGUAGUCA | Chimp | [299-321] ORF |
| 1221 | UUGACUACUGGGAUUAUGUUGUU | AACAACAUAAUCCCAGUAGUCAA | Chimp | [298-320] ORF |
| 1222 | UAGGGACAGAUGUAUUCAUCCUG | CAGGAUGAAUACAUCUGUCCCUA | | [2148-2170] 3'UTR |
| 1223 | GUAGGGACAGAUGUAUUCAUCCU | AGGAUGAAUACAUCUGUCCCUAC | | [2147-2169] 3'UTR |
| 1224 | CGUAGGGACAGAUGUAUUCAUCC | GGAUGAAUACAUCUGUCCCUACG | | [2146-2168] 3'UTR |
| 1225 | CAAUCUUUAUAGAAUUGGGCCAA | UUGGCCCAAUUCUAUAAAGAUUG | | [2296-2318] 3'UTR |
| 1226 | CCAAUCUUUAUAGAAUUGGGCCA | UGGCCCAAUUCUAUAAAGAUUGG | | [2295-2317] 3'UTR |
| 1227 | GCCAAUCUUUAUAGAAUUGGGCC | GGCCCAAUUCUAUAAAGAUUGGC | | [2294-2316] 3'UTR |
| 1228 | AGCCAAUCUUUAUAGAAUUGGGC | GCCCAAUUCUAUAAAGAUUGGCU | | [2293-2315] 3'UTR |
| 1229 | AAGCCAAUCUUUAUAGAAUUGGG | CCCAAUUCUAUAAAGAUUGGCUU | | [2292-2314] 3'UTR |
| 1230 | GUUGUCCUUUUUCCACUAACAGU | ACUGUUAGUGGAAAAAGGACAAC | | [2440-2462] 3'UTR |
| 1231 | GUCCUAAAAAGGGAAAAUAUAUA | UAUAUAUUUUCCCUUUUUAGGAC | | [779-801] ORF + 3'UTR |
| 1232 | AUUUAGCCUAUCAAAACUUCCAA | UUGGAAGUUUUGAUAGGCUAAAU | | [1213-1235] 3'UTR |

TABLE E-continued additional 23 mers

| Number | Sense siRNA | AntiSense siRNA | Other Sp | Hum-34222182 ORF: 204-785 |
|---|---|---|---|---|
| 1233 | CUAAACUCUUCAAAUGCUUGGAA | UUCCAAGCAUUUGAAGAGUUUAG | | [2259-2281] 3'UTR |
| 1234 | ACUAAACUCUUCAAAUGCUUGGA | UCCAAGCAUUUGAAGAGUUUAGU | | [2258-2280] 3'UTR |
| 1235 | AACUAAACUCUUCAAAUGCUUGG | CCAAGCAUUUGAAGAGUUUAGUU | | [2257-2279] 3'UTR |
| 1236 | AAACUAAACUCUUCAAAUGCUUG | CAAGCAUUUGAAGAGUUUAGUUU | | [2256-2278] 3'UTR |
| 1237 | CAAACUAAACUCUUCAAAUGCUU | AAGCAUUUGAAGAGUUUAGUUUG | | [2255-2277] 3'UTR |
| 1238 | UGCGAGGUUGUGUUAUGCACGUG | CACGUGCAUAACACAACCUCGCA | | [511-533] ORF |
| 1239 | UUGCGAGGUUGUGUUAUGCACGU | ACGUGCAUAACACAACCUCGCAA | | [510-532] ORF |
| 1240 | UCAACUUGCCAGAAUUUGGUUAA | UUAACCAAAUUCUGGCAAGUUGA | Chimp | [357-379] ORF |
| 1241 | CAAAAGCUUGUGGUGCCAUUUCA | UGAAAUGGCACCACAAGCUUUUG | | [1419-1441] 3'UTR |
| 1242 | ACAAAAGCUUGUGGUGCCAUUUC | GAAAUGGCACCACAAGCUUUUGU | | [1418-1440] 3'UTR |
| 1243 | AACAAAAGCUUGUGGUGCCAUUU | AAAUGGCACCACAAGCUUUUGUU | | [1417-1439] 3'UTR |
| 1244 | CAACAAAAGCUUGUGGUGCCAUU | AAUGGCACCACAAGCUUUUGUUG | | [1416-1438] 3'UTR |
| 1245 | GCAAGGCUUUCAUAUCCUUGCUG | CAGCAAGGAUAUGAAAGCCUUGC | | [2050-2072] 3'UTR |
| 1246 | AGCAAGGCUUUCAUAUCCUUGCU | AGCAAGGAUAUGAAAGCCUUGCU | | [2049-2071] 3'UTR |
| 1247 | CAGCAAGGCUUUCAUAUCCUUGC | GCAAGGAUAUGAAAGCCUUGCUG | | [2048-2070] 3'UTR |
| 1248 | UCAGCAAGGCUUUCAUAUCCUUG | CAAGGAUAUGAAAGCCUUGCUGA | | [2047-2069] 3'UTR |
| 1249 | UUCAGCAAGGCUUUCAUAUCCUU | AAGGAUAUGAAAGCCUUGCUGAA | | [2046-2068] 3'UTR |
| 1250 | AAGAUACUACAAAGCCAAUCUUU | AAAGAUUGGCUUUGUAGUAUCUU | | [2281-2303] 3'UTR |
| 1251 | UCAGCUCAGGAUUUCGACUUGUU | AACAAGUCGAAAUCCUGAGCUGA | | [712-734] ORF |
| 1252 | GCAGUGUUAUCUCAUCUCUGGGC | GCCCAGAGAUGAGAUAACACUGC | | [1706-1728] 3'UTR |
| 1253 | GGCAGUGUUAUCUCAUCUCUGGG | CCCAGAGAUGAGAUAACACUGCC | | [1705-1727] 3'UTR |
| 1254 | UGGCAGUGUUAUCUCAUCUCUGG | CCAGAGAUGAGAUAACACUGCCA | | [1704-1726] 3'UTR |
| 1255 | AUGGCAGUGUUAUCUCAUCUCUG | CAGAGAUGAGAUAACACUGCCAU | | [1703-1725] 3'UTR |
| 1256 | CAUGGCAGUGUUAUCUCAUCUCU | AGAGAUGAGAUAACACUGCCAUG | | [1702-1724] 3'UTR |
| 1257 | AUCUUUAUAGAAUUGGGCCAAGA | UCUUGGCCCAAUUCUAUAAAGAU | | [2298-2320] 3'UTR |
| 1258 | AAUCUUUAUAGAAUUGGGCCAAG | CUUGGCCCAAUUCUAUAAAGAUU | | [2297-2319] 3'UTR |
| 1259 | CCCAUUUUUGUACAGAAUUGAAU | AUUCAAUUCUGUACAAAAUGGG | | [1006-1028] 3'UTR |
| 1260 | UCCCAUUUUUGUACAGAAUUGAA | UUCAAUUCUGUACAAAAUGGGA | | [1005-1027] 3'UTR |
| 1261 | AUCCCAUUUUUGUACAGAAUUGA | UCAAUUCUGUACAAAAUGGGAU | | [1004-1026] 3'UTR |
| 1262 | GAUCCCAUUUUUGUACAGAAUUG | CAAUUCUGUACAAAAUGGGAUC | | [1003-1025] 3'UTR |
| 1263 | AGAUCCCAUUUUUGUACAGAAUU | AAUUCUGUACAAAAUGGGAUCU | | [1002-1024] 3'UTR |
| 1264 | GUGUGUAGUUGAUUACUCUUCCA | UGGAAGAGUAAUCAACUACACAC | | [1552-1574] 3'UTR |
| 1265 | UGUGUGUAGUUGAUUACUCUUCC | GGAAGAGUAAUCAACUACACACA | | [1551-1573] 3'UTR |
| 1266 | UUGUGUGUAGUUGAUUACUCUUC | GAAGAGUAAUCAACUACACACAA | | [1550-1572] 3'UTR |
| 1267 | UUUGUGUGUAGUUGAUUACUCUU | AAGAGUAAUCAACUACACACAAA | | [1549-1571] 3'UTR |
| 1268 | UUUUGUGUGUAGUUGAUUACUCU | AGAGUAAUCAACUACACACAAAA | | [1548-1570] 3'UTR |
| 1269 | GUAAAUGAGAAAUAUUACGGCAA | UUGCCGUAAUAUUUCUCAUUUAC | | [1336-1358] 3'UTR |

TABLE E-continued additional 23 mers

| Number | Sense siRNA | AntiSense siRNA | Other Sp | Hum-34222182 ORF: 204-785 |
|---|---|---|---|---|
| 1270 | AUGCACCCAGAUUUUUUCCACCU | AGGUGGAAAAAAUCUGGGUGCAU | | [1899-1921] 3'UTR |
| 1271 | CAUGCACCCAGAUUUUUUCCACC | GGUGGAAAAAAUCUGGGUGCAUG | | [1898-1920] 3'UTR |
| 1272 | UAGAUCCCAUUUUUGUACAGAAU | AUUCUGUACAAAAAUGGGAUCUA | | [1001-1023] 3'UTR |
| 1273 | AUAGAUCCCAUUUUUGUACAGAA | UUCUGUACAAAAAUGGGAUCUAU | | [1000-1022] 3'UTR |
| 1274 | CAGAAUUGCUGGACUGUGGCUAU | AUAGCCACAGUCCAGCAAUUCUG | Chimp | [250-272] ORF |
| 1275 | UCAGAAUUGCUGGACUGUGGCUA | UAGCCACAGUCCAGCAAUUCUGA | Chimp | [249-271] ORF |
| 1276 | UUCAGAAUUGCUGGACUGUGGCU | AGCCACAGUCCAGCAAUUCUGAA | Chimp | [248-270] ORF |
| 1277 | UUUCAGAAUUGCUGGACUGUGGC | GCCACAGUCCAGCAAUUCUGAAA | Chimp | [247-269] ORF |
| 1278 | AUUUCAGAAUUGCUGGACUGUGG | CCACAGUCCAGCAAUUCUGAAAU | Chimp | [246-268] ORF |
| 1279 | UUUGACUACUGGGAUUAUGUUGU | ACAACAUAAUCCCAGUAGUCAAA | Chimp | [297-319] ORF |
| 1280 | UUUUGACUACUGGGAUUAUGUUG | CAACAUAAUCCCAGUAGUCAAAA | Chimp | [296-318] ORF |
| 1281 | AUUUUGACUACUGGGAUUAUGUU | AACAUAAUCCCAGUAGUCAAAAU | Chimp | [295-317] ORF |
| 1282 | GAGAAUUGCUCAAGAUGUCCUGC | GCAGGACAUCUUGAGCAAUUCUC | Chimp, Ms | [461-483] ORF |
| 1283 | AGAGAAUUGCUCAAGAUGUCCUG | CAGGACAUCUUGAGCAAUUCUCU | Chimp, Ms | [460-482] ORF |
| 1284 | CAGAGAAUUGCUCAAGAUGUCCU | AGGACAUCUUGAGCAAUUCUCUG | Chimp, Ms | [459-481] ORF |
| 1285 | UGUAGAACUGUUGUCCUUUUUCC | GGAAAAGGACAACAGUUCUACA | | [2431-2453] 3'UTR |
| 1286 | AUGUAGAACUGUUGUCCUUUUUC | GAAAAGGACAACAGUUCUACAU | | [2430-2452] 3'UTR |
| 1287 | GAUGUAGAACUGUUGUCCUUUUU | AAAAGGACAACAGUUCUACAUC | | [2429-2451] 3'UTR |
| 1288 | CGAUGUAGAACUGUUGUCCUUUU | AAAGGACAACAGUUCUACAUCG | | [2428-2450] 3'UTR |
| 1289 | CCAUUUUGUACAGAAUUGAAUG | CAUUCAAUUCUGUACAAAAUGG | | [1007-1029] 3'UTR |
| 1290 | CUUAAUCUCAGAUGAACCAUUUC | GAAAUGGUUCAUCUGAGAUUAAG | | [1677-1699] 3'UTR |
| 1291 | GCUUAAUCUCAGAUGAACCAUUU | AAAUGGUUCAUCUGAGAUUAAGC | | [1676-1698] 3'UTR |
| 1292 | UGCUUAAUCUCAGAUGAACCAUU | AAUGGUUCAUCUGAGAUUAAGCA | | [1675-1697] 3'UTR |
| 1293 | GAAUUUGGUUAAAAUGCUGGAGA | UCUCCAGCAUUUUAACCAAAUUC | Chimp | [368-390] ORF |
| 1294 | AGAAUUUGGUUAAAAUGCUGGAG | CUCCAGCAUUUUAACCAAAUUCU | Chimp | [367-389] ORF |
| 1295 | CAGAAUUUGGUUAAAAUGCUGGA | UCCAGCAUUUUAACCAAAUUCUG | Chimp | [366-388] ORF |
| 1296 | CCAGAAUUUGGUUAAAAUGCUGG | CCAGCAUUUUAACCAAAUUCUGG | Chimp | [365-387] ORF |
| 1297 | UUUUUAGACAGGAAGGUAGGAUU | AAUCCUACCUUCCUGUCUAAAAA | | [1274-1296] 3'UTR |
| 1298 | UUGAAGUAUCUCUCCUUAACCCC | GGGGUUAAGGAGAGAUACUUCAA | | [1740-1762] 3'UTR |
| 1299 | AUUGAAGUAUCUCUCCUUAACCC | GGGUUAAGGAGAGAUACUUCAAU | | [1739-1761] 3'UTR |
| 1300 | AAUUGAAGUAUCUCUCCUUAACC | GGUUAAGGAGAGAUACUUCAAUU | | [1738-1760] 3'UTR |
| 1301 | GAAUUGAAGUAUCUCUCCUUAAC | GUUAAGGAGAGAUACUUCAAUUC | | [1737-1759] 3'UTR |
| 1302 | GGAAUUGAAGUAUCUCUCCUUAA | UUAAGGAGAGAUACUUCAAUUCC | | [1736-1758] 3'UTR |
| 1303 | CUUUGACUCUCUUGCCUGUUAUG | CAUAACAGGCAAGAGAGUCAAAG | | [2466-2488] 3'UTR |
| 1304 | UCUUUGACUCUCUUGCCUGUUAU | AUAACAGGCAAGAGAGUCAAAGA | | [2465-2487] 3'UTR |
| 1305 | AUCUUUGACUCUCUUGCCUGUUA | UAACAGGCAAGAGAGUCAAAGAU | | [2464-2486] 3'UTR |
| 1306 | UAUCUUUGACUCUCUUGCCUGUU | AACAGGCAAGAGAGUCAAAGAUA | | [2463-2485] 3'UTR |

TABLE E-continued additional 23 mers

| Number | Sense siRNA | AntiSense siRNA | Other Sp | Hum-34222182 ORF: 204-785 |
|---|---|---|---|---|
| 1307 | UUAUCUUUGACUCUCUUGCCUGU | ACAGGCAAGAGAGUCAAAGAUAA | | [2462-2484] 3'UTR |
| 1308 | UGUGGCUAUCACCCAGAGAGCCU | AGGCUCUCUGGGUGAUAGCCACA | Chimp | [264-286] ORF |
| 1309 | CUGUGGCUAUCACCCAGAGAGCC | GGCUCUCUGGGUGAUAGCCACAG | Chimp | [263-285] ORF |
| 1310 | ACUGUGGCUAUCACCCAGAGAGC | GCUCUCUGGGUGAUAGCCACAGU | Chimp | [262-284] ORF |
| 1311 | GACUGUGGCUAUCACCCAGAGAG | CUCUCUGGGUGAUAGCCACAGUC | Chimp | [261-283] ORF |
| 1312 | GGACUGUGGCUAUCACCCAGAGA | UCUCUGGGUGAUAGCCACAGUCC | Chimp | [260-282] ORF |
| 1313 | AUAAAGGCCUUAUUUUUGUCUU | AAGACAAAAAUAAGGCCUUUAU | | [1945-1967] 3'UTR |
| 1314 | CAGUGUUAUCUCAUCUCUGGGCU | AGCCCAGAGAUGAGAUAACACUG | | [1707-1729] 3'UTR |
| 1315 | UGCAACUGGCAGUUUGAGCAGCA | UGCUGCUCAAACUGCCAGUUGCA | Dog, Chimp | [209-231] ORF |
| 1316 | UUGCAACUGGCAGUUUGAGCAGC | GCUGCUCAAACUGCCAGUUGCAA | Dog, Chimp | [208-230] ORF |
| 1317 | GAUUAUUUCAUGAUUGGGUAGUA | UACUACCCAAUCAUGAAAUAAUC | | [804-826] 3'UTR |
| 1318 | AGAUGCCUUUAUAAGCUCAGUUU | AAACUGAGCUUAUAAAGGCAUCU | | [1461-1483] 3'UTR |
| 1319 | UAGAUGCCUUUAUAAGCUCAGUU | AACUGAGCUUAUAAAGGCAUCUA | | [1460-1482] 3'UTR |
| 1320 | UUAGAUGCCUUUAUAAGCUCAGU | ACUGAGCUUAUAAAGGCAUCUAA | | [1459-1481] 3'UTR |
| 1321 | UUUAGAUGCCUUUAUAAGCUCAG | CUGAGCUUAUAAAGGCAUCUAAA | | [1458-1480] 3'UTR |
| 1322 | UUUUAGAUGCCUUUAUAAGCUCA | UGAGCUUAUAAAGGCAUCUAAAA | | [1457-1479] 3'UTR |
| 1323 | GUUAAGCUCCAAAGGUUCACUGU | ACAGUGAACCUUUGGAGCUUAAC | | [2349-2371] 3'UTR |
| 1324 | UGUUAAGCUCCAAAGGUUCACUG | CAGUGAACCUUUGGAGCUUAACA | | [2348-2370] 3'UTR |
| 1325 | UUGUUAAGCUCCAAAGGUUCACU | AGUGAACCUUUGGAGCUUAACAA | | [2347-2369] 3'UTR |
| 1326 | AUUGUUAAGCUCCAAAGGUUCAC | GUGAACCUUUGGAGCUUAACAAU | | [2346-2368] 3'UTR |
| 1327 | UAUUGUUAAGCUCCAAAGGUUCA | UGAACCUUUGGAGCUUAACAAUA | | [2345-2367] 3'UTR |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08614311B2). An electronic copy of the "Sequence Listing" will also be available from the USPTO upon request and payment of the fee set forth in 37 CFR 1.19(b)(3).

What is claimed is:

1. A double-stranded RNA compound having the following structure:

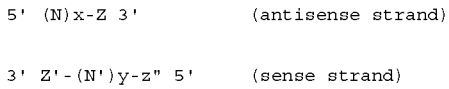

```
5'  (N)x-Z 3'           (antisense strand)

3'  Z'-(N')y-z" 5'      (sense strand)
``` wherein each of N and N' is a ribonucleotide which may be unmodified or modified, or is an unconventional moiety;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present;

wherein z" may be present or absent, but if present is a capping moiety covalently attached at the 5' terminus of (N')y;

wherein each of x and y is 19;

wherein (N)x comprises at least five unmodified and at least five 2'-O-methyl sugar modified ribonucleotides in an alternating pattern beginning at the 3' end and at least nine 2'-O-methyl sugar modified ribonucleotides in total and each remaining N is an unmodified ribonucleotide;

wherein (N')y comprises at least one unconventional moiety selected from the group consisting of a modified deoxyribonucleotide, an unmodified deoxyribonucleotide, a mirror nucleotide, and a nucleotide joined to an adjacent nucleotide by a 2'-5' internucleotide phosphate bond;

wherein the sequence of (N')y is 5' ACGUGAACUUG-GAAAUUGA (SEQ ID NO:6898); and wherein the sequence of (N)x is 5' UCAAUUUCCAAGUUCACGU 3' (SEQ ID NO:6914).

2. The double-stranded RNA compound of claim 1, wherein (N)x comprises 2'-O-methyl sugar modified ribonucleotides at positions 1, 3, 5, 7, 9, 11, 13, 15, 17 and 19.

3. The double-stranded RNA compound of claim 1, wherein (N)x comprises 2'-O-methyl sugar modified ribonucleotides at positions 2, 4, 6, 8, 11, 13, 15, 17, and 19.

4. The double-stranded RNA compound of claim 1, wherein (N')y comprises a mirror nucleotide.

5. The double-stranded RNA compound of claim 4, wherein the mirror nucleotide is present at position 18.

6. The double-stranded RNA compound of claim 5, wherein (N')y further comprises a mirror nucleotide at position 17.

7. The double-stranded RNA compound of claim 1 or 5, wherein (N')y comprises a deoxyribonucleotide at position 15.

8. The double-stranded RNA compound of claim 1, wherein each of (N)x and (N')y is unphosphorylated or phosphorylated at the 5' terminus and the 3' terminus.

9. The double-stranded RNA compound of claim 8, wherein (N)x is unphosphorylated at the 3' terminus.

10. The double-stranded RNA compound of claim 1, wherein z" is present.

11. The double-stranded RNA compound of claim 1 having the structure:

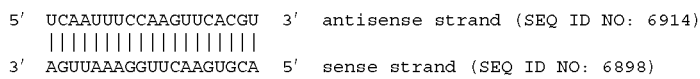

```
5'  UCAAUUUCCAAGUUCACGU  3'   antisense strand (SEQ ID NO: 6914)
    |||||||||||||||||||
3'  AGUUAAAGGUUCAAGUGCA  5'   sense strand (SEQ ID NO: 6898)
``` wherein each of A, C, U and G is an unmodified or a 2'-O-methyl sugar modified ribonucleotide or may be replaced by an unconventional moiety; and wherein in 5'-3' order each A, C, U, G or unconventional moiety is joined to the next A, C, U, G or unconventional moiety by a phosphodiester bond.

12. A composition comprising the double-stranded RNA compound of claim 1 or 11; and a pharmaceutically acceptable carrier.

13. The double-stranded RNA compound of claim 1, wherein the covalent bond joining each consecutive N or N' is a phosphodiester bond.

14. The double-stranded RNA compound of claim 11, wherein the sense strand comprises at least one unconventional moiety which is a mirror nucleotide.

15. The double-stranded RNA compound of claim 14, wherein the mirror nucleotide is L-DNA.

16. The double-stranded RNA compound of claim 15, wherein the L-DNA is present at position 18 of the sense strand.

17. The double-stranded RNA compound of claim 15, wherein the L-DNA is present at positions 17 and 18 of the sense strand.

18. The double-stranded RNA compound of claim 10, wherein z" is selected from the group consisting of an abasic ribose moiety, a deoxyribose moiety; an inverted abasic ribose moiety, a deoxyribose moiety; C6-amino-Pi; and a mirror nucleotide.

19. The double-stranded RNA compound of claim 16 or 17, wherein the L-DNA is L-deoxyribocytidine.

* * * * *